(12) United States Patent
Hu et al.

(10) Patent No.: US 10,662,203 B2
(45) Date of Patent: May 26, 2020

(54) PYRIDO[2,3-B]INDOLE COMPOUNDS FOR THE TREATMENT AND PROPHYLAXIS OF BACTERIAL INFECTION

(71) Applicant: Hoffmann-La Roche Inc., Little Falls, NJ (US)

(72) Inventors: Yimin Hu, Shanghai (CN); Chengang Zhou, Shanghai (CN); Mingwei Zhou, Shanghai (CN); Houguang Shi, Shanghai (CN); Yongqiang Liu, Shanghai (CN); Hong Shen, Shanghai (CN); Maarten Vercruysse, Basel (CH); Shixiang Yan, Shanghai (CN); Xuefei Tan, Shanghai (CN); Xianfeng Lin, Shanghai (CN); Fabian Dey, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/941,313

(22) Filed: Mar. 30, 2018

(65) Prior Publication Data

US 2018/0327425 A1    Nov. 15, 2018

(30) Foreign Application Priority Data

Mar. 30, 2017  (WO) ................ PCT/CN2017/078810
Oct. 19, 2017  (WO) ................ PCT/CN2017/106920
Feb. 11, 2018  (WO) ................ PCT/CN2018/076251

(51) Int. Cl.
  *C07D 519/00*   (2006.01)
  *C07D 471/04*   (2006.01)
  *A61P 31/04*    (2006.01)

(52) U.S. Cl.
  CPC ............ *C07D 519/00* (2013.01); *A61P 31/04* (2018.01); *C07D 471/04* (2013.01)

(58) Field of Classification Search
  CPC ..... C07D 519/00; C07D 471/04; A61P 31/04; A61K 31/4375
  See application file for complete search history.

(56) References Cited

FOREIGN PATENT DOCUMENTS

| WO | 99/55677 A1 | 11/1999 | |
|---|---|---|---|
| WO | 2010/136817 A1 | 12/2010 | |
| WO | WO-2010136817 A1 * | 12/2010 | ........... C07D 471/04 |
| WO | 2011/032050 A2 | 3/2011 | |
| WO | 2012/125746 A1 | 9/2012 | |
| WO | WO-2012125746 A1 * | 9/2012 | ........... C07D 487/04 |
| WO | 2014/043272 A1 | 3/2014 | |
| WO | 2015/038661 A1 | 3/2015 | |

OTHER PUBLICATIONS

ISR of PCT/EP2017/079857 (dated Jan. 25, 2018).
ISR of PCT/EP2018/057709 (dated Jun. 19, 2018).

* cited by examiner

*Primary Examiner* — Amanda L Aguirre
(74) *Attorney, Agent, or Firm* — Bradley E. Davis

(57) ABSTRACT

The present invention relates to novel compounds of formula (I),

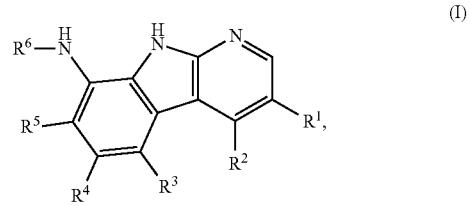

wherein $R^1$, $R^2$, $R^3$, $R^4$, $R^5$ and $R^6$ are as described herein, and their pharmaceutically acceptable salt, enantiomer or diastereomer thereof, and compositions including the compounds and methods of using the compounds.

27 Claims, 1 Drawing Sheet

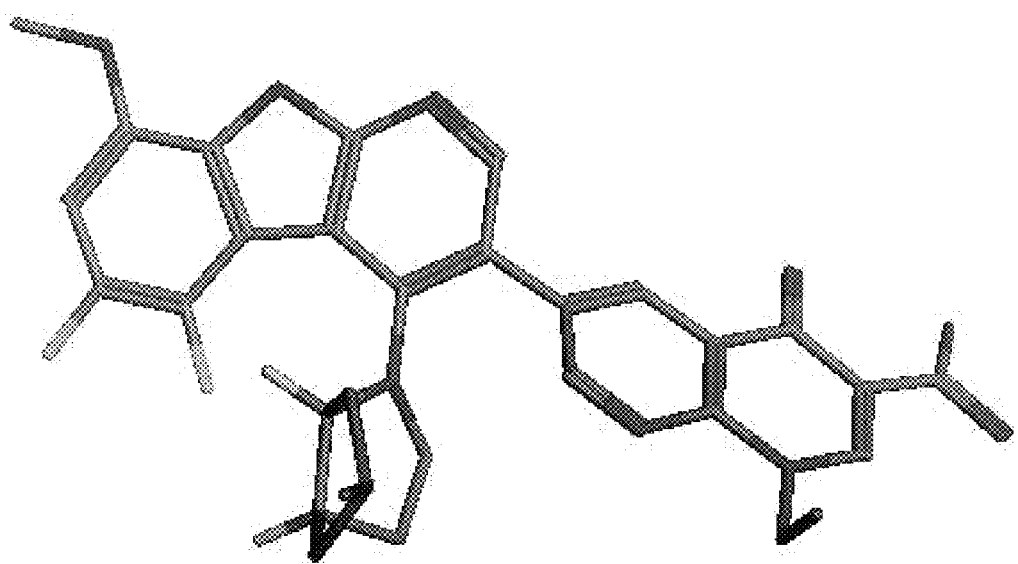

PYRIDO[2,3-B]INDOLE COMPOUNDS FOR THE TREATMENT AND PROPHYLAXIS OF BACTERIAL INFECTION

RELATED APPLICATIONS

This application claims priority to International Application Number PCT/CN2018/076251, filed Feb. 11, 2018, International Application Number PCT/CN2017/078810, filed Mar. 30, 2017 and International Application Number PCT/CN2017/106920, filed Oct. 19, 2017 each of which are incorporated herein by reference in its entirety.

The present invention relates to organic compounds useful for therapy and/or prophylaxis in a mammal, and in particular to inhibitors of DNA gyrase and/or topoisomerase IV useful for treatment and/or prophylaxis of bacterial infection.

FIELD OF THE INVENTION

Bacterial infections pose a continuing medical problem because anti-bacterial drugs eventually engender resistance in the bacteria on which they are used. Bacterial resistance against virtually all current antibiotic drugs are increasing. Many forms of antibiotic resistance can even cross international boundaries and spread with remarkable speed. Thus novel classes of antibacterial compounds are urgently needed.

One target for development of anti-bacterial drugs has been DNA gyrase and topoisomerase IV (bacterial type IIA topoisomerases), which are essential to cell life, that solve DNA topological problems resulting from the replication, transcription, and recombination of DNA. DNA Gyrase controls DNA supercoiling and relieves topological stress that occurs when the DNA strands are untwisted such as during replication. Topoisomerase IV primarily resolves linked chromosome dimers at the conclusion of DNA replication. Both enzymes can introduce double stranded DNA breaks; pass a second DNA strand through the break and rejoining the broken strands. The activity of both enzymes is driven by the binding and hydrolysis of ATP. Bacterial DNA gyrase consists of two A (GyrA) and two B (GyrB) subunits. Binding and cleavage of the DNA is associated with GyrA, whereas ATP is bound and hydrolyzed by GyrB. Bacterial Topoisomerase IV is also a hetero-tetramer that consists of two C (ParC) and two E (ParE) subunits. The latter subunits bind ATP like GyrB in order to supply energy necessary for catalytic turnover of the enzymes.

Inhibition of DNA gyrase and topoisomerase IV has potential for the development of broad-spectrum antibiotics. The enzymes are highly conserved across a broad range of gram-positive and gram-negative pathogens. There are two classes of antibiotics that demonstrated such mechanism of action. The first, well-represented by the quinolones, inhibits GyrA and ParC subunits by stabilizing the cleaved DNA-enzyme complex, thus inhibiting overall gyrase function, leading to cell death. Novobiocin, the only marketed drug in the second class, exerts its effect by blocking the ATPase activity of the enzymes. Novobiocin was identified in 1950s. But its use declined rapidly and it was eventually withdrawn from the market, mainly due to its low permeability in many bacteria strains, rise of spontaneous resistance development, and the development of more effective drugs, such as penicillinase-stable penicillins and the first cephalosporins in 1960s and 1970s.

Recently, strong inhibition of DNA gyrase and/or topoisomerase IV has been recognized to be important for low resistance development in bacterial strains treated by inhibitors of the enzymes. Inhibitors of bacterial DNA gyrase and/or topoisomerase IV with different mechanism of action compare to the widely used quinolones will exhibit minimal cross resistance, and will be potentially useful in combating quinolone resistance that has increased significantly in the past few years.

SUMMARY OF THE INVENTION

The present invention relates to novel compounds of formula (I),

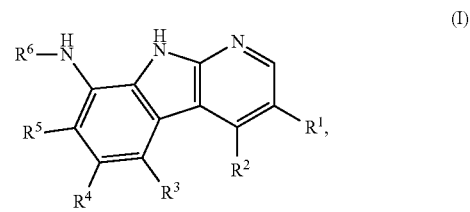

(I)

wherein
$R^1$ is

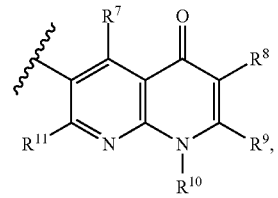

wherein
$R^7$ is H;
$R^8$ is carboxy;
$R^9$ is H;
$R^{10}$ is $(C_{1-6}alkyl)_2(C_{1-6}alkylamino)C_{1-6}alkyl$, $(C_{1-6}alkyl)_2(pyrrolidinyl)C_{1-6}alkyl$, $(C_{1-6}alkyl)_2$ amino, $(C_{1-6}alkyl)_2amino(phenyl)C_{1-6}alkyl$, $(C_{1-6}alkyl)_2aminoC_{1-6}alkyl$, $(C_{1-6}alkylamino)C_{1-6}alkyl$, $(C_{1-6}alkylpiperazinyl)C_{1-6}alkyl$, $(C_{1-6}alkylpiperidinyl)C_{1-6}alkyl$, $(C_{1-6}alkylpyrrolidinyl)C_{1-6}alkyl$, (hydroxyC_{1-6}alkyl)_2C_{1-6}alkyl$, $(hydroxyC_{1-6}alkyl)C_{1-6}$ alkyl, $(hydroxyC_{3-7}cycloalkyl)C_{1-6}alkyl$, amino, aminoC_{1-6}alkyl, $C_{1-6}alkoxyC_{1-6}alkyl$, $C_{1-6}alkoxyC_{1-6}$ alkylamino, $C_{1-6}alkyl$, $C_{1-6}alkylamino$, $C_{1-6}alkylheterocyclyl$, $C_{3-7}cycloalkyl$, $C_{3-7}cycloalkylamino$, dihydroxyC_{1-6}alkyl, haloC_{1-6}alkylamino, hydroxyC_{1-6}alkyl, heterocyclylC_{1-6}alkyl, heterocyclyl or heterocyclyl amino;
$R^{11}$ is H;
$R^2$ is $(C_{1-6}alkyl)_2amino$, $C_{1-6}alkylamino$, $C_{1-6}alkoxyC_{1-6}alkyl(C_{1-6}alkyl)amino$ or heterocyclyl;
$R^3$ is H, halogen, cyano or $C_{1-6}alkoxy$;
$R^4$ is H, halogen or haloC_{1-6}alkyl;
$R^5$ is H or halogen;
$R^6$ is $C_{1-6}alkyl$;
or a pharmaceutically acceptable salt, or enantiomer or diastereomer thereof.

Objects of the present invention are novel compounds of formula (I), their manufacture, medicaments based on a compound in accordance with the invention and their production as well as the use of compounds of formula (I) for the treatment or prophylaxis of bacterial infection. The use of compounds of formula (I) as DNA gyrase and/or topoisomerase IV inhibitors is also one of the objections of present invention. The compounds of formula (I) showed superior anti-bacterial activity, good solubility, good $CC_{50}$ profiles, improved microsomal stability and/or improved PK profile.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

Definitions

The term "$C_{1-6}$alkyl" denotes a saturated, linear or branched chain alkyl group containing 1 to 6, particularly 1 to 4 carbon atoms, for example methyl, ethyl, propyl, isopropyl, n-butyl, isobutyl, tert-butyl and the like. Particular "$C_{1-6}$alkyl" groups are methyl, ethyl and propyl.

The term "$C_{1-6}$alkoxy" denotes a group of the formula $C_{1-6}$alkyl-O—. Examples of $C_{1-6}$alkoxy group include, but not limited to, methoxy, ethoxy, n-propoxy, isopropoxy, n-butoxy, isobutoxy and tert-butoxy. Particular "$C_{1-6}$alkoxy" groups are methoxy, ethoxy and isopropoxy.

The term "halogen" and "halo" are used interchangeably herein and denote fluoro, chloro, bromo, or iodo.

The term "halo$C_{1-6}$alkyl" denotes an alkyl group wherein at least one of the hydrogen atoms of the alkyl group has been replaced by same or different halogen atoms, particularly fluoro atom. Examples of halo$C_{1-6}$alkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, difluoromethyl, trifluoromethyl and trifluoroethyl.

The term "halopyrrolidinyl" denotes a pyrrolidinyl substituted once, twice or three times by halogen. Examples of halopyrrolidinyl include, but not limited to, difluoropyrrolidinyl.

The term "heterocyclyl" denotes a monovalent saturated or partly unsaturated mono-, bicyclic or tricyclic ring system of 3 to 12 ring atoms, comprising 1, 2, or 3 ring heteroatoms selected from N, O and S, the remaining ring atoms being carbon. In particular embodiments, heterocyclyl is a monovalent saturated or partly unsaturated monocyclic or bicyclic ring system of 4 to 10 ring atoms, comprising 1, 2, or 3 ring heteroatoms selected from N, O and S, the remaining ring atoms being carbon. Examples for monocyclic saturated heterocyclyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Bicyclic heterocyclyl can be spiro ring, fused ring or bridged ring. Examples for bicyclic heterocyclyl are decahydronaphthyridine; azabicyclo[3.2.0]heptanyl; octahydrocyclopenta[b]pyrrolyl; octahydrocyclopenta[c]pyrrolyl; 1,3,3a,4,6,6a-hexahydrofuro[3,4-c]pyrrolyl; 1,3,3a,4,6,6a-hexahydropyrrolo[3,4-c]pyrrolyl; 1,7-diazaspiro[3.4]octanyl; 1,7-diazaspiro[4.4]nonanyl; 2,3,3a,4,6,6a-hexahydrofuro[2,3-c]pyrrolyl; 2,3,3a,4,6,6a-hexahydropyrrolo[2,3-c]pyrrolyl; 2,3,3a,5,6,6a-hexahydropyrrolo[3,2-b]pyrrolyl; 2,3,3a,4,6,6a-hexahydropyrrolo[3,4-b]pyrrolyl; 2,3,3a,5,6,6a-hexahydropyrrolo[3,2-b]pyrrolyl; 2,3,4a,5,7,7a-hexahydropyrrolo[3,4-b][1,4]oxazinyl; 2,6-diazabicyclo[3.2.0]heptanyl; 2,6-diazaspiro[3.4]octanyl; 2,7-diazaspiro[4.4]nonanyl; 2,8-diazaspiro[4.5]decanyl; 2,9-diazaspiro[4.5]decanyl; 3,3a,4,5,6,6a-hexahydro-1H-cyclopenta[c]pyrrolyl; 3,3a,4,5,7,7a-hexahydro-2H-pyrrolo[2,3-c]pyridinyl; 3,3a,4,6,7,7a-hexahydro-2H-pyrrolo[3,2-c]pyridinyl; 3,3a,5,6,7,7a-hexahydro-2H-pyrrolo[3,2-b]pyridinyl; 3,4,4a,5,7,7a-hexahydro-2H-pyrrolo[3,4-b]pyridinyl; 3,4,6,6a-tetrahydro-2H-pyrrolo[2,3-c]pyrrolyl; 3,4,6,6a-tetrahydro-2H-pyrrolo[3,4-b]pyrrolyl; 3,4,6,7,8,8a-hexahydro-1H-pyrrolo[1,2-a]pyrazinyl; 3,6-diazabicyclo[3.2.0]heptanyl; 3,8-diazabicyclo[4.2.0]octanyl; 3,7-diazabicyclo[4.2.0]octanyl; 2,7-diazabicyclo[4.2.0]octanyl; 3-azabicyclo[3.1.0]hexanyl; 5-azaspiro[2.4]heptanyl; 5-oxa-2,8-diazaspiro[3.5]nonanyl; 6-azaspiro[3.4]octanyl; 6-oxa-2,9-diazaspiro[4.5]decanyl; hexahydro-1H-isoindol-2(3H)-yl; hexahydro-1H-pyrrolo[3,4-b]pyridin-6(2H)-yl; hexahydropyrazino[2,1-c][1,4]oxazin-8(1H)-yl; hexahydropyrrolo[3,4-b][1,4]oxazin-6(2H)-yl; hexahydropyrrolo[3,4-b]pyrrol-1(2H)-yl; oxaazabicyclo[2.2.1]heptanyl; and oxaazabicyclo[3.1.1]heptanyl. Examples for partly unsaturated heterocyclyl are dihydrofuryl, imidazolinyl, dihydro-oxazolyl, tetrahydro-pyridinyl, or dihydropyranyl. Monocyclic or bicyclic heterocyclyl can be further substituted once, twice or three times by hydroxy$C_{1-6}$alkyl, ($C_{1-6}$alkoxy$C_{1-6}$alkyl($C_{1-6}$alkyl)amino)$C_{1-6}$alkyl, ($C_{1-6}$alkyl)$_2$amino, ($C_{1-6}$alkyl)$_2$amino$C_{1-6}$alkyl, ($C_{3-7}$cycloalkyl($C_{1-6}$alkyl)amino)$C_{1-6}$alkyl, ($C_{3-7}$cycloalkylamino)$C_{1-6}$alkyl, amino, amino$C_{1-6}$alkyl, $C_{1-6}$alkoxy, $C_{1-6}$alkoxy$C_{1-6}$alkyl, $C_{1-6}$alkoxy$C_{1-6}$alkyl($C_{1-6}$alkyl)amino, $C_{1-6}$alkyl, $C_{1-6}$alkyl, ($C_{1-6}$alkyl)2amino, $C_{3-7}$cycloalkyl, $C_{3-7}$cycloalkyl($C_{1-6}$alkyl)amino, $C_{3-7}$cycloalkylamino, halo$C_{1-6}$alkyl, halogen, hydroxy, hydroxy$C_{1-6}$alkyl, hydroxy$C_{1-6}$alkyl($C_{1-6}$alkyl)amino, morpholino$C_{1-6}$alkyl, pyrrolidinyl or pyrrolidinyl$C_{1-6}$alkyl.

The term "cis-isomers" and "trans-isomers" denote the relative stereochemistry of the molecule or moiety. For example: Intermediate C42

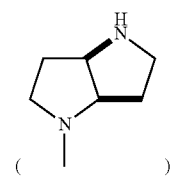

as the "cis-isomers" refers to a mixture of

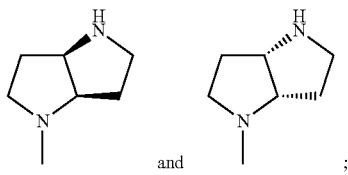

similarly, Intermediate C50

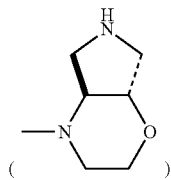

as the "trans-isomers" refers to a mixture of

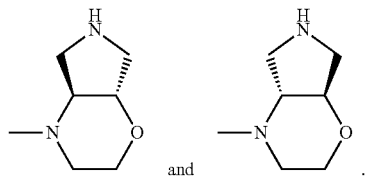

The way of showing relative stereochemistry also applies to the final compound.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

Inhibitors of DNA Gyrase and/or Topoisomerase IV

The present invention relates to a compound of formula (I),

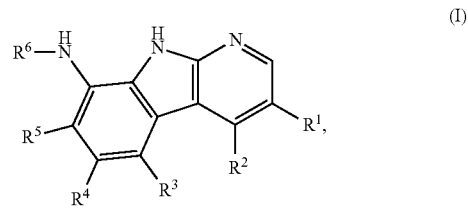

wherein
$R^1$ is

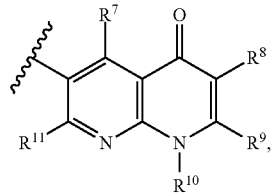

wherein
$R^7$ is H;
$R^8$ is carboxy;
$R^9$ is H;
$R^{10}$ is $(C_{1-6}alkyl)_2(C_{1-6}alkylamino)C_{1-6}alkyl$, $(C_{1-6}alkyl)_2(pyrrolidinyl)C_{1-6}alkyl$, $(C_{1-6}alkyl)_2amino$, $(C_{1-6}alkyl)_2amino(phenyl)C_{1-6}alkyl$, $(C_{1-6}alkyl)_2aminoC_{1-6}alkyl$, $(C_{1-6}alkylamino)C_{1-6}alkyl$, $(C_{1-6}alkylpiperazinyl)C_{1-6}alkyl$, $(C_{1-6}alkylpiperidinyl)C_{1-6}alkyl$, $(C_{1-6}alkylpyrrolidinyl)C_{1-6}alkyl$, $(hydroxyC_{1-6}alkyl)_2C_{1-6}alkyl$, $(hydroxyC_{1-6}alkyl)C_{1-6}alkyl$, $(hydroxyC_{3-7}cycloalkyl)C_{1-6}alkyl$, amino, $aminoC_{1-6}alkyl$, $C_{1-6}alkoxy$ $C_{1-6}alkyl$, $C_{1-6}alkoxyC_{1-6}alkylamino$, $C_{1-6}alkyl$, $C_{1-6}alkylamino$, $C_{1-6}alkylheterocyclyl$, $C_{3-7}cycloalkyl$, $C_{3-7}cycloalkylamino$, $dihydroxyC_{1-6}alkyl$, $haloC_{1-6}alkylamino$, $hydroxyC_{1-6}alkyl$, $heterocyclylC_{1-6}alkyl$, heterocyclyl or heterocyclyl amino;
$R^{11}$ is H;
$R^2$ is $(C_{1-6}alkyl)_2amino$, $C_{1-6}alkylamino$, $C_{1-6}alkoxy$ $C_{1-6}alkyl(C_{1-6}alkyl)amino$ or heterocyclyl;
$R^3$ is H, halogen, cyano or $C_{1-6}alkoxy$;
$R^4$ is H, halogen or $haloC_{1-6}alkyl$;

$R^5$ is H or halogen;
$R^6$ is $C_{1-6}$alkyl;
or a pharmaceutically acceptable salt, or enantiomer or diastereomer thereof.

A further embodiment of present invention is (ii) a compound of formula (I) according to (i), wherein $R^1$ is

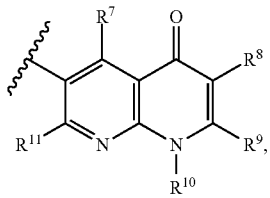

wherein
$R^7$ is H;
$R^8$ is carboxy;
$R^9$ is H;
$R^{10}$ is $(C_{1-6}alkyl)_2(C_{1-6}alkylamino)C_{1-6}alkyl$, $(C_{1-6}alkyl)_2(pyrrolidinyl)C_{1-6}alkyl$, $(C_{1-6}alkyl)_2amino$, $(C_{1-6}alkyl)_2amino(phenyl)C_{1-6}alkyl$, $(C_{1-6}alkyl)_2aminoC_{1-6}alkyl$, $(C_{1-6}alkylamino)C_{1-6}alkyl$, $(C_{1-6}alkylpiperazinyl)C_{1-6}alkyl$, $(C_{1-6}alkylpiperidinyl)C_{1-6}alkyl$, $(C_{1-6}alkylpyrrolidinyl)C_{1-6}alkyl$, $(hydroxyC_{1-6}alkyl)_2C_{1-6}alkyl$, $(hydroxyC_{1-6}alkyl)C_{1-6}alkyl$, $(hydroxyC_{3-7}cycloalkyl)C_{1-6}alkyl$, amino, $aminoC_{1-6}alkyl$, $C_{1-6}alkoxy$ $C_{1-6}alkyl$, $C_{1-6}alkoxyC_{1-6}alkylamino$, $C_{1-6}alkyl$, $C_{1-6}alkylamino$, $C_{1-6}alkylpyrrolidinyl$, $C_{3-7}cycloalkyl$, $C_{3-7}cycloalkylamino$, $dihydroxyC_{1-6}alkyl$, $haloC_{1-6}alkylamino$, $hydroxyC_{1-6}alkyl$, morpholino$C_{1-6}alkyl$, morpholinyl, morpholinyl$C_{1-6}alkyl$, $oxazolylC_{1-6}alkyl$, oxopiperazinyl $C_{1-6}alkyl$, $pyrazinylC_{1-6}alkyl$, $pyridinylC_{1-6}alkyl$, pyrrolidinyl, $pyrrolidinylC_{1-6}alkyl$, tetrahydrofuranyl, $tetrahydrofuranylC_{1-6}alkyl$ or tetrahydropyranyl amino;
$R^{11}$ is H;
$R^2$ is $(C_{1-6}alkyl)_2amino$;
$C_{1-6}alkoxyC_{1-6}alkyl(C_{1-6}alkyl)amino$;
$C_{1-6}alkylamino$;
1,3,3a,4,6,6a-hexahydrofuro[3,4-c]pyrrolyl;
1,3,3a,4,6,6a-hexahydropyrrolo[3,4-c]pyrrolyl substituted by $C_{1-6}alkyl$;
1,4-diazepanyl substituted by $C_{1-6}alkyl$;
1,4-oxazepanyl substituted by $(C_{1-6}alkyl)_2amino$ $C_{1-6}alkyl$;
1,7-diazaspiro[3.4]octanyl substituted by $C_{1-6}alkyl$;
1,7-diazaspiro[4.4]nonanyl substituted by $C_{1-6}alkyl$;
2,3,3a,4,6,6a-hexahydrofuro[2,3-c]pyrrolyl substituted by $(C_{1-6}alkyl)_2amino$, $(C_{1-6}alkyl)_2aminoC_{1-6}alkyl$ or hydroxy;
2,3,3a,4,6,6a-hexahydropyrrolo[2,3-c]pyrrolyl substituted by one or two substituents independently selected from $haloC_{1-6}alkyl$, halogen, hydroxy $C_{1-6}alkyl$, $C_{1-6}alkoxyC_{1-6}alkyl$, $C_{3-7}cycloalkyl$ and $C_{1-6}alkyl$;
2,3,3a,5,6,6a-hexahydropyrrolo[3,2-b]pyrrolyl substituted by $C_{1-6}alkyl$;
2,3,4a,5,7,7a-hexahydropyrrolo[3,4-b][1,4]oxazinyl substituted by $C_{1-6}alkyl$;
2,6-diazabicyclo[3.2.0]heptanyl substituted by $C_{1-6}alkyl$;
2,6-diazaspiro[3.4]octanyl substituted by $C_{1-6}alkyl$;
2,7-diazaspiro[4.4]nonanyl substituted by $C_{1-6}alkyl$;
2,8-diazaspiro[4.5]decanyl substituted by $C_{1-6}alkyl$;
2,9-diazaspiro[4.5]decanyl substituted by hydroxy $C_{1-6}alkyl$, $C_{1-6}alkoxyC_{1-6}alkyl$ or $C_{1-6}alkyl$;
3,3a,4,5,6,6a-hexahydro-1H-cyclopenta[c]pyrrolyl substituted by $(C_{1-6}alkyl)_2aminoC_{1-6}alkyl$ or $(C_{1-6}alkyl)_2amino$;
3,3a,4,5,7,7a-hexahydro-2H-pyrrolo[2,3-c]pyridinyl substituted by $C_{1-6}alkyl$;
3,3a,4,6,7,7a-hexahydro-2H-pyrrolo[3,2-c]pyridinyl substituted by $C_{1-6}alkyl$;
3,3a,5,6,7,7a-hexahydro-2H-pyrrolo[3,2-b]pyridinyl substituted by $C_{1-6}alkyl$;
3,4,4a,5,7,7a-hexahydro-2H-pyrrolo[3,4-b]pyridinyl substituted by one or two substituents independently selected from hydroxy and $C_{1-6}alkyl$;
3,4,6,6a-tetrahydro-2H-pyrrolo[2,3-c]pyrrolyl substituted twice by $C_{1-6}alkyl$;
3,4,6,6a-tetrahydro-2H-pyrrolo[3,4-b]pyrrolyl substituted by one or two substituents independently selected from halogen and $C_{1-6}alkyl$;
3,4,6,7,8,8a-hexahydro-1H-pyrrolo[1,2-a]pyrazinyl;
3,6-diazabicyclo[3.2.0]heptanyl substituted by $C_{1-6}alkyl$;
3,8-diazabicyclo[4.2.0]octanyl substituted by $C_{1-6}alkyl$;
3-azabicyclo[3.1.0]hexanyl substituted by $(C_{1-6}alkyl)_2amino$;
5-azaspiro[2.4]heptanyl substituted by $(C_{1-6}alkyl)_2aminoC_{1-6}alkyl$ or $(C_{1-6}alkyl)_2amino$;
5-oxa-2,8-diazaspiro[3.5]nonanyl;
6-azaspiro[3.4]octanyl substituted by $(C_{1-6}alkyl)_2amino$;
6-oxa-2,9-diazaspiro[4.5]decanyl substituted by $C_{1-6}alkyl$;
hexahydro-1H-isoindol-2(3H)-yl substituted by $(C_{1-6}alkyl)_2amino$;
hexahydro-1H-pyrrolo[3,4-b]pyridin-6(2H)-yl substituted by $C_{1-6}alkyl$;
hexahydropyrazino[2,1-c][1,4]oxazin-8(1H)-yl;
hexahydropyrrolo[3,4-b][1,4]oxazin-6(2H)-yl substituted by $C_{1-6}alkyl$;
morpholinyl, said morpholinyl being unsubstituted or substituted by $(C_{1-6}alkyl)_2aminoC_{1-6}alkyl$, $hydroxyC_{1-6}alkyl$, $C_{1-6}alkoxyC_{1-6}alkyl$ or $C_{1-6}alkyl$;
oxaazabicyclo[2.2.1]heptanyl;
oxaazabicyclo[3.1.1]heptanyl;
oxazepanyl;
piperazinyl substituted by $haloC_{1-6}alkyl$, $C_{3-7}cycloalkyl$ or $C_{1-6}alkyl$;
piperidinyl, said piperidinyl being unsubstituted or substituted with one or two substituents independently selected from $(C_{1-6}alkyl)_2amino$, $(C_{1-6}alkyl)_2aminoC_{1-6}alkyl$, $C_{1-6}alkoxy$, $C_{1-6}alkoxy$ $C_{1-6}alkyl(C_{1-6}alkyl)amino$, halogen, hydroxy, $hydroxyC_{1-6}alkyl(C_{1-6}alkyl)amino$ and pyrrolidinyl;
pyrazolyl substituted once or twice by substituents independently selected from $aminoC_{1-6}alkyl$ and $haloC_{1-6}alkyl$;
pyrrolidinyl said pyrrolidinyl being unsubstituted or substituted with one, two or three substituents independently selected from $(C_{1-6}alkoxyC_{1-6}alkyl(C_{1-6}alkyl))C_{1-6}alkyl$, $(C_{1-6}alkyl)_2amino$, $(C_{1-6}alkyl)_2aminoC_{1-6}alkyl$, $(C_{3-7}cycloalkyl(C_{1-6}alkyl)amino)C_{1-6}alkyl$, $(C_{3-7}cycloalkylamino)$ $C_{1-6}alkyl$, amino, $aminoC_{1-6}alkyl$, $C_{1-6}alkoxy$, $C_{1-6}$alkoxy$C_{1-6}$alkyl($C_{1-6}$alkyl)amino, $C_{1-6}$alkyl, $C_{3-7}$cycloalkyl($C_{1-6}$alkyl)amino, $C_{3-7}$cycloalkylamino, halo$C_{1-6}$alkyl, halogen, hydroxy, hydroxy$C_{1-6}$alkyl, hydroxy$C_{1-6}$alkyl($C_{1-6}$alkyl)amino, morpholino$C_{1-6}$alkyl and pyrrolidinyl $C_{1-6}$alkyl; or thiomorpholinyl;

$R^3$ is H, halogen, cyano or $C_{1-6}$alkoxy;

$R^4$ is H, halogen or halo$C_{1-6}$alkyl;

$R^5$ is H or halogen;

$R^6$ is $C_{1-6}$alkyl;

or a pharmaceutically acceptable salt, or enantiomer or diastereomer thereof.

A further embodiment of present invention is (iii) a compound of formula (I) according to (ii), wherein $R^1$ is

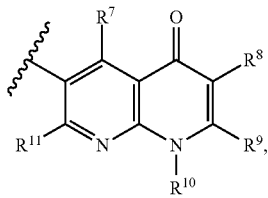

wherein $R^7$ is H;

$R^8$ is carboxy;

$R^9$ is H;

$R^{10}$ is (diethylamino)ethyl, (dimethylamino)butyl, (dimethylamino)ethyl, (dimethylamino)isopentyl, (dimethylamino)isopropyl, (dimethylamino)methylpropyl, (ethylpyrrolidinyl)methyl, (hydroxycyclopropyl)methyl, (hydroxymethyl)$_2$ethyl, (hydroxymethyl)ethyl, (methylamino)ethyl, (methylpiperazinyl)ethyl, (methylpiperidinyl)methyl, amino, amino(methyl)propyl, aminoisopentyl, cyclopropyl, cyclopropylamino, dihydroxypropyl, dimethyl(methylamino)ethyl, dimethyl(pyrrolidinyl)ethyl, dimethylamino, dimethylamino(phenyl)ethyl, ethyl, ethylamino, ethylpyrrolidinyl, hydroxy(methyl)propyl, hydroxypropyl, methoxyethyl, methoxyethylamino, methoxymethyl, methyl, methylamino, methylpyrrolidinyl, morpholinylethyl, morpholinyl, morpholinylmethyl, oxazolylmethyl, oxopiperazinylethyl, pyrazinylmethyl, pyridinylmethyl, pyrrolidinyl, pyrrolidinylmethyl, tetrahydrofuranyl, tetrahydrofuranylmethyl, tetrahydropyranylamino or trifluoroethylamino;

$R^{11}$ is H;

$R^2$ is dimethylamino; ((cyclopropyl(methyl)amino)methyl)pyrrolidinyl; ((cyclopropylamino)methyl)pyrrolidinyl; ((diethylamino)methyl)morpholinyl; ((dimethylamino)methyl)fluoropiperidinyl; ((dimethylamino)methyl)fluoropyrrolidinyl; ((dimethylamino)methyl)hydroxypyrrolidinyl; ((dimethylamino)methyl)methylpyrrolidinyl; ((dimethylamino)methyl)morpholinyl; ((dimethylamino)methyl)piperidinyl; ((dimethylamino)methyl)pyrrolidinyl; ((methoxyethyl(methyl)amino)methyl)pyrrolidinyl; cyclopropyl(methyl)amino)pyrrolidinyl; (cyclopropylamino)pyrrolidinyl; (dimethylamino)fluoropyrrolidinyl; (dimethylamino)hexahydro-1H-isoindol-2(3H)-yl; (dimethylamino)hydroxypyrrolidinyl; (dimethylamino)methoxypyrrolidinyl; (dimethylamino)methyl-1,4-oxazepanyl; (dimethylamino)methyl-2,3,3a,4,6,6a-hexahydrofuro[2,3-c]pyrrolyl; (dimethylamino)methyl-3,3a,4,5,6,6a-hexahydro-1H-cyclopenta[c]pyrrolyl; (dimethylamino)methyl-3,3-difluoropyrrolidinyl; (dimethylamino)methyl-5-azaspiro[2.4]heptanyl; (dimethylamino)methylpyrrolidinyl; (dimethylamino)piperidinyl; (dimethylamino)pyrrolidinyl; (hydroxyethyl(methyl)amino)piperidinyl; (hydroxyethyl(methyl)amino)pyrrolidinyl; (hydroxyethyl)morpholinyl; (hydroxyethyl)pyrrolidinyl; (hydroxymethyl)pyrrolidinyl; (methoxyethyl(methyl)amino)piperidinyl; (methoxyethyl(methyl)amino)pyrrolidinyl; (methoxymethyl)morpholinyl; (morpholinylmethyl)pyrrolidinyl; (pyrrolidinylmethyl)pyrrolidinyl; (trifluoromethyl)piperazinyl; (trifluoromethyl)pyrazolyl; 1,3,3a,4,6,6a-hexahydrofuro[3,4-c]pyrrolyl; 3,4,6,7,8,8a-hexahydro-1H-pyrrolo[1,2-a]pyrazinyl; 3a-(fluoromethyl)-5-methyl-2,3,3a,4,6,6a-hexahydropyrrolo[2,3-c]pyrrolyl; 3a-fluoro-5-methyl-2,3,3a,4,6,6a-hexahydropyrrolo[2,3-c]pyrrolyl; 5-oxa-2,8-diazaspiro[3.5]nonanyl; amino(trifluoromethyl)pyrrolidinyl; aminomethyl(trifluoromethyl)pyrazolyl; cyclopropyl-2,3,3a,4,6,6a-hexahydropyrrolo[2,3-c]pyrrolyl; cyclopropylpiperazinyl; difluoropyrrolidinyl; dimethyl-3,4,6,6a-tetrahydro-2H-pyrrolo[2,3-c]pyrrolyl; dimethylamino-2,3,3a,4,6,6a-hexahydrofuro[2,3-c]pyrrolyl; dimethylamino-3,3a,4,5,6,6a-hexahydro-1H-cyclopenta[c]pyrrolyl; dimethylamino-3-azabicyclo[3.1.0]hexanyl; dimethylamino-5-azaspiro[2.4]heptanyl; dimethylamino-6-azaspiro[3.4]octanyl; ethyl-2,3,3a,4,6,6a-hexahydropyrrolo[2,3-c]pyrrolyl; ethylpiperazinyl; fluoro(aminomethyl)pyrrolidinyl; fluoro(hydroxy)pyrrolidinyl; fluoro(methyl)-3,4,6,6a-tetrahydro-2H-pyrrolo[3,4-b]pyrrolyl; hexahydropyrazino[2,1-c][1,4]oxazin-8(1H)-yl; hydroxy(methyl)-3,4,4a,5,7,7a-hexahydro-2H-pyrrolo[3,4-b]pyridinyl; hydroxy(methyl)pyrrolidinyl; hydroxy(trifluoromethyl)pyrrolidinyl; hydroxy-2,3,3a,4,6,6a-hexahydrofuro[2,3-c]pyrrolyl; hydroxyethyl-2,3,3a,4,6,6a-hexahydropyrrolo[2,3-c]pyrrolyl; hydroxyethyl-2,9-diazaspiro[4.5]decanyl; hydroxymethyl(methyl)pyrrolidinyl; hydroxypiperidinyl; hydroxypropyl-2,3,3a,4,6,6a-hexahydropyrrolo[2,3-c]pyrrolyl; hydroxypyrrolidinyl; isopropylpiperazinyl; methoxyethyl(methyl)amino; methoxyethyl-2,3,3a,4,6,6a-hexahydropyrrolo[2,3-c]pyrrolyl; methoxyethyl-2,9-diazaspiro[4.5]decanyl; methoxypiperidinyl; methyl(propyl)amino; methyl-1,3,3a,4,6,6a-hexahydropyrrolo[3,4-c]pyrrolyl; methyl-1,4-diazepanyl; methyl-1,7-diazaspiro[3.4]octanyl; methyl-1,7-diazaspiro[4.4]nonanyl; methyl-2,3,3a,4,6,6a-hexahydropyrrolo[2,3-c]pyrrolyl; methyl-2,3,3a,5,6,6a-hexahydropyrrolo[3,2-b]pyrrolyl; methyl-2,3,4a,5,7,7a-hexahydropyrrolo[3,4-b][1,4]oxazinyl; methyl-2,6-diazabicyclo[3.2.0]heptanyl; methyl-2,6-diazaspiro[3.4]octanyl; methyl-2,7-diazaspiro[4.4]nonanyl; methyl-2,8-diazaspiro[4.5]decanyl; methyl-2,9-diazaspiro[4.5]decanyl; methyl-3,3a,4,5,7,7a-hexahydro-2H-pyrrolo[2,3-c]pyridinyl; methyl-3,3a,4,6,7,7a-hexahydro-2H-pyrrolo[3,2-c]pyridinyl; methyl-3,3a,5,6,7,7a-hexahydro-2H-pyrrolo[3,2-b]pyridinyl; methyl-3,4,4a,5,7,7a-hexahydro-2H-pyrrolo[3,4-b]pyridinyl; methyl-3,6-diazabicyclo[3.2.0]heptanyl; methyl-3,8-diazabicyclo[4.2.0]octanyl; methyl-6-oxa-2,9-diazaspiro[4.5]decanyl; methylamino; methylhexahydro-1H-pyrrolo[3,4-b]pyridin-6(2H)-yl; methylhexahydropyrrolo[3,4-b][1,4]

oxazin-6(2H)-yl; methylmorpholinyl; methylpiperazinyl; methylpyrrolidinyl; morpholinyl; oxaazabicyclo[2.2.1]heptanyl; oxaazabicyclo[3.1.1]heptanyl; oxazepanyl; piperidinyl; pyrrolidinyl; pyrrolidinylpiperidinyl; or thiomorpholinyl;

$R^3$ is H, fluoro, chloro, cyano or methoxy;
$R^4$ is H, fluoro, chloro or trifluoromethyl;
$R^5$ is H, fluoro or chloro;
$R^6$ is methyl or ethyl;
or a pharmaceutically acceptable salt, or enantiomer or diastereomer thereof.

A further embodiment of present invention is (iv) a compound of formula (I) according to (ii), wherein $R^{10}$ is $C_{1-6}$alkyl or $C_{1-6}$alkylamino.

A further embodiment of present invention is (v) a compound of formula (I) according to (iv), wherein $R^{10}$ is methyl or methylamino.

A further embodiment of present invention is (vi) a compound of formula (I) according to (iv), wherein $R^2$ is 2,3,3a,4,6,6a-hexahydropyrrolo[2,3-c]pyrrolyl substituted by $C_{1-6}$alkyl; pyrrolidinyl substituted by $(C_{1-6}$alkyl$)_2$amino; 3,3a,4,5,6,6a-hexahydro-1H-cyclopenta[c]pyrrolyl substituted by $(C_{1-6}$alkyl$)_2$amino; 2,3,3a,4,6,6a-hexahydrofuro[2,3-c]pyrrolyl substituted by $(C_{1-6}$alkyl$)_2$amino; or 2,3,4a,5,7,7a-hexahydropyrrolo[3,4-b][1,4]oxazinyl substituted by $C_{1-6}$alkyl.

A further embodiment of present invention is (vii) a compound of formula (I) according to (vi), wherein $R^2$ is (dimethylamino)pyrrolidinyl; methyl-2,3,3a,4,6,6a-hexahydropyrrolo[2,3-c]pyrrolyl; dimethylamino-3,3a,4,5,6,6a-hexahydro-1H-cyclopenta[c]pyrrolyl; dimethylamino-2,3,3a,4,6,6a-hexahydrofuro[2,3-c]pyrrolyl; or methyl-2,3,4a,5,7,7a-hexahydropyrrolo[3,4-b][1,4]oxazinyl.

A further embodiment of present invention is (viii) a compound of formula (I) according to (vi), wherein $R^4$ is halogen.

A further embodiment of present invention is (ix) a compound of formula (I) according to (viii), wherein $R^4$ is fluoro or chloro.

A further embodiment of present invention is (x) a compound of formula (I) according to (viii), wherein $R^5$ is H.

A further embodiment of present invention is (xi) a compound of formula (I) according to (ii), wherein
$R^1$ is

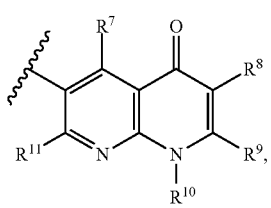

wherein
$R^7$ is H;
$R^8$ is carboxy;
$R^9$ is H;
$R^{10}$ is $C_{1-6}$alkyl or $C_{1-6}$alkylamino;
$R^{11}$ is H;
$R^2$ is 2,3,3a,4,6,6a-hexahydropyrrolo[2,3-c]pyrrolyl substituted by $C_{1-6}$alkyl; pyrrolidinyl substituted by $(C_{1-6}$alkyl$)_2$amino; 3,3a,4,5,6,6a-hexahydro-1H-cyclopenta[c]pyrrolyl substituted by $(C_{1-6}$alkyl$)_2$amino; 2,3,3a,4,6,6a-hexahydrofuro[2,3-c]pyrrolyl substituted by $(C_{1-6}$alkyl$)_2$amino; or 2,3,4a,5,7,7a-hexahydropyrrolo[3,4-b][1,4]oxazinyl substituted by $C_{1-6}$alkyl;
$R^3$ is H, halogen or cyano;
$R^4$ is halogen;
$R^5$ is H;
$R^6$ is $C_{1-6}$alkyl;
or a pharmaceutically acceptable salt, or enantiomer or diastereomer thereof.

A further embodiment of present invention is (xii) a compound of formula (I) according to (xi), wherein
$R^1$ is

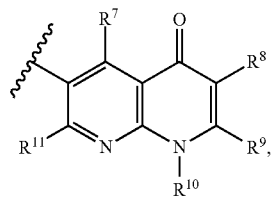

wherein
$R^7$ is H;
$R^8$ is carboxy;
$R^9$ is H;
$R^{10}$ is methyl or methylamino;
$R^{11}$ is H;
$R^2$ is (dimethylamino)pyrrolidinyl; methyl-2,3,3a,4,6,6a-hexahydropyrrolo[2,3-c]pyrrolyl; dimethylamino-3,3a,4,5,6,6a-hexahydro-1H-cyclopenta[c]pyrrolyl; dimethylamino-2,3,3a,4,6,6a-hexahydrofuro[2,3-c]pyrrolyl; or methyl-2,3,4a,5,7,7a-hexahydropyrrolo[3,4-b][1,4]oxazinyl;
$R^3$ is H, fluoro, chloro or cyano;
$R^4$ is fluoro or chloro;
$R^5$ is H;
$R^6$ is methyl;
or a pharmaceutically acceptable salt, or enantiomer or diastereomer thereof.

A further embodiment of present invention is (xiii) a compound of formula (I) according to (ii), wherein
$R^1$ is

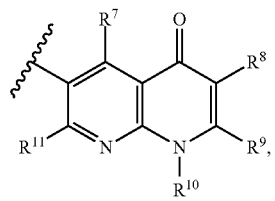

wherein
$R^7$ is H;
$R^8$ is carboxy;
$R^9$ is H;
$R^{10}$ is $(C_{1-6}$alkylpyrrolidinyl)$C_{1-6}$alkyl, (hydroxy$C_{1-6}$alkyl)$C_{1-6}$alkyl, amino$C_{1-6}$alkoxy$C_{1-6}$alkyl, $C_{1-6}$alkoxy$C_{1-6}$alkylamino, $C_{1-6}$alkyl, $C_{1-6}$alkylamino, halo$C_{1-6}$alkylamino, morpholinyl or pyrrolidinyl;
$R^{11}$ is H;
$R^2$ is $(C_{1-6}$alkyl$)_2$amino; 1,3,3a,4,6,6a-hexahydropyrrolo[3,4-c]pyrrolyl substituted by $C_{1-6}$alkyl;

1,4-oxazepanyl substituted by (C$_{1-6}$alkyl)$_2$amino C$_{1-6}$alkyl;
1,7-diazaspiro[3.4]octanyl substituted by C$_{1-6}$alkyl;
2,3,3a,4,6,6a-hexahydrofuro[2,3-c]pyrrolyl substituted by (C$_{1-6}$alkyl)$_2$aminoC$_{1-6}$alkyl;
2,3,3a,4,6,6a-hexahydropyrrolo[2,3-c]pyrrolyl substituted by one or two substituents independently selected from haloC$_{1-6}$alkyl, halogen, hydroxy C$_{1-6}$alkyl, C$_{1-6}$alkoxyC$_{1-6}$alkyl and C$_{1-6}$alkyl;
2,3,3a,5,6,6a-hexahydropyrrolo[3,2-b]pyrrolyl substituted by C$_{1-6}$alkyl;
2,3,4a,5,7,7a-hexahydropyrrolo[3,4-b][1,4]oxazinyl substituted by C$_{1-6}$alkyl;
2,6-diazabicyclo[3.2.0]heptanyl substituted by C$_{1-6}$alkyl;
2,7-diazaspiro[4.4]nonanyl substituted by C$_{1-6}$alkyl;
2,8-diazaspiro[4.5]decanyl substituted by C$_{1-6}$alkyl;
2,9-diazaspiro[4.5]decanyl substituted by C$_{1-6}$alkoxyC$_{1-6}$alkyl or C$_{1-6}$alkyl;
3,3a,4,5,6,6a-hexahydro-1H-cyclopenta[c]pyrrolyl substituted by (C$_{1-6}$alkyl)$_2$amino;
3,3a,4,5,7,7a-hexahydro-2H-pyrrolo[2,3-c]pyridinyl substituted by C$_{1-6}$alkyl;
3,3a,4,6,7,7a-hexahydro-2H-pyrrolo[3,2-c]pyridinyl substituted by C$_{1-6}$alkyl;
3,3a,5,6,7,7a-hexahydro-2H-pyrrolo[3,2-b]pyridinyl substituted by C$_{1-6}$alkyl;
3,4,4a,5,7,7a-hexahydro-2H-pyrrolo[3,4-b]pyridinyl substituted by C$_{1-6}$alkyl;
3,4,6,6a-tetrahydro-2H-pyrrolo[2,3-c]pyrrolyl substituted twice by C$_{1-6}$alkyl;
3,4,6,6a-tetrahydro-2H-pyrrolo[3,4-b]pyrrolyl substituted by one or two substituents independently selected from halogen and C$_{1-6}$alkyl;
3,4,6,7,8,8a-hexahydro-1H-pyrrolo[1,2-a]pyrazinyl;
3,6-diazabicyclo[3.2.0]heptanyl substituted by C$_{1-6}$alkyl;
3,8-diazabicyclo[4.2.0]octanyl substituted by C$_{1-6}$alkyl;
5-azaspiro[2.4]heptanyl substituted by (C$_{1-6}$alkyl)$_2$aminoC$_{1-6}$alkyl or (C$_{1-6}$alkyl)$_2$amino;
hexahydro-1H-isoindol-2(3H)-yl substituted by (C$_{1-6}$alkyl)$_2$amino;
hexahydro-1H-pyrrolo[3,4-b]pyridin-6(2H)-yl substituted by C$_{1-6}$alkyl;
hexahydropyrazino[2,1-c][1,4]oxazin-8(1H)-yl;
morpholinyl, said morpholinyl being unsubstituted or substituted by (C$_{1-6}$alkyl)$_2$aminoC$_{1-6}$alkyl;
piperazinyl substituted by C$_{1-6}$alkyl;
piperidinyl substituted by (C$_{1-6}$alkyl)$_2$amino, (C$_{1-6}$alkyl)$_2$aminoC$_{1-6}$alkyl, C$_{1-6}$alkoxyC$_{1-6}$alkyl (C$_{1-6}$alkyl)amino, hydroxyC$_{1-6}$alkyl(C$_{1-6}$alkyl)amino or pyrrolidinyl; or
pyrrolidinyl substituted by one, two or three substituents independently selected from (C$_{1-6}$alkyl)$_2$amino, (C$_{1-6}$alkoxyC$_{1-6}$alkyl(C$_{1-6}$alkyl)amino)C$_{1-6}$alkyl, (C$_{1-6}$alkyl)$_2$amino, (C$_{1-6}$alkyl)$_2$aminoC$_{1-6}$alkyl, C$_{1-6}$alkoxy, C$_{1-6}$alkoxyC$_{1-6}$alkyl(C$_{1-6}$alkyl)amino, C$_{1-6}$alkyl, halogen, hydroxy, hydroxyC$_{1-6}$alkyl (C$_{1-6}$alkyl)amino or pyrrolidinylC$_{1-6}$alkyl;
R$^3$ is H, halogen or cyano;
R$^4$ is H, halogen or haloC$_{1-6}$alkyl;
R$^5$ is H or halogen;
R$^6$ is C$_{1-6}$alkyl;
or a pharmaceutically acceptable salt, or enantiomer or diastereomer thereof.

A further embodiment of present invention is (xiv) a compound of formula (I) according to (xiii), wherein R$^1$ is

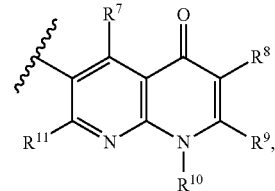

wherein
R$^7$ is H;
R$^8$ is carboxy;
R$^9$ is H;
R$^{10}$ is amino, C$_{1-6}$alkoxyC$_{1-6}$alkyl, C$_{1-6}$alkoxy C$_{1-6}$alkylamino, C$_{1-6}$alkyl, C$_{1-6}$alkylamino, halo C$_{1-6}$alkylamino or hydroxyC$_{1-6}$alkyl;
R$^{11}$ is H;
R$^2$ is 1,4-oxazepanyl substituted by (C$_{1-6}$alkyl)$_2$amino C$_{1-6}$alkyl;
1,7-diazaspiro[3.4]octanyl substituted by C$_{1-6}$alkyl;
2,3,3a,4,6,6a-hexahydrofuro[2,3-c]pyrrolyl substituted by (C$_{1-6}$alkyl)$_2$aminoC$_{1-6}$alkyl;
2,3,3a,4,6,6a-hexahydropyrrolo[2,3-c]pyrrolyl substituted by one or two substituents independently selected from haloC$_{1-6}$alkyl, halogen, hydroxy C$_{1-6}$alkyl, C$_{1-6}$alkoxyC$_{1-6}$alkyl and C$_{1-6}$alkyl;
2,3,3a,5,6,6a-hexahydropyrrolo[3,2-b]pyrrolyl substituted by C$_{1-6}$alkyl;
2,6-diazabicyclo[3.2.0]heptanyl substituted by C$_{1-6}$alkyl;
3,3a,4,5,7,7a-hexahydro-2H-pyrrolo[2,3-c]pyridinyl substituted by C$_{1-6}$alkyl;
3,3a,4,6,7,7a-hexahydro-2H-pyrrolo[3,2-c]pyridinyl substituted by C$_{1-6}$alkyl;
3,3a,5,6,7,7a-hexahydro-2H-pyrrolo[3,2-b]pyridinyl substituted by C$_{1-6}$alkyl;
3,4,6,6a-tetrahydro-2H-pyrrolo[2,3-c]pyrrolyl substituted twice by C$_{1-6}$alkyl;
3,4,6,6a-tetrahydro-2H-pyrrolo[3,4-b]pyrrolyl substituted by one or two substituents independently selected from halogen and C$_{1-6}$alkyl;
hexahydro-1H-isoindol-2(3H)-yl substituted by (C$_{1-6}$alkyl)$_2$amino;
hexahydro-1H-pyrrolo[3,4-b]pyridin-6(2H)-yl substituted by C$_{1-6}$alkyl;
morpholinyl substituted by (C$_{1-6}$alkyl)$_2$amino C$_{1-6}$alkyl;
piperidinyl substituted by (C$_{1-6}$alkyl)$_2$amino, (C$_{1-6}$alkyl)$_2$aminoC$_{1-6}$alkyl, C$_{1-6}$alkoxyC$_{1-6}$alkyl (C$_{1-6}$alkyl)amino, hydroxyC$_{1-6}$alkyl(C$_{1-6}$alkyl)amino or pyrrolidinyl; or
pyrrolidinyl substituted by one or two substituents independently selected from (C$_{1-6}$alkoxyC$_{1-6}$alkyl (C$_{1-6}$alkyl)amino)C$_{1-6}$alkyl, (C$_{1-6}$alkyl)$_2$amino, (C$_{1-6}$alkyl)$_2$aminoC$_{1-6}$alkyl, C$_{1-6}$alkoxy, C$_{1-6}$alkyl, halogen, hydroxy or pyrrolidinylC$_{1-6}$alkyl;
R$^3$ is H, halogen or cyano;
R$^4$ is H or halogen;
R$^5$ is H or halogen;
R$^6$ is C$_{1-6}$alkyl;
or a pharmaceutically acceptable salt, or enantiomer or diastereomer thereof.

A further embodiment of present invention is (xv) a compound of formula (I) according to (xiv), wherein
$R^1$ is

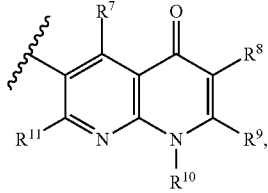

wherein
$R^7$ is H;
$R^8$ is carboxy;
$R^9$ is H;
$R^{10}$ is (hydroxymethyl)ethyl, amino, ethyl, ethylamino, methoxyethylamino, methoxymethyl, methyl, methylamino, trifluoroethylamino;
$R^{11}$ is H;
$R^2$ is ((diethylamino)methyl)morpholinyl; ((dimethylamino)methyl)fluoropyrrolidinyl; ((dimethylamino)methyl)hydroxypyrrolidinyl; ((dimethylamino)methyl)methylpyrrolidinyl; ((dimethylamino)methyl)morpholinyl; ((dimethylamino)methyl)piperidinyl; ((dimethylamino)methyl)pyrrolidinyl; ((methoxyethyl(methyl)amino)methyl)pyrrolidinyl; (dimethylamino)hexahydro-1H-isoindol-2(3H)-yl; (dimethylamino)hydroxypyrrolidinyl; (dimethylamino)methoxypyrrolidinyl; (dimethylamino)methyl-1,4-oxazepanyl; (dimethylamino)methyl-2,3,3a,4,6,6a-hexahydrofuro[2,3-c]pyrrolyl; (dimethylamino)methylpyrrolidinyl; (dimethylamino)piperidinyl; (dimethylamino)pyrrolidinyl; (hydroxyethyl(methyl)amino)piperidinyl; (methoxyethyl(methyl)amino)piperidinyl; (pyrrolidinylmethyl)pyrrolidinyl; 3a-(fluoromethyl)-5-methyl-2,3,3a,4,6,6a-hexahydropyrrolo[2,3-c]pyrrolyl; dimethyl-3,4,6,6a-tetrahydro-2H-pyrrolo[2,3-c]pyrrolyl; ethyl-2,3,3a,4,6,6a-hexahydropyrrolo[2,3-c]pyrrolyl; fluoro(methyl)-3,4,6,6a-tetrahydro-2H-pyrrolo[3,4-b]pyrrolyl; hydroxyethyl-2,3,3a,4,6,6a-hexahydropyrrolo[2,3-c]pyrrolyl; hydroxypropyl-2,3,3a,4,6,6a-hexahydropyrrolo[2,3-c]pyrrolyl; methoxyethyl-2,3,3a,4,6,6a-hexahydropyrrolo[2,3-c]pyrrolyl; methyl-1,7-diazaspiro[3.4]octanyl; methyl-2,3,3a,4,6,6a-hexahydropyrrolo[2,3-c]pyrrolyl; methyl-2,3,3a,5,6,6a-hexahydropyrrolo[3,2-b]pyrrolyl; methyl-2,6-diazabicyclo[3.2.0]heptanyl; methyl-3,3a,4,5,7,7a-hexahydro-2H-pyrrolo[2,3-c]pyridinyl; methyl-3,3a,4,6,7,7a-hexahydro-2H-pyrrolo[3,2-c]pyridinyl; methyl-3,3a,5,6,7,7a-hexahydro-2H-pyrrolo[3,2-b]pyridinyl; methylhexahydro-1H-pyrrolo[3,4-b]pyridin-6(2H)-yl; or pyrrolidinylpiperidinyl;
$R^3$ is H, fluoro or cyano;
$R^4$ is H, fluoro or chloro;
$R^5$ is H or fluoro;
$R^6$ is methyl or ethyl;
or a pharmaceutically acceptable salt, or enantiomer or diastereomer thereof.

A further embodiment of present invention is (xvi) a compound of formula (I) according to (ii), wherein
$R^1$ is

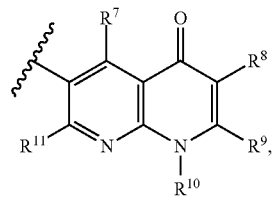

wherein
$R^7$ is H;
$R^8$ is carboxy;
$R^9$ is H;
$R^{10}$ is $(C_{1-6}alkylamino)C_{1-6}alkyl$, $(C_{1-6}alkylpiperidinyl)C_{1-6}alkyl$, $(hydroxyC_{1-6}alkyl)_2C_{1-6}alkyl$, $(hydroxyC_{1-6}alkyl)C_{1-6}alkyl$, $aminoC_{1-6}alkyl$, $C_{1-6}alkoxyC_{1-6}alkylamino$, $C_{1-6}alkyl$, $C_{1-6}alkylamino$, $hydroxyC_{1-6}alkyl$, morpholinyl, $morpholinylC_{1-6}alkyl$, $pyrazinylC_{1-6}alkyl$, pyrrolidinyl, $pyrrolidinylC_{1-6}alkyl$;
$R^{11}$ is H;
$R^2$ is $(C_{1-6}alkyl)_2amino$;
$C_{1-6}alkoxyC_{1-6}alkyl(C_{1-6}alkyl)amino$;
$C_{1-6}alkylamino$;
1,4-oxazepanyl substituted by $(C_{1-6}alkyl)_2aminoC_{1-6}alkyl$;
1,7-diazaspiro[3.4]octanyl substituted by $C_{1-6}alkyl$;
2,3,3a,4,6,6a-hexahydropyrrolo[2,3-c]pyrrolyl substituted by $C_{1-6}alkyl$;
2,6-diazaspiro[3.4]octanyl substituted by $C_{1-6}alkyl$;
2,7-diazaspiro[4.4]nonanyl substituted by $C_{1-6}alkyl$;
2,8-diazaspiro[4.5]decanyl substituted by $C_{1-6}alkyl$;
2,9-diazaspiro[4.5]decanyl substituted by $hydroxyC_{1-6}alkyl$;
3,3a,4,5,7,7a-hexahydro-2H-pyrrolo[2,3-c]pyridinyl substituted by $C_{1-6}alkyl$;
3,3a,4,6,7,7a-hexahydro-2H-pyrrolo[3,2-c]pyridinyl substituted by $C_{1-6}alkyl$;
3,8-diazabicyclo[4.2.0]octanyl substituted by $C_{1-6}alkyl$;
hexahydropyrazino[2,1-c][1,4]oxazin-8(1H)-yl;
hexahydropyrrolo[3,4-b][1,4]oxazin-6(2H)-yl substituted by $C_{1-6}alkyl$;
morpholinyl, said morpholinyl being unsubstituted or substituted by $(C_{1-6}alkyl)_2aminoC_{1-6}alkyl$ or $C_{1-6}alkyl$;
piperidinyl substituted by hydroxy, $(C_{1-6}alkyl)_2aminoC_{1-6}alkyl$ or $(C_{1-6}alkyl)_2amino$;
pyrazolyl substituted twice by $aminoC_{1-6}alkyl$ and $haloC_{1-6}alkyl$;
pyrrolidinyl substituted by $(C_{1-6}alkyl)_2amino$, $(C_{1-6}alkyl)_2aminoC_{1-6}alkyl$, $aminoC_{1-6}alkyl$, $C_{1-6}alkyl$, $haloC_{1-6}alkyl$, halogen, hydroxy, $hydroxyC_{1-6}alkyl$ or $pyrrolidinylC_{1-6}alkyl$; or
thiomorpholinyl;
$R^3$ is H, halogen or cyano;
$R^4$ is H or halogen;
$R^5$ is H or halogen;
$R^6$ is $C_{1-6}alkyl$;
or a pharmaceutically acceptable salt, or enantiomer or diastereomer thereof.

A further embodiment of present invention is (xvii) a compound of formula (I) according to (xvi), wherein $R^1$ is

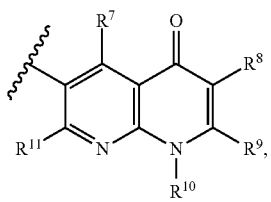

wherein
$R^7$ is H;
$R^8$ is carboxy;
$R^9$ is H;
$R^{10}$ is (hydroxymethyl)$_2$ethyl, (hydroxymethyl)ethyl, (methylamino)ethyl, (methylpiperidinyl)methyl, amino(methyl)propyl, aminoisopentyl, ethyl, hydroxy(methyl)propyl, hydroxypropyl, methoxyethylamino, methyl, methylamino, morpholinyl, morpholinylmethyl, pyrazinylmethyl, pyrrolidinyl or pyrrolidinylmethyl;
$R^{11}$ is H;
$R^2$ is ((diethylamino)methyl)morpholinyl; ((dimethylamino)methyl)morpholinyl; ((dimethylamino)methyl)piperidinyl; ((dimethylamino)methyl)pyrrolidinyl; (dimethylamino)methyl-1,4-oxazepanyl; (dimethylamino)methylpyrrolidinyl; (dimethylamino)piperidinyl; (dimethylamino)pyrrolidinyl; (hydroxyethyl)pyrrolidinyl; (hydroxymethyl)pyrrolidinyl; (pyrrolidinylmethyl)pyrrolidinyl; aminomethyl(trifluoromethyl)pyrazolyl; dimethylamino; fluoro(aminomethyl)pyrrolidinyl; fluoro(hydroxy)pyrrolidinyl; hexahydropyrazino[2,1-c][1,4]oxazin-8(1H)-yl; hydroxy(trifluoromethyl)pyrrolidinyl; hydroxyethyl-2,9-diazaspiro[4.5]decanyl; hydroxypiperidinyl; hydroxypyrrolidinyl; methoxyethyl(methyl)amino; methyl-1,7-diazaspiro[4.4]nonanyl; methyl-2,3,3a,4,6,6a-hexahydropyrrolo[2,3-c]pyrrolyl; methyl-2,6-diazaspiro[3.4]octanyl; methyl-2,7-diazaspiro[4.4]nonanyl; methyl-2,8-diazaspiro[4.5]decanyl; methyl-3,3a,4,5,7,7a-hexahydro-2H-pyrrolo[2,3-c]pyridinyl; methyl-3,3a,4,6,7,7a-hexahydro-2H-pyrrolo[3,2-c]pyridinyl; methyl-3,8-diazabicyclo[4.2.0]octanyl; methylamino; methylhexahydropyrrolo[3,4-b][1,4]oxazin-6(2H)-yl; methylmorpholinyl; morpholinyl; or thiomorpholinyl;
$R^3$ is H, fluoro, chloro or cyano;
$R^4$ is H, fluoro or chloro;
$R^5$ is H or fluoro;
$R^6$ is methyl or ethyl;
or a pharmaceutically acceptable salt, or enantiomer or diastereomer thereof.

The present invention relates to (i') a compound of formula (I),

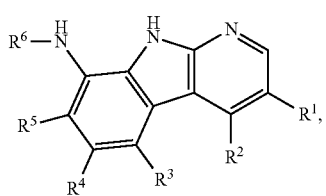

(I)

wherein
$R^1$ is

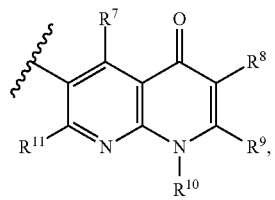

wherein
$R^7$ is H;
$R^8$ is carboxy;
$R^9$ is H;
$R^{10}$ is $(C_{1-6}alkyl)_2$amino(phenyl)$C_{1-6}$alkyl, $(C_{1-6}alkyl)_2$amino$C_{1-6}$alkyl, $(C_{1-6}alkylamino)C_{1-6}$alkyl, $(C_{1-6}alkylpiperazinyl)C_{1-6}$alkyl, $(C_{1-6}alkylpiperidinyl)C_{1-6}$alkyl, $(C_{1-6}alkylpyrrolidinyl)C_{1-6}$alkyl, $(hydroxyC_{1-6}alkyl)_2C_{1-6}$alkyl, amino$C_{1-6}$alkyl, $C_{1-6}$alkoxy$C_{1-6}$alkyl, $C_{1-6}$alkyl, $C_{1-6}$alkylamino, $C_{1-6}$alkylpyrrolidinyl, hydroxy$C_{1-6}$alkyl, morpholinyl, morpholinyl$C_{1-6}$alkyl, pyrazinyl$C_{1-6}$alkyl, pyridinyl$C_{1-6}$alkyl, pyrrolidinyl, pyrrolidinyl$C_{1-6}$alkyl, pyrrolidinyl$C_{1-6}$alkyl, tetrahydrofuranyl or tetrahydrofuranyl$C_{1-6}$alkyl;
$R^{11}$ is H;
$R^2$ is $(C_{1-6}alkyl)_2$amino, $C_{1-6}$alkylamino, $C_{1-6}$alkoxy $C_{1-6}$alkyl$(C_{1-6}$alkyl)amino or heterocyclyl;
$R^3$ is H or halogen;
$R^4$ is halogen;
$R^5$ is H or halogen;
$R^6$ is $C_{1-6}$alkyl;
or a pharmaceutically acceptable salt, or enantiomer or diastereomer thereof.

A further embodiment of present invention is a compound of formula (I), wherein
$R^1$ is

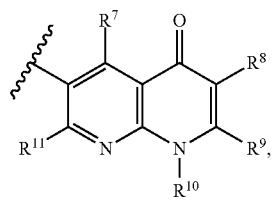

wherein
$R^7$ is H;
$R^8$ is carboxy;
$R^9$ is H;
$R^{10}$ is $C_{1-6}$alkyl, pyrrolidinyl, $(C_{1-6}$alkylpyrrolidinyl)$C_{1-6}$alkyl, pyrrolidinyl$C_{1-6}$alkyl or morpholinyl $C_{1-6}$alkyl;
$R^{11}$ is H;
$R^2$ is $(C_{1-6}alkyl)_2$amino, $(C_{1-6}alkyl)_2$amino$C_{1-6}$alkylpyrrolidinyl, amino$C_{1-6}$alkyl(halo$C_{1-6}$alkyl)pyrazolyl, oxaazabicyclo[2.2.1]heptanyl, $C_{1-6}$alkoxy$C_{1-6}$alkyl $(C_{1-6}$alkyl)amino, $C_{1-6}$alkoxy$C_{1-6}$alkylmorpholinyl, halo$C_{1-6}$alkylpiperazinyl, halopyrrolidinyl or morpholinyl;

$R^3$ is H or halogen;
$R^4$ is halogen;
$R^5$ is H;
$R^6$ is $C_{1-6}$alkyl;
or pharmaceutically acceptable salt, or enantiomer or diastereomer thereof.

A further embodiment of present invention is a compound of formula (I), wherein
$R^1$ is

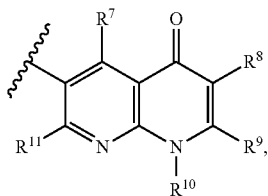

wherein
$R^7$ is H;
$R^8$ is carboxy;
$R^9$ is H;
$R^{10}$ is (ethylpyrrolidinyl)methyl, dimethyl(pyrrolidinyl)ethyl, ethyl, methyl, morpholinylmethyl, pyrrolidinyl or pyrrolidinylmethyl;
$R^{11}$ is H;
$R^2$ is (dimethylamino)methylpyrrolidinyl, (methoxymethyl)morpholinyl, (trifluoromethyl)piperazinyl, aminomethyl(trifluoromethyl)pyrazolyl, oxaazabicyclo[2.2.1]heptanyl, difluoropyrrolidinyl, dimethylamino, methoxyethyl(methyl)amino, methyl(propyl)amino or morpholinyl;
$R^3$ is H or fluoro;
$R^4$ is fluoro;
$R^5$ is H;
$R^6$ is methyl or ethyl;
or pharmaceutically acceptable salt, or enantiomer or diastereomer thereof.

A further embodiment of present invention is (ii') a compound of formula (I), wherein
$R^1$ is

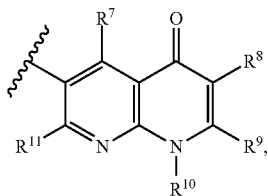

wherein
$R^7$ is H;
$R^8$ is carboxy;
$R^9$ is H;
$R^{10}$ is $(C_{1-6}$alkyl$)_2$amino(phenyl)$C_{1-6}$alkyl, $(C_{1-6}$alkyl$)_2$amino$C_{1-6}$alkyl, $(C_{1-6}$alkylamino)$C_{1-6}$alkyl, $(C_{1-6}$alkylpiperazinyl)$C_{1-6}$alkyl, $(C_{1-6}$alkylpiperidinyl)$C_{1-6}$alkyl, $(C_{1-6}$alkylpyrrolidinyl)$C_{1-6}$alkyl, (hydroxy$C_{1-6}$alkyl$)_2C_{1-6}$alkyl, amino$C_{1-6}$alkyl, $C_{1-6}$alkoxy$C_{1-6}$alkyl, $C_{1-6}$alkyl, $C_{1-6}$alkylamino, $C_{1-6}$alkylpyrrolidinyl, hydroxy$C_{1-6}$alkyl, morpholinyl, morpholinyl$C_{1-6}$alkyl, pyrazinyl$C_{1-6}$alkyl, pyridinyl$C_{1-6}$alkyl, pyrrolidinyl, pyrrolidinyl $C_{1-6}$alkyl, pyrrolidinyl$C_{1-6}$alkyl, tetrahydrofuranyl or tetrahydrofuranyl$C_{1-6}$alkyl;
$R^{11}$ is H;
$R^2$ is $(C_{1-6}$alkyl$)_2$amino;
$C_{1-6}$alkylamino;
$C_{1-6}$alkoxy$C_{1-6}$alkyl($C_{1-6}$alkyl)amino;
oxaazabicyclo[2.2.2]heptanyl;
oxazepanyl;
1,3,3a,4,6,6a-hexahydrofuro[3,4-c]pyrrolyl;
2,3,3a,4,6,6a-hexahydropyrrolo[2,3-c]pyrrolyl substituted by $C_{1-6}$alkyl;
morpholinyl, said morpholinyl being unsubstituted or substituted by $C_{1-6}$alkyl, $C_{1-6}$alkoxy$C_{1-6}$alkyl or $(C_{1-6}$alkyl$)_2$amino$C_{1-6}$alkyl;
piperazinyl substituted by halo$C_{1-6}$alkyl;
piperidinyl, said piperidinyl being unsubstituted or substituted by hydroxy, $C_{1-6}$alkoxy or $(C_{1-6}$ alkyl$)_2$amino$C_{1-6}$alkyl;
pyrazolyl, said pyrazolyl being unsubstituted or substituted with one or two substituents independently selected from halo$C_{1-6}$alkyl and amino$C_{1-6}$alkyl;
pyrrolidinyl, said pyrrolidinyl being unsubstituted or substituted with one or two substituents independently selected from $(C_{1-6}$alkyl$)_2$amino, $(C_{1-6}$ alkyl$)_2$amino$C_{1-6}$alkyl, amino, amino$C_{1-6}$alkyl, $C_{1-6}$alkyl, halo$C_{1-6}$alkyl, halogen, hydroxy and hydroxy$C_{1-6}$alkyl; or
thiomorpholinyl;
$R^3$ is H or halogen;
$R^4$ is halogen;
$R^5$ is H or halogen;
$R^6$ is $C_{1-6}$alkyl;
or a pharmaceutically acceptable salt, or enantiomer or diastereomer thereof.

A further embodiment of present invention according to (ii') is (iii') a compound of formula (I), wherein
$R^1$ is

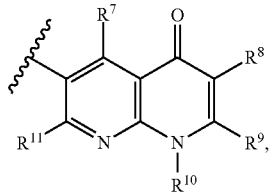

wherein
$R^7$ is H;
$R^8$ is carboxy;
$R^9$ is H;
$R^{10}$ is dimethylamino(phenyl)ethyl, (dimethylamino)ethyl, (dimethylamino)isopentyl, (dimethylamino)isopropyl, (diethylamino)ethyl, (dimethylamino)butyl, (methylamino)ethyl, (methylpiperazinyl)ethyl, (methylpiperidinyl)methyl, (ethylpyrrolidinyl)methyl, (hydroxymethyl)$_2$ethyl, amino(methyl)propyl, aminoisopentyl, methoxyethyl, methyl, ethyl, methylamino, methylpyrrolidinyl, hydroxy(methyl)propyl, (hydroxymethyl)ethyl, hydroxypropyl, morpholinyl, morpholinylmethyl, pyrazinylmethyl, pyridinylmethyl, pyrrolidinyl, pyrrolidinylmethyl, dimethyl(pyrrolidinyl)ethyl, tetrahydrofuranyl or tetrahydrofuranylmethyl;

$R^{11}$ is H;

$R^2$ is dimethylamino, methyl(propyl)amino, 1,3,3a,4,6,6a-hexahydrofuro[3,4-c]pyrrolyl, 5-methyl-2,3,3a,4,6,6a-hexahydropyrrolo[2,3-c]pyrrolyl, methoxyethyl(methyl)amino, methylamino, morpholinyl, (methoxymethyl)morpholinyl, methylmorpholinyl, (dimethylamino)methylmorpholinyl, oxaazabicyclo[2.2.1]heptanyl, oxazepanyl, (trifluoromethyl)piperazinyl, methoxypiperidinyl, hydroxypiperidinyl, piperidinyl, (dimethylamino)methylpiperidinyl, aminomethyl(trifluoromethyl)pyrazolyl, (trifluoromethyl)pyrazolyl, (dimethylamino)methylpyrrolidinyl, difluoropyrrolidinyl, fluoro(aminomethyl)pyrrolidinyl, hydroxy(trifluoromethyl)pyrrolidinyl, amino(trifluoromethyl)pyrrolidinyl, pyrrolidinyl, hydroxypyrrolidinyl, (hydroxymethyl)pyrrolidinyl, hydroxy(methyl)pyrrolidinyl, (hydroxyethyl)pyrrolidinyl, (dimethylamino)pyrrolidinyl, fluoro(hydroxy)pyrrolidinyl, hydroxymethyl(methyl)pyrrolidinyl or thiomorpholinyl;

$R^3$ is H or fluoro;

$R^4$ is fluoro;

$R^5$ is H, fluoro or chloro;

$R^6$ is methyl, trideuteriomethyl or ethyl;

or a pharmaceutically acceptable salt, or enantiomer or diastereomer thereof.

A further embodiment of present invention according to (ii') or (iii') is (iv') a compound of formula (I), wherein $R^{10}$ is $(C_{1-6}alkyl)_2aminoC_{1-6}alkyl$, $aminoC_{1-6}alkyl$, $C_{1-6}alkyl$, $C_{1-6}alkylamino$, $C_{1-6}alkylpyrrolidinyl$ or $pyridinylC_{1-6}alkyl$.

A further embodiment of present invention according to any one of (ii') to (iv') is (v') a compound of formula (I), wherein $R^{10}$ is methyl, ethyl, (dimethylamino)ethyl, pyridinylmethyl, methylamino, aminoisopentyl, (diethylamino)ethyl, (dimethylamino)butyl or methylpyrrolidinyl.

A further embodiment of present invention according to any one of (ii') to (v') is (vi') a compound of formula (I), wherein $R^2$ is $(C_{1-6}alkyl)_2amino$;
$C_{1-6}alkoxyC_{1-6}alkyl(C_{1-6}alkyl)amino$;
oxazepanyl;
2,3,3a,4,6,6a-hexahydropyrrolo[2,3-c]pyrrolyl substituted by $C_{1-6}alkyl$;
morpholinyl, said morpholinyl being unsubstituted or substituted by $C_{1-6}alkyl$ or $C_{1-6}alkoxyC_{1-6}alkyl$;
piperidinyl substituted by $(C_{1-6}alkyl)_2aminoC_{1-6}alkyl$; or
pyrrolidinyl, said pyrrolidinyl being unsubstituted or substituted by $(C_{1-6}alkyl)_2amino$, $(C_{1-6}alkyl)_2aminoC_{1-6}alkyl$ or $hydroxyC_{1-6}alkyl$.

A further embodiment of present invention according to any one of (ii') to (vi') is (vii') a compound of formula (I), wherein $R^2$ is (dimethylamino)methylpiperidinyl, (dimethylamino)methylpyrrolidinyl, (dimethylamino)pyrrolidinyl, (hydroxymethyl)pyrrolidinyl, (methoxymethyl)morpholinyl, 5-methyl-2,3,3a,4,6,6a-hexahydropyrrolo[2,3-c]pyrrolyl, dimethylamino, methoxyethyl(methyl)amino, methylmorpholinyl, morpholinyl, oxazepanyl or pyrrolidinyl.

A further embodiment of present invention according to (ii') is (viii') a compound of formula (I), wherein $R^1$ is

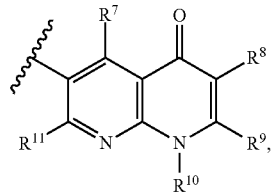

wherein
$R^7$ is H;
$R^8$ is carboxy;
$R^9$ is H;
$R^{10}$ is $C_{1-6}alkyl$;
$R^{11}$ is H;
$R^2$ is 2,3,3a,4,6,6a-hexahydropyrrolo[2,3-c]pyrrolyl substituted by $C_{1-6}alkyl$; morpholinyl substituted by $(C_{1-6}alkyl)_2aminoC_{1-6}alkyl$; or pyrrolidinyl substituted by $(C_{1-6}alkyl)_2amino$ or $(C_{1-6}alkyl)_2aminoC_{1-6}alkyl$;
$R^3$ is H or halogen;
$R^4$ is halogen;
$R^5$ is H or halogen;
$R^6$ is $C_{1-6}alkyl$;
or a pharmaceutically acceptable salt, or enantiomer or diastereomer thereof.

A further embodiment of present invention according to (viii') is (ix') a compound of formula (I), wherein $R^1$ is

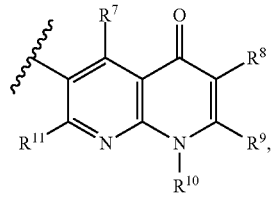

wherein
$R^7$ is H;
$R^8$ is carboxy;
$R^9$ is H;
$R^{10}$ is methyl;
$R^{11}$ is H;
$R^2$ is 5-methyl-2,3,3a,4,6,6a-hexahydropyrrolo[2,3-c]pyrrolyl, (dimethylamino)methylmorpholinyl, (dimethylamino)methylpyrrolidinyl or (dimethylamino)pyrrolidinyl;
$R^3$ is H or fluoro;
$R^4$ is fluoro;
$R^5$ is H or fluoro;
$R^6$ is methyl;
or a pharmaceutically acceptable salt, or enantiomer or diastereomer thereof.

Another embodiment of present invention is that compounds of formula (I) are selected from:

6-[4-(dimethylamino)-5,6-difluoro-8-(methylamino)-9H-pyrido[2,3-b]indol-3-yl]-1-methyl-4-oxo-1,8-naphthyridine-3-carboxylic acid;

6-[4-(dimethylamino)-5,6-difluoro-8-(methylamino)-9H-pyrido[2,3-b]indol-3-yl]-4-oxo-1-pyrrolidin-3-yl-1,8-naphthyridine-3-carboxylic acid;

6-[4-(dimethylamino)-5,6-difluoro-8-(methylamino)-9H-pyrido[2,3-b]indol-3-yl]-1-(morpholin-3-ylmethyl)-4-oxo-1,8-naphthyridine-3-carboxylic acid;

6-[4-(dimethylamino)-5,6-difluoro-8-(methylamino)-9H-pyrido[2,3-b]indol-3-yl]-1-[(1-ethylpyrrolidin-2-yl)methyl]-4-oxo-1,8-naphthyridine-3-carboxylic acid;

6-[5,6-difluoro-8-(methylamino)-4-(2-oxa-5-azabicyclo[2.2.1]heptan-5-yl)-9H-pyrido[2,3-b]indol-3-yl]-1-ethyl-4-oxo-1,8-naphthyridine-3-carboxylic acid;

6-[5,6-difluoro-4-[2-methoxyethyl(methyl)amino]-8-(methylamino)-9H-pyrido[2,3-b]indol-3-yl]-1-ethyl-4-oxo-1,8-naphthyridine-3-carboxylic acid;

6-[5,6-difluoro-8-(methylamino)-4-[methyl(propyl)amino]-9H-pyrido[2,3-b]indol-3-yl]-1-ethyl-4-oxo-1,8-naphthyridine-3-carboxylic acid;

6-[5,6-difluoro-8-(methylamino)-4-morpholino-9H-pyrido[2,3-b]indol-3-yl]-1-methyl-4-oxo-1,8-naphthyridine-3-carboxylic acid;

6-[5,6-difluoro-8-(methylamino)-4-[3-(trifluoromethyl)piperazin-1-yl]-9H-pyrido[2,3-b]indol-3-yl]-1-methyl-4-oxo-1,8-naphthyridine-3-carboxylic acid;

6-[5,6-difluoro-4-[2-(methoxymethyl)morpholin-4-yl]-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-morpholino-9H-pyrido[2,3-b]indol-3-yl]-4-oxo-1-(pyrrolidin-2-ylmethyl)-1,8-naphthyridine-3-carboxylic acid;

6-[4-[2-[(dimethylamino)methyl]pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-[(2R)-2-[(dimethylamino)methyl]pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-[(2S)-2-[(dimethylamino)methyl]pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-[4-(aminomethyl)-3-(trifluoromethyl)pyrazol-1-yl]-8-(ethylamino)-6-fluoro-9H-pyrido[2,3-b]indol-3-yl]-1-ethyl-4-oxo-1,8-naphthyridine-3-carboxylic acid;

6-[4-(3,3-difluoropyrrolidin-1-yl)-6-fluoro-8-(methylamino)-9H-pyrido[2,3-b]indol-3-yl]-1-methyl-4-oxo-1,8-naphthyridine-3-carboxylic acid;

6-[4-(Dimethylamino)-6-fluoro-8-(methylamino)-9H-pyrido[2,3-b]indol-3-yl]-1-(1,1-dimethyl-2-pyrrolidin-1-yl-ethyl)-4-oxo-1,8-naphthyridine-3-carboxylic acid;

6-[4-(Dimethylamino)-5,6-difluoro-8-(methylamino)-9H-pyrido[2,3-b]indol-3-yl]-1-ethyl-4-oxo-1,8-naphthyridine-3-carboxylic acid;

6-[4-(Dimethylamino)-6-fluoro-8-(methylamino)-9H-pyrido[2,3-b]indol-3-yl]-1-ethyl-4-oxo-1,8-naphthyridine-3-carboxylic acid;

6-[4-(Dimethylamino)-6,7-difluoro-8-(methylamino)-9H-pyrido[2,3-b]indol-3-yl]-1-ethyl-4-oxo-1,8-naphthyridine-3-carboxylic acid;

6-[4-(Dimethylamino)-5,6-difluoro-8-(methylamino)-9H-pyrido[2,3-b]indol-3-yl]-4-oxo-1-tetrahydrofuran-3-yl-1,8-naphthyridine-3-carboxylic acid;

6-[4-(Dimethylamino)-5,6-difluoro-8-(methylamino)-9H-pyrido[2,3-b]indol-3-yl]-1-[2-(dimethylamino)ethyl]-4-oxo-1,8-naphthyridine-3-carboxylic acid;

6-[4-[3-(Aminomethyl)-3-fluoro-pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-(Dimethylamino)-5,6-difluoro-8-(methylamino)-9H-pyrido[2,3-b]indol-3-yl]-1-(2-methoxyethyl)-4-oxo-1,8-naphthyridine-3-carboxylic acid;

6-[6-Fluoro-4-[3-hydroxy-3-(trifluoromethyl)pyrrolidin-1-yl]-8-(methylamino)-9H-pyrido[2,3-b]indol-3-yl]-1-methyl-4-oxo-1,8-naphthyridine-3-carboxylic acid;

6-[4-(Dimethylamino)-5,6-difluoro-8-(methylamino)-9H-pyrido[2,3-b]indol-3-yl]-1-[2-(methylamino)ethyl]-4-oxo-1,8-naphthyridine-3-carboxylic acid;

6-[4-[3-Amino-3-(trifluoromethyl)pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[8-(Ethylamino)-6-fluoro-4-[3-(trifluoromethyl)pyrazol-1-yl]-9H-pyrido[2,3-b]indol-3-yl]-4-oxo-1-pyrrolidin-3-yl-1,8-naphthyridine-3-carboxylic acid;

6-[4-(Dimethylamino)-5,6-difluoro-8-(methylamino)-9H-pyrido[2,3-b]indol-3-yl]-1-[2-(4-methylpiperazin-1-yl)ethyl]-4-oxo-1,8-naphthyridine-3-carboxylic acid;

6-[4-(Dimethylamino)-5,6-difluoro-8-(methylamino)-9H-pyrido[2,3-b]indol-3-yl]-4-oxo-1-(4-pyridylmethyl)-1,8-naphthyridine-3-carboxylic acid;

6-[5,6-Difluoro-8-(methylamino)-4-morpholino-9H-pyrido[2,3-b]indol-3-yl]-1-(morpholin-3-ylmethyl)-4-oxo-1,8-naphthyridine-3-carboxylic acid;

6-[4-(Dimethylamino)-5,6-difluoro-8-(methylamino)-9H-pyrido[2,3-b]indol-3-yl]-1-[(1-methyl-4-piperidyl)methyl]-4-oxo-1,8-naphthyridine-3-carboxylic acid;

6-[5,6-Difluoro-4-[2-methoxyethyl(methyl)amino]-8-(methylamino)-9H-pyrido[2,3-b]indol-3-yl]-1-methyl-4-oxo-1,8-naphthyridine-3-carboxylic acid;

6-[8-(Ethylamino)-6-fluoro-4-morpholino-9H-pyrido[2,3-b]indol-3-yl]-4-oxo-1-pyrrolidin-3-yl-1,8-naphthyridine-3-carboxylic acid;

6-[5,6-Difluoro-8-(methylamino)-4-morpholino-9H-pyrido[2,3-b]indol-3-yl]-1-(2-hydroxy-2-methyl-propyl)-4-oxo-1,8-naphthyridine-3-carboxylic acid;

6-[5,6-Difluoro-8-(methylamino)-4-[(2S)-2-methylmorpholin-4-yl]-9H-pyrido[2,3-b]indol-3-yl]-1-methyl-4-oxo-1,8-naphthyridine-3-carboxylic acid;

6-[6-Fluoro-4,8-bis(methylamino)-9H-pyrido[2,3-b]indol-3-yl]-1-(morpholin-3-ylmethyl)-4-oxo-1,8-naphthyridine-3-carboxylic acid;

1-(2-Amino-2-methyl-propyl)-6-[5,6-difluoro-8-(methylamino)-4-morpholino-9H-pyrido[2,3-b]indol-3-yl]-4-oxo-1,8-naphthyridine-3-carboxylic acid;

6-[5,6-Difluoro-8-(methylamino)-4-morpholino-9H-pyrido[2,3-b]indol-3-yl]-4-oxo-1-(tetrahydrofuran-2-ylmethyl)-1,8-naphthyridine-3-carboxylic acid;

6-[5,6-Difluoro-4-(4-methoxy-1-piperidyl)-8-(methylamino)-9H-pyrido[2,3-b]indol-3-yl]-1-methyl-4-oxo-1,8-naphthyridine-3-carboxylic acid;

6-[5,6-Difluoro-4-[2-methoxyethyl(methyl)amino]-8-(methylamino)-9H-pyrido[2,3-b]indol-3-yl]-1-(morpholin-3-ylmethyl)-4-oxo-1,8-naphthyridine-3-carboxylic acid;

6-[5,6-Difluoro-8-(methylamino)-4-morpholino-9H-pyrido[2,3-b]indol-3-yl]-1-(morpholin-2-ylmethyl)-4-oxo-1,8-naphthyridine-3-carboxylic acid;

6-[5,6-Difluoro-4-(4-hydroxy-1-piperidyl)-8-(methylamino)-9H-pyrido[2,3-b]indol-3-yl]-1-methyl-4-oxo-1,8-naphthyridine-3-carboxylic acid;

6-[6-Fluoro-8-(methylamino)-4-morpholino-9H-pyrido[2,3-b]indol-3-yl]-1-[2-hydroxy-1-(hydroxymethyl)-1-methyl-ethyl]-4-oxo-1,8-naphthyridine-3-carboxylic acid;

6-[6-Fluoro-8-(methylamino)-4-morpholino-9H-pyrido[2,3-b]indol-3-yl]-1-(2-hydroxy-1-methyl-ethyl)-4-oxo-1,8-naphthyridine-3-carboxylic acid;

6-[6-Fluoro-8-(methylamino)-4-pyrrolidin-1-yl-9H-pyrido[2,3-b]indol-3-yl]-1-methyl-4-oxo-1,8-naphthyridine-3-carboxylic acid;

6-[6-Fluoro-4-(3-hydroxypyrrolidin-1-yl)-8-(methylamino)-9H-pyrido[2,3-b]indol-3-yl]-1-methyl-4-oxo-1,8-naphthyridine-3-carboxylic acid;

6-[6-Fluoro-8-(methylamino)-4-morpholino-9H-pyrido[2,3-b]indol-3-yl]-1-methyl-4-oxo-1,8-naphthyridine-3-carboxylic acid;

6-[6-Fluoro-8-(methylamino)-4-[(2R)-2-methylmorpholin-4-yl]-9H-pyrido[2,3-b]indol-3-yl]-1-methyl-4-oxo-1,8-naphthyridine-3-carboxylic acid;

6-[6-Fluoro-8-(methylamino)-4-[(2S)-2-methylmorpholin-4-yl]-9H-pyrido[2,3-b]indol-3-yl]-1-methyl-4-oxo-1,8-naphthyridine-3-carboxylic acid;

6-[5,6-Difluoro-8-(methylamino)-4-morpholino-9H-pyrido[2,3-b]indol-3-yl]-1-(2-hydroxy-1-methyl-ethyl)-4-oxo-1,8-naphthyridine-3-carboxylic acid;

6-[6-Fluoro-8-(methylamino)-4-morpholino-9H-pyrido[2,3-b]indol-3-yl]-1-(methylamino)-4-oxo-1,8-naphthyridine-3-carboxylic acid;

6-[6-Fluoro-8-(methylamino)-4-morpholino-9H-pyrido[2,3-b]indol-3-yl]-1-(2-hydroxypropyl)-4-oxo-1,8-naphthyridine-3-carboxylic acid;

6-[6-Fluoro-4-[3-(hydroxymethyl)pyrrolidin-1-yl]-8-(methylamino)-9H-pyrido[2,3-b]indol-3-yl]-1-methyl-4-oxo-1,8-naphthyridine-3-carboxylic acid;

6-[4-(Dimethylamino)-6,7-difluoro-8-(methylamino)-9H-pyrido[2,3-b]indol-3-yl]-4-oxo-1-pyrrolidin-3-yl-1,8-naphthyridine-3-carboxylic acid;

6-[6-Fluoro-8-(methylamino)-4-(1-piperidyl)-9H-pyrido[2,3-b]indol-3-yl]-1-methyl-4-oxo-1,8-naphthyridine-3-carboxylic acid;

1-(2-Amino-3-methyl-butyl)-6-[5,6-difluoro-8-(methylamino)-4-morpholino-9H-pyrido[2,3-b]indol-3-yl]-4-oxo-1,8-naphthyridine-3-carboxylic acid;

6-[6-Fluoro-8-(methylamino)-4-morpholino-9H-pyrido[2,3-b]indol-3-yl]-4-oxo-1-(pyrazin-2-ylmethyl)-1,8-naphthyridine-3-carboxylic acid;

6-[6-Fluoro-4-(3-hydroxy-3-methyl-pyrrolidin-1-yl)-8-(methylamino)-9H-pyrido[2,3-b]indol-3-yl]-1-methyl-4-oxo-1,8-naphthyridine-3-carboxylic acid;

6-[6-Fluoro-8-(methylamino)-4-(1,4-oxazepan-4-yl)-9H-pyrido[2,3-b]indol-3-yl]-1-methyl-4-oxo-1,8-naphthyridine-3-carboxylic acid;

6-[4-[2-[(Dimethylamino)methyl]morpholin-4-yl]-5,6-difluoro-8-(methylamino)-9H-pyrido[2,3-b]indol-3-yl]-1-methyl-4-oxo-1,8-naphthyridine-3-carboxylic acid;

6-[4-(1,3,3a,4,6,6a-Hexahydrofuro[3,4-c]pyrrol-5-yl)-6-fluoro-8-(methylamino)-9H-pyrido[2,3-b]indol-3-yl]-1-methyl-4-oxo-1,8-naphthyridine-3-carboxylic acid;

6-[7-Chloro-6-fluoro-8-(methylamino)-4-morpholino-9H-pyrido[2,3-b]indol-3-yl]-1-methyl-4-oxo-1,8-naphthyridine-3-carboxylic acid;

6-[5,6-Difluoro-8-(methylamino)-4-pyrrolidin-1-yl-9H-pyrido[2,3-b]indol-3-yl]-4-oxo-1-pyrrolidin-3-yl-1,8-naphthyridine-3-carboxylic acid;

6-[6-Fluoro-8-(methylamino)-4-thiomorpholino-9H-pyrido[2,3-b]indol-3-yl]-1-methyl-4-oxo-1,8-naphthyridine-3-carboxylic acid;

6-[6-Fluoro-4-[3-(2-hydroxyethyl)pyrrolidin-1-yl]-8-(methylamino)-9H-pyrido[2,3-b]indol-3-yl]-1-methyl-4-oxo-1,8-naphthyridine-3-carboxylic acid;

6-[7-Chloro-4-(dimethylamino)-6-fluoro-8-(methylamino)-9H-pyrido[2,3-b]indol-3-yl]-4-oxo-1-pyrrolidin-3-yl-1,8-naphthyridine-3-carboxylic acid;

1-[2-(Dimethylamino)-2-methyl-propyl]-6-[6-fluoro-8-(methylamino)-4-morpholino-9H-pyrido[2,3-b]indol-3-yl]-4-oxo-1,8-naphthyridine-3-carboxylic acid;

1-[2-(Dimethylamino)-1-methyl-ethyl]-6-[6-fluoro-8-(methylamino)-4-morpholino-9H-pyrido[2,3-b]indol-3-yl]-4-oxo-1,8-naphthyridine-3-carboxylic acid;

6-[6-Fluoro-8-(methylamino)-4-morpholino-9H-pyrido[2,3-b]indol-3-yl]-1-morpholino-4-oxo-1,8-naphthyridine-3-carboxylic acid;

6-[4-(Dimethylamino)-5,6-difluoro-8-(methylamino)-9H-pyrido[2,3-b]indol-3-yl]-1-(methylamino)-4-oxo-1,8-naphthyridine-3-carboxylic acid;

1-[2-(Diethylamino)ethyl]-6-[5,6-difluoro-8-(methylamino)-4-morpholino-9H-pyrido[2,3-b]indol-3-yl]-4-oxo-1,8-naphthyridine-3-carboxylic acid;

6-[5,6-Difluoro-8-(methylamino)-4-morpholino-9H-pyrido[2,3-b]indol-3-yl]-1-[2-(dimethylamino)-2-phenyl-ethyl]-4-oxo-1,8-naphthyridine-3-carboxylic acid;

6-[4-[3-(Dimethylamino)pyrrolidin-1-yl]-6-fluoro-8-(methylamino)-9H-pyrido[2,3-b]indol-3-yl]-1-methyl-4-oxo-1,8-naphthyridine-3-carboxylic acid;

6-[6,7-Difluoro-8-(methylamino)-4-pyrrolidin-1-yl-9H-pyrido[2,3-b]indol-3-yl]-4-oxo-1-pyrrolidin-3-yl-1,8-naphthyridine-3-carboxylic acid;

6-[5,6-Difluoro-4-[(2S)-2-(hydroxymethyl)pyrrolidin-1-yl]-8-(methylamino)-9H-pyrido[2,3-b]indol-3-yl]-1-methyl-4-oxo-1,8-naphthyridine-3-carboxylic acid;

6-[4-[2-[(Dimethylamino)methyl]morpholin-4-yl]-6,7-difluoro-8-(methylamino)-9H-pyrido[2,3-b]indol-3-yl]-1-methyl-4-oxo-1,8-naphthyridine-3-carboxylic acid;

6-[5,6-Difluoro-8-(methylamino)-4-morpholino-9H-pyrido[2,3-b]indol-3-yl]-1-[2-(dimethylamino)butyl]-4-oxo-1,8-naphthyridine-3-carboxylic acid;

6-[4-[3-[(Dimethylamino)methyl]-1-piperidyl]-5,6-difluoro-8-(methylamino)-9H-pyrido[2,3-b]indol-3-yl]-1-methyl-4-oxo-1,8-naphthyridine-3-carboxylic acid;

6-[6-Fluoro-8-(methylamino)-4-morpholino-9H-pyrido[2,3-b]indol-3-yl]-1-(1-methylpyrrolidin-3-yl)-4-oxo-1,8-naphthyridine-3-carboxylic acid;

6-[5,6-Difluoro-4-[trans-3-fluoro-4-hydroxy-pyrrolidin-1-yl]-8-(methylamino)-9H-pyrido[2,3-b]indol-3-yl]-1-methyl-4-oxo-1,8-naphthyridine-3-carboxylic acid;

6-[5,6-difluoro-4-[trans-3-hydroxy-4-methyl-pyrrolidin-1-yl]-8-(methylamino)-9H-pyrido[2,3-b]indol-3-yl]-1-methyl-4-oxo-1,8-naphthyridine-3-carboxylic acid;

6-[5,6-Difluoro-4-[3-(hydroxymethyl)-3-methyl-pyrrolidin-1-yl]-8-(methylamino)-9H-pyrido[2,3-b]indol-3-yl]-1-methyl-4-oxo-1,8-naphthyridine-3-carboxylic acid;

6-[4-[cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-[cis-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-(methylamino)-4-oxo-1,8-naphthyridine-3-carboxylic acid;

6-[4-(dimethylamino)-5,6-difluoro-8-(methylamino)-9H-pyrido[2,3-b]indol-3-yl]-1-(oxazol-5-ylmethyl)-4-oxo-1,8-naphthyridine-3-carboxylic acid;

6-[4-[cis-3-[(dimethylamino)methyl]-2,3,3a,4,6,6a-hexahydrofuro[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid;

(S)-6-(5,6-difluoro-8-(methylamino)-4-(pyrrolidin-1-yl)-9H-pyrido[2,3-b]indol-3-yl)-4-oxo-1-(pyrrolidin-3-yl)-1,4-dihydro-1,8-naphthyridine-3-carboxylic acid;

6-(4-(6-((dimethylamino)methyl)-1,4-oxazepan-4-yl)-6-fluoro-8-(methylamino)-9H-pyrido[2,3-b]indol-3-yl)-1-methyl-4-oxo-1,4-dihydro-1,8-naphthyridine-3-carboxylic acid;

6-(4-(dimethylamino)-5,6-difluoro-8-(methylamino)-9H-pyrido[2,3-b]indol-3-yl)-4-oxo-1-((tetrahydro-2H-pyran-4-yl)amino)-1,4-dihydro-1,8-naphthyridine-3-carboxylic acid;

6-(4-(3-((dimethylamino)methyl)-3-fluoropyrrolidin-1-yl)-6-fluoro-8-(methylamino)-9H-pyrido[2,3-b]indol-3-yl)-1-(methylamino)-4-oxo-1,4-dihydro-1,8-naphthyridine-3-carboxylic acid;

6-(4-(3-((dimethylamino)methyl)-3-fluoropyrrolidin-1-yl)-5,6-difluoro-8-(methylamino)-9H-pyrido[2,3-b]indol-3-yl)-1-(methylamino)-4-oxo-1,4-dihydro-1,8-naphthyridine-3-carboxylic acid;

6-(4-(3-((dimethylamino)methyl)piperidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

1-cyclopropyl-6-[4-(dimethylamino)-5,6-difluoro-8-(methylamino)-9H-pyrido[2,3-b]indol-3-yl]-4-oxo-1,8-naphthyridine-3-carboxylic acid;

6-[4-[(cis-5-(2-methoxyethyl)-2,3,3a,4,6,6a-hexahydropyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-(5,6-difluoro-8-(methylamino)-4-thiomorpholino-9H-pyrido[2,3-b]indol-3-yl)-1-methyl-4-oxo-1,4-dihydro-1,8-naphthyridine-3-carboxylic acid;

6-(5,6-difluoro-8-(methylamino)-4-thiomorpholino-9H-pyrido[2,3-b]indol-3-yl)-4-oxo-1-(pyrrolidin-3-yl)-1,4-dihydro-1,8-naphthyridine-3-carboxylic acid;

6-(4-(3-((cyclopropyl(methyl)amino)methyl)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-(4-(3-((dimethylamino)methyl)-3-hydroxypyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-(3-((dimethylamino)methyl)-3-methylpyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-(3-((dimethylamino)methyl)-3-methylpyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-[4-[cis-5-methyl-2,3,3a,4,6,6a-hexahydropyrrolo[2,3-c]pyrrol-1-yl]-6,7-difluoro-8-(methylamino)-9H-pyrido[2,3-b]indol-3-yl]-1-methyl-4-oxo-1,8-naphthyridine-3-carboxylic acid;

6-(4-(3-(dimethylamino)pyrrolidin-1-yl)-8-(ethylamino)-5,6-difluoro-9H-pyrido[2,3-b]indol-3-yl)-1-methyl-4-oxo-1,4-dihydro-1,8-naphthyridine-3-carboxylic acid;

6-(5,7-difluoro-8-(methylamino)-4-morpholino-9H-pyrido[2,3-b]indol-3-yl)-1-methyl-4-oxo-1,4-dihydro-1,8-naphthyridine-3-carboxylic acid;

6-(4-(3-((dimethylamino)methyl)pyrrolidin-1-yl)-8-(ethylamino)-5,6-difluoro-9H-pyrido[2,3-b]indol-3-yl)-1-methyl-4-oxo-1,4-dihydro-1,8-naphthyridine-3-carboxylic acid;

6-(4-(dimethylamino)-5,7-difluoro-8-(methylamino)-9H-pyrido[2,3-b]indol-3-yl)-4-oxo-1-(pyrrolidin-3-yl)-1,4-dihydro-1,8-naphthyridine-3-carboxylic acid;

6-(4-(3-((dimethylamino)methyl)-3-fluoropyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-(3-((dimethylamino)methyl)-3-fluoropyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-(6-fluoro-8-(methylamino)-4-(cis-1-methylhexahydro-1H-pyrrolo[3,4-b]pyridin-6(2H)-yl)-9H-pyrido[2,3-b]indol-3-yl)-1-methyl-4-oxo-1,4-dihydro-1,8-naphthyridine-3-carboxylic acid;

6-(6-fluoro-8-(methylamino)-4-(cis-1-methylhexahydro-1H-pyrrolo[3,4-b]pyridin-6(2H)-yl)-9H-pyrido[2,3-b]indol-3-yl)-1-(methylamino)-4-oxo-1,4-dihydro-1,8-naphthyridine-3-carboxylic acid;

6-(6-fluoro-8-(methylamino)-4-(cis-4-methylhexahydropyrrolo[3,4-b][1,4]oxazin-6(2H)-yl)-9H-pyrido[2,3-b]indol-3-yl)-1-methyl-4-oxo-1,4-dihydro-1,8-naphthyridine-3-carboxylic acid;

6-(6-fluoro-8-(methylamino)-4-(cis-4-methylhexahydropyrrolo[3,4-b][1,4]oxazin-6(2H)-yl)-9H-pyrido[2,3-b]indol-3-yl)-1-(methylamino)-4-oxo-1,4-dihydro-1,8-naphthyridine-3-carboxylic acid;

6-(4-(3-(cyclopropylamino)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-(4-(3-(cyclopropylamino)pyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-(3-(cyclopropyl(methyl)amino)pyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(5-chloro-4-(dimethylamino)-6-fluoro-8-(methylamino)-9H-pyrido[2,3-b]indol-3-yl)-1-methyl-4-oxo-1,4-dihydro-1,8-naphthyridine-3-carboxylic acid;

6-(4-(3-(cyclopropyl(methyl)amino)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

1-(cyclopropylamino)-6-(4-(dimethylamino)-5,6-difluoro-8-(methylamino)-9H-pyrido[2,3-b]indol-3-yl)-4-oxo-1,4-dihydro-1,8-naphthyridine-3-carboxylic acid;

6-[4-(3a-fluoro-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-(3a-fluoro-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-(methylamino)-4-oxo-1,8-naphthyridine-3-carboxylic acid;

6-(5-chloro-4-(3-((dimethylamino)methyl)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-[4-[cis-5-methyl-2,3,3a,4,6,6a-hexahydropyrrolo[2,3-c]pyrrol-1-yl]-8-(ethylamino)-6-(trifluoromethyl)-9H-pyrido[2,3-b]indol-3-yl]-1-(methylamino)-4-oxo-1,8-naphthyridine-3-carboxylic acid;

6-[4-[3a-(fluoromethyl)-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-[3a-(fluoromethyl)-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-(methylamino)-4-oxo-1,8-naphthyridine-3-carboxylic acid;

6-(4-(3,3-difluoropyrrolidin-1-yl)-6-fluoro-8-(methylamino)-9H-pyrido[2,3-b]indol-3-yl)-1-ethyl-4-oxo-1,4-dihydro-1,8-naphthyridine-3-carboxylic acid;

6-(8-(ethylamino)-6-fluoro-4-(3-(trifluoromethyl)-1H-pyrazol-1-yl)-9H-pyrido[2,3-b]indol-3-yl)-1-methyl-4-oxo-1,4-dihydro-1,8-naphthyridine-3-carboxylic acid;

6-(4-(6-oxa-3-azabicyclo[3.1.1]heptan-3-yl)-5,6-difluoro-8-(methylamino)-9H-pyrido[2,3-b]indol-3-yl)-1-ethyl-4-oxo-1,4-dihydro-1,8-naphthyridine-3-carboxylic acid;

6-(5,6-difluoro-4-(3-hydroxy-3-(trifluoromethyl)pyrrolidin-1-yl)-8-(methylamino)-9H-pyrido[2,3-b]indol-3-yl)-1-methyl-4-oxo-1,4-dihydro-1,8-naphthyridine-3-carboxylic acid;

6-(4-(dimethylamino)-5,6-difluoro-8-(methylamino)-9H-pyrido[2,3-b]indol-3-yl)-1-(1-methylpyrrolidin-3-yl)-4-oxo-1,4-dihydro-1,8-naphthyridine-3-carboxylic acid;

6-(5,6-difluoro-4-((2-methoxyethyl)(methyl)amino)-8-(methylamino)-9H-pyrido[2,3-b]indol-3-yl)-1-methyl-4-oxo-1,4-dihydro-1,8-naphthyridine-3-carboxylic acid;

6-(6-fluoro-8-(methylamino)-4-(3-methylpyrrolidin-1-yl)-9H-pyrido[2,3-b]indol-3-yl)-1-methyl-4-oxo-1,4-dihydro-1,8-naphthyridine-3-carboxylic acid;

6-(5,6-difluoro-4-(hexahydropyrazino[2,1-c][1,4]oxazin-8(1H)-yl)-8-(methylamino)-9H-pyrido[2,3-b]indol-3-yl)-1-methyl-4-oxo-1,4-dihydro-1,8-naphthyridine-3-carboxylic acid;

6-(4-(3-((dimethylamino)methyl)pyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-(3-((cyclopropylamino)methyl)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-(4-(3-((cyclopropylamino)methyl)pyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(6-chloro-4-(2-((dimethylamino)methyl)morpholino)-8-(methylamino)-9H-pyrido[2,3-b]indol-3-yl)-1-methyl-4-oxo-1,4-dihydro-1,8-naphthyridine-3-carboxylic acid;

6-(6-chloro-4-(3-(dimethylamino)pyrrolidin-1-yl)-8-(methylamino)-9H-pyrido[2,3-b]indol-3-yl)-1-methyl-4-oxo-1,4-dihydro-1,8-naphthyridine-3-carboxylic acid;

6-(4-(dimethylamino)-8-(ethylamino)-5,6-difluoro-9H-pyrido[2,3-b]indol-3-yl)-4-oxo-1-(pyrrolidin-3-yl)-1,4-dihydro-1,8-naphthyridine-3-carboxylic acid;

6-(6-fluoro-4-(3-(((2-methoxyethyl)(methyl)amino)methyl)pyrrolidin-1-yl)-8-(methylamino)-9H-pyrido[2,3-b]indol-3-yl)-1-methyl-4-oxo-1,4-dihydro-1,8-naphthyridine-3-carboxylic acid;

6-(5,6-difluoro-4-(3-(((2-methoxyethyl)(methyl)amino)methyl)pyrrolidin-1-yl)-8-(methylamino)-9H-pyrido[2,3-b]indol-3-yl)-1-methyl-4-oxo-1,4-dihydro-1,8-naphthyridine-3-carboxylic acid;

6-(4-(4-((dimethylamino)methyl)-3,3-difluoropyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-(4-((dimethylamino)methyl)-3,3-difluoropyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-[4-(dimethylamino)-5,6-difluoro-8-(methylamino)-9H-pyrido[2,3-b]indol-3-yl]-1-(3-hydroxy-1-methyl-propyl)-4-oxo-1,4-dihydro-1,8-naphthyridine-3-carboxylic acid;

6-(4-(dimethylamino)-5,6-difluoro-8-(methylamino)-9H-pyrido[2,3-b]indol-3-yl)-1-((1-hydroxycyclopropyl)methyl)-4-oxo-1,4-dihydro-1,8-naphthyridine-3-carboxylic acid;

6-(4-(dimethylamino)-5,6-difluoro-8-(methylamino)-9H-pyrido[2,3-b]indol-3-yl)-1-(2-morpholinoethyl)-4-oxo-1,4-dihydro-1,8-naphthyridine-3-carboxylic acid;

6-(4-(dimethylamino)-5,6-difluoro-8-(methylamino)-9H-pyrido[2,3-b]indol-3-yl)-4-oxo-1-(2-(3-oxopiperazin-1-yl)ethyl)-1,4-dihydro-1,8-naphthyridine-3-carboxylic acid;

6-(4-(2-((diethylamino)methyl)morpholino)-5,6-difluoro-8-(methylamino)-9H-pyrido[2,3-b]indol-3-yl)-1-methyl-4-oxo-1,4-dihydro-1,8-naphthyridine-3-carboxylic acid;

(S)-6-(4-(dimethylamino)-5,6-difluoro-8-(methylamino)-9H-pyrido[2,3-b]indol-3-yl)-4-oxo-1-(pyrrolidin-3-yl)-1,4-dihydro-1,8-naphthyridine-3-carboxylic acid;

(R)-6-(5,6-difluoro-4-(3-hydroxypyrrolidin-1-yl)-8-(methylamino)-9H-pyrido[2,3-b]indol-3-yl)-1-methyl-4-oxo-1,4-dihydro-1,8-naphthyridine-3-carboxylic acid;

6-(4-trans-(3-(dimethylamino)-4-methylpyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-[4-[(2S)-2-[(dimethylamino)methyl]pyrrolidin-1-yl]-6-fluoro-8-(methylamino)-9H-pyrido[2,3-b]indol-3-yl]-4-oxo-1-(2,2,2-trifluoroethylamino)-1,8-naphthyridine-3-carboxylic acid;

6-[4-[(2S)-2-[(dimethylamino)methyl]pyrrolidin-1-yl]-6-fluoro-8-(methylamino)-9H-pyrido[2,3-b]indol-3-yl]-4-oxo-1-(tetrahydropyran-4-ylamino)-1,8-naphthyridine-3-carboxylic acid;

(R)-6-(4-(dimethylamino)-5,6-difluoro-8-(methylamino)-9H-pyrido[2,3-b]indol-3-yl)-4-oxo-1-(pyrrolidin-3-yl)-1,4-dihydro-1,8-naphthyridine-3-carboxylic acid;

(R)-6-(5,6-difluoro-8-(methylamino)-4-(pyrrolidin-1-yl)-9H-pyrido[2,3-b]indol-3-yl)-4-oxo-1-(pyrrolidin-3-yl)-1,4-dihydro-1,8-naphthyridine-3-carboxylic acid;

(S)-6-(4-(6-((dimethylamino)methyl)-5-azaspiro[2.4]heptan-5-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-((3S,4S)-3-(dimethylamino)-4-methoxypyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-((3S,4S)-3-(dimethylamino)-4-fluoropyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-((3R,4S)-3-(dimethylamino)-4-methylpyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

(S)-6-(4-(2-((dimethylamino)methyl)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

(S)-6-(5,6-difluoro-4-(3-hydroxypyrrolidin-1-yl)-8-(methylamino)-9H-pyrido[2,3-b]indol-3-yl)-1-methyl-4-oxo-1,4-dihydro-1,8-naphthyridine-3-carboxylic acid;

(S)-6-(5,6-difluoro-4-(3-(hydroxymethyl)pyrrolidin-1-yl)-8-(methylamino)-9H-pyrido[2,3-b]indol-3-yl)-1-methyl-4-oxo-1,4-dihydro-1,8-naphthyridine-3-carboxylic acid;

(R)-6-(5,6-difluoro-4-(3-(hydroxymethyl)pyrrolidin-1-yl)-8-(methylamino)-9H-pyrido[2,3-b]indol-3-yl)-1-methyl-4-oxo-1,4-dihydro-1,8-naphthyridine-3-carboxylic acid;

(S)-6-(4-(2-((dimethylamino)methyl)pyrrolidin-1-yl)-8-(ethylamino)-5,6-difluoro-9H-pyrido[2,3-b]indol-3-yl)-1-methyl-4-oxo-1,4-dihydro-1,8-naphthyridine-3-carboxylic acid;

6-(4-trans-(3-(dimethylamino)-4-methylpyrrolidin-1-yl)-5,
6-difluoro-8-(methylamino)-9H-pyrido[2,3-b]indol-3-
yl)-1-methyl-4-oxo-1,4-dihydro-1,8-naphthyridine-3-car-
boxylic acid;

6-(4-trans-(3-(dimethylamino)-4-fluoropyrrolidin-1-yl)-5,6-
difluoro-8-(methylamino)-9H-pyrido[2,3-b]indol-3-yl)-
1-methyl-4-oxo-1,4-dihydro-1,8-naphthyridine-3-carbox-
ylic acid;

6-(4-trans-(3-(dimethylamino)-4-fluoropyrrolidin-1-yl)-6-
fluoro-8-(methylamino)-9H-pyrido[2,3-b]indol-3-yl)-1-
methyl-4-oxo-1,4-dihydro-1,8-naphthyridine-3-carbox-
ylic acid;

6-(4-trans-(3-(dimethylamino)-4-methoxypyrrolidin-1-yl)-
5,6-difluoro-8-(methylamino)-9H-pyrido[2,3-b]indol-3-
yl)-1-methyl-4-oxo-1,4-dihydro-1,8-naphthyridine-3-car-
boxylic acid;

6-(4-trans-(3-(dimethylamino)-4-methoxypyrrolidin-1-yl)-
6-fluoro-8-(methylamino)-9H-pyrido[2,3-b]indol-3-yl)-
1-methyl-4-oxo-1,4-dihydro-1,8-naphthyridine-3-carbox-
ylic acid;

(S)-6-(4-(2-((dimethylamino)methyl)pyrrolidin-1-yl)-6,7-
difluoro-8-(methylamino)-9H-pyrido[2,3-b]indol-3-yl)-
1-methyl-4-oxo-1,4-dihydro-1,8-naphthyridine-3-carbox-
ylic acid;

(S)-6-(5,6-difluoro-8-(methylamino)-4-(3-(pyrrolidin-1-yl-
methyl)pyrrolidin-1-yl)-9H-pyrido[2,3-b]indol-3-yl)-1-
methyl-4-oxo-1,4-dihydro-1,8-naphthyridine-3-carbox-
ylic acid;

(S)-6-(5,6-difluoro-8-(methylamino)-4-(3-(morpholinom-
ethyl)pyrrolidin-1-yl)-9H-pyrido[2,3-b]indol-3-yl)-1-
methyl-4-oxo-1,4-dihydro-1,8-naphthyridine-3-carbox-
ylic acid;

6-(4-((3aR,4R,7aS)-4-(dimethylamino)hexahydro-1H-
isoindol-2(3H)-yl)-5,6-difluoro-8-(methylamino)-9H-
pyrido[2,3-b]indol-3-yl)-1-methyl-4-oxo-1,4-dihydro-1,
8-naphthyridine-3-carboxylic acid;

6-[8-(ethylamino)-6-fluoro-4-morpholino-9H-pyrido[2,3-b]
indol-3-yl]-4-oxo-1-pyrrolidin-3-yl-1,8-naphthyridine-3-
carboxylic acid;

6-[5,6-difluoro-8-(methylamino)-4-morpholino-9H-pyrido
[2,3-b]indol-3-yl]-1-(2,3-dihydroxypropyl)-4-oxo-1,8-
naphthyridine-3-carboxylic acid;

6-[4-(dimethylamino)-5,6-difluoro-8-(methylamino)-9H-
pyrido[2,3-b]indol-3-yl]-1-[2-(dimethylamino)-2-
methyl-propyl]-4-oxo-1,8-naphthyridine-3-carboxylic
acid;

6-[4-(dimethylamino)-5,6-difluoro-8-(methylamino)-9H-
pyrido[2,3-b]indol-3-yl]-1-morpholino-4-oxo-1,8-naph-
thyridine-3-carboxylic acid;

6-[5,6-difluoro-8-(methylamino)-4-morpholino-9H-pyrido
[2,3-b]indol-3-yl]-1-(dimethylamino)-4-oxo-1,8-naph-
thyridine-3-carboxylic acid;

6-[4-[2-[(dimethylamino)methyl]morpholin-4-yl]-5,6-dif-
luoro-8-(methylamino)-9H-pyrido[2,3-b]indol-3-yl]-1-
(methylamino)-4-oxo-1,8-naphthyridine-3-carboxylic
acid;

6-[4-[4-(dimethylamino)-1-piperidyl]-5,6-difluoro-8-(meth-
ylamino)-9H-pyrido[2,3-b]indol-3-yl]-1-methyl-4-oxo-1,
8-naphthyridine-3-carboxylic acid;

6-[4-[4-[(dimethylamino)methyl]-1-piperidyl]-5,6-difluoro-
8-(methylamino)-9H-pyrido[2,3-b]indol-3-yl]-1-methyl-
4-oxo-1,8-naphthyridine-3-carboxylic acid;

6-[6-fluoro-8-(methylamino)-4-(4-methylpiperazin-1-yl)-
9H-pyrido[2,3-b]indol-3-yl]-1-methyl-4-oxo-1,8-naph-
thyridine-3-carboxylic acid;

6-[6-fluoro-8-(methylamino)-4-(4-methyl-1,4-diazepan-1-
yl)-9H-pyrido[2,3-b]indol-3-yl]-1-methyl-4-oxo-1,8-
naphthyridine-3-carboxylic acid;

6-[4-[3-[(dimethylamino)methyl]-1-piperidyl]-5,6-difluoro-
8-(methylamino)-9H-pyrido[2,3-b]indol-3-yl]-1-(methyl-
amino)-4-oxo-1,8-naphthyridine-3-carboxylic acid;

6-[6-fluoro-8-(methylamino)-4-[cis-5-methyl-2,3,3a,4,6,6a-
hexahydropyrrolo[2,3-c]pyrrol-1-yl]-9H-pyrido[2,3-b]in-
dol-3-yl]-1-methyl-4-oxo-1,8-naphthyridine-3-carbox-
ylic acid;

6-[6-fluoro-4-(cis-1-methyl-3,3a,4,6,7,7a-hexahydro-2H-
pyrrolo[3,2-c]pyridin-5-yl)-8-(methylamino)-9H-pyrido
[2,3-b]indol-3-yl]-1-methyl-4-oxo-1,8-naphthyridine-3-
carboxylic acid;

6-[5,6-difluoro-8-(methylamino)-4-[cis-5-methyl-2,3,3a,4,
6,6a-hexahydropyrrolo[2,3-c]pyrrol-1-yl]-9H-pyrido[2,
3-b]indol-3-yl]-1-(methylamino)-4-oxo-1,8-naphthyri-
dine-3-carboxylic acid;

6-[5,6-difluoro-8-(methylamino)-4-(9-methyl-2,9-diaz-
aspiro[4.5]decan-2-yl)-9H-pyrido[2,3-b]indol-3-yl]-1-
methyl-4-oxo-1,8-naphthyridine-3-carboxylic acid;

6-[4-[3-(dimethylamino)-1-piperidyl]-5,6-difluoro-8-(meth-
ylamino)-9H-pyrido[2,3-b]indol-3-yl]-1-(methylamino)-
4-oxo-1,8-naphthyridine-3-carboxylic acid;

6-[5,6-difluoro-8-(methylamino)-4-[cis-1-methyl-2,3,3a,4,
6,6a-hexahydropyrrolo[2,3-c]pyrrol-5-yl]-9H-pyrido[2,
3-b]indol-3-yl]-1-methyl-4-oxo-1,8-naphthyridine-3-car-
boxylic acid;

6-[5,6-difluoro-8-(methylamino)-4-[cis-1-methyl-2,3,3a,4,
6,6a-hexahydropyrrolo[2,3-c]pyrrol-5-yl]-9H-pyrido[2,
3-b]indol-3-yl]-1-(methylamino)-4-oxo-1,8-naphthyri-
dine-3-carboxylic acid;

6-[5,6-difluoro-4-[9-(2-hydroxyethyl)-2,9-diazaspiro[4.5]
decan-2-yl]-8-(methylamino)-9H-pyrido[2,3-b]indol-3-
yl]-1-methyl-4-oxo-1,8-naphthyridine-3-carboxylic acid;

6-[5,6-difluoro-4-[9-(2-methoxyethyl)-2,9-diazaspiro[4.5]
decan-2-yl]-8-(methylamino)-9H-pyrido[2,3-b]indol-3-
yl]-1-methyl-4-oxo-1,8-naphthyridine-3-carboxylic acid;

6-[5,6-difluoro-4-(cis-1-methyl-3,3a,4,5,7,7a-hexahydro-
2H-pyrrolo[2,3-c]pyridin-6-yl)-8-(methylamino)-9H-
pyrido[2,3-b]indol-3-yl]-1-methyl-4-oxo-1,8-naphthyri-
dine-3-carboxylic acid;

6-[5,6-difluoro-4-[3-[2-methoxyethyl(methyl)amino]-1-pi-
peridyl]-8-(methylamino)-9H-pyrido[2,3-b]indol-3-yl]-
1-methyl-4-oxo-1,8-naphthyridine-3-carboxylic acid;

6-[5,6-difluoro-4-[3-[2-methoxyethyl(methyl)amino]pyrro-
lidin-1-yl]-8-(methylamino)-9H-pyrido[2,3-b]indol-3-
yl]-1-methyl-4-oxo-1,8-naphthyridine-3-carboxylic acid;

6-[5,6-difluoro-4-(cis-1-methyl-3,3a,4,5,7,7a-hexahydro-
2H-pyrrolo[2,3-c]pyridin-6-yl)-8-(methylamino)-9H-pyri
do[2,3-b]indol-3-yl]-1-(methylamino)-4-oxo-1,8-naph-
thyridine-3-carboxylic acid;

6-[5,6-difluoro-4-[3-[2-hydroxyethyl(methyl)amino]pyrro-
lidin-1-yl]-8-(methylamino)-9H-pyrido[2,3-b]indol-3-
yl]-1-methyl-4-oxo-1,8-naphthyridine-3-carboxylic acid;

6-[5,6-difluoro-4-[3-[2-hydroxyethyl(methyl)amino]-1-pip-
eridyl]-8-(methylamino)-9H-pyrido[2,3-b]indol-3-yl]-1-
methyl-4-oxo-1,8-naphthyridine-3-carboxylic acid;

6-[5,6-difluoro-8-(methylamino)-4-(9-methyl-6-oxa-2,9-di-
azaspiro[4.5]decan-2-yl)-9H-pyrido[2,3-b]indol-3-yl]-1-
methyl-4-oxo-1,8-naphthyridine-3-carboxylic acid;

6-[5,6-difluoro-8-(methylamino)-4-(4-pyrrolidin-1-yl-1-pi-
peridyl)-9H-pyrido[2,3-b]indol-3-yl]-1-methyl-4-oxo-1,
8-naphthyridine-3-carboxylic acid;

6-[4-(4-cyclopropylpiperazin-1-yl)-5,6-difluoro-8-(methyl-
amino)-9H-pyrido[2,3-b]indol-3-yl]-1-methyl-4-oxo-1,8-
naphthyridine-3-carboxylic acid;

6-[5,6-difluoro-8-(methylamino)-4-[cis-5-(2-hydroxy-ethyl)-2,3,3a,4,6,6a-hexahydropyrrolo[2,3-c]pyrrol-1-yl]-9H-pyrido[2,3-b]indol-3-yl]-1-methyl-4-oxo-1,8-naphthyridine-3-carboxylic acid;

6-[5,6-difluoro-8-(methylamino)-4-[cis-5-methyl-2,3,3a,4,6,6a-hexahydropyrrolo[2,3-c]pyrrol-1-yl]-9H-pyrido[2,3-b]indol-3-yl]-1-(2-hydroxy-1-methyl-ethyl)-4-oxo-1,8-naphthyridine-3-carboxylic acid;

6-[4-[7-(dimethylamino)-5-azaspiro[2.4]heptan-5-yl]-5,6-difluoro-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-pyrrolidin-1-yl-9H-pyrido[2,3-b]indol-3-yl]-1-methyl-4-oxo-1,8-naphthyridine-3-carboxylic acid;

6-[6-fluoro-8-(methylamino)-4-[cis-1-methyl-2,3,3a,4,6,6a-hexahydropyrrolo[2,3-c]pyrrol-5-yl]-9H-pyrido[2,3-b]indol-3-yl]-1-methyl-4-oxo-1,8-naphthyridine-3-carboxylic acid;

6-[6-fluoro-8-(methylamino)-4-[cis-1-methyl-2,3,3a,4,6,6a-hexahydropyrrolo[2,3-c]pyrrol-5-yl]-9H-pyrido[2,3-b]indol-3-yl]-1-(methylamino)-4-oxo-1,8-naphthyridine-3-carboxylic acid;

6-[6-fluoro-4-(cis-1-methyl-3,3a,4,5,7,7a-hexahydro-2H-pyrrolo[2,3-c]pyridin-6-yl)-8-(methylamino)-9H-pyrido[2,3-b]indol-3-yl]-1-methyl-4-oxo-1,8-naphthyridine-3-carboxylic acid;

6-[6-fluoro-4-(cis-1-methyl-3,3a,4,5,7,7a-hexahydro-2H-pyrrolo[2,3-c]pyridin-6-yl)-8-(methylamino)-9H-pyrido[2,3-b]indol-3-yl]-1-(methylamino)-4-oxo-1,8-naphthyridine-3-carboxylic acid;

6-[5,6-difluoro-8-(methylamino)-4-(cis-8-methyl-3,8-diaz-abicyclo[4.2.0]octan-3-yl)-9H-pyrido[2,3-b]indol-3-yl]-1-methyl-4-oxo-1,8-naphthyridine-3-carboxylic acid;

6-[5,6-difluoro-8-(methylamino)-4-(cis-8-methyl-3,8-diaz-abicyclo[4.2.0]octan-3-yl)-9H-pyrido[2,3-b]indol-3-yl]-1-(methylamino)-4-oxo-1,8-naphthyridine-3-carboxylic acid;

6-[4-[3-(dimethylamino)-1-piperidyl]-5,6-difluoro-8-(methylamino)-9H-pyrido[2,3-b]indol-3-yl]-1-methyl-4-oxo-1,8-naphthyridine-3-carboxylic acid;

6-[6-fluoro-8-(methylamino)-4-morpholino-9H-pyrido[2,3-b]indol-3-yl]-1-[(1 S)-2-hydroxy-1-methyl-ethyl]-4-oxo-1,8-naphthyridine-3-carboxylic acid;

6-[4-[(2 S)-2-[(dimethylamino)methyl]pyrrolidin-1-yl]-5,6-difluoro-8-(methylamino)-9H-pyrido[2,3-b]indol-3-yl]-1-(methylamino)-4-oxo-1,8-naphthyridine-3-carboxylic acid;

6-[4-cis-(4R)-[(dimethylamino)methyl]-3,3a,4,5,6,6a-hexahydro-1H-cyclopenta[c]pyrrol-2-yl]-5,6-difluoro-8-(methylamino)-9H-pyrido[2,3-b]indol-3-yl]-1-methyl-4-oxo-1,8-naphthyridine-3-carboxylic acid;

6-[4-[(8aS)-3,4,6,7,8,8a-hexahydro-1H-pyrrolo[1,2-a]pyrazin-2-yl]-5,6-difluoro-8-(methylamino)-9H-pyrido[2,3-b]indol-3-yl]-1-methyl-4-oxo-1,8-naphthyridine-3-carboxylic acid;

6-[4-[(8aR)-3,4,6,7,8,8a-hexahydro-1H-pyrrolo[1,2-a]pyrazin-2-yl]-5,6-difluoro-8-(methylamino)-9H-pyrido[2,3-b]indol-3-yl]-1-methyl-4-oxo-1,8-naphthyridine-3-carboxylic acid;

6-[4-cis-(4R)-(dimethylamino)-3,3a,4,5,6,6a-hexahydro-1H-cyclopenta[c]pyrrol-2-yl]-5,6-difluoro-8-(methylamino)-9H-pyrido[2,3-b]indol-3-yl]-1-methyl-4-oxo-1,8-naphthyridine-3-carboxylic acid;

6-[4-[cis-3-(dimethylamino)-4-hydroxy-pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-[cis-3-(dimethylamino)-4-hydroxy-pyrrolidin-1-yl]-5,6-difluoro-8-(methylamino)-9H-pyrido[2,3-b]indol-3-yl]-1-(methylamino)-4-oxo-1,8-naphthyridine-3-carboxylic acid;

6-[5,6-difluoro-4-[2-(2-hydroxyethyl)morpholin-4-yl]-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-(4-methylpiperazin-1-yl)-9H-pyrido[2,3-b]indol-3-yl]-1-methyl-4-oxo-1,8-naphthyridine-3-carboxylic acid;

6-[5,6-difluoro-8-(methylamino)-4-[cis-2-methyl-1,3,3a,4,6,6a-hexahydropyrrolo[3,4-c]pyrrol-5-yl]-9H-pyrido[2,3-b]indol-3-yl]-1-methyl-4-oxo-1,8-naphthyridine-3-carboxylic acid;

6-[5,6-difluoro-8-(methylamino)-4-(2-methyl-2,6-diaz-aspiro[3.4]octan-6-yl)-9H-pyrido[2,3-b]indol-3-yl]-1-methyl-4-oxo-1,8-naphthyridine-3-carboxylic acid;

6-[5,6-difluoro-8-(methylamino)-4-(7-methyl-2,7-diaz-aspiro[4.4]nonan-2-yl)-9H-pyrido[2,3-b]indol-3-yl]-1-methyl-4-oxo-1,8-naphthyridine-3-carboxylic acid;

6-[5,6-difluoro-8-(methylamino)-4-(1-methyl-1,8-diaz-aspiro[4.5]decan-8-yl)-9H-pyrido[2,3-b]indol-3-yl]-1-methyl-4-oxo-1,8-naphthyridine-3-carboxylic acid;

6-[5,6-difluoro-8-(methylamino)-4-(2-methyl-2,8-diaz-aspiro[4.5]decan-8-yl)-9H-pyrido[2,3-b]indol-3-yl]-1-methyl-4-oxo-1,8-naphthyridine-3-carboxylic acid;

6-[5,6-difluoro-4-(1-methyl-3,4,4a,5,7,7a-hexahydro-2H-pyrrolo[3,4-b]pyridin-6-yl)-8-(methylamino)-9H-pyrido[2,3-b]indol-3-yl]-1-methyl-4-oxo-1,8-naphthyridine-3-carboxylic acid;

6-[4-(4-ethylpiperazin-1-yl)-5,6-difluoro-8-(methylamino)-9H-pyrido[2,3-b]indol-3-yl]-1-methyl-4-oxo-1,8-naphthyridine-3-carboxylic acid;

6-[5,6-difluoro-4-(4-isopropylpiperazin-1-yl)-8-(methylamino)-9H-pyrido[2,3-b]indol-3-yl]-1-methyl-4-oxo-1,8-naphthyridine-3-carboxylic acid;

6-[5,6-difluoro-4-(4-methyl-2,3,4a,5,7,7a-hexahydropyrrolo[3,4-b][1,4]oxazin-6-yl)-8-(methylamino)-9H-pyrido[2,3-b]indol-3-yl]-1-methyl-4-oxo-1,8-naphthyridine-3-carboxylic acid;

6-[5,6-difluoro-4-(4-methyl-2,3,4a,5,7,7a-hexahydropyrrolo[3,4-b][1,4]oxazin-6-yl)-8-(methylamino)-9H-pyrido[2,3-b]indol-3-yl]-1-(methylamino)-4-oxo-1,8-naphthyridine-3-carboxylic acid;

6-[5,6-difluoro-8-(methylamino)-4-(1-methyl-1,7-diaz-aspiro[3.4]octan-7-yl)-9H-pyrido[2,3-b]indol-3-yl]-1-methyl-4-oxo-1,8-naphthyridine-3-carboxylic acid;

6-[5,6-difluoro-8-(methylamino)-4-(1-methyl-1,7-diaz-aspiro[3.4]octan-7-yl)-9H-pyrido[2,3-b]indol-3-yl]-1-(methylamino)-4-oxo-1,8-naphthyridine-3-carboxylic acid;

6-[5,6-difluoro-8-(methylamino)-4-(1-methyl-1,7-diaz-aspiro[4.4]nonan-7-yl)-9H-pyrido[2,3-b]indol-3-yl]-1-methyl-4-oxo-1,8-naphthyridine-3-carboxylic acid;

6-[5,6-difluoro-8-(methylamino)-4-(1-methyl-1,7-diaz-aspiro[4.4]nonan-7-yl)-9H-pyrido[2,3-b]indol-3-yl]-1-(methylamino)-4-oxo-1,8-naphthyridine-3-carboxylic acid;

6-[5,6-difluoro-4-(cis-4-methyl-2,3,4a,5,7,7a-hexahydropyrrolo[3,4-b][1,4]oxazin-6-yl)-8-(methylamino)-9H-pyrido[2,3-b]indol-3-yl]-1-methyl-4-oxo-1,8-naphthyridine-3-carboxylic acid;

6-[5,6-difluoro-4-(cis-4-methyl-2,3,4a, 5,7,7a-hexahydropyrrolo[3,4-b][1,4]oxazin-6-yl)-8-(methylamino)-9H-pyrido[2,3-b]indol-3-yl]-1-(methylamino)-4-oxo-1,8-naphthyridine-3-carboxylic acid;

6-[5,6-difluoro-4-(5-methyl-3,3a,4,6,7,7a-hexahydro-2H-pyrrolo[3,2-c]pyridin-1-yl)-8-(methylamino)-9H-pyrido[2,3-b]indol-3-yl]-1-methyl-4-oxo-1,8-naphthyridine-3-carboxylic acid;

6-[5,6-difluoro-4-(5-methyl-3,3a,4,6,7,7a-hexahydro-2H-pyrrolo[3,2-c]pyridin-1-yl)-8-(methylamino)-9H-pyrido[2,3-b]indol-3-yl]-1-(methylamino)-4-oxo-1,8-naphthyridine-3-carboxylic acid;

6-[5,6-difluoro-4-(cis-1-methyl-2,3,3a, 5,6,6a-hexahydropyrrolo[3,2-b]pyrrol-4-yl)-8-(methylamino)-9H-pyrido[2,3-b]indol-3-yl]-1-methyl-4-oxo-1,8-naphthyridine-3-carboxylic acid;

6-[5,6-difluoro-4-(4-methyl-3,3a, 5,6,7,7a-hexahydro-2H-pyrrolo[3,2-b]pyridin-1-yl)-8-(methylamino)-9H-pyrido[2,3-b]indol-3-yl]-1-methyl-4-oxo-1,8-naphthyridine-3-carboxylic acid;

6-[5,6-difluoro-4-(4-methyl-3,3a, 5,6,7,7a-hexahydro-2H-pyrrolo[3,2-b]pyridin-1-yl)-8-(methylamino)-9H-pyrido[2,3-b]indol-3-yl]-1-(methylamino)-4-oxo-1,8-naphthyridine-3-carboxylic acid;

6-[5,6-difluoro-8-(methylamino)-4-(cis-6-methyl-2,6-diazabicyclo[3.2.0]heptan-2-yl)-9H-pyrido[2,3-b]indol-3-yl]-1-methyl-4-oxo-1,8-naphthyridine-3-carboxylic acid;

6-[5,6-difluoro-4-(cis-1-methyl-2,3,3a,5,6,6a-hexahydropyrrolo[3,2-b]pyrrol-4-yl)-8-(methylamino)-9H-pyrido[2,3-b]indol-3-yl]-1-(methylamino)-4-oxo-1,8-naphthyridine-3-carboxylic acid;

6-[5,6-difluoro-8-(methylamino)-4-[(2S)-2-methylmorpholin-4-yl]-9H-pyrido[2,3-b]indol-3-yl]-4-oxo-1-[(1S)-2-hydroxy-1-methyl-ethyl]-1,8-naphthyridine-3-carboxylic acid;

(1R)-6-[5,6-difluoro-8-(methylamino)-4-[(2S)-2-methylmorpholin-4-yl]-9H-pyrido[2,3-b]indol-3-yl]-4-oxo-1-pyrrolidin-3-yl-1,8-naphthyridine-3-carboxylic acid;

6-[5,6-difluoro-8-(methylamino)-4-[cis-6-methyl-3,6-diazabicyclo[3.2.0]heptan-3-yl]-9H-pyrido[2,3-b]indol-3-yl]-1-methyl-4-oxo-1,8-naphthyridine-3-carboxylic acid;

6-[4-[(3S)-3-(dimethylamino)pyrrolidin-1-yl]-6-fluoro-8-(methylamino)-9H-pyrido[2,3-b]indol-3-yl]-1-methyl-4-oxo-1,8-naphthyridine-3-carboxylic acid;

6-[4-[(3S)-3-(dimethylamino)pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-[(3S)-3-[(dimethylamino)methyl]pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-[(3R)-3-[(dimethylamino)methyl]pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-[(3R)-3-(dimethylamino)pyrrolidin-1-yl]-5,6-difluoro-8-(methylamino)-9H-pyrido[2,3-b]indol-3-yl]-1-(methylamino)-4-oxo-1,8-naphthyridine-3-carboxylic acid;

6-[4-[(3R)-3-(dimethylamino)pyrrolidin-1-yl]-5,6-difluoro-8-(methylamino)-9H-pyrido[2,3-b]indol-3-yl]-1-(ethylamino)-4-oxo-1,8-naphthyridine-3-carboxylic acid;

6-[6-fluoro-8-(methylamino)-4-pyrrolidin-1-yl-9H-pyrido[2,3-b]indol-3-yl]-4-oxo-1-pyrrolidin-3-yl-1,8-naphthyridine-3-carboxylic acid;

6-[4-[cis-1-(3-hydroxypropyl)-2,3,3a,4,6,6a-hexahydropyrrolo[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid;

6-[4-[cis-1-(2-hydroxyethyl)-2,3,3a,4,6,6a-hexahydropyrrolo[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid;

6-(4-(1-(dimethylamino)-6-azaspiro[3.4]octan-6-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-((1R,5 S,6S)-6-(dimethylamino)-3-azabicyclo[3.1.0]hexan-3-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-[4-[cis-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-(methylamino)-4-oxo-1,8-naphthyridine-3-carboxylic acid;

6-[4-[cis-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-methyl-4-oxo-1,8-naphthyridine-3-carboxylic acid;

6-[4-[cis-5-methyl-2,3,3a,4,6,6a-hexahydropyrrolo[2,3-c]pyrrol-1-yl]-6-chloro-5-fluoro-8-(methylamino)-9H-pyrido[2,3-b]indol-3-yl]-1-(methylamino)-4-oxo-1,8-naphthyridine-3-carboxylic acid;

6-[4-[cis-5-methyl-2,3,3a,4,6,6a-hexahydropyrrolo[2,3-c]pyrrol-1-yl]-6-chloro-5-fluoro-8-(methylamino)-9H-pyrido[2,3-b]indol-3-yl]-1-methyl-4-oxo-1,8-naphthyridine-3-carboxylic acid;

6-[4-[cis-5-methyl-2,3,3a,4,6,6a-hexahydropyrrolo[2,3-c]pyrrol-1-yl]-5-chloro-6-fluoro-8-(methylamino)-9H-pyrido[2,3-b]indol-3-yl]-1-(methylamino)-4-oxo-1,8-naphthyridine-3-carboxylic acid;

6-(5-chloro-6-fluoro-8-(methylamino)-4-morpholino-9H-pyrido[2,3-b]indol-3-yl)-1-methyl-4-oxo-1,4-dihydro-1,8-naphthyridine-3-carboxylic acid;

6-[4-[cis-5-methyl-2,3,3a,4,6,6a-hexahydropyrrolo[2,3-c]pyrrol-1-yl]-5-chloro-6-fluoro-8-(methylamino)-9H-pyrido[2,3-b]indol-3-yl]-1-methyl-4-oxo-1,8-naphthyridine-3-carboxylic acid;

6-[4-(3a,5-dimethyl-3,4,6,6a-tetrahydro-2H-pyrrolo[2,3-c]pyrrol-1-yl)-6-fluoro-8-(methylamino)-9H-pyrido[2,3-b]indol-3-yl]-1-methyl-4-oxo-1,8-naphthyridine-3-carboxylic acid;

6-[4-(3a,5-dimethyl-3,4,6,6a-tetrahydro-2H-pyrrolo[2,3-c]pyrrol-1-yl)-6-fluoro-8-(methylamino)-9H-pyrido[2,3-b]indol-3-yl]-1-(methylamino)-4-oxo-1,8-naphthyridine-3-carboxylic acid;

6-[4-[cis-5-methyl-2,3,3a,4,6,6a-hexahydropyrrolo[2,3-c]pyrrol-1-yl]-5-cyano-6-fluoro-8-(methylamino)-9H-pyrido[2,3-b]indol-3-yl]-1-methyl-4-oxo-1,8-naphthyridine-3-carboxylic acid;

6-[4-[cis-5-methyl-2,3,3a,4,6,6a-hexahydropyrrolo[2,3-c]pyrrol-1-yl]-5-cyano-6-fluoro-8-(methylamino)-9H-pyrido[2,3-b]indol-3-yl]-1-(methylamino)-4-oxo-1,8-naphthyridine-3-carboxylic acid;

6-[6-chloro-4-(cis-3-hydroxy-2,3,3a,4,6,6a-hexahydrofuro[2,3-c]pyrrol-5-yl)-8-(methylamino)-9H-pyrido[2,3-b]indol-3-yl]-1-methyl-4-oxo-1,8-naphthyridine-3-carboxylic acid;

6-[6-chloro-4-[cis-3-(dimethylamino)-2,3,3a,4,6,6a-hexahydrofuro[2,3-c]pyrrol-5-yl]-8-(methylamino)-9H-pyrido[2,3-b]indol-3-yl]-1-methyl-4-oxo-1,8-naphthyridine-3-carboxylic acid;

6-[6-chloro-8-(methylamino)-4-(cis-8-methyl-3,8-diazabicyclo[4.2.0]octan-3-yl)-9H-pyrido[2,3-b]indol-3-yl]-1-methyl-4-oxo-1,8-naphthyridine-3-carboxylic acid;

6-[4-[(cis-5-ethyl-2,3,3a,4,6,6a-hexahydropyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-(dimethylamino)-5,6-difluoro-8-(methylamino)-9H-pyrido[2,3-b]indol-3-yl]-1-[(3S)-1-ethylpyrrolidin-3-yl]-4-oxo-1,8-naphthyridine-3-carboxylic acid;

6-[4-[cis-1-cyclopropyl-2,3,3a,4,6,6a-hexahydropyrrolo[2,3-c]pyrrol-5-yl]-5,6-difluoro-8-(methylamino)-9H-pyrido[2,3-b]indol-3-yl]-1-(methylamino)-4-oxo-1,8-naphthyridine-3-carboxylic acid;

6-[4-[3-[(dimethylamino)methyl]-3-fluoro-1-piperidyl]-5,6-difluoro-8-(methylamino)-9H-pyrido[2,3-b]indol-3-yl]-1-methyl-4-oxo-1,8-naphthyridine-3-carboxylic acid;

6-[4-[cis-1-cyclopropyl-2,3,3a,4,6,6a-hexahydropyrrolo[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-[cis-(4R)-4-(dimethylamino)-3,3a,4,5,6,6a-hexahydro-1H-cyclopenta[c]pyrrol-2-yl]-9H-pyrido[2,3-b]indol-3-yl]-1-(methylamino)-4-oxo-1,8-naphthyridine-3-carboxylic acid;

6-[6-chloro-8-(methylamino)-4-[cis-(4R)-(dimethylamino)-3,3a,4,5,6,6a-hexahydro-1H-cyclopenta[c]pyrrol-2-yl]-9H-pyrido[2,3-b]indol-3-yl]-1-methyl-4-oxo-1,8-naphthyridine-3-carboxylic acid;

6-[4-[cis-3-(dimethylamino)-2,3,3a,4,6,6a-hexahydrofuro[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid;

6-[5,6-difluoro-4-(cis-3-hydroxy-2,3,3a,4,6,6a-hexahydrofuro[2,3-c]pyrrol-5-yl)-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-[cis-(4S)-4-(dimethylamino)-3,3a,4,5,6,6a-hexahydro-1H-cyclopenta[c]pyrrol-2-yl]-9H-pyrido[2,3-b]indol-3-yl]-1-methyl-4-oxo-1,8-naphthyridine-3-carboxylic acid;

6-[4-[cis-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-ethyl-4-oxo-1,8-naphthyridine-3-carboxylic acid;

6-[4-[cis-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-(ethylamino)-4-oxo-1,8-naphthyridine-3-carboxylic acid;

6-[4-[cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-(ethylamino)-4-oxo-1,8-naphthyridine-3-carboxylic acid;

6-(5,6-dichloro-4-(cis-(4R)-4-(dimethylamino)hexahydrocyclopenta[c]pyrrol-2(1H)-yl)-8-(methylamino)-9H-pyrido[2,3-b]indol-3-yl)-1-methyl-4-oxo-1,4-dihydro-1,8-naphthyridine-3-carboxylic acid;

6-[4-[cis-5-methyl-2,3,3a,4,6,6a-hexahydropyrrolo[2,3-c]pyrrol-1-yl]-5,6-dichloro-8-(methylamino)-9H-pyrido[2,3-b]indol-3-yl]-1-methyl-4-oxo-1,8-naphthyridine-3-carboxylic acid;

6-[4-[cis-5-methyl-2,3,3a,4,6,6a-hexahydropyrrolo[2,3-c]pyrrol-1-yl]-6-fluoro-5-methoxy-8-(methylamino)-9H-pyrido[2,3-b]indol-3-yl]-1-methyl-4-oxo-1,8-naphthyridine-3-carboxylic acid;

6-[4-[cis-1-methyl-2,3,3a,4,6,6a-hexahydropyrrolo[2,3-c]pyrrol-5-yl]-6-fluoro-5-methoxy-8-(methylamino)-9H-pyrido[2,3-b]indol-3-yl]-1-methyl-4-oxo-1,8-naphthyridine-3-carboxylic acid;

6-(6-fluoro-8-(methylamino)-4-(5-oxa-2,8-diazaspiro[3.5]nonan-8-yl)-9H-pyrido[2,3-b]indol-3-yl)-1-methyl-4-oxo-1,4-dihydro-1,8-naphthyridine-3-carboxylic acid;

6-(6-fluoro-8-(methylamino)-4-(cis-6-methylhexahydropyrrolo[3,4-b][1,4]oxazin-4(4aH)-yl)-9H-pyrido[2,3-b]indol-3-yl)-1-methyl-4-oxo-1,4-dihydro-1,8-naphthyridine-3-carboxylic acid;

6-[4-[(3aS,6aS)-5-methyl-2,3,3a,4,6,6a-hexahydropyrrolo[2,3-c]pyrrol-1-yl]-5-cyano-6-fluoro-8-(methylamino)-9H-pyrido[2,3-b]indol-3-yl]-1-methyl-4-oxo-1,8-naphthyridine-3-carboxylic acid;

6-[4-[(3aS,6aS)-5-methyl-2,3,3a,4,6,6a-hexahydropyrrolo[2,3-c]pyrrol-1-yl]-5-cyano-6-fluoro-8-(methylamino)-9H-pyrido[2,3-b]indol-3-yl]-1-(methylamino)-4-oxo-1,8-naphthyridine-3-carboxylic acid;

6-[4-(3,3-Difluoropyrrolidin-1-yl)-5,6-difluoro-8-(methylamino)-9H-pyrido[2,3-b]indol-3-yl]-1-methyl-4-oxo-1,8-naphthyridine-3-carboxylic acid;

6-[4-(3,3-Difluoropyrrolidin-1-yl)-5,6-difluoro-8-(methylamino)-9H-pyrido[2,3-b]indol-3-yl]-1-[2-(dimethylamino)ethyl]-4-oxo-1,8-naphthyridine-3-carboxylic acid;

6-(4-(3,3-difluoropyrrolidin-1-yl)-5,6-difluoro-8-(methylamino)-9H-pyrido[2,3-b]indol-3-yl)-1-(1-methylpyrrolidin-3-yl)-4-oxo-1,4-dihydro-1,8-naphthyridine-3-carboxylic acid;

6-[4-[cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-(2-methoxyethylamino)-4-oxo-1,8-naphthyridine-3-carboxylic acid;

6-[4-[(cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-amino-4-oxo-1,8-naphthyridine-3-carboxylic acid;

6-(4-(dimethylamino)-5,6-difluoro-8-(methylamino)-9H-pyrido[2,3-b]indol-3-yl)-4-oxo-1-((2,2,2-trifluoroethyl)amino)-1,4-dihydro-1,8-naphthyridine-3-carboxylic acid;

6-(4-(dimethylamino)-5,6-difluoro-8-(methylamino)-9H-pyrido[2,3-b]indol-3-yl)-1-(2-methyl-1-(methylamino)propan-2-yl)-4-oxo-1,4-dihydro-1,8-naphthyridine-3-carboxylic acid;

6-[4-[(cis-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-amino-4-oxo-1,8-naphthyridine-3-carboxylic acid;

6-[4-[cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-(methoxymethyl)-4-oxo-1,8-naphthyridine-3-carboxylic acid;

6-(4-(trans-1-(dimethylamino)-5-azaspiro[2.4]heptan-5-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-(cis-1-(dimethylamino)-5-azaspiro[2.4]heptan-5-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-((2S,4S)-2-((dimethylamino)methyl)-4-fluoropyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-[5,6-difluoro-8-(methylamino)-4-[(3aS,6aS)-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylic acid;

6-[5,6-difluoro-8-(methylamino)-4-[(3aR,6aR)-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylic acid;

6-[4-[(2 S)-2-[(dimethylamino)methyl]morpholin-4-yl]-6-fluoro-8-(methylamino)-9H-pyrido[2,3-b]indol-3-yl]-1-methyl-4-oxo-1,8-naphthyridine-3-carboxylic acid;

6-[4-[(2R)-2-[(dimethylamino)methyl]morpholin-4-yl]-6-fluoro-8-(methylamino)-9H-pyrido[2,3-b]indol-3-yl]-1-methyl-4-oxo-1,8-naphthyridine-3-carboxylic acid;

6-[4-[(3aS,6aS)-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-[(3 aR,6aR)-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-[(3aS,6aS)-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-methyl-4-oxo-1,8-naphthyridine-3-carboxylic acid;

6-[4-[(3aS,6aS)-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-(methylamino)-4-oxo-1,8-naphthyridine-3-carboxylic acid;

6-[4-[(3R)-3-(dimethylamino)-1-piperidyl]-5,6-difluoro-8-(methylamino)-9H-pyrido[2,3-b]indol-3-yl]-1-methyl-4-oxo-1,8-naphthyridine-3-carboxylic acid;

6-[4-[(3S)-3-(dimethylamino)-1-piperidyl]-5,6-difluoro-8-(methylamino)-9H-pyrido[2,3-b]indol-3-yl]-1-methyl-4-oxo-1,8-naphthyridine-3-carboxylic acid;

6-[4-[(3aR,6aR)-1-methyl-2,3,3a,4,6,6a-hexahydropyrrolo[2,3-c]pyrrol-5-yl]-5,6-difluoro-8-(methylamino)-9H-pyrido[2,3-b]indol-3-yl]-1-(methylamino)-4-oxo-1,8-naphthyridine-3-carboxylic acid;

6-[4-[(3aS,6aS)-1-methyl-2,3,3a,4,6,6a-hexahydropyrrolo[2,3-c]pyrrol-5-yl]-5,6-difluoro-8-(methylamino)-9H-pyrido[2,3-b]indol-3-yl]-1-(methylamino)-4-oxo-1,8-naphthyridine-3-carboxylic acid;

6-[4-[(3aR,6aR)-1-methyl-2,3,3a,4,6,6a-hexahydropyrrolo[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid;

6-[4-[(3aR,6aR)-3a-fluoro-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-[(3 aS,6aS)-3a-fluoro-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-[(3aR,6aR)-3a-fluoro-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-(methylamino)-4-oxo-1,8-naphthyridine-3-carboxylic acid;

6-[4-[(3 aS,6aS)-3a-fluoro-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-(methylamino)-4-oxo-1,8-naphthyridine-3-carboxylic acid;

6-[4-[(3 aS,6aS)-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-methyl-4-oxo-1,8-naphthyridine-3-carboxylic acid;

6-[4-[(3aR,6aR)-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-methyl-4-oxo-1,8-naphthyridine-3-carboxylic acid;

6-[4-[(3 aS,6aS)-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-(methylamino)-4-oxo-1,8-naphthyridine-3-carboxylic acid;

6-[4-[(3aR,6aR)-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-(methylamino)-4-oxo-1,8-naphthyridine-3-carboxylic acid;

6-[4-[(4aS,7aR)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-(methylamino)-4-oxo-1,8-naphthyridine-3-carboxylic acid;

6-[4-[(4aR,7aS)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-(methylamino)-4-oxo-1,8-naphthyridine-3-carboxylic acid;

6-[4-[(4aS,7aR)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-methyl-4-oxo-1,8-naphthyridine-3-carboxylic acid;

6-[4-[(4aR,7aS)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-methyl-4-oxo-1,8-naphthyridine-3-carboxylic acid;

6-[4-[(3aR,6aR)-1-methyl-2,3,3a,4,6,6a-hexahydropyrrolo[2,3-c]pyrrol-5-yl]-6-chloro-8-(methylamino)-9H-pyrido[2,3-b]indol-3-yl]-1-methyl-4-oxo-1,8-naphthyridine-3-carboxylic acid;

6-[4-[(3 aS,6aS)-1-methyl-2,3,3a,4,6,6a-hexahydropyrrolo[2,3-c]pyrrol-5-yl]-6-chloro-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-[(5R)-9-methyl-6-oxa-2,9-diazaspiro[4.5]decan-2-yl]-9H-pyrido[2,3-b]indol-3-yl]-1-methyl-4-oxo-1,8-naphthyridine-3-carboxylic acid 6-[5,6-difluoro-8-(methylamino)-4-[(5 S)-9-methyl-6-oxa-2,9-diazaspiro[4.5]decan-2-yl]-9H-pyrido[2,3-b]indol-3-yl]-1-methyl-4-oxo-1,8-naphthyridine-3-carboxylic acid;

6-[4-[(3aR,6aR)-1-methyl-2,3,3a,4,6,6a-hexahydropyrrolo[2,3-c]pyrrol-5-yl]-6-fluoro-8-(methylamino)-9H-pyrido[2,3-b]indol-3-yl]-1-(methylamino)-4-oxo-1,8-naphthyridine-3-carboxylic acid;

6-[4-[(3 aS,6aS)-1-methyl-2,3,3a,4,6,6a-hexahydropyrrolo[2,3-c]pyrrol-5-yl]-6-fluoro-8-(methylamino)-9H-pyrido[2,3-b]indol-3-yl]-1-(methylamino)-4-oxo-1,8-naphthyridine-3-carboxylic acid;

6-[4-[(3aR,7aR)-1-methyl-3,3a,4,5,7,7a-hexahydro-2H-pyrrolo[2,3-c]pyridin-6-yl]-6-fluoro-8-(methylamino)-9H-pyrido[2,3-b]indol-3-yl]-1-methyl-4-oxo-1,8-naphthyridine-3-carboxylic acid;

6-[4-[(3 aS,7aS)-1-methyl-3,3a,4,5,7,7a-hexahydro-2H-pyrrolo[2,3-c]pyridin-6-yl]-6-fluoro-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-[(3aR,4R,6aS)-4-(dimethylamino)-3,3a,4,5,6,6a-hexahydro-1H-cyclopenta[c]pyrrol-2-yl]-9H-pyrido[2,3-b]indol-3-yl]-1-(methylamino)-4-oxo-1,8-naphthyridine-3-carboxylic acid;

6-[5,6-difluoro-8-(methylamino)-4-[(3 aS,4R,6aR)-4-(dimethylamino)-3,3a,4,5,6,6a-hexahydro-1H-cyclopenta[c]pyrrol-2-yl]-9H-pyrido[2,3-b]indol-3-yl]-1-(methylamino)-4-oxo-1,8-naphthyridine-3-carboxylic acid;

6-[4-[(3aR,4S,6aS)-4-(dimethylamino)-3,3a,4,5,6,6a-hexahydro-1H-cyclopenta[c]pyrrol-2-yl]-6-chloro-8-(methylamino)-9H-pyrido[2,3-b]indol-3-yl]-1-methyl-4-oxo-1,8-naphthyridine-3-carboxylic acid;

6-[4-[(3 aS,4S,6aR)-4-(dimethylamino)-3,3a,4,5,6,6a-hexahydro-1H-cyclopenta[c]pyrrol-2-yl]-6-chloro-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-[(4aR,7aR)-4-hydroxy-1-methyl-3,4,4a,5,7,7a-hexahydro-2H-pyrrolo[3,4-b]pyridin-6-yl]-9H-pyrido[2,3-b]indol-3-yl]-1-methyl-4-oxo-1,8-naphthyridine-3-carboxylic acid;

6-[5,6-difluoro-8-(methylamino)-4-[(4aS,7aS)-4-hydroxy-1-methyl-3,4,4a,5,7,7a-hexahydro-2H-pyrrolo[3,4-b]pyridin-6-yl]-9H-pyrido[2,3-b]indol-3-yl]-1-methyl-4-oxo-1,8-naphthyridine-3-carboxylic acid;

6-[6-fluoro-8-(methylamino)-4-[(4aS,7aR)-4-methyl-2,3,4a,5,7,7a-hexahydropyrrolo[3,4-b][1,4]oxazin-6-yl]-9H-pyrido[2,3-b]indol-3-yl]-1-methyl-4-oxo-1,8-naphthyridine-3-carboxylic acid;

6-[4-[(4aR,7aS)-4-methyl-2,3,4a,5,7,7a-hexahydropyrrolo[3,4-b][1,4]oxazin-6-yl]-6-fluoro-8-(methylamino)-9H-pyrido[2,3-b]indol-3-yl]-1-methyl-4-oxo-1,8-naphthyridine-3-carboxylic acid;

6-[6-fluoro-8-(methylamino)-4-[(4aS,7aR)-4-methyl-2,3,4a,5,7,7a-hexahydropyrrolo[3,4-b][1,4]oxazin-6-yl]-9H-pyrido[2,3-b]indol-3-yl]-1-(methylamino)-4-oxo-1,8-naphthyridine-3-carboxylic acid;

6-[4-[(4aR,7aS)-4-methyl-2,3,4a,5,7,7a-hexahydropyrrolo[3,4-b][1,4]oxazin-6-yl]-6-fluoro-8-(methylamino)-9H-pyrido[2,3-b]indol-3-yl]-1-(methylamino)-4-oxo-1,8-naphthyridine-3-carboxylic acid;

6-[4-[(4aS,7aS)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-methyl-4-oxo-1,8-naphthyridine-3-carboxylic acid;

6-[4-[(4aR,7aR)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-methyl-4-oxo-1,8-naphthyridine-3-carboxylic acid;

(S)-6-(5,6-difluoro-8-(methylamino)-4-(3-(trifluoromethyl)piperazin-1-yl)-9H-pyrido[2,3-b]indol-3-yl)-1-methyl-4-oxo-1,4-dihydro-1,8-naphthyridine-3-carboxylic acid;

(R)-6-(5,6-difluoro-8-(methylamino)-4-(3-(trifluoromethyl)piperazin-1-yl)-9H-pyrido[2,3-b]indol-3-yl)-1-methyl-4-oxo-1,4-dihydro-1,8-naphthyridine-3-carboxylic acid;

(R)-6-(4-(2-((dimethylamino)methyl)morpholino)-5,6-difluoro-8-(methylamino)-9H-pyrido[2,3-b]indol-3-yl)-1-methyl-4-oxo-1,4-dihydro-1,8-naphthyridine-3-carboxylic acid; or (S)-6-(4-(2-((dimethylamino)methyl)morpholino)-5,6-difluoro-8-(methylamino)-9H-pyrido[2,3-b]indol-3-yl)-1-methyl-4-oxo-1,4-dihydro-1,8-naphthyridine-3-carboxylic acid;

or a pharmaceutically acceptable salt, or enantiomer or diastereomer thereof.

Synthesis

Scheme 1

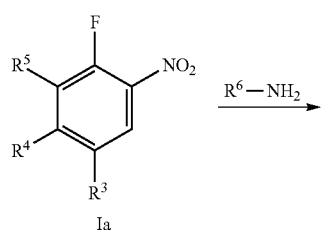

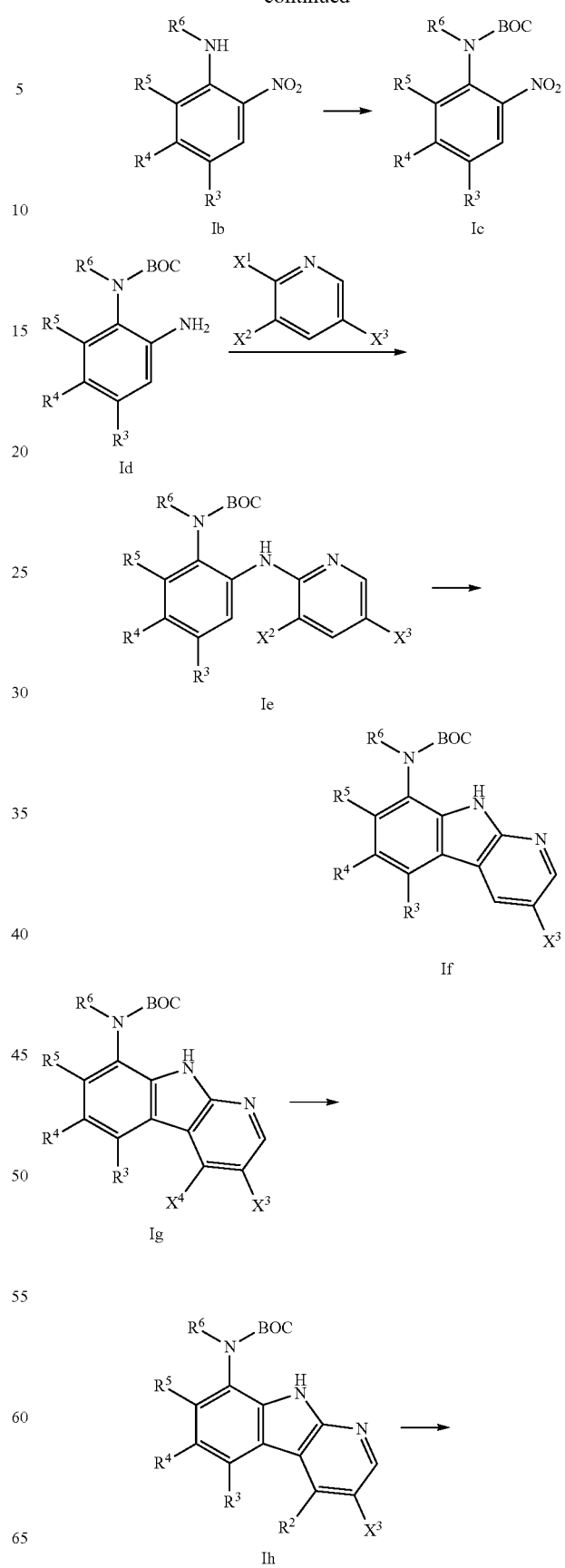

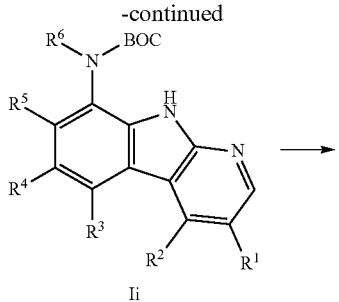

Ii

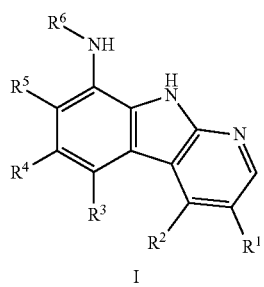

I wherein $X^1$, $X^2$, $X^3$ and $X^4$ are halogen.

Compound of formula (I) can be prepared according to Scheme 1. Nucleophilic substitution of ortho-fluoro nitrobenzene (Ia) with amine $R^6$—$NH_2$ affords aniline (Ib). The aniline (Ib) can be protected with di-tert-butyl carbonate to give the protected aniline (Ic). The nitro group in aniline (Ic) can be reduced by a reducing agent, such as $H_2$ with palladium catalysts, to give the compound of formula (Id). Coupling of the compound of formula (Id) with tri-halogenated pyridine can be achieved using palladium catalysts and phosphine ligands to give compound of formula (Ie). Cyclization of compound of formula (Ie) using palladium catalysts and phosphine ligands gives compound of formula (If). Compound of formula (Ig) can be obtained from formula (If) through oxidation of the pyridine followed by halogenation, such as treatment of $POCl_3$ or $POBr_3$. Compound of formula (Ig) can also be obtained by additional halogenation of compound of formula (Ig) (when $R^3$ is H) with halogenating reagent, such as NCS, followed by di-tert-butyl carbonate re-protection.

Compound of formula (I) can be prepared according to Scheme 1. Coupling of compound of formula (Ig) to introduce $R^2$ can be achieved either through nucleophilic substitution with amine and a base for certain C—N bond formation (with $R_2$ bearing a nucleophilic N), or a Buchwald-Hartwig Cross Coupling Reaction for certain C—N bond formation (with $R^2$ bearing a basic N), or a palladium catalyzed Suzuki coupling for C—C bond formation (with $R^2$ as a boronic ester or boronic acid), to give compound of formula (Ih). Further coupling of compound of formula (Ih) to introduce $R^1$ can be achieved using a palladium catalyzed Suzuki coupling to give compound of formula (Ii). Chiral separation can be achieved in compound of formula (Ih) or compound of formula (Ii). Some special compound of formula (Ii) need reverse the Suzuki coupling for C—C bond formation by converting compound of formula (Ih) to compound of formula (Ij) as a boronic ester or boronic acid then coupling with $R^1$ halide. Deprotection of compound of formula (Ii) in the presence of an acid, such as trifluoroacetic acid, affords compound of formula (I).

Scheme 2

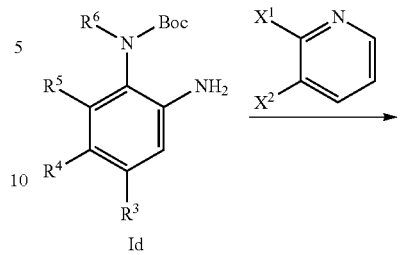

Id

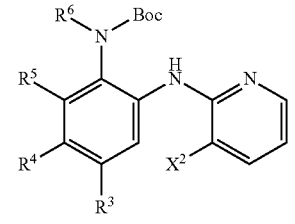

Ik

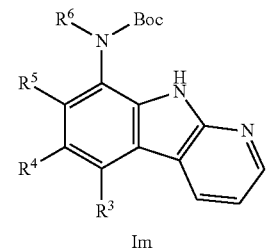

Im

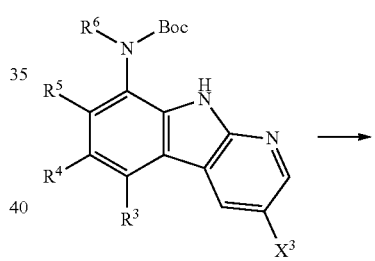

If

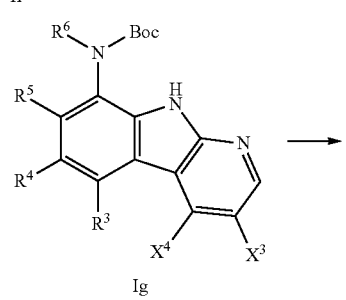

Ig

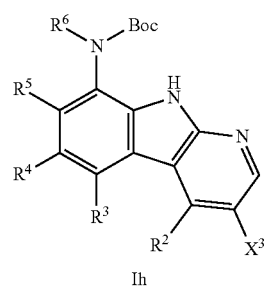

Ih

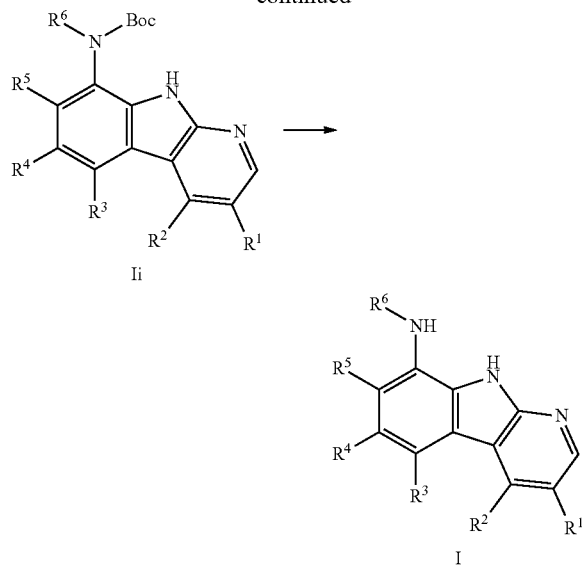

wherein $X^1$, $X^2$, $X^3$ and $X^4$ are halogen.

Alternatively, compound of formula (I) can be prepared according to Scheme 2. Coupling of the compound of formula (Id) with di-halogenated pyridine can be achieved using palladium catalyst and phosphine ligands to give compound of formula (Ik). Cyclization of compound of formula (Ik) using palladium catalyst and phosphine ligands gives compound of formula (Im). Compound of formula (Im) can be subject to halogenation using halogenating reagent, such as NCS, NBS, or NIS, to give compound of formula (If), which subsequently undergoes oxidation of the pyridine followed by halogenation, such as treatment of $POCl_3$ or $POBr_3$. Alternatively, compound of formula (If) can be obtained by treatment of compound of formula (If) (when $R^3$ is H) with halogenating reagent, such as NBS, to give compound of formula (If) (when $R^3$ is halogen, in particular bromo). Compound of formula (If) can further be obtained by converting compound of formula (If) (when $R^3$ is halogen, in particular bromo) to compound of formula (If) (when $R^3$ is CN, OMe, etc) via palladium mediated substitution or aromatic nucleophilic substitution.

Coupling of compound of formula (Ig) to introduce $R^2$ can be achieved either through nucleophilic substitution with amine and a base for certain C—N bond formation (with $R_2$ bearing a nucleophilic N), or a Buchwald-Hartwig Cross Coupling Reaction for certain C—N bond formation (with $R^2$ bearing a basic N), or a palladium catalyzed Suzuki coupling for C—C bond formation (with $R^2$ as a boronic ester or boronic acid), to give compound of formula (Ih). Further coupling of compound of formula (Ih) to introduce $R^1$ can be achieved using a palladium catalyzed Suzuki coupling to give compound of formula (Ii). Chiral separation can be achieved in compound of formula (Ih) or compound of formula (Ii). Some special compound of formula (Ii) need to reverse the Suzuki coupling for C—C bond formation by converting compound of formula (Ih) to compound of formula (Ij) as a boronic ester or boronic acid then coupling with $R^1$ halide. Deprotection of compound of formula (Ii) in the presence of an acid, such as trifluoroacetic acid, affords compound of formula (I).

This invention also relates to a process for the preparation of a compound of formula (I) comprising the reaction of compound of formula (Ii),

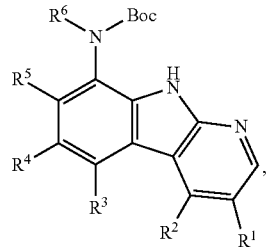

with an acid, which can be for example trifluoroacetic acid;

wherein $R^1$ to $R^6$ are defined above. A compound of formula (I) when manufactured according to the above process is also an object of the invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to reduced bacterial load or improve host survival through the inhibition of bacterial DNA gyrase and/or Topoisomerase IV. For example, such amount may be below the amount that is toxic to normal cells, or the mammal as a whole.

In one example, the pharmaceutically effective amount of the compound of the invention administered parenterally per dose will be in the range of about 0.1 to 1000 mg/kg, alternatively about 1 to 100 mg/kg of patient body weight per day. In another embodiment, oral unit dosage forms, such as tablets and capsules, preferably contain from about 5 to about 5000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 10 to 500 mg of the compound of the invention compounded with about 40 to 400 mg anhydrous lactose, about 5 to 50 mg sodium croscarmellose, about 5 to 50 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 to 1000 mg) of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I), or a stereoisomer or pharmaceutically acceptable salt thereof. In a further embodiment includes a pharmaceutical composition comprising a compound of formula (I), or a stereoisomer or pharmaceutically acceptable salt thereof, together with a pharmaceutically acceptable carrier or excipient.

Another embodiment includes a pharmaceutical composition comprising a compound of formula (I) for use in the treatment and/or prophylaxis of bacterial infections.

In some embodiments, the compounds of this invention may be administered, as part of a single or multiple dosage regimen, orally, parenterally, by inhalation spray, topically, rectally, nasally, buccally, vaginally, or via an implanted reservoir. The term parenteral as used includes subcutaneous, intracutaneous, intravenous, intramuscular, intra-articular, intrasynovial, intrasternal, intrathecal, intralesional and intracranial injection or infusion techniques. Typically, the pharmaceutical compositions of the invention will be administered from about 1 to 5 times per day or alternatively, as a continuous infusion upon improvement of a patient's condition.

Indications and Methods of Treatment

The compounds of the invention are useful for treatment and/or prophylaxis of bacterial infection in humans or other animals by administering to the subject in need of a therapeutically effective amount of compound of formula (I), or a pharmaceutically acceptable salt, or enantiomer or diastereomer thereof. The compounds and methods of the invention are particularly well suited for human patients infected by pathogens that include *Staphylococcus aureus, Escherichia coli, Klebsiella pneumoniae, Acinetobacter baumannii* and *Pseudomonas aeruginosa*. Examples of bacterial organisms that may also be controlled by the compounds of the invention include, but not limited to, the following Gram-Positive and Gram-Negative organisms: *Streptococcus pneumoniae, Streptococcus pyogenes, Enterococcus faecalis, Enterococcus faecium, Enterobacter* spp. species, *Proteus* spp. species, *Serratia marcescens, Staphylococcus aureus,* Coag. Neg. *Staphylococci, Haemophilus influenzae, Bacillus anthraces, Mycoplasma pneumoniae, Moraxella catarrhalis, Chlamydophila pneumoniae, Chlamydia trachomatis, Legionella pneumophila, Mycobacterium tuberculosis, Helicobacter pylori, Staphylococcus saprophyticus, Staphylococcus epidermidis, Francisella tularensis, Yersinia pestis, Clostridium difficile, Bacteroides* spp. species *Neisseria gonorrhoeae, Neisseria meningitidis, Burkholderia pseudomallei, Burkholderia mallei, Borrelia burgdorferi, Mycobacterium avium* complex, *Mycobacterium abscessus, Mycobacterium kansasii, E. coli* and *Mycobacterium ulcerans*.

Examples of bacterial infections may include, but not limited to, upper respiratory infections, lower respiratory infections, ear infections, pleuropulmonary and bronchial infections, complicated urinary tract infections, uncomplicated urinary tract infections, intra-abdominal infections, cardiovascular infections, a blood stream infection, sepsis, bacteremia, CNS infections, skin and soft tissue infections, GI infections, bone and joint infections, genital infections, eye infections, or granulomatous infections. Examples of specific bacterial infections include, but not limited to, uncomplicated skin and skin structure infections (uSSSI), complicated skin and skin structure infections (cSSSI), catheter infections, pharyngitis, sinusitis, otitis extema, otitis media, bronchitis, empyema, pneumonia, community-acquired bacterial pneumoniae (CABP), hospital-acquired pneumonia (HAP), hospital-acquired bacterial pneumonia, ventilator-associated pneumonia (VAP), diabetic foot infections, vancomycin resistant enterococci infections, cystitis and pyelonephritis, renal calculi, prostatitis, peritonitis, complicated intra-abdominal infections (cIAI) and other inter-abdominal infections, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, an infection in cystic fibrosis patients or an infection of febrile neutropenic patients.

Furthermore, the invention relates to the use of a compound of formula (I) for the treatment and/or prophylaxis of bacterial infection. The invention relates to the use of a compound of formula (I) for the preparation of a medicament for the treatment and/or prophylaxis of bacterial infection. Another embodiment includes a method for the treatment or prophylaxis of bacterial infection which method comprises administering an effective amount of a compound of formula (I), or pharmaceutically acceptable salt, or enantiomer or diastereomer thereof.

BRIEF DESCRIPTION OF THE FIGURE

FIGURE. Crystal analysis of Example 3.01A

EXAMPLES

The invention will be more fully understood by reference to the following examples. They should not, however, be construed as limiting the scope of the invention.

ABBREVIATIONS

Abbreviations used herein are as follows:
ACN or MeCN acetonitrile
AcOK potassium acetate
$[\alpha]D_{20}$ optical rotation at 20 degrees Celsius
$B_2Pin_2$ Bis(pinacolato)diboron
BINAP 2,2'-Bis(diphenylphosphino)-1,1'-binaphthalene
BOMCl benzylchloromethyl ester
CAMHB Caution-Adjusted Mueller Hinton Broth
calc'd calculated
$CC_{50}$ concentration results in the death of 50 percent of the cells
CL clearance
Ct cycle threshold
d day
DBU 1,8-Diazabicyclo[5.4.0]undec-7-ene
DCM dichloromethane
DHP dihydropyran
DIAD diisopropyl azodicarboxylate
DIPEA N,N-diisopropylethylamine
EDTA-k2 edathamil
EtOAc or EA ethyl acetate
FA formic acid
h(s) or hr(s) hour
HATU: 1-[Bis(dimethylamino)methylene]-1H-1,2,3-triazolo[4,5-b]pyridinium 3-oxid hexafluorophosphate
HPLC: high performance liquid chromatography
HPLC-UV: high performance liquid chromatography with ultraviolet detector
IV intravenous
LAH lithium aluminum hydride
LDA lithium diisopropylamide
NADPH nicotinamide adenine dinucleotide phosphate
MIC minimum inhibitory concentration
OD optical density
Pd-Ad$_2$nBuP Biphenyl Chloro[(di(1-adamantyl)-N-butylphosphine)-2-(2-aminobiphenyl)]palladium(II)
PE petroleum ether
PBS phosphate buffered saline
Precat precatalyst
prep-HPLC preparative high performance liquid chromatography
qPCR quantitative polymerase chain reaction
qRT-PCR quantitative real-time polymerase chain reaction
rel relative
rt room temperature
rpm revolutions per minute
SEM 2-methoxyethyl(trimethyl)silane
SFC supercritical fluid chromatography
SM starting material
TLC Thin Layer Chromatography
UV ultraviolet detector
wt weight

GENERAL EXPERIMENTAL CONDITIONS

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp $C_{18}$ (5 μm, OBD™ 30×100 mm) column.

Chiral Separation was conducted on Thar 350 preparative SFC using ChiralPak AD-10μ (200×50 mm I.D.) with mobile phase A for $CO_2$ and B for ethanol. LC/MS spectra were obtained using a Waters UPLC-SQD Mass. Standard LC/MS conditions were as follows (running time: 3 minutes):

Acidic condition: A: 0.1% formic acid and 1% acetonitrile in $H_2O$; B: 0.1% formic acid in acetonitrile;

Basic condition: A: 0.05% $NH_3$—$H_2O$ in $H_2O$; B: acetonitrile.

Mass spectra (MS): generally only ions which indicate the parent mass are reported, and unless otherwise stated the mass ion quoted is the positive mass ion $(M+H)^+$.

NMR Spectra were obtained using Bruker Avance 400 MHz.

All reactions involving air-sensitive reagents were performed under an argon atmosphere. Reagents were used as received from commercial suppliers without further purification unless otherwise noted.

PREPARATIVE EXAMPLES

Intermediate A1 tert-Butyl N-(3,4-dichloro-6-fluoro-9H-pyrido[2,3-b]indol-8-yl)-N-methyl-carbamate

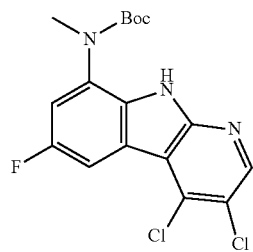 [SMILES: CN(C(=O)OC(C)(C)C)c1cc(F)cc2c1[nH]c1ncc(Cl)c(Cl)c12]

The titled compound was synthesized according to the following scheme:

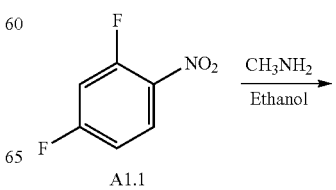

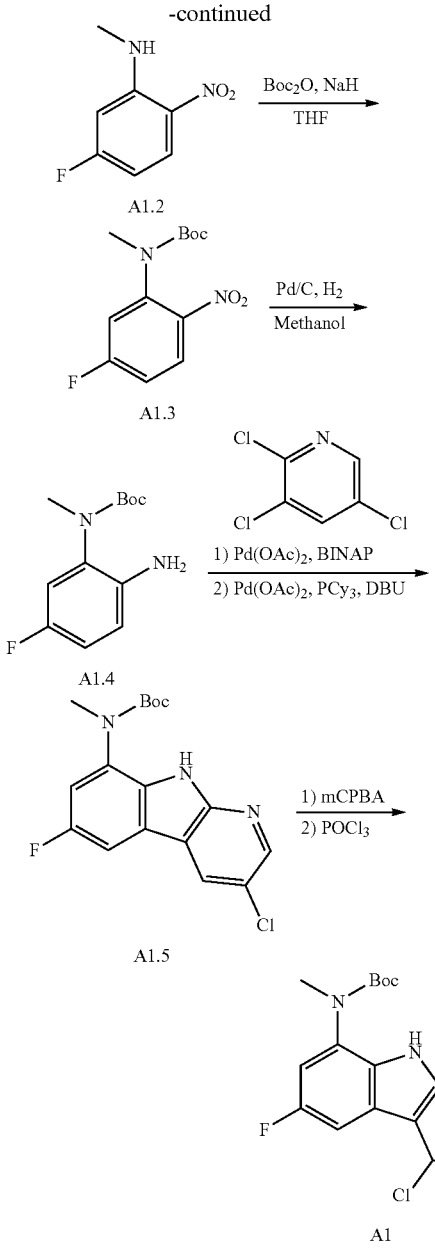

Step (a) Preparation of
5-Fluoro-N-methyl-2-nitro-aniline (Compound
A1.2)

Methylamine solution (355 g, 2.866 mol, 25% in ethanol) was added dropwise to 2,4-difluoronitrobenzene (147 g, 0.924 mol) at 0° C. over 15 min. After completion of the addition, the reaction mixture was stirred at 0° C. for 2 h. The solution was diluted with ethanol (500 mL) and poured into 2 L of ice-water. The resulting precipitates were collected by filtration and dried in vacuo to give 5-fluoro-N-methyl-2-nitro-aniline (143 g, 63% yield) as a yellow solid.

Step (b) Preparation of tert-Butyl N-(5-fluoro-2-nitro-phenyl)-N-methyl-carbamate (Compound A1.3)

To the suspension of sodium hydride (141 g, 3.5 mol, 60% dispersion in mineral oil) in dry tetrahydrofuran (2.0 L) was added 5-fluoro-N-methyl-2-nitro-aniline (60 g, 0.35 mol, compound A1.2) portion wise at 0° C. The solution was stirred at 0° C. for 1 h. Then the solution of di-tert-butyl dicarbonate (115 g, 0.53 mol) in tetrahydrofuran (0.5 L) was added dropwise and the reaction continued for another 15 h at 15° C. The reaction mixture was poured into 1.6 L of ice-water and extracted with EtOAc (1.6 L) two times. The combined organic layer was dried over sodium sulfate and concentrated in vacuo. The crude product was purified by flash chromatography (silica gel, 1-5% ethyl acetate in petroleum ether) to give tert-butyl N-(5-fluoro-2-nitro-phenyl)-N-methyl-carbamate (70 g, 73% yield) as a yellow solid. MS (ESI): 293.0 ([M+Na]$^+$), 171.0 ([M-C$_4$H$_8$—CO$_2$+H]$^+$).

Step (c) Preparation of tert-Butyl N-(2-amino-5-fluoro-phenyl)-N-methyl-carbamate (Compound A1.4)

To the solution of tert-butyl N-(5-fluoro-2-nitro-phenyl)-N-methyl-carbamate (70.0 g, 259 mmol, compound A1.3) in methanol (1.0 L) was added palladium on carbon (5.0 g, 10 wt. % loading). The reaction mixture was stirred at 16° C. for 18 h under H$_2$ atmosphere (50 psi). The remaining palladium catalyst was removed by filtration. The filtrate was concentrated in vacuo to give tert-butyl N-(2-amino-5-fluoro-phenyl)-N-methyl-carbamate (60 g, 96% yield) as a white solid. MS (ESI): 263.1 ([M+Na]$^+$), 185.0 ([M-C$_4$H$_8$+H]$^+$), 141.0 ([M-C$_4$H$_8$—CO$_2$+H]$^+$).

Step (d) Preparation of tert-Butyl N-(3-chloro-6-fluoro-9H-pyrido[2,3-b]indol-8-yl)-N-methyl-carbamate (Compound A1.5)

To the solution of tert-butyl N-(2-amino-5-fluoro-phenyl)-N-methyl-carbamate (80.0 g, 333 mmol, compound A1.4) and 2,3,5-trichloropyridine (66.8 g, 366 mmol, CAS: 16063-70-0) in dioxane (2.0 L) were added cesium carbonate (217 g, 666 mmol), palladium(II) acetate (3.74 g, 16.7 mmol), and BINAP (20.7 g, 33.3 mmol, CAS: 98327-87-8). Reaction continued at 120° C. for 16 h under nitrogen atmosphere. Then the reaction mixture was cooled to room temperature and diluted with EtOAc (800 mL). The precipitate was removed by filtration. The filtrate was concentrated in vacuo and the residue was purified by flash chromatography (silica gel, 0.2% to 5% EtOAc in petroleum ether) to give tert-butyl N-[2-[(3,5-dichloro-2-pyridyl)amino]-5-fluoro-phenyl]-N-methyl-carbamate (75 g, 58% yield). MS (ESI): 390.1 ([{$^{37}$Cl}M+H]$^+$), 388.1 ([{$^{37}$Cl+$^{35}$Cl}M+H]$^+$), 386.1 ([{$^{35}$Cl}M+H]$^+$).

To the solution of tert-butyl N-[2-[(3,5-dichloro-2-pyridyl)amino]-5-fluoro-phenyl]-N-methyl-carbamate (5.0 g, 12.95 mmol) and DBU (3.94 g, 25.9 mmol, CAS: 6674-22-2) in the mixture of o-xylene (7.5 mL) and N,N-Dimethylacetamide (7.5 mL) were added palladium(II) acetate (727 mg, 3.24 mmol) and tricyclohexylphosphine tetrafluoroborate (2.38 g, 6.48 mmol) under nitrogen atmosphere. The reaction mixture was stirred at 160° C. for 6 h, then cooled to room temperature and poured into water (100 mL). Then the mixture was extracted with EtOAc (200 mL) and the organic layer was collected and washed with water (50 mL) two times and brine (30 mL) two times, dried over sodium sulfate. The organic layer was concentrated in vacuo and the residue was purified by flash chromatography (silica gel, 0.5% to 20% EtOAc in dichloromethane) to give tert-butyl N-(3-chloro-6-fluoro-9H-pyrido[2,3-b]indol-8- yl)-N-methyl-carbamate (873 mg, 19.3% yield) as a yellow solid. MS (ESI): 352.1 ([{$^{37}$Cl}M+H]$^+$), 350.1 ([{$^{35}$Cl}M+H]$^+$).

Step (e) Preparation of tert-Butyl N-(3,4-dichloro-6-fluoro-9H-pyrido[2,3-b]indol-8-yl)-N-methyl-carbamate (Intermediate A1)

To the solution of tert-butyl N-(3-chloro-6-fluoro-9H-pyrido[2,3-b]indol-8-yl)-N-methyl-carbamate (4.8 g, 13.7 mmol, compound A1.5) in dichloromethane (200 mL) was added 3-chloroperbenzoic acid (9.47 g, 54.9 mmol) at 0° C. under nitrogen atmosphere. Reaction continued at 30° C. for 12 h. The reaction mixture was poured into sodium sulfite aqueous solution (10%, 150 mL) and stirred for 1 h followed by extraction with ethyl acetate (750 mL) three times. The combined organic layer was washed by sodium bicarbonate aqueous solution (5N, 200 mL) and brine (250 mL), then dried over sodium sulfate and concentrated in vacuo to give tert-butyl N-(3-chloro-6-fluoro-1-oxido-9H-pyrido[2,3-b]indol-1-ium-8-yl)-N-methyl-carbamate (4.8 g, 96% yield) as a brown solid. MS (ESI): 368.1 ([{$^{37}$Cl}M+H]$^+$), 366.1 ([{$^{35}$Cl}M+H]$^+$).

To the solution of tert-butyl N-(3-chloro-6-fluoro-1-oxido-9H-pyrido[2,3-b]indol-1-ium-8-yl)-N-methyl-carbamate (4.8 g, 13.1 mmol) in dimethylformamide (100 mL) was added phosphorus(V) oxychloride (22.1 g, 144 mmol) dropwise at −5° C. The mixture was stirred at −5° C. to 0° C. for 1 h then poured into sodium bicarbonate aqueous solution (saturated, 350 mL) at 0° C. The mixture was extracted by EtOAc (500 mL) three times and the combined organic layer was washed with water (200 mL) three times and brine (150 ml) two times, dried over sodium sulfate and concentrated in vacuo. The crude product was washed with methanol (120 mL) to give tert-butyl N-(3,4-dichloro-6-fluoro-9H-pyrido[2,3-b]indol-8-yl)-N-methyl-carbamate (2.16 g, 42.9% yield) as a pale yellow solid. MS (ESI): 388.1 ([{$^{37}$Cl+$^{37}$Cl}M+H]$^+$), 386.1 ([{$^{37}$Cl+$^{35}$Cl}M+H]$^+$), 384.1 ([{$^{35}$Cl+$^{35}$Cl}M+H]$^+$). $^1$H NMR (400 MHz, DMSO-d$^6$) δppm: 12.55 (s, 1H), 8.65 (s, 1H), 8.05 (d, J=7.0 Hz, 1H) 7.49 (dd, J=10.3, 2.5 Hz, 1H) 3.26 (s, 3H) 1.19-1.62 (m, 9H).

Intermediate A2 tert-Butyl N-(3,4-dichloro-6-fluoro-9H-pyrido[2,3-b]indol-8-yl)-N-ethyl-carbamate

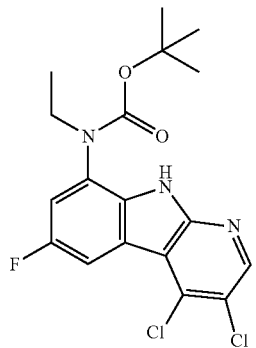 [SMILES: CCN(C(=O)OC(C)(C)C)c1cc(F)cc2c1[nH]c1ncc(Cl)c(Cl)c12]

tert-Butyl N-(3,4-dichloro-6-fluoro-9H-pyrido[2,3-b]indol-8-yl)-N-ethyl-carbamate (Intermediate A2) was prepared in analogy to Intermediate A1, by replacing methylamine solution with ethylamine solution (30% in ethanol) in step (a). MS (ESI): 402.0 ([{$^{37}$Cl+$^{37}$Cl}M+H]$^+$), 400.0 ([{$^{37}$Cl+$^{35}$Cl}M+H]$^+$), 398.0 ([{$^{35}$Cl+$^{35}$Cl}M+H]$^+$). $^1$H NMR (400 MHz, DMSO-d$^6$) δ ppm: 12.57 (s, 1H), 8.65 (s, 1H), 8.08 (d, 1H) 7.42 (m, 1H) 3.67 (br, 2H) 1.06-1.51 (m, 12H).

Intermediate A3 tert-Butyl N-(3,4-dichloro-5,6-difluoro-9H-pyrido[2,3-b]indol-8-yl)-N-methyl-carbamate

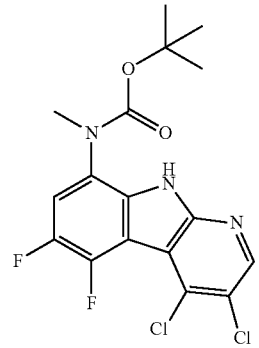 [SMILES: CN(C(=O)OC(C)(C)C)c1cc(F)c(F)c2c1[nH]c1ncc(Cl)c(Cl)c12]

tert-Butyl N-(3,4-dichloro-5,6-difluoro-9H-pyrido[2,3-b]indol-8-yl)-N-methyl-carbamate (Intermediate A3) was prepared in analogy to Intermediate A1, by replacing 2,4-difluoronitrobenzene with 2,4,5-trifluoronitrobenzene in step (a). MS (ESI): 406.1 ([{$^{37}$Cl+$^{37}$Cl}M+H]$^+$), 404.1 ([{$^{37}$Cl+$^{35}$Cl}M+H]$^+$), 402.1 ([{$^{35}$Cl+$^{35}$Cl}M+H]$^+$). $^1$H NMR (400 MHz, DMSO-d$^6$) δ ppm: 12.84 (br. s, 1H), 8.64 (s, 1H), 7.70 (m, 1H), 3.22 (s, 3H), 1.22-1.50 (m, 9H).

Intermediate A4 tert-Butyl N-(3,4-dichloro-6,7-difluoro-9H-pyrido[2,3-b]indol-8-yl)-N-methyl-carbamate

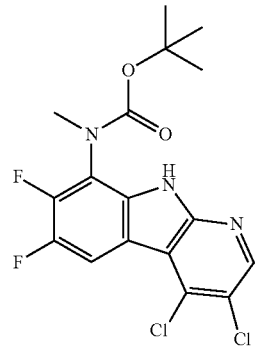 [SMILES: CN(C(=O)OC(C)(C)C)c1c(F)c(F)cc2c1[nH]c1ncc(Cl)c(Cl)c12]

tert-Butyl N-(3,4-dichloro-6,7-difluoro-9H-pyrido[2,3-b]indol-8-yl)-N-methyl-carbamate (Intermediate A4) was prepared in analogy to Intermediate A1, by replacing 2,4-difluoronitrobenzene with 2,3,4-trifluoronitrobenzene in step (a). MS (ESI): 406.2 ([{$^{37}$Cl+$^{37}$Cl}M+H]$^+$), 404.2 ([{$^{37}$Cl+$^{35}$Cl}M+H]$^+$), 402.1 ([{$^{35}$Cl+$^{35}$Cl}M+H]$^+$). $^1$H NMR (400 MHz, DMSO-d$^6$) δ ppm: 12.61 (br. s, 1H), 8.59 (s, 1H), 8.26 (m, 1H), 3.04 (s, 3H), 1.22-1.50 (m, 9H).

Intermediate A5 tert-Butyl N-methyl-N-(3,4,7-trichloro-6-fluoro-9H-pyrido[2,3-b]indol-8-yl)carbamate

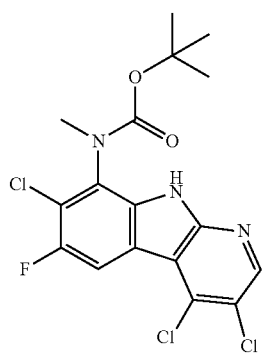 [SMILES: CN(C(=O)OC(C)(C)C)c1c(Cl)c(F)cc2c1[nH]c1ncc(Cl)c(Cl)c12]

tert-Butyl N-methyl-N-(3,4,7-trichloro-6-fluoro-9H-pyrido[2,3-b]indol-8-yl)carbamate (Intermediate A5) was prepared in analogy to Intermediate A1, by replacing 2,4-difluoronitrobenzene with 3-chloro-2,4-Difluoronitrobenzene in step (a). MS (ESI): 420.0 ([{$^{37}$Cl+$^{35}$Cl+$^{35}$Cl}M+H]$^+$), 418.0 ([{$^{35}$Cl+$^{35}$Cl+$^{35}$Cl}M+H]$^+$).

Intermediate A6 tert-Butyl N-(3,4-dichloro-5,6-difluoro-9H-pyrido[2,3-b]indol-8-yl)-N-(trideuteriomethyl)carbamate

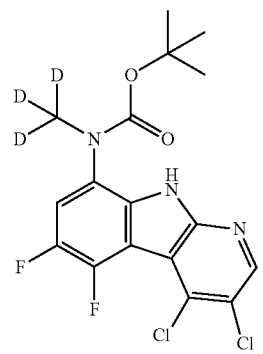 [SMILES: [2H]C([2H])([2H])N(C(=O)OC(C)(C)C)c1cc(F)c(F)c2c1[nH]c1ncc(Cl)c(Cl)c12]

tert-Butyl N-(3,4-dichloro-5,6-difluoro-9H-pyrido[2,3-b]indol-8-yl)-N-(trideuteriomethyl)carbamate (Intermediate A6) was prepared in analogy to Intermediate A1, by replacing 2,4-difluoronitrobenzene with 2,4,5-trifluoronitrobenzene, methylamine solution with methyl-d3-amine hydrochloride in step (a) and by adding 3 equivalents of DIPEA, and reacting at 30° C. for 15 h. MS (ESI): 407.1 ([{$^{37}$Cl+$^{35}$Cl}M+H]$^+$), 405.1 ([{$^{35}$Cl+$^{35}$Cl}M+H]$^+$).

Intermediate A7 tert-Butyl (3,4-dichloro-5,6-difluoro-9H-pyrido[2,3-b]indol-8-yl)(ethyl)carbamate

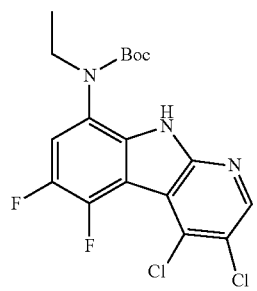

tert-Butyl (3,4-dichloro-5,6-difluoro-9H-pyrido[2,3-b]indol-8-yl)(ethyl)carbamate (Intermediate A7) was prepared in analogy to Intermediate A1, by replacing 2,4-difluoronitrobenzene with 2,4,5-trifluoronitrobenzene, methylamine solution with ethylamine solution (30% in ethanol) in step (a) $^1$H NMR (400 MHz, DMSO-d6) δ: 12.86 (br. s, 1H), 8.66 (s, 1H), 7.65 (dd, J=11.54, 6.78 Hz, 1H), 3.44~3.90 (m, 2H), 0.86~1.75 (m, 12H). MS (ESI): 416.1 ({$^{35}$Cl}M+H)$^+$, 418.1 ({$^{37}$Cl}M+H)+, 438.1 ({$^{35}$Cl}M+Na)$^+$.

Intermediate A8 tert-Butyl (3,4-dichloro-5,7-difluoro-9H-pyrido[2,3-b]indol-8-yl)(methyl)carbamate

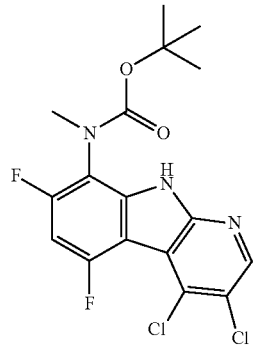 [SMILES: CN(C(=O)OC(C)(C)C)c1c(F)cc(F)c2c1[nH]c1ncc(Cl)c(Cl)c12]

tert-Butyl (3,4-dichloro-5,7-difluoro-9H-pyrido[2,3-b]indol-8-yl)(methyl)carbamate (Intermediate A8) was prepared in analogy to Intermediate A1, by replacing 2,4-difluoro-1-nitrobenzene with 1,2,5-trifluoro-3-nitrobenzene in step (a). MS (ESI): 402.0 ([{$^{37}$Cl+$^{37}$Cl}M+H]$^+$).

Intermediate A9 tert-Butyl methyl(3,4,5-trichloro-6-fluoro-9H-pyrido[2,3-b]indol-8-yl)carbamate

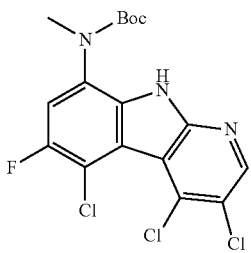 [SMILES: CN(C(=O)OC(C)(C)C)c1cc(F)c(Cl)c2c1[nH]c1ncc(Cl)c(Cl)c12]

The titled compound was synthesized according to the following scheme:

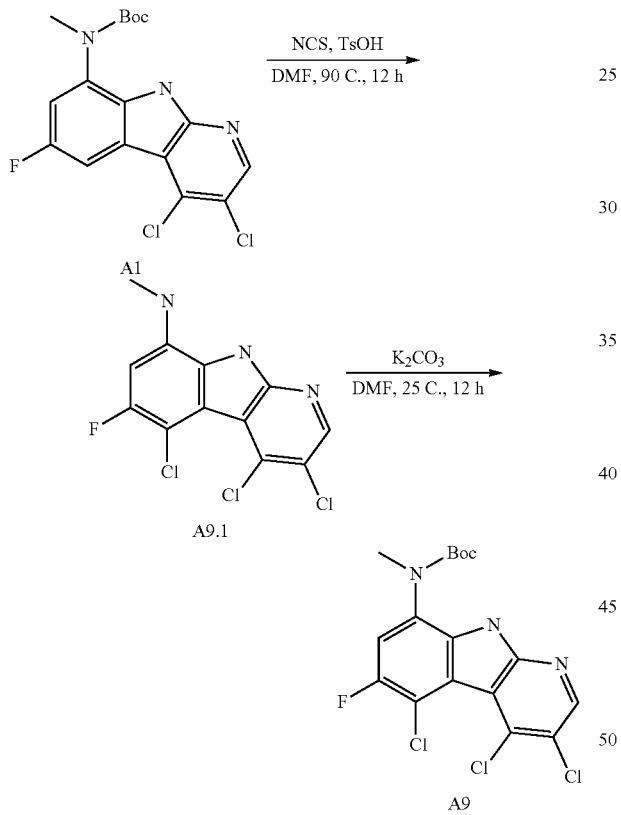

Step (a) Preparation of 3,4,5-trichloro-6-fluoro-N-methyl-9H-pyrido[2,3-b]indol-8-amine (Compound A9.1)

To a stirred solution of tert-butyl (3,4-dichloro-6-fluoro-9H-pyrido[2,3-b]indol-8-yl)(methyl)carbamate (Intermediate A1, 5.0 g, 13.02 mmol) in DMF (150.0 mL) was added 1-chloropyrrolidine-2,5-dione (2.27 g, 39.06 mmol) and 4-methylbenzenesulfonic acid (4.48 mg, 26.04 mmol). The mixture was stirred at 90° C. for 12 h until LCMS showed the starting material was completely consumed. The reaction mixture was cooled back to r.t., and concentrated in vacuo. The crude product was purified by silica gel flash chromatography (petroleum ether:EtOAc=10:1~1:1) to give 3,4,5-trichloro-6-fluoro-N-methyl-9H-pyrido[2,3-b]indol-8-amine (3.0 g; yield: 71.9%) as a yellow solid. MS (ESI): 319.9 (M+H]$^+$).

Step (b) Preparation of tert-butyl methyl(3,4,5-trichloro-6-fluoro-9H-pyrido[2,3-b]indol-8-yl)carbamate (Intermediate A9)

To a stirred solution of 3,4,5-trichloro-6-fluoro-N-methyl-9H-pyrido[2,3-b]indol-8-amine (3.0 g, 9.416 mmol) and K$_2$CO$_3$ (6.5 g, 47.08 mmol) in DMF (60.0 mL) was added di-tert-butyl dicarbonate (6.2 g, 28.25 mmol). The mixture was stirred at 25° C. for 12 h until TLC (petroleum ether:EtOAc=10:1) and LCMS showed the starting material was consumed completely. The reaction mixture was concentrated in vacuo and residue was purified by silica gel flash chromatography (petroleum ether:EtOAc=20:1~10:1) to give tert-butyl methyl(3,4,5-trichloro-6-fluoro-9H-pyrido[2,3-b]indol-8-yl)carbamate (2.1 g; 53.8% yield) as a yellow solid. MS (ESI): 418.0 ([$^{35}$Cl]M+H]$^+$), 317.9 {M-56}+H]$^+$). $^1$H NMR (400 MHz, DMSO-d$_6$) δ ppm 9.75 (s, 1H), 8.59 (s, 1H), 7.27-7.30 (m, 1H), 3.37 (s, 3H), 1.43 (m, 9H).

Intermediate A10 tert-Butyl (3,4-dichloro-6-(trifluoromethyl)-9H-pyrido[2,3-b]indol-8-yl)(ethyl)carbamate

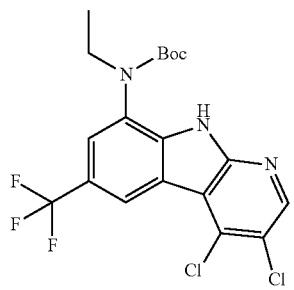 [SMILES: CCN(C(=O)OC(C)(C)C)c1cc(C(F)(F)F)cc2c1[nH]c1ncc(Cl)c(Cl)c12]

tert-Butyl (3,4-dichloro-6-(trifluoromethyl)-9H-pyrido[2,3-b]indol-8-yl)(ethyl)carbamate (Intermediate A10) was prepared in analogy to Intermediate A1, by replacing 2,4,5-trifluoronitrobenzene with 2-fluoro-1-nitro-4-(trifluoromethyl)benzene, methylamine solution with ethanamine solution in step (a). MS (ESI): 448.0 ([$^{35}$Cl]M+H]$^+$), 450.0 ([$^{37}$Cl]M+H]$^+$), 392.0 {M-56}+H]$^+$).

$^1$H NMR (400 MHz, DMSO-d6) δ ppm 12.96 (br s, 1H), 8.69~8.74 (m, 1H), 8.71 (s, 1H), 8.57 (s, 1H), 7.74 (s, 1H), 3.53~3.97 (m, 2H), 1.40~1.61 (m, 3H), 1.02~1.26 (m, 9H).

Intermediate A12 tert-Butyl (3-bromo-4-chloro-5,6-difluoro-9H-pyrido[2,3-b]indol-8-yl)(methyl)carbamate

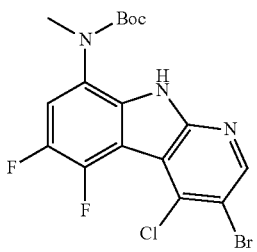 [SMILES: CN(C(=O)OC(C)(C)C)c1cc(F)c(F)c2c1[nH]c1ncc(Br)c(Cl)c12]

The titled compound was synthesized according to the following scheme:

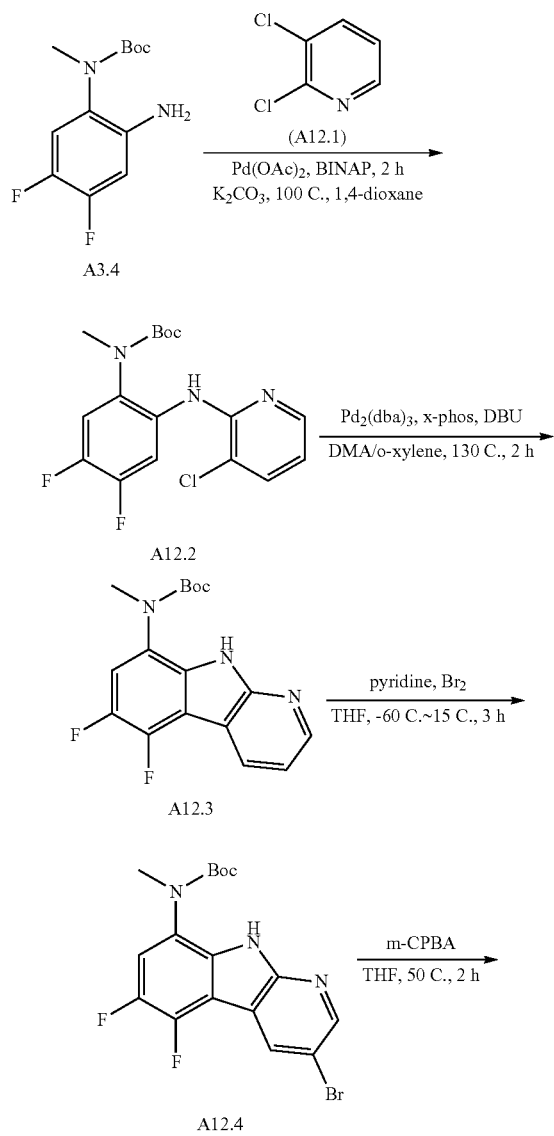

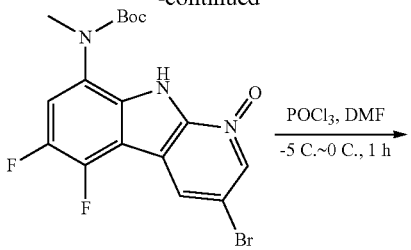

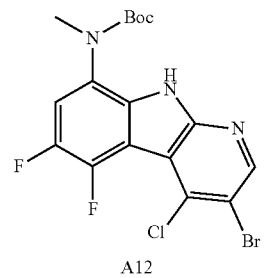

Step (a) Preparation of tert-butyl (2-((3-chloropyridin-2-yl)amino)-4,5-difluorophenyl)(methyl)carbamate (Compound A12.2)

To a stirred solution of tert-butyl (2-amino-4,5-difluorophenyl)(methyl)carbamate (142.0 g, 0.550 mol, compound A3.4) and 2,3-dichloropyridine (81.4 g, 0.550 mol, compound A12.1) in dioxane (1.5 L) was added cesium carbonate (358.6 g, 1.10 mol). The mixture was degassed with nitrogen for 2 min before palladium(II) acetate (12.3 g, 0.055 mol) and BINAP (68.5 g, 0.110 mmol, CAS: 98327-87-8) were added under nitrogen. The resulting suspension was then heated to 110° C. and stirred for 3 h. The reaction mixture was then cooled back to r.t., and diluted with EtOAc (1.0 L) and filtered. The filtrate was concentrated in vacuo to give a crude product, which was purified by silica gel flash chromatography (petroleum ether:EtOAc=500:1~20:1) to give tert-butyl (2-((3-chloropyridin-2-yl)amino)-4,5-difluorophenyl)(methyl)carbamate (175.0 g, 6.1% yield) as a white solid. MS (ESI): 370.1 ([{$^{35}$Cl}M+H]$^+$), 372.1 ([{$^{37}$Cl}M+H]$^+$).

Step (d) Preparation of tert-butyl (5,6-difluoro-9H-pyrido[2,3-b]indol-8-yl)(methyl)carbamate (Compound A12.3)

tert-Butyl (2-((3-chloropyridin-2-yl)amino)-4,5-difluorophenyl)(methyl)carbamate (175.0 g, 473.24 mmol, compound 12.2), Pd$_2$(dba)$_3$ (65.0 g, 71.0 mmol, CAS: 51364-51-3), x-phos (67.7 g, 142.0 mmol, CAS: 564483-18-7) and DBU (144.0 g, 946.5 mmol, CAS: 6674-22-2) were dissolved in a mixture solution of o-xylene/DMA (v/v=1:1, 260.0 mL). After the mixture solution was degassed with nitrogen for 5 min, it was heated at 130° C. for 3 h before cooled back to r.t. and diluted with EtOAc (500 mL). The mixture was filtered to remove part of catalyst and ligand and the filtrate was poured into water (1.0 L) and extracted with EtOAc (2.0 L) three times. The combined organic phase was washed with aq. calcium chloride solution (1N, 500 mL) four times, brine (500 mL) twice, and dried over anhy. sodium sulfate and concentrated in vacuo to give a crude product. It was then recrystallized with MeOH (800 mL) to give tert-butyl (5,6-difluoro-9H-pyrido[2,3-b]indol- 8-yl)(methyl)carbamate (110.0 g, 69.73% yield) as a white solid. The mother liquid was purified by silica gel flash chromatography (petroleum ether:EtOAc=50:1~1:1) to give additional tert-butyl (5,6-difluoro-9H-pyrido[2,3-b]indol-8-yl)(methyl)carbamate (35.0 g, yield: 22.2%) as a white solid. In total, the title compound (145.0 g, yield: 91.92%) was obtained. MS (ESI): 334.1 ([M+H]$^+$).

Step (e) Preparation of tert-butyl (3-bromo-5,6-difluoro-9H-pyrido[2,3-b]indol-8-yl)(methyl)carbamate (Compound A12.4)

To a stirred solution of tert-butyl (5,6-difluoro-9H-pyrido[2,3-b]indol-8-yl)(methyl)carbamate (140.0 g, 0.420 mol) and pyridine (166.1 g, 2.1 mol) in tetrahydrofuran (2.0 L) was added bromine (335.6 g, 2.1 mol) at −60° C. After the addition, the mixture was warmed up and stirred at 15° C. for 2 h. After LCMS showed starting material was consumed, the mixture was added dropwise into aq. sodium sulfite solution (5.0 L, 10%) and adjusted pH=8.0 with aq. sodium carbonate solution at 0° C. and stirred at 25° C. for additional 1 h. The mixture was extracted by EtOAc (2.0 L) three times. The organic layer was then washed with aq. sodium carbonate solution (1.0 L) twice and brine (1.0 L) three times. Separated organic layer was dried over anhy. sodium sulfate, filtered, and concentrated in vacuo to give a crude product which was recrystallized with MeOH (1.0 L) to give tert-butyl (3-bromo-5,6-difluoro-9H-pyrido[2,3-b]indol-8-yl)(methyl)carbamate (150.0 g, 86.6% yield) as a yellow solid. MS (ESI): 412.1 ([{$^{79}$Br}M+H]$^+$), 414.1 ([{$^{81}$Br}M+H]$^+$).

Step (f) Preparation of 3-bromo-8-((tert-butoxycarbonyl)(methyl)amino)-5,6-difluoro-9H-pyrido[2,3-b]indole 1-oxide (Compound A12.5)

To a stirred solution of tert-butyl (3-bromo-5,6-difluoro-9H-pyrido[2,3-b]indol-8-yl)(methyl)carbamate (150.0 g, 363.9 mmol, compound A12.4) in tetrahydrofuran (1.2 L) was added 3-chlorobenzoperoxoic acid (148.0 g, 727.8 mmol, 85% wt). The mixture was degassed with nitrogen for 2 min before stirred at 50° C. for 2 h. After TLC (petroleum ether:EtOAc=2:1) showed the starting material was consumed completely, the reaction was cooled back to r.t. and the mixture was poured into aq. sodium sulfite solution (6.0 L, 10%) and stirred for 1 h. The resulting precipitate was collected by filtration and washed by aq. sodium sulfite solution (1.0 L, 5%). The filter cake was evaporated to dryness under reduced pressure to give 3-bromo-8-((tert-butoxycarbonyl)(methyl)amino)-5,6-difluoro-9H-pyrido[2,3-b]indole 1-oxide (150.0 g, 96.3% yield) as a yellow solid. LCMS.MS (ESI): 428.1 ([{$^{79}$Br}M+H]$^+$), 430.1 ([{$^{81}$Br}M+H]$^+$).

Step (g) Preparation of tert-butyl (3-bromo-4-chloro-5,6-difluoro-9H-pyrido[2,3-b]indol-8-yl)(methyl)carbamate (Intermediate A12)

To a stirred solution of 3-bromo-8-((tert-butoxycarbonyl)(methyl)amino)-5,6-difluoro-9H-pyrido[2,3-b]indole 1-oxide (150 g, 0.35 mol) in dimethylformamide/tetrahydrofuran (2.5 L, v/v=1:1) was added phosphorus(V) oxychloride (421.3 g, 2.75 mol) dropwise under ice-salt baths. The mixture was stirred at −5° C.~0° C. for 4 h until TLC (petroleum ether:EtOAc=2:1) showed the starting material was consumed completely. The mixture was poured into saturated aq. solution of sodium carbonate (5.0 L) under 0° C. and extracted with EtOAc (3.0 L) twice. The combined organic layer was washed with saturated aq. solution of sodium carbonate (1.0 L) twice, aq. calcium chloride solution (1N, 1.5 L) four times, and brine (1.0 L) twice. The organic layer was dried over anhy. sodium sulfate, filtered, and concentrated in vacuo to give a crude product, which was recrystallized with MeOH (1.2 L) to give tert-butyl (3-bromo-4-chloro-5,6-difluoro-9H-pyrido[2,3-b]indol-8-yl)(methyl)carbamate (142.0 g, yield: 90.76%) as a white solid. $^1$H NMR (400 MHz, DMSO-d6) δ: 12.85 (br. s., 1H), 8.75 (s, 1H), 7.69~7.74 (dd, J=11.6, 6.8 Hz, 1H), 3.22 (s, 3H), 1.22~1.50 (m, 9H). MS (ESI): 446.0 ([{$^{79}$Br} M+H]$^+$), 448.0 ([{$^{81}$Br} M+H]$^+$).

Intermediate A13 tert-Butyl N-(4-chloro-6-fluoro-3-iodo-9H-pyrido[2,3-b]indol-8-yl)-N-methyl-carbamate

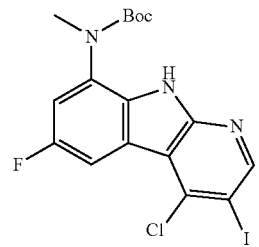 [SMILES: CN(C(=O)OC(C)(C)C)c1cc(F)cc2c1[nH]c1ncc(I)c(Cl)c12]

The titled compound was synthesized according to the following scheme:

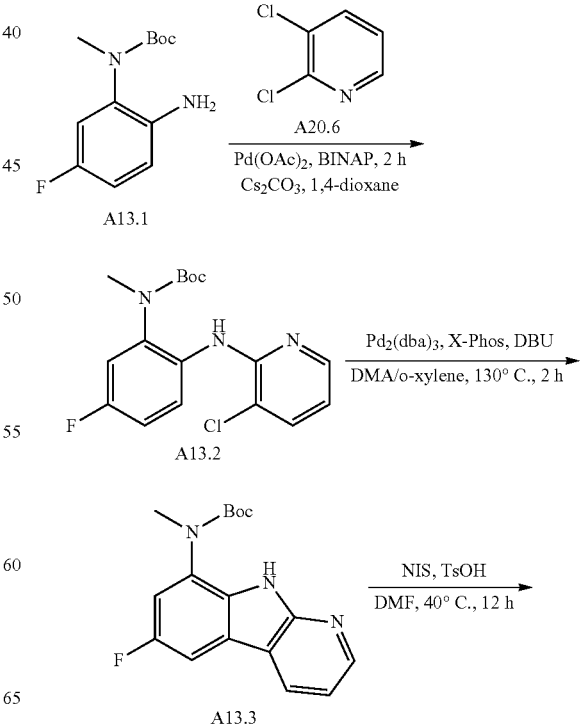

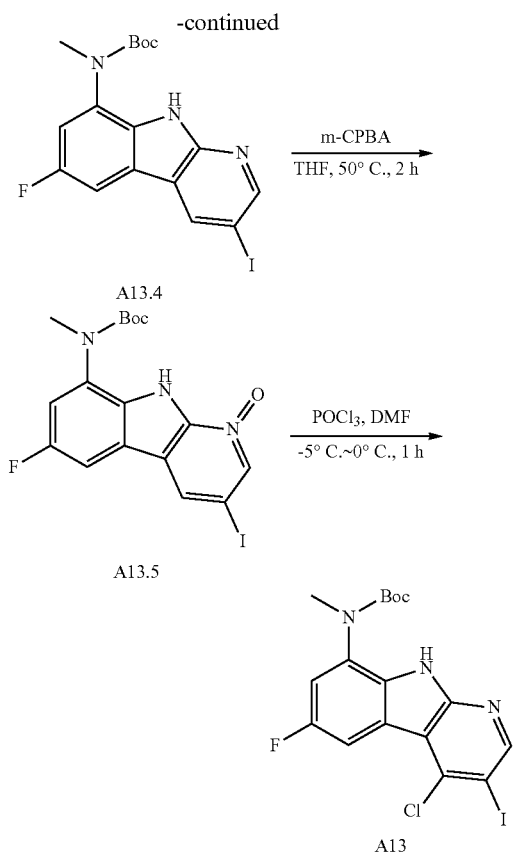

Step (a) Preparation of tert-butyl (2-((3-chloropyridin-2-yl)amino)-5-fluorophenyl)(methyl)carbamate (Compound A13.2)

To a solution of tert-butyl (2-amino-5-fluorophenyl)(methyl)carbamate (24.0 g, 99.9 mol, compound A1.4) and 2,3-dichloropyridine (13.3 g, 89.9 mmol) in dioxane (500.0 mL) was added cesium carbonate (65.0 g, 199.8 mmol). The mixture was degassed with nitrogen for 2 min followed by the addition of palladium(II) acetate (2.24 g, 9.99 mmol) and BINAP (12.8 g, 19.98 mmol, CAS: 98327-87-8) under nitrogen. Afterwards, the suspension was heated to 100° C. and stirred for 3 h. After LCMS showed the starting material was consumed completely, the reaction mixture was cooled down to room temperature and diluted with EtOAc (2.0 L) and filtered. The filtrate was concentrated in vacuo to give a crude product, which was purified by silica gel flash chromatography (petroleum ether:EtOAc=500:1~20:1) to give tert-butyl (2-((3-chloropyridin-2-yl)amino)-5-fluorophenyl)(methyl)carbamate (16.0 g, 78.4% yield) as a yellow solid. MS (ESI): 296.0 ([$\{^{35}Cl\}$M-t-Bu+H]$^+$), 252.0 ([$\{^{35}Cl\}$M-Boc+H]$^+$), 374.0 ([$\{^{35}Cl\}$M+Na]$^+$).

Step (b) Preparation of tert-butyl (6-fluoro-9H-pyrido[2,3-b]indol-8-yl)(methyl)carbamate (Compound A13.3)

A mixture of tert-butyl (2-((3-chloropyridin-2-yl)amino)-5-fluorophenyl)(methyl)carbamate (22.8 g, 64.77 mmol), Pd$_2$(dba)$_3$ (11.9 g, 12.95 mmol, CAS: 51364-51-3), x-phos (12.4 g, 25.91 mmol, CAS: 564483-18-7) and DBU (19.7 g, 129.5 mmol, CAS: 6674-22-2) were dissolved in a mixed solution of o-xylene/N,N-Dimethylacetamide (v/v=1:1, 40.0 mL). The mixture solution was degassed with nitrogen for 5 min before was heated at 130° C. and stirred for 2 h. After TLC (petroleum ether/EtOAc=5:1) showed the stating material was consumed completely, the reaction mixture was cooled down to room temperature and diluted with EtOAc (200 mL) and filtered. The filtrate was poured into water (200 mL) and extracted with EtOAc (200 mL) three times. The combined organic layer was washed with aq. CaCl$_2$ solution (1 N, 200 m L×3) and brine (200 mL) twice. The organic layer was then dried over anhy. sodium sulfate, filtered, and concentrated in vacuo to give a crude product, which was recrystallized with MeOH (200 mL) to give tert-butyl (6-fluoro-9H-pyrido[2,3-b]indol-8-yl)(methyl)carbamate (16.0 g, 78.4% yield) as a yellow solid. MS (ESI): 316.0 ([$\{^{35}Cl\}$M+H]$^+$), 260.0 ([$\{^{35}Cl\}$M-t-Bu+H]$^+$).

Step (c) Preparation of tert-butyl (6-fluoro-3-iodo-9H-pyrido[2,3-b]indol-8-yl)(methyl)carbamate (Compound A13.4)

To a solution of tert-butyl (6-fluoro-9H-pyrido[2,3-b]indol-8-yl)(methyl)carbamate (12.0 g, 38.1 mmol) in DMF (120 mL) was added N-iodosuccinimide (19.7 g, 87.5 mmol) and p-toluenesulfonic acid monohydrate (2.9 g, 15.2 mmol). The resulting reaction mixture was stirred at 40° C. for 12 h until LCMS showed the starting material was consumed completely. After cooled down to room temperature, the reaction mixture was poured into aq. Na$_2$SO$_3$ solution (10%, 500 mL) and stirred for 2 h. The mixture was then filtered, and the filter cake was washed with aq. Na$_2$SO$_3$ solution (10%, 200 mL) and water (200 mL). After trituration with MeOH (100 mL), it gave tert-butyl (6-fluoro-3-iodo-9H-pyrido[2,3-b]indol-8-yl)(methyl)carbamate (13.5 g, 78.8% yield) as a yellow solid. MS (ESI): 441.9 ([$\{^{35}Cl\}$M+H]$^+$), 385.8 ([$\{^{35}Cl\}$M-t-Bu+H]$^+$).

Step (d) Preparation of 8-((tert-butoxycarbonyl)(methyl)amino)-6-fluoro-3-iodo-9H-pyrido[2,3-b]indole 1-oxide (Compound A13.5)

To a solution of tert-butyl (6-fluoro-3-iodo-9H-pyrido[2,3-b]indol-8-yl)(methyl)carbamate (11.0 g, 24.93 mmol) in THF (120 mL) was added 3-chloroperoxyoxybenzoic acid (8.6 g, 49.86 mmol) and the resulting mixture solution was stirred at 50° C. for 2 h. After LCMS showed the starting material was consumed completely, the reaction mixture was cooled down to room temperature and poured into aq. Na$_2$SO$_3$ solution (10%, 200 mL) and stirred for 2 h. The mixture solution was then filtered, and the filter cake was washed with aq. Na$_2$SO$_3$ solution (10%, 100 mL), water (100 mL), and dried under vacuum to give 8-((tert-butoxycarbonyl)(methyl)amino)-6-fluoro-3-iodo-9H-pyrido[2,3-b]indole 1-oxide (12 g, 26.24 mmol, 85.08% yield) as a yellow solid. MS (ESI): 457.9 ([$\{^{35}Cl\}$M+H]$^+$), 401.9 ([$\{^{35}Cl\}$M-t-Bu+H]$^+$), 479.9 ([$\{^{35}Cl\}$M+Na]$^+$).

Step (e) Preparation of tert-butyl N-(4-chloro-6-fluoro-3-iodo-9H-pyrido[2,3-b]indol-8-yl)-N-methyl-carbamate (Intermediate A13)

To a solution of tert-butyl N-(6-fluoro-3-iodo-1-oxido-9H-pyrido[2,3-b]indol-1-ium-8-yl)-N-methyl-carbamate (0.15 mL, 21.2 mmol) in THF (100 mL) and N,N-dimethylformamide (100 mL) was added phosphorus oxychloride (27.3 mL, 292.9 mmol) dropwise at −5° C. After the addition, the reaction mixture was stirred at −5° C. for 3 h until LCMS showed the starting material was consumed completely. The mixture was poured into sat. aq. NaHCO$_3$ solution (1000 mL) to form a white suspension. After filtration, the filter cake was washed with satd. aq. NaHCO$_3$ solution (300 mL) and water (300 mL) to give a crude yellow product, which was purified by trituration with MeOH (100 mL) to give tert-butyl N-(4-chloro-6-fluoro-3-iodo-9H-pyrido[2,3-b]indol-8-yl)-N-methyl-carbamate (7.5 g, 52.27% yield) as a light yellow solid. MS (ESI): 476.0 ([{$^{35}$Cl}M+H]$^+$), 419.9 ([{$^{35}$Cl}M-t-Bu+H]$^+$).

Intermediate A14 tert-butyl (3-bromo-4,6-dichloro-5-fluoro-9H-pyrido[2,3-b]indol-8-yl)(methyl)carbamate

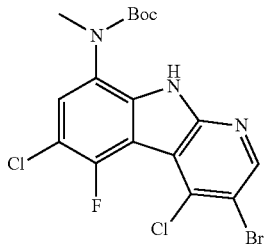 [SMILES: CN(C(=O)OC(C)(C)C)c1cc(Cl)c(F)c2c1[nH]c1ncc(Br)c(Cl)c12]

tert-butyl (3-bromo-4,6-dichloro-5-fluoro-9H-pyrido[2,3-b]indol-8-yl)(methyl)carbamate (Intermediate A14) was prepared in analogy to Intermediate A12, by replacing tert-butyl (2-amino-4,5-difluorophenyl)(methyl)carbamate with tert-butyl (2-amino-5-chloro-4-fluorophenyl)(methyl)carbamate, in step (a). MS (ESI): 464.0 ([{$^{37}$Cl+$^{35}$Cl}M+H]$^+$), 462.0 ([{$^{35}$Cl+$^{35}$Cl}M+H]$^+$). $^1$H NMR (300 MHz, CHLOROFORM-d) δ=8.72 (s, 1H), 7.42 (d, J=6.0 Hz, 1H), 3.37 (s, 3H), 1.41 (br d, 9H).

Intermediate A16 tert-Butyl (3,4-dichloro-5-cyano-6-fluoro-9H-pyrido[2,3-b]indol-8-yl)(methyl)carbamate

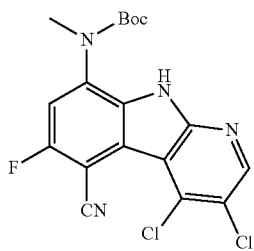 [SMILES: CN(C(=O)OC(C)(C)C)c1cc(F)c(C#N)c2c1[nH]c1ncc(Cl)c(Cl)c12]

The titled compound was synthesized according to the following scheme:

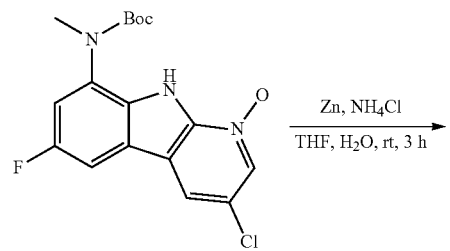
A16.1

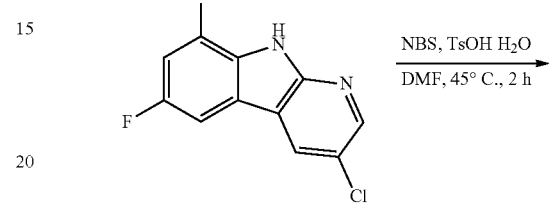
A16.2

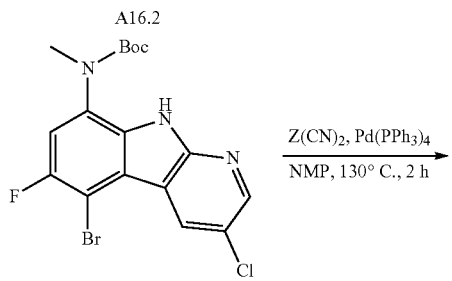
A16.3

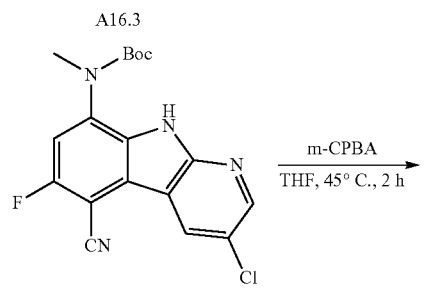
A16.4

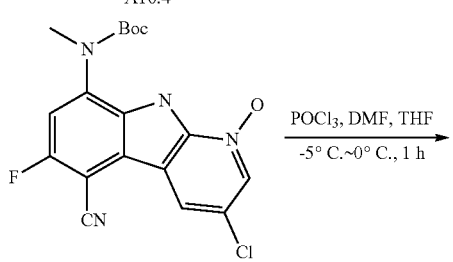
A16.5

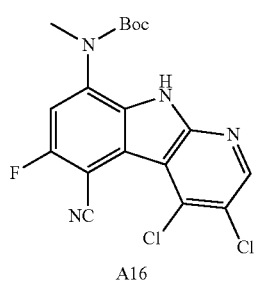
A16

Step (a) Preparation of 5-Fluoro-N-methyl-2-nitro-aniline (Compound A16.2)

To a solution of 8-((tert-butoxycarbonyl)(methyl)amino)-3-chloro-6-fluoro-9H-pyrido[2,3-b]indole 1-oxide (compound A16.1, 5.0 g, 13.67 mmol) in THF/H$_2$O (100.0 mL, v/v=8:1) was added NH$_4$Cl (5.8 g, 109.36 mmol) and Zn powder (4.47 g, 68.35 mmol), and the resulting reaction mixture was stirred at 25° C. for 3 h. After LCMS showed that the starting material was consumed completely, the reaction mixture was diluted with EtOAc (200 mL) and filtered. The filtrate was washed with brine (100 mL) three times and The combined organic layer was dried over anhy. Na$_2$SO$_4$, filtered, and concentrated in vacuo to give a crude product of tert-butyl (3-chloro-6-fluoro-9H-pyrido[2,3-b]indol-8-yl)(methyl)carbamate (4.5 g, 94.1% yield) as a white solid, which was used directly in the next step without further purification. MS (ESI): 350.2 ([$\{^{37}Cl\}$M+H]$^+$), 352.2 ([$\{^{35}Cl\}$M+H]$^+$).

Step (b) Preparation of tert-butyl (5-bromo-3-chloro-6-fluoro-9H-pyrido[2,3-b]indol-8-yl)(methyl)carbamate (Compound A16.3)

To a solution of tert-butyl (3-chloro-6-fluoro-9H-pyrido[2,3-b]indol-8-yl)(methyl)carbamate (4.5 g, 12.86 mmol) in anhydrous DMF (60.0 mL) was added NBS (4.58 g, 25.72 mmol) and TsOH.H$_2$O (1.22 g, 6.43 mmol). The reaction mixture was stirred at 45° C. for 2 h until LCMS showed the starting material was consumed completely. The reaction mixture was then poured into aq. Na$_2$SO$_3$ solution (10%, 200.0 mL) and adjusted to pH=8 with aq. Na$_2$CO$_3$ solution. The mixture was stirred at 25° C. for 0.5 h before it was extracted with EtOAc (150 mL) three times. The organic layer was washed with satd. aq. CaCl$_2$ solution (100.0 mL) four times, brine (100.0 mL) three times, dried over anhy. Na$_2$SO$_4$, filtered, and concentrated in vacuo to give a crude product. It was recrystallized with MeOH (40.0 mL) to give tert-butyl (5-bromo-3-chloro-6-fluoro-9H-pyrido[2,3-b]indol-8-yl)(methyl)carbamate (4.8 g, 87.04% yield) as a yellow solid. MS (ESI): 428.0 ([$\{^{79}Br\}$M+H]$^+$), 430.0 ([$\{^{81}Cl\}$M+H]$^+$).

Step (c) Preparation of tert-butyl (3-chloro-5-cyano-6-fluoro-9H-pyrido[2,3-b]indol-8-yl)(methyl)carbamate (Compound A16.4)

To a solution of tert-butyl (5-bromo-3-chloro-6-fluoro-9H-pyrido[2,3-b]indol-8-yl)(methyl)carbamate (1.3 g, 3.03 mmol), Zn(CN)$_2$ (1.42 g, 12.13 mmol) in NMP (10.0 mL) was added Pd(PPh$_3$)$_4$(350.0 mg, 0.303 mmol) in glovebox under argon. The resulting reaction mixture was stirred at 130° C. for 2 h under argon. After LCMS showed the starting material was consumed completely, the reaction mixture was diluted with EtOAc (200 mL) and filtered. The filtrate was washed with brine (80 mL) three times, and the organic layer was dried over anhy. Na$_2$SO$_4$, filtered, and concentrated in vacuo to give a crude product, which was recrystallized with MeOH to give tert-butyl (3-chloro-5-cyano-6-fluoro-9H-pyrido[2,3-b]indol-8-yl)(methyl)carbamate (1.0 g, 87.98% yield) as a yellow solid. MS (ESI): 375.0 ([$\{^{35}Cl\}$M+H]$^+$), 377.0 ([$\{^{37}Cl\}$M+H]$^+$).

Step (d) Preparation of 8-((tert-butoxycarbonyl)(methyl)amino)-3-chloro-5-cyano-6-fluoro-9H-pyrido[2,3-b]indole 1-oxide (Compound A16.5)

To a solution of tert-butyl (3-chloro-5-cyano-6-fluoro-9H-pyrido[2,3-b]indol-8-yl)(methyl)carbamate (1.0 g, 2.67 mmol) in THF (10.0 mL) was added m-CPBA (1.08 g, 5.34 mmol, 85% wt). The reaction mixture was degassed with nitrogen for 2 min before it was stirred at 45° C. for 2 h. After TLC (petroleum ether:EtOAc=2:1) showed the starting material was consumed completely, the reaction mixture was poured into aq. Na$_2$SO$_3$ solution (10%, 50.0 mL) and stirred for 1 h. The resulting precipitate was collected by filtration and the filter cake was washed with 5% aq. Na$_2$SO$_3$ solution (5%, 50.0 mL). The filter cake was dried under vacuum to give a crude product of 8-((tert-butoxycarbonyl)(methyl)amino)-3-chloro-5-cyano-6-fluoro-9H-pyrido[2,3-b]indole 1-oxide (1.0 g, 95.9% yield) as a yellow solid, which was used directly in the next step without further purification. MS (ESI): 391.1 ([$\{^{35}Cl\}$M+H]$^+$), 393.1 ([$\{^{37}Cl\}$M+H]$^+$).

Step (e) Preparation of tert-butyl (3,4-dichloro-5-cyano-6-fluoro-9H-pyrido[2,3-b]indol-8-yl)(methyl)carbamate (Intermediate A16)

To a solution of 8-((tert-butoxycarbonyl)(methyl)amino)-3-chloro-5-cyano-6-fluoro-9H-pyrido[2,3-b]indole 1-oxide (1.0 g, 2.56 mmol) in DMF/THF (10.0 mL, v/v=1:1) was added POCl$_3$ (4.26 g, 27.8 mmol) dropwise under ice-salt bath and the resulting reaction mixture was stirred at -5° C.~0° C. for 1 h. After TLC (petroleum ether:EtOA=2:1) and TLC showed the starting material was consumed completely, the reaction mixture was poured into satd. aq. NaHCO$_3$ solution (100 mL) at 0° C. and subsequently extracted with EtOAc (200 mL) twice. The combined organic layer was washed with satd. aq. NaHCO$_3$ solution (50.0 mL) twice, aq. CaCl$_2$ solution (1 N, 50 mL) four times and brine (50 mL) twice. The organic layer was dried over anhy. Na$_2$SO$_4$, filtered, and concentrated in vacuo to give a crude product, which was purified by silica gel flash chromatography (petroleum ether:EtOAc=100:1~2:1, 20% DCM as additive) to give tert-butyl (3,4-dichloro-5-cyano-6-fluoro-9H-pyrido[2,3-b]indol-8-yl)(methyl)carbamate (900.0 mg, 85.94% yield) as a yellow solid. MS (ESI): 409.2 ([$\{^{35}Cl\}$M+H]$^+$), 411.2 ([$\{^{37}Cl\}$M+H]$^+$).

Intermediate A17 tert-butyl (3,4-dichloro-6-fluoro-5-methoxy-9H-pyrido[2,3-b]indol-8-yl)(methyl)carbamate

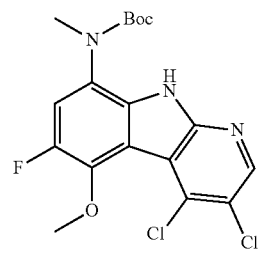 [SMILES: COc1c(F)cc(N(C)C(=O)OC(C)(C)C)c2[nH]c3ncc(Cl)c(Cl)c3c12]

The titled compound was synthesized according to the following scheme:

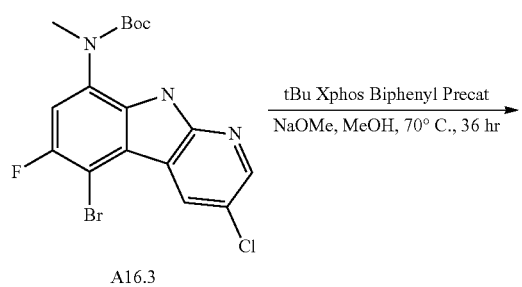

A16.3

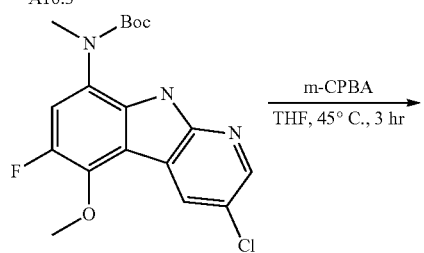

A17.1

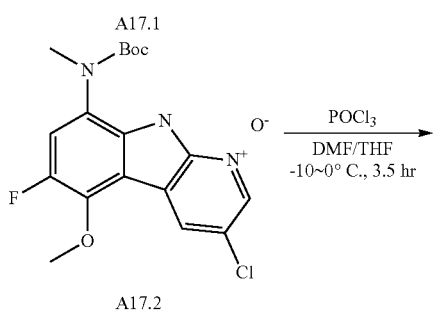

A17.2

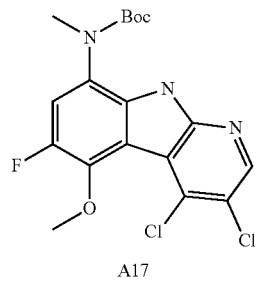

A17

Step (a) tert-butyl (3-chloro-6-fluoro-5-methoxy-9H-pyrido[2,3-b]indol-8-yl)(methyl)carbamate (Compound A17.1)

To a solution of tert-butyl (5-bromo-3-chloro-6-fluoro-9H-pyrido[2,3-b]indol-8-yl)(methyl)carbamate (850 mg, 1.98 mmol, compound A16.3) in MeOH (10 mL) was added t-Bu Xphos Biphenyl Precat (G3) (100 mg, 0.126 mmol, CAS #1447963-75-8) and NaOMe (300 mg, 5.55 mmol), then the resulting mixture was stirred at 70° C. for 36 hrs under Argon. Then the mixture was cooled to room temperature, a lot of precipitate was formed. The mixture was filtered, the filter cake was washed with H$_2$O (20 mL) and dried in vacuo to give tert-butyl (3-chloro-6-fluoro-5-methoxy-9H-pyrido[2,3-b]indol-8-yl)(methyl)carbamate (680 mg, 90.2%) as white solid. MS (ESI): 382.1 ([{$^{37}$Cl}M+H]$^+$), 380.1 ([{$^{35}$Cl}M+H]$^+$). $^1$H NMR (400 MHz, DMSO-d$^6$) δppm: 12.21 (s, 1H), 8.48 (s, 1H), 8.42 (s, 1H), 7.42 (d, J=13.6 Hz, 1H), 4.16 (s, 3H), 3.20 (d, 3H), 1.23 (s, 9H).

Step (b) 8-((tert-butoxycarbonyl)(methyl)amino)-3-chloro-6-fluoro-5-methoxy-9H-pyrido[2,3-b]indole 1-oxide (Compound A17.2)

To a mixture of tert-butyl (3-chloro-6-fluoro-5-methoxy-9H-pyrido[2,3-b]indol-8-yl) (methyl)carbamate (680 mg, 1.79 mmol, compound A17.1) in THF (10 mL) was added m-CPBA (730 mg, 3.60 mmol), then the resulting mixture was stirred at 40° C. for 3 hrs. Then the mixture was cooled to room temperature and then poured into Na$_2$SO$_3$ (aq. 10%, 100 mL), a lot of precipitate was formed. The mixture was filtered, the filter cake was washed with H$_2$O (20 mL) and dried in vacuo to give 8-((tert-butoxycarbonyl)(methyl)amino)-3-chloro-6-fluoro-5-methoxy-9H-pyrido[2,3-b]indole 1-oxide (720 mg, crude) as yellow solid which was used in the next step without any further purification. MS (ESI): 398.0 ([{$^{37}$Cl}M+H]$^+$), 36.0 ([{$^{35}$Cl}M+H]$^+$). $^1$H NMR (400 MHz, DMSO-d$^6$) δppm: 8.64 (s, 1H), 8.09 (s, 1H), 7.46-7.42 (d, J=13.6 Hz, 1H), 4.17 (s, 3H), 3.24 (s, 3H), 1.28 (s, 9H).

Step (c) tert-butyl (3,4-dichloro-6-fluoro-5-methoxy-9H-pyrido[2,3-b]indol-8-yl)(methyl)carbamate (Intermediate A17)

To a mixture of 8-((tert-butoxycarbonyl)(methyl)amino)-3-chloro-6-fluoro-5-methoxy-9H-pyrido[2,3-b]indole 1-oxide (660 mg, 1.64 mmol, compound A17.1) in THF/DMF (20.0 mL, 1/1) was added POCl$_3$ (3.02 g, 17.50 mmol) at −10~0° C., then the resulting mixture was stirred at this temperature for 3.5 hrs. The mixture was added dropwise into sat. NaHCO$_3$ (100 mL) solution, which was then extracted with EtOAc (80 mL) three times. The organic layers were dried over anhydrous Na$_2$SO$_4$, filtered and concentrated to give a crude material, which was purified by silica gel column with Petroleum Ether/EtOAc from 20/1 to 8/1 to give tert-butyl (3,4-dichloro-6-fluoro-5-methoxy-9H-pyrido[2,3-b]indol-8-yl)(methyl)carbamate (480.0 mg, purity-70%, yield: 45.3%) as yellow solid. MS (ESI): 418.1 ([{$^{37}$Cl+$^{37}$Cl}M+H]$^+$), 416.1 ([{$^{37}$Cl+$^{35}$Cl}M+H]$^+$), 414.1 ([{$^{35}$Cl+$^{35}$Cl}M+H]$^+$). $^1$H NMR (400 MHz, DMSO-d$^6$) δppm: 9.93 (s, 1H), 8.53 (s, 1H), 7.25-7.24 (d, J=13.6 Hz, 1H), 4.10 (s, 3H), 3.50 (s, 3H), 1.35 (s, 9H).

Intermediate A18 tert-butyl (3-bromo-4,5,6-trichloro-9H-pyrido[2,3-b]indol-8-yl)(methyl)carbamate

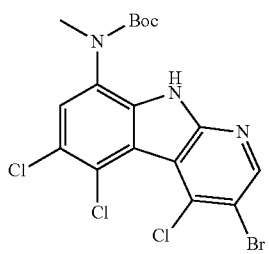 [SMILES: CN(C(=O)OC(C)(C)C)c1cc(Cl)c(Cl)c2c1[nH]c1ncc(Br)c(Cl)c12]

The titled compound was synthesized according to the following scheme:

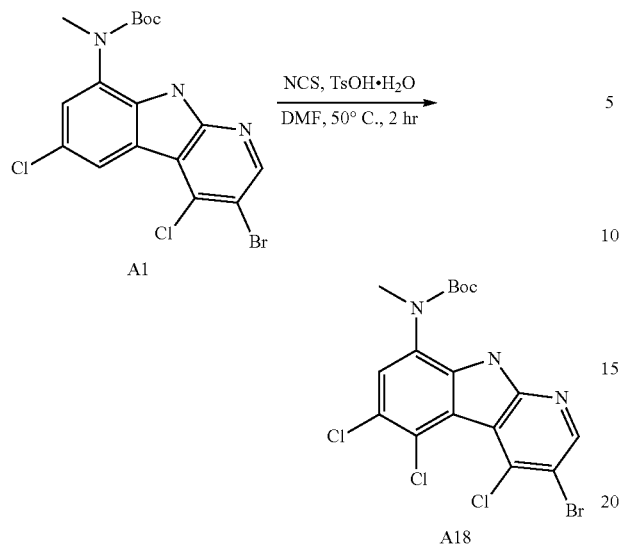

A1

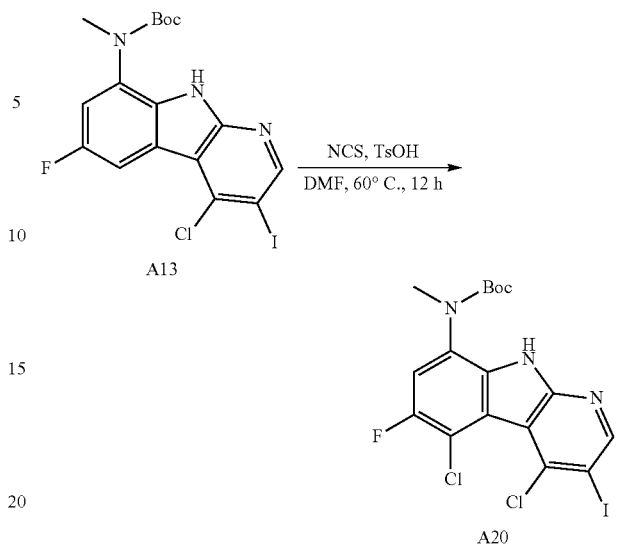

A13

A18

A20

Preparation of tert-butyl (3-bromo-4,5,6-trichloro-9H-pyrido[2,3-b]indol-8-yl)(methyl)carbamate (Intermediate A18)

To a solution of tert-butyl (3-bromo-4,6-dichloro-9H-pyrido[2,3-b]indol-8-yl)(methyl)carbamate (250.0 mg, 0.624 mmol) in DMF (6.0 mL) was added TsOH.H2O (65.0 mg, 0.342 mmol) and NCS (170.0 mg, 1.27 mmol), then the resulting mixture was stirred at 50° C. for 5 hr. Then the mixture was purified by reverse column (PR 18) with H$_2$O (0.225% TFA)-MeCN (65% MeCN in H$_2$O to 90% MeCN in H$_2$O) to give tert-butyl (3-bromo-4,5,6-trichloro-9H-pyrido[2,3-b]indol-8-yl)(methyl)carbamate (240.0 mg, 89.1%) as white solid. MS (ESI): 484.0 ([{$^{35}$Cl+$^{37}$Cl+$^{37}$Cl+$^{81}$Br}M+H]$^+$ or [{$^{37}$Cl+$^{37}$Cl+$^{37}$Cl+$^{79}$Br}M+H]$^+$), 482.0 ([{$^{35}$Cl+$^{35}$Cl+$^{37}$Cl+$^{81}$Br}M+H]$^+$ or [{$^{35}$Cl+$^{37}$Cl+$^{37}$C+$^{79}$Br}M+H]$^+$), 480.0 ([{$^{35}$Cl+$^{35}$Cl+$^{35}$Cl+$^{81}$Br}M+H]$^+$ or [{$^{35}$Cl+$^{35}$Cl+$^{37}$C+$^{79}$Br}M+H]$^+$), 478.0 ([{$^{35}$Cl+$^{35}$Cl+$^{35}$Cl+$^{79}$Br}M+H]$^+$). $^1$H NMR (400 MHz, CDCl$_3$) δppm: 9.71 (s, 1H), 8.67 (s, 1H), 7.51 (s, 1H) 3.35 (s, 3H) 1.42 (s, 9H).

Intermediate A20 tert-Butyl (4,5-dichloro-6-fluoro-3-iodo-9H-pyrido [2,3-b]indol-8-yl)(methyl)carbamate Preparation of tert-butyl (4,5-dichloro-6-fluoro-3-iodo-9H-pyrido[2,3-b]indol-8-yl)(methyl)carbamate (Intermediate A20)

To a solution of tert-butyl (4-chloro-6-fluoro-3-iodo-9H-pyrido[2,3-b]indol-8-yl)(methyl) carbamate (Intermediate A13, 3.0 g, 6.30 mmol) in DMF (90.0 mL) was added NCS (1.68 g, 12.6 mmol) and TsOH (0.975 g, 5.67 mmol). The resulting reaction mixture was stirred at 60° C. for 12 h. After LCMS showed the starting material was consumed completely, the reaction mixture was poured into aq. Na$_2$SO$_3$ solution (10%, 500 mL) and stirred for 2 h. The mixture solution was then filtered, and the filter cake was washed with aq. Na$_2$SO$_3$ solution (10%, 200 mL), water (200 mL), and triturated with MeOH (100 mL) to give a crude product. It was then purified by silica gel flash column (petroleum ether:EtOAc=3:1) to give tert-butyl (4,5-dichloro-6-fluoro-3-iodo-9H-pyrido[2,3-b]indol-8-yl) (methyl)carbamate (1.5 g, 46.9% yield) as a yellow solid. MS (ESI): 510.1. $^1$H NMR (400 MHz, DMSO-d$_6$) δ: 12.89 (br s, 1H), 8.89 (d, J=3.1 Hz, 1H), 7.69 (br d, J=10.3 Hz, 1H), 3.22 (br s, 3H), 1.21 (br s, 9H).

Intermediate B1

[8-(1,1-Dimethyl-2-pyrrolidin-1-yl-ethyl)-6-ethoxycarbonyl-5-oxo-1,8-naphthyridin-3-yl]boronic acid

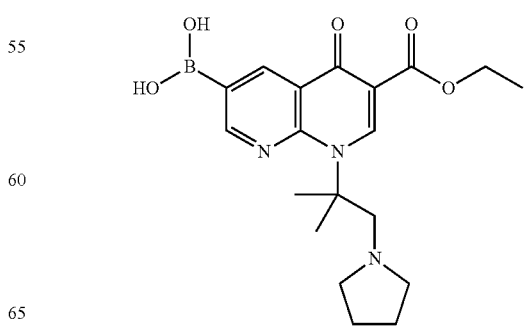

The titled compound was synthesized according to the following scheme:

The titled compound was synthesized according to the following scheme:

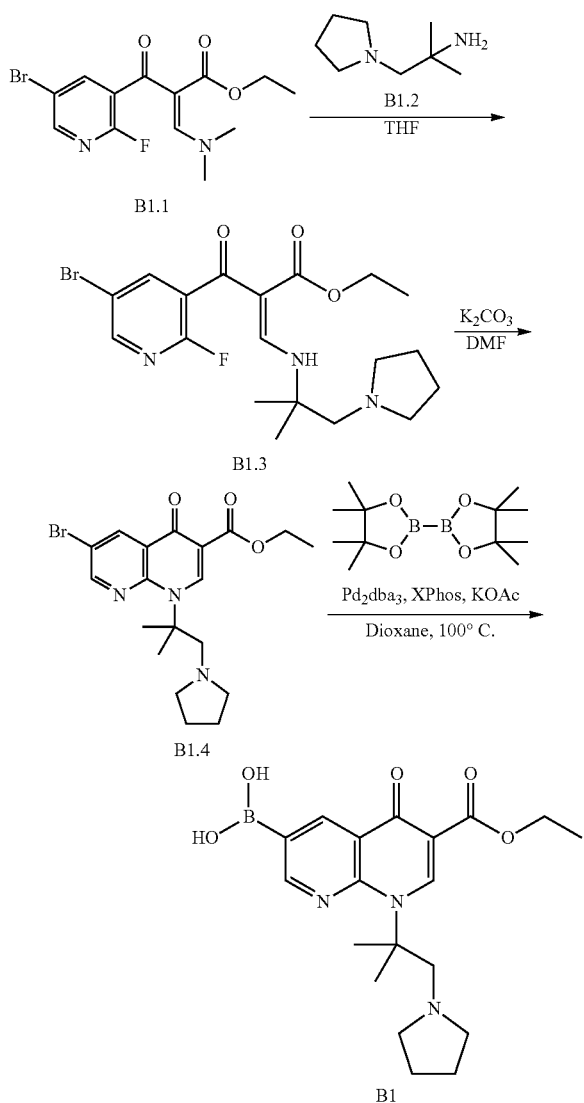

Step (a) Ethyl (Z)-2-(5-bromo-2-fluoro-pyridine-3-carbonyl)-3-(dimethylamino)prop-2-enoate (Compound B1.1)

Compound B 1.1 was prepared according to the procedure disclosed in WO 2010/136817 A1. MS (ESI): 347.0 ([{$^{81}$Br}M+H]$^+$), 345.0 ([{$^{79}$Br}M+H]$^+$ Step (b) 2-Methyl-1-pyrrolidin-1-yl-propan-2-amine (Compound B1.2)

Compound B 1.2 was prepared according to the procedure disclosed in US 2004/0176380 A1. $^1$H NMR (400 MHz, DMSO-d6) δppm: 8.00 (br. s, 2H) 2.66 (s, 3H), 2.61 (s, 3H) 1.69 (s, 4H) 1.19-1.26 (m, 6H)

Step (c) Ethyl (Z)-2-(5-bromo-2-fluoro-pyridine-3-carbonyl)-3-[(1,1-dimethyl-2-pyrrolidin-1-yl-ethyl)amino]prop-2-enoate (Compound B1.3)

A stirred solution of ethyl (Z)-2-(5-bromo-2-fluoro-pyridine-3-carbonyl)-3-(dimethylamino)prop-2-enoate (compound B1.1, 0.6 g, 1.74 mmol) and 2-methyl-1-pyrrolidin-1-yl-propan-2-amine (compound B1.2, 0.27 g, 2.09 mmol) in THF (15 mL) was heated to 70° C. and stirred for 3 h. Afterwards, the solution was cooled down to room temperature and concentrated in vacuo to give a crude product of ethyl (Z)-2-(5-bromo-2-fluoro-pyridine-3-carbonyl)-3-[(1,1-dimethyl-2-pyrrolidin-1-yl-ethyl)amino]prop-2-enoate (0.74 g, 96% yield) as yellow oil. It was then used directly in the next step without further purification. MS (ESI): 444.2 ([{$^{81}$Br}M+H]$^+$), 442.2 ([{$^{79}$Br}M+H]$^+$ Step (d) Ethyl 6-bromo-1-(1,1-dimethyl-2-pyrrolidin-1-yl-ethyl)-4-oxo-1,8-naphthyridine-3-carboxylate (Compound B1.4)

A solution of ethyl (Z)-2-(5-bromo-2-fluoro-pyridine-3-carbonyl)-3-[(1,1-dimethyl-2-pyrrolidin-1-yl-ethyl)amino]prop-2-enoate (compound B1.3, 0.74 g, 1.68 mmol) and K$_2$CO$_3$ (0.72 g, 5.21 mmol) in DMF (20 mL) was heated to 70° C. and stirred for 16 h. The reaction was then cooled to room temperature and poured into water (50 mL) and extracted with EtOAc (50 mL) twice. The combined organics was washed with brine (50 mL), dried over anhy. sodium sulfate, filtered, and concentrated in vacuo to give a crude product, which was then purified by silica gel flash chromatography (1-2% methanol in dichloromethane) to give ethyl 6-bromo-1-(1,1-dimethyl-2-pyrrolidin-1-yl-ethyl)-4-oxo-1,8-naphthyridine-3-carboxylate (210 mg, 30% yield) as a pale yellow solid. $^1$H NMR (400 MHz, CDCl$_3$) δppm: 9.00 (s, 1H), 8.93 (d, J=2.6 Hz, 1H), 8.76 (d, J=2.6 Hz, 1H), 4.44 (q, J=7.2 Hz, 2H), 3.37 (s, 2H), 2.27 (m, 4H), 1.88 (s, 6H) 1.58 (m, 4H), 1.43 (t, J=7.2 Hz, 3H). MS (ESI): 424.1 ([{$^{81}$Br}M+H]$^+$), 422.1 ([{$^{79}$Br}M+H]$^+$ Step (e) [8-(1,1-Dimethyl-2-pyrrolidin-1-yl-ethyl)-6-ethoxycarbonyl-5-oxo-1,8-naphthyridin-3-yl]boronic acid (Intermediate B1)

A mixture of ethyl 6-bromo-1-(1,1-dimethyl-2-pyrrolidin-1-yl-ethyl)-4-oxo-1,8-naphthyridine-3-carboxylate (compound B1.4, 200 mg, 0.47 mmol), bis(pinacolato)diboron (240 mg, 0.95 mmol), tris(dibenzylideneacetone)dipalladium(0) (217 mg, 0.24 mmol), XPhos (113 mg, 0.24 mmol), and potassium acetate (140 mg, 1.42 mmol) was dissolved in dioxane (3.0 mL). The solution was degassed with argon for 5 min before stirred at 100° C. for 2 h. The reaction mixture was cooled back to room temperature and precipitate was removed by filtration. The filtrate was concentrated under reduced pressure to give a crude product, which was then purified by reverse phase HPLC to give [8-(1,1-dimethyl-2-pyrrolidin-1-yl-ethyl)-6-ethoxycarbonyl-5-oxo-1,8-naphthyridin-3-yl]boronic acid as a yellow solid (80 mg, 44% yield). MS (ESI): 388.2 ([M+H]$^+$)

Intermediate B2

(6-Ethoxycarbonyl-8-methyl-5-oxo-1,8-naphthyridin-3-yl)boronic acid

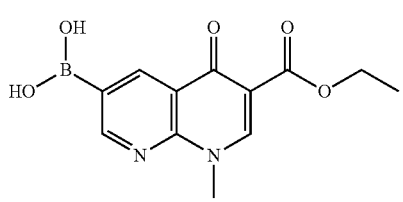 [SMILES: CCOC(=O)c1cn(C)c2ncc(B(O)O)cc2c1=O]

The title compound was prepared in analogy to Intermediate B1 by replacing 2-methyl-1-pyrrolidin-1-yl-propan-2-amine (compound B1.2) with methylamine in step (c). MS (ESI): 277.1 ([M+H]⁺)

Intermediate B3

(6-Ethoxycarbonyl-8-ethyl-5-oxo-1,8-naphthyridin-3-yl)boronic acid

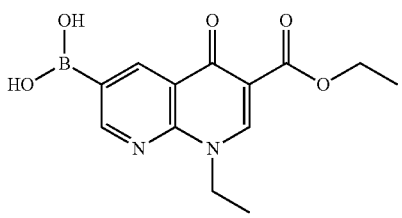 [SMILES: CCOC(=O)c1cn(CC)c2ncc(B(O)O)cc2c1=O]

The title compound was prepared in analogy to Intermediate B1 by replacing 2-methyl-1-pyrrolidin-1-yl-propan-2-amine (compound B1.2) with ethylamine in step (c). MS (ESI): 291.1 ([M+H]⁺)

Intermediate B4

[6-Ethoxycarbonyl-8-[(1-ethylpyrrolidin-2-yl)methyl]-5-oxo-1,8-naphthyridin-3-yl]boronic acid

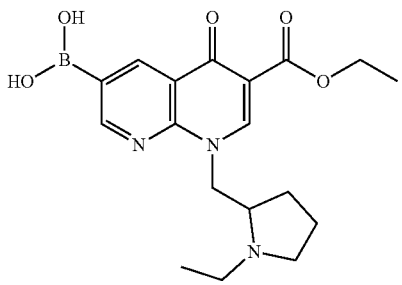 [SMILES: CCOC(=O)c1cn(CC2CCCN2CC)c2ncc(B(O)O)cc2c1=O]

The titled compound was synthesized according to the following scheme:

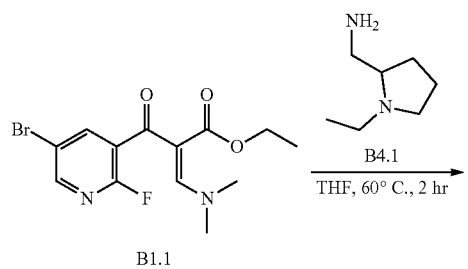

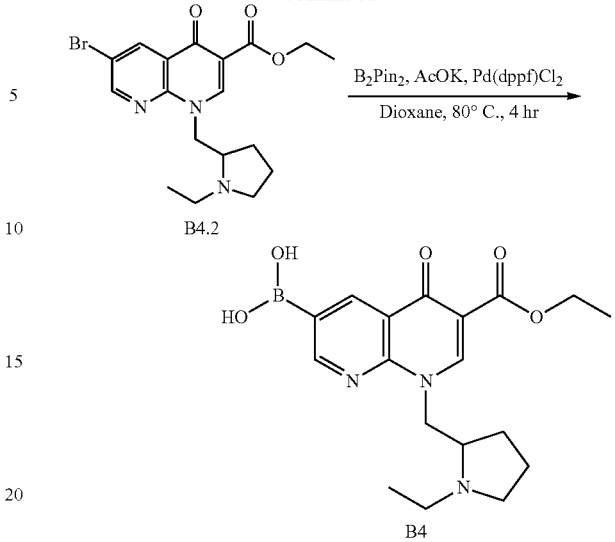

Step (a) Ethyl (Z)-2-(5-bromo-2-fluoro-pyridine-3-carbonyl)-3-(dimethylamino)prop-2-enoate (Compound B1.1)

Compound B1.1 was prepared according to the procedure disclosed in WO 2010/136817 A1. MS (ESI): 347.0 ([{⁸¹Br}M+H]⁺), 345.0 ([{⁷⁹Br}M+H]⁺

Step (b) Ethyl 6-bromo-1-[(1-ethylpyrrolidin-2-yl)methyl]-4-oxo-1,8-naphthyridine-3-carboxylate (Compound B4.2)

To a solution of ethyl (Z)-2-(5-bromo-2-fluoro-pyridine-3-carbonyl)-3-(dimethylamino)prop-2-enoate (compound B1.1, 800.0 mg, 2.24 mmol) in THF (10.0 mL) was added (1-ethylpyrrolidin-2-yl)methanamine (compound B4.1, 500.0 mg, 1.74 mmol) and the resulting mixture was stirred at 60° C. for 2 h. Afterwards, the reaction mixture was poured into water (100 mL) and extracted with EtOAc (40 mL) three times. The combined organics was washed then with satd. aq. NH₄Cl solution (40 mL) three times, brine (40 mL) three times, filtered and concentrated in vacuo to give a crude product, which was purified by reverse phase HPLC to give ethyl 6-bromo-1-[(1-ethylpyrrolidin-2-yl)methyl]-4-oxo-1,8-naphthyridine-3-carboxylate (620.0 mg, 68% yield) as a white solid. MS (ESI): 408.0 ([{⁸¹Br}M+H]⁺), 410.0 ([{⁷⁹Br}M+H]⁺

Step (c) [6-Ethoxycarbonyl-8-[(1-ethylpyrrolidin-2-yl)methyl]-5-oxo-1,8-naphthyridin-3-yl]boronic acid (Intermediate B4)

To a stirred solution of ethyl 6-bromo-1-[(1-ethylpyrrolidin-2-yl)methyl]-4-oxo-1,8-naphthyridine-3-carboxylate (compound B4.2, 300.0 mg, 0.735 mmol), B₂Pin₂ (250.0 mg, 0.984 mmol) in dioxane (10.0 mL) was added Pd(dppf)Cl₂ (90.0 mg, 0.123 mmol) and AcOK (250.0 mg, 2.55 mmol). The resulting reaction mixture was stirred at 80° C. under N₂ for 4 h. After it was cooled back to room temperature, the reaction mixture was filtered and the filter cake was washed with EtOAc (20 mL) two times. The filtrate was then concentrated in vacuo to give a crude product, which was purified by reverse HPLC to give [6-ethoxycarbonyl- 8-[(1-ethylpyrrolidin-2-yl)methyl]-5-oxo-1,8-naphthyridin-3-yl]boronic acid (150.0 mg, 54.7% yield) as a white solid. MS (ESI): 374.1 ([M+H]$^+$)

Intermediate B5

[8-[(4-tert-Butoxycarbonylmorpholin-3-yl)methyl]-6-ethoxycarbonyl-5-oxo-1,8-naphthyridin-3-yl]boronic acid

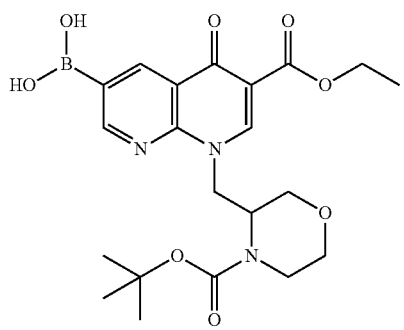 [SMILES: CCOC(=O)c1cn(CC2COCCN2C(=O)OC(C)(C)C)c2ncc(B(O)O)cc2c1=O]

The title compound was prepared in analogy to Intermediate B4 by replacing (1-ethylpyrrolidin-2-yl)methanamine (compound B4.1) with tert-butyl 3-(aminomethyl)morpholine-4-carboxylate in step (b). MS (ESI): 462.1 ([M+H]$^+$)

Intermediate B6

[8-(1-tert-Butoxycarbonylpyrrolidin-3-yl)-6-ethoxycarbonyl-5-oxo-1,8-naphthyridin-3-yl]boronic acid

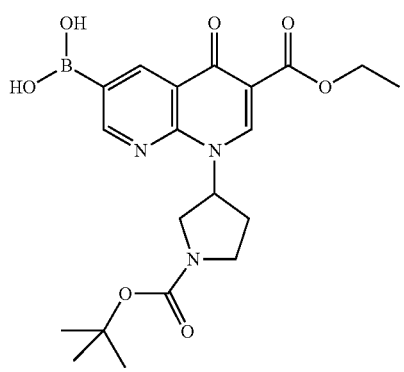 [SMILES: CCOC(=O)c1cn(C2CCN(C(=O)OC(C)(C)C)C2)c2ncc(B(O)O)cc2c1=O]

The title compound was prepared in analogy to Intermediate B1 by replacing 2-methyl-1-pyrrolidin-1-yl-propan-2-amine (compound B1.2) with tert-butyl 3-aminopyrrolidine-1-carboxylate in step (c). MS (ESI): 432.2 ([M+H]$^+$)

Intermediate B7

[8-[(1-tert-Butoxycarbonylpyrrolidin-2-yl)methyl]-6-ethoxycarbonyl-5-oxo-1,8-naphthyridin-3-yl]boronic acid

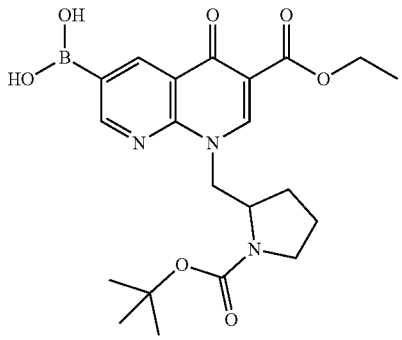 [SMILES: CCOC(=O)c1cn(CC2CCCN2C(=O)OC(C)(C)C)c2ncc(B(O)O)cc2c1=O]

The title compound was prepared in analogy to Intermediate B1 by replacing 2-methyl-1-pyrrolidin-1-yl-propan-2-amine (compound B1.2) with tert-butyl 2-(aminomethyl)pyrrolidine-1-carboxylate in step (c). MS (ESI): 446.2 ([M+H]$^+$)

Intermediate B8

[6-Ethoxycarbonyl-8-[(4-methoxyphenyl)methyl]-5-oxo-1,8-naphthyridin-3-yl]boronic acid

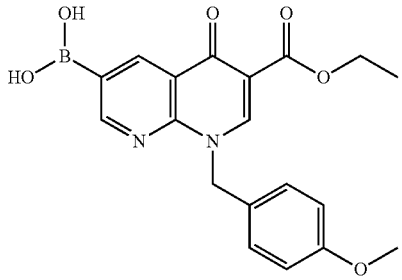 [SMILES: CCOC(=O)c1cn(Cc2ccc(OC)cc2)c2ncc(B(O)O)cc2c1=O]

The title compound was prepared in analogy to Intermediate B4 by replacing (1-ethylpyrrolidin-2-yl)methanamine (compound B4.1) with 1-(4-methoxyphenyl)methanamine in step (b). MS (ESI): 383.0 ([M+H]$^+$)

Intermediate B9

[6-Ethoxycarbonyl-8-(1-methylpyrrolidin-3-yl)-5-oxo-1,8-naphthyridin-3-yl]boronic acid

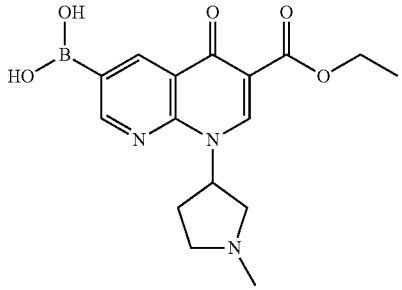 [SMILES: CCOC(=O)c1cn(C2CCN(C)C2)c2ncc(B(O)O)cc2c1=O]

The title compound was prepared in analogy to Intermediate B1 by replacing 2-methyl-1-pyrrolidin-1-yl-propan-2-amine (compound B1.2) with 1-methylpyrrolidin-3-amine in step (c). MS (ESI): 346.1 ([M+H]$^+$)

Intermediate B10

(6-Ethoxycarbonyl-5-oxo-8-tetrahydrofuran-3-yl-1,8-naphthyridin-3-yl)boronic acid

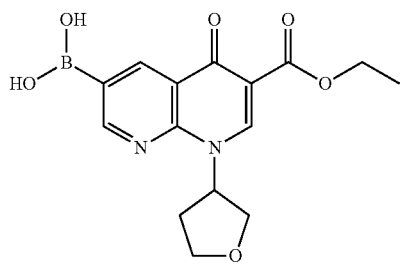 [SMILES: CCOC(=O)c1cn(C2CCOC2)c2ncc(B(O)O)cc2c1=O]

The title compound was prepared in analogy to Intermediate B1 by replacing 2-methyl-1-pyrrolidin-1-yl-propan-2-amine (compound B1.2) with tetrahydrofuran-3-amine in step (c). MS (ESI): 333.1 ([M+H]$^+$)

Intermediate B11

[8-[2-(Dimethylamino)ethyl]-6-ethoxycarbonyl-5-oxo-1,8-naphthyridin-3-yl]boronic acid

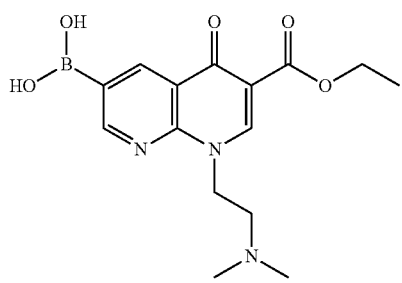 [SMILES: CCOC(=O)c1cn(CCN(C)C)c2ncc(B(O)O)cc2c1=O]

The title compound was prepared in analogy to Intermediate B1 by replacing 2-methyl-1-pyrrolidin-1-yl-propan-2-amine (compound B1.2) with 2-dimethylaminoethylamine in step (c). MS (ESI): 334.1 ([M+H]$^+$)

Intermediate B12

[6-Ethoxycarbonyl-8-(2-methoxyethyl)-5-oxo-1,8-naphthyridin-3-yl]boronic acid

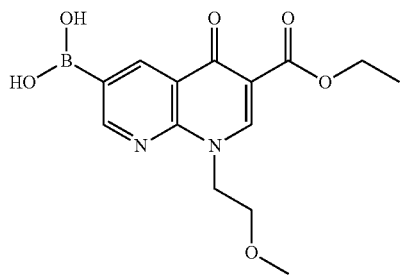 [SMILES: CCOC(=O)c1cn(CCOC)c2ncc(B(O)O)cc2c1=O]

The title compound was prepared in analogy to Intermediate B1 by replacing 2-methyl-1-pyrrolidin-1-yl-propan-2-amine (compound B1.2) with 2-methoxyethyl amine in step (c). MS (ESI): 321.1 ([M+H]$^+$)

Intermediate B13

[8-[2-[tert-Butoxycarbonyl(methyl)amino]ethyl]-6-ethoxycarbonyl-5-oxo-1,8-naphthyridin-3-yl]boronic acid

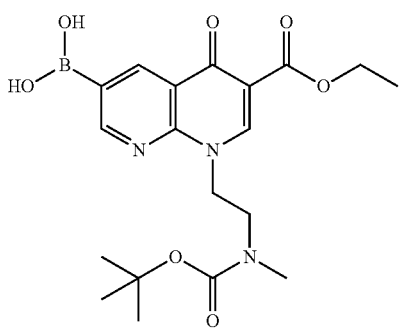 [SMILES: CCOC(=O)c1cn(CCN(C)C(=O)OC(C)(C)C)c2ncc(B(O)O)cc2c1=O]

The title compound was prepared in analogy to Intermediate B4 by replacing (1-ethylpyrrolidin-2-yl)methanamine (compound B4.1) with N-(2-aminoethyl)-N-methyl-carbamic acid 1,1-dimethylethyl ester in step (b). MS (ESI): 420.2 ([M+H]$^+$)

Intermediate B14

[6-Ethoxycarbonyl-8-[2-(4-methylpiperazin-1-yl)ethyl]-5-oxo-1,8-naphthyridin-3-yl]boronic acid

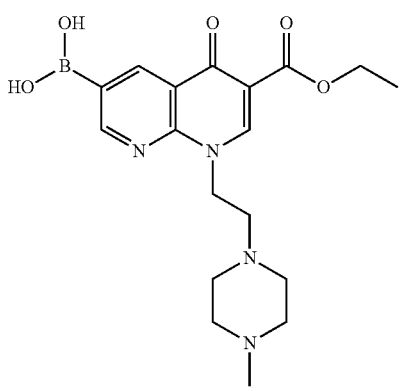 [SMILES: CCOC(=O)c1cn(CCN2CCN(C)CC2)c2ncc(B(O)O)cc2c1=O]

The title compound was prepared in analogy to Intermediate B4 by replacing (1-ethylpyrrolidin-2-yl)methanamine (compound B4.1) with 2-(4-methyl-1-piperazinyl)ethanamine in step (b). MS (ESI): 389.2 ([M+H]$^+$).

Intermediate B15

[6-Ethoxycarbonyl-5-oxo-8-(4-pyridylmethyl)-1,8-naphthyridin-3-yl]boronic acid

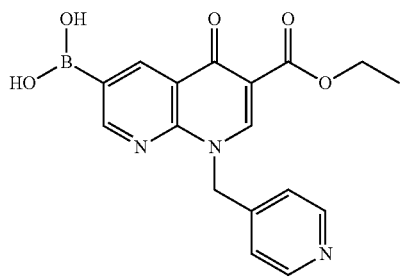 [SMILES: CCOC(=O)c1cn(Cc2ccncc2)c2ncc(B(O)O)cc2c1=O]

The title compound was prepared in analogy to Intermediate B4 by replacing (1-ethylpyrrolidin-2-yl)methanamine (compound B4.1) with 4-pyridinemethaneamine in step (b). MS (ESI): 354.1 ([M+H]$^+$).

Intermediate B16

[6-Ethoxycarbonyl-8-[(1-methyl-4-piperidyl)methyl]-5-oxo-1,8-naphthyridin-3-yl]boronic acid

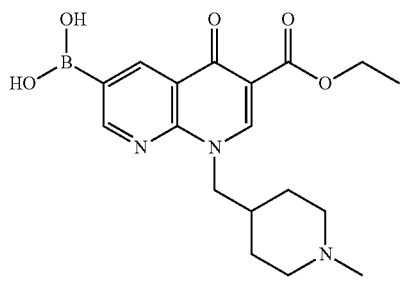 [SMILES: CCOC(=O)c1cn(CC2CCN(C)CC2)c2ncc(B(O)O)cc2c1=O]

The title compound was prepared in analogy to Intermediate B4 by replacing (1-ethylpyrrolidin-2-yl)methanamine (compound B4.1) with (1-methylpiperidin-4-yl)methanamine in step (b). MS (ESI): 374.2 ([M+H]$^+$).

Intermediate B17

[6-Ethoxycarbonyl-8-(2-hydroxy-2-methyl-propyl)-5-oxo-1,8-naphthyridin-3-yl]boronic acid

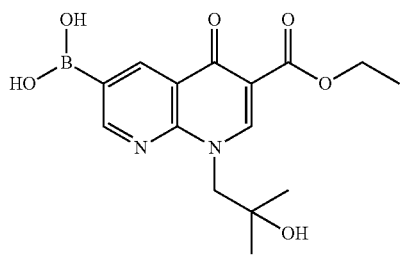 [SMILES: CCOC(=O)c1cn(CC(C)(C)O)c2ncc(B(O)O)cc2c1=O]

The titled compound was synthesized according to the following scheme:

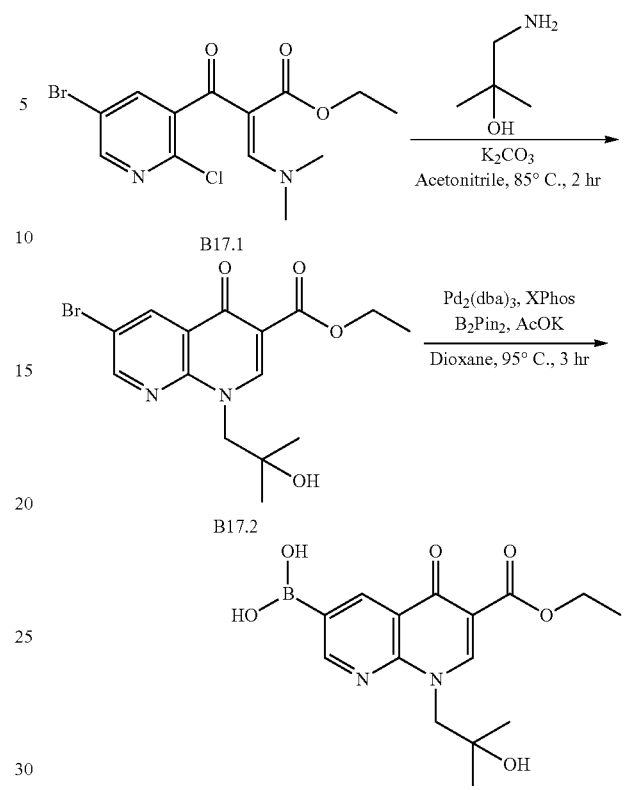

Step (a) Ethyl (Z)-2-(5-bromo-2-chloro-pyridine-3-carbonyl)-3-(dimethylamino)prop-2-enoate (Compound B17.1)

Compound B 17.1 was prepared according to the procedure disclosed in WO 2006/050942 A1. MS (ESI): 361.0 ([{$^{79}$Br+$^{35}$Cl}M+H]$^+$).

Step (b) Ethyl 6-bromo-1-(2-hydroxy-2-methyl-propyl)-4-oxo-1,8-naphthyridine-3-carboxylate (Compound B17.2)

To a stirred solution of ethyl (Z)-2-(5-bromo-2-chloro-pyridine-3-carbonyl)-3-(dimethylamino)prop-2-enoate (compound B17.1, 425.0 mg, 1.18 mmol) in acetonitrile (12.0 mL) were added DIPEA (411 μL, 2.35 mmol) and 1-amino-2-methylpropan-2-ol (210 mg, 2.35 mmol). The resulting mixture was heated at 85° C. for 2 h before it was cooled back to room temperature. K$_2$CO$_3$ (325 mg, 2.35 mmol) was added to the reaction mixture and the solution was stirred at 85° C. for another 12 h. After cooling back to room temperature, the reaction mixture was poured into water (100 mL) and extracted with EtOAc (40 mL) three times. The combined organics was washed with satd. aq. NH$_4$Cl solution (40 mL) three times, brine (40 mL), filtered and concentrated in vacuo to give a crude product, which was then purified by silica gel flash chromatography (0-5% MeOH in DCM) to give ethyl 6-bromo-1-(2-hydroxy-2-methyl-propyl)-4-oxo-1,8-naphthyridine-3-carboxylate (220.0 mg, 51% yield) as an off-white solid. MS (ESI): 371.0 ([{$^{81}$Br}M+H]$^+$), 369.0 ([{$^{79}$Br}M+H]$^+$ c) [6-Ethoxycarbonyl-8-(2-hydroxy-2-methyl-propyl)-5-oxo-1,8-naphthyridin-3-yl]boronic acid (Intermediate B17)

To a stirred solution of ethyl 6-bromo-1-(2-hydroxy-2-methyl-propyl)-4-oxo-1,8-naphthyridine-3-carboxylate (compound B17.2, 190.0 mg, 0.515 mmol) and $B_2Pin_2$ (261.0 mg, 1.03 mmol) in dioxane (12.0 mL) were added $Pd_2(dba)_3$ (47.1 mg, 0.052 mmol), Xphos (49.1 mg, 0.103 mmol), and AcOK (152.0 mg, 1.54 mmol). After stirred at 95° C. under $N_2$ for 3 h, the reaction mixture was filtered and the filter cake was washed with EtOAc (20 mL) two times. The filtrate was concentrated in vacuo to give a crude product, which was purified by reverse phase HPLC to give [6-ethoxycarbonyl-8-(2-hydroxy-2-methyl-propyl)-5-oxo-1,8-naphthyridin-3-yl]boronic acid (105.0 mg, 61% yield) as an off-white solid. MS (ESI): 335.1 ([M+H]$^+$).

Intermediate B18

[8-[2-(tert-Butoxycarbonylamino)-2-methyl-propyl]-6-ethoxycarbonyl-5-oxo-1,8-naphthyridin-3-yl]boronic acid

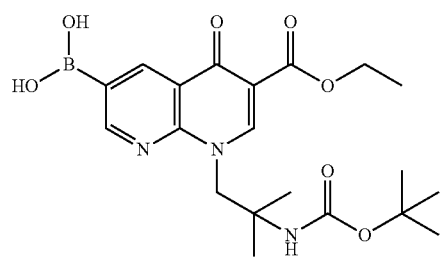 [SMILES: CCOC(=O)c1cn(CC(C)(C)NC(=O)OC(C)(C)C)c2ncc(B(O)O)cc2c1=O]

The title compound was prepared in analogy to Intermediate B17 by replacing 1-amino-2-methylpropan-2-ol with tert-butyl N-(1-amino-2-methylpropan-2-yl)carbamate in step (b). MS (ESI): 434.2 ([M+H]$^+$).

Intermediate B19

[6-Ethoxycarbonyl-5-oxo-8-(tetrahydrofuran-2-ylmethyl)-1,8-naphthyridin-3-yl]boronic acid

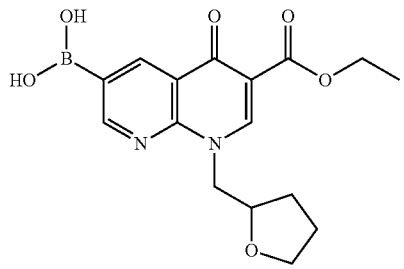 [SMILES: CCOC(=O)c1cn(CC2CCCO2)c2ncc(B(O)O)cc2c1=O]

The title compound was prepared in analogy to Intermediate B17 by replacing 1-amino-2-methylpropan-2-ol with tetrahydrofurfurylamine in step (b). MS (ESI): 347.1 ([M+H]$^+$)

Intermediate B20

[8-[(4-tert-Butoxycarbonylmorpholin-2-yl)methyl]-6-ethoxycarbonyl-5-oxo-1,8-naphthyridin-3-yl]boronic acid

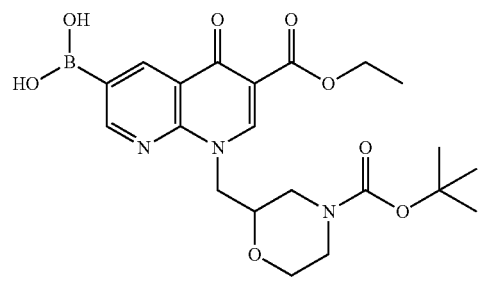 [SMILES: CCOC(=O)c1cn(CC2CN(C(=O)OC(C)(C)C)CCO2)c2ncc(B(O)O)cc2c1=O]

The title compound was prepared in analogy to Intermediate B4 by replacing (1-ethylpyrrolidin-2-yl)methanamine (compound B4.1) with 4-Boc-2-(aminomethyl)morpholine in step (b). MS (ESI): 462.2 ([M+H]$^+$).

Intermediate B21

[6-Ethoxycarbonyl-8-[1-methyl-2-tetrahydropyran-2-yloxy-1-(tetrahydropyran-2-yloxymethyl)ethyl]-5-oxo-1,8-naphthyridin-3-yl]boronic acid

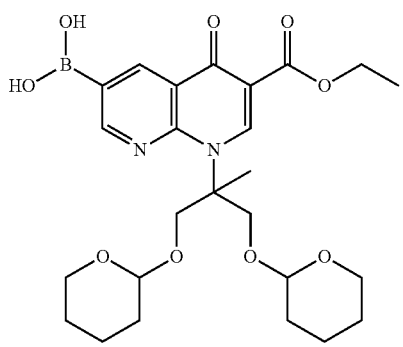 [SMILES: CCOC(=O)c1cn(C(C)(COC2CCCCO2)COC2CCCCO2)c2ncc(B(O)O)cc2c1=O]

The titled compound was synthesized according to the following scheme:

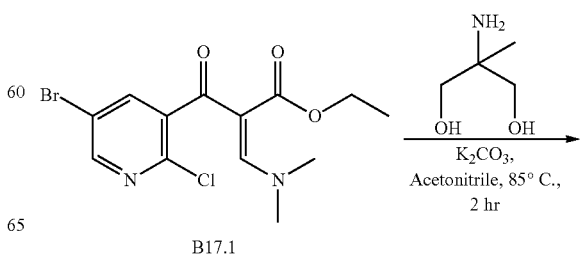

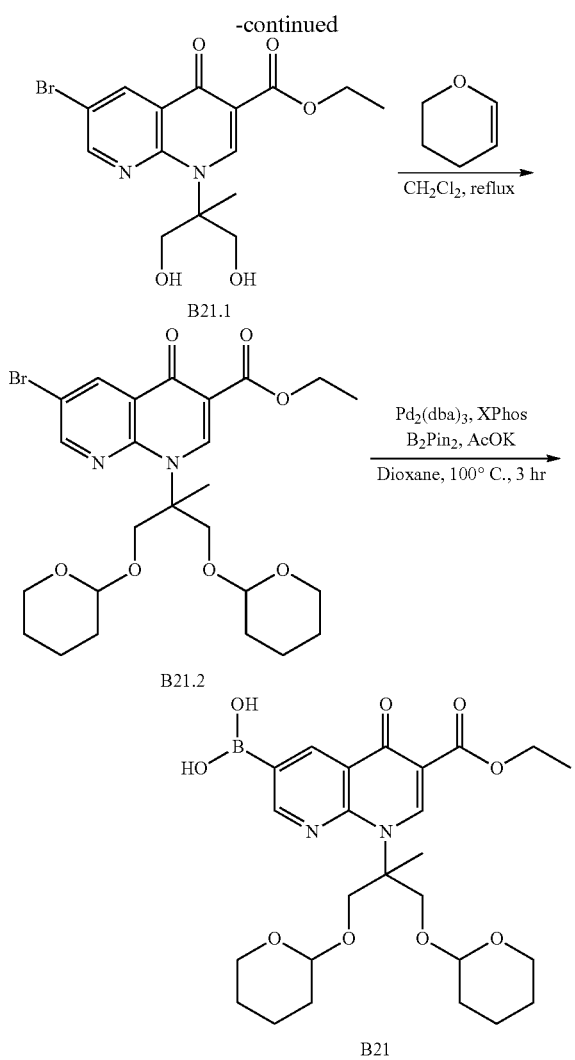

Step (a) Ethyl 6-bromo-1-[2-hydroxy-1-(hydroxymethyl)-1-methyl-ethyl]-4-oxo-1,8-naphthyridine-3-carboxylate (Compound B21.1)

Compound B21.1 was prepared in analogy to compound B17.2 by replacing 1-amino-2-methylpropan-2-ol with 2-amino-2-methylpropane-1,3-diol. MS (ESI): 387.1 ([{$^{81}$Br}M+H]$^+$), 385.1 ([{$^{79}$Br}M+H]$^+$.

Step (b) Ethyl 6-bromo-1-[1-methyl-2-tetrahydropyran-2-yloxy-1-(tetrahydropyran-2-yloxymethyl)ethyl]-4-oxo-1,8-naphthyridine-3-carboxylate (Compound 21.2)

To a 100 mL round-bottom flask were added DHP (578 μL, 6.32 mmol), ethyl 6-bromo-1-[2-hydroxy-1-(hydroxymethyl)-1-methyl-ethyl]-4-oxo-1,8-naphthyridine-3-carboxylate (compound B21.1, 406 mg, 1.05 mmol) and p-toluenesulfonic acid monohydrate (20 mg, 0.11 mmol) and DCM (20 mL). The resulting light yellow solution was heated at 45° C. for 15 h before cooled back to room temperature. Volatiles were removed under reduced pressure and the crude product was purified by silica gel flash chromatography (0% to 5% MeOH in DCM) to afford ethyl 6-bromo-1-[1-methyl-2-tetrahydropyran-2-yl oxy-1-(tetrahydropyran-2-yloxymethyl)ethyl]-4-oxo-1,8-naphthyridine-3-carboxylate (580 mg, 1.05 mmol, 99% yield) as a yellow solid. MS (ESI): 555.2 ([{$^{81}$Br}M+H]$^+$), 553.2 ([{$^{79}$Br}M+H]$^+$.

Step (c) [6-Ethoxycarbonyl-8-[1-methyl-2-tetrahydropyran-2-yloxy-1-(tetrahydropyran-2-yloxymethyl)ethyl]-5-oxo-1,8-naphthyridin-3-yl]boronic acid (Intermediate B21)

To a stirred solution of ethyl 6-bromo-1-[1-methyl-2-tetrahydropyran-2-yloxy-1-(tetrahydropyran-2-yloxymethyl)ethyl]-4-oxo-1,8-naphthyridine-3-carboxylate (compound B21.2, 580 mg, 1.05 mmol) and B$_2$Pin$_2$ (535 mg, 2.11 mmol) in dioxane (14.0 mL) were added Pd$_2$(dba)$_3$ (96.5 mg, 0.105 mmol), Xphos (100 mg, 0.211 mmol), and AcOK (310 mg, 3.16 mmol). The reaction mixture was heated at 100° C. under N$_2$ in a microwave reactor for 3 h. After cooled back to room temperature, the reaction mixture was filtered, and the filter cake was washed with EtOAc (20 mL) two times. The filtrate was concentrated in vacuo to give a crude product, which was purified by reverse phase HPLC to give [6-ethoxycarbonyl-8-[1-methyl-2-tetrahydropyran-2-yloxy-1-(tetrahydropyran-2-yloxymethyl)ethyl]-5-oxo-1,8-naphthyridin-3-yl]boronic acid (196 mg, 36% yield) as a light yellow solid. MS (ESI): 519.3 ([M+H]$^+$).

Intermediate B22

[6-Ethoxycarbonyl-8-(1-methyl-2-tetrahydropyran-2-yloxy-ethyl)-5-oxo-1,8-naphthyridin-3-yl]boronic acid

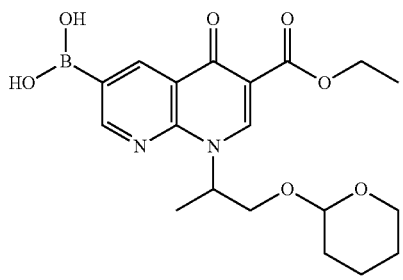 [SMILES: CCOC(=O)c1cn(C(C)COC2CCCCO2)c2ncc(B(O)O)cc2c1=O]

The title compound was prepared in analogy to Intermediate B21 by replacing 2-amino-2-methylpropane-1,3-diol with 2-aminopropan-1-ol in step (a). MS (ESI): 405.2 ([M+H]$^+$).

Intermediate B23

[8-[tert-Butoxycarbonyl(methyl)amino]-6-ethoxycarbonyl-5-oxo-1,8-naphthyridin-3-yl]boronic acid

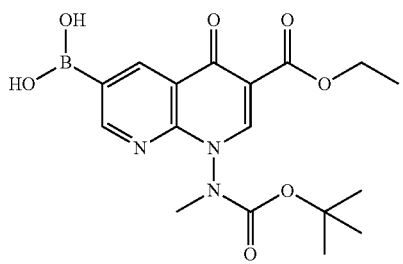 [SMILES: CCOC(=O)c1cn(N(C)C(=O)OC(C)(C)C)c2ncc(B(O)O)cc2c1=O]

The title compound was prepared in analogy to Intermediate B17 by replacing 1-amino-2-methylpropan-2-ol with tert-butyl 1-methylhydrazinecarboxylate in step (b). MS (ESI): 392.3 ([M+H]$^+$).

Intermediate B24

[6-Ethoxycarbonyl-5-oxo-8-(2-tetrahydropyran-2-yloxypropyl)-1,8-naphthyridin-3-yl]boronic acid

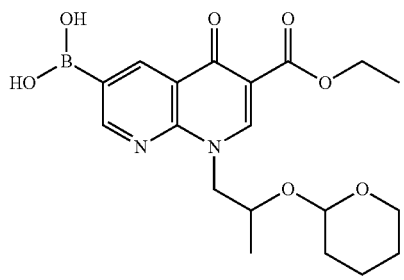 [SMILES: CCOC(=O)c1cn(CC(C)OC2CCCCO2)c2ncc(B(O)O)cc2c1=O]

The title compound was prepared in analogy to Intermediate B21 by replacing 2-amino-2-methylpropane-1,3-diol with 1-aminopropan-2-ol in step (a). MS (ESI): 405.2 ([M+H]$^+$)

Intermediate B25

[6-Ethoxycarbonyl-8-[(1S)-1-(hydroxymethyl)-2,2-dimethyl-propyl]-5-oxo-1,8-naphthyridin-3-yl]boronic acid

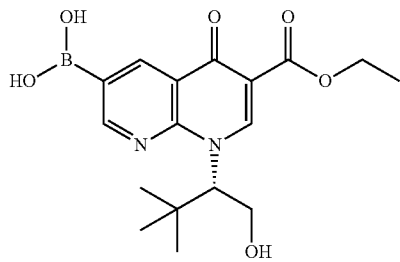 [SMILES: CCOC(=O)c1cn([C@H](CO)C(C)(C)C)c2ncc(B(O)O)cc2c1=O]

The title compound was prepared in analogy to Intermediate B4 by replacing (1-ethylpyrrolidin-2-yl)methanamine (compound B4.1) with (S)-tert-Leucinol in step (b). MS (ESI): 363.2 ([M+H]$^+$).

Intermediate B26

[8-[2-(tert-Butoxycarbonylamino)-3-methyl-butyl]-6-ethoxycarbonyl-5-oxo-1,8-naphthyridin-3-yl]boronic acid

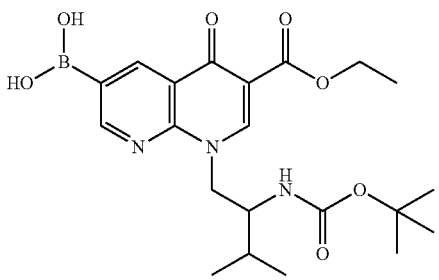 [SMILES: CCOC(=O)c1cn(CC(NC(=O)OC(C)(C)C)C(C)C)c2ncc(B(O)O)cc2c1=O]

The title compound was prepared in analogy to Intermediate B4 by replacing (1-ethylpyrrolidin-2-yl)methanamine (compound B4.1) with 2-methyl-2-propanyl (1-amino-3-methyl-2-butanyl)carbamate in step (b), a reaction time of 12 h in step (b), and a reaction temperature at 100° C. for 12 h in step (c). MS (ESI): 448.2 ([M+H]$^+$).

Intermediate B27

[6-Ethoxycarbonyl-5-oxo-8-(pyrazin-2-ylmethyl)-1,8-naphthyridin-3-yl]boronic acid

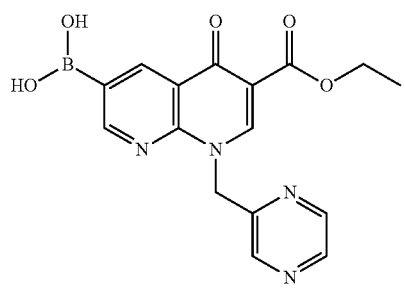 [SMILES: CCOC(=O)c1cn(Cc2cnccn2)c2ncc(B(O)O)cc2c1=O]

The title compound was prepared in analogy to Intermediate B4 by replacing (1-ethylpyrrolidin-2-yl)methanamine (compound B4.1) with pyrazin-2-ylmethanamine, and reacting at refluxing temperature in step (b). MS (ESI): 355.1 ([M+H]$^+$).

Intermediate B28

[8-[2-(Dimethylamino)-2-methyl-propyl]-6-ethoxycarbonyl-5-oxo-1,8-naphthyridin-3-yl]boronic acid

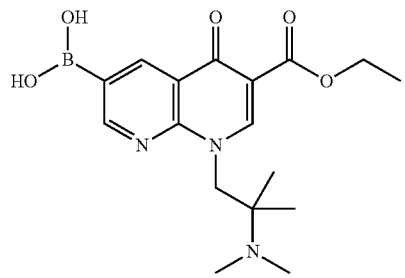 [SMILES: CCOC(=O)c1cn(CC(C)(C)N(C)C)c2ncc(B(O)O)cc2c1=O]

The title compound was prepared in analogy to Intermediate B17 by replacing 1-amino-2-methylpropan-2-ol with 2-N,2-N,2-trimethylpropane-1,2-diamine in step (b). MS (ESI): 362.1 ([M+H]$^+$)

Intermediate B29

[8-[2-(Dimethylamino)-1-methyl-ethyl]-6-ethoxycarbonyl-5-oxo-1,8-naphthyridin-3-yl]boronic acid

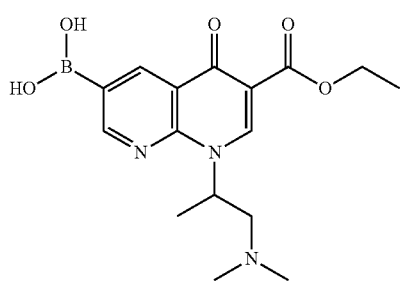 [SMILES: CCOC(=O)c1cn(C(C)CN(C)C)c2ncc(B(O)O)cc2c1=O]

The title compound was prepared in analogy to Intermediate B17 by replacing 1-amino-2-methylpropan-2-ol with N1,N1-dimethylpropane-1,2-diamine in step (b). MS (ESI): 348.1 ([M+H]$^+$).

Intermediate B30

(6-Ethoxycarbonyl-8-morpholino-5-oxo-1,8-naphthyridin-3-yl)boronic acid

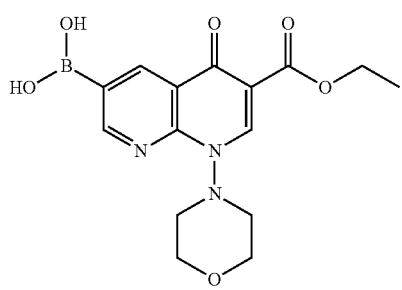 [SMILES: CCOC(=O)c1cn(N2CCOCC2)c2ncc(B(O)O)cc2c1=O]

The title compound was prepared in analogy to Intermediate B17 by replacing 1-amino-2-methylpropan-2-ol with morpholin-4-amine in step (b). MS (ESI): 348.1 ([M+H]$^+$).

Intermediate B31

[8-(Dimethylamino)-6-ethoxycarbonyl-5-oxo-1,8-naphthyridin-3-yl]boronic acid

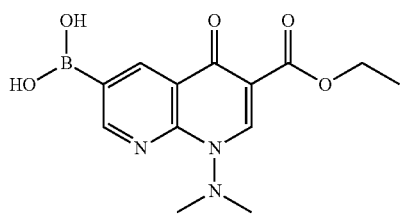 [SMILES: CCOC(=O)c1cn(N(C)C)c2ncc(B(O)O)cc2c1=O]

The title compound was prepared in analogy to Intermediate B17 by replacing 1-amino-2-methylpropan-2-ol with 1,1-dimethylhydrazine hydrochloride in step (b). MS (ESI): 306.1 ([M+H]$^+$).

Intermediate B32

[8-[2-(Diethylamino)ethyl]-6-ethoxycarbonyl-5-oxo-1,8-naphthyridin-3-yl]boronic acid

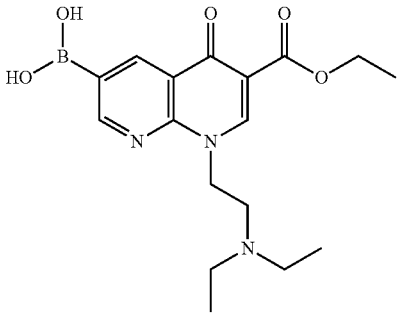 [SMILES: CCOC(=O)c1cn(CCN(CC)CC)c2ncc(B(O)O)cc2c1=O]

The title compound was prepared in analogy to Intermediate B17 by replacing 1-amino-2-methylpropan-2-ol with N1,N1-diethylethane-1,2-diamine in step (b). MS (ESI): 362.1 ([M+H]$^+$).

Intermediate B33

[8-[2-(Dimethylamino)-2-phenyl-ethyl]-6-ethoxycarbonyl-5-oxo-1,8-naphthyridin-3-yl]boronic acid

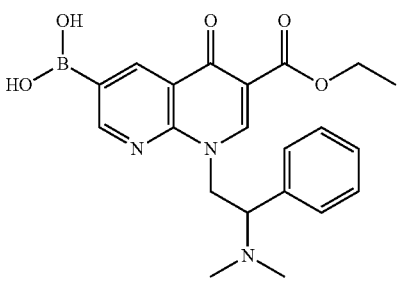 [SMILES: CCOC(=O)c1cn(CC(c2ccccc2)N(C)C)c2ncc(B(O)O)cc2c1=O]

The title compound was prepared in analogy to Intermediate B17 by replacing 1-amino-2-methylpropan-2-ol with N1,N1-dimethyl-1-phenylethane-1,2-diamine in step (b). MS (ESI): 410.0 ([M+H]$^+$).

Intermediate B34

[8-[2-(Dimethylamino)butyl]-6-ethoxycarbonyl-5-oxo-1,8-naphthyridin-3-yl]boronic acid

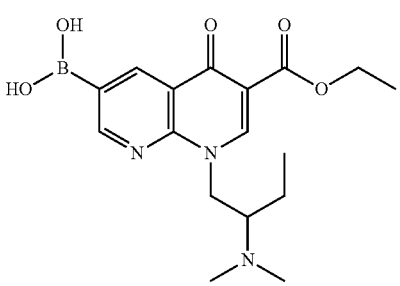 [SMILES: CCOC(=O)c1cn(CC(CC)N(C)C)c2ncc(B(O)O)cc2c1=O]

The title compound was prepared in analogy to Intermediate B17 by replacing 1-amino-2-methylpropan-2-ol with 2-N,2-N-dimethylbutane-1,2-diamine in step (b). MS (ESI): 362.2 ([M+H]⁺).

Intermediate B35

6-Borono-1-[tert-butoxycarbonyl(ethyl)amino]-4-oxo-1,8-naphthyridine-3-carboxylic acid

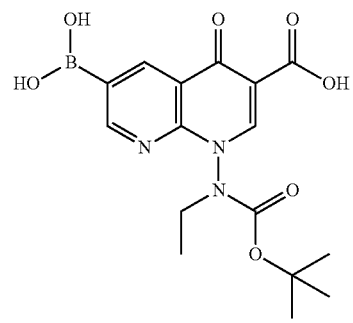 [SMILES: CCN(C(=O)OC(C)(C)C)n1cc(C(=O)O)c(=O)c2cc(B(O)O)cnc21]

The title compound was prepared in analogy to Intermediate B1 by replacing 2-methyl-1-pyrrolidin-1-yl-propan-2-amine (compound B1.2) with tert-butyl 1-ethyl hydrazinecarboxylate in step (c). MS (ESI): 406.1 ([M+H]⁺)

Intermediate B36

[6-Ethoxycarbonyl-8-(oxazol-5-ylmethyl)-5-oxo-1,8-naphthyridin-3-yl]boronic acid

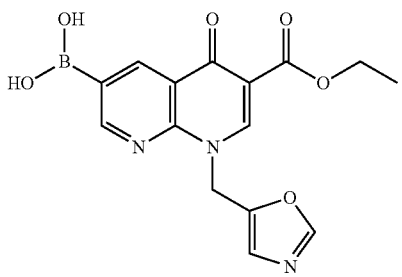 [SMILES: CCOC(=O)c1cn(Cc2cnco2)c2ncc(B(O)O)cc2c1=O]

The titled compound was synthesized according to the following scheme:

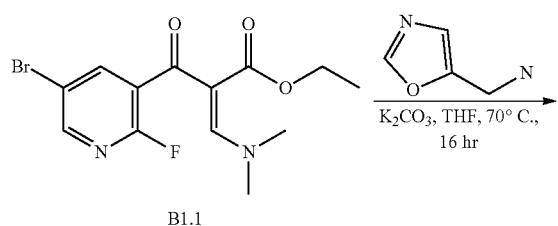

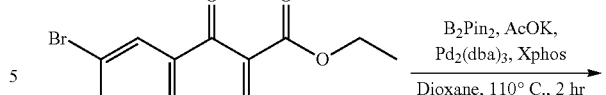

B36.2

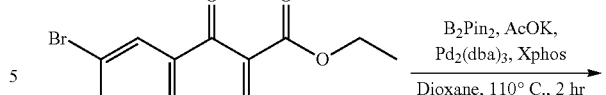

B36

Step (a) Ethyl 6-bromo-1-(oxazol-5-ylmethyl)-4-oxo-1,8-naphthyridine-3-carboxylate (Compound B36.2)

A mixture solution of ethyl (Z)-2-(5-bromo-2-fluoro-pyridine-3-carbonyl)-3-(dimethylamino)prop-2-enoate (compound B1.1 (600 mg, 1.74 mmol), oxazol-5-ylmethanamine (compound B1087.1, 205 mg, 2.09 mmol) and K₂CO₃ (720 mg, 5.21 mmol) in THF (10.0 mL) was stirred at 70° C. for 16 h. After cooled down to room temperature, the reaction mixture was diluted with EtOAc (30 mL), washed with brine (30 mL) twice. The organic layer was dried over anhy. Na₂SO₄, filtered and concentrated in vacuo to give a crude product, which was triturated with MTBE (5 mL) to give ethyl 6-bromo-1-(oxazol-5-ylmethyl)-4-oxo-1,8-naphthyridine-3-carboxylate (120 mg, 18.25% yield) as a yellow solid. MS (ESI): 380.0 ([{⁸¹Br}M+H]⁺), 378.0 ([{⁷⁹Br}M+H]⁺).

Step (b) [6-Ethoxycarbonyl-8-(oxazol-5-ylmethyl)-5-oxo-1,8-naphthyridin-3-yl]boronic acid (Intermediate B36)

A mixture solution of ethyl 6-bromo-1-(oxazol-5-ylmethyl)-4-oxo-1,8-naphthyridine-3-carboxylate (compound B36.2, 100 mg, 0.260 mmol), B₂Pin₂ (80 mg, 0.320 mmol), AcOK (78 mg, 0.790 mmol), Xphos (25 mg, 0.050 mmol) and Pd₂(dba)₃ (24 mg, 0.030 mmol) in 1,4-dioxane (2.0 mL) was stirred at 110° C. for 2 h. After cooled down to room temperature, the mixture solution was diluted with DCM (30 mL) and filtered. The filtrate was concentrated in vacuo to give a crude product, which was triturated with MTBE (5 mL) and ether (5 mL) to give [6-ethoxycarbonyl-8-(oxazol-5-ylmethyl)-5-oxo-1,8-naphthyridin-3-yl]boronic acid (80 mg, 88.18% yield) as a yellow solid. MS (ESI): 344.1 ([M+H]⁺).

Intermediate B37

(R)-Ethyl 1-(1-(tert-butoxycarbonyl)pyrrolidin-3-yl)-4-oxo-6-(4,4,5,5-tetramethyl-1,3,2-dioxaborolan-2-yl)-1,4-dihydro-1,8-naphthyridine-3-carboxylate

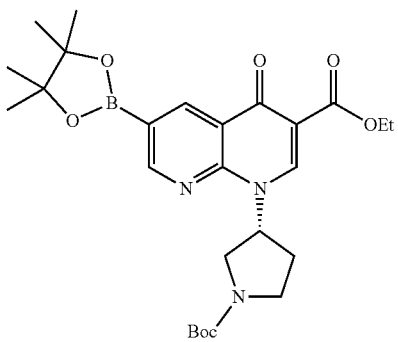 [SMILES: CCOC(=O)c1cn([C@@H]2CCN(C(=O)OC(C)(C)C)C2)c2ncc(B3OC(C)(C)C(C)(C)O3)cc2c1=O]

The title compound was prepared in analogy to Intermediate B17 by replacing 1-amino-2-methylpropan-2-ol with (R)-tert-butyl 3-aminopyrrolidine-1-carboxylate in step (b). MS (ESI): 432.1 ([M-82+H]$^+$).

Intermediate B38

(8-((tert-Butoxycarbonyl)(tetrahydro-2H-pyran-4-yl)amino)-6-(ethoxycarbonyl)-5-oxo-5,8-dihydro-1,8-naphthyridin-3-yl)boronic acid

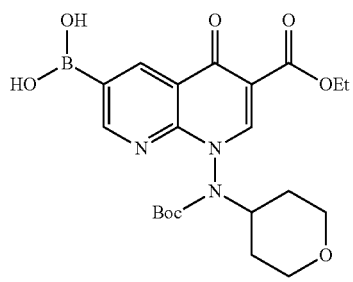 [SMILES: CCOC(=O)c1cn(N(C(=O)OC(C)(C)C)C2CCOCC2)c2ncc(B(O)O)cc2c1=O]

The titled compound was synthesized according to the following scheme:

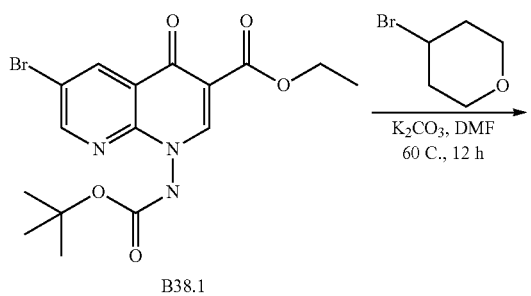

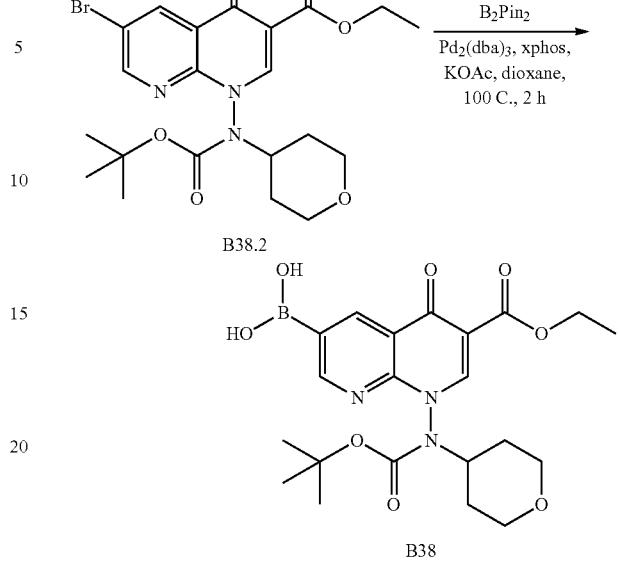

Step (a) Ethyl (Z)-2-(5-bromo-2-fluoro-pyridine-3-carbonyl)-3-(dimethylamino)prop-2-enoate (Compound B38.1)

Compound B38.1 was prepared in analogy to compound B4.2 by replacing (1-ethylpyrrolidin-2-yl)methanamine with tert-butyl hydrazinecarboxylate in step (b). MS (ESI): 415.0 ([{$^{81}$Br}M+H]$^+$), 412.0 ([{$^{79}$Br}M+H]$^+$)

Step (b) Ethyl 6-bromo-1-((tert-butoxycarbonyl)(tetrahydro-2H-pyran-4-yl)amino)-4-oxo-1,4-dihydro-1,8-naphthyridine-3-carboxylate (Compound B38.2)

To a stirred solution of ethyl 6-bromo-1-(tert-butoxycarbonylamino)-4-oxo-1,8-naphthyridine-3-carboxylate (compound B38.1, 540.0 mg, 1.31 mmol) and 4-bromo-tetrahydropyran (1.08 g, 6.55 mmol) in DMF (20 mL) was added potassium carbonate (905.1 mg, 6.55 mmol) under nitrogen atmosphere. The mixture was stirred at 70° C. for 24 h before it was cooled back to room temperature and filtered. The filtrate was concentrated in vacuo to give a crude product, which was then purified by Prep-HPLC to give ethyl 6-bromo-1-[tert-butoxycarbonyl(tetrahydropyran-4-yl)amino]-4-oxo-1,8-naphthyridine-3-carboxylate (530 mg, 77% yield) as a brown solid. MS (ESI): 498.1 ([{$^{81}$Br}M+H]$^+$), 496.1 ([{$^{79}$Br}M+H]$^+$).

Step (c) (8-((tert-Butoxycarbonyl)(tetrahydro-2H-pyran-4-yl)amino)-6-(ethoxycarbonyl)-5-oxo-5,8-dihydro-1,8-naphthyridin-3-yl)boronic acid (Intermediate B38)

To a stirred solution of B$_2$Pin$_2$ (429.7 mg, 1.69 mmol), ethyl 6-bromo-1-[tert-butoxycarbonyl (tetrahydropyran-4-yl)amino]-4-oxo-1,8-naphthyridine-3-carboxylate (compound B1095.2, 420.0 mg, 0.850 mmol), Xphos (80.6 mg, 0.170 mmol, 0.200 eq) and Pd$_2$(dba)$_3$ (77.49 mg, 0.080 mmol) in 1,4-dioxane (15 mL), was added AcOK (0.16 mL, 2.54 mmol) under N$_2$. The reaction mixture was stirred at 100° C. for 4 h until starting material was consumed completely. The reaction mixture was cooled to room temperature and concentrated in vacuo. The residue was resuspended in H₂O (50 mL) and extracted with DCM (20 mL) three times. The combined organic layer was concentrated under reduced pressure to give a crude product, which was purified by Prep-HPLC to give [8-[tert-butoxycarbonyl(tetrahydropyran-4-yl)amino]-6-ethoxycarbonyl-5-oxo-1,8-naphthyridin-3-yl]boronic acid (230.0 mg, 57% yield) as a yellow solid. MS (ESI): 462.2 ([M+H]$^+$).

Intermediate B39

[6-Ethoxycarbonyl-8-(3-hydroxy-1-methyl-propyl)-5-oxo-1,8-naphthyridin-3-yl] boronic acid

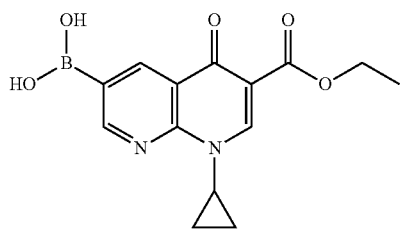 [SMILES: CCOC(=O)c1cn(C2CC2)c2ncc(B(O)O)cc2c1=O]

The title compound was prepared in analogy to Intermediate B36 by replacing oxazol-5-ylmethanamine (compound B36.1) with cyclopropanamine, and using triethylamine as base in step (a). MS (ESI): 303.2 ([M+H]$^+$).

Intermediate B40

Ethyl 1-((tert-butoxycarbonyl)(cyclopropyl)amino)-4-oxo-6-(4,4,5,5-tetramethyl-1,3,2-dioxaborolan-2-yl)-1,4-dihydro-1,8-naphthyridine-3-carboxylate

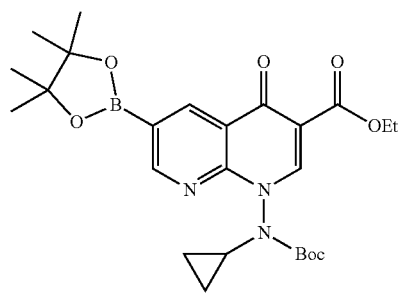 [SMILES: CCOC(=O)c1cn(N(C(=O)OC(C)(C)C)C2CC2)c2ncc(B3OC(C)(C)C(C)(C)O3)cc2c1=O]

The title compound was prepared in analogy to Intermediate B1 by replacing 2-methyl-1-pyrrolidin-1-yl-propan-2-amine (compound B1.2) with tert-butyl 1-cyclopropylhydrazinecarboxylate in step (c). MS (ESI): 418.1 ([M+H]$^+$)

Intermediate B41

[6-Ethoxycarbonyl-8-(3-hydroxy-1-methyl-propyl)-5-oxo-1,8-naphthyridin-3-yl] boronic acid

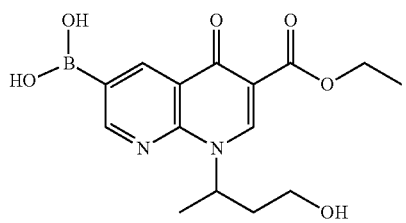 [SMILES: CCOC(=O)c1cn(C(C)CCO)c2ncc(B(O)O)cc2c1=O]

The title compound was prepared in analogy to Intermediate B36 by replacing oxazol-5-ylmethanamine (compound B36.1) with 3-aminobutan-1-ol, and using triethylamine as base in step (a). MS (ESI): 335.1 ([M+H]$^+$).

Intermediate B42

(6-(Ethoxycarbonyl)-8-((1-hydroxycyclopropyl)methyl)-5-oxo-5,8-dihydro-1,8-naphthyridin-3-yl) boronic acid

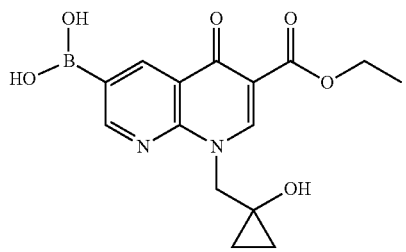 [SMILES: CCOC(=O)c1cn(CC2(O)CC2)c2ncc(B(O)O)cc2c1=O]

The title compound was prepared in analogy to Intermediate B36 by replacing oxazol-5-ylmethanamine (compound B36.1) with 1-(aminomethyl)cyclopropanol in step (a). MS (ESI): 333.2 ([M+H]$^+$).

Intermediate B43

(6-(Ethoxycarbonyl)-8-(2-morpholinoethyl)-5-oxo-5,8-dihydro-1,8-naphthyridin-3-yl)boronic acid

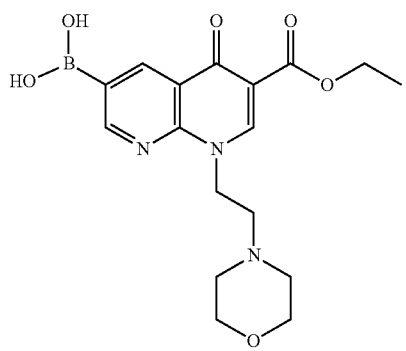 [SMILES: CCOC(=O)c1cn(CCN2CCOCC2)c2ncc(B(O)O)cc2c1=O]

The title compound was prepared in analogy to Intermediate B4 by replacing (1-ethylpyrrolidin-2-yl)methanamine (compound B4.1) with 2-morpholinoethanamine in step (b). MS (ESI): 376.0 ([M+H]+).

Intermediate B44

(6-(Ethoxycarbonyl)-5-oxo-8-(2-(3-oxopiperazin-1-yl)ethyl)-5,8-dihydro-1,8-naphthyridin-3-yl)boronic acid

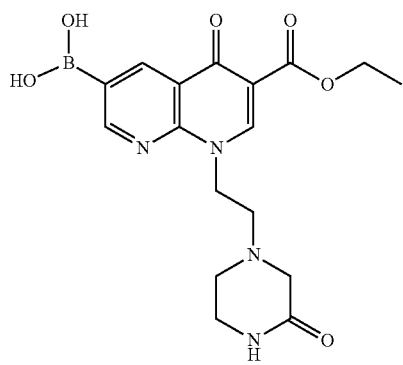 [SMILES: CCOC(=O)c1cn(CCN2CCNC(=O)C2)c2ncc(B(O)O)cc2c1=O]

The titled compound was synthesized according to the following scheme:

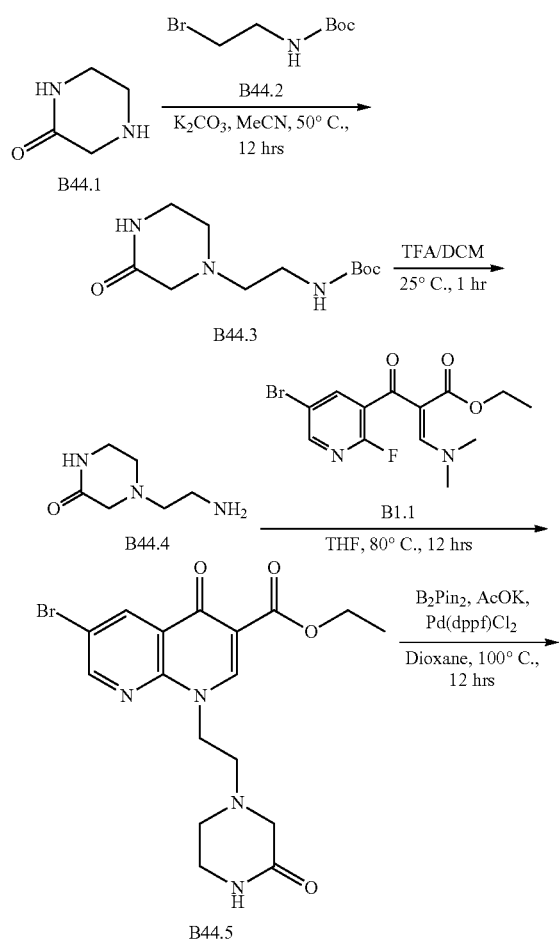

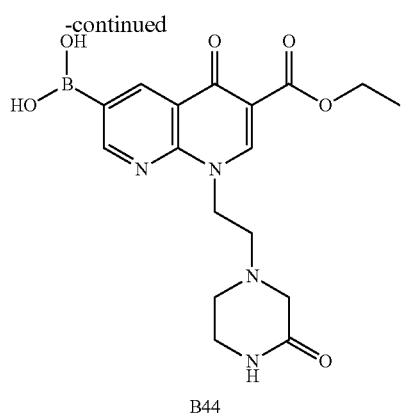

B44

Step (a) tert-Butyl (2-(3-oxopiperazin-1-yl)ethyl)carbamate (Compound B44.3)

To a stirred solution of piperazin-2-one (compound B44.1, 4.5 g, 44.95 mmol) and $K_2CO_3$ (12.42 g, 89.89 mmol) in MeCN (100 mL) was added tert-butyl N-(2-bromoethyl (compound B44.2, 10.07 g, 44.95 mmol) and the resulting mixture was heated to 50° C. and stirred at this temperature for 12 h. After cooling to room temperature, the mixture was filtered and the filtrate was concentrated in vacuo to give a crude product, which was purified by silica gel flash chromatography (0-10% MeOH in DCM) to give tert-butyl (2-(3-oxopiperazin-1-yl)ethyl)carbamate (8.7 g, yield: 67.54%) as light-yellow oil. $^1$H NMR (400 MHz, CDCl$_3$) δppm: 6.56 (s, 1H), 4.96 (s, 1H), 3.40-3.38 (m, 2H), 3.28-3.26 (m, 2H), 3.16 (s, 2H), 2.70 (t, J=5.6 Hz, 2H), 2.56 (t, J=6.0 Hz, 2H), 1.46 (s, 9H).

Step (b) 4-(2-Aminoethyl)piperazin-2-one (Compound B44.4)

To a solution of tert-butyl (2-(3-oxopiperazin-1-yl)ethyl) carbamate (compound B44.3, 2.0 g, 8.22 mmol) in DCM (85.0 mL) was added TFA (4.7 mL) at 0° C. The mixture was then warmed up to 25° C. and stirred for 1 h before it was concentrated under reduced pressure to give a residue. The residue was diluted with MeOH (50 mL) and adjusted to pH=8~9 with basic resin. The mixture was filtered and the filtrate was concentrated in vacuo to give 4-(2-aminoethyl) piperazin-2-one (1.0 g, yield: 71.01%) as a white solid. $^1$H NMR (400 MHz, MeOD-d$^4$) δppm: 3.38-3.36 (t, J=5.2 Hz, 2H), 3.18 (s, 2H), 3.10-3.08 (m, 2H), 2.77-2.71 (m, 4H).

Step (c) Ethyl 6-bromo-4-oxo-1-(2-(3-oxopiperazin-1-yl)ethyl)-1,4-dihydro-1,8-naphthyridine-3-carboxylate (Compound B44.5)

The title compound was prepared in analogy to Intermediate B4 by replacing (1-ethylpyrrolidin-2-yl)methanamine (compound B4.1) with 4-(2-aminoethyl)piperazin-2-one (compound B1201.4), and reaction temperature at 80° C. for 12 h in step (b). MS (ESI): 424.9 ([{$^{81}$Br}M+H]+), 423.0 ([{$^{79}$Br}M+H]+).

Step (d) (6-(Ethoxycarbonyl)-5-oxo-8-(2-(3-oxopiperazin-1-yl)ethyl)-5,8-dihydro-1,8-naphthyridin-3-yl)boronic acid (Intermediate B44)

The title compound was prepared in analogy to Intermediate B4, with reaction temperature at 100° C. for 12 h in step (c). ¹H NMR (400 MHz, DMSO-d⁶) δppm: 9.05 (d, J=2.0 Hz, 1H), 8.96 (d, J=2.0 Hz, 1H), 8.80 (s, 1H), 4.67 (m, 2H), 4.27-4.21 (m, 2H), 3.10 (s, 3H), 3.01 (s, 2H), 2.74-2.50 (m, 4H), 1.29 (t, J=7.2 Hz, 3H).

Intermediate B45

(8-((tert-Butoxycarbonyl)(2,2,2-trifluoroethyl)amino)-6-(ethoxycarbonyl)-5-oxo-5,8-dihydro-1,8-naphthyridin-3-yl)boronic acid

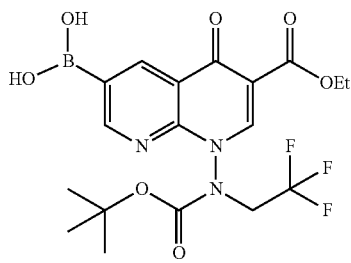 [SMILES: CCOC(=O)c1cn(N(CC(F)(F)F)C(=O)OC(C)(C)C)c2ncc(B(O)O)cc2c1=O]

The title compound was prepared in analogy to Intermediate B38 by replacing 4-bromo-tetrahydropyran with 2-bromo-1,1,1-trifluoroethane in step (b). MS (ESI): 460.1 ([M+H]⁺).

Intermediate B46

(S)-Ethyl 1-(1-(tert-butoxycarbonyl)pyrrolidin-3-yl)-4-oxo-6-(4,4,5,5-tetramethyl-1,3,2-dioxaborolan-2-yl)-1,4-dihydro-1,8-naphthyridine-3-carboxylate

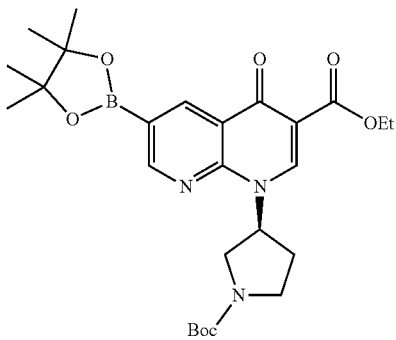 [SMILES: CCOC(=O)c1cn([C@H]2CCN(C(=O)OC(C)(C)C)C2)c2ncc(B3OC(C)(C)C(C)(C)O3)cc2c1=O]

The title compound was prepared in analogy to Intermediate B17 by replacing (R)-tert-butyl 3-aminopyrrolidine-1-carboxylate with (S)-tert-butyl 3-aminopyrrolidine-1-carboxylate in step (b). MS (ESI): 432.1 ([M-82+H]⁺).

Intermediate B47

[8-[(2,2-Dimethyl-1,3-dioxolan-4-yl)methyl]-6-ethoxycarbonyl-5-oxo-1,8-naphthyridin-3-yl]boronic acid

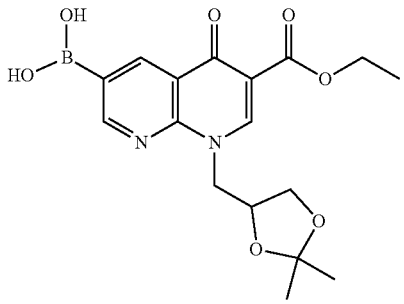 [SMILES: CCOC(=O)c1cn(CC2COC(C)(C)O2)c2ncc(B(O)O)cc2c1=O]

The title compound was prepared in analogy to Intermediate B1 by replacing 2-methyl-1-pyrrolidin-1-yl-propan-2-amine (compound B1.2) with (2,2-dimethyl-1,3-dioxolan-4-yl)methanamine in step (c). MS (ESI): 377.2 ([M+H]⁺)

Intermediate B48

Ethyl 6-bromo-1-((tert-butoxycarbonyl)(2,2,2-trifluoroethyl)amino)-4-oxo-1,4-dihydro-1,8-naphthyridine-3-carboxylate

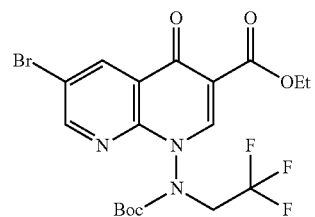 [SMILES: CCOC(=O)c1cn(N(CC(F)(F)F)C(=O)OC(C)(C)C)c2ncc(Br)cc2c1=O]

The titled compound was synthesized according to the following scheme:

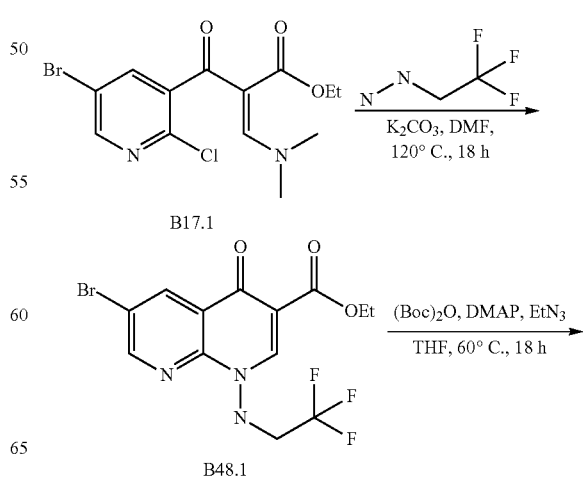

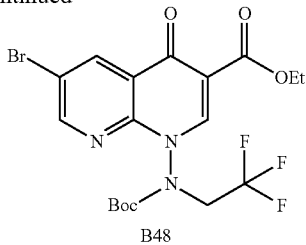

Step (a) Ethyl 6-bromo-4-oxo-1-((2,2,2-trifluoroethyl)amino)-1,4-dihydro-1,8-naphthyridine-3-carboxylate (Compound B48.1)

To a solution of ethyl 2-(5-bromo-2-chloronicotinoyl)-3-(dimethylamino)acrylate in DMF (5 mL) was added 2,2,2-trifluoroethylhydrazine (0.16 g, 1.38 mmol) and K$_2$CO$_3$ (573.3 mg, 4.15 mmol). The resulting mixture was stirred at 120° C. for 18 h before it was cooled back to room temperature. The mixture was poured into water (200 mL) and extracted by EtOAc (100 mL) three times. The combined organic layer was washed with brine (100 mL) twice, dried over anhy. Na$_2$SO$_4$, filtered, concentrated in vacuo to give a crude product, which was recrystallized in EtOAc (20 mL) to give ethyl 6-bromo-4-oxo-1-((2,2,2-trifluoroethyl)amino)-1,4-dihydro-1,8-naphthyridine-3-carboxylate (100.0 mg, 18.35% yield) as a white solid. MS (ESI): 394.1 ([{$^{79}$Br}M+H]$^+$), 396.0 ([{$^{81}$Br}M+H]$^+$).

Step (b) Ethyl 6-bromo-1-((tert-butoxycarbonyl)(2,2,2-trifluoroethyl)amino)-4-oxo-1,4-dihydro-1,8-naphthyridine-3-carboxylate (Intermediate B48)

To a stirred solution of ethyl 6-bromo-4-oxo-1-((2,2,2-trifluoroethyl)amino)-1,4-dihydro-1,8-naphthyridine-3-carboxylate (compound B4003A.1, 100.0 mg, 0.250 mmol) in DCM (5 mL) was added Et$_3$N (37.0 mg, 0.370 mmol) and (Boc)$_2$O (276.8 mg, 1.27 mmol). The resulting mixture was stirred at 15° C. for 15 h until LCMS showed the reaction was completed. The reaction mixture was then concentrated to dryness under reduced pressure and the residue was purified by silica gel flash chromatography (10% EtOAc in hexane) to give ethyl 6-bromo-1-((tert-butoxycarbonyl)(2,2,2-trifluoroethyl)amino)-4-oxo-1,4-dihydro-1,8-naphthyridine-3-carboxylate (50.0 mg, 39.87% yield) as a yellow solid. MS (ESI): 494.1 ([{$^{79}$Br}M+H]$^+$), 496.0 ([{$^{81}$Br}M+H]$^+$)

Intermediate C1 tert-Butyl N-[[3-(trifluoromethyl)-1H-pyrazol-4-yl]methyl]carbamate

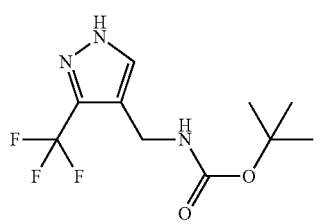 [SMILES: CC(C)(C)OC(=O)NCc1c[nH]nc1C(F)(F)F]

The titled compound was synthesized according to the following scheme:

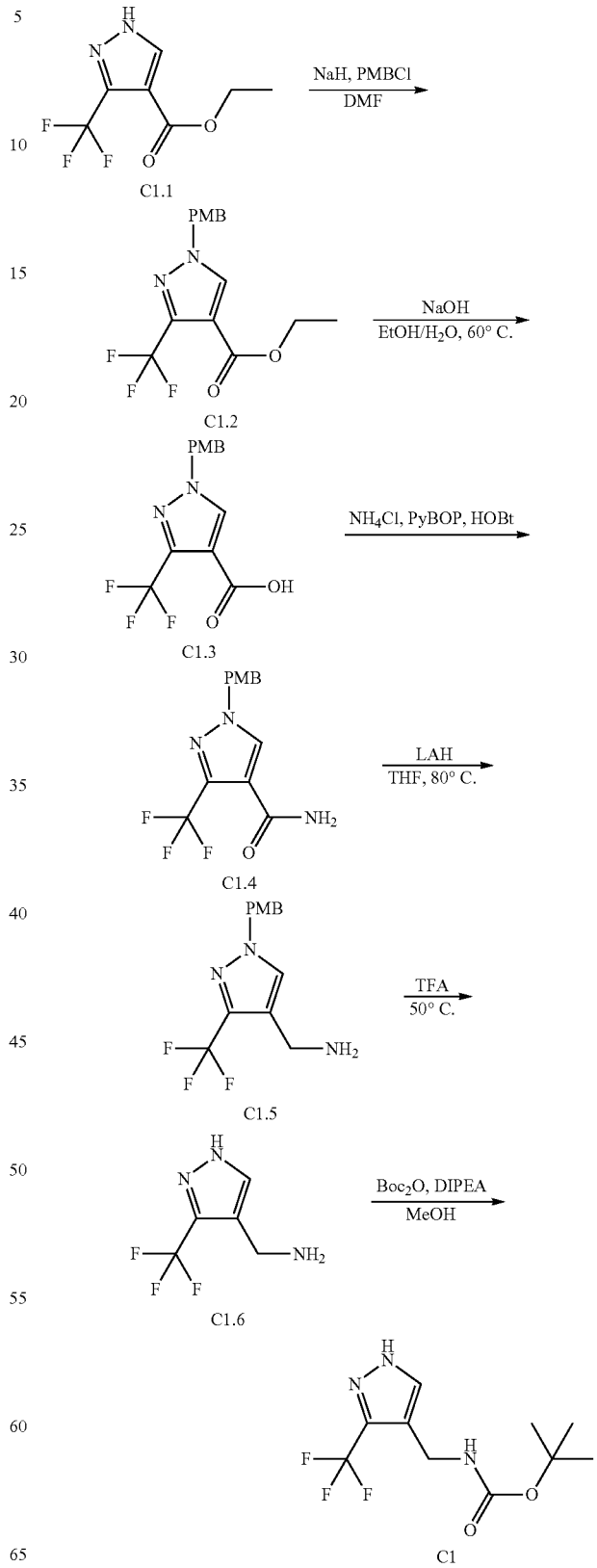

Step (a) Preparation of ethyl 1-[(4-methoxyphenyl)methyl]-3-(trifluoromethyl)pyrazole-4-carboxylate (Compound C1.2)

To a stirred solution of ethyl 3-(trifluoromethyl)-1H-pyrazole-4-carboxylate (compound C1.1, 4.0 g, 19.2 mmol) in dry DMF (50.0 mL) was added NaH (1.5 g, 38.5 mmol) at 0° C. and stirred at 0° C. for 1 h before a solution of PMBCl (3.6 g, 23.1 mmol) in DMF was added. The reaction was then warmed up to room temperature and stirred for 3 h. It was then poured into water (100 mL), and extracted with EtOAc (200 mL) twice. The combined organic layer was dried over anhy. $Na_2SO_4$, filtered, and concentrated in vacuo to give a crude product, which was then purified by silica gel flash chromatography (petroleum ether:EtOAc=20:1-5:1) to give ethyl 1-[(4-methoxyphenyl)methyl]-3-(trifluoromethyl)pyrazole-4-carboxylate (3.8 g, 60% yield) as a yellow solid. MS (ESI): 329.2 ([M+H]$^+$).

Step (b) Preparation of 1-[(4-methoxyphenyl)methyl]-3-(trifluoromethyl)pyrazole-4-carboxylic acid (Compound C1.3)

A stirred mixture solution of ethyl 1-[(4-methoxyphenyl)methyl]-3-(trifluoromethyl)pyrazole-4-carboxylate (3.8 g, 11.3 mmol) and NaOH (9.0 g, 225 mmol) in EtOH (30.0 mL) and water (15.0 mL) was stirred at 60° C. for 2 h. After the reaction was cooled to room temperature, HCl (28% in water) was added dropwise to the mixture and adjust pH=3. The reaction mixture was then concentrated in vacuo. The residue was re-dissolved in EtOAc (100 mL) and washed with water (100 mL). The separated organic layer was dried over anhy. $Na_2SO_4$, filtered, and concentrated in vacuo. Further drying under high vacuum gave 1-[(4-methoxyphenyl)methyl]-3-(trifluoromethyl)pyrazole-4-carboxylic acid (3.3 g, 97% yield) as a yellow solid. MS (ESI): 301.2 ([M+H]$^+$).

Step (c) Preparation of 1-[(4-methoxyphenyl)methyl]-3-(trifluoromethyl)pyrazole-4-carboxamide (compound C1.4)

A mixture solution of 1-[(4-methoxyphenyl)methyl]-3-(trifluoromethyl)pyrazole-4-carboxylic acid (3.2 g, 10.7 mmol), $NH_4Cl$ (2.85 g, 53.3 mmol), HOBt (1.73 g, 12.8 mmol), PyBOP (6.66 g, 12.8 mmol), and DIPEA (8.25 g, 64.0 mmol) in DMF (30.0 mL) was stirred at 30° C. under $N_2$ atmosphere for 1 h. Then, the reaction mixture was poured into water (100.0 mL) and extracted with EtOAc (100 mL) three times. The combined organic layer was dried over anhy. $Na_2SO_4$, filtered, and concentrated in vacuo to give a crude product, which was then purified by Prep-HPLC to give 1-[(4-methoxyphenyl)methyl]-3-(trifluoromethyl)pyrazole-4-carboxamide (3.0 g, 94% yield) as yellow oil. MS (ESI): 300.2 ([M+H]$^+$).

Step (d) Preparation of [1-[(4-methoxyphenyl)methyl]-3-(trifluoromethyl)pyrazol-4-yl]methanamine (Compound C1.5)

To a stirred solution of 1-[(4-methoxyphenyl)methyl]-3-(trifluoromethyl)pyrazole-4-carboxamide (2.9 g, 9.7 mmol) in dry THF (25.0 mL) was added LAH (1.84 g, 48.5 mmol) at 0° C. After the addition, the reaction mixture was warmed up to 80° C. under $N_2$ atmosphere and stirred for 2 h. It was then cooled back to 0° C. and added water (1.8 mL), 15% aqueous NaOH solution (3.6 mL), and water (1.8 mL) sequentially. The mixture solution was diluted with ethyl acetate (200 mL) and filtered. The filtrate was dried over anhy. $Na_2SO_4$, filtered, and concentrated in vacuo. Further drying under high vacuum gave [1-[(4-methoxyphenyl)methyl]-3-(trifluoromethyl)pyrazol-4-yl]methanamine (2.6 g, 94% yield) as colorless oil. MS (ESI): 286.2 ([M+H]$^+$).

Step (e) Preparation of [3-(trifluoromethyl)-1H-pyrazol-4-yl]methanamine (Compound C$_{1-6}$)

To a solution of [1-[(4-methoxyphenyl)methyl]-3-(trifluoromethyl)pyrazol-4-yl]methanamine (2.5 g, 8.8 mmol) in MeCN (40 mL) and water (10.0 mL) was added ceric ammonium nitrate (19.2 g, 35.0 mmol). The resulting reaction mixture was stirred at room temperature for 2 h, and then basified to pH=9 with aq. NaOH solution and diluted with MeOH (400 mL). The reaction mixture was filtered and the filtrate was concentrated in vacuo. Further drying under high vacuum gave crude [3-(trifluoromethyl)-1H-pyrazol-4-yl]methanamine (1.5 g) as a yellow solid. It was used directly in the next step without further purification.

Step (f) Preparation of tert-butyl N-[[3-(trifluoromethyl)-1H-pyrazol-4-yl]methyl]carbamate (Intermediate C1)

A mixture solution of [3-(trifluoromethyl)-1H-pyrazol-4-yl]methanamine (1.5 g, 8.5 mmol), Boc$_2$O (2.78 g, 12.7 mmol) and DIPEA (3.28 g, 25.4 mmol) in MeOH (50.0 mL) was stirred at room temperature for 1 h. Afterwards, the reaction mixture was concentrated in vacuo poured into water (100 mL), and extracted with EtOAc (100 mL) three times. The combined organic layer was washed with brine (50 mL) twice, dried over anhy. $Na_2SO_4$, filtered, and concentrated in vacuo to give a crude product, which was purified by Prep-HPLC to give tert-butyl N-[[3-(trifluoromethyl)-1H-pyrazol-4-yl]methyl]carbamate (1.05 g, 47% yield) as a white solid. MS (ESI): 266.3 ([M+H]$^+$).

Intermediate C2 cis-1-(3,3a,4,5,6,6a-Hexahydro-2H-furo[2,3-c]pyrrol-3-yl)-N,N-dimethyl-methanamine hydrochloride

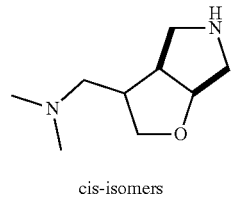

cis-isomers

The titled compound was synthesized according to the following scheme:

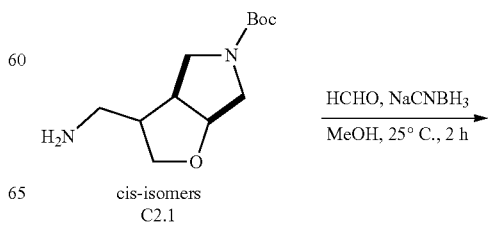

cis-isomers
C2.1

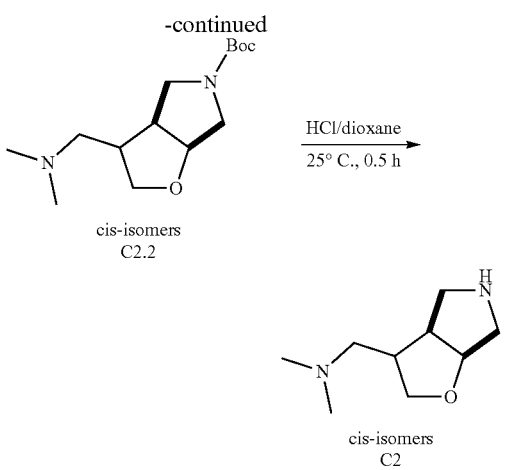

cis-isomers
C2.2

HCl/dioxane
25° C., 0.5 h cis-isomers
C2

Step (a) cis-tert-Butyl-3-[(dimethylamino)methyl]-2,3,3a,4,6,6a-hexahydrofuro[2,3-c] pyrrole-5-carboxylate (Compound C2.2)

To a stirred solution of cis-tert-butyl 3-(aminomethyl) tetrahydro-2H-furo[2,3-c]pyrrole-5(3H)-carboxylate (compound C2.1, 240 mg, 0.99 mmol) in methanol (2 mL) was added sodium cyanoborohydride (370 mg, 5.94 mmol) and paraformaldehyde (583 mg, 5.94 mmol) and the resulting mixture solution was stirred at 25° C. for 2 h. The reaction mixture was then diluted with EtOAc (50 mL), washed with water (20 mL) and brine (20 mL). The organic layer was dried over anhy. Na$_2$SO$_4$, filtered and concentrated in vacuo to give cis-tert-butyl-3-[(dimethylamino)methyl]-2,3,3a,4,6,6a-hexahydrofuro[2,3-c]pyrrole-5-carboxylate (200 mg, 74.68% yield) as light yellow oil, which was used directly in the next step without further purification. MS (ESI): 271.2 ([M+H]$^+$).

Step (b) cis-1-(3,3a,4,5,6,6a-Hexahydro-2H-furo[2,3-c]pyrrol-3-yl)-N,N-dimethyl-methanamine hydrochloride (Intermediate C2)

A solution of cis-tert-butyl-3-[(dimethylamino)methyl]-2,3,3a,4,6,6a-hexahydrofuro[2,3-c]pyrrole-5-carboxylate (compound C1092.2, 200 mg, 0.740 mmol) in HCl/dioxane (0.18 mL, 0.740 mmol) was stirred at 25° C. for 0.5 h. Afterwards, the reaction mixture was concentrated under reduced pressure to give a crude product of cis-1-(3,3a,4,5,6,6a-hexahydro-2H-furo[2,3-c]pyrrol-3-yl)-N,N-dimethyl-methanamine hydrochloride (130 mg, 85.02% yield) as a colorless gum, which was used directly in the next step without further purification.

Intermediate C3

1-(3-Fluoropyrrolidin-3-yl)-N,N-dimethylmethanamine hydrochloride

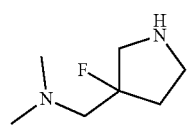

The titled compound was synthesized according to the following scheme:

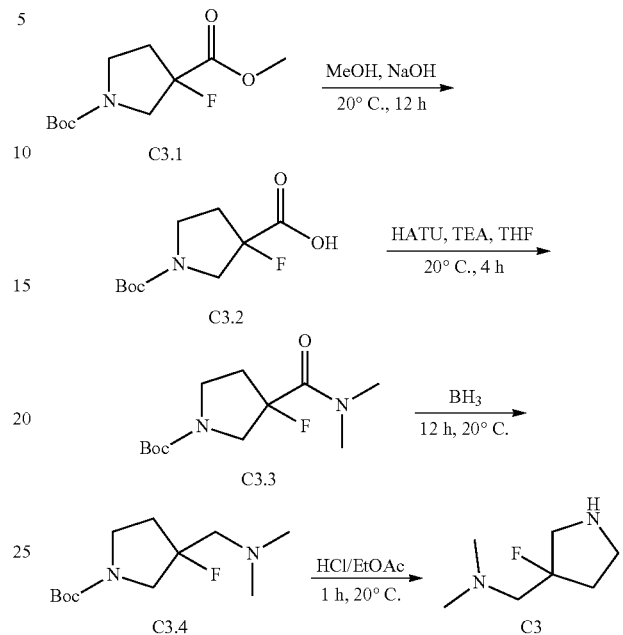

Step (a) Preparation of 1-(tert-butoxycarbonyl)-3-fluoropyrrolidine-3-carboxylic acid (Compound C3.2)

To a solution of 1-tert-butyl 3-methyl 3-fluoropyrrolidine-1,3-dicarboxylate (3.5 g, 14.2 mmol) in methanol (10.0 mL) and water (2.0 mL) was added sodium hydroxide (1.7 g, 42.5 mmol), and the reaction mixture was stirred at 20° C. for 12 h. Afterwards, the mixture was diluted with DCM (100 mL), adjusted pH=3.0 with aq. HCl solution (2 M in water), and extracted with DCM (100 mL). The separated organic layer was dried over anhy. Na$_2$SO$_4$, filtered, and concentrated in vacuo to give a crude product of 1-(tert-butoxycarbonyl)-3-fluoropyrrolidine-3-carboxylic acid (3.2 g, 13.7 mmol, 96.9% yield) as a white solid, which was used directly in the next step without further purification. MS (ESI): 329.2 ([M+H]$^+$).

Step (b) Preparation of tert-butyl 3-(dimethylcarbamoyl)-3-fluoropyrrolidine-1-carboxylate (Compound C3.3)

A mixture solution of 1-(tert-butoxycarbonyl)-3-fluoropyrrolidine-3-carboxylic acid (2.9 g, 12.4 mmol, 1.0 eq), HATU (6.1 g, 16.2 mmol, 1.3 eq), dimethylamine hydrochloride (5.1 g, 62.2 mmol, 5.0 eq) and DIPEA (6.5 mL, 37.3 mmol, 3.0 eq) in anhydrous THF (10.0 mL) was stirred at 20° C. for 4 h Afterwards, the mixture was diluted with DCM (100 mL), poured into water (50 mL), and extracted with DCM (100 mL). The separated organic layer was washed with brine (50 mL), dried over anhy. Na$_2$SO$_4$, filtered, and concentrated in vacuo to give a crude product of tert-butyl 3-(dimethylcarbamoyl)-3-fluoropyrrolidine-1-carboxylate (1.9 g, 7.2 mmol, 57.5% yield) as colorless oil, which was used directly in the next step without further purification. MS (ESI): 205.1 ([M+H-tBu]$^+$).

Step (c) Preparation of tert-butyl 3-((dimethyl-amino)methyl)-3-fluoropyrrolidine-1-carboxylate (Compound C3.4)

To a stirred solution of tert-butyl 3-(dimethylcarbamoyl)-3-fluoropyrrolidine-1-carboxylate (1.8 g, 6.9 mmol) in anhydrous THF (8.0 mL) was added borane-methyl sulfide complex (10 M in dimethylsulfane, 8.0 mL, 80.0 mmol) at 0° C. The reaction mixture was then warmed up to 20° C. and stirred at 20° C. for 12.0 h. The mixture was poured into ice-MeOH (100 mL) and stirred for 1 h before it was concentrated in vacuo to give a crude product of tert-butyl 3-((dimethylamino)methyl)-3-fluoropyrrolidine-1-carboxylate (1.2 g, 4.9 mmol, 70.5% yield) as colorless oil, which was used directly in the next step without further purification. MS (ESI): 247.1 ([M+H]$^+$).

Step (d) Preparation of 1-(3-fluoropyrrolidin-3-yl)-N,N-dimethylmethanamine hydrochloride (Intermediate C3)

A mixture solution of tert-butyl 3-((dimethylamino)methyl)-3-fluoropyrrolidine-1-carboxylate (1.2 g, 4.9 mmol) in HCl/ethyl acetate (10.0 mL, 40.0 mmol) was stirred at 20° C. for 2 h. Afterwards, The reaction mixture was concentrated under reduced pressure to give a crude product, which was recrystallized from (MeOH:EtOAc=1:10, 10.0 mL) to give 1-(3-fluoropyrrolidin-3-yl)-N,N-dimethylmethanamine hydrochloride (0.9 g, 4.2 mmol, 85.2% yield) as a white solid. MS (ESI): 147.1 ([M+H]$^+$).

Intermediate C4

N,N-dimethyl-1-(3-piperidyl) methanamine hydrochloride

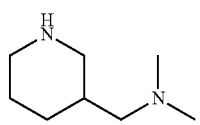

The titled compound was synthesized according to the following scheme:

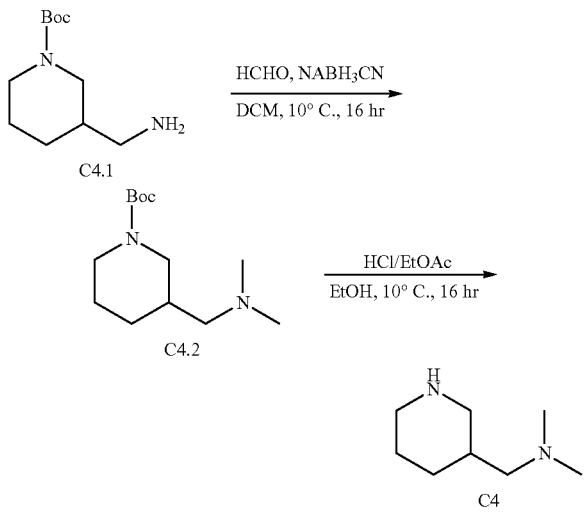

Step (a) tert-Butyl 3-[(dimethylamino) methyl] piperidine-1-carboxylate (Compound C4.2)

To a stirred solution of tert-butyl 3-(aminomethyl)piperidine-1-carboxylate (compound C4.1, 5.0 g, 23.33 mmol) in DCM (50 mL) was added formaldehyde (9.47 g, 116.65 mmol) and sodium cyanoborohydride (7.33 g, 116.7 mmol) and the resulting mixture was stirred at 10° C. for 16 h. The mixture was then diluted with DCM (150 mL), washed with water (50 mL), brine (50 mL), dried over anhy. Na$_2$SO$_4$, filtered, and concentrated in vacuo to give a crude product, which was purified by silica gel flash chromatography (DCM:MeOH=50:1) to give tert-butyl 3-[(dimethylamino) methyl] piperidine-1-carboxylate (1.8 g, 25.47% yield) as colorless oil. MS (ESI): 243.2 ([M+H]$^+$).

Step (b) N,N-Dimethyl-1-(3-piperidyl) methanamine hydrochloride (Compound C4)

To a solution of tert-butyl 3-[(dimethylamino) methyl] piperidine-1-carboxylate (compound C4.2, 1.8 g, 7.43 mmol) in EtOAc (20 mL) was added HCl/EtOAc (5.0 mL, 4 M) and the resulting mixture was stirred at 10° C. for 16 h. The mixture solution was then concentrated in vacuo to give N,N-dimethyl-1-(3-piperidyl) methanamine hydrochloride (1.3 g, 97.95% yield) as a white solid, which was used directly in the next step without further purification. MS (ESI): 143.4 ([M+H]$^+$).

Intermediate C5 cis-5-(2-Methoxyethyl)-2,3,3a,4,6,6a-hexahydro-1H-pyrrolo[2,3-c]pyrrole

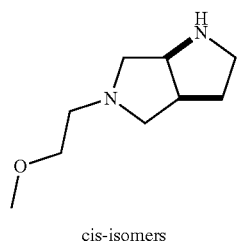

cis-isomers

The titled compound was synthesized according to the following scheme:

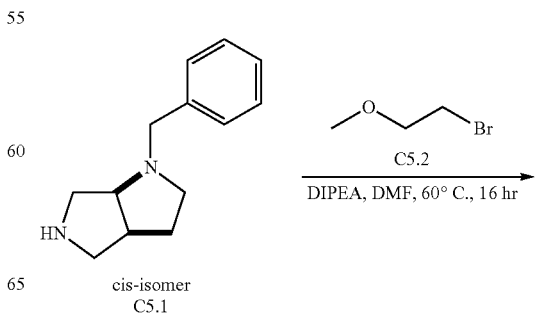

109
-continued

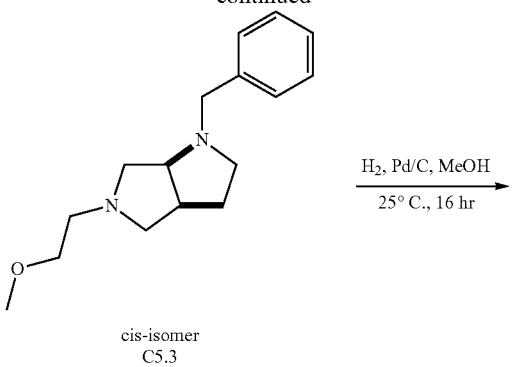

cis-isomer
C5.3

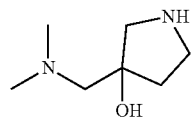

H₂, Pd/C, MeOH
25° C., 16 hr cis-isomer
C5

Step (a) cis-1-Benzyl-5-(2-methoxyethyl)-2,3,3a,4,6,6a-hexahydropyrrolo[2,3-c]pyrrole (Compound C5.3)

To a stirred solution of cis-1-benzyl-3,3a,4,5,6,6a-hexahydro-2H-pyrrolo[2,3-c]pyrrole (compound C5.1, 500 mg, 2.47 mmol) in DMF (5 mL) was added N,N-diisopropylethylamine (959 mg, 7.42 mmol) and 2-bromoethyl methyl ether (compound C5.2, 412 mg, 2.96 mmol) and the resulting mixture solution was stirred at 60° C. for 16 h. After cooled back to room temperature, the reaction mixture was diluted with EtOAc (80 mL), washed with water (30 mL), brine (30 mL) three times, dried over anhy. Na₂SO₄, filtered, and concentrated in vacuo to give a crude product, which was then purified by Prep-TLC (petroleum ether:EtOAc=3:1) to give cis-1-benzyl-5-(2-methoxyethyl)-2,3,3a,4,6,6a-hexahydropyrrolo[2,3-c]pyrrole (3) (350 mg, 53.3% yield) as yellow oil. MS (ESI): 261.1 ([M+H]⁺).

Step (b) cis-5-(2-Methoxyethyl)-2,3,3a,4,6,6a-hexahydro-1H-pyrrolo[2,3-c]pyrrole (Intermediate C5)

To a stirred solution of cis-1-benzyl-5-(2-methoxyethyl)-2,3,3a,4,6,6a-hexahydropyrrolo[2,3-c]pyrrole (compound C5.3, 350 mg, 1.34 mmol) in methanol (5 mL) was added palladium (100 mg, 0.47 mmol) under N₂ atmosphere. After suspension was degassed and purged with H₂ for 3 times, the reaction mixture was stirred under H₂ (760 mmHg) at 25° C. for 16 h. The mixture was then filtered and the filtrate was concentrated in vacuo to give cis-5-(2-methoxyethyl)-2,3,3a,4,6,6a-hexahydro-1H-pyrrolo[2,3-c]pyrrole (120 mg, 52.43% yield) as yellow oil, which was used directly in the next step without further purification.

110

Intermediate C6

3-((Dimethylamino)methyl)pyrrolidin-3-ol

The titled compound was synthesized according to the following scheme: NaH, DMSO Dimethylamine

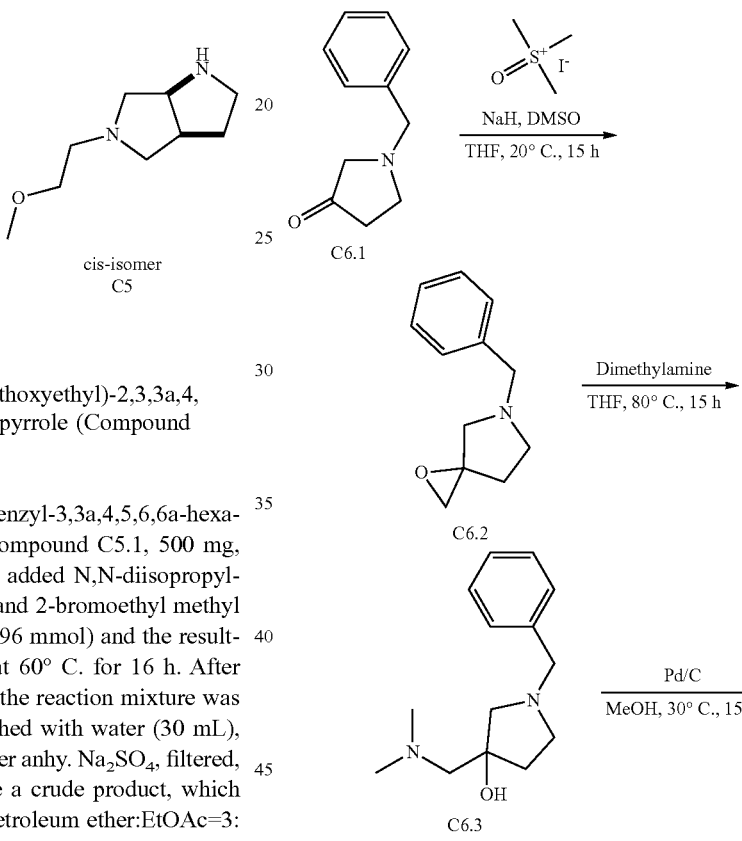

Step (a) Preparation of 5-benzyl-1-oxa-5-azaspiro[2.4]heptane (Compound C6.2)

To a stirred solution of trimethylsulfoxonium iodide (2.5 g, 11.4 mmol) in DMSO (20 mL) was added NaH (328.7 mg, 13.7 mmol) at 0° C. The resulting mixture was stirred at 0° C. for 1 h before 1-benzyl-3-pyrrolidinone (2.0 g, 11.4 mmol) was added. The resulting mixture was stirred at 20° C. for additional 15 h until TLC (petroleum ether:EtOAc=3:1) showed the reaction was completed. Water (50 mL) was added and the resulting mixture was extracted with EtOAc (20 mL) three times. The combined organic layer was washed with brined, dried over anhy. Na₂SO₄, filtered and concentrated in vacuo to give a crude product, which was purified by silica gel flash chromatography (petroleum ether: EtOAc=from 5:1 to 3:1) to give 5-benzyl-1-oxa-5-azaspiro [2.4]heptane (800 mg, 37.04% yield) as yellow oil. ¹H NMR (400 MHz, CHLOROFORM-d) δ 7.40-7.31 (m, 4H), 7.30-7.24 (m, 1H), 4.14 (q, J=7.2 Hz, 1H), 3.72-3.60 (m, 2H), 2.89-2.85 (m, 2H), 2.85-2.77 (m, 2H), 2.77-2.68 (m, 1H), 2.61 (d, J=10.7 Hz, 1H), 2.22 (td, J=7.2, 14.1 Hz, 1H), 2.00-1.88 (m, 1H).

Step (b) Preparation of 1-benzyl-3-((dimethylamino)methyl)pyrrolidin-3-ol (Compound C6.3)

To a solution of 5-benzyl-1-oxa-5-azaspiro[2.4]heptane (800 mg, 4.23 mmol) in water (5 mL) was added dimethylamine in water (10.0 mL, 42.27 mmol). The resulting mixture was stirred at 80° C. for 15 h until TLC (petroleum ether:EtOAc=5:1) showed the reaction was completed. Solvent was concentrated in vacuo to give a crude product of 1-benzyl-3-((dimethylamino)methyl)pyrrolidin-3-ol (800 mg, 80.76% yield) as yellow oil, which was used directly in the next step without further purification. ¹H NMR (400 MHz, CHLOROFORM-d) δ 7.37-7.15 (m, 5H), 6.67-6.55 (m, 1H), 3.82-3.69 (m, 2H), 2.94-2.69 (m, 4H), 2.60-2.51 (m, 2H), 2.46-2.27 (m, 6H), 1.93-1.80 (m, 2H).

Step (C) Preparation of 3-((dimethylamino)methyl) pyrrolidin-3-ol (Intermediate C6)

To a stirred solution of 1-benzyl-3-((dimethylamino) methyl)pyrrolidin-3-ol (800.0 mg, 3.41 mmol) in methanol (5 mL) was added Pd/C (100.0 mg, 0.940 mmol). The resulting mixture was stirred at 30° C. for 15 h under H₂ atmosphere until TLC (DCM:MeOH=10:1) showed the starting material was fully consumed. Catalyst was filtered off and solvent was concentrated under reduced pressure to give a crude product of 3-((dimethylamino)methyl)pyrrolidin-3-ol (300 mg, 2.08 mmol, 60.94% yield) as yellow oil, which was used directly in the next step without further purification.

Intermediate C7

[8-[2-(Dimethylamino)-2-phenyl-ethyl]-6-ethoxycarbonyl-5-oxo-1,8-naphthyridin-3-yl]boronic acid

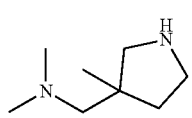

The title compound was prepared in analogy to Intermediate C3 by replacing 1-(tert-butoxycarbonyl)-3-fluoropyrrolidine-3-carboxylic acid with 1-(tert-butoxycarbonyl)-3-methylpyrrolidine-3-carboxylic acid in step (b). MS (ESI): 143.1 ([M+H]⁺).

Intermediate C8 cis-5-Methyloctahydropyrrolo[2,3-c]pyrrole

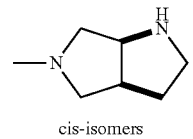

cis-isomers

The titled compound was synthesized according to the following scheme:

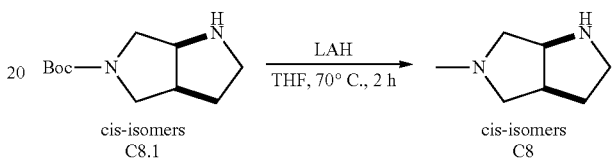

cis-isomers
C8.1 cis-isomers
C8

Step (a) Preparation of cis-5-methyloctahydropyrrolo[2,3-c]pyrrole (Intermediate C8)

To a stirred solution of LAH (4.02 g, 105.99 mmol) in THF (50 mL) was added cis-tert-butyl hexahydropyrrolo[2,3-c]pyrrole-5(1H)-carboxylate (4.5 g, 21.2 mmol) at 0° C., and the resulting reaction mixture was stirred at 70° C. for 2 h under N₂ until TLC (DCM/MeOH=10/1) showed starting material was consumed completely. The reaction mixture was then cooled back to 0° C. and quenched by the addition of H₂O (5 mL), followed by 15% aqueous NaOH solution (5 mL), H₂O (15 mL), and MgSO₄ (10 g). After being stirred at 25° C. for 1 h, the reaction mixture was filtered and the filtrate was concentrated under reduced pressure to give cis-5-methyloctahydropyrrolo[2,3-c]pyrrole (2.6 g, 20.6 mmol, 97.19% yield) as yellow oil. ¹H NMR (400 MHz, CHCl₃-d) δ ppm 3.66-3.79 (m, 1H), 2.89-3.02 (m, 1H), 2.75 (dt, J=11.19, 6.50 Hz, 1H), 2.65 (dtd, J=12.40, 8.35, 8.35, 4.39 Hz, 1H), 2.46-2.54 (m, 2H), 2.38-2.45 (m, 1H), 2.34 (dd, J=9.28, 4.14 Hz, 1H), 2.27 (s, 3H), 1.85 (ddt, J=12.42, 8.78, 6.33, 6.33 Hz, 1H), 1.45-1.56 (m, 1H), 1.43 (s, 1H), 1.21-1.31 (m, 1H).

Intermediate C9 cis-1-Methyloctahydro-1H-pyrrolo[3,4-b]pyridine

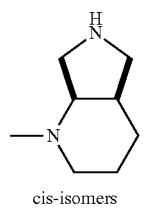

cis-isomers

The titled compound was synthesized according to the following scheme:

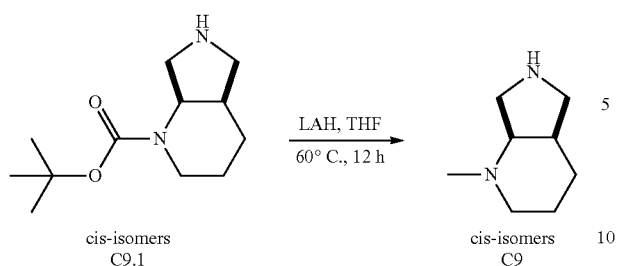

Step (a) Preparation of cis-1-methyloctahydro-1H-pyrrolo[3,4-b]pyridine (Intermediate C9)

To a solution of LAH (0.5 g, 13.3 mmol) in anhydrous THF (10.0 mL) was added cis-tert-butyl-2,3,4,4a,5,6,7,7a-octahydropyrrolo[3,4-b]pyridine-1-carboxylate (1.0 g, 4.4 mmol), and the reaction mixture was stirred at 60° C. for 2 h. The reaction mixture was diluted with THF (10.0 mL), followed by the addition of water (0.6 mL) at 0° C., and aq. NaOH solution (1.5 M, 1.2 mL). The reaction mixture was filtered, and filtrate was concentrated in vacuo to give a crude product of cis-rac-1-methyl-2,3,4,4a,5,6,7,7a-octahydropyrrolo[3,4-b]pyridine (0.6 g, 4.3 mmol, 96.8% yield) as yellow oil. It was used directly in the next step without further purification. MS (ESI): 141.1 ([M+H]$^+$).

Intermediate C10 cis-4-Methyloctahydropyrrolo[3,4-b][1,4]oxazine

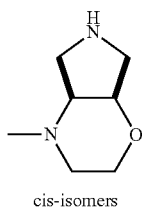

The titled compound was synthesized according to the following scheme:

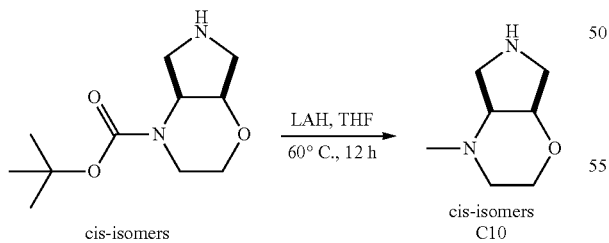

Preparation of cis-4-methyloctahydropyrrolo[3,4-b][1,4]oxazine (Intermediate C10)

To a solution of LAH (0.3 g, 8.8 mmol) in anhydrous THF (15.0 mL) was added cis-tert-butyl-3,4a,5,6,7,7a-hexahydro-2H-pyrrolo[3,4-b][1,4]oxazine-4-carboxylate (1.0 g, 4.38 mmol), and the reaction mixture was stirred at 60° C. for 2 h. The reaction mixture was diluted with THF (10.0 mL), followed by the addition of water (0.6 mL) at 0° C., and then aq. NaOH solution (1.5 M, 1.2 mL). The mixture solution was then filtered, and the filtrate was concentrated in vacuo to give a crude product of cis-4-methyl-3,4a,5,6,7,7a-hexahydro-2H-pyrrolo[3,4-b][1,4]oxazine (0.6 g, 4.2 mmol, 96.3% yield) as yellow oil, which was used directly in the next step without further purification. MS (ESI): 143.1 ([M+H]$^+$).

Intermediate C11

N-cyclopropyl-N-methylpyrrolidin-3-amine

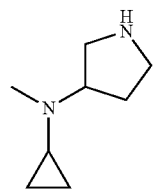

The titled compound was synthesized according to the following scheme:

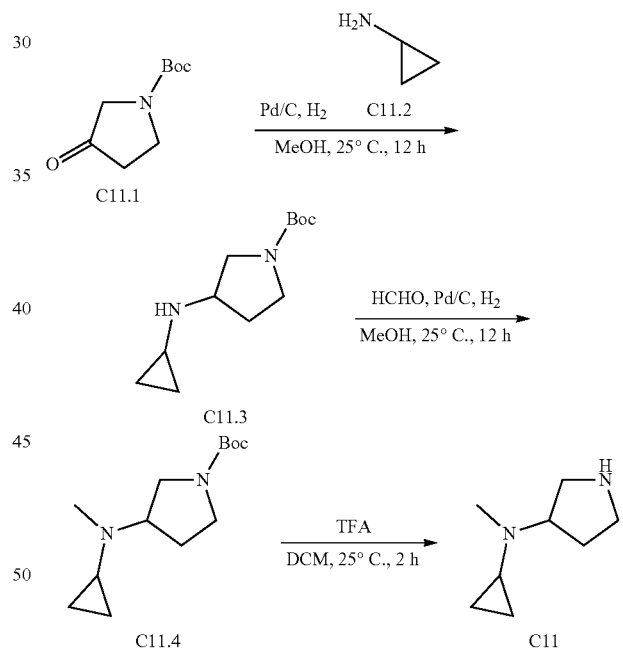

Step (a) Preparation of tert-butyl 3-(cyclopropylamino)pyrrolidine-1-carboxylate (Compound C11.3)

To a solution of tert-butyl 3-oxopyrrolidine-1-carboxylate (4.0 g, 21.6 mmol) and cyclopropanamine (9.86 g, 172.8 mmol) in MeOH (20.0 mL) was added Pd/C (2.0 g, 50% in H$_2$O).

Then the suspension was degassed under vacuum and purged with H$_2$ several times. The reaction mixture was stirred at 25° C. for 12 h under H$_2$ (20 psi) until TLC (petroleum ether:EtOAc=2:1, stained by I$_2$) showed the SM was consumed completely. The mixture was filtered and the filtrate was evaporated under reduced pressure to give a crude product of tert-butyl 3-(cyclopropylamino)pyrrolidine-1-carboxylate (4.5 g, yield: 92.07%) as pale yellow oil, which was used directly in the next step without further purification. MS (ESI): 227.1 ([M+H]$^+$), 171.1 ([{M-56}+H]$^+$).

Step (b) Preparation of tert-butyl 3-(cyclopropyl (methyl)amino)pyrrolidine-1-carboxylate (Compound C11.4)

To a solution of tert-butyl 3-(cyclopropylamino)pyrrolidine-1-carboxylate (4.5 g, 19.88 mmol) and HCHO (20.0 mL, 37% in water) in MeOH (60.0 mL) was added Palladium on carbon (2.0 g 10 wt. % loading). Then the suspension was degassed under vacuum and purged with H$_2$ several times. The reaction mixture was stirred at 25° C. for 12 h under H$_2$ (20 psi) until TLC (petroleum ether:EtOAc=2:1, stained by I$_2$) showed the SM was consumed completely. The mixture was filtered and the filtrate was evaporated under reduced pressure to give a crude product, which was purified by silica gel flash chromatography (petroleum ether: EtOAc=100:1~1:1, 0.5% NH$_3$.H$_2$O as additive) to give tert-butyl 3-(cyclopropyl(methyl)amino)pyrrolidine-1-carboxylate (3.5 g, 73.24% yield) as pale yellow oil. MS (ESI): 241.1 ([M+H]$^+$).

Step (c) Preparation of N-cyclopropyl-N-methylpyrrolidin-3-amine (compound C11)

A solution of tert-butyl 3-(cyclopropyl(methyl)amino) pyrrolidine-1-carboxylate (3.5 g, 14.56 mmol) in DCM (15 mL) was added TFA (10 mL) and the resulting reaction mixture was stirred at 25° C. for 2 h until LCMS showed starting material was consumed completely. The mixture was then concentrated under reduced pressure to dryness. The residue was re-dissolved in toluene and basified to pH=8 with aq. K$_2$CO$_3$ solution The mixture was filtered and the filtrate was concentrated in vacuo to give a crude product of N-cyclopropyl-N-methylpyrrolidin-3-amine (1.5 g, 73.46% yield), which was used directly in the next step without further purification. MS (ESI): 141.1 ([M+H]$^+$).

Intermediate C12

3a-Fluoro-5-methyloctahydropyrrolo[2,3-c]pyrrole

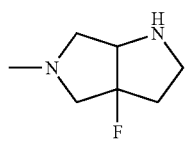

The titled compound was synthesized according to the following scheme:

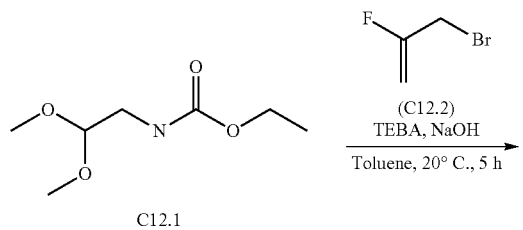

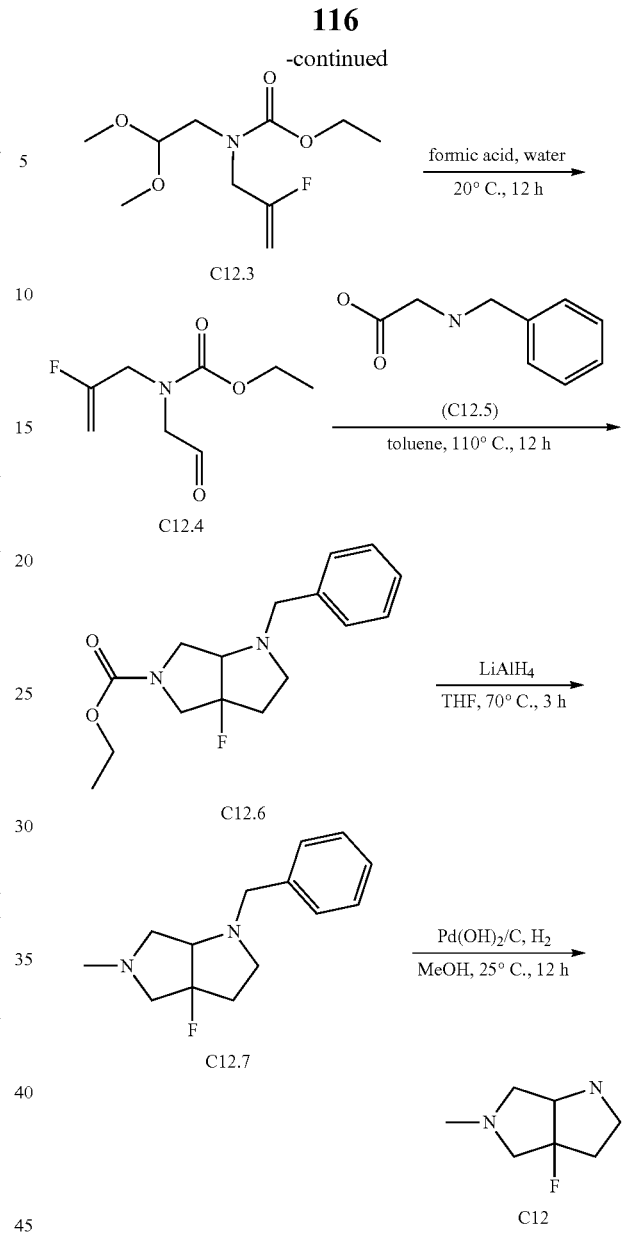

Step (a) Preparation of ethyl (2,2-dimethoxyethyl)(2-fluoroallyl) carbamate (Compound C12.3)

To a solution of ethyl (2,2-dimethoxyethyl)carbamate (3.2 g, 18.06 mmol, compound C12.1), sodium hydroxide (5.06 g, 126.42 mmol) and triethylbenzylammoniumchloride (206.0 mg, 0.903 mmol) in toluene (20.0 mL) was added 3-bromo-2-fluoroprop-1-ene (3.0 g, 21.67 mmol) at 25° C. under argon in glovebox. The resulting reaction mixture was stirred at 25° C. for 5 h under argon until TLC (petroleum ether/EtOAc=5:1, stained by I$_2$) showed the starting material was consumed completely. The mixture solution was then poured into water (100 mL) and extracted by EtOAc (300 mL) twice. The separated organic layer was washed by brine (100 mL) twice, dried with anhy. Na$_2$SO$_4$, filtered, and concentrated in vacuo to give a crude product of ethyl (2,2-dimethoxyethyl)(2-fluoroallyl)carbamate (4.0 g, 94.15% yield) as pale yellow oil, which was used directly in the next step without further purification.

Step (b) Preparation of ethyl (2-fluoroallyl)(2-oxoethyl)carbamate (Compound C12.4)

A stirred solution of ethyl (2,2-dimethoxyethyl)(2-fluoroallyl) carbamate (4.0 g, 17.0 mmol, compound C12.3) in aq. formic acid (35.0 mL, 85% in $H_2O$) was stirred at 25° C. for 2 h. After TLC (petroleum ether/EtOAc=5:1, stained by alkaline solution of $KMnO_4$) showed starting material was consumed completely, the reaction mixture was evaporated to dryness under the reduced pressure. The residue was re-dissolved in EtOAc and basified to pH=7 with aq. potassium carbonate solution The mixture solution was then filtered and the filtrate was concentrated in vacuo to give a crude product of ethyl (2-fluoroallyl)(2-oxoethyl)carbamate (3.0 g, 93.26% yield), which was used directly in the next step without further purification.

Step (c) Preparation of ethyl 1-benzyl-3a-fluorohexahydropyrrolo[2,3-c]pyrrole-5(1H)-carboxylate (compound C12.6)

A mixture solution of ethyl (2-fluoroallyl)(2-oxoethyl) carbamate (3.0 g, 15.86 mmol, compound C12.4) and 2-(benzylamino)acetic acid (2.88 g, 17.44 mmol) in toluene (75.0 mL) was stirred at 120° C. in a Dean-Stark apparatus for 24 h. After TLC (petroleum ether/EtOAc=2:1, stained by alkaline solution of KMnO4) showed starting material was consumed completely, the reaction mixture was evaporated to dryness under reduced pressure to give a crude product, which was purified by Prep-HPLC (TFA as additive) to give ethyl 1-benzyl-3a-fluorohexahydropyrrolo[2,3-c]pyrrole-5 (1H)-carboxylate (2.8 g, 60.40% yield) as pale yellow oil. MS (ESI): 293.2 ([M+H]$^+$).

Step (d) Preparation of 1-benzyl-3a-fluoro-5-methyloctahydropyrrolo[2,3-c]pyrrole (Compound C12.7)

To a stirred solution of ethyl 1-benzyl-3a-fluorohexahydropyrrolo[2,3-c]pyrrole-5(1H)-carboxylate (2.8 g, 9.58 mmol, compound C12.6) in tetrahydrofuran (30.0 mL) was added $LiAlH_4$ (1.82 g, 47.9 mmol) slowly under ice-water bath. After the addition, the resulting reaction mixture was stirred at 70° C. for 2 h before diluted with tetrahydrofuran (200 mL). To this solution was then slowly added $H_2O$ (1.82 mL), aq. NaOH solution (3.64 mL, 15% in $H_2O$) and $H_2O$ (1.82 mL) sequentially under ice-water bath. Afterwards, the mixture solution was extracted with EtOAc (300 mL), and the separated organic layer was dried over anhy. $Na_2SO_4$, filtered, and concentrated in vacuo to give a crude product of 1-benzyl-3a-fluoro-5-methyloctahydropyrrolo[2,3-c]pyrrole (2.0 g, 89.12% yield), which was used directly in the next step without further purification. MS (ESI): 235.2 ([M+H]$^+$).

Step (e) Preparation of 3a-fluoro-5-methyloctahydropyrrolo[2,3-c]pyrrole (Compound C12)

To a solution of 1-benzyl-3a-fluoro-5-methyloctahydropyrrolo[2,3-c]pyrrole (1.9 g, 8.11 mmol, compound C12.7) in MeOH (20.0 mL) was added palladium hydroxide on carbon (1.0 g 10% wt.). After the suspension was degassed under vacuum and purged with $H_2$ several times, the reaction mixture was stirred at 25° C. for 12 h under $H_2$ (20 psi). The reaction mixture was filtered through Celite and the filtrate was evaporated to dryness under reduced pressure to give a crude product of 3a-fluoro-5-methyloctahydropyrrolo[2,3-c]pyrrole (1.0 g, 85.53% yield) as pale yellow oil, which was used directly in the next step without further purification. $^1$H NMR (400 MHz, DMSO-d6) δ ppm: 3.47~3.64 (m, 1H), 2.88~3.07 (m, 2H), 2.70~2.83 (m, 1H), 2.53~2.67 (m, 2H), 2.43 (m, 1H), 2.25 (s, 3H), 2.03~2.22 (m, 1H), 1.78~1.94 (m, 2H). MS (ESI): 145.1 ([M+H]$^+$).

Intermediate C13

3a-(Fluoromethyl)-5-methyloctahydropyrrolo[2,3-c]pyrrole

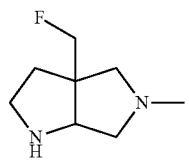

The titled compound was synthesized according to the following scheme:

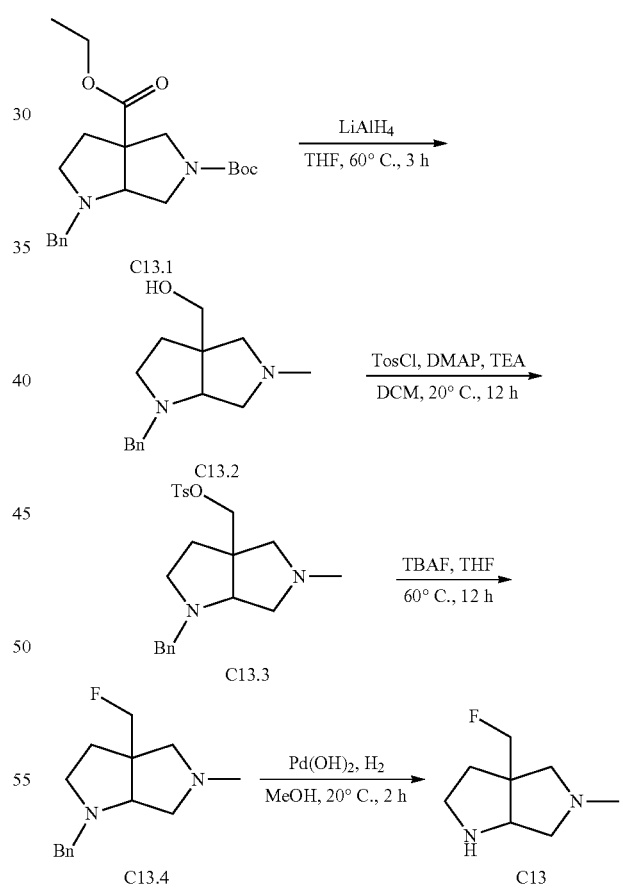

Step (a) Preparation of (1-benzyl-5-methyloctahydropyrrolo[2,3-c]pyrrol-3a-yl)methanol (Compound C13.2)

To a solution of 5-tert-butyl 3a-ethyl 1-benzylhexahydropyrrolo[2,3-c]pyrrole-3a,5(1H)-dicarboxylate (800 mg, 2.14 mmol compound C13.1) in THF (2.0 mL) was added LiAlH$_4$ (815 mg, 21.4 mmol) and the resulting reaction mixture was stirred at 60° C. for 3 h. After LCMS showed the starting material was consumed completely, the reaction was cooled down to 0° C., poured into EtOAc (10.0 mL) with addition of MgSO$_4$, and then stirred for 1 h. The mixture solution was then filtered and the filtrate was evaporated to dryness under reduced pressure to give a crude product of (1-benzyl-5-methyloctahydropyrrolo[2,3-c]pyrrol-3a-yl)methanol (450 mg) as colourless oil, which was used directly in the next step without further purification. MS (ESI): 247.1 (M+H)$^+$.

Step (b) Preparation of (1-benzyl-5-methyloctahydropyrrolo[2,3-c]pyrrol-3a-yl)methyl 4-methylbenzenesulfonate (Compound C13.3)

To a solution of (1-benzyl-5-methyloctahydropyrrolo[2,3-c]pyrrol-3a-yl)methanol (210.0 mg, 0.854 mmol compound C13.2) in DCM (1.0 mL) was added TosCl (486.6 mg, 2.56 mmol), DMAP (52.1 mg, 0.427 mmol) and TEA (258.6 mg, 2.56 mmol). The resulting reaction mixture was stirred at 20° C. for 12 h before poured into water (50 mL) and extracted with EtOAc (50 mL). The separated organic layer was then washed with aq. CaCl$_2$ solution (1N, 100 mL) twice and brine (100 mL) twice. The organic layer was dried over anhy. Na$_2$SO$_4$, filtered, and concentrated in vacuo to give a crude product, which was purified by Prep-TLC (petroleum ether:EtOAc=1:4) to give (1-benzyl-5-methyl-octahydropyrrolo[2,3-c]pyrrol-3a-yl)methyl 4-methylbenzenesulfonate (453.5 mg, 66.4% yield) as yellow oil. MS (ESI): 401.1 (M+H)$^+$ Step (c) Preparation of 1-benzyl-3a-(fluoromethyl)-5-methyloctahydropyrrolo[2,3-c]pyrrole (Compound C13.4)

To a solution of (1-benzyl-5-methyloctahydropyrrolo[2,3-c]pyrrol-3a-yl)methyl 4-methylbenzenesulfonate (447.3 mg, 1.12 mmol C13.3) in THF (10 mL) was added TBAF (11.2 mL, 11.2 mmol, 1M in THF) and the resulting reaction mixture was stirred at 60° C. for 12 h. After LCMS showed the starting material was consumed completely, the reaction mixture was poured into water (100 mL), and extracted with EtOAc (100 mL) three times. The combined organic layer was dried over anhy. Na$_2$SO$_4$, filtered, and concentrated in vacuo to give a crude product, which was purified by silica gel flash chromatography (100% EtOAc) to give 1-benzyl-3a-(fluoromethyl)-5-methyloctahydropyrrolo[2,3-c]pyrrole (205 mg, 74.0% yield) as a yellow solid. MS (ESI): 249.1 (M+H)$^+$ Step (d) Preparation of 3a-(fluoromethyl)-5-methyl-octahdropyrrolo[2,3-c]pyrrole (Intermediate C13)

To a solution of 1-benzyl-3a-(fluoromethyl)-5-methyloctahydropyrrolo[2,3-c]pyrrole (205 mg, 0.83 mmol C13.4) in MeOH was added Pd(OH)$_2$ on carbon (12 mg, 0.083 mmol, 10% w.t). After the suspension was degassed under vacuum and purged with H$_2$ several times, the reaction mixture was stirred at 60° C. for 12 h under H$_2$ (50 psi). After reaction was cooled down to room temperature, the mixture solution was filtered through Celite and the filter cake was washed with MeOH (30 mL) four times. The filtrate was evaporated to dryness under reduced pressure to give a crude product of 3a-(fluoromethyl)-5-methyloctahydropyrrolo[2,3-c]pyrrole (101 mg, 77.1% yield) as colorless oil. MS (ESI): 159.2 ([M+H]$^+$)

Intermediate C14

2-Methoxy-N-methyl-N-(pyrrolidin-3-ylmethyl)ethanamine dihydrochloride

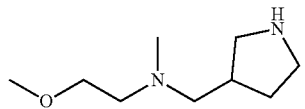

The titled compound was synthesized according to the following scheme:

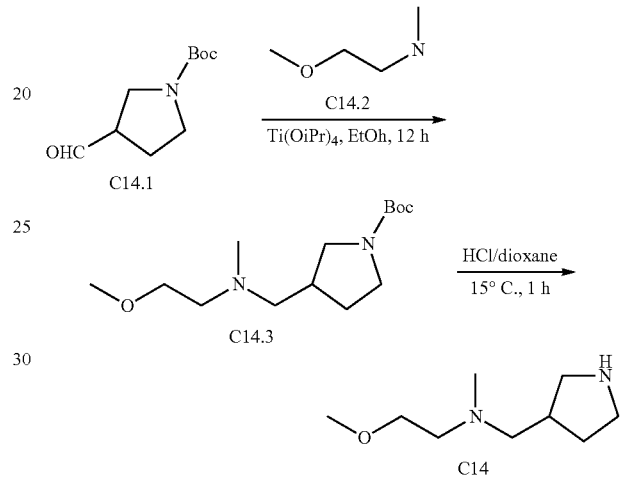

Step (a) Preparation of tert-butyl 3-(((2-methoxyethyl)(methyl)amino)methyl)pyrrolidine-1-carboxylate (Compound C14.3)

To a solution of tert-butyl 3-formylpyrrolidine-1-carboxylate (2.0 g, 22.5 mmol) and 2-methoxy-N-methylethanamine (2.0 g, 10.1 mmol) in EtOH (40.0 mL) was added tetraisopropoxytitanium (4.0 g, 14.1 mmol) under nitrogen atmosphere. The resulting reaction mixture was stirred at 15° C. for 12 h before sodium borohydride (1.6 g, 42.3 mmol) was added to the reaction mixture. Afterwards, the mixture was stirred at 15° C. for another 12 h before LCMS showed the starting material was consumed completely. The reaction mixture was then poured into water (250 mL) and filtered. The filtrate was extracted with EtOAc (100 mL) three times and the organic layer was washed with brine (100 mL) three times, dried over anhy. Na$_2$SO$_4$, filtered, and concentrated in vacuo to give a crude product, which was purified by silica gel flash chromatography (DCM:MeOH=20:1-10:1) to give tert-butyl 3-(((2-methoxyethyl)(methyl)amino)methyl)pyrrolidine-1-carboxylate (2.5 g, 92.6% yield) as light yellow oil. $^1$H NMR (400 MHz, DMSO-d$_6$) δ ppm 3.37~3.40 (t, 2H), 3.34 (s, 2H), 3.28~3.32 (m, 1H), 3.27 (s, 3H), 3.23 (s, 1H), 2.50 (s, 1H), 2.46~2.48 (s, 1H), 2.26~2.28 (m, 2H), 2.18 (s, 3H), 1.84~1.87 (m, 1H), 1.48~1.50 (m, 1H), 1.24 (s, 9H).

Step (b) Preparation of 2-methoxy-N-methyl-N-(pyrrolidin-3-ylmethyl)ethanamine dihydrochloride (Intermediate C14)

A solution of tert-butyl 3-(((2-methoxyethyl)(methyl)amino)methyl)pyrrolidine-1-carboxylate (2.5 g, 9.178 mmol) in HCl/dioxane (4M, 25.0 mL) was stirred at 15° C. for 1 h. After LCMS showed the starting material was consumed completely, the reaction mixture was concentrated in vacuo to give a crude product of 2-methoxy-N-methyl-N-(pyrrolidin-3-ylmethyl)ethanamine dihydrochloride (1.5 g, yield: 93.8%) as thick yellow oil, which was used directly in the next step without further purification. MS (ESI): 173.1 ([M+H]$^+$).

Intermediate C15

1-(4,4-Difluoropyrrolidin-3-yl)-N,N-dimethylmethanamine

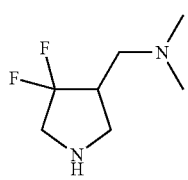

The titled compound was synthesized according to the following scheme:

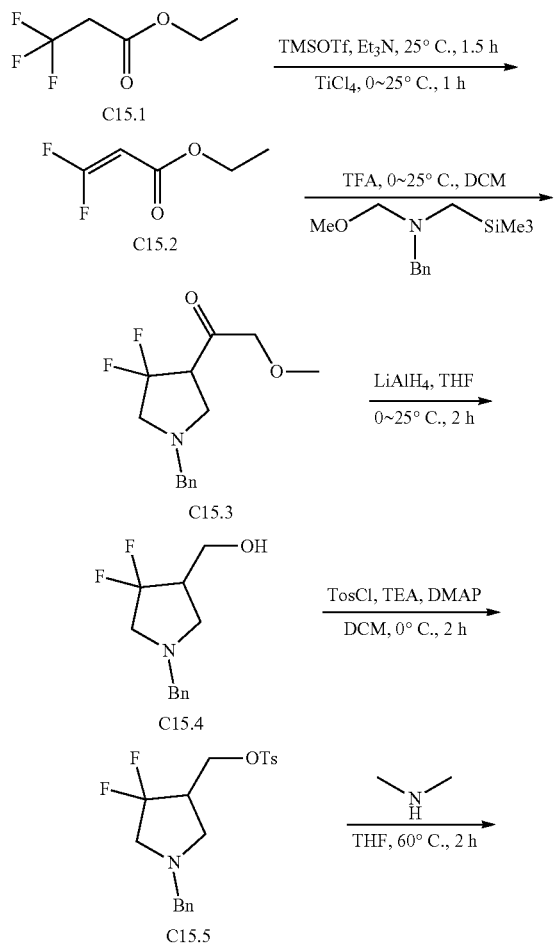

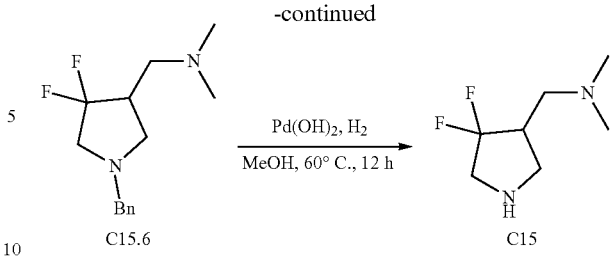

Step (a) Preparation of ethyl 3,3-difluoroacrylate (Compound C15.2)

To a stirred mixture solution of ethyl 3,3,3-trifluoropropanoate (10.0 g, 64.1 mmol) and Et$_3$N (7.8 g, 76.9 mmol) in CHCl$_3$ (100.0 mL) was added TMSOTf (17.4 g, 76.9 mmol) dropwise in an ice-water batch. After the addition, TiCl$_4$ (9.61 mL, 1.0 M in DCM) was added. The resulting reaction mixture was allowed to warmed up to room temperature and stirred at 25° C. for 1 h. The reaction was re-cooled in an ice bath before it was quenched with water (100 mL). The organic layer was separated, dried over anhy. MgSO$_4$, filtered, and concentrated in vacuo to give a crude product of ethyl 3,3-difluoroacrylate as oil, which was used directly in the next step without further purification.

Step (b) Preparation of ethyl 1-benzyl-4,4-difluoropyrrolidine-3-carboxylate (Compound C15.3)

To a stirred solution of ethyl 3,3-difluoroacrylate (1.0 g, 4.4 mmol) (5.0 g, 36.8 mmol) in CHCl$_3$ (20.0 mL) was added N-benzyl-1-methoxy-N-((trimethylsilyl)methyl)methanamine (1.3 g, 55.1 mmol) and TFA (0.5 mL) in an ice-water bath. The resulting reaction mixture was stirred at 0° C. for 1 h before allowed to warmed up to 25° C. and stirred for another 2 h. The reaction was before it was quenched by adding sat. NaHCO$_3$ solution. The mixture solution was then poured into water (50 mL) and extracted with EtOAc (50 mL). The organic layer was washed with aq. CaCl$_2$ solution (1N, 100 mL) twice, brine (100 mL) twice, dried over anhy. Na$_2$SO$_4$, filtered and concentrated in vacuo to give a crude product, which was purified by silica gel flash chromatography (petroleum ether:EtOAc=40:1~20:1) to give ethyl 1-benzyl-4,4-difluoropyrrolidine-3-carboxylate (10.9 g, 74.7% yield). MS (ESI): 270.1 ([M+H]$^+$)

Step (c) Preparation of (1-benzyl-4,4-difluoropyrrolidin-3-yl)methanol (Compound C15.4)

To a stirred solution of ethyl 1-benzyl-4,4-difluoropyrrolidine-3-carboxylate (4.0 g, 14.9 mmol) in THF (20 mL) was added LiAlH$_4$ (5.6 g, 148.6 mmol) at 0° C. After the addition, the reaction mixture was allowed to warm up to room temperature and stirred at 25° C. for 2 h before the reaction was quenched. The reaction mixture was then poured into water and extracted with EtOAc. The organic layer was washed with aq. CaCl$_2$ solution (1N, 50 mL) twice, brine (50 mL) twice dried over anhy. Na$_2$SO$_4$, filtered, and concentrated in vacuo to give (1-benzyl-4,4-difluoropyrrolidin-3-yl)methanol (3.1 g, 91.7% yield) as yellow oil. MS (ESI): 228.1 ([M+H]$^+$)

Step (d) Preparation of (1-benzyl-4,4-difluoropyrrolidin-3-yl)methyl 4-methylbenzenesulfonate (Compound C15.5)

To a solution of (1-benzyl-4,4-difluoropyrrolidin-3-yl)methanol (1.0 g, 4.4 mmol) in DCM (10.0 mL) was added TosCl (1.3 g, 6.6 mmol), TEA (1.3 g, 13.2 mmol) and DMAP (0.16 g, 1.32 mmol). The resulting reaction mixture was stirred at 0° C. for 2 h until LCMS showed the starting material was consumed completely. The mixture solution was then concentrated under reduced pressure to give a crude product, which was purified by prep-HPLC (0.1% TFA as additive) to give (1-benzyl-4,4-difluoropyrrolidin-3-yl)methyl 4-methylbenzenesulfonate (1.2 g, 70.6% yield) as colorless oil. MS (ESI): 382.0 ([M+H]$^+$)

Step (e) Preparation of 1-(1-benzyl-4,4-difluoropyrrolidin-3-yl)-N,N-dimethylmethanamine (Compound C15.6)

To a stirred solution of (1-benzyl-4,4-difluoropyrrolidin-3-yl)methyl 4-methylbenzenesulfonate (1.2 g, 3.15 mmol) in THF (10 mL) was added dimethylamine (30.0 mL, 2M in THF) and the resulting reaction mixture was stirred at 60° C. for 2 h. After LCMS showed the starting material was consumed completely, the mixture solution was then concentrated in vacuo to give a crude product, which was purified by prep-HPLC (0.5% TFA in water) to give 1-(1-benzyl-4,4-difluoropyrrolidin-3-yl)-N,N-dimethylmethanamine (0.65 g, 81.2% yield) as colorless oil. MS (ESI): 255.1 ([M+H]$^+$)

Step (f) Preparation of 1-(4,4-difluoropyrrolidin-3-yl)-N,N-dimethylmethanamine (compound C15)

A stirred solution of 1-(1-benzyl-4,4-difluoropyrrolidin-3-yl)-N,N-dimethylmethanamine (0.65 g, 2.56 mmol) and Pd(OH)$_2$ (0.36 g, 0.26 mmol) in MeOH (15.0 mL) was stirred at 60° C. for 12 h under H$_2$ (50 psi). After LCMS showed the starting material was consumed completely, the reaction was cooled down to room temperature and filtered through Celite. After washing the filter cake with MeOH (30 mL) four times, combined filtrated was evaporated to dryness under reduced pressure to give a crude product of 1-(4,4-difluoropyrrolidin-3-yl)-N,N-dimethylmethanamine (0.79 g) as colorless oil, which was used directly in the next step without further purification. MS (ESI): 165.1 ([M+H]$^+$).

Intermediate C16

N-ethyl-N-(morpholin-2-ylmethyl)ethanamine hydrochloride

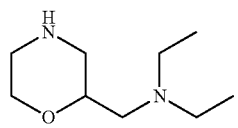

The titled compound was synthesized according to the following scheme:

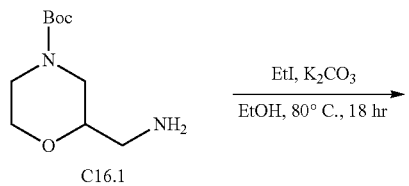

C16.1

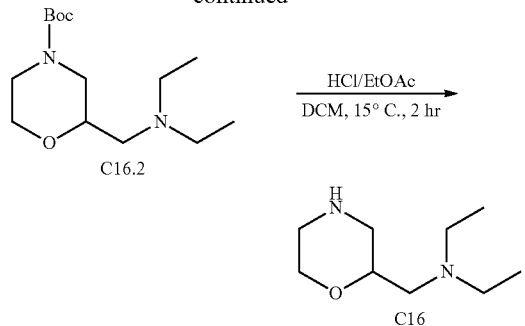

Step (a) tert-Butyl 2-((diethylamino)methyl)morpholine-4-carboxylate (Compound C16.2)

To a solution of tert-butyl 2-(aminomethyl)morpholine-4-carboxylate (250.0 mg, 1.16 mmol, compound C16.1) in EtOH (10.0 mL) was added K$_2$CO$_3$ (800.0 mg, 5.79 mmol) and EtI (900 mg, 5.77 mmol). The resulting reaction mixture was stirred at 80° C. for 18 h before it was cooled back to room temperature and filtered. The filtrate was concentrated in vacuo to give a residual, which was re-dissolved in EtOAc/MTBE (50 mL, 1:5) and stirred at ambient temperature for 15 min. Then mixture solution was filtered and the filtrate was concentrated in vacuo to give tert-butyl 2-((diethylamino)methyl)morpholine-4-carboxylate (163.0 mg, 51.8% yield) as colorless gum. $^1$H NMR (400 MHz, CDCl$_3$) δppm: 3.91-3.84 (m, 2H), 3.64 (m 1H), 3.52-3.47 (m, 2H), 2.89 (m, 1H), 2.60-2.53 (m, 6H), 2.41-2.41 (m, 1H), 1.45 (s, 9H), 1.03-1.00 (m, 6H).

Step (b) N-ethyl-N-(morpholin-2-ylmethyl)ethanamine hydrochloride (Intermediate C16)

To a solution of tert-butyl 2-((diethylamino)methyl)morpholine-4-carboxylate (163.0 mg, 0.598 mmol, compound C16.2) in DCM (3.0 mL) was added HCl/EtOAc (3M, 2.0 mL) and the resulting reaction mixture was stirred at 15° C. for 2 h. The reaction mixture was then concentrated in vacuo to give a crude product of N-ethyl-N-(morpholin-2-ylmethyl)ethanamine hydrochloride (130.0 mg) as a yellow solid. $^1$H NMR (400 MHz, CDCl$_3$) δppm: 10.41 (s, 1H), 9.81 (m, 2H), 4.33 (s, 1H), 3.96 (m, 1H), 3.85 (m, 1H), 3.38 (m, 1H), 3.28 (m, 2H), 3.18-3.12 (m, 5H), 2.95 (m, 1H), 2.81 (m, 1H), 1.24-1.17 (m, 6H).

Intermediate C17 trans-N,N,-4-trimethylpyrrolidin-3-amine hydrochloride

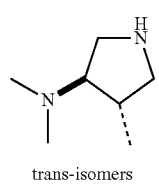

trans-isomers

The title compound was prepared in analogy to Intermediate C4 by replacing tert-butyl 3-(aminomethyl)piperidine- 1-carboxylate with trans-tert-butyl 3-amino-4-methylpyrrolidine-1-carboxylate in step (a). MS (ESI): 129.1 ([M+H]+).

Intermediate C18

(S)—N,N-dimethyl-1-(pyrrolidin-2-yl)methanamine dihydrochloride

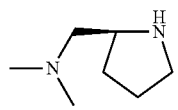

The titled compound was synthesized according to the following scheme:

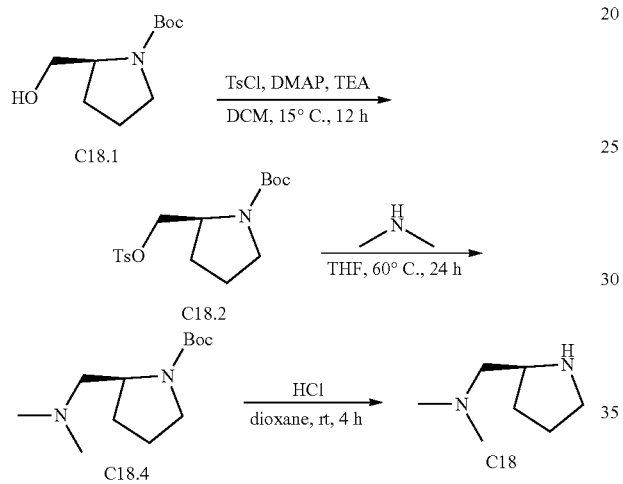

Step (a) Preparation of (S)-tert-butyl 2-((tosyloxy)methyl)pyrrolidine-1-carboxylate (Compound C18.2)

To a solution of (S)-tert-butyl 2-(hydroxymethyl)pyrrolidine-1-carboxylate (55.0 g, 273.27 mmol), 4-methylbenzene-1-sulfonyl chloride (57.3 g, 300.6 mmol) and triethylamine (83.0 g, 819.8 mmol) in DCM (200.0 mL) was added N,N-dimethylpyridin-4-amine (6.7 g, 1.49 mmol). The resulting mixture was stirred at 15° C. for 4 h until TLC (petroleum ether/EtOAc=3:1) showed the SM was consumed completely. The mixture was then diluted with EtOAc (500 mL) and filtered. The filtrate was concentrated in vacuo to give a crude product which was purified by silica gel flash chromatography (petroleum ether:EtOAc=50:1~3:1) to give (S)-tert-butyl 2-((tosyloxy)methyl)pyrrolidine-1-carboxylate (93.0 g, 95.74% yield) as pale yellow oil. MS (ESI): 256.2 ([M-100]+H]+, 300.2 ([M-56]+H]+.

Step (b) Preparation of (S)-tert-butyl 2-((dimethylamino)methyl)pyrrolidine-1-carboxylate (Compound C18.4)

A mixture solution of (S)-tert-butyl 2-((tosyloxy)methyl)pyrrolidine-1-carboxylate (93.0 g, 261.64 mmol, compound C18.2) and dimethylamine in THF (2 M, 1.0 L) was stirred in an auto calve at 60° C. for 24 h. After TLC (petroleum ether/EtOAc=1:3, 0.5% NH3.H2O as additive, stained by I2) showed starting material was consumed completely, the reaction mixture was diluted with EtOAc (400 mL) and filtered. The filtrate was concentrated in vacuo to give a crude product, which was purified by silica gel flash chromatography (petroleum ether:EtOAc=50:1~1:5, 0.5% NH3.H2O as additive) to give (S)-tert-butyl 2-((dimethylamino)methyl)pyrrolidine-1-carboxylate (51.0 g, 85.37% yield) as pale yellow oil. MS (ESI): 229.2 ([M+H])+.

Step (c) Preparation of (S)—N,N-dimethyl-1-(pyrrolidin-2-yl)methanamine dihydrochloride (Compound C18)

A solution of (S)-tert-butyl 2-((dimethylamino)methyl)pyrrolidine-1-carboxylate (51.0 g, 56.93 mmol) in HCl/dioxane (4 M, 300.0 mL) was stirred at 15° C. for 4 h. After LCMS showed starting material was consumed completely, the reaction mixture was evaporated to dryness under reduced pressure to give a crude product of (S)—N,N-dimethyl-1-(pyrrolidin-2-yl)methanamine dihydrochloride (44.0 g, 97.94% yield) as a pale yellow solid, which was used directly in the next step without further purification. MS (ESI): 129.1 ([M+H])+.

Intermediate C19

(S)—N,N-dimethyl-1-(5-azaspiro[2.4]heptan-6-yl)methanamine hydrochloride

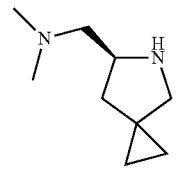

The title compound was prepared in analogy to Intermediate C3 by replacing 1-(tert-butoxycarbonyl)-3-fluoropyrrolidine-3-carboxylic acid with (S)-5-(tert-butoxycarbonyl)-5-azaspiro[2.4]heptane-6-carboxylic acid in step (b). MS (ESI): 154.1 ([M+H]+).

Intermediate C20

(3S,4S)-4-Methoxy-N,N-dimethylpyrrolidin-3-amine hydrochloride

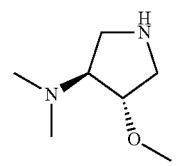

The title compound was prepared in analogy to Intermediate C4 by replacing tert-butyl 3-(aminomethyl)piperidine-1-carboxylate with (3S,4S)-tert-butyl 3-amino-4-methoxypyrrolidine-1-carboxylate in step (a). MS (ESI): 145.1 ([M+H]+).

Intermediate C21

(3S,4S)-4-Fluoro-N,N-dimethylpyrrolidin-3-amine hydrochloride

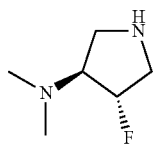

The title compound was prepared in analogy to Intermediate C4 by replacing tert-butyl 3-(aminomethyl)piperidine-1-carboxylate with (3S,4S)-tert-butyl 3-amino-4-fluoropyrrolidine-1-carboxylate in step (a). MS (ESI): 133.1 ([M+H]$^+$).

Intermediate C22

(3R,4S)—N,N,-4-trimethylpyrrolidin-3-amine hydrochloride

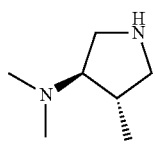

The title compound was prepared in analogy to Intermediate C4 by replacing tert-butyl 3-(aminomethyl)piperidine-1-carboxylate with (3R,4S)-tert-butyl 3-amino-4-methylpyrrolidine-1-carboxylate in step (a). MS (ESI): 129.1 ([M+H]$^+$).

Intermediate C23

1-((2S,4S)-4-Fluoropyrrolidin-2-yl)-N,N-dimethylmethanamine hydrochloride

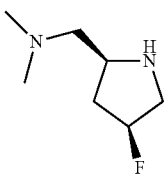

The title compound was prepared in analogy to Intermediate C3 by replacing 1-(tert-butoxycarbonyl)-3-fluoropyrrolidine-3-carboxylic acid with (2S,4S)-1-(tert-butoxycarbonyl)-4-fluoropyrrolidine-2-carboxylic acid in step (b). MS (ESI): 147.1 ([M+H]$^+$).

Intermediate C24 trans-4-Fluoro-N,N-dimethylpyrrolidin-3-amine hydrochloride

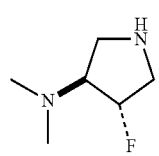

trans-isomers

The title compound was prepared in analogy to Intermediate C4 by replacing tert-butyl 3-(aminomethyl)piperidine-1-carboxylate with trans-tert-butyl 3-amino-4-fluoropyrrolidine-1-carboxylate in step (a). MS (ESI): 133.1 ([M+H]$^+$).

Intermediate C25 trans-4-Methoxy-N,N-dimethylpyrrolidin-3-amine hydrochloride

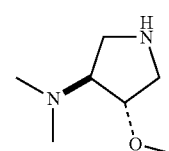

trans-isomers

The title compound was prepared in analogy to Intermediate C4 by replacing tert-butyl 3-(aminomethyl)piperidine-1-carboxylate with trans-tert-butyl 3-amino-4-methoxypyrrolidine-1-carboxylate in step (a). MS (ESI): 145.1 ([M+H]$^+$).

Intermediate C26

(R)-1-(Pyrrolidin-3-ylmethyl)pyrrolidine hydrochloride

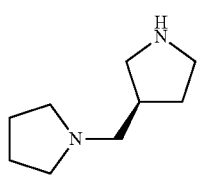 [SMILES: C1CCN(C[C@@H]2CCNC2)C1]

The titled compound was synthesized according to the following scheme:

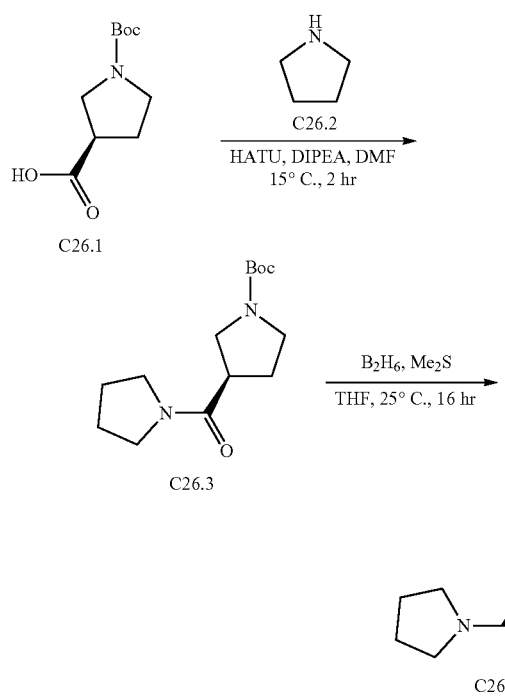

Intermediate C27

(R)-4-(Pyrrolidin-3-ylmethyl)morpholine

The titled compound was synthesized according to the following scheme:

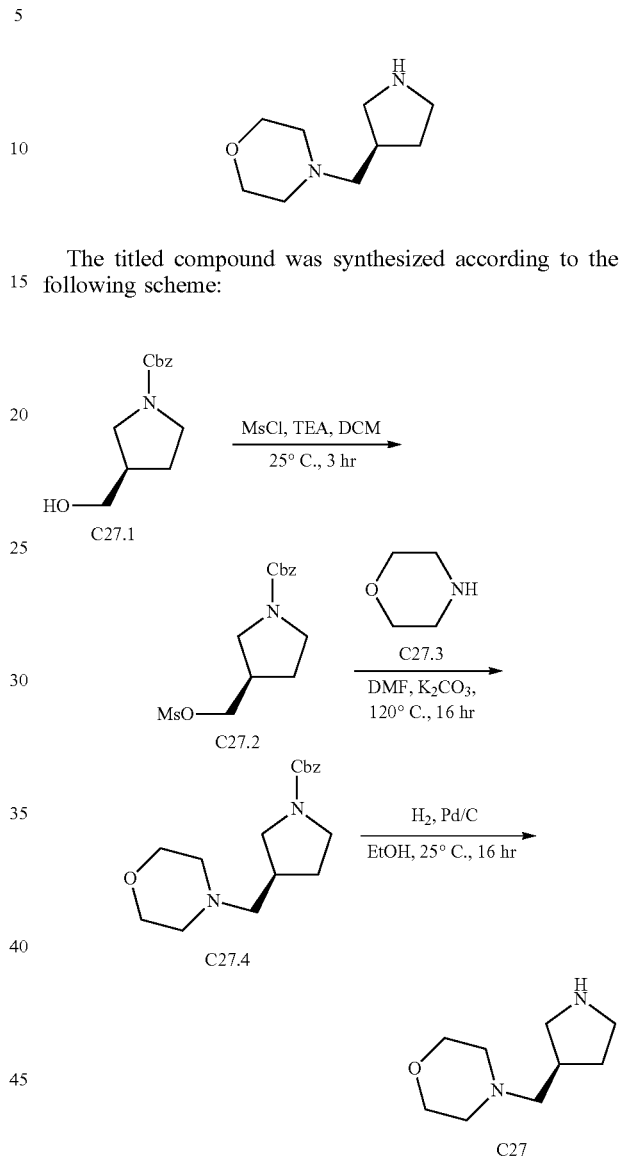

Step (a) (R)-tert-Butyl 3-(pyrrolidine-1-carbonyl)pyrrolidine-1-carboxylate (Compound C26.3)

A solution of (R)-1-(tert-butoxycarbonyl)pyrrolidine-3-carboxylic acid (1.01 g, 4.69 mmol, compound C26.1) and HATU (1.90 g, 5.00 mmol) in DMF (10.0 mL) was stirred at 15° C. for 15 min before pyrrolidine (390.0 mg, 5.48 mmol, compound C26.2) was added and the resulting mixture was stirred at 15° C. for another 15 min. DIPEA (1.25 g, 9.67 mmol) was then added and the resulting mixture was stirred at 15° C. for another 90 min. The reaction mixture was poured into water (150 mL) and extracted with EtOAc (100 mL) twice. The organic layer was washed with brine, dried over anhy. $Na_2SO_4$, filtered, and concentrated in vacuo to give a crude product which was purified by silica gel flash chromatography (10-50% EtOAc in petroleum ether) to give (R)-tert-butyl 3-(pyrrolidine-1-carbonyl)pyrrolidine-1-carboxylate (1.10 g, 87.4% yield) as colorless gum. $^1$H NMR (400 MHz, $CDCl_3$) δppm: 3.58-3.54 (m, 1H), 3.48-3.44 (m 4H), 3.34-3.30 (m, 2H), 3.08 (m, 1H), 2.20 (m, 1H), 1.97 (m, 3H), 1.88 (m, 3H), 1.44 (s, 9H).

Step (b) (R)-1-(Pyrrolidin-3-ylmethyl)pyrrolidine hydrochloride (Compound C26)

To a solution of (R)-tert-butyl 3-(pyrrolidine-1-carbonyl)pyrrolidine-1-carboxylate (300.0 mg, 1.12 mmol, compound C26.3) in THF (10 mL) was added $B_2H_6.Me_2S$ (10 M, 0.2 mL, 2.0 mmol), and the resulting mixture was stirred at 25° C. for 16 h. Afterwards, the reaction mixture was acidified by adding aq. HCl solution (2 M, 15 mL) and stirred at 25° C. for additional 2 h. The reaction mixture was then adjusted to pH=7~8 with satd. aq. solution and extracted with EtOAc/MeOH (90/1, 50 mL). Separated organic layer was dried over anhy. $Na_2SO_4$, filtered and concentrated in vacuo to give a crude product of (R)-1-(pyrrolidin-3-ylmethyl)pyrrolidine hydrochloride (150 mg), which was used directly in the next step without further purification.

Step (a) (R)-Benzyl 3-(((methylsulfonyl)oxy)methyl)pyrrolidine-1-carboxylate (Compound C27.2)

A mixture solution of (R)-benzyl 3-(hydroxymethyl)pyrrolidine-1-carboxylate (467.61 mg, 1.99 mmol, compound C27.1) and TEA (0.55 mL, 3.97 mmol) in DCM (5 mL) cooled at 0° C. was added MsCl (0.68 mL, 8.82 mmol) dropwise. After the addition, the resulting mixture solution was stirred at 25° C. for 3 h before aq. citric acid solution (10%, 10 mL) was added. The separated organic layer was then washed with satd. aq. $NaHCO_3$ solution, dried with anhy. $Na_2SO_4$, filtered and concentrated in vacuo to give a crude product of (R)-benzyl 3-(((methylsulfonyl)oxy)methyl)pyrrolidine-1-carboxylate (480 mg, 69.36% yield) as colorless oil. $^1$H NMR (400 MHz, $CDCl_3$) δppm: 7.35-7.21 (m, 5H), 5.06 (s, 2H), 4.14-4.12 (m, 1H), 4.08-4.06 (m, 1H), 3.59-3.52 (m, 1H), 3.52-3.42 (m, 1H), 3.40-3.31 (m, 1H), 3.21-3.12 (m, 1H), 2.94 (s, 3H), 2.63-2.54 (m, 1H), 2.06-1.97 (m, 1H), 1.79-1.61 (m, 1H).

Step (b) (S)-Benzyl 3-(morpholinomethyl)pyrrolidine-1-carboxylate (Compound C27.4)

A mixture solution of (R)-benzyl 3-(((methyl sulfonyl)oxy)methyl)pyrrolidine-1-carboxylate (480.0 mg, 1.53 mmol, compound C27.2) and morpholine (1.33 g, 15.32 mmol, compound C27.3) in DMF (1 mL) was stirred at 120° C. for 16 h. After cooled back to room temperature, the reaction mixture was concentrated in vacuo to give a crude product, which was purified by Prep-HPLC (0.1% FA in H$_2$O) to give (S)-benzyl 3-(morpholinomethyl)pyrrolidine-1-carboxylate (420 mg, 85.58% yield) as orange oil. $^1$H NMR (400 MHz, CDCl$_3$) δppm: 7.38-7.33 (m, 5H), 5.15 (s, 2H), 3.76 (m, 4H), 3.71-3.47 (m, 2H), 3.45-3.33 (m, 1H), 3.18-3.07 (m, 1H), 2.66-2.38 (m, 7H), 2.12-1.99 (m, 1H), 1.75-1.56 (m, 1H).

Step (c) (R)-4-(Pyrrolidin-3-ylmethyl)morpholine (Intermediate C27)

A solution of (S)-benzyl 3-(morpholinomethyl)pyrrolidine-1-carboxylate (360.0 mg, 1.18 mmol, compound C27.4) and Pd/C (120.0 mg, 10% wt.) in EtOH (10 mL) was stirred at 25° C. for 16 h under H$_2$ (760 mmHg). Afterwards, the reaction mixture was filtered through Celite and the filtrate was concentrated in vacuo to give a crude product of (R)-4-(pyrrolidin-3-ylmethyl)morpholine (200 mg, 84.43% yield) as yellow oil. $^1$H NMR (400 MHz, CDCl$_3$) δppm: 3.71 (m, 4H), 3.13-3.05 (m, 1H), 3.04-2.92 (m, 3H), 2.70-2.62 (m, 1H), 2.52-2.39 (m, 4H), 2.34-2.30 (m, 2H), 2.00-1.88 (m, 1H), 1.52-1.39 (m, 1H).

Intermediate C28

(3aR,4R,7aS)—N,N-dimethyloctahydro-1H-isoindol-4-amine

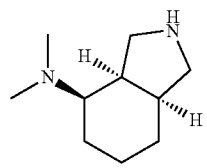

The titled compound was synthesized according to the following scheme:

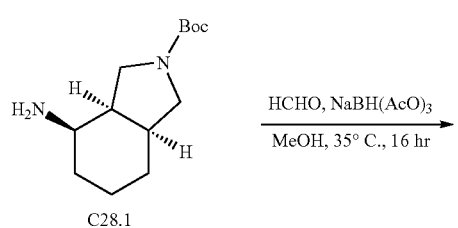

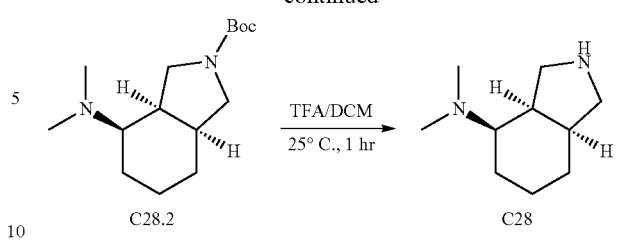

Step (a) (3aR,4R,7aS)-tert-Butyl 4-(dimethylamino)hexahydro-H-isoindole-2(3H)-carboxylate (Compound C28.2)

A mixture solution of (3aR,4R,7aS)-tert-butyl 4-amino-hexahydro-1H-isoindole-2(3H)-carboxylate (300.0 mg, 1.25 mmol, compound C28.1), HCHO (362.0 mg, 12.48 mmol, 37% in water) and NaBH(AcO)$_3$ (78.0 mg, 1.25 mmol) in DCM (10 mL) was stirred at 50° C. for 16 h. After cooled to room temperature, to the reaction mixture was added H$_2$O (10 mL) and EtOAc (20 mL). The organic layer was separated, dried with anhy. Na$_2$SO$_4$, filtered, and concentrated in vacuo to give a crude product of (3aR,4R,7aS)-tert-butyl 4-(dimethylamino)hexahydro-1H-isoindole-2(3H)-carboxylate (230 mg, 0.86 mmol, 63.85% yield) as light yellow oil. MS (ESI): 269.1 ([M+H]$^+$). It was used directly in the next step without further purification.

Step (b) (3aR,4R,7aS)—N,N-dimethyloctahydro-1H-isoindol-4-amine (Intermediate C28)

A solution of (3aR,4R,7aS)-tert-butyl 4-(dimethylamino)hexahydro-1H-isoindole-2(3H)-carboxylate (200.0 mg, 0.750 mmol, compound C28.2) and TFA (1.15 mL, 14.9 mmol) in DCM (2 mL) was stirred at 25° C. for 1 h. Afterwards, the reaction mixture was concentrated in vacuo to give a crude product of (3aR,4R,7aS)—N,N-dimethyloctahydro-1H-isoindol-4-amine (180 mg). It was used directly in the next step without further purification.

Intermediate C29

2-(2,7-Diazaspiro[4.5]decan-7-yl)ethanol

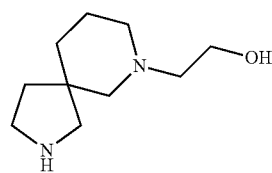 [SMILES: OCCN1CCCC2(CCNC2)C1]

The titled compound was synthesized according to the following scheme

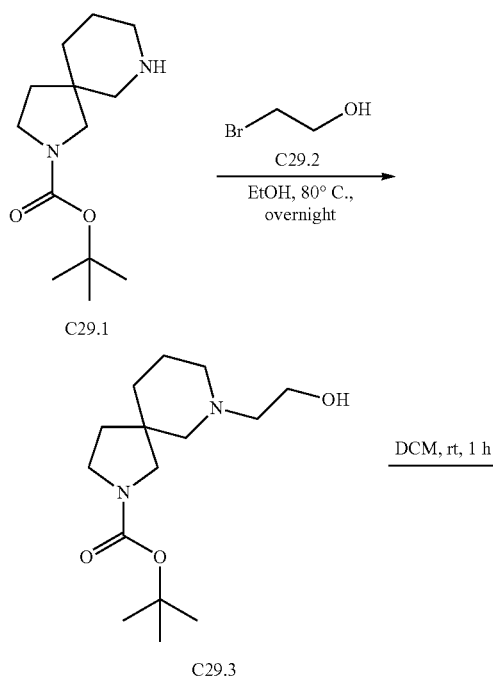

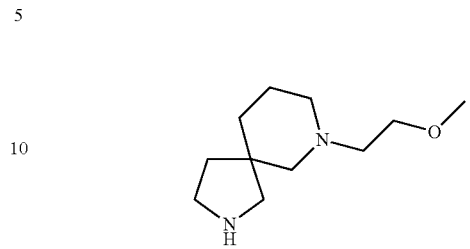

Step (a) tert-Butyl 9-(2-hydroxyethyl)-2,9-diazaspiro[4.5]decane-2-carboxylate (Compound C29.3)

To a 100 mL round-bottom flask was charged with tert-butyl 2,7-diazaspiro[4.5]decane-2-carboxylate (300 mg, 1.25 mmol), 2-bromoethan-1-ol (187 mg, 1.5 mmol), DIPEA (242 mg, 327 µL, 1.87 mmol), and EtOH (12 mL). The resulting reaction mixture was heated to 80° C. and stirred overnight. After cooled to the room temperature, the reaction mixture was concentrated in vacuo to give a crude product of tert-butyl 7-(2-hydroxyethyl)-2,7-diazaspiro[4.5]decane-2-carboxylate (355 mg, 100% yield). MS (ESI): 285.2 ([M+H]$^+$). It was used directly in the next step without further purification.

Step (b) 2-(2,7-Diazaspiro[4.5]decan-7-yl)ethanol (Compound C29)

To a 100 mL round-bottom flask charged with tert-butyl 7-(2-hydroxyethyl)-2,7-diazaspiro[4.5]decane-2-carboxylate (355 mg, 1.25 mmol) in DCM (6 ml) was added TFA (2.85 g, 1.92 ml, 25 mmol). The resulting reaction mixture was stirred at room temperature for 1 h before concentrated in vacuo to give a crude product of 2-(2,7-diazaspiro[4.5]decan-7-yl)ethan-1-ol (230 mg, 100% yield), which was used directly in the next step without further purification. MS (ESI): 185.2 ([M+H]$^+$).

Intermediate C30

7-(2-Methoxyethyl)-2,7-diazaspiro[4.5]decane

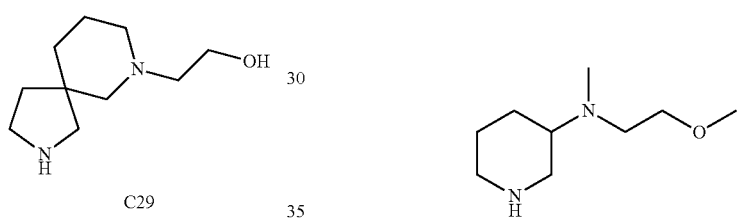

The title compound was prepared in analogy to Intermediate C29 by replacing 2-bromoethan-1-ol with 1-bromo-2-methoxy-ethane in step (a). MS (ESI): 199.2 ([M+H]$^+$).

Intermediate C31

N-(2-methoxyethyl)-N-methyl-piperidin-3-amine

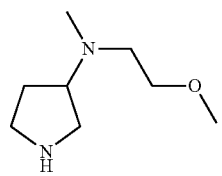

The title compound was prepared in analogy to Intermediate C29 by replacing tert-butyl 2,7-diazaspiro[4.5]decane-2-carboxylate with tert-butyl 3-(methylamino)piperidine-1-carboxylate and 2-bromoethan-1-ol with 1-bromo-2-methoxy-ethane in step (a). MS (ESI): 173.2 ([M+H]$^+$).

Intermediate C32

N-(2-methoxyethyl)-N-methyl-pyrrolidin-3-amine

The title compound was prepared in analogy to Intermediate C29 by replacing tert-butyl 2,7-diazaspiro[4.5]decane-2-carboxylate with tert-butyl 3-(methylamino)pyrrolidine-1-carboxylate and 2-bromoethan-1-ol with 1-bromo-2-methoxy-ethane in step (a) in step (a). MS (ESI): 159.2 ([M+H]$^+$).

Intermediate C33

2-[Methyl(pyrrolidin-3-yl)amino]ethanol

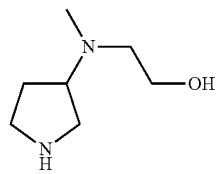

The title compound was prepared in analogy to Intermediate C29 by replacing tert-butyl 2,7-diazaspiro[4.5]decane-2-carboxylate with tert-butyl 3-(methylamino)pyrrolidine-1-carboxylate in step (a). MS (ESI): 145.2 ([M+H]$^+$).

Intermediate C34

2-[Methyl(3-piperidyl)amino]ethanol

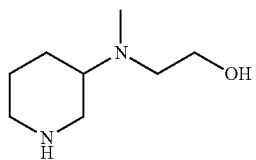

The title compound was prepared in analogy to Intermediate C29 by replacing tert-butyl 2,7-diazaspiro[4.5]decane-2-carboxylate with tert-butyl 3-(methylamino)piperidine-1-carboxylate in step (a). MS (ESI): 159.2 ([M+H]$^+$).

Intermediate C35 cis-2-(2,3,3a,4,6,6a-Hexahydro-1H-pyrrolo[2,3-c]pyrrol-5-yl)ethanol

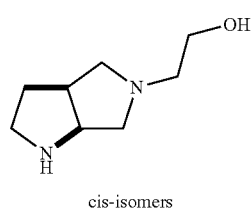

cis-isomers

The title compound was prepared in analogy to Intermediate C5 by replacing bromo-2-methoxy-ethane with 2-bromoethan-1-ol in step (a). MS (ESI): 157.2 ([M+H]$^+$).

Intermediate C36

N,N-dimethyl-5-azaspiro[2.4]heptan-7-amine

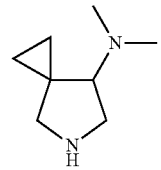

The titled compound was synthesized according to the following scheme

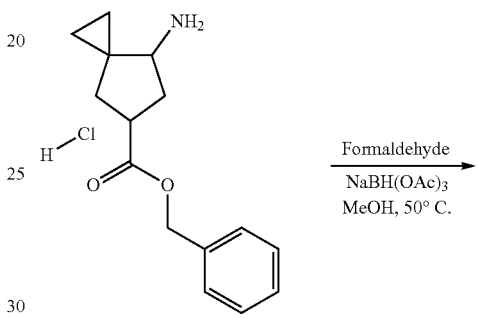

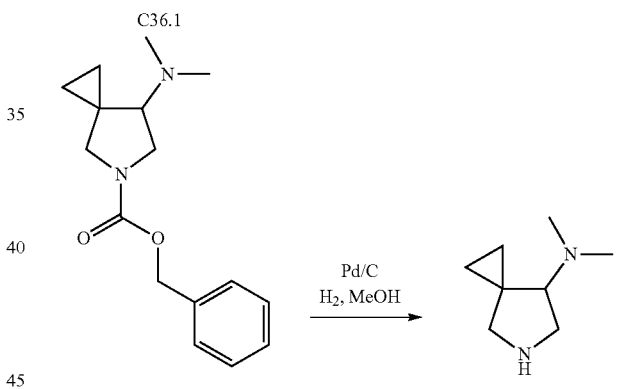

Step (a) Benzyl 7-(dimethylamino)-5-azaspiro[2.4]heptane-5-carboxylate (Compound C36.2)

In a 100 mL round-bottom flask, benzyl 7-amino-5-azaspiro[2.4]heptane-5-carboxylate hydrochloride (500 mg, 1.77 mmol), formaldehyde (319 mg, 10.6 mmol) and NaBH(OAc)$_3$ (2.25 g, 10.6 mmol) were dissolved in MeOH (2.5 mL) to give a colorless solution. The reaction mixture was heated to 50° C. and stirred for 15 h. After cooled to room temperature, the reaction mixture was concentrated in vacuo and poured into satd. aq. NaHCO$_3$ solution (25 mL) and extracted with EtOAc (25 mL) three times. The combined organic layer was washed with brine (25 mL), dried over anhy. Na$_2$SO$_4$, filtered, and concentrated in vacuo to give a crude product, which was then purified by silica gel flash chromatography (0% to 10% MeOH in DCM) to give benzyl 7-(dimethylamino)-5-azaspiro[2.4]heptane-5-carboxylate (460 mg, 94.8% yield). MS (ESI): 275.3 ([M+H]$^+$).

Step (b) N,N-dimethyl-5-azaspiro[2.4]heptan-7-amine (Intermediate C36)

To a solution of benzyl 7-(dimethylamino)-5-azaspiro[2.4]heptane-5-carboxylate (480 mg, 1.75 mmol) in MeOH (15 mL) was added Pd/C (93.1 mg, 875 μmol). After the suspension was degassed under vacuum and purged with H₂ several times, the reaction mixture was stirred at room temperature for 1 h. The reaction mixture was filtered through Celite and the filtrate was concentrated in vacuo to give a crude product of N,N-dimethyl-5-azaspiro[2.4]heptan-7-amine (66 mg, 26.9% yield), which was used directly in the next step without further purification. MS (ESI): 141.3 ([M+H]⁺).

Intermediate C37 cis-(4R)—N,N-dimethyl-1,2,3,3a,4,5,6,6a-octahydrocyclopenta[c]pyrrol-4-yl]methanamine

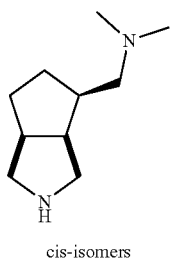

cis-isomers

The title compound was prepared in analogy to Intermediate C2 by replacing cis-tert-butyl 3-(aminomethyl)tetrahydro-2H-furo[2,3-c]pyrrole-5 (3H)-carboxylate with cis-tert-butyl-(4R)-(aminomethyl)-3,3a,4,5,6,6a-hexahydro-1H-cyclopenta[c]pyrrole-2-carboxylate in step (a). MS (ESI): 169.2 ([M+H]⁺).

Intermediate C38 cis-(4R)—N,N-dimethyl-1,2,3,3a,4,5,6,6a-octahydrocyclopenta[c]pyrrol-4-amine

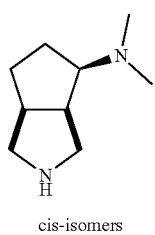

cis-isomers

The title compound was prepared in analogy to Intermediate C2 by replacing cis-tert-butyl 3-(aminomethyl)tetrahydro-2H-furo[2,3-c]pyrrole-5 (3H)-carboxylate with cis-tert-butyl-(4R)-amino-3,3a,4,5,6,6a-hexahydro-1H-cyclopenta[c]pyrrole-2-carboxylate in step (a). MS (ESI): 155.2 ([M+H]⁺)

Intermediate C39 cis-4-(Dimethylamino)pyrrolidin-3-ol

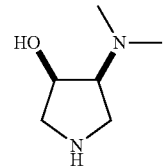

The title compound was prepared in analogy to Intermediate C2 by replacing cis-tert-butyl 3-(aminomethyl)tetrahydro-2H-furo[2,3-c]pyrrole-5 (3H)-carboxylate with tert-butyl cis-3-amino-4-hydroxy-pyrrolidine-1-carboxylate in step (a). MS (ESI): 131.2 ([M+H]⁺).

Intermediate C40

4-Methyl-3,4a,5,6,7,7a-hexahydro-2H-pyrrolo[3,4-b][1,4]oxazine dihydrochloride

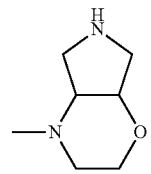

The titled compound was synthesized according to the following scheme:

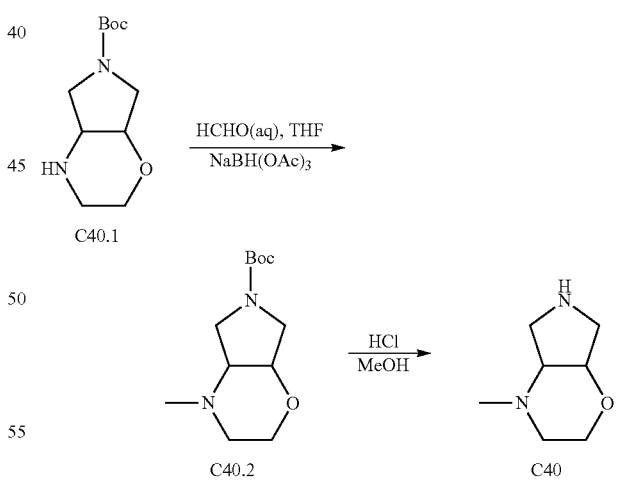

Step (a) tert-Butyl 4-methyl-2,3,4a, 5,7,7a-hexahydropyrrolo[3,4-b][1,4]oxazine-6-carboxylate (Compound C40.2)

To the solution of tert-butyl 3,4,4a,5,7,7a-hexahydro-2H-pyrrolo[3,4-b][1,4]oxazine-6-carboxylate (1.0 g, 4.39 mmol, compound C40.1) in THF (5.0 mL) was added aq. formaldehyde solution (1.8 mL, 17.6 mmol, 30%) at room temperature. The reaction mixture was stirred at room temperature for 6 h before sodium triacetoxyborohydride (4.66 g, 21.95 mmol) was added. The resulting mixture solution was stirred at room temperature for another 12 h, before it was poured into water (20 mL), and extracted with DCM (100 mL) twice. The combined organic layer was dried over anhy. Na$_2$SO$_4$, filtered, and concentrated in vacuo to give a crude product of tert-butyl 4-methyl-2,3,4a,5,7,7a-hexahydropyrrolo[3,4-b][1,4]oxazine-6-carboxylate (0.95 g, 90% yield) as oil, which was used directly in the next step without further purification. MS (ESI): 243.2 ([M+H]$^+$).

Step (b) 4-Methyl-3,4a,5,6,7,7a-hexahydro-2H-pyrrolo[3,4-b][1,4]oxazine (Intermediate C40)

To a solution of tert-butyl 4-methyl-2,3,4a,5,7,7a-hexahydropyrrolo[3,4-b][1,4]oxazine-6-carboxylate (0.95 g, 3.95 mmol) in MeOH (5.0 mL) was added HCl solution (2M in MeOH, 10 mL) at 0° C. The reaction mixture was then stirred at room temperature for 2 h before it was concentrated in vacuo to give a crude product of 4-methyl-3,4a,5,6,7,7a-hexahydro-2H-pyrrolo[3,4-b][1,4]oxazine (0.85 g, 100% yield) as a white solid. MS (ESI): 143.2 ([M+H]$^+$).

Intermediate C41 cis-4-Methyl-3,4a,5,6,7,7a-hexahydro-2H-pyrrolo[3,4-b][1,4]oxazine dihydrochloride

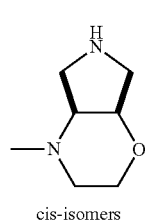

cis-isomers

The title compound was prepared in analogy to Intermediate C40 by replacing tert-butyl 3,4,4a, 5,7,7a-hexahydro-2H-pyrrolo[3,4-b][1,4]oxazine-6-carboxylate with cis-tert-butyl 3,4,4a,5,7,7a-hexahydro-2H-pyrrolo[3,4-b][1,4]oxazine-6-carboxylate in step (a). MS (ESI): 143.2 ([M+H]$^+$).

Intermediate C42 cis-4-Methyl-2,3,3a,5,6,6a-hexahydro-1H-pyrrolo[3,2-b]pyrrole

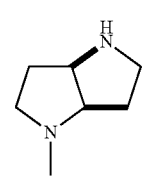

The title compound was prepared in analogy to Intermediate C40 by replacing tert-butyl 3,4,4a, 5,7,7a-hexahydro-2H-pyrrolo[2,3-c][1,4]oxazine-6-carboxylate with cis-tert-butyl 2,3,3a,5,6,6a-hexahydro-1H-pyrrolo[3,2-b]pyrrole-4-carboxylate in step (a). MS (ESI): 127.2 ([M+H]$^+$).

Intermediate C43

4-Methyl-1,2,3,3a,5,6,7,7a-octahydropyrrolo[3,2-b]pyridine dihydrochloride

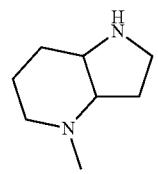

The title compound was prepared in analogy to Intermediate C40 by replacing tert-butyl 3,4,4a, 5,7,7a-hexahydro-2H-pyrrolo[3,4-b][1,4]oxazine-6-carboxylate with tert-butyl 2,3,3a,4,5,6,7,7a-octahydropyrrolo[3,2-b]pyridine-1-carboxylate in step (a). MS (ESI): 141.2 ([M+H]$^+$).

Intermediate C44 cis-6-Methyl-2,6-diazabicyclo[3.2.0]heptane dihydrochloride

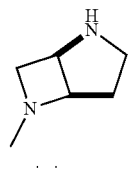

cis-isomers

The title compound was prepared in analogy to Intermediate C40 by replacing tert-butyl 3,4,4a, 5,7,7a-hexahydro-2H-pyrrolo[3,4-b][1,4]oxazine-6-carboxylate with cis-tert-butyl 2,6-diazabicyclo[3.2.0]heptane-2-carboxylate in step (a). MS (ESI): 113.2 ([M+H]$^+$).

Intermediate C45 cis-1-(3-((tert-butyldiphenylsilyl)oxy)propyl)octahydropyrrolo[2,3-c]pyrrole

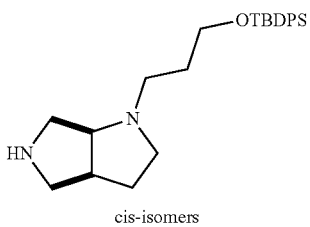

cis-isomers

The titled compound was synthesized according to the following scheme:

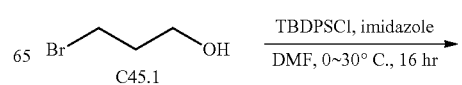

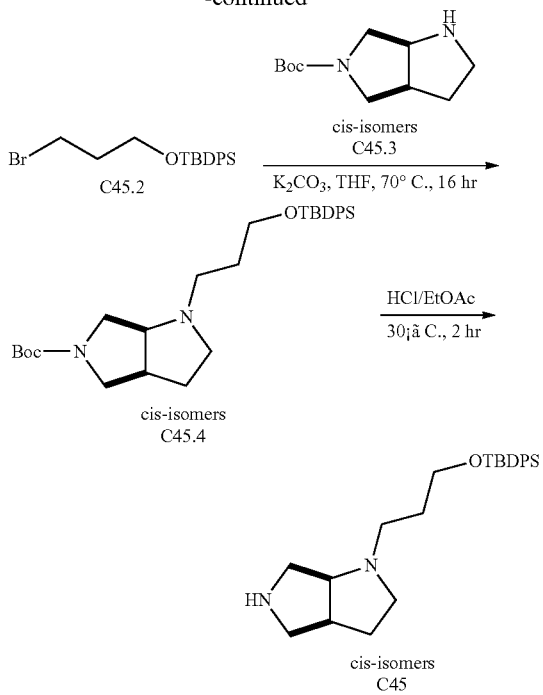

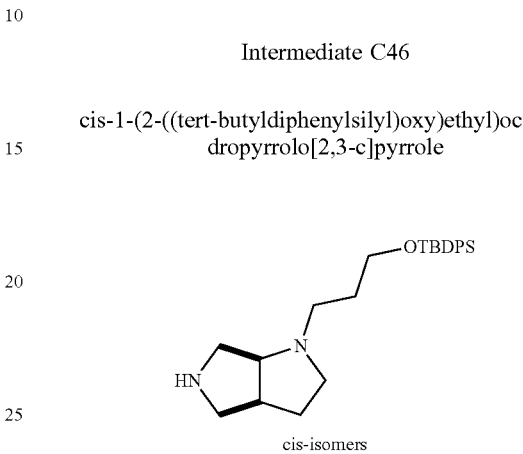

Step (a) 3-Bromopropoxy-tert-butyl-diphenyl-silane (Compound C45.2)

To a solution of 3-bromo-1-propanol (10 g, 71.95 mmol, compound C45.1), imidazole (9.8 g, 143.9 mmol) in DMF (40 mL) was added tert-butylchlorodiphenylsilane (19.8 g, 71.95 mmol) at 0° C., then the mixture was stirred at 30° C. for 16 h. The reaction mixture was diluted with EtOAc (300 mL) and washed with brine (100 mL) twice. The combined organic layer was dried over anhy. Na$_2$SO$_4$, filtered and concentrated in vacuo to give product crude product, which was then purified by silica gel flash chromatography (2~5% EtOAc in petroleum ether) to give 3-bromopropoxy-tert-butyl-diphenyl-silane (20 g, 73.66% yield) as colorless oil.

Step (b) cis-tert-butyl 1-(3-((tert-butyldiphenylsilyl)oxy)propyl)hexahydropyrrolo[2,3-c]pyrrole-5(1H)-carboxylate (Compound C45.4)

A solution of cis-tert-butyl hexahydropyrrolo[2,3-c]pyrrole-5(1H)-carboxylate (500.0 mg, 2.36 mmol, compound C45.3), 3-bromopropoxy-tert-butyl-diphenyl-silane (1000 mg, 2.83 mmol, compound C45.2) and potassium carbonate (650 mg, 4.71 mmol) in THF (5 mL) was stirred at 70° C. for 16 h. After cooled down to room temperature, EtOAc (50 mL) was added and the mixture solution was washed with brine (30 mL) twice. The combined organic layer was dried over anhy. Na$_2$SO$_4$, filtered and concentrated in vacuo to give a crude product, which was then purified by silica gel flash chromatography (5~10% EtOAc in petroleum ether) to give cis-tert-butyl 1-(3-((tert-butyldiphenyl silyl)oxy)propyl) hexahydropyrrolo[2,3-c]pyrrole-5(1H)-carboxylate (700 mg, 58.42% yield) as yellow oil. MS (ESI): 509.2 ([M+H]$^+$).

Step (c) cis-1-(3-(tert-butyldiphenylsilyl)oxy)propyl)octahydropyrrolo[2,3-c]pyrrole (Intermediate C45)

To a solution of 1-(3-((tert-butyldiphenylsilyl)oxy)propyl)hexahydropyrrolo[2,3-c]pyrrole-5(1H)-carboxylate (700.0 mg, 1.38 mmol, compound C45.4) in EtOAc (5 mL) was added HCl/EtOAc solution (1.75 mL, 7 mmol), then the mixture was stirred at 30° C. for 2 h. Afterwards, the reaction mixture was concentrated in vacuo to give a crude product which was purified by Prep-HPLC (C18, 5% to 60% MeCN in H$_2$O, 0.1% formic acid as addictive) and gave cis-1-(3-((tert-butyldiphenylsilyl)oxy)propyl)octahydropyrrolo[2,3-c]pyrrole (300 mg, 0.730 mmol, 53.36% yield) as colorless oil. MS (ESI): 409.2 ([M+H]$^+$).

Intermediate C46 cis-1-(2-((tert-butyldiphenylsilyl)oxy)ethyl)octahydropyrrolo[2,3-c]pyrrole

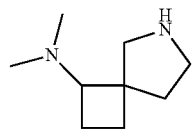

The title compound was prepared in analogy to Intermediate C45 by replacing 3-bromo-1-propanol (compound C45.1) with 2-bromoethanol. MS (ESI): 395.2 ([M+H]$^+$).

Intermediate C47

N,N-dimethyl-6-azaspiro[3.4]octan-1-amine hydrochloride

The titled compound was synthesized according to the following scheme:

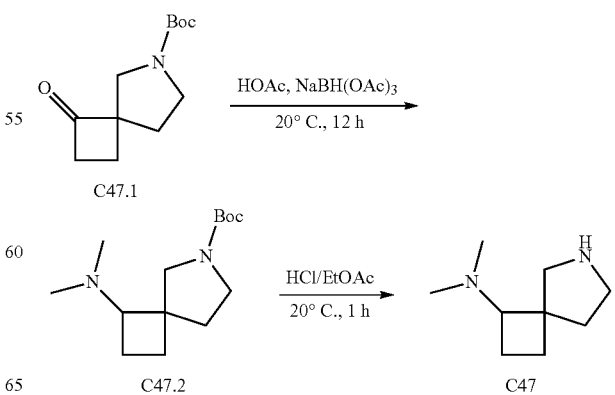

Step (a) Preparation of tert-butyl 1-(dimethyl-amino)-6-azaspiro[3.4]octane-6-carboxylate (Compound C47.2)

To a mixture of tert-butyl 1-oxo-6-azaspiro[3.4]octane-6-carboxylate (800.0 mg, 3.55 mmol) and dimethylamine in THF (15.0 mL, 30.0 mmol) was added acetic acid (21.3 mg, 0.36 mmol), and the reaction mixture was stirred for at 20° C. 2 h before sodium triacetoxyborohydride (2.3 g, 10.6 mmol) was added to the reaction mixture, and stirred for another 12 h. After LCMS showed the starting material was consumed completely, the mixture solution was diluted with DCM (200 mL), poured into water (100 mL), and extracted with DCM (100 mL) twice. The combined organic layer was washed with brine (100 mL), dried over anhy.Na$_2$SO$_4$, filtered, concentrated in vacuo to give a crude product, which was purified by silica gel flash chromatography (DCM:MeOH=10:1) to give tert-butyl 3-(dimethylamino)-6-azaspiro[3.4]octane-6-carboxylate (800 mg, 88.5% yield) as yellow oil. MS (ESI): 255.1 ([M+H]$^+$).

Step (b) Preparation of N,N-dimethyl-6-azaspiro[3.4]octan-1-amine hydrochloride (Intermediate C47)

A solution of tert-butyl 1-(dimethylamino)-6-azaspiro[3.4]octane-6-carboxylate (750.0 mg, 2.9 mmol) in HCl/EtOAc (10.0 mL, 40.0 mmol) was stirred at 20° C. for 1 h. After LCMS showed the starting material was consumed completely, the mixture was concentrated in vacuo to give a crude product of N,N-dimethyl-6-azaspiro[3.4]octan-3-amine hydrochloride (565 mg, 99.48% yield), which was used directly in the next step without further purification. MS (ESI): 151.1 ([M+H]$^+$).

Intermediate C48

(1R,5S,6S)—N,N-dimethyl-3-azabicyclo[3.1.0]hexan-6-amine

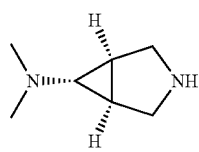

The title compound was prepared in analogy to Intermediate C2 by replacing cis-tert-butyl 3-(aminomethyl)tetrahydro-2H-furo[2,3-c]pyrrole-5 (3H)-carboxylate with (1R, 5S,6S)-tert-butyl 6-amino-3-azabicyclo[3.1.0]hexane-3-carboxylate in step (a). MS (ESI): 127.1 ([M+H]$^+$).

Intermediate C49

3a,5-Dimethyloctahydropyrrolo[2,3-c]pyrrole

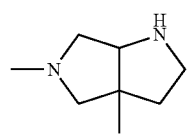

The titled compound was synthesized according to the following scheme:

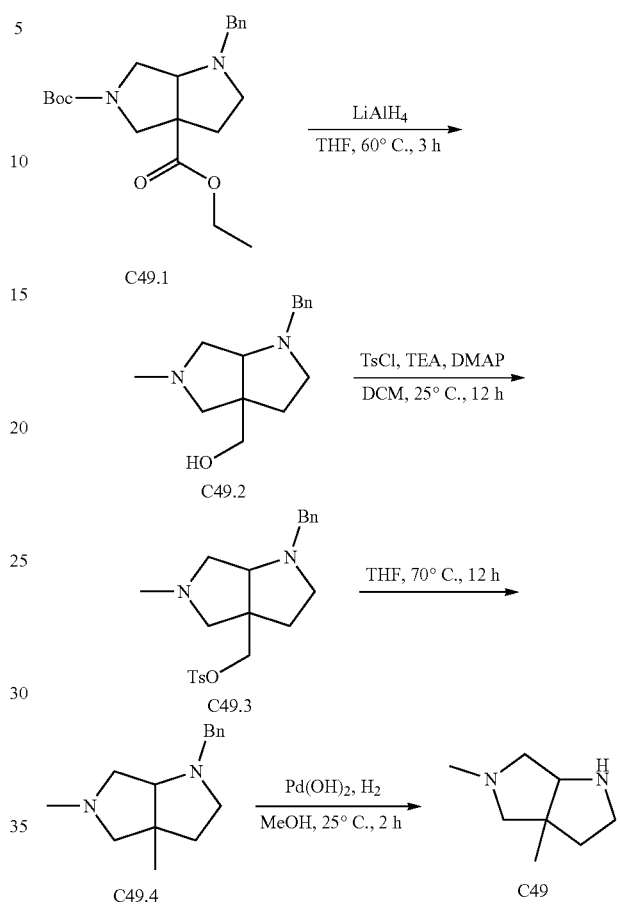

Step (a) Preparation of (1-benzyl-5-methyloctahydropyrrolo[2,3-c]pyrrol-3a-yl)methanol (Compound C49.2)

To a stirred solution of 5-tert-butyl 3a-ethyl 1-benzyl-hexahydropyrrolo[2,3-c]pyrrole-3a,5(1H)-dicarboxylate (800 mg, 2.14 mmol compound C49.1) in THF (2.0 mL) was added LiAlH$_4$ (815 mg, 21.4 mmol) and the resulting reaction mixture was stirred at 60° C. for 3 h. After LCMS showed the starting material was consumed completely, the reaction was cooled down to 0° C., and poured into EtOAc (10.0 mL), followed by the addition of MgSO$_4$. The resulting mixture was stirred at 0° C. for 1 h before it was filtered. The filtrate was then concentrated in vacuo to give a crude product of (1-benzyl-5-methyloctahydropyrrolo[2,3-c]pyrrol-3a-yl)methanol (450 mg) as colourless oil, which was used directly in the next step without further purification. MS (ESI): 247.1 (M+H)$^+$.

Step (b) Preparation of (1-benzyl-5-methyloctahydropyrrolo[2,3-c]pyrrol-3a-yl)methyl 4-methylbenzenesulfonate (Compound C49.3)

To a solution of (1-benzyl-5-methyl octahydropyrrolo[2,3-c]pyrrol-3a-yl)methanol (700.0 mg, 2.84 mmol, compound C49.2), TsCl (650 mg, 3.41 mmol) and TEA (862.2 mg, 8.52 mmol) in DCM (5.0 mL) was added DMAP (69 mg, 0.568 mmol) and the resulting mixture was stirred at 25° C. for 3 h. After LCMS showed the starting material was consumed completely, the mixture was diluted with EtOAc (50 mL) and filtered. The filtrate was concentrated in vacuo to give a crude product of (1-benzyl-5-methyloctahydropyrrolo[2,3-c]pyrrol-3a-yl)methyl 4-methylbenzenesulfonate (900 mg, 79.1% yield) as yellow oil. MS (ESI): 401.1 (M+H)⁺. It was used directly in the next step without further purification.

Step (c) Preparation of 1-benzyl-3a,5-dimethyloctahydropyrrolo[2,3-c]pyrrole (Compound C49.4)

To a solution of (1-benzyl-5-methyloctahydropyrrolo[2,3-c]pyrrol-3a-yl)methyl 4-methylbenzenesulfonate (900 mg, 2.25 mmol, compound C49.4) in THF (15 mL) was added LiAlH₄ (853 mg, 22.5 mmol) slowly at 0° C. After completion of addition, the mixture was stirred at 70° C. for 12 h. After TLC (petroleum ether/EtOAc=2/1, 1% NH₃.H₂O as additive) showed the starting material was consumed completely, the mixture was diluted with THF (300 mL) followed by the addition of H₂O (0.85 mL), aq. NaOH solution (1.70 mL, 10%), H₂O (0.85 mL), and EtOAc (300 mL) in an ice-water bath. The mixture solution was filtered, and separated organic layer was dried over anhy. Na₂SO₄, filtered, and concentrated in vacuo to give a crude product, which was purified by silica gel flash chromatography (petroleum ether:EtOAc=10:1~1:2, 1% NH₃.H₂O as additive) to give 1-benzyl-3a,5-dimethyloctahydropyrrolo[2,3-c]pyrrole (400 mg, 77.28% yield) as yellow oil. MS (ESI): 231.0 (M+H)⁺.

Step (d) Preparation of 3a,5-dimethyloctahydropyrrolo[2,3-c]pyrrole (Intermediate C49)

To a solution of 1-benzyl-3a,5-dimethyloctahydropyrrolo[2,3-c]pyrrole (400 mg, 0.52 mmol) in EtOH (5 mL) was added Pd(OH)₂/C (400 mg). The suspension was degassed under vacuum and purged with H₂ several times before it was stirred at 60° C. for 2 h under H₂ (20 psi). After LCMS showed the starting material was consumed completely, the mixture was filtered through Celite and the filtrate was evaporated under reduced pressure to give a crude product of 3a,5-dimethyloctahydropyrrolo[2,3-c]pyrrole (200 mg, 82.1% yield) as pale yellow oil, which was used directly in the next step without further purification. MS (ESI): 141.0 ([M+H]⁺).

Intermediate C50 trans-4-Methyl-3,4a,5,6,7,7a-hexahydro-2H-pyrrolo[3,4-b][1,4]oxazine; dihydrochloride

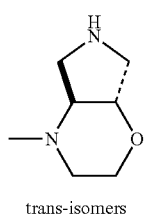

trans-isomers

The title compound was prepared in analogy to Intermediate C40 by replacing tert-butyl 3,4,4a,5,7,7a-hexahydro-2H-pyrrolo[3,4-b][1,4]oxazine-6-carboxylate with trans-tert-butyl 3,4,4a,5,7,7a-hexahydro-2H-pyrrolo[3,4-b][1,4]oxazine-6-carboxylate in step (a). MS (ESI): 143.2 ([M+H]⁺).

Intermediate C51 cis-N,N-dimethyl-3,3a,4,5,6,6a-hexahydro-2H-furo[2,3-c]pyrrol-3-amine

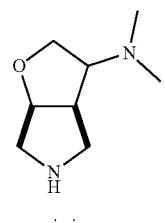

cis-isomers

The titled compound was synthesized according to the following scheme

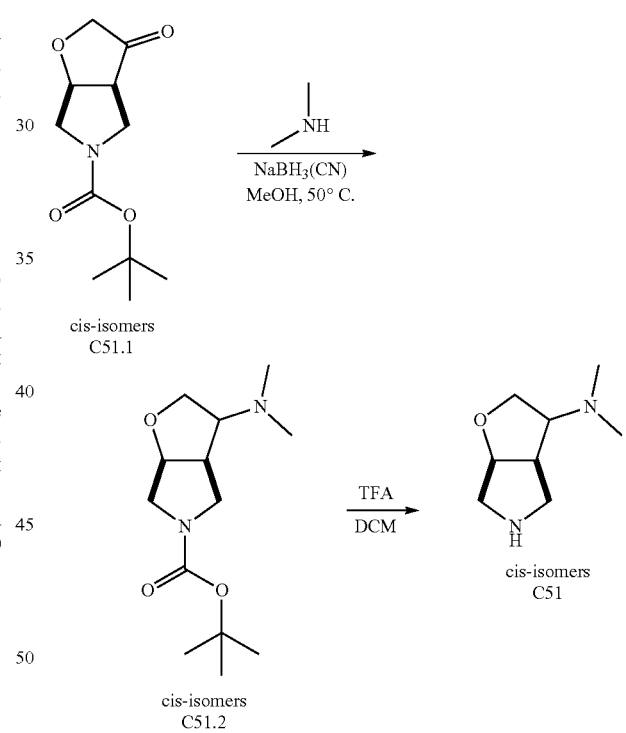

Step (a) cis-tert-butyl 3-(dimethylamino)-2,3,3a,4,6,6a-hexahydrofuro[2,3-c]pyrrole-5-carboxylate(Compound C51.2)

In a 50 mL round-bottom flask, dimethylamine hydrochloride (502 mg, 6.16 mmol) and tert-butyl 3-oxohexahydro-5H-furo[2,3-c]pyrrole-5-carboxylate (350 mg, 1.54 mmol) were dissolved in MeOH (10 mL) to give a colorless solution. The reaction mixture was heated to 50° C. and stirred for 1 h before it was cooled to room temperature and added sodium cyanoborohydride (387 mg, 6.16 mmol). The reaction mixture was re-heated to 50° C. and stirred for 15 h. After cooled to room temperature, the reaction mixture was concentrated under reduced pressure and satd aq. NaHCO$_3$ solution (25 mL) and extracted with DCM/isopropanol (3/1) (25 mL) three times. The combined organic layer was washed with brine (5 mL), dried over anhy. Na$_2$SO$_4$, filtered, and concentrated in vacuo to give a crude product of obtain tert-butyl 3-(dimethylamino)hexahydro-5H-furo[2,3-c]pyrrole-5-carboxylate (395 mg, 100% yield), which was used directly in the next step without further purification. MS (ESI): 256.8 ([M+H]$^+$).

Step (b) cis-N,N-dimethyl-3,3a,4,5,6,6a-hexahydro-2H-furo[2,3-c]pyrrol-3-amine (Intermediate C51)

To a stirred solution of tert-butyl 3-(dimethylamino)hexahydro-5H-furo[2,3-c]pyrrole-5-carboxylate (190 mg, 741 µmol) in DCM (6 mL) was added TFA (3.38 g, 2.28 ml, 29.6 mmol) was added. The resulting reaction mixture was stirred at room temperature for 1 h before concentrated in vacuo to give a crude product of N,N-dimethylhexahydro-2H-furo[2,3-c]pyrrol-3-amine bis(2,2,2-trifluoroacetate) (285 mg, 100% yield), which was used directly in the next step without further purification. MS (ESI): 156.8 ([M+H]$^+$).

Intermediate C52 cis-3,3a,4,5,6,6a-hexahydro-2H-furo[2,3-c]pyrrol-3-ol

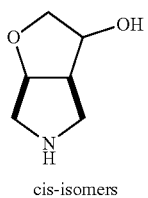
cis-isomers

The titled compound was synthesized according to the following scheme

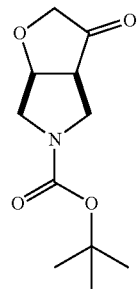 
cis-isomers
C52.1

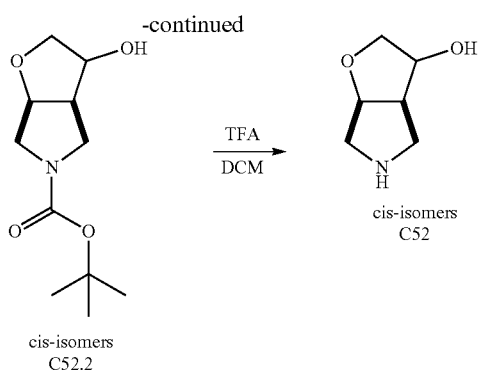
cis-isomers
C52.2

Step (a) cis-tert-butyl 3-hydroxy-2,3,3a,4,6,6a-hexahydrofuro[2,3-c]pyrrole-5-carboxylate (Compound C52.2)

To a stirred solution of cis-tert-butyl 3-oxohexahydro-5H-furo[2,3-c]pyrrole-5-carboxylate (150 mg, 660 µmol) in MeOH (10 mL) was added NaBH$_4$, and the resulting reaction mixture was stirred at room temperature for 1 h. Afterwards, the reaction mixture was concentrated under reduced pressure and the residue was poured into H$_2$O (25 mL) and extracted with EtOAc (25 mL) three times. The combined organic layer was washed with brine (25 mL), dried over anhy. Na$_2$SO$_4$, filtered, and concentrated in vacuo to give a crude product of cis-tert-butyl 3-hydroxyhexahydro-5H-furo[2,3-c]pyrrole-5-carboxylate (151 mg, 99.8% yield), which was used directly in the next step without further purification. MS (ESI): 230.3 ([M+H]$^+$).

Step (b) cis-3,3a,4,5,6,6a-hexahydro-2H-furo[2,3-c]pyrrol-3-ol (Intermediate C52)

To a solution of tert-butyl 3-hydroxyhexahydro-5H-furo[2,3-c]pyrrole-5-carboxylate (151 mg, 659 µmol) in DCM (6 mL) was added TFA (3.75 g, 2.54 mL, 32.9 mmol), and the resulting reaction mixture was stirred at room temperature for 1 h. Afterwards, the reaction mixture was concentrated in vacuo to give a crude product of cis-hexahydro-2H-furo[2,3-c]pyrrol-3-ol, which was used directly in the next step without further purification. MS (ESI): 130.3 ([M+H]$^+$).

Intermediate C53 cis-5-Ethyl-2,3,3a,4,6,6a-hexahydro-1H-pyrrolo[2,3-c]pyrrole

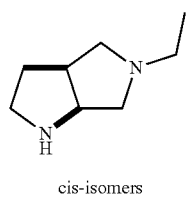
cis-isomers

The title compound was prepared in analogy to Intermediate C3 by replacing bromo-2-methoxy-ethane with iodoethane in step (a). MS (ESI): 141.2 ([M+H]$^+$).

Intermediate C54 cis-1-Cyclopropyl-3,3a,4,5,6,6a-hexahydro-2H-pyrrolo[2,3-c]pyrrole

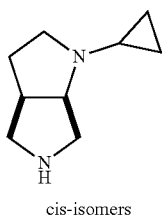

cis-isomers

The titled compound was synthesized according to the following scheme

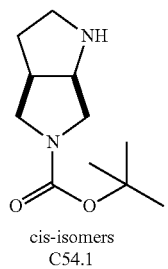

cis-isomers
C54.1

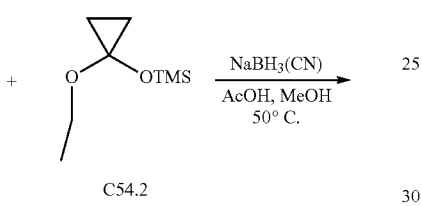

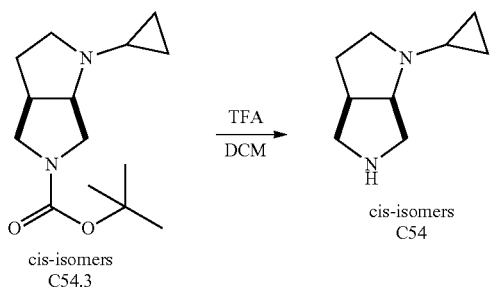

Step (a) cis-tert-butyl 1-cyclopropyl-2,3,3a,4,6,6a-hexahydropyrrolo[2,3-c]pyrrole-5-carboxylate (Compound C54.3)

In a 100 mL round-bottomed flask, (1-ethoxycyclopropoxy)trimethylsilane (411 mg, 2.36 mmol), cis-tert-butyl hexahydropyrrolo[3,4-b]pyrrole-5(1H)-carboxylate (250 mg, 1.18 mmol), sodium cyanoborohydride (222 mg, 3.53 mmol), and AcOH (84.9 mg, 80.9 µl, 1.41 mmol) were dissolved in MeOH (20 mL). The resulting reaction mixture was heated to 50° C. and stirred for 5 h before it was cooled down to room temperature and concentrated under reduced pressure. The residue was poured into satd. aq. NaHCO₃ solution (50 mL) and extracted with EtOAc (25 mL) three times. The combined organic layer was with brine (25 mL), dried over anhy. Na₂SO₄, filtered, and concentrated in vacuo to give a crude product of cis-tert-butyl 1-cyclopropylhexahydropyrrolo[3,4-b]pyrrole-5(1H)-carboxylate (180 mg, 713 µmol, 60.6% yield), which was used directly in the next step without further purification. MS (ESI): 253.5 ([M+H]⁺).

Step (b) cis-1-cyclopropyl-3,3a,4,5,6,6a-hexahydro-2H-pyrrolo[2,3-c]pyrrole (Intermediate C54)

To a solution of tert-butyl 1-cyclopropylhexahydropyrrolo[3,4-b]pyrrole-5(1H)-carboxylate (180 mg, 713 µmol) in DCM (6 mL) was added TFA (4.07 g, 2.75 mL, 35.7 mmol). The resulting reaction mixture was stirred at room temperature for 30 min before concentrated in vacuo to give a crude product of cis-1-cyclopropyloctahydropyrrolo[3,4-b]pyrrole 2,2,2-trifluoroacetate (190 mg, 100% yield), which was used directly in the next step without further purification. MS (ESI):153.2 ([M+H]⁺).

Intermediate C55

1-(3-Fluoro-3-piperidyl)-N,N-dimethyl-methanamine

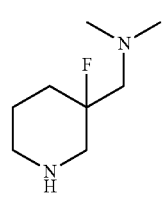

The title compound was prepared in analogy to Intermediate C2 by replacing cis-tert-butyl 3-(aminomethyl)tetrahydro-2H-furo[2,3-c]pyrrole-5 (3H)-carboxylate with tert-butyl 3-(aminomethyl)-3-fluoro-piperidine-1-carboxylate in step (a). MS (ESI): 161.2 ([M+H]⁺).

Intermediate C56 cis-(4S)—N,N-dimethyl-1,2,3,3a,4,5,6,6a-octahydrocyclopenta[c]pyrrol-4-amine

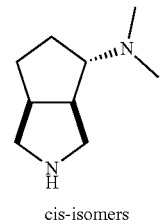

cis-isomers

The title compound was prepared in analogy to Intermediate C2 by replacing cis-tert-butyl 3-(aminomethyl)tetrahydro-2H-furo[2,3-c]pyrrole-5 (3H)-carboxylate with cis-tert-butyl-(4S)-amino3,3a,4,5,6,6a-hexahydro-1H-cyclopenta[c]pyrrole-2-carboxylate in step (a). MS (ESI): 155.2 ([M+H]⁺).

Intermediate C57 cis-1-Methyl-2,3,4,4a,5,6,7,7a-octahydropyrrolo[3,4-b]pyridin-4-ol

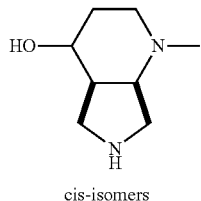

cis-isomers

The titled compound was synthesized according to the following scheme

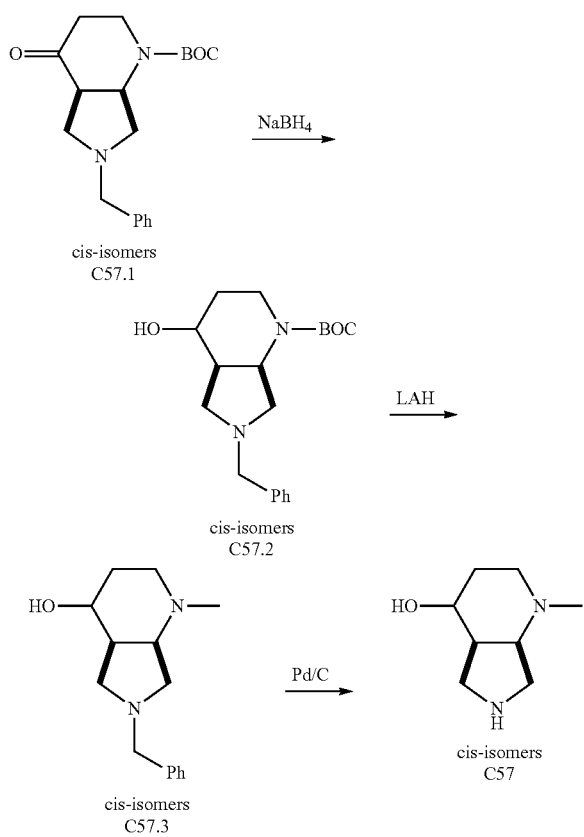

Step (a) cis-1-amino-6-(aminomethyl)-3,4,4a,5,7,7a-hexahydro-2H-pyrrolo[3,4-b]pyridin-4-ol (Compound C57.2)

To a solution of cis-1-amino-6-(aminomethyl)-2,3,4a,5,7,7a-hexahydropyrrolo[3,4-b]pyridin-4-one (250 mg, 757 μmol) in MeOH (15 mL) was added NaBH$_4$ (85.9 mg, 2.27 mmol). The resulting reaction mixture was stirred at room temperature for 1 h before it was concentrated in vacuo. The residue was poured into satd. aq. NH$_4$Cl solution (25 mL) and extracted with EtOAc (25 mL) three times. The combined organic layer was washed with brine (25 mL), dried over anhy. Na$_2$SO$_4$, filtered, and concentrated in vacuo to give a crude product of cis-1-amino-6-(aminomethyl)-3,4,4a,5,7,7a-hexahydro-2H-pyrrolo[3,4-b]pyridin-4-ol (252 mg, 100% yield), which was used directly in the next step without further purification. MS (ESI): 333.6 ([M+H]$^+$).

Step (b) cis-6-(aminomethyl)-1-methyl-3,4,4a,5,7,7a-hexahydro-2H-pyrrolo[3,4-b]pyridin-4-ol (Compound C57.3)

To a 25 mL microwave vial was added cis-1-amino-6-(aminomethyl)-3,4,4a,5,7,7a-hexahydro-2H-pyrrolo[3,4-b]pyridin-4-ol (230 mg, 692 μmol) and LiAlH$_4$ (1.38 ml, 3.46 mmol) in THF (12 mL). The vial was capped and heated in the microwave reactor at 80° C. for 1 h. After cooled down to room temperature, satd. aq. Na$_2$SO$_4$ solution (0.6 mL) added to quench the reaction. The reaction mixture was filtered through glass fiber paper and the filtrate was concentrated in vacuo to give a crude product of cis-6-(aminomethyl)-1-methyl-3,4,4a,5,7,7a-hexahydro-2H-pyrrolo[3,4-b]pyridin-4-ol (170 mg, 690 μmol, 99.7% yield), which was used directly in the next step without further purification. MS (ESI): 248.2 ([M+H]$^+$).

Step (c) cis-6-(aminomethyl)-1-methyl-3,4,4a,5,7,7a-hexahydro-2H-pyrrolo[3,4-b]pyridin-4-ol (Intermediate C57)

To a solution of cis-6-(aminomethyl)-1-methyl-3,4,4a,5,7,7a-hexahydro-2H-pyrrolo[3,4-b]pyridin-4-ol (170 mg, 690 μmol) in MeOH (20 mL) was added Pd(OH)$_2$/C (29.1 mg, 207 μmol). The reaction was degassed under vacuum and purged with H$_2$ balloon three times before it was stirred at room temperature for 1 h. Afterwards, the reaction mixture was filtered through glass fiber paper and the filtrate was concentrated in vacuo to give a crude product of 1-methyl-2,3,4,4a,5,6,7,7a-octahydropyrrolo[3,4-b]pyridin-4-ol (108 mg, 100% yield), which was used directly in the next step without further purification. MS (ESI): 157.1 ([M+H]$^+$).

Intermediate C58 cis-6-Methyloctahydropyrrolo[3,4-b][1,4]oxazine

cis-isomers

The titled compound was synthesized according to the following scheme:

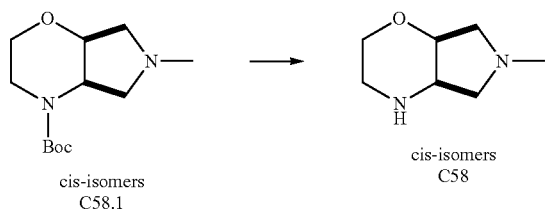

Preparation of cis-6-methyloctahydropyrrolo[3,4-b][1,4]oxazine (Intermediate C58)

cis-tert-Butyl 6-methylhexahydropyrrolo[3,4-b][1,4]oxazine-4(4aH)-carboxylate hydrochloride (900 mg, 3.4 mmol) was neutralized by $K_2CO_3$ in methanol, which was filtered and concentrated to afford the free amine. The free amine in 5 mL THF was added to a suspension of lithium aluminum hydride (516 mg, 13.6 mmol) in THF (40 mL), the mixture was stirred at 70° C. for 3 h under $N_2$. The reaction was quenched with 1 g of water and 1 mL of 3 M NaOH solution. The separated organic layer was dried over $MgSO_4$, filtered and the filtrate was concentrated to give cis-6-methyloctahydropyrrolo[3,4-b][1,4]oxazine (Intermediate C58) (450 mg, 3.16 mmol, 93.1% yield) as a yellow oil. H NMR: (400 MHz, CHLOROFORM-d) δ ppm 3.91 (td, J=5.14, 2.01 Hz, 1H), 3.75-3.81 (m, 1H), 3.45 (ddd, J=11.26, 9.07, 3.89 Hz, 1H), 3.33 (td, J=7.06, 4.96 Hz, 1H), 3.07 (ddd, J=13.30, 8.91, 4.77 Hz, 1H), 2.82-2.88 (m, 2H) 2.61-2.70 (m, 3H), 2.38 (s, 3H).

Example 1.01

6-[4-(Dimethylamino)-5,6-difluoro-8-(methylamino)-9H-pyrido[2,3-b]indol-3-yl]-1-methyl-4-oxo-1,8-naphthyridine-3-carboxylic acid

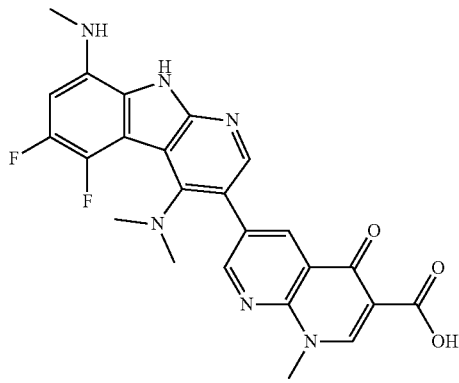 [SMILES: CNc1cc(F)c(F)c2c1[nH]c1ncc(-c3cnc4c(c3)c(=O)c(C(=O)O)cn4C)c(N(C)C)c12]

Step (a) Preparation of tert-butyl N-[3-chloro-4-(dimethylamino)-5,6-difluoro-9H-pyrido[2,3-b]indol-8-yl]-N-methyl-carbamate

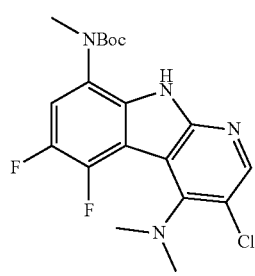 [SMILES: CN(C)c1c(Cl)cnc2[nH]c3c(N(C)C(=O)OC(C)(C)C)cc(F)c(F)c3c12]

To a solution of tert-Butyl N-(3,4-dichloro-5,6-difluoro-9H-pyrido[2,3-b]indol-8-yl)-N-methyl-carbamate (Intermediate A3, 100.0 mg, 0.25 mmol, as the "CORE" in table 1) and DIPEA (320 mg, 2.48 mmol) in DMSO (2.0 mL) was added N-methylmethanamine hydrochloride (203 mg, 2.48 mmol, as the "AMINE" in table 1), the reaction solution was stirred at 110° C. for 12 h. The mixture was poured into water (50 mL) and extracted by EtOAc (100 mL) two times. The organic layer was washed by brine (50 mL) two times, dried over anhy. $Na_2SO_4$, filtered, and concentrated under reduced pressure to give a crude product, which was purified by Prep-TLC (petroleum ether:EtOAc=2:1) to give tert-butyl N-[3-chloro-4-(dimethylamino)-5,6-difluoro-9H-pyrido[2,3-b]indol-8-yl]-N-methyl-carbamate (90.0 mg, 88% yield) as a yellow solid in 96% of purity. MS (ESI): 411.3 ($[\{^{35}Cl\}M+H]^+$), 413.2 ($[\{^{37}Cl\}M+H]^+$).

Step (b) Preparation of ethyl 6-[8-[tert-butoxycarbonyl(methyl)amino]-4-(dimethylamino)-5,6-difluoro-9H-pyrido[2,3-b]indol-3-yl]-1-methyl-4-oxo-1,8-naphthyridine-3-carboxylate

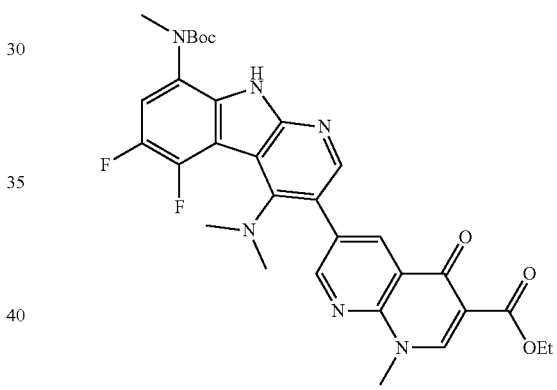

A solution of tert-butyl N-[3-chloro-4-(dimethylamino)-5,6-difluoro-9H-pyrido[2,3-b]indol-8-yl]-N-methyl-carbamate (90 mg, 0.219 mmol), (6-ethoxycarbonyl-8-methyl-5-oxo-1,8-naphthyridin-3-yl)boronic acid (Intermediate B2, 121.0 mg, 0.438 mmol, as the "BORONIC REAGENT" in table 1) and $K_3PO_4$ (186 mg, 0.876 mmol) in THF/$H_2O$ (4.0 mL, v/v=20:1 as the "SOLVENT" in table 1), and then $Ad_2nBuP$ Biphenyl (30 mg, 0.044 mmol, as the "CATALYST" in table 1) was added to the mixture in glove box under argon. The reaction mixture was stirred at 70° C. for 12 h under argon. The mixture was poured into water (50 mL) and extracted by EtOAc (100 mL) two times. The organic layer was washed by brine (50 mL) two times, dried with anhy. $Na_2SO_4$, filtered, and concentrated under reduced pressure to give a crude product, which was purified by Prep-TLC (DCM:MeOH=30:1) to give ethyl 6-[8-[tert-butoxycarbonyl(methyl)amino]-4-(dimethylamino)-5,6-difluoro-9H-pyrido[2,3-b]indol-3-yl]-1-methyl-4-oxo-1,8-naphthyridine-3-carboxylate (100 mg, 75% yield) as a yellow solid. MS (ESI): 607.1 (M+H)$^+$.

Step (c) Preparation of 6-[8-[tert-butoxycarbonyl (methyl)amino]-4-(dimethylamino)-5,6-difluoro-9H-pyrido[2,3-b]indol-3-yl]-1-methyl-4-oxo-1,8-naphthyridine-3-carboxylic acid

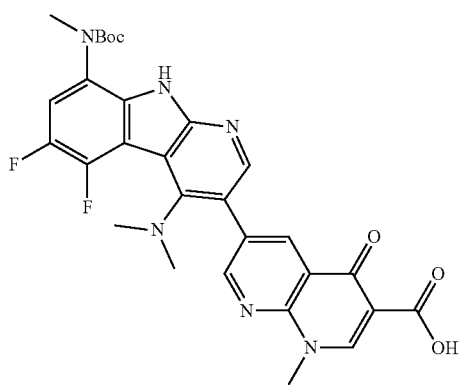 [SMILES: CCOC(=O)c1cn(C)c2ncc(-c3cnc4[nH]c5c(N(C)C(=O)OC(C)(C)C)cc(F)c(F)c5c4c3N(C)C)cc2c1=O]

A solution of ethyl 6-[8-[tert-butoxycarbonyl(methyl)amino]-4-(dimethylamino)-5,6-difluoro-9H-pyrido[2,3-b]indol-3-yl]-1-methyl-4-oxo-1,8-naphthyridine-3-carboxylate (100 mg, 0.165 mmol) and NaOH (198.0 mg, 4.95 mmol) were dissolved in a mixture of THF/H$_2$O (3.0 mL, V/V=3/1). The reaction mixture was stirred at 30° C. for 12 h. After LCMS showed starting material was consumed completely, the reaction mixture was diluted with DCM (50 mL) and H$_2$O (10 mL), and adjusted to 15 pH=6 with 1N HCl aqueous solution, and extracted with DCM/MeOH (10:1, 50 mL) three times. The combined organic phase washed with brine (50 mL) two times, dried over anhy. Na$_2$SO$_4$, filtered, and concentrated in vacuo to give a crude product of 6-[8-[tert-butoxycarbonyl(methyl)amino]-4-(dimethylamino)-5,6-difluoro-9H-pyrido[2,3-b]indol-3-yl]-1-methyl-4-oxo-1,8-naphthyridine-3-carboxylic acid (90 mg, 94% yield) as a yellow solid, which was used directly in the next step without further purification. MS (ESI): 579.4 (M+H)$^+$.

Step (d) Preparation of 6-[4-(dimethylamino)-5,6-difluoro-8-(methylamino)-9H-pyrido[2,3-b]indol-3-yl]-1-methyl-4-oxo-1,8-naphthyridine-3-carboxylic acid (Example 1.01)

To a solution of 6-[8-[tert-butoxycarbonyl(methyl)amino]-4-(dimethylamino)-5,6-difluoro-9H-pyrido[2,3-b]indol-3-yl]-1-methyl-4-oxo-1,8-naphthyridine-3-carboxylic acid (88 mg, 0.152 mmol) in dry DCM (2.0 mL) was added TFA (1.0 mL). The reaction mixture was stirred at 15° C. for 1 h before it was concentrated in vacuo to give a crude product, which was purified by Prep-HPLC (0.5% TFA in water) to give 6-[4-(dimethylamino)-5,6-difluoro-8-(methylamino)-9H-pyrido[2,3-b]indol-3-yl]-1-methyl-4-oxo-1,8-naphthyridine-3-carboxylic acid (34 mg, 47% yield) as a yellow solid in 99.6% of purity. $^1$H NMR (400 MHz, DMSO-d$_6$) δ: 11.76 (s, 1H), 9.29 (s, 1H), 9.07~9.08 (d, 1H), 8.60~8.60 (d, 1H), 8.25 (s, 1H), 6.56~6.61 (m, 1H), 4.18 (s, 3H), 2.90 (s, 3H), 2.73~2.73 (m, 6H). MS (ESI): 479.3 (M+H)$^+$.

The following examples were prepared in analogy to Example 1.01, replacing tert-Butyl N-(3,4-dichloro-5,6-difluoro-9H-pyrido[2,3-b]indol-8-yl)-N-methyl-carbamate (Intermediate A3) with the "CORE" in step (a), N-methylmethanamine hydrochloride with the "AMINE" in step (a), THF/H$_2$O with the "SOLVENT" in step (b), Ad$_2$nBuP Biphenyl with the "CATALYST" in step (b) and (6-ethoxycarbonyl-8-methyl-5-oxo-1,8-naphthyridin-3-yl)boronic acid with the "BORONIC REAGENT" in step (b) by the reagents indicated in Table 1.

TABLE 1

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.02 | 6-[4-(dimethylamino)-5,6-difluoro-8-(methylamino)-9H-pyrido[2,3-b]indol-3-yl]-4-oxo-1-pyrrolidin-3-yl-1,8-naphthyridine-3-carboxylic acid | CORE: Intermediate A3<br>AMINE: Dimethylamine hydrochloride<br>BORONIC REAGENT: Intermediate B6<br>CATALYST: Pd-Ad$_2$nBuP Biphenyl Precat (CAS#: 1375477-29-4)<br>SOLVENT: THF/H$_2$O | $^1$H NMR (400 MHz, Methanol-d4): δ ppm: 9.22 (s, 1 H), 9.03 (s, 1 H) 8.66 (s, 1 H), 8.24 (s, 1 H), 6.63-6.58 (m, 1 H), 5.99-5.96 (m, 1 H) 3.83-3.75 (m, 3 H), 3.38-3.35 (m, 1 H), 2.90 (s, 3 H), 2.76-2.67 (m, 6 H), 2.52 (m, 2 H)<br>MS: 534.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.03 | 6-[4-(dimethylamino)-5,6-difluoro-8-(methylamino)-9H-pyrido[2,3-b]indol-3-yl]-1-(morpholin-3-ylmethyl)-4-oxo-1,8-naphthyridine-3-carboxylic acid | CORE: Intermediate A3<br>AMINE: Dimethylamine hydrochloride<br>BORONIC REAGENT: Intermediate B5<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 11.75 (brs, 1H), 9.14 (s, 1H), 9.04 (d, 1H), 8.62 (d, 1H), 8.26 (s, 1H), 8.20 (s, 1H), 6.59 (m, 1H), 5.67 (m, 1H), 4.79 (m, 1H), 4.43-4.59 (m, 1H), 3.82 (m, 1H), 3.62 (m, 1H), 3.23 (m, 1H), 2.91 (m, 3H), 2.74 (s, 6H).<br>MS: 546.2 ([M+H]$^+$) |
| 1.04 | 6-[4-(dimethylamino)-5,6-difluoro-8-(methylamino)-9H-pyrido[2,3-b]indol-3-yl]-1-[(1-ethylpyrrolidin-2-yl)methyl]-4-oxo-1,8-naphthyridine-3-carboxylic acid | CORE: Intermediate A3<br>AMINE: Dimethylamine hydrochloride<br>BORONIC REAGENT: Intermediate B3<br>CATALYST: Pd-Ad$_2$nBuP Biphenyl Precat (CAS#: 1375477-29-4)<br>SOLVENT: EtOH/H$_2$O | $^1$H NMR (400 MHz, DMSO-d6): δ ppm: 12.39 (brs, 1H), 11.17 (brs, 1H), 9.41 (s, 1H), 9.05 (d, J = 2.4 Hz, 1H), 8.66-8.65 (d, 1H), 8.22 (s, 1H), 6.61 (m, 1H), 5.20-5.10 (m, 2H), 4.01 (m, 1H), 3.23-3.12 (m, 4H), 2.88 (s, 3H), 2.77 (s, 6H), 1.99-1.94 (m, 4H), 1.33-1.30 (t, 3H).<br>MS: 576.1 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.05 | 6-[5,6-difluoro-8-(methylamino)-4-(2-oxa-5-azabicyclo[2.2.1]heptan-5-yl)-9H-pyrido[2,3-b]indol-3-yl]-1-ethyl-4-oxo-1,8-naphthyridine-3-carboxylic acid | CORE: Intermediate A3 AMINE: 2-oxa-5-azabicyclo[2.2.1]heptane BORONIC REAGENT: Intermediate B3 CATALYST: Pd-Ad$_2$nBuP Biphenyl Precat (CAS#: 1375477-29-4) SOLVENT: THF/H$_2$O | $^1$H NMR (400 MHz, DMSO-d6): δ ppm: 12.24 (s, 1 H), 9.29 (s, 1 H), 9.18~9.19 (m, 1 H), 8.71~8.74 (m, 1 H), 8.217 (s, 1 H), 6.57~6.62 (m, 1 H), 4.85 (s, 2 H), 4.72~4.74 (m, 2 H), 4.40 (s, 1 H), 3.63~3.65 (m, 1 H), 3.55~3.57 (m, 1 H), 3.12~3.15 (m, 1 H), 2.888 (s, 3 H), 1.83~1.85 (m, 1 H), 1.72~1.74 (m, 1 H), 1.46~1.49 (m, 3 H). MS: 547.2 ([M + H]$^+$) |
| 1.06 | 6-[5,6-difluoro-4-[2-methoxyethyl(methyl)amino]-8-(methylamino)-9H-pyrido[2,3-b]indol-3-yl]-1-ethyl-4-oxo-1,8-naphthyridine-3-carboxylic acid | CORE: Intermediate A3 AMINE: 2-methoxy-N-methyl-ethanamine BORONIC REAGENT: Intermediate B3 CATALYST: Pd-Ad$_2$nBuP Biphenyl Precat (CAS#: 1375477-29-4) SOLVENT: THF/H$_2$O | $^1$H NMR (400 MHz, DMSO-d6): δ ppm: 11.88 (s, 1 H), 9.28 (s, 1 H), 9.10~9.11 (m, 1 H), 8.73~8.74 (m, 1 H), 8.24~8.26 (m, 1 H), 6.56~6.61 (m, 1 H), 4.71~4.77 (m, 2 H), 3.38~3.41 (m, 2 H), 3.16 (s, 2 H), 3.10~3.11 (s, 3H), 2.89 (s, 3 H), 2.84 (s, 3 H) 2.51 (s, 3 H), 1.47~1.51 (m, 3 H). MS: 537.2 ([M + H]$^+$) |
| 1.07 | 6-[5,6-difluoro-8-(methylamino)-4-[methyl(propyl)amino]-9H-pyrido[2,3-b]indol-3-yl]-1-ethyl-4-oxo-1,8-naphthyridine-3-carboxylic acid | CORE: Intermediate A3 AMINE: N-methylpropan-1-amine BORONIC REAGENT: Intermediate B3 CATALYST: Pd-Ad$_2$nBuP Biphenyl Precat (CAS#: 1375477-29-4) SOLVENT: THF/H$_2$O | $^1$H NMR (400 MHz, DMSO-d6): δ ppm: 11.84 (s, 1 H), 9.28 (s, 1 H), 9.07 (s, 1 H), 8.62~8.62 (m, 1 H), 8.27 (s, 1 H), 6.56~6.61 (m, 1 H), 4 71~4.77 (m, 2 H), 2.99 (s, 3 H), 2.89 (s, 3H), 2.60~2.63 (m, 3 H), 1.46~1.50 (m, 3 H), 1.32~1.39 (m, 2 H), 0.59~0.63 (m, 3 H). MS: 521.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.08 | 6-[5,6-difluoro-8-(methylamino)-4-morpholino-9H-pyrido[2,3-b]indol-3-yl]-1-methyl-4-oxo-1,8-naphthyridine-3-carboxylic acid | CORE: Intermediate A3<br>AMINE: morpholine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 11.88 (s, 1H), 9.29 (s, 1H), 9.12~9.13 (d, 1H), 8.71~8.72 (d, 1H), 8.24 (s, 1H), 6.59~6.64 (m, 13.6 Hz, 1H), 4.18 (s, 3H), 3.58 (s, 4H), 2.93 (s, 4H), 2.90 (s, 3H)<br>MS: 521.1 ([M+H]$^+$) |
| 1.09 | 6-[5,6-difluoro-8-(methylamino)-4-[3-(trifluoromethyl)piperazin-1-yl]-9H-pyrido[2,3-b]indol-3-yl]-1-methyl-4-oxo-1,8-naphthyridine-3-carboxylic acid | CORE: Intermediate A3<br>AMINE: 2-(trifluoromethyl)piperazine hydrochloride<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 12.00 (s, 1 H), 9.28 (s, 1 H), 9.16 (s, 1 H), 8.69~8.69 (m, 1 H), 8.26 (s, 1 H), 6.60-6.65 (m, 1 H), 4.11~4.13 (m, 8H), 3.17~3.24 (m, 3 H), 2.91 (s, 3 H).<br>MS: 588.3 ([M + H]$^+$) |
| 1.10 | 6-[5,6-difluoro-4-[2-(methoxymethyl)morpholin-4-yl]-8-(methylamino)-9H-pyrido[2,3-b]indol-3-yl]-1-methyl-4-oxo-1,8-naphthyridine-3-carboxylic acid | CORE: Intermediate A3<br>AMINE: 2-(methoxymethyl)morpholine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 11.93 (s, 1H), 9.26 (s, 1H), 9.09 (s, 1H), 8.70 (s, 1H), 8.27-8.24 (m, 1H), 6.63-6.58 (m, 1H), 5.75 (s, 1H), 4.17 (s, 3H), 3.67-3.64 (m, 2H), 3.22-3.20 (m, 2H), 3.16-3.15 (m, 1H), 3.12 (s, 3H), 3.05 (m, 1H), 2.90 (s, 3H), 2.85 (m, 2H), 2.66 (m, 1H).<br>MS: 565.0 ([M + H]$^+$) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.11 | 6-[5,6-difluoro-8-(methylamino)-4-morpholino-9H-pyrido[2,3-b]indol-3-yl]-4-oxo-1-(pyrrolidin-2-ylmethyl)-1,8-naphthyridine-3-carboxylic acid | CORE: Intermediate A3<br>AMINE: morpholine<br>BORONIC REAGENT: Intermediate B7<br>CATALYST: Pd-Ad₂nBuP Biphenyl Precat (CAS#: 1375477-294)<br>SOLVENT: THF/H₂O | ¹H NMR (400 MHz, DMSO-d6): δ ppm: 9.29 (s, 1 H), 9.10 (s, 1 H), 8.75 (s, 1 H), 8.23 (s, 1 H), 6.67-6.62 (dd, 1 H), 5.07-5.04 (d, 2 H), 4.79 (m, 1 H), 4.01 (m, 1H), 3.29 (m, 2 H), 3.13-3.11 (m, 2 H), 2.90 (m, 8 H), 2.23-1.93 (m, 4 H), 1.78 (m, 1 H).<br>MS: 590.6 ([M + H]⁺) |
| 1.12 | 6-[4-[2-[(dimethylamino)methyl]pyrrolidin-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: N,N-dimethyl-1-pyrrolidin-2-yl-methanamine<br>BORONIC REAGENT: Intermediate B2<br>CATALYST: Pd-Ad₂nBuP Biphenyl Precat (CAS#: 1375477-294)<br>SOLVENT: THF/H₂O | ¹H NMR (400 MHz, DMSO-d6): δ ppm: 11.91 (s, 1H), 9.31 (s, 1H), 9.09~9.10 (d, 1H), 8.70~8.71 (d, 1H), 8.384 (s, 1H), 6.59~6.64 (m, 1H), 4.174 (s, 3H), 3.292~3.330 (t, 1H), 2.90 (s, 4H) 2.72~2.76 (t, 1H), 2.33~2.59 (m, 4H), 1.93 (s, 1H), 1.92 (s, 1H), 1.73 (s, 2H).<br>MS: 562.1 ([M + H]⁺) |
| 1.13 | 6-[4-[(2R)-2-[(dimethylamino)methyl]pyrrolidin-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: N,N-dimethyl-1-[(2R)-pyrrolidin-2-yl]methanamine hydrochloride<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, DMSO-d6): δ ppm: 9.03 (s, 1 H), 8.93 (s, 1 H), 8.58 (s, ¹ H), 8.18 (s, 1 H), 6.52~6.57 (m, 1 H), 5.87 (s, 1 H), 4.06 (s, 3H), 3.15 (m, 1 H), 2.88~2.89 (m, 3 H), 2.54~2.58 (m, 2 H), 1.76~1.96 (m, 5 H), 1.67 (s, 6 H), 1.48 (m, 1 H).<br>MS: 562.1 ([M + H]⁺) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.14 | 6-[4-[(2S)-2-[(dimethylamino)methyl]pyrrolidin-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: N,N-dimethyl-1-[(2S)-pyrrolidin-2-yl]methanamine hydrochloride<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 11.85 (br s, 1 H), 9.22 (s, 1 H), 9.05~9.06 (d, 1 H), 8.665 (d, 1 H), 8.23 (s, 1 H), 6.54~6.59 (m, 1 H), 5.75~5.76 (br d, 1 H), 4.15 (s, 3 H), 3.55~3.60 (m, 1 H), 3.18 (m, 1 H), 2.89~2.90 (d, 3 H), 2.52~2.54 (m, 1 H), 1.72~2.03 (m, 11 H), 1.52 (br s, 1 H)<br>MS: 562.2 ([M + H]$^+$) |
| 1.15 | 6-[4-[4-(aminomethyl)-3-(trifluoromethyl)pyrazol-1-yl]-8-(ethylamino)-6-fluoro-9H-pyrido[2,3-b]indol-3-yl]-1-ethyl-4-oxo-1,8-naphthyridine-3-carboxylic acid | CORE: Intermediate A2<br>AMINE: tert-butyl N-[[3-(trifluoromethyl)-1H-pyrazol-4-yl]methyl]carbamate (Intermediate C1)<br>BORONIC REAGENT: Intermediate B3<br>CATALYST: Pd$_2$(dba)$_3$ (CAS#: 51364-51-3); x-phos (CAS#: 564483-18-7)<br>SOLVENT: Dioxane/H$_2$O | $^1$H NMR (400 MHz, DMSO-d6): δ ppm: 9.07 (s, 1 H), 8.79 (s, 1 H), 8.70 (s, 1 H), 8.30~8.39 (m, 2 H), 6.47~6.49 (m, 1 H), 6.02~6.04 (m, 1 H), 4.65~4.70 (m, 2 H) 4.24 (s, 2 H), 3.27~3.29 (m, 2 H), 1.50~1.54 (m, 3 H), 1.40~1.44 (m, 3 H)<br>MS: 609.2 ([M + H]$^+$) |
| 1.16 | 6-[4-(3,3-difluoropyrrolidin-1-yl)-6-fluoro-8-(methylamino)-9H-pyrido[2,3-b]indol-3-yl]-1-methyl-4-oxo-1,8-naphthyridine-3-carboxylic acid | CORE: Intermediate A1<br>AMINE: 3,3-Difluoropyrrolidine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 11.73 (s, 1 H), 9.27 (s, 1 H), 9.14~9.15 (m, 1 H), 8.71~8.71 (m, 1 H), 8.26 (s, 1 H), 6.84~6.87 (m, 1 H), 6.46~6.49 (m, 1 H), 4.17 (s, 3 H), 3.53~3.60 (m, 2 H), 3.36~3.39 (m, 2 H), 2.93 (s, 3 H), 2.40~2.50 (m, 2 H).<br>MS: 523.1 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
| --- | --- | --- | --- |
| 1.17 | 6-[4-(Dimethylamino)-6-fluoro-8-(methylamino)-9H-pyrido[2,3-b]indol-3-yl]-1-(1,1-dimethyl-2-pyrrolidin-1-yl-ethyl)-4-oxo-1,8-naphthyridine-3-carboxylic acid | CORE: Intermediate A1<br>AMINE: Dimethylamine hydrochloride<br>BORONIC REAGENT: Intermediate B1<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d4) δ ppm: 9.24 (s, 1H), 9.09 (s, 1H), 8.76 (s, 1H), 8.25 (m, 1H), 6.98 (s, 1H), 6.50 (s, 1H), 4.67 (s, 2H), 3.79 (m, 2H), 3.17 (m, 2H), 3.01 (m, 9H), 2.17 (s, 6H), 2.05 (m, 4H)<br>MS: 572.2 ([M + H]$^+$) |
| 1.18 | 6-[4-(Dimethylamino)-5,6-difluoro-8-(methylamino)-9H-pyrido[2,3-b]indol-3-yl]-1-ethyl-4-oxo-1,8-naphthyridine-3-carboxylic acid | CORE: Intermediate A3<br>AMINE: Dimethylamine hydrochloride<br>BORONIC REAGENT: Intermediate B3<br>CATALYST: Pd$_2$(dba)$_3$ (CAS#: 51364-51-3); x-phos (CAS#: 564483-18-7)<br>SOLVENT: Dioxane/H$_2$O | $^1$H NMR (400 MHz, CDCl$_3$) δ ppm: 14.93 (br s, 1H), 9.05 (s, 1H), 8.87 (d, 1H), 8.77 (d, 1H), 7.87 (s, 1H), 6.62 (m, 1H), 4.72 (m, 2H), 3.04 (m, 9H), 1.65 (t, 3H).<br>MS: 493.3 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.19 | 6-[4-(Dimethylamino)-6-fluoro-8-(methylamino)-9H-pyrido[2,3-b]indol-3-yl]-1-ethyl-4-oxo-1,8-naphthyridine-3-carboxylic acid | CORE: Intermediate A1<br>AMINE: Dimethylamine hydrochloride<br>BORONIC REAGENT: Intermediate B3<br>CATALYST: Pd$_2$(dba)$_3$ (CAS#: 51364-51-3); X-phos (CAS#: 564483-18-7)<br>SOLVENT: Dioxane/H$_2$O | $^1$H NMR (400 MHz, DMSO-d6) δ ppm: 12.94 (br s, 1H), 9.31 (s, 1H), 9.10 (s, 1H), 8.73 (s, 1H), 8.30 (s, 1H), 7.02 (m, 1H), 6.52 (m, 1H), 4.75 (m, 2H), 2.91 (s, 9H), 1.48 (t, 3H).<br>MS: 475.2 ([M + H]$^+$) |
| 1.20 | 6-[4-(Dimethylamino)-6,7-difluoro-8-(methylamino)-9H-pyrido[2,3-b]indol-3-yl]-1-ethyl-4-oxo-1,8-naphthyridine-3-carboxylic acid | CORE: Intermediate A4<br>AMINE: Dimethylamine hydrochloride<br>BORONIC REAGENT: Intermediate B3<br>CATALYST: Pd$_2$(dba)$_3$ (CAS#: 51364-51-3); X-phos (CAS#: 564483-18-7)<br>SOLVENT: Dioxane/H$_2$O | $^1$H NMR (400 MHz, DMSO-d6) δ ppm: 11.76 (br s, 1H), 9.28 (s, 1H), 9.06 (s, 1H), 8.59 (s, 1H), 8.24 (s, 1H), 7.25 (m, 1H), 4.75 (m, 2H), 3.12 (d, 3H), 2.79 (s, 6H), 1.49 (t, 3H).<br>MS: 493.1 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.21 | 6-[4-(Dimethylamino)-5,6-difluoro-8-(methylamino)-9H-pyrido[2,3-b]indol-3-yl]-4-oxo-1-tetrahydroduran-3-yl-1,8-naphthyridine-3-carboxylic acid | CORE: Intermediate A3<br>AMINE: Dimethylamine hydrochloride<br>BORONIC REAGENT: Intermediate B10<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.80 (s, 1H), 9.08 (d, J = 2.8 Hz, 1H), 8.97 (s, 1H), 8.63 (d, J = 2.8 Hz, 1H), 8.27 (s, 1H), 6.60 (m, 1H), 6.34 (br s, 1H), 4.32 (d, J = 10.5 Hz, 1H), 4.18 (m, 2H), 4.00 (m, 1H), 3.88 (m, 1H), 2.90 (s, 3H), 2.73~2.75 (m, 7H), 2.51 (m, 1H), 2.30 (m, 1H)<br>MS: 535.1 ([M + H]$^+$) |
| 1.22 | 6-[4-(Dimethylamino)-5,6-difluoro-8-(methylamino)-9H-pyrido[2,3-b]indol-3-yl]-1-[2-(dimethylamino)ethyl]-4-oxo-1,8-naphthyridine-3-carboxylic acid | CORE: Intermediate A3<br>AMINE: Dimethylamine hydrochloride<br>BORONIC REAGENT: Intermediate B11<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.82 (s, 1H), 9.35 (s, 1H), 9.03 (d, J = 2.4 Hz, 1H), 8.63 (d, J = 2.4 Hz, 1H), 8.24 (s, 1H), 6.59 (m, 1H), 5.07 (m, 2H), 3.74 (m, 2H), 2.95 (s, 6H), 2.90 (s, 3H), 2.76 (s, 3H), 2.75 (s, 3H)<br>MS: 536.1 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.23 | 6-[4-[3-(Aminomethyl)-3-fluoro-pyrrolidin-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: tert-butyl N-[(3-Fluoropyrrolidin-3-yl)methyl]carbamate (PharmaBlock, catalog #: PBN20120604)<br>BORONIC REAGENT: Intermediate B2<br>CATALYST: XPhos Pd G2 (Sigma-Aldrich, Catalog #: 741825)<br>SOLVENT: THF/H$_2$O | $^1$H NMR (400 MHz, DMSO-d6) δ ppm: 11.82 (s, 1H), 9.22 (s, 1H), 9.05 (d, J = 2.4 Hz, 1H), 8.62 (d, J = 2.4 Hz, 1H), 8.25 (s, 1H), 7.96 (br, 2H), 6.55 (m, 1H), 4.10 (s, 3H), 3.25~3.50 (m, 6H), 2.84 (s, 3H), 2.08 (m, 2H).<br>MS: 552.2 ([M + H]$^+$) |
| 1.24 | 6-[4-(Dimethylamino)-5,6-difluoro-8-(methylamino)-9H-pyrido[2,3-b]indol-3-yl]-1-(2-methoxyethyl)-4-oxo-1,8-naphthyridine-3-carboxylic acid | CORE: Intermediate A3<br>AMINE: Dimethylamine hydrochloride<br>BORONIC REAGENT: Intermediate B12<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 12.95 (br. s, 1H), 9.14 (s, 1H), 9.06 (s, 1H), 8.68 (s, 1H), 8.26 (s, 1H), 7.41 (m, 1H), 6.66 (m, 1H), 4.91 (m, 2H), 3.81 (m, 2H), 3.28 (s, 3H), 2.88 (s, 3H), 2.81 (s, 6H).<br>MS: 523.1 ([M + H]$^+$) |
| 1.25 | 6-[6-Fluoro-4-[3-hydroxy-3-(trifluoromethyl)pyrrolidin-1-yl]-8-(methylamino)-9H-pyrido[2,3-b]indol-3-yl]-1-methyl-4-oxo-1,8-naphthyridine-3-carboxylic acid | CORE: Intermediate A1<br>AMINE: 3-Trifluoromethyl-pyrrolidin-3-ol<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.68 (s, 1H), 9.26 (s, 1H), 9.13 (d, J = 2.0 Hz, 1H), 8.69 (d, J = 2.0 Hz, 1H), 8.26 (s, 1H), 7.08 (m, 1H) 6.47 (m, 1H), 4.16 (s, 3H), 3.45 (m, 2H), 3.29 (m, 2H), 2.92 (s, 3H), 2.16 (m, 1H), 2.05 (m, 1H).<br>MS: 571.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.26 | 6-[4-(Dimethylamino)-5,6-difluoro-8-(methylamino)-9H-pyrido[2,3-b]indol-3-yl]-1-[2-(methylamino)ethyl]-4-oxo-1,8-naphthyridine-3-carboxylic acid | CORE: Intermediate A3<br>AMINE: Dimethylamine hydrochloride<br>BORONIC REAGENT: Intermediate B13<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.86 (s, 1H), 9.11 (s, 1H), 9.00 (s, 1H), 8.58 (s, 1H), 8.24 (s, 1H), 6.57 (m, 1H), 5.79 (m, 1H), 4.74 (m, 2H), 3.00 (m, 2H), 3.29 (m, 2H), 2.90 (s, 3H), 2.72 (s, 3H), 2.68 (s, 3H), 2.33 (s, 3H).<br>MS: 521.8 ([M + H]$^+$) |
| 1.27 | 6-[4-[3-Amino-3-(trifluoromethyl)pyrrolidin-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Benzyl (3-(trifluoromethyl)Pyrrolidin-3-Y1)Carbamate Hydrochloride<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.91 (s, 1H), 9.31 (s, 1H), 9.14 (d, J = 2.0 Hz, 1H), 8.71 (d, J = 2.0 Hz, 1H), 8.21 (s, 1H), 6.62 (m, 1H), 4.18 (s, 3H), 2.91 (m, 5H), 2.68 (m, 1H), 2.35 (m, 2H), 2.03 (m, 1H).<br>MS: 588.3 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.28 | 6-[8-(Ethylamino)-6-fluoro-4-[3-(trifluoro-methyl)pyrazol-1-yl]-9H-pyrido[2,3-b]indol-3-yl]-4-oxo-1-pyrrolidin-3-yl-1,8-naphthyridine-3-carboxylic acid | CORE: Intermediate A2<br>AMINE: 3-(Trifluoro-methyl)pyrazole<br>BORONIC REAGENT: Intermediate B6<br>CATALYST: XPhos Pd G2 (Sigma-Aldrich, Catalog #: 741825)<br>SOLVENT: THF/H$_2$O | $^1$H NMR (400 MHz, DMSO-d6): δ ppm: 12.13 (s, 1H), 9.10 (s, 1H), 8.84 (d, 1H), 8.77 (s, 1H), 8.37 (d, 1H), 8.27 (s, 1H), 7.04 (d, 1H), 6.45 (m, 1H), 5.95 (m, 2H), 5.69 (m, 1H), 3.62 (m, 4H), 3.20 (m, 2H), 2.53 (m, 2H), 2.36 (m, 2H), 1.26 (t, 3H).<br>MS: 621.7 ([M + H]$^+$) |
| 1.29 | 6-[4-(Dimethylamino)-5,6-difluoro-8-(methylamino)-9H-pyrido[2,3-b]indol-3-yl]-1-[2-(4-methylpiperazin-1-yl)ethyl]-4-oxo-1,8-naphthyridine-3-carboxylic acid | CORE: Intermediate A3<br>AMINE: Dimethylamine hydrochloride<br>BORONIC REAGENT: Intermediate B14<br>CATALYST: cataCXium® A Pd G2 (Sigma-Aldrich, Catalog #: 761311)<br>SOLVENT: THF/H$_2$O | $^1$H NMR (400 MHz, DMSO-d6) δ ppm: 11.79 (s, 1H), 9.10 (s, 1H), 8.98 (s, 1H), 8.57 (s, 1H), 8.39 (s, 1H), 8.23 (s, 1H), 6.57 (m, 1H), 5.71 (m, 1H), 4.78 (m, 2H), 2.89 (s, 3H), 2.74 (s, 6H), 2.33 (m, 4H), 2.10 (m, 6H), 2.07 (s, 3H).<br>MS: 591.0 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.30 | 6-[4-(Dimethylamino)-5,6-difluoro-8-(methylamino)-9H-pyrido[2,3-b]indol-3-yl]-4-oxo-1-(4-pyridyl-methyl)-1,8-naphthyridine-3-carboxylic acid | CORE: Intermediate A3<br>AMINE: Dimethylamine hydrochloride<br>BORONIC REAGENT: Intermediate B15<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 12.85 (br s, 1H), 9.51 (s, 1H), 8.88 (m, 3H), 8.69 (d, J = 2.4 Hz, 1H), 8.19 (s, 1H), 7.99 (m, 2H), 6.65 (m, 1H), 6.21 (s, 2H), 2.87 (s,3H), 2.76 (d, 6H).<br>MS: 556.1 ([M + H]$^+$) |
| 1.31 | 6-[5,6-Difluoro-8-(methylamino)-4-morpholino-9H-pyrido[2,3-b]indol-3-yl]-1-(morpholin-3-ylmethyl)-4-oxo-1,8-naphthyridine-3-carboxylic acid | CORE: Intermediate A3<br>AMINE: Morpholine<br>BORONIC REAGENT: Intermediate B5<br>CATALYST: XPhos Pd G2 (Sigma-Aldrich, Catalog #: 741825)<br>SOLVENT: THF/H$_2$O | $^1$H NMR (400 MHz, DMSO-d6): δ ppm: 11.88 (br s, 1H), 9.13 (m, 2H), 8.73 (d, 1H), 8.28 (s, 1H), 6.63 (m, 1H), 5.72 (m, 1H), 4.95 (m, 1H), 4.58 (m, 1H), 3.85 (m, 1H), 3.74 (m, 1H), 3.54 (m, 4H), 2.91 (m, 9H), 2.66 (m, 2H).<br>MS: 606.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.32 | 6-[4-(Dimethylamino)-5,6-difluoro-8-(methylamino)-9H-pyrido[2,3-b]indol-3-yl]-1-[(1-methyl-4-piperidyl)methyl]-4-oxo-1,8-naphthyridine-3-carboxylic acid | CORE: Intermediate A3<br>AMINE: Dimethylamine hydrochloride<br>BORONIC REAGENT: Intermediate B16<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 12.37 (br s, 1H), 10.31 (br s, 1H), 9.32 (s, 1H), 9.06 (m, 1H), 8.68 (d, J = 2.8 Hz, 1H), 8.25 (d, J = 2.8 Hz, 1H), 6.64 (m, 1H), 4.68 (m, 2H), 3.37 (m, 2H), 2.89 (s, 3H), 2.85 (m, 2H), 2.79 (s, 6H), 2.68 (s, 3H), 2.24 (m, 1H), 1.80 (m, 2H), 1.73 (m, 2H).<br>MS: 576.2 ([M + H]$^+$) |
| 1.33 | 6-[5,6-Difluoro-4-[2-methoxyethyl(methyl)amino]-8-(methylamino)-9H-pyrido[2,3-b]indol-3-yl]-1-methyl-4-oxo-1,8-naphthyridine-3-carboxylic acid | CORE: Intermediate A3<br>AMINE: N-(2-Methoxyethyl)methyl amine<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 9.22 (s, 1H), 9.08 (s, 1H), 8.69 (s, 1H), 8.21 (s, 1H), 6.57 (m, 1H), 5.72 (s, 1H), 4.15 (s, 3H), 3.55 (m, 2H), 3.20 (s, 3H), 3.08 (m, 2H), 2.90 (s, 3H), 2.87 (s, 3H).<br>MS: 523.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.34 | 6-[8-(Ethylamino)-6-fluoro-4-morpholino-9H-pyrido[2,3-b]indol-3-yl]-4-oxo-1-pyrrolidin-3-yl-1,8-naphthyridine-3-carboxylic acid | CORE: Intermediate A2<br>AMINE: 3-Morpholine<br>BORONIC REAGENT: Intermediate B6<br>CATALYST: XPhos Pd G2 (Sigma-Aldrich, Catalog #: 741825)<br>SOLVENT: THF/H$_2$O | $^1$H NMR (400 MHz, DMSO-d6): δ ppm: 11.66 (s, 1H), 9.35 (s, 1H), 9.13 (s, 1H), 8.70 (d, 1H), 8.21 (s, 1H), 7.10 (m, 1H), 6.49 (m, 1H), 6.18 (m, 1H), 5.79 (m, 1H), 3.72 (m, 4H), 3.20 (m, 6H), 2.95 (m, 5H), 2.05 (m, 1H), 1.33 (t, 3H).<br>MS: 572.3 ([M + H]$^+$) |
| 1.35 | 6-[5,6-Difluoro-8-(methylamino)-4-morpholino-9H-pyrido[2,3-b]indol-3-yl]-1-(2-hydroxy-2-methyl-propyl)-4-oxo-1,8-naphthyridine-3-carboxylic acid | CORE: Intermediate A3<br>AMINE: Morpholine<br>BORONIC REAGENT: Intermediate B17<br>CATALYST: XPhos Pd G2 (Sigma-Aldrich, Catalog #: 741825)<br>SOLVENT: THF/H$_2$O | $^1$H NMR (400 MHz, DMSO-d6): δ ppm: 14.75 (s, 1H), 11.89 (s, 1H), 9.15 (s, 1H), 9.10 (s, 1H), 8.73 (s, 1H), 8.31 (s, 1H), 6.63 (m, 1H), 5.70 (m, 1H), 5.05 (m, 1H), 4.75 (m, 2H), 3.53 (m, 4H), 3.39 (m, 1H), 2.94 (m, 4H), 2.90 (s, 3H), 1.14 (s, 6H).<br>MS: 579.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.36 | 6-[5,6-Difluoro-8-(methylamino)-4-[(2S)-2-methyl-morpholin-4-yl]-9H-pyrido[2,3-b]indol-3-yl]-1-methyl-4-oxo-1,8-naphthyridine-3-carboxylic acid | CORE: Intermediate A3<br>AMINE: (S)-2-Methylmorpholine<br>BORONIC REAGENT: Intermediate B2<br>CATALYST: Pd$_2$(dba)$_3$ (CAS#: 51364-51-3); XPhos (CAS#: 564483-18-7)<br>SOLVENT: Dioxane/H$_2$O | $^1$H NMR (400 MHz, DMSO-d6) δ ppm: 14.77 (s, 1H), 11.88 (s, 1H), 9.30 (s, 1H), 9.13 (d, 1H), 8.73 (d, 1H), 8.25 (s, 1H), 6.63 (m, 1H), 5.70 (s, 1H), 4.19 (s, 3H), 3.62 (m, 3H), 3.05 (m, 1H), 2.90 (s, 3H), 2.67 (m, 2H), 2.61 (m, 1H), 0.92 (s, 3H).<br>MS: 535.1 ([M + H]$^+$) |
| 1.37 | 6-[6-Fluoro-4,8-bis(methylamino)-9H-pyrido[2,3-b]indol-3-yl]-1-(morpholin-3-ylmethyl)-4-oxo-1,8-naphthyridine-3-carboxylic acid | CORE: Intermediate A1<br>AMINE: Methylamine<br>BORONIC REAGENT: Intermediate B5<br>CATALYST: XPhos Pd G2 (Sigma-Aldrich, Catalog #: 741825)<br>SOLVENT: Ethanol/H$_2$O | $^1$H NMR (400 MHz, DMSO-d6): δ ppm: 9.11 (m, 2H), 8.64 (d, 1H), 8.02 (s, 1H), 7.51 (m, 1H), 6.40 (m, 1H), 4.77 (m, 1H), 4.48 (m, 1H), 3.81 (m, 1H), 3.39 (m, 1H), 3.23 (m, 4H), 2.90 (s, 3H), 2.81 (m, 1H), 2.54 (m, 5H).<br>MS: 532.1 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.38 | 1-(2-Amino-2-methylpropyl)-6-[5,6-difluoro-8-(methylamino)-4-morpholino-9H-pyrido[2,3-b]indol-3-yl]-4-oxo-1,8-naphthyridine-3-carboxylic acid | CORE: Intermediate A3<br>AMINE: Morpholine<br>BORONIC REAGENT: Intermediate B18<br>CATALYST: XPhos Pd G2 (Sigma-Aldrich, Catalog #: 741825)<br>SOLVENT: THF/H$_2$O | $^1$H NMR (400 MHz, DMSO-d6) δ ppm: 11.95 (br s, 1H), 9.28 (s, 1H), 9.06 (m, 1H), 8.71 (d, 1H), 8.30 (s, 1H), 6.63 (m, 1H), 5.71 (d, 1H), 4.69 (s, 2H), 3.54 (s, 3H), 2.91 (m, 8H), 1.11 (s, 6H).<br>MS: 578.2 ([M + H]$^+$) |
| 1.39 | 6-[5,6-Difluoro-8-(methylamino)-4-morpholino-9H-pyrido[2,3-b]indol-3-yl]-4-oxo-1-(tetrahydrofuran-2-ylmethyl)-1,8-naphthyridine-3-carboxylic acid | CORE: Intermediate A3<br>AMINE: Morpholine<br>BORONIC REAGENT: Intermediate B19<br>CATALYST: XPhos Pd G2 (Sigma-Aldrich, Catalog #: 741825)<br>SOLVENT: THF/H$_2$O | $^1$H NMR (400 MHz, DMSO-d6) δ ppm: 14.69 (s, 1H), 11.88 (br s, 1H), 9.19 (s, 1H), 9.12 (d, 1H), 8.74 (d, 1H), 8.27 (s, 1H), 6.63 (m, 1H), 5.71 (d, 1H), 5.02 (m, 1H), 4.58 (m, 1H), 4.34 (m, 1H), 3.89 (m, 1H), 3.69 (m, 1H), 3.58 (s, 3H), 2.92 (m, 7H), 1.68-2.09 (m, 4H).<br>MS: 591.5 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.40 | 6-[5,6-Difluoro-4-(4-methoxy-1-piperidyl)-8-(methylamino)-9H-pyrido[2,3-b]indol-3-yl]-1-methyl-4-oxo-1,8-naphthyridine-3-carboxylic acid | CORE: Intermediate A3<br>AMINE: 4-Methoxypiperidine<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.88 (br s, 1H), 9.25 (s, 1H), 9.08 (s, 1H), 8.68 (s, 1H), 8.22 (s, 1H), 6.59 (m, 1H), 5.71 (s, 1H), 4.16 (s, 3H), 3.22 (s, 3H), 3.20 (m, 2H), 2.87 (m, 5H), 1.76 (m, 2H), 1.39 (m, 2H).<br>MS: 549.2 ([M + H]$^+$) |
| 1.41 | 6-[5,6-Difluoro-4-[2-methoxyethyl(methyl)amino]-8-methylamino)-9H-pyrido[2,3-b]indol-3-yl]-1-(morpholin-3-ylmethyl)-4-oxo-1,8-naphthyridine-3-carboxylic acid | CORE: Intermediate A3<br>AMINE: N-(2-Methoxyethyl)methyl amine<br>BORONIC REAGENT: Intermediate B5<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 12.95 (br s, 1H), 9.96 (br s, 1H), 9.77 (br s. 1H), 9.27 (s, 1H), 9.08 (d, 1H), 8.79 (d, 1H), 8.21 (s, 1H), 6.68 (m, 1H), 4.94 (m, 2H), 4.13 (m, 3H), 3.46 (s, 3H), 3.33 (m, 1H), 3.16 (s, 3H), 2.89 (m, 1H), 2.80 (s, 3H), 2.50 (s, 3H).<br>MS: 608.0 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.42 | 6-[5,6-Difluoro-8-(methylamino)-4-morpholino-9H-pyrido[2,3-b]indol-3-yl]-1-(morpholin-2-ylmethyl)-4-oxo-1,8-naphthyridine-3-carboxylic acid | CORE: Intermediate A3<br>AMINE: Morpholine<br>BORONIC REAGENT: Intermediate B20<br>CATALYST: XPhos Pd G2 (Sigma-Aldrich, Catalog #: 741825)<br>SOLVENT: THF/H$_2$O | $^1$H NMR (400 MHz, DMSO-d6) δ ppm: 11.96 (br s, 1H), 9.15 (d, 1H), 9.11 (s, 1H), 8.70 (s, 1H), 8.29 (d, 2H), 6.61 (m, 1H), 5.75 (m, 1H), 4.92 (m, 1H), 4.57 (m, 1H), 3.86 (m, 1H), 3.75 (m, 2H), 3.57 (m, 4H), 2.94 (m, 9H), 2.68 (m, 2H).<br>MS: 606.0 ([M + H]$^+$) |
| 1.43 | 6-[5,6-Difluoro-4-(4-hydroxy-1-piperidyl)-8-(methylamino)-9H-pyrido[2,3-b]indol-3-yl]-1-methyl-4-oxo-1,8-naphthyridine-3-carboxylic acid | CORE: Intermediate A3<br>AMINE: 4-Hydroxypiperidine<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.88 (br s, 1H), 9.24 (s, 1H), 9.07 (s, 1H), 8.67 (s, 1H), 8.21 (s, 1H), 6.60 (m, 1H), 5.72 (s, 1H), 4.61 (s, 1H), 4.16 (s, 3H), 3.05 (m, 2H), 2.90 (m, 5H), 1.61 (m, 2H), 1.40 (m, 2H).<br>MS: 535.3 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.44 | 6-[6-Fluoro-8-(methylamino)-4-morpholino-9H-pyrido[2,3-b]indol-3-yl]-1-[2-hydroxy-1-hydroxy-methyl)-1-methyl-ethyl]-4-oxo-1,8-naphthyridine-3-carboxylic acid 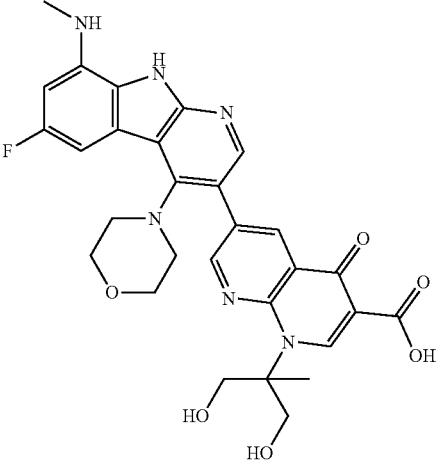 | CORE: Intermediate A1<br>AMINE: Morpholine<br>BORONIC REAGENT: Intermediate B21<br>CATALYST: XPhos Pd G2 (Sigma-Aldrich, Catalog #: 741825)<br>SOLVENT: THF/H$_2$O | $^1$H NMR (400 MHz, DMSO-d6): δ ppm: 14.70 (s, 1H), 11.57 (s, 1H), 9.20 (s, 1H), 9.08 (d, 1H), 8.70 (d, 1H), 8.23 (s, 1H), 7.12 (m, 1H), 6.49 (m, 1H), 5.95 (m, 1H), 5.24 (m, 2H), 4.41 (m, 2H), 4.09 (m, 2H), 3.72 (m, 4H), 2.99 (m, 4H), 2.93 (s, 3H), 1.89 (s, 3H).<br>MS: 577.3 ([M + H]$^+$) |
| 1.45 | 6-[6-Fluoro-8-(methylamino)-4-morpholino-9H-pyrido[2,3-b]indol-3-yl]-1-(2-hydroxy-1-methyl-ethyl)-4-oxo-1,8-naphthyridine-3-carboxylic acid 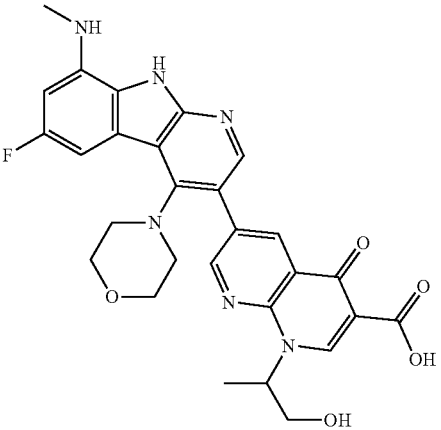 | CORE: Intermediate A1<br>AMINE: Morpholine<br>BORONIC REAGENT: Intermediate B22<br>CATALYST: XPhos Pd G2 (Sigma-Aldrich, Catalog #: 741825)<br>SOLVENT: THF/H$_2$O | $^1$H NMR (400 MHz, DMSO-d6): δ ppm: 14.74 (br s, 1H), 11.59 (s, 1H), 9.12 (m, 2H), 8.71 (d, 1H), 8.22 (s, 1H), 7.12 (m, 1H), 6.48 (m, 1H), 5.94 (m, 2H), 5.23 (m, 1H), 3.84 (m, 2H), 2.96 (m, 6H), 1.60 (s, 3H).<br>MS: 547.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.46 | 6-[6-Fluoro-8-(methylamino)-4-pyrrolidin-1-yl-9H-pyrido[2,3-b]indol-3-yl]-1-methyl-4-oxo-1,8-naphthyridine-3-carboxylic acid | CORE: Intermediate A1<br>AMINE: pyrrolidine<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.69 (s, 1H), 9.28 (s, 1H), 9.14 (d, 1H), 8.70 (d, 1H), 8.23 (s, 1H), 6.82 (m, 1H), 6.46 (m, 1H), 4.18 (s, 3H), 3.23 (m, 4H), 2.93 (s, 3H), 1.85 (m, 4H).<br>MS: 487.1 ([M + H]$^+$) |
| 1.47 | 6-[6-Fluoro-4-(3-hydroxypyrrolidin-1-yl)-8-methyl-amino)-9H-pyrido[2,3-b]indol-3-yl]-1-methyl-4-oxo-1,8-naphthyridine-3-carboxylic acid | CORE: Intermediate A1<br>AMINE: 3-Pyrrolidinol<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.67 (br s, 1H), 9.29 (s, 1H), 9.14 (s, 1H), 8.70 (d, 1H), 8.24 (s, 1H), 7.09 (m, 1H), 6.45 (m, 1H), 4.30 (m, 1H), 4.15 (s, 3H), 3.29 (m, 2H), 3.15 (m, 2H), 2.92 (s, 3H), 1.96 (m, 1H), 1.78 (m, 1H).<br>MS: 503.0 ([M + H]$^+$) |
| 1.48 | 6-[6-Fluoro-8-(methylamino)-4-morpholino-9H-pyrido[2,3-b]indol-3-yl]-1-methyl-4-oxo-1,8-naphthyridine-3-carboxylic acid | CORE: Intermediate A1<br>AMINE: Morpholine<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.59 (s, 1H), 9.29 (s, 1H), 9.13 (d, J = 2.4 Hz, 1H), 8.68 (d, J = 2.4 Hz, 1H), 8.21 (s, 1H), 7.11 (m, 1H), 6.47 (m, 1H), 4.19 (s, 3H), 3.71 (m, 4H), 2.97 (m, 4H), 2.93 (s, 3H).<br>MS: 503.1 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.49 | 6-[6-Fluoro-8-(methylamino)-4-[(2R)-2-methyl-morpholin-4-yl]-9H-pyrido[2,3-b]indol-3-yl]-1-methyl-4-oxo-1,8-naphthyridine-3-carboxylic acid | CORE: Intermediate A1<br>AMINE: (R)-2-Methylmorpholine<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.61 (s, 1H), 9.28 (s, 1H), 9.10 (d, J = 2.4 Hz, 1H), 8.67 (d, J = 2.4 Hz, 1H), 8.21 (s, 1H), 7.08 (m, 1H), 6.47 (m, 1H), 4.18 (s, 3H), 3.76 (m, 2H), 3.65 (m, 1H), 3.21 (m, 1H), 2.95 (m, 1H), 2.93 (s, 3H), 2.75 (m, 1H), 2.54 (m, 1H), 1.00 (d, J = 2.4 Hz, 3H).<br>MS: 517.1 ([M + H]$^+$) |
| 1.50 | 6-[6-Fluoro-8-(methylamino)-4-[(2S)-2-methyl-morpholin-4-yl]-9H-pyrido[2,3-b]indol-3-yl]-1-methyl-4-oxo-1,8-naphthyridine-3-carboxylic acid | CORE: Intermediate A1<br>AMINE: (S)-2-Methylmorpholine<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 14.77 (br s, 1H), 11.61 (s, 1H), 9.30 (s, 1H), 9.12 (m, 1H), 8.69 (d, 1H), 8.21 (s, 1H), 7.11 (m, 1H), 6.48 (m, 1H), 4.20 (s, 3H), 3.77 (m, 3H), 3.21 (m, 1H), 2.94 (s, 3H), 2.68 (m, 1H), 2.57 (m, 1H), 2.34 (m, 1H), 1.01 (d, 3H).<br>MS: 517.2 ([M + H]$^+$) |
| 1.51 | 6-[5,6-Difluoro-8-(methylamino)-4-morpholino-9H-pyrido[2,3-b]indol-3-yl]-1-(2-hydroxy-1-methyl-ethyl)-4-oxo-1,8-naphthyridine-3-carboxylic acid | CORE: Intermediate A3<br>AMINE: Morpholine<br>BORONIC REAGENT: Intermediate B22<br>CATALYST: XPhos Pd G2 (Sigma-Aldrich, Catalog #: 741825)<br>SOLVENT: THF/H$_2$O | 1H NMR (400 MHz, DMSO-d6) δ ppm: 9.11 (m, 2H), 8.75 (d, 1H), 8.26 (s, 1H), 6.64 (m, 1H), 5.94 (br s, 1H), 3.90 (m, 1H), 3.84 (m, 1H), 3.59 (m, 5H), 2.95 (m, 4H), 2.90 (s, 3H), 1.60 (d, 3H)<br>MS: 565.2 ([M + H]$^+$) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.52 | 6-[6-Fluoro-8-(methylamino)-4-morpholino-9H-pyrido[2,3-b]indol-3-yl]-1-(methylamino)-4-oxo-1,8-naphthyridine-3-carboxylic acid 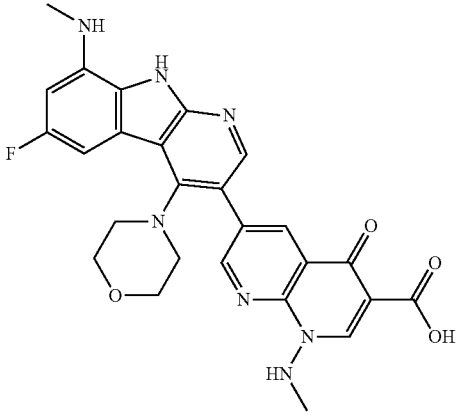 | CORE: Intermediate A1<br>AMINE: Morpholine<br>BORONIC REAGENT: Intermediate B23<br>CATALYST: XPhos Pd G2 (Sigma-Aldrich, Catalog #: 741825)<br>SOLVENT: THF/H₂O | ¹H NMR (400 MHz, DMSO-d6) δ ppm: 9.14 (d, 1H), 9.05 (s, 1H), 8.71 (d, 1H), 8.22 (s, 1H), 7.11 (m, 1H), 6.49 (m, 1H), 3.71 (m, 5H), 2.95 (m, 7H), 2.93 (s, 3H).<br>MS: 518.2 ([M + H]⁺) |
| 1.53 | 6-[6-Fluoro-8-(methylamino)-4-morpholino-9H-pyrido[2,3-b]indol-3-yl]-1-(2-hydroxypropyl)-4-oxo-1,8-naphthyridine-3-carboxylic acid 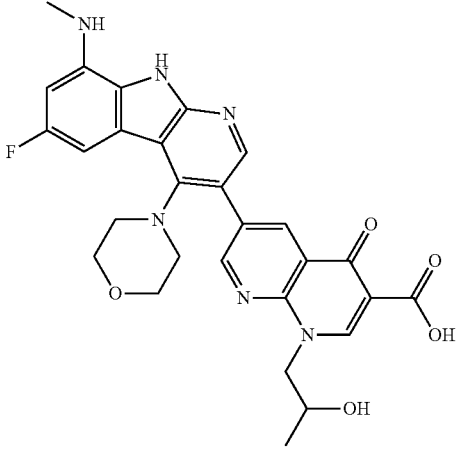 | CORE: Intermediate A1<br>AMINE: Morpholine<br>BORONIC REAGENT: Intermediate B24<br>CATALYST: XPhos Pd G2 (Sigma-Aldrich, Catalog #: 741825)<br>SOLVENT: THF/H₂O | ¹H NMR (400 MHz, DMSO-d6) δ ppm: 9.09 (d, 2H), 8.69 (d, 1H), 8.22 (s, 1H), 7.11 (m, 1H), 6.49 (m, 1H), 4.95 (m, 1H), 4.29 (m, 1H), 4.12 (m, 1H), 3.71 (m, 4H), 2.97 (m, 4H), 2.93 (s, 3H), 1.24 (d, 3H).<br>MS: 547.4 ([M + H]⁺) |
| 1.54 | 6-[6-Fluoro-4-[3-(hydroxymethyl)pyrrolidin-1-yl]-8-(methylamino)-9H-pyrido[2,3-b]indol-3-yl]-1-methyl-4-oxo-1,8-naphthyridine-3-carboxylic acid 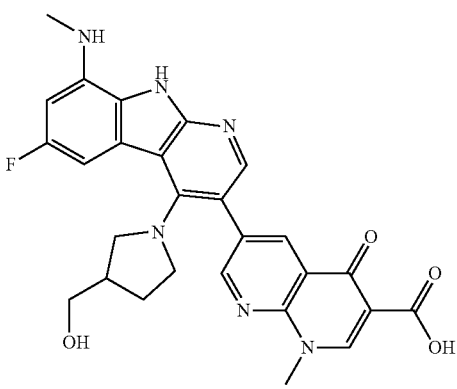 | CORE: Intermediate A1<br>AMINE: Pyrrolidin-3-ylmethanol<br>BORONIC REAGENT: Intermediate B2<br>CATALYST: cataCXium® A Pd G2 (Sigma-Aldrich, Catalog #: 761311)<br>SOLVENT: THF/H₂O | ¹H NMR (400 MHz, DMSO-d6) δ ppm: 11.51 (s, 1H), 9.23 (s, 1H), 9.07 (s, 1H), 8.61 (s, 1H), 8.18 (s, 1H), 6.77 (m, 1H), 6.43 (m, 1H), 5.91 (br s, 1H), 4.67 (br s, 1H), 4.15 (s, 3H), 3.32 (m, 2H), 3.16 (m, 1H), 2.91 (m, 4H), 2.84 (m, 1H), 2.35 (m, 1H), 1.95 (m, 1H), 1.60 (m, 1H).<br>MS: 517.2 ([M + H]⁺) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.55 | 6-[4-(Dimethylamino)-6,7-difluoro-8-(methylamino)-9H-pyrido[2,3-b]indol-3-yl]-4-oxo-1-pyrrolidin-3-yl-1,8-naphthyridine-3-carboxylic acid | CORE: Intermediate A4<br>AMINE: Dimethylamine hydrochloride<br>BORONIC REAGENT: Intermediate B6<br>CATALYST: cataCXium® A Pd G2 (Sigma-Aldrich, Catalog #: 761311)<br>SOLVENT: THF/H$_2$O | $^1$H NMR (400 MHz, DMSO-d6): δ ppm: 11.78 (s, 1H), 9.24 (s, 1 H), 9.05 (s, 1 H) 8.66 (d, 1 H), 8.23 (s, 1 H), 7.28 (m, 1H), 6.01 (m, 1 H), 3.39 (m, 1H), 3.13 (s, 3H), 2.81 (s, 6H), 2.66 (m, 2H), 2.53 (m, 4H).<br>MS: 534.1 ([M + H]$^+$) |
| 1.56 | 6-[6-Fluoro-8-(methylamino)-4-(1-piperidyl)-9H-pyrido[2,3-b]indol-3-yl]-1-methyl-4-oxo-1,8-naphthyridine-3-carboxylic acid | CORE: Intermediate A1<br>AMINE: Piperidine<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.62 (s, 1H), 9.29 (s, 1H), 9.11 (s, 1H), 8.67 (d, 1H), 8.18 (s, 1H), 7.13 (m, 1H), 6.48 (m, 1H), 4.19 (s, 3H), 2.95 (m, 7H), 1.60 (m, 4H), 1.48 (m, 2H).<br>MS: 501.1 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.57 | 1-(2-Amino-3-methylbutyl)-6-[5,6-difluoro-8-(methylamino)-4-morpholino-9H-pyrido[2,3-b]indol-3-yl]-4-oxo-1,8-naphthyridine-3-carboxylic acid 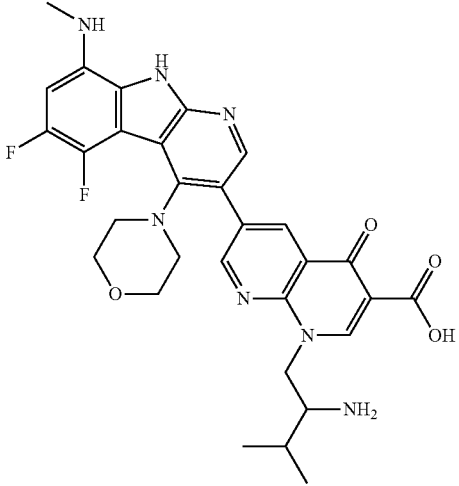 | CORE: Intermediate A3<br>AMINE: Morpholine<br>BORONIC REAGENT: Intermediate B26<br>CATALYST: XPhos Pd G2 (Sigma-Aldrich, Catalog #: 741825)<br>SOLVENT: THF/H$_2$O | $^1$H NMR (400 MHz, DMSO-d6) δ ppm: 9.25 (s, 1H), 9.11 (d, 1H), 8.72 (d, 1H), 8.29 (d, 1H), 6.63 (m, 1H), 5.72 (br s, 1H), 5.09 (m, 1H), 4.20 (m, 1H), 3.58 (m, 4H), 3.08 (m, 1H), 2.95 (s, 3H), 2.90 (m, 3H), 1.83 (m, 1H), 1.03 (d, 6H).<br>MS: 592.2 ([M + H]$^+$) |
| 1.58 | 6-[6-Fluoro-8-(methylamino)-4-morpholino-9H-pyrido[2,3-b]indol-3-yl]-4-oxo-1-(pyrazin-2-ylmethyl)-1,8-naphthyridine-3-carboxylic acid 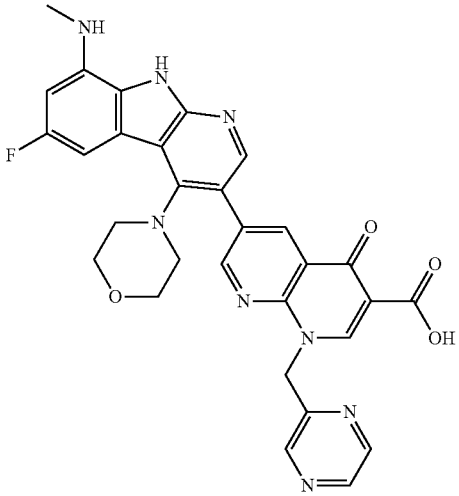 | CORE: Intermediate A1<br>AMINE: Morpholine<br>BORONIC REAGENT: Intermediate B27<br>CATALYST: cataCXium ® A Pd G2 (Sigma-Aldrich, Catalog #: 761311)<br>SOLVENT: THF/H$_2$O | $^1$H NMR (400 MHz, DMSO-d6 + D$_2$O) δ ppm: 9.34 (s, 1H), 8.87 (s, 2H), 8.61 (s, 1H), 8.53 (s, 1H), 8.46 (s, 1H), 8.31 (s, 1H), 8.12 (s, 1H), 7.04 (d, 1H), 6.44 (d, 1H), 6.08 (s, 2H), 3.59 (m, 4H), 2.88 (m, 7H).<br>MS: 581.1 ([M + H]$^+$) |

| No. | Compound Name and Structure | CORE, AMINE, BORONIC REAGENT, CATALYST and SOLVENT | ¹H NMR and MS (ESI) |
|---|---|---|---|
| 1.59 | 6-[6-Fluoro-4-(3-hydroxy-3-methyl-pyrrolidin-1-yl)-8-(methylamino)-9H-pyrido[2,3-b]indol-3-yl]-1-methyl-4-oxo-1,8-naphthyridine-3-carboxylic acid | CORE: Intermediate A1<br>AMINE: 3-Methylpyrrolidin-3-ol<br>BORONIC REAGENT: Intermediate B2<br>CATALYST: cataCXium® A Pd G2 (Sigma-Aldrich, Catalog #: 761311)<br>SOLVENT: THF/H₂O | ¹H NMR (400 MHz, DMSO-d6) δ ppm: 11.77 (br s, 1H), 9.28 (s, 1H), 9.17 (d, 1H), 8.71 (d, 1H), 8.23 (s, 1H), 7.11 (m, 1H), 6.45 (m, 1H), 4.17 (s, 3H), 3.27 (m, 2H), 2.91 (s, 3H), 2.52 (m, 1H), 2.34 (m, 1H), 1.78 (m, 2H), 1.23 (s, 3H).<br>MS: 517.2 ([M + H]⁺) |
| 1.60 | 6-[6-Fluoro-8-(methylamino)-4-(1,4-oxazepan-4-yl)-9H-pyrido[2,3-b]indol-3-yl]-1-methyl-4-oxo-1,8-naphthyridine-3-carboxylic acid | CORE: Intermediate A1<br>AMINE: 1,4-Oxazepane<br>BORONIC REAGENT: Intermediate B2<br>CATALYST: cataCXium® A Pd G2 (Sigma-Aldrich, Catalog #: 761311)<br>SOLVENT: THF/H₂O | ¹H NMR (400 MHz, DMSO-d6) δ ppm: 14.82 (br s, 1H), 11.55 (s, 1H), 9.29 (s, 1H), 9.14 (d, 1H), 8.72 (d, 1H), 8.31 (s, 1H), 7.30 (m, 1H), 6.47 (m, 1H), 5.90 (br s, 1H), 4.19 (s, 3H), 3.80 (m, 2H), 3.67 (m, 2H), 3.47 (m, 2H), 3.06 (m, 2H), 2.93 (s, 3H), 1.73 (m, 2H).<br>MS: 517.2 ([M + H]⁺) |
| 1.61 | 6-[4-[2-[(Dimethylamino)methyl]morpholin-4-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: N,N-Dimethyl-1-morpholin-2-ylmethanamine<br>BORONIC REAGENT: Intermediate B2<br>CATALYST: cataCXium® A Pd G2 (Sigma-Aldrich, Catalog #: 761311)<br>SOLVENT: THF/H₂O | ¹H NMR (400 MHz, DMSO-d6) δ ppm: 11.89 (br s, 1H), 9.29 (s, 1H), 9.12 (d, 1H), 8.73 (s, 1H), 8.24 (s, 1H), 6.22 (m, 1H), 5.72 (d, 1H), 4.19 (s, 3H), 3.65 (m, 2H), 3.50 (m, 1H), 3.18 (m, 1H), 2.91 (d, 3H), 2.84 (m, 2H), 2.68 (m, 1H), 2.15 (m, 2H), 2.04 (s, 6H).<br>MS: 578.4 ([M + H]⁺) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.62 | 6-[4-(1,3,3a,4,6,6a-Hexahydrofuro[3,4-c]pyrrol-5-yl)-6-fluoro-8-(methylamino)-9H-pyrido[2,3-b]indol-3-yl]-1-methyl-4-oxo-1,8-naphthyridine-3-carboxylic acid | CORE: Intermediate A1<br>AMINE: 3,3a,4,5,6,6a-Hexahydro-1H-furo[3,4-c]pyrrole, hydrochloride<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.61 (s, 1H), 9.29 (s, 1H), 9.10 (d, 1H), 8.68 (d, 1H), 8.18 (s, 1H), 7.03 (m, 1H), 6.45 (m, 1H), 4.18 (s, 3H), 3.60 (m, 4H), 2.92 (m, 7H), 2.53 (m, 2H).<br>MS: 529.2 ([M + H]$^+$) |
| 1.63 | 6-[7-Chloro-6-fluoro-8-(methylamino)-4-morpholino-9H-pyrido[2,3-b]indol-3-yl]-1-methyl-4-oxo-1,8-naphthyridine-3-carboxylic acid | CORE: Intermediate A5<br>AMINE: Morpholine<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.87 (s, 1H), 9.31 (s, 1H), 9.14 (d, 1H), 8.70 (s, 1H), 8.25 (s, 1H), 7.48 (m, 1H), 4.20 (s, 3H), 3.72 (m, 4H), 3.15 (s, 3H), 2.95 (m, 4H).<br>MS: 539.0 ([{$^{37}$Cl}M + H]$^+$), 537.0 ([{$^{35}$Cl}M + H]$^+$) |
| 1.64 | 6-[4-(Dimethylamino)-5,6-difluoro-8-(trideuteriomethylamino)-9H-pyrido[2,3-b]indol-3-yl]-4-oxo-1-pyrrolidin-3-yl-1,8-naphthyridine-3-carboxylic acid | CORE: Intermediate A6<br>AMINE: Dimethylamine hydrochloride<br>BORONIC REAGENT: Intermediate B6<br>CATALYST: cataCXium ® A Pd G2 (Sigma-Aldrich, Catalog #: 761311)<br>SOLVENT: THF/H$_2$O | $^1$H NMR (400 MHz, DMSO-d6): δ ppm: 14.64 (br s, 1H), 11.77 (s, 1H), 9.25 (s, 1 H), 9.05 (s, 1 H) 8.67 (s, 1 H), 8.24 (s, 1 H), 6.61 (m, 1 H), 6.02 (m, 1 H), 5.66 (m, 1H), 3.77 (m, 3 H), 3.38 (m, 2H), 2.77 (s, 6H), 2.34 (m, 2 H).<br>MS: 537.2 ([M + H]$^+$) |

| No. | Compound Name and Structure | CORE, AMINE, BORONIC REAGENT, CATALYST and SOLVENT | ¹H NMR and MS (ESI) |
|---|---|---|---|
| 1.65 | 6-[5,6-Difluoro-8-(methylamino)-4-pyrrolidin-1-yl-9H-pyrido[2,3-b]indol-3-yl)-4-oxo-1-pyrrolidin-3-yl-1,8-naphthyridine-3-carboxylic acid | CORE: Intermediate A3<br>AMINE: Pyrrolidine<br>BORONIC REAGENT: Intermediate B6<br>CATALYST: cataCXium ® A Pd G2 (Sigma-Aldrich, Catalog #: 761311)<br>SOLVENT: THF/H₂O | ¹H NMR (400 MHz, DMSO-d6): δ ppm: 11.89 (s, 1H), 9.23 (s, 1 H), 9.09 (d, 1 H) 8.74 (d, 1 H), 8.26 (s, 1 H), 6.60 (m, 1H), 6.01 (m, 1 H), 3.77 (m, 3H), 3.18 (m, 4H), 2.90 (s, 3H), 2.66 (m, 2H), 2.53 (m, 2H), 1.81 (m, 4H).<br>MS: 560.2 ([M + H]⁺) |
| 1.66 | 6-[6-Fluoro-8-(methylamino)-4-thiomorpholino-9H-pyrido[2,3-b]indol-3-yl]-1-methyl-4-oxo-1,8-naphthyridine-3-carboxylic acid | CORE: Intermediate A1<br>AMINE: Thiomorpholine<br>BORONIC REAGENT: Intermediate B2<br>CATALYST: cataCXium ® A Pd G2 (Sigma-Aldrich, Catalog #: 761311)<br>SOLVENT: THF/H₂O | ¹H NMR (400 MHz, DMSO-d6) δ ppm: 11.60 (s, 1H), 9.27 (s, 1H), 9.11 (d, 1H), 8.69 (d, 1H), 8.25 (s, 1H), 7.19 (m, 1H), 6.47 (m, 1H), 4.18 (s, 3H), 3.20 (m, 4H), 2.93 (s, 3H), 2.68 (m, 4H).<br>MS: 519.2 ([M + H]⁺) |
| 1.67 | 6-[6-Fluoro-4-[3-(2-hydroxyethyl)pyrrolidin-1-yl]-8-(methylamino)-9H-pyrido[2,3-b]indol-3-yl]-1-methyl-4-oxo-1,8-naphthyridine-3-carboxylic acid | CORE: Intermediate A1<br>AMINE: 3-(2-Hydroxyethyl)pyrrolidine hydrochloride<br>BORONIC REAGENT: Intermediate B2<br>CATALYST: cataCXium ® A Pd G2 (Sigma-Aldrich, Catalog #: 761311)<br>SOLVENT: THF/H₂O | ¹H NMR (400 MHz, DMSO-d6) δ ppm: 11.88 (s, 1H), 9.29 (s, 1H), 9.17 (d, 1H), 8.73 (d, 1H), 8.25 (s, 1H), 6.89 (m, 1H), 6.46 (m, 1H), 4.17 (s, 3H), 3.50 (m, 1H), 3.29 (m, 4H), 3.01 (m, 1H), 2.92 (s, 3H), 2.20 (m, 1H), 2.00 (m, 1H), 1.47 (m, 4H).<br>MS: 519.2 ([M + H]⁺) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.68 | 6-[7-Chloro-4-(dimethylamino)-6-fluoro-8-(methylamino)-9H-pyrido[2,3-b]indol-3-yl]-4-oxo-1-pyrrolidin-3-yl-1,8-naphthyridine-3-carboxylic acid | CORE: Intermediate A5<br>AMINE: Dimethylamine hydrochloride<br>BORONIC REAGENT: Intermediate B6<br>CATALYST: cataCXium ® A Pd G2 (Sigma-Aldrich, Catalog #: 761311)<br>SOLVENT: THF/H$_2$O | $^1$H NMR (400 MHz, DMSO-d6): δ ppm: 11.83 (s, 1H), 9.25 (s, 1 H), 9.05 (s, 1 H) 8.68 (s, 1 H), 8.27 (s, 1 H), 7.40 (d, 1 H), 6.01 (m, 1 H), 3.80 (m, 4H), 3.39 (m, 1H), 3.15 (s, 3H), 2.82 (s, 6H), 2.68 (m, 1H), 2.53 (m, 1H).<br>MS: 550.1 ([{$^{35}$Cl}M + H]$^+$), 552.1 ([{$^{37}$Cl}M + H]$^+$). |
| 1.69 | 1-[2-(Dimethylamino)-2-methyl-propyl]-6-[6-fluoro-8-(methylamino)-4-morpholino-9H-pyrido[2,3-b]indol-3-yl]-4-oxo-1,8-naphthyridine-3-carboxylic acid | CORE: Intermediate A1<br>AMINE: Morpholine<br>BORONIC REAGENT: Intermediate B28<br>CATALYST: XPhos Pd G2 (Sigma-Aldrich, Catalog #: 741825)<br>SOLVENT: THF/H$_2$O | $^1$H NMR (400 MHz, DMSO-d6) δ ppm: 9.08 (d, 1H), 8.96 (s, 1H), 8.69 (d, 1H), 8.25 (s, 1H), 7.11 (m, 1H), 6.49 (m, 1H), 4.81 (s, 2H), 3.68 (m, 4H), 2.95 (m, 4H), 2.93 (s, 3H), 2.28 (s, 6H), 0.96 (s, 6H).<br>MS: 588.1 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.70 | 1-[2-(Dimethylamino)-1-methyl-ethyl]-6-[6-fluoro-8-(methylamino)-4-morpholino-9H-pyrido[2,3-b]indol-3-yl]-4-oxo-1,8-naphthyridine-3-carboxylic acid | CORE: Intermediate A1<br>AMINE: Morpholine<br>BORONIC REAGENT: Intermediate B29<br>CATALYST: XPhos Pd G2 (Sigma-Aldrich, Catalog #: 741825)<br>SOLVENT: THF/H$_2$O | $^1$H NMR (400 MHz, DMSO-d6) δ ppm: 9.11 (d, 1H), 9.07 (s, 1H), 8.70 (d, 1H), 8.25 (s, 1H), 7.12 (m, 1H), 6.49 (m, 1H), 6.03 (br s, 1H), 3.70 (m, 4H), 3.14 (m, 1H), 2.97 (m, 4H), 2.93 (s, 3H), 2.28 (s, 6H), 2.61 (m, 2H), 2.15 (s, 6H), 1.58 (d, 3H).<br>MS: 574.3 ([M + H]$^+$) |
| 1.71 | 6-[6-Fluoro-8-(methylamino)-4-morpholino-9H-pyrido[2,3-b]indol-3-yl]-1-morpholino-4-oxo-1,8-naphthyridine-3-carboxylic acid | CORE: Intermediate A1<br>AMINE: Morpholine<br>BORONIC REAGENT: Intermediate B30<br>CATALYST: XPhos Pd G2 (Sigma-Aldrich, Catalog#: 741825)<br>SOLVENT: THF/H$_2$O | $^1$H NMR (400 MHz, DMSO-d6) δ ppm: 9.11 (d, 1H), 9.06 (s, 1H), 8.68 (d, 1H), 8.21 (s, 1H), 7.12 (m, 1H), 6.49 (m, 1H), 4.16 (m, 2H), 3.92 (m, 2H), 3.78 (m, 2H), 3.72 (m, 4H), 3.38 (m, 2H), 2.99 (m, 4H), 2.93 (s, 3H).<br>MS: 574.3 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.72 | 6-[4-(Dimethylamino)-5,6-difluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: Dimethylamine hydrochloride<br>BORONIC REAGENT: Intermediate B23<br>CATALYST: XPhos Pd G2 (Sigma-Aldrich, Catalog #: 741825)<br>SOLVENT: THF/H$_2$O | $^1$H NMR (400 MHz, DMSO-d6) δ ppm: 9.08 (d, 1H), 9.03 (s, 1H), 8.63 (d, 1H), 8.26 (s, 1H), 6.60 (m, 1H), 2.97 (s, 3H), 2.90 (s, 3H), 2.74 (d, 6H).<br>MS: 494.5 ([M + H]$^+$) |
| 1.73 | 1-[2-(Dimethylamino)ethyl]-6-[5,6-difluoro-8-(methylamino)-4-morpholino-9H-pyrido[2,3-b]indol-3-yl]-4-oxo-1,8-naphthyridine-3-carboxylic acid | CORE: Intermediate A3<br>AMINE: Morpholine<br>BORONIC REAGENT: Intermediate B32<br>CATALYST: XPhos Pd G2 (Sigma-Aldrich, Catalog #: 741825)<br>SOLVENT: THF/H$_2$O | $^1$H NMR (400 MHz, DMSO-d6) δ ppm: 9.10 (d, 1H), 9.07 (s, 1H), 8.72 (d, 1H), 8.28 (s, 1H), 6.64 (m, 1H), 4.76 (m, 2H), 3.55 (m, 4H), 2.95 (m, 4H), 2.90 (s, 3H), 2.80 (m, 2H), 2.47 (m, 4H), 0.73 (t, 6H).<br>MS: 606.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.74 | 6-[5,6-Difluoro-8-(methylamino)-4-morpholino-9H-pyrido[2,3-b]indol-3-yl]-1-[2-(dimethylamino)-2-phenyl-ethyl]-4-oxo-1,8-naphthyridine-3-carboxylic acid | CORE: Intermediate A3<br>AMINE: Morpholine<br>BORONIC REAGENT: Intermediate B33<br>CATALYST: XPhos Pd G2 (Sigma-Aldrich, Catalog #: 741825)<br>SOLVENT: THF/H$_2$O | $^1$H NMR (400 MHz, DMSO-d6) δ ppm: 9.09 (s, 1H), 8.99 (s, 1H), 8.68 (d, 1H), 8.29 (s, 1H), 7.35 (m, 3H), 7.24 (m, 2H), 6.64 (m, 1H), 5.29 (m, 1H), 4.97 (m, 1H), 4.04 (m, 1H), 3.58 (m, 4H), 2.94 (m, 4H), 2.90 (s, 3H), 2.15 (s, 6H).<br>MS: 654.5 ([M + H]$^+$) |
| 1.75 | 6-[4-[3-(Dimethylamino)pyrrolidin-1-yl]-6-fluoro-8-(methylamino)-9H-pyrido[2,3-b]indol-3-yl]-1-methyl-4-oxo-1,8-naphthyridine-3-carboxylic acid | CORE: Intermediate A1<br>AMINE: N,N-Dimethylpyrrolidin-3-amine, dihydrochloride<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.68 (s, 1H), 10.12 (br s, 1H), 9.29 (s, 1H), 9.12 (d, 1H), 8.68 (s, 1H), 8.25 (s, 1H), 6.79 (m, 1H), 6.47 (m, 1H), 4.17 (s, 3H), 3.93 (m, 1H), 3.39 (m, 4H), 3.12 (m, 1H), 2.92 (s, 3H), 2.76 (s, 3H), 2.64 (s, 3H), 2.11 (m, 1H).<br>MS: 530.1 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.76 | 6-[6,7-Difluoro-8-(methylamino)-4-pyrrolidin-1-yl-9H-pyrido[2,3-b]indol-3-yl]-4-oxo-1-pyrrolidin-3-yl-1,8-naphthyridine-3-carboxylic acid | CORE: Intermediate A4<br>AMINE: Pyrrolidine<br>BORONIC REAGENT: Intermediate B6<br>CATALYST: cataCXium ® A Pd G2 (Sigma-Aldrich, Catalog #: 761311)<br>SOLVENT: THF/H$_2$O | $^1$H NMR (400 MHz, DMSO-d6): δ ppm: 12.12 (br s, 1H), 9.48 (br s, 1H), 9.23 (s, 1 H), 9.12 (s, 1 H) 8.73 (d, 1 H), 8.22 (s, 1 H), 7.09 (m, 1H), 6.01 (m, 1H), 3.92 (m, 1 H), 3.79 (m, 4H), 3.39 (m, 1H), 3.26 (m,4H), 3.12 (s, 3H), 2.68 (m, 1H), 1.84 (m, 4H).<br>MS: 560.2 ([M + H]$^+$) |
| 1.77 | 6-[5,6-Difluoro-4-[(2S)-2-(hydroxymethyl)pyrrolidin-1-yl]-8-(methylamino)-9H-pyrido[2,3-b]indol-3-yl]-1-methyl-4-oxo-1,8-naphthyridine-3-carboxylic acid | CORE: Intermediate A3<br>AMINE: L-Prolinol<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.89 (br s, 1H), 9.17 (s, 1H), 9.05 (s, 1H), 8.68 (s, 1H), 8.22 (s, 1H), 6.57 (m, 1H), 5.79 (br s, 1H), 4.12 (s, 3H), 3.09 (m, 1H), 2.89 (s, 3H), 2.54 (m, 2H), 1.75 (m, 4H).<br>MS: 535.0 ([M + H]$^+$) |
| 1.78 | 6-[4-[2-[(Dimethylamino)methyl]morpholin-4-yl]-6,7-difluoro-8-(methylamino)-9H-pyrido[2,3-b]indol-3-yl]-1-methyl-4-oxo-1,8-naphthyridine-3-carboxylic acid | CORE: Intermediate A4<br>AMINE: N,N-Dimethyl-1-morpholin-2-ylmethanamine<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.76 (s, 1H), 9.23 (s, 1H), 9.06 (d, 1H), 8.60 (s, 1H), 8.15 (s, 1H), 7.29 (m, 1H), 5.52 (br s, 1H), 4.16 (s, 3H), 3.90 (m, 1H), 3.71 (m, 2H), 3.33 (m, 1H), 3.12 (m, 3H), 2.86 (m, 1H), 2.54 (m, 3H), 2.39 (m, 1H), 2.21 (s, 6H).<br>MS: 578.4 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.79 | 6-[5,6-Difluoro-8-(methylamino)-4-morpholino-9H-pyrido[2,3-b]indol-3-yl]-1-[2-(dimethylamino)butyl]-4-oxo-1,8-naphthyridine-3-carboxylic acid | CORE: Intermediate A3<br>AMINE: Morpholine<br>BORONIC REAGENT: Intermediate B34<br>CATALYST: XPhos Pd G2 (Sigma-Aldrich, Catalog #: 741825)<br>SOLVENT: Dioxane/H$_2$O | $^1$H NMR (400 MHz, Methanol-d4) δ ppm: 9.08 (s, 1H), 8.83 (s, 1H), 8.27 (s, 1H), 8.26 (s, 1H), 6.63 (m, 1H), 5.02 (m, 1H), 4.60 (m, 1H), 3.71 (m, 4H), 3.23 (m, 1H), 3.07 (m, 4H), 3.00 (s, 3H), 2.52 (s, 6H), 1.89 (m, 1H), 1.53 (m, 1H), 1.17 (m, 3H).<br>MS: 606.1 ([M + H]$^+$) |
| 1.80 | 6-[4-[3-[(Dimethylamino)methyl]-1-piperidyl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: N,N-Dimethyl-1-piperidin-3-ylmethanamine<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, Methanol-d4) δ ppm: 9.09 (s, 1H), 8.98 (d, 1H), 8.81 (d, 1H), 8.20 (s, 1H), 6.55 (m, 1H), 4.13 (s, 3H), 2.91 (m, 9H), 2.76 (s, 3H), 2.74 (s, 3H), 2.15 (m, 1H), 1.71 (m, 1H), 1.52 (m, 1H), 1.36 (m, 1H), 1.06 (m, 1H).<br>MS: 576.1 ([M + H]$^+$) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.81 | 6-[6-Fluoro-8-(methylamino)-4-morpholino-9H-pyrido[2,3-b]indol-3-yl]-1-(1-methylpyrrolidin-3-yl)-4-oxo-1,8-naphthyridine-3-carboxylic acid | CORE: Intermediate A1<br>AMINE: Morpholine<br>BORONIC REAGENT: Intermediate B9<br>CATALYST: XPhos Pd G2 (Sigma-Aldrich, Catalog #: 741825)<br>SOLVENT: Dioxane/H$_2$O | ¹H NMR (400 MHz, Methanol-d4) δ ppm: 8.97 (s, 1H), 8.73 (s, 1H), 8.16 (s, 1H), 8.06 (s, 1H), 7.14 (d, 1H), 6.41 (m, 1H), 3.73 (m, 6H), 3.00 (m, 5H), 2.91 (m, 5H), 2.77 (m, 5H).<br>MS: 572.0 ([M + H]$^+$) |
| 1.82 | 6-[5,6-Difluoro-4-[trans-3-fluoro-4-hydroxy-pyrrolidin-1-yl]-8-(methylamino)-9H-pyrido[2,3-b]indol-3-yl]-1-methyl-4-oxo-1,8-naphthyridine-3-carboxylic acid | CORE: Intermediate A3<br>AMINE: trans-4-Fluoro-3-hydroxypyrrolidine Hydrochloride<br>BORONIC REAGENT: Intermediate B2<br>CATALYST: cataCXium® A Pd G2 (Sigma-Aldrich, Catalog #: 761311)<br>SOLVENT: THF/H$_2$O | ¹H NMR (400 MHz, DMSO-d6) δ ppm: 12.05 (br s, 1H), 9.28 (s, 1H), 9.17 (d, 1H), 8.73 (d, 1H), 8.24 (s, 1H), 6.60 (m, 1H), 4.82 (m, 1H), 4.23 (m, 4H), 3.71 (m, 1H), 3.43 (m, 1H), 3.32 (m, 1H), 3.04 (m, 1H), 2.90 (s, 3H).<br>MS: 539.1 ([M + H]$^+$) |
| 1.83 | 6-[5,6-difluoro-4-[trans-3-hydroxy-4-methyl-pyrrolidin-1-yl]-8-(methylamino)-9H-pyrido[2,3-b]indol-3-yl]-1-methyl-4-oxo-1,8-naphthyridine-3-carboxylic acid | CORE: Intermediate A3<br>AMINE: trans-4-Methyl-pyrrolidin-3-ol Hydrochloride<br>BORONIC REAGENT: Intermediate B2<br>CATALYST: cataCXium® A Pd G2 (Sigma-Aldrich, Catalog #: 761311)<br>SOLVENT: THF/H$_2$O | ¹H NMR (400 MHz, DMSO-d6) δ ppm: 12.03 (br s, 1H), 9.29 (s, 1H), 9.17 (d, 1H), 8.73 (d, 1H), 8.27 (s, 1H), 6.60 (m, 1H), 4.18 (s, 3H), 3.70 (m, 1H), 3.48 (m, 2H), 2.97 (m, 2H), 2.90 (s, 3H), 1.97 (m, 1H), 0.88 (d, 3H).<br>MS: 535.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.84 | 6-[5,6-Difluoro-4-[3-(hydroxymethyl-3-methyl-pyrrolidin-1-yl]-8-(methylamino)-9H-pyrido[2,3-b]indol-3-yl]-1-methyl-4-oxo-1,8-naphthyridine-3-carboxylic acid | CORE: Intermediate A3<br>AMINE: (3-Methylpyrrolidin-3-yl)methanol Hydrochloride<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 12.11 (br s, 1H), 9.29 (s, 1H), 9.16 (d, 1H), 8.71 (d, 1H), 8.25 (s, 1H), 6.59 (m, 1H), 4.17 (s, 3H), 3.28 (m, 3H), 3.05 (m, 3H), 2.89 (s, 3H), 1.73 (m, 1H), 1.48 (m, 1H), 0.85 (s, 3H).<br>MS: 549.2 ([M + H]$^+$) |
| 1.85 | 6-[4-[cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: cis-5-Methyl-1H-hexahydropyrrolo[2,3-c]pyrrole<br>BORONIC REAGENT: Intermediate B2<br>CATALYST: cataCXium ® A Pd G2 (Sigma-Aldrich, Catalog #: 761311)<br>SOLVENT: Dioxane/H$_2$O | $^1$H NMR (400 MHz, Methanol-d) δ ppm: 9.01 (br s, 1H), 8.94 (br s, 1H), 8.62 (br s, 1H), 8.07-8.23 (m, 1H), 6.52 (dd, J = 6.24, 12.96 Hz, 1H), 4.10 (br s, 3H), 3.33-3.66 (m, 4H), 3.02-3.13 (m, 1H), 2.84-2.93 (m, 4H), 2.60-2.77 (m, 4H), 2.03-2.29 (m, 1H), 1.72-1.89 (m, 1H), 0.97-1.07 (m, 1H).<br>MS: 560.2 ([M + H]$^+$) |
| 1.86 | 6-[4-[cis-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: Intermediate C8<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, Methanol-d) δ ppm: 9.20 (s, 1H), 9.11 (s, 1H), 8.87 (s, 1H), 8.29 (s, 1H), 7.00 (m, 1H), 6.58 (m, 1H), 4.45 (m, 1H), 4.13 (m, 1H), 3.84 (m, 1H), 3.40-3.51 (m, 2H), 3.15 (m, 2H), 3.09 (s, 3H), 3.04 (s, 3H), 2.81 (m, 4H), 2.44 (m, 1H), 2.06 (m, 1H).<br>MS: 557.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.87 | 6-[4-(dimethylamino)-5,6-difluoro-8-(methylamino)-9H-pyrido[2,3-b]indol-3-yl]-1-(oxazol-5-ylmethyl)-4-oxo-1,8-naphthyridine-3-carboxylic acid | CORE: Intermediate A3<br>AMINE: Dimethylamine hydrochloride<br>BORONIC REAGENT: Intermediate B36<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.78 (s, 1H), 9.43 (s, 1H), 9.07 (d, J = 2.4 Hz, 1H), 8.62 (d, J = 2.4 Hz, 1H), 8.38 (s, 1H), 8.27 (s, 1H), 7.37 (s, 1H), 6.62-6.57 (m, 1H), 6.08 (s, 2H), 2.91 (s, 3H), 2.73 (s, 6H).<br>MS: 546.4 ([M + H]$^+$). |
| 1.88 | 6-[4-[cis-3-[(dimethylamino)methyl]-2,3,3a,4,6,6a-hexahydrofuro[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C2<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.92 (s, 1H), 9.48 (m, 1H), 9.29 (s, 1H), 9.13 (d, 1H), 8.69 (d, 1H), 8.37 (s, 1H), 6.64-6.59 (m, 1H), 4.62 (s, 1H), 4.17 (s, 3H), 3.86 (m, 1H), 3.59 (m, 3H), 3.28 (m, 1H), 3.13 (m, 2H), 2.98 (m, 2H), 2.90 (s, 3H), 2.82 (m, 1H), 2.74 (s, 6H), 2.67 (m, 1H).<br>MS: 604.2 ([M + H]$^+$). |

| No. | Compound Name and Structure | CORE, AMINE, BORONIC REAGENT, CATALYST and SOLVENT | ¹H NMR and MS (ESI) |
|---|---|---|---|
| 1.89 | (S)-6-(5,6-difluoro-8-(methylamino)-4-(pyrrolidin-1-yl)-9H-pyrido[2,3-b]indol-3-yl)-4-oxo-1-(pyrrolidin-3-yl)-1,4-dihydro-1,8-naphthyridine-3-carboxylic acid | CORE: Intermediate A3<br>AMINE: pyrrolidine<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, DMSO-d₆) δ ppm 12.00 (s, 1 H), 9.39 (s, 1 H), 9.22 (s, 1 H), 9.00-9.14 (m, 2 H), 8.75 (d, J = 2.384 Hz, 1 H), 8.26 (s, 1 H), 6.59 (dd, J = 13.55, 6.27 Hz, 1 H), 5.94-6.05 (m, 1 H), 3.66-3.92 (m, 3 H), 3.37 (s, 1 H), 3.21 (s, 4 H), 2.89 (s, 3 H), 2.60-2.73 (m, 1 H), 2.52-2.58 (m, 1 H), 1.79 (s, 4 H). MS (ESI): 560.2 ([M + H]⁺). |
| 1.90 | 6-(4-(6-((dimethylamino)methyl)-1,4-oxazepan-4-yl)-6-fluoro-8-(methylamino)-9H-pyrido[2,3-b]indol-3-yl)-1-methyl-4-oxo-1,4-dihydro-1,8-naphthyridine-3-carboxylic acid | CORE: Intermediate A1<br>AMINE: N,N-dimethyl-1-(1,4-oxazepan-6-yl)methanamine hydrochloride<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, DMSO-d₆) δ ppm 11.64 (s, 1H), 9.314 (s, 1H), 8.99-9.16 (m, 2 H), 8.76 (d, J = 2.259 Hz, 1 H), 8.36 (s, 1 H), 7.30 (d, J = 10.039 Hz, 1 H), 6.48 (dd, J = 12.109, 2.070 Hz, 1 H), 4.19 (s, 3 H), 3.98 (s, 1 H), 3.67-3.85 (m, 3 H), 3.09-3.20 (m, 1 H), 3.02 (s, 2H), 2.93 (s, 3 H), 2.82 (br s, 1 H), 2.57 (d, J = 4.643 Hz, 3 H), 2.52-2.55 (m, 5 H), 2.10 (d, J = 16.187 Hz, 1 H) MS (ESI): 574.2 ([M + H]⁺). |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.91 | 6-(4-(dimethylamino)-5,6-difluoro-8-(methylamino)-9H-pyrido[2,3-b]indol-3-yl)-4-oxo-1-((tetrahydro-2H-pyran-4-yl)amino)-1,4-dihydro-1,8-naphthyridine-3-carboxylic acid | CORE: Intermediate A3<br>AMINE: dimethylamine hydrochloride<br>BORONIC REAGENT: Intermediate B38<br>CATALYST: Pd-Ad$_2$nBuP Biphenyl Precat (CAS#: 1375477-29-4)<br>SOLVENT: THF/H$_2$O | ¹H NMR (400 MHz, DMSO-d$_6$) δ ppm 11.77 (s, 1 H), 9.11 (d, J = 2.384 Hz, 1 H), 8.90 (s, 1 H), 8.63 (d, J = 2.259 Hz, 1 H), 8.26 (s, 1 H), 6.60 (dd, J = 13.490, 6.211 Hz, 1 H), 3.89 (br d, J = 11.670 Hz, 2 H), 3.59-3.60 (m, 1 H), 3.23-3.34 (m, 2 H), 2.90 (s, 3 H), 2.74 (d, J = 2.008 Hz, 6 H), 1.75 (br d, J = 10.666 Hz, 2 H), 1.47-1.59 (m, 2 H).<br>MS (ESI): 564.2 ([M + H]$^+$). |
| 1.92 | 6-(4-(3-((dimethylamino)methyl)-3-fluoropyrrolidin-1-yl)-6-fluoro-8-(methylamino)-9H-pyrido[2,3-b]indol-3-yl)-1-(methylamino)-4-oxo-1,4-dihydro-1,8-naphthyridine-3-carboxylic acid | CORE: Intermediate A1<br>AMINE: Intermediate C3<br>BORONIC REAGENT: Intermediate B23<br>CATALYST: Pd-Ad$_2$nBuP Biphenyl Precat (CAS#: 1375477-29-4)<br>SOLVENT: THF/H$_2$O | ¹H NMR (400 MHz, DMSO-d6): δ ppm: 11.640 (s, 1 H), 9.638 (br s, 1 H), 9.166 (d, J = 2.259 Hz, 1 H), 9.074 (s, 1 H), 8.729 (d, J = 2.384 Hz, 1 H), 8.306 (s, 1 H), 6.908 (br d, J = 8.282 Hz, 1 H), 6.483 (dd, J = 11.984, 1.945 Hz, 1 H), 3.565 (br s, 6 H), 3.264~3.427 (m, 2 H), 2.979 (s, 3 H), 2.938 (s, 3 H), 2.825 (br d, J = 4.643 Hz, 6 H).<br>MS: 577.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.93 | 6-(4-(3-((dimethylamino)methyl)-3-fluoropyrrolidin-1-yl)-5,6-difluoro-8-(methylamino)-9H-pyrido[2,3-b]indol-3-yl)-1-(methylamino)-4-oxo-1,4-dihydro-1,8-naphthyridine-3-carboxylic acid 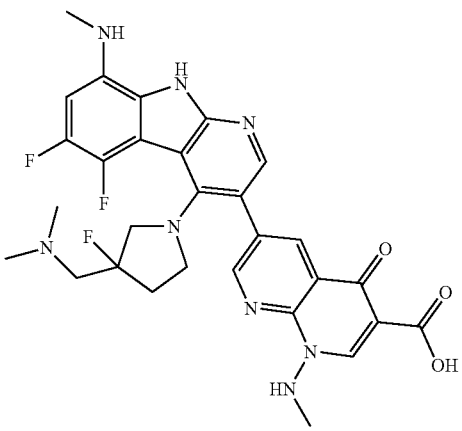 | CORE: Intermediate A3<br>AMINE: Intermediate C3<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 11.92 (s, 1 H), 9.60 (br d, J = 2.38 Hz, 1 H), 9.15 (d, J = 2.26 Hz, 1 H), 9.07 (s, 1 H), 8.74 (d, J = 2.26 Hz, 1 H), 8.36 (s, 1 H), 6.63 (dd, J = 13.49, 6.33 Hz, 1 H), 3.40~3.68 (m, 6 H), 3.29~3.40 (m, 2 H), 2.97 (s, 3 H), 2.92 (s, 3 H), 2.79 (br s, 6 H).<br>MS: 595.2 ([M + H]$^+$) |
| 1.94 | 6-(4-(3-((dimethylamino)methyl)piperidin-1-yl)-6-fluoro-8-(methylamino)-9H-pyrido[2,3-b]indol-3-yl)-1-methyl-4-oxo-1,4-dihydro-1,8-naphthyridine-3-carboxylic acid 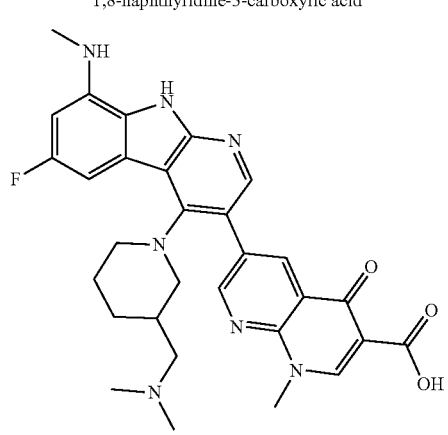 | CORE: Intermediate A1<br>AMINE: Intermediate C4<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.60 (s, 1H), 9.31 (s, 1H), 9.09-9.15 (m, 2H), 8.68 (s, 1H), 8.22 (s, 1H), 7.12-7.09 (d, J = 12.0 Hz, 1H), 6.49-6.46 (d, J = 12.0 Hz, 1H), 4.18 (s, 3H), 3.13 (m, 3H), 2.92 (m, 6H), 2.72-2.69 (m, 6H), 2.13 (m, 1H), 1.80 (m, 1H), 1.67 (m, 2H), 1.05 (m, 1H).<br>MS: 558.3 ([M + H]$^+$). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.95 | 1-cyclopropyl-6-[4-(dimethylamino)-5,6-difluoro-8-(methylamino)-9H-pyrido[2,3-b]indol-3-yl]-4-oxo-1,8-naphthyridine-3-carboxylic acid | CORE: Intermediate A3<br>AMINE: Dimethylamine hydrochloride<br>BORONIC REAGENT: Intermediate B39<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 14.62 (br s, 1H), 11.74 (s, 1H), 9.10 (s, 1H), 8.91 (s, 1H), 8.59 (s, 1H), 8.26 (s, 1H), 6.60-6.55 (m, 1H), 5.66 (s, 1H), 3.99-3.96 (m, 1H), 2.90 (s, 3H), 2.73 (s, 6H), 1.28-1.23 (m, 4H).<br>MS: 505.2 ([M + H]$^+$). |
| 1.96 | 6-[4-[(cis-5-(2-methoxyethyl)-2,3,3a,4,6,6a-hexahydro-pyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C5<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 14.66 (s, 1H), 11.89 (m, 1H), 9.45 (m, 1H), 9.32 (s, 1H), 9.14-9.11 (m, 1H), 8.70 (s, 1H), 8.32-8.20 (m, 1H), 6.67-6.60 (m, 1H), 4.26-4.19 (m, 4H), 3.82-3.58 (m, 1H), 3.36-3.31 (m, 2H), 3.26-2.99 (m, 8H), 2.95-2.78 (m, 5H), 2.63 (m, 1H), 2.18-2.04 (m, 1H), 1.91-1.75 (m, 1H).<br>$^1$H NMR (400 MHz, DMSO-d6, T = 80° C.) δ ppm: 11.68 (s, 1H), 9.21 (s, 1H), 9.10 (d, J = 2.4 Hz, 1H), 8.72 (d, J = 2.4 Hz, 1H), 8.27-8.25 (m, 1H), 6.64-6.59 (m, 1H), 4.21 (m, 4H), 3.79-3.65 (m, 2H), 3.49 (m, 3H), 3.46-3.37 (m, 3H), 2.95 (s, 3 H), 2.52 (m, 4H), 2.45 (m, 2 H), 2.16 (m, 1H), 1.84 (m, 1H).<br>MS: 604.1 ([M + H]$^+$). |
| 1.97 | 6-(5,6-difluoro-8-(methylamino)-4-thiomorpholino-9H-pyrido[2,3-b]indol-3-yl)-1-methyl-4-oxo-1,4-dihydro-1,8-naphthyridine-3-carboxylic acid | CORE: Intermediate A3<br>AMINE: thiomorpholine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6) δ ppm 14.77 (br s, 1 H), 11.93 (br s, 1 H), 9.29 (s, 1H), 9.13 (br s, 1 H), 8.75 (s, 1 H), 8.30 (br s, 1 H), 6.59-6.66 (m, 1 H), 5.75 (br s, 1 H), 4.19 (s, 3 H), 2.91 (br s, 3 H), 1.19~1.44 (m, 8 H)<br>MS (ESI): 537.2 ([M + H]$^+$). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
| --- | --- | --- | --- |
| 1.98 | 6-(5,6-difluoro-8-(methylamino)-4-thiomorpholino-9H-pyrido[2,3-b]indol-3-yl)-4-oxo-1-(pyrrolidin-3-yl)-1,4-dihydro-1,8-naphthyridine-3-carboxylic acid | CORE: Intermediate A3<br>AMINE: thiomorpholine<br>BORONIC REAGENT: Intermediate B6<br>CATALYST: Pd-Ad$_2$nBuP Biphenyl Precat (CAS#: 1375477-29-4)<br>SOLVENT: THF/H$_2$O | $^1$H NMR $^1$H NMR (400 MHz, DMSO-d$_6$) δ ppm 11.98 (s, 1 H), 9.30 (s, 2 H), 9.17 (d, J = 2.3 Hz, 1 H), 8.86 (d, J = 2.3 Hz, 1 H), 8.36 (s, 1 H), 6.70 (dd, J = 13.3, 6.3 Hz, 1 H), 6.13 (dd, J = 13.2, 7.2 Hz, 1 H), 3.76~3.87 (m, 2 H), 3.17~3.53 (m, 4H), 2.97 (s, 3 H), 2.69~2.77 (m, 1 H), 2.58~2.64 (m, 2 H), 2.30~2.53 (m, 1 H), 1.16~1.61 (m, 3 H). MS (ESI): 592.1 ([M + H]$^+$). |
| 1.99 | 6-(4-(3-(((cyclopropyl(methyl)amino)methyl)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid | CORE: Intermediate A1<br>AMINE: N-methyl-N-(pyrrolidin-3-ylmethyl)cyclopropanamine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) δ 11.76 (s, 1H), 9.29 (s, 1H), 9.15 (d, J = 2.3 Hz, 1H), 8.70 (d, J = 2.4 Hz, 1H), 8.26 (s, 1H), 6.83 (dd, J = 1.8, 9.9 Hz, 1H), 6.46 (dd, J = 2.0, 12.2 Hz, 1H), 4.17 (s, 3H), 3.37-3.20 (m, 5H), 3.01-2.87 (m, 4H), 2.85-2.72 (m, 5H), 2.16 (br, J = 5.5, 11.7 Hz, 1H), 1.70 (br s, 1H), 0.85-0.66 (m, 4H) MS (ESI): 570.2 ([M + H]$^+$). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.100 | 6-(4-(3-((dimethylamino)methyl)-3-hydroxypyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C6<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6) δ 14.80 (br s, 1H), 11.84 (s, 1H), 9.30 (s, 1H), 9.13 (d, J = 2.3 Hz, 1H), 9.05 (br s, 1H), 8.68 (d, J = 2.4 Hz, 1H), 8.22 (s, 1H), 6.60 (dd, J = 6.2, 13.4 Hz, 1H), 5.42 (br s, 1H), 4.17 (s, 3H), 3.26-3.17 (m, 4H), 3.03 (br d, J = 9.7 Hz, 2H), 2.90 (s, 3H), 2.79 (br d, J = 4.6 Hz, 3H), 2.71 (br d, J = 4.6 Hz, 3H), 2.05-1.91 (m, 2H)<br>MS (ESI): 578.3 ([M + H]$^+$). |
| 1.101 | 6-(4-(3-((dimethylamino)methyl)-3-methylpyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C7<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) 14.75 (s, 1H), 15.19-14.22 (m, 1H), 11.90 (s, 1H), 9.31 (s, 1H), 9.14 (d, J = 2.3 Hz, 1H), 9.00 (br s, 1H), 8.69 (d, J = 2.3 Hz, 1H), 8.27 (s, 1H), 6.61 (dd, J = 6.3, 13.4 Hz, 1H), 4.17 (s, 3H), 3.34-3.29 (m, 1H), 3.13-3.04 (m, 4H), 2.93 (br s, 1H), 2.90 (s, 3H), 2.82-2.74 (m, 1H), 2.81-2.74 (m, 1H), 2.77 (br d, J = 4.3 Hz, 1H), 2.65 (br d, J = 4.0 Hz, 3H), 1.88-1.80 (m, 1H), 1.78-1.68 (m, 1H), 1.00 (s, 3H)<br>MS (ESI): 576.1 ([M + H]$^+$). |
| 1.102 | 6-(4-(3-((dimethylamino)methyl)-3-methylpyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid | CORE: Intermediate A1<br>AMINE: Intermediate C7<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) 11.75 (br s, 1H), 9.29 (s, 1H), 9.16 (d, J = 2.3 Hz, 2H), 8.70 (d, J = 2.3 Hz, 1H), 8.25 (s, 1H), 6.84 (br d, J = 10.1 Hz, 1H), 6.47 (dd, J = 1.8, 12.0 Hz, 1H), 4.17 (s, 3H), 3.42-3.41 (m, 1H), 3.24-3.11 (m, 3H), 3.10-3.01 (m, 2H), 2.92 (s, 3H), 2.79 (br s, 3H), 2.66 (br s, 3H), 1.92-1.81 (m, 2H), 1.22 (br s, 1H), 1.11 (s, 3H)<br>MS (ESI): 558.2 ([M + H]$^+$). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.103 | 6-[4-[cis-5-methyl-2,3,3a,4,6,6a-hexahydropyrrolo[2,3-c]pyrrol-1-yl]-6,7-difluoro-8-(methylamino)-9H-pyrido[2,3-b]indol-3-yl]-1-methyl-4-oxo-1,8-naphthyridine-3-carboxylic acid | CORE: Intermediate A4<br>AMINE: Intermediate C8<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6) δ ppm 11.80-11.96 (m, 1 H), 9.94 (s, 1 H), 9.26 (s, 1 H), 9.08 (d, J = 3.26 Hz, 1 H), 8.61 (d, J = 7.78 Hz, 1 H), 8.18 (d, J = 6.49 Hz, 1 H), 7.14-7.23 (m, 1 H), 4.18 (s, 3 H), 3.94-4.08 (m, 1 H), 3.75-3.91 (m, 1 H), 3.49-3.70 (m, 1 H), 3.33-3.48 (m, 1 H), 3.16-3.29 (m, 1 H), 3.13 (d, J = 4.14 Hz, 3 H), 2.61-3.00 (m, 6 H), 2.10-2.31 (m, 1 H), 1.81-2.06 (m, 1 H).<br>MS (ESI): 560.2 ([M + H]$^+$). |
| 1.104 | 6-(4-(3-(dimethylamino)pyrrolidin-1-yl)-8-(ethylamino)-5,6-difluoro-9H-pyrido[2,3-b]indol-3-yl)-1-methyl-4-oxo-1,4-dihydro-1,8-naphthyridine-3-carboxylic acid | CORE: Intermediate A7<br>AMINE: N,N-dimethylpyrrolidin-3-amine (CAS#: 69478-75-7)<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 12.03-12.02 (m, 1H), 9.80~9.92 (m, 1H), 9.31 (s, 1H), 9.13~9.14 (m, 1H), 8.70 (s, 1H), 8.31~8.35 (m, 1H), 6.62~6.67 (m, 1H), 4.19 (s, 3H), 3.90~3.98 (m, 1H), 3.70~3.79 (m, 1H), 3.36 (m, 1H), 3.23~3.25 (m, 3H), 3.08~3.11 (m, 1H), 2.74~2.75 (m, 3H), 2.63~2.64 (m, 3H), 2.23~2.30 (m, 1H), 1.96~1.98 (m, 1H), 1.30~1.34 (m, 3H).<br>MS: 562.3 ([M + H]$^+$) |
| 1.105 | 6-(5,7-difluoro-8-(methylamino)-4-morpholino-9H-pyrido[2,3-b]indol-3-yl)-1-methyl-4-oxo-1,4-dihydro-1,8-naphthyridine-3-carboxylic acid | CORE: Intermediate A8<br>AMINE: morpholine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 14.68-14.79 (br, 1H), 12.16 (s, 1H), 9.30 (s, 1H), 9.12~9.13 (m, 1H), 8.72 (s, 1H), 8.21~8.25 (m, 1H), 6.99~7.05 (m, 1H), 4.19 (s, 3H), 3.56 (m, 4H), 2.98~2.99 (m, 3H), 2.93 (s, 4H).<br>MS: 521.2 ([M + H]$^+$) |

… TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.106 | 6-(4-(3-((dimethylamino)methyl)pyrrolidin-1-yl)-8-(ethylamino)-5,6-difluoro-9H-pyrido[2,3-b]indol-3-yl)-1-methyl-4-oxo-1,4-dihydro-1,8-naphthyridine-3-carboxylic acid 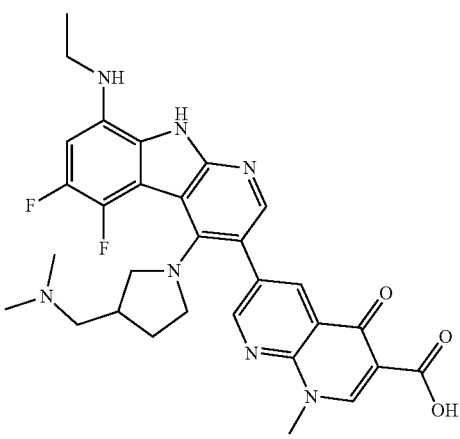 | CORE: Intermediate A7<br>AMINE: N,N-dimethyl-1-(pyrrolidin-3-yl)methanamine (CAS#: 99724-17-1)<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 12.02 (s, 1H), 9.31 (s, 2H), 9.13~9.15 (m, 1H), 8.70 (s, 1H), 8.31~8.33 (m, 1H), 6.61~6.66 (m, 1H), 4.45 (s, 3H), 3.41 (m, 1H), 3.21~3.26 (m, 4H), 3.07~3.08 (m, 1H), 2.90~2.92 (m, 1H), 2.71~2.72 (m, 6H), 2.08~2.10 (m, 1H), 1.61~1 68 (m, 1H), 1.30~1.33 (m, 3H).<br>MS: 576.3 ([M + H]$^+$) |
| 1.107 | 6-(4-(dimethylamino)-5,7-difluoro-8-(methylamino)-9H-pyrido[2,3-b]indol-3-yl)-4-oxo-1-(pyrrolidin-3-yl)-1,4-dihydro-1,8-naphthyridine-1-carboxylic acid 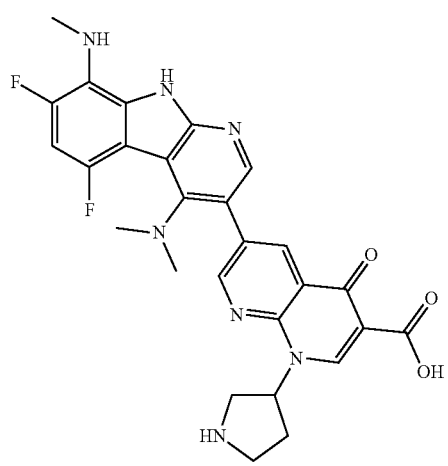 | CORE: Intermediate A8<br>AMINE: Dimethylamine hydrochloride<br>BORONIC REAGENT: Intermediate B6<br>CATALYST: Pd-Ad$_2$nBuP Biphenyl Precat (CAS#: 1375477-29-4)<br>SOLVENT: THF/H$_2$O | $^1$H NMR (400 MHz, Methanol-d4): δ ppm 11.98~12.21 (m, 1 H), 9.36~9.50 (m, 1 H), 9.21~9.26 (m, 1 H), 9.00~9.12 (m, 2 H), 8.64~8.69 (m, 1 H), 8.22 (s, 1 H), 6.94~7.05 (m, 1 H), 5.94~6.08 (m, 1 H), 3.63~3.88 (m, 3 H), 3.32~3.43 (m, 1 H), 2.99 (d, J = 2.87 Hz, 3 H), 2.72~2.79 (m, 7 H), 2.66~2.69 (m, 1 H), 2.31~2.38 (m, 1 H).<br>MS: 534.2 ([M + H]$^+$) |

TABLE 1-continued

Compound synthesis and characterization

| No. | Compound Name and Structure | CORE, AMINE, BORONIC REAGENT, CATALYST and SOLVENT | ¹H NMR and MS (ESI) |
| --- | --- | --- | --- |
| 1.108 | 6-(4-(3-((dimethylamino)methyl)-3-fluoropyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C3<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 mHz, DMSO-d6): δ ppm: 11.80~11.83 (s, 1H), 9.38~9.40 (m, 1H), 9.34 (s, 1H), 9.22~9.22 (m, 1H), 8.44~8.46 (m, 1H), 7.37~7.39 (m, 1H), 6.49~6.55 (m, 1H), 4.02 (s, 3H), 3.43~3.54 (m, 2H), 2.95 (s, 3H), 2.92 (m, 1H), 2.77~2.78 (m, 3H), 2.68~2.69 (m, 3H), 2.34 (s, 1H), 1.60~1.61 (m, 1H), 1.24~1.29 (m, 1H), 1.11 (m, 1H), 0.94~1.10 (m, 1H). MS: 580.3 ([M + H]⁺) |
| 1.109 | 6-(4-(3-((dimethylamino)methyl)-3-fluoropyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid | CORE: Intermediate A1<br>AMINE: Intermediate C3<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, Methanol-d4): δ ppm: 9.19~9.22 (m, 2H), 8.88 (s, 1H), 8.25 (s, 1H), 7.31~7.35 (m, 1H), 5.82 (s, 1H), 3.94~4.09 (m, 3H), 3.51~3.53 (m, 1H), 3.21 (s, 3H), 3.09 (s, 6H), 2.78~2.87 (m, 2H). MS: 562.3 ([M + H]⁺) |
| 1.110 | 6-(6-fluoro-8-(methylamino)-4-(cis-1-methyl-hexahydro-1H-pyrrolo[3,4-b]pyridin-6(2H)-yl)-9H-pyrido[2,3-b]indol-3-yl)-1-methyl-4-oxo-1,4-dihydro-1,8-naphthyridine-3-carboxylic acid | CORE: Intermediate A1<br>AMINE: Intermediate C9<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, DMSO-d6): δ ppm: 11.80~12.03 (m, 1H), 9.30 (s, 1H), 9.16 (s, 1H), 8.73~8.74 (m, 1H), 8.20~8.33 (m, 1H), 6.87~7.03 (m, 1H), 6.46~6.49 (m, 1H), 4.18 (m, 6H), 3.40~4.11 (m, 4H), 2.92 (s, 3H), 2.66 (m, 4H), 1.66~1.76 (m, 4H). MS: 556.3 ([M + H]⁺) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.111 | 6-(6-fluoro-8-(methylamino)-4-(cis-1-methyl-hexahydro-1H-pyrrolo[3,4-b]pyridin-6(2H)-yl)-9H-pyrido[2,3-b]indol-3-yl)-1-(methylamino)-4-oxo-1,4-dihydro-1,8-naphthyridine-3-carboxylic acid | CORE: Intermediate A1<br>AMINE: Intermediate C9<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 11.84~12.09 (s, 1H), 10.07~10.08 (m, 1H), 9.19 (s, 1H), 9.06 (s, 1H), 8.77~8.78 (m, 1H), 8.22~8.36 (m, 1H), 6.89~7.04 (m, 1H), 6.47~6.50 (m, 1H), 3.39~4.18 (m, 8H), 2.98 (s, 3H), 2.92 (s, 3H), 2.66 (m, 3H), 1.39~1.76 (m, 4H).<br>MS: 571.3 ([M + H]$^+$) |
| 1.112 | 6-(6-fluoro-8-(methylamino)-4-(cis-4-methyl-hexahydropyrrolo[3,4-b][1,4]oxazin-6(2H)-yl)-9H-pyrido[2,3-b]indol-3-yl)-1-methyl-4-oxo-1,4-dihydro-1,8-naphthyridine-3-carboxylic acid | CORE: Intermediate A1<br>AMINE: Intermediate C10<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 11.68 (s, 1H), 9.30 (s, 1H), 9.15~9.19 (m, 1H), 8.72~8.76 (m, 1H), 8.31 (s, 1H), 7.07~7.09 (m, 1H), 6.47~6.50 (m, 1H), 4.35~4.49 (m, 1H), 4.18 (s, 3H), 3.94~4.00 (m, 2H), 3.69 (m, 2H), 3.45~3.49 (m, 3H), 3.29~3.32 (m, 3H), 2.93 (s, 3H), 2.68~2.69 (m, 2H).<br>MS: 558.2 ([M + H]$^+$) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.113 | 6-(6-fluoro-8-(methylamino)-4-(cis-4-methyl-hexahydropyrrolo[3,4-b][1,4]oxazin-6(2H)-yl)-9H-pyrido[2,3-b]indol-3-yl)-1-(methylamino)-4-oxo-1,4-dihydro-1,8-naphthyridine-3-carboxylic acid | CORE: Intermediate A1<br>AMINE: Intermediate C10<br>BORONIC REAGENT: Intermediate B23<br>CATALYST: Pd-Ad₂nBuP Biphenyl Precat (CAS#: 1375477-29-4)<br>SOLVENT: THF/H₂O | ¹H NMR (400 MHz, DMSO-d6): δ ppm: 11.69 (s, 1H), 9.17 (s, 1H), 9.06 (s, 1H), 8.75~8.76 (m, 1H), 8.36 (s, 1H), 7.06~7.09 (m, 1H), 6.47~6.50 (m, 1H), 4.36 (m, 1H), 3.97~4.02 (m, 2H), 3.68 (m, 3H), 3.31~3.45 (m, 5H), 2.98 (m, 3H), 2.93 (m, 3H), 2.68~2.68 (m, 2H). MS: 573.2 ([M + H]⁺) |
| 1.114 | 6-(4-(3-(cyclopropylamino)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid | CORE: Intermediate A1<br>AMINE: tert-butyl cyclopropyl(pyrrolidin-3-yl)carbamate<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, DMSO-d6) δ ppm: 11.76 (s, 1 H), 9.31 (s, 1 H), 8.94~9.15 (m, 3 H), 8.71~8.75 (d, J = 2.4 Hz, 1 H), 8.23 (s, 1 H), 6.85~6.88 (dd, J = 9.6, 2.0 Hz, 1 H), 6.46~6.49 (dd, J = 12.0, 2.0 Hz, 1 H), 4.18 (s, 3H), 3.92 (br s, 1 H), 3.54 (m, 1 H), 3.36~3.45 (m, 2 H), 3.13 (m, 1 H), 2.93 (s, 3 H), 2.68 (m, 1 H), 2.32~2.44 (m, 1 H), 2.06 (m, 1 H), 0.67~0.75 (m, 4 H). MS (ESI): 542.3 ([M + H]⁺), 271.6 ([M/2 + H]⁺). |
| 1.115 | 6-(4-(3-(cyclopropylamino)pyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: tert-butyl cyclopropyl(pyrrolidin-3-yl)carbamate<br>BORONIC REAGENT: Intermediate B2<br>CATALYST Pd-Ad₂nBuP Biphenyl Precat (CAS#: 1375477-29-4)<br>SOLVENT: THF/H₂O | ¹H NMR (400 MHz, DMSO-d6) δ ppm: 11.938 (s, 1 H), 9.307 (s, 1 H), 8.900~9.138 (m, 3 H), 8.684~8.690 (d, J = 2.4 Hz, 1 H), 8.285 (s, 1 H), 6.6587~6.636 (dd, J = 13.6, 6.4 Hz, 1 H), 4.186 (s, 3 H), 3.785 (br s, 1 H), 3.498~3.585 (m, 1 H), 3.231~3.435 (m, 2 H), 2.986 (br t, J = 8.4 Hz, 1 H), 2.638 (br s, 1 H), 2.283~2.403 (m, 1 H), 1.879~2.019 (m, 1 H), 0.629~0.722 (m, 4 H) MS (ESI): 560.2 ([M + H]⁺), 280.6 ([M/2 + H]⁺). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.116 | 6-(4-(3-(cyclopropyl(methyl)amino)pyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C11<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6) δ: 11.92 (s, 1 H), 9.29 (s, 1 H), 9.14 (s, 1 H), 8.70~8.71 (d, J = 2.0, 1 H), 8.30 (s, 1 H), 6.59~6.64 (m, 1 H), 4.17 (s, 3 H), 3.99~4.01 (m, 1 H), 3.17~3.27 (m, 2 H), 2.90 (s, 3 H), 2.77 (s, 5 H), 2.33~2.40 (m, 2 H), 1.97 (s, 1 H), 0.53~0.75 (m, 1 H).<br>MS (ESI): 574.2 ([M + H]$^+$). |
| 1.117 | 6-(5-chloro-4-(dimethylamino)-6-fluoro-8-(methylamino)-9H-pyrido[2,3-b]indol-3-yl)-1-methyl-4-oxo-1,4-dihydro-1,8-naphthyridine-3-carboxylic acid | CORE: Intermediate A9<br>AMINE: Dimethylamine hydrochloride<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) δ ppm 11.72 (br s, 1 H), 9.21 (s, 1 H), 9.00 (s, 1 H), 8.52 (d, J = 1.8 Hz, 1 H), 8.17 (s, 1 H), 6.57 (d, J =1 2.3 Hz, 1 H), 4.13 (s, 3 H), 2.90 (s, 3 H), 2.67 (s, 6 H).<br>MS: 495.0 ([M + H]$^+$), 517.0 ([M + Na]$^+$). |
| 1.118 | 6-(4-(3-(cyclopropyl(methyl)amino)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid | CORE: Intermediate A1<br>AMINE: Intermediate C11<br>BORONIC REAGENT: Intermediate B2<br>CATALYST: Pd-Ad2$_n$BuP Biphenyl Precat (CAS#: 1375477-29-4)<br>SOLVENT: THF/H$_2$O | $^1$H NMR (400 MHz, DMSO-d$_6$) δ: 11.670 (s, 1H), 9.307 (s, 1H), 9.154 (s, 1H), 8.717 (s, 1H), 8.244 (s, 1H), 6.806~6.830 (d, J = 9.6 Hz, 1H), 6.464~6.494 (d, J = 12.0 Hz, 1H), 4.178 (s, 3H), 4.112 (s, 4H), 2.924 (s, 3H), 2.791 (s, 5 H), 2.064 (m, 2H), 0.532~0.752 (m, 4H).<br>MS: 556.2 ([M + H]$^+$), 278.6 ([M/2 + H]$^+$). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.119 | 1-(cyclopropylamino)-6-(4-(dimethylamino)-5,6-difluoro-8-(methylamino)-9H-pyrido[2,3-b]indol-3-yl)-4-oxo-1,4-dihydro-1,8-naphthyridine-3-carboxylic acid | CORE: Intermediate A3<br>AMINE: Dimethylamine<br>BORONIC REAGENT: Intermediate B40<br>CATALYST: cataCXium ® A Pd G2 (Sigma-Aldrich, Catalog #: 761311)<br>SOLVENT: THF/H$_2$O | $^1$H NMR (400 MHz, DMSO): δ 11.81 (s, 1 H), 9.12~9.13 (m, 1 H), 8.93 (s, 1 H), 8.64~8.64 (m, 1 H), 8.28 (m, 2 H), 6.56~6.61 (m, 1 H), 3.15~3.18 (m, 1 H), 2.90 (s, 3 H), 2.75~2.78 (m, 6 H), 0.71~0.77 (m, 2 H), 0.59~0.62 (m, 2 H). MS (ESI): 460.1 ([M + H]$^+$). |
| 1.120 | 6-[4-(3a-fluoro-5-methyl-3,4,6,6a-tetrahydro-2H-pyrrolo[2,3-c]pyrrol-1-yl)-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C12<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6) δ ppm: 11.98 (s, 1 H), 9.32 (s, 1 H), 9.14~9.15 (d, J = 2.0 Hz, 1 H), 8.74~8.75 (d, J = 2.4 Hz, 1 H), 8.29 (s, 1 H), 6.63~6.68 (dd, J = 13.4, 6.4 Hz, 1 H), 4.19 (s, 3 H), 3.72 (m, 5 H), 3.37~3.41 (m, 1 H), 2.92 (s, 3 H), 2.68~2.72 (m, 4 H), 2.26~2.29 (m, 1 H) MS (ESI): 578.3 ([M + H]$^+$), 289.7 ([M/2 + H]$^+$). |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.121 | 6-[4-(3a-fluoro-5-methyl-3,4,6,6a-tetrahydro-2H-pyrrolo[2,3-c]pyrrol-1-yl)-5,6-difluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: Intermediate C12<br>BORONIC REAGENT: Intermediate B23<br>CATALYST: Pd-Ad$_2$nBuP Biphenyl Precat (CAS#: 1375477-29-4)<br>SOLVENT: THF/H$_2$O | ¹H NMR (400 MHz, DMSO-d6) δ ppm: 12.00 (s, 1 H), 9.16~9.17 (d, J = 2.4 Hz, 1 H), 9.09 (s, 1 H), 8.79 (d, J = 2.0 Hz, 1 H), 8.32 (s, 1 H), 6.63~6.68 (dd, J = 13.6, 6.4 Hz, 1 H), 3.90~3.94 (m, 4 H), 3.74 (m, 1 H), 3.41~3.52 (m, 2 H), 2.92~2.97 (m, 6 H), 2.71~2.80 (m, 4 H), 2.23~2.34 (m, 1 H)<br>MS (ESI): 593.3 ([M + H]$^+$), 297.2 ([M/2 + H]$^+$). |
| 1.122 | 6-(5-chloro-4-(3-((dimethylamino)methyl)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid | CORE: Intermediate A9<br>AMINE: N,N-dimethyl-1-(pyrrolidin-3-yl)methanamine<br>BORONIC REAGENT: Intermediate B2<br>CATALYST: cataCXium ® A Pd G2 (Sigma-Aldrich, Catalog #: 761311)<br>SOLVENT: THF/H$_2$O | ¹H NMR (400 MHz, Methanol-d4): δ 12.01 (s, 1 H), 9.41 (s, 1 H), 9.30 (s, 1 H), 9.14~9.15 (d, J = 2.4 Hz, 1 H), 8.68~8.69 (d, J = 2.0 Hz, 1 H), 8.25 (s, 1 H), 6.62~6.65 (m, 1 H), 4.18 (s, 3 H), 3.18 (m, 3 H), 2.93 (m, 4 H), 2.68~2.73 (m, 7 H), 2.53 (m, 4H), 2.03~2.08 (m, 1 H), 1.59~1.76 (m, 1 H).<br>MS: 521.1 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.123 | 6-[4-[cis-5-methyl-2,3,3a,4,6,6a-hexahydropyrrolo[2,3-c]pyrrol-1-yl]-8-(ethylamino)-6-(trifluoromethyl)-9H-pyrido[2,3-b]indol-3-yl]-1-(methylamino)-4-oxo-1,8-naphthyridine-3-carboxylic acid | CORE: Intermediate A12<br>AMINE: Intermediate C8<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) δ ppm 12.14 (br s, 1 H), 9.78-10.03 (m, 1 H), 9.01~9.18 (m, 2 H), 8.74 (br s, 1 H), 8.31 (br d, J = 6.8 Hz, 1 H), 7.32~7.47 (m, 1 H), 6.81 (s, 1 H), 4.20 (br s, 1 H), 3.97~4.08 (m, 1 H), 3.94~4.10 (m, 1 H), 3.42~3.53 (m, 3 H), 3.34~3.36 (m, 1 H), 3.24 (br d, J = 10.9 Hz, 1 H), 3.14~3.19 (m, 1 H), 2.99 (s, 3 H), 2.86~3.12 (m, 1 H), 2.61~2.69 (m, 1 H), 2.654 (br d, J = 14.4 Hz, 3 H), 2.57~2.72 (m, 1 H), 2.08~2.36 (m, 1 H), 1.85 (br d, J = 16.8 Hz, 1 H), 1.31~1.38 (m, 3 H).<br>MS (ESI): 621.3 ([M + H]$^+$), 311.3 ([M/2 + H]$^+$). . |
| 1.124 | 6-[4-[3a-(fluoromethyl)-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: C13<br>BORONIC REAGENT: Intermediate B2<br>CATALYST: cataCXium ® A Pd G2 (Sigma-Aldrich, Catalog #: 761311)<br>SOLVENT: THF/H$_2$O | 1H NMR (400 MHz, DMSO): δ 11.94~11.96 (m, 1 H), 9.33 (s, 1 H), 9.13~9.14 (m, 1 H) (m, 1 H), 8.70~8.73 (m, 1 H), 8.73 (m, 1 H), 6.63~6.68 (m, 1 H), 4.32 (m, 1 H), 4.14~4.23 (m, 1 H), 3.96~4.01 (m, 2 H), 3.83 (m, 1 H), 2.98 (m, 1 H), 2.92 (s, 3 H), 2.78~2.82 (m, 1 H), 2.67~2.70 (m, 4 H), 2.13~2.30 (m, 1 H), 1.95 (m, 1 H).<br>MS: 592.0 ([M + H]+) |

| No. | Compound Name and Structure | CORE, AMINE, BORONIC REAGENT, CATALYST and SOLVENT | $^1$H NMR and MS (ESI) |
|---|---|---|---|
| 1.125 | 6-[4-[3a-(fluoromethyl)-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: C13<br>BORONIC REAGENT: Intermediate B23<br>CATALYST: cataCXium ® A Pd G2 (Sigma-Aldrich, Catalog #: 761311)<br>SOLVENT: THF/H$_2$O | $^1$H NMR (400 MHz, DMSO): δ 11.96~11.98 (m, 1 H), 9.13~9.15 (m, 1 H), 9.09 (s, 1 H), 8.76 (s, 1 H), 8.28~8.30 (m, 1 H), 6.63~6.68 (m, 1 H), 4.30~4.33 (m, 2 H), 4.30~4.33 (m, 2 H), 4.03~4.27 (m, 2 H), 3.87~3.97 (m, 2 H), 2.92~2.98 (m, 2 H), 2.83 (s, 3 H), 2.78 (s, 3 H), 2.70 (m, 1 H), 2.68 (m, 3 H), 2.13 (m, 1 H), 1.93~1.96 (m, 1 H).<br>MS: 607.0 ([M + H]$^+$) |
| 1.126 | 6-(4-(3,3-difluoropyrrolidin-1-yl)-6-fluoro-8-(methylamino)-9H-pyrido[2,3-b]indol-1-yl)-1-ethyl-4-oxo-1,4-dihydro-1,8-naphthyridine-3-carboxylic acid | CORE: Intermediate A1<br>AMINE: 3,3-Difluoropyrrolidine<br>BORONIC REAGENT: Intermediate B3<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 14.77 (s, 1 H), 11.65 (s, 1H), 9.30 (s, 1H), 9.14 (s, 1H), 8.71~8.72 (m, 1H), 8.27 (s, 1H), 6.85~6.87 (m, 1H), 6.46~6.49 (m, 1H), 5.99 (s, 1H), 4.73~4.78 (m, 2H), 3.50~3.57 (m, 4H), 2.93 (s, 3H), 2.67~2.68 (m, 1H), 2.33~2.50 (m, 1H), 1.23~1.50 (m, 3H).<br>MS: 537.3 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.127 | 6-(8-(ethylamino)-6-fluoro-4-(3-(trifluoromethyl)-1H-pyrazol-1-yl)-9H-pyrido[2,3-b]indol-3-yl)-1-methyl-4-oxo-1,4-dihydro-1,8-naphthyridine-3-carboxylic acid | CORE: Intermediate A2<br>AMINE: 3-(trifluoromethyl)-1H-pyrazole<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, Methanol-d4): δ 9.20 (s, 1 H), 8.90 (s, 1 H), 8.84 (s, 1 H), 8.37 (s, 1 H), 8.32 (s, 1 H), 7.09 (s, 1 H), 6.47~6.50 (d, J = 12.0 Hz, 1 H), 5.73~5.75 (d, J = 8.4 Hz, 1 H), 4.086 (s, 3H), 3.25 (m, 2 H), 1.30~1.33 (m, 3 H).<br>MS: 566.1 ([M + H]$^+$) |
| 1.128 | 6-(4-(6-oxa-3-azabicyclo[3.1.1]heptan-3-yl)-5,6-difluoro-8-(methylamino)-9H-pyrido[2,3-b]indol-3-yl)-1-ethyl-4-oxo-1,4-dihydro-1,8-naphthyridine-3-carboxylic acid | CORE: Intermediate A3<br>AMINE: 6-oxa-3-azabicyclo[3.1.1]heptanes<br>BORONIC REAGENT: Intermediate B3<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 11.95 (s, 1H), 9.28~9.30 (d, J = 7.2 Hz, 1H), 9.12~9.13 (d, J = 2.4 Hz, 1H), 8.74~8.76 (m, 3H), 8.42 (s, 1H), 6.62~6.67 (m, 1H), 4.72~4.75 (m, 2H), 4.43~4.44 (m, 2H), 3.68~3.71 (m, 2H), 3.09~3.39 (m, 2H), 2.89 (s, 3H), 2.68 (m, 1H), 2.33 (m, 1H), 1.45~1.48 (m, 3H).<br>MS: 547.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
| --- | --- | --- | --- |
| 1.129 | 6-(5,6-difluoro-4-(3-hydroxy-3-(trifluoromethyl)pyrrolidin-1-yl)-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: 3-(trifluoromethyl)pyrrolidin-3-ol<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 9.03 (s, 2H), 8.74 (s, 1H), 8.10 (s, 1H), 6.49~6.54 (m, 1H), 4.09 (s, 3H), 3.84~3.86 (m, 1H), 3.39~3.48 (m, 3H), 2.76~2.87 (m, 3H), 2.18~2.21 (m, 1H), 1.83~1.87 (m, 1H).<br>MS: 589.2 ([M + H]$^+$) |
| 1.130 | 6-(4-(dimethylamino)-5,6-difluoro-8-(methylamino)-9H-pyrido[2,3-b]indol-3-yl)-1-(1-methylpyrrolidin-3-yl)-4-oxo-1,4-dihydro-1,8-naphthyridine-3-carboxylic acid | CORE: Intermediate A3<br>AMINE: Dimethylamine hydrochloride<br>BORONIC REAGENT: Intermediate B6<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d4) δ ppm 9.19 (s, 1 H), 9.10 (s, 1 H), 8.81~8.82 (d, J = 2.0 Hz, 1 H), 8.19 (s, 1 H), 6.62~6.67 (dd, J = 13.2, 6.0 Hz, 1 H), 5.81~5.87 (br s, 1 H), 4.19~4.39 (m, 2 H), 3.79~3.83 (m, 1 H), 3.46~3.50 (m, 1 H), 3.16 (s, 3 H), 2.84~3.00 (m, 11 H)<br>MS (ESI): 548.2 (M + H)$^+$, 274.6 (M/2 + H)$^+$. |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.131 | 6-(5,6-difluoro-8-(trideuteriomethylamino)-4-morpholino-9H-pyrido[2,3-b]indol-3-yl)-1-methyl-4-oxo-1,4-dihydro-1,8-naphthyridine-3-carboxylic acid | CORE: Intermediate A6<br>AMINE: morpholine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) δ 11.89 (s, 1H), 9.30 (s, 1H), 9.13 (d, J = 2.4 Hz, 1H), 8.72 (d, J = 2.4 Hz, 1H), 8.24 (s, 1H), 6.62 (dd, J = 6.1, 13.2 Hz, 1H), 4.19 (s, 3H), 3.57-3.52 (m, 4H), 2.94 (s, 4H)<br>MS (ESI): 364.0 ([M + H]$^+$). |
| 1.132 | 6-(5,6-difluoro-4-((2-methoxyethyl)(methyl)amino)-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: 2-methoxy-N-methylethanamine<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, Methanol-d4): δ: 9.22 (s, 1 H), 9.08 (s, 1 H), 8.69 (s, 1 H), 8.21 (s, 1 H), 6.55~6.60 (m, 1 H), 5.721 (s, 1 H), 4.15 (s, 3 H), 3.54~3.55 (m, 2 H), 3.54 (s, 3 H), 3.51~3.53 (m, 2 H), 3.06~3.10 (m, 3 H), 2.844 (s, 3 H).<br>MS: 566.1 ([M + H]$^+$) |
| 1.133 | 6-(6-fluoro-8-(methylamino)-4-(3-methylpyrrolidin-1-yl)-9H-pyrido[2,3-b]indol-3-yl)-1-methyl-4-oxo-1,4-dihydro-1,8-naphthyridine-3-carboxylic acid | CORE: Intermediate A1<br>AMINE: 3-methylpyrrolidine<br>BORONIC REAGENT: Intermediate B2<br>CATALYST Pd-Ad$_2$nBuP Biphenyl Precat (CAS#: 1375477-29-4)<br>SOLVENT: THF/H$_2$O | $^1$H NMR (400 MHz, DMSO-d$_6$) δ ppm 11.79 (s, 1 H), 9.28 (s, 1 H), 9.16 (d, J = 2.38 Hz, 1 H), 8.72 (d, J = 2.25 Hz, 1 H), 8.24 (s, 1 H), 6.88 (d, J = 10.415 Hz, 1 H), 6.46 (dd, J = 12.04, 2.13 Hz, 1 H), 4.17 (s, 3 H), 3.41-3.54 (m, 1 H), 3.23-3.36 (m, 2 H), 2.85-2.96 (m, 4 H), 2.24 (dd, J = 14.24, 6.46 Hz, 1 H), 2.00 (dd, J = 11.35, 5.08 Hz, 1 H), 1.41-1.54 (m, 1 H), 0.95 (d, J = 6.65 Hz, 3 H).<br>MS (ESI): 501.1 ([M + H]$^+$). |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.134 | 6-(5,6-difluoro-4-(hexahydropyrazino[2,1-c][1,4]oxazin-8(1H)-yl)-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: octahydropyrazino[2,1-c][1,4]oxazine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | 1H NMR (400 MHz, DMSO-d6) δ ppm 12.00 (s, 1 H), 9.34 (s, 1 H), 9.14 (s, 1 H), 8 76 (s, 1 H), 8.24 (s, 1 H), 6.66 (dd, J = 13.36, 6.21 Hz, 1 H), 4.21 (s, 3 H), 3 .96 (d, J = 11.17 Hz, 2 H), 3.86 (d, J = 11.29 Hz, 2 H), 3.63 (t, J = 12.05 Hz, 2 H), 3.22-3.42 (m, 7 H), 2.91 (s, 3 H).<br>MS (ESI): 576.1 ([M + H]$^+$). |
| 1.135 | 6-(4-(3-((dimethylamino)methyl)pyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: N,N-dimethyl-1-(pyrrolidin-3-yl)methanamine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | 1H NMR (400 MHz, DMSO-d6): δ ppm: 11.91 (s, 1 H), 9.31 (s, 2 H), 9.11~9.16 (m, 1 H), 8.67~8.72 (m, 1 H), 8.32 (s, 1 H), 6.55~6.66 (m, 1 H), 4.14~4.21 (m, 3 H), 3.31~3.46 (m, 2 H), 3.16~3.29 (m, 2 H), 3.01~3.11 (m, 2 H), 2.906 (s, 4 H), 2.68~2.75 (m, 6 H), 2.02~2.16 (m, 1 H), 1.54~1.68 (m, 1 H).<br>MS: 632.2 ([M + H]$^+$) |
| 1.136 | 6-(4-(3-((cyclopropylamino)methyl)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid | CORE: Intermediate A1<br>AMINE: tert-butyl cyclopropyl(pyrrolidin-3-ylmethyl)carbamate<br>BORONIC REAGENT: Intermediate B2<br>CATALYST: Pd-Ad$_2$nBuP Biphenyl Precat (CAS#: 1375477-29-4)<br>SOLVENT: THF/H$_2$O | ¹H NMR (400 MHz, DMSO-d6) δ ppm: 11.92 (br s, 1 H), 9.28 (s, 1 H), 9.14~9.15 (d, J = 2.0 Hz, 1 H), 8.69~8.77 (m, 3 H), 8.26 (s, 1 H), 6.83~6.86 (br d, J = 8.8 Hz, 1 H), 6.45~6.48 (br d, J = 12.0 Hz, 1 H), 4.17 (s, 3 H), 3.35~3.46 (m, 3 H), 2.98~3.04 (m, 3 H), 2.92 (s, 3 H), 2.55~2.65 (m, 2 H), 2.11~2.12 (br dd, J = 12.0, 5.2 Hz, 1 H), 1.71~1.72 (m, 1 H), 0.68~0.75 (m, 4 H)<br>MS (ESI): 556.2 ([M + H]$^+$). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.137 | 6-(4-(3-((cyclopropylamino)methyl)pyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: tert-butyl cyclopropyl(pyrrolidin-3-ylmethyl)carbamate<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6) δ ppm: 11.93 (s, 1 H), 9.30 (s, 1 H), 9.12~9.13 (d, J = 2.4 Hz, 1 H), 8.60~8.69 (m, 3 H), 8.31 (s, 1 H), 6.58~6.64 (dd, J = 13.2, 6.4 Hz, 1 H), 4.18 (s, 3H), 3.41 (br t, J = 8.4 Hz, 1 H), 3.20~3.24 (br t, J = 6.4 Hz, 2 H), 2.90~3.03 (m, 6 H), 2.54~2.68 (m, 2 H), 2.05~2.07 (br dd, J = 11.0, 5.5 Hz, 1 H), 1.62 (m, 1 H), 0.69~0.74 (m, 4 H)<br>MS (ESI): 574.2 ([M + H]$^+$). |
| 1.138 | 6-(6-chloro-4-(2-((dimethylamino)methyl)morpholino)-8-(methylamino)-9H-pyrido[2,3-b]indol-3-yl)-1-methyl-4-oxo-1,4-dihydro-1,8-naphthyridine-3-carboxylic acid | CORE: Intermediate A11<br>AMINE: N,N-dimethyl-1-(morpholin-2-yl)methanamine<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, Methanol-d4): δ 11.79 (s, 1 H), 9.50 (s, 2 H), 9.33 (s, 1 H), 9.16 (s, 1 H), 8.70 (s, 1 H), 8.25 (s, 1 H), 7.40 (s, 1 H), 6.61 (s, 1 H), 4.20 (s, 3 H), 4.09 (m, 1 H), 3.94 (m, 2 H), 3.12~3.20 (m, 1 H), 3.059~3.07 (m, 3 H), 2.94 (s, 3 H), 2.77~2.80 (m, 6 H), 2.53~2.53 (m, 2 H).<br>MS: 576.3 ({$^{35}$Cl}M + H)$^+$ |
| 1.139 | 6-(6-chloro-4-(3-(dimethylamino)pyrrolidin-1-yl)-8-(methylamino)-9H-pyrido[2,3-b]indol-3-yl)-1-methyl-4-oxo-1,4-dihydro-1,8-naphthyridine-3-carboxylic acid | CORE: Intermediate A11<br>AMINE: N,N-dimethylpyrrolidin-3-amine<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, Methanol-d4): δ 11.84 (s, 1 H), 10.01 (s, 1 H), 9.31 (s, 1 H), 9.14~9.14 (d, J = 2.4 Hz, 1 H), 8.70~8.70 (d, J = 2.4 Hz, 1 H), 8.27 (s, 1 H), 7.05 (s, 1 H), 6.60~6.60 (m, 1 H), 4.19 (s, 3 H), 4.10 (m, 1 H), 3.39~3.50 (m, 3 H), 3.12 (m, 1 H), 2.93 (m, 3 H), 2.77 (m, 3 H), 2.64 (m, 3 H), 2.39~2.64 (m, 2 H), 2.10~2.11 (m, 1 H).<br>MS: 546.2 ({$^{35}$Cl}M + H)$^+$ |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.140 | 6-(4-(dimethylamino)-8-(ethylamino)-5,6-difluoro-9H-pyrido[2,3-b]indol-3-yl)-4-oxo-1-(pyrrolidin-3-yl)-1,4-dihydro-1,8-naphthyridine-3-carboxylic acid | CORE: Intermediate A7<br>AMINE: N,N-dimethylamine<br>BORONIC REAGENT: Intermediate B6<br>CATALYST cataCXium ® A Pd G2 (Sigma-Aldrich, Catalog #: 761311)<br>SOLVENT: THF/H$_2$O | $^1$H NMR (400 MHz, DMSO): δ 11.86 (s, 1 H), 9.24 (m, 2 H), 8.99~9.05 (m, 2 H), 8.67~8.67 (m, 1 H), 8.25 (s, 1 H), 6.60~6.64 (m, 1 H), 6.01~6.04 (m, 1 H), 3.76 (m, 3H), 3.20~3.26 (m, 4 H), 2.76~2.76 (m, 6 H), 2.66~2.68 (m, 1 H), 2.53~2.56 (m, 2 H) 1.30~1.33 (m, 2 H). MS: 548.1 ([M + H]$^+$). |
| 1.141 | 6-(6-fluoro-4-(3-(((2-methoxyethyl)(methyl)amino)methyl)pyrrolidin-1-yl)-8-(methylamino)-9H-pyrido[2,3-b]indol-3-yl)-1-methyl-4-oxo-1,4-dihydro-1,8-naphthyridine-3-carboxylic acid | CORE: Intermediate A1<br>AMINE: Intermediate C14<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) δ ppm 11.81 (s, 1 H), 9.28 (s, 1 H), 9.13~9.14 (d, J = 2.4 Hz, 1 H), 8.67~8.68 (d, J = 2.4 Hz, 1 H), 8.25 (s, 1 H), 6.81~6.84 (m, 1 H), 6.43~6.47 (m, 1 H), 4.17 (s, 3 H), 3.43~3.45 (m, 1 H), 3.34 (s, 2H), 3.33 (s, 2 H), 3.31 (s, 3 H), 3.23 (s, 3 H), 3.18 (s, 1 H), 2.91 (s, 4 H), 2.73 (s, 3 H), 2.54 (s, 1 H), 2.15 (s, 1 H), 1.68~1.72 (m, 1 H). MS (ESI): 588.2 ([M + H]$^+$), 610.2 ([M + Na]$^+$). |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.142 | 6-(5,6-difluoro-4-(3-(((2-methoxyethyl)(methyl)amino) methyl)pyrrolidin-1-yl)-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C14<br>BORONIC REAGENT: Intermediate B2<br>CATALYST: Pd-Ad$_2$nBuP Biphenyl Precat (CAS#: 1375477-29-4)<br>SOLVENT: THF/H$_2$O | ¹H NMR (400 MHz, DMSO-d$_6$) δ ppm 11.81 (s, 1 H), 9.23 (s, 1 H), 9.07 (s, 1 H), 8.64 (s, 1 H), 8.25 (s, 1 H), 6.55~6.60 (m, 1 H), 5.70~5.71 (d, J = 4.8 Hz, 1 H), 4.14 (s, 3 H), 3.18~3.21 (m, 4H), 3.10 (s, 3 H), 2.89~2.90 (m, 3 H), 2.81~2.89 (m, 1 H), 2.22~2.33 (m, 6 H), 2.03 (s, 3 H), 1.89~1.99 (m, 1H), 1.50-1.51 (m, 1H).<br>MS (ESI): 606.3 ([M + H]⁺). |
| 1.143 | 6-(4-(4-((dimethylamino)methyl)-3,3-difluoro-pyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: C15<br>BORONIC REAGENT: Intermediate B2<br>CATALYST: cataCXium ® A Pd G2 (Sigma-Aldrich, Catalog #: 761311)<br>SOLVENT: THF/H$_2$O | ¹H NMR (400 MHz, DMSO): δ 11.99 (s, 1 H), 9.48 (s, 1 H), 9.16~9.16 (m, 1 H), 8.77 (m, 1 H), 8.38 (s, 1 H), 6.63~6.68 (m, 1 H), 4.19 (s, 3 H), 3.75~3.79 (m, 6 H), 3.12~3.24 (m, 4 H), 2.92 (s, 3 H), 2.79 (m, 6 H), 2.53 (m, 2 H).<br>MS: 460.1 ([M + H]⁺). |
| 1.144 | 6-(4-(4-((dimethylamino)methyl)-3,3-difluoro-pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid | CORE: Intermediate A1<br>AMINE: C15<br>BORONIC REAGENT: Intermediate B2<br>CATALYST: cataCXium ® A Pd G2 (Sigma-Aldrich, Catalog #: 761311)<br>SOLVENT: THF/H$_2$O | ¹H NMR (400 MHz, Methanol-d4): δ 11.73 (s, 1 H), 11.66 (s, 2 H), 9.62 (s, 1 H), 9.32 (s, 1 H), 9.17~9.18 (d, J = 2.4 Hz, 1 H), 8.75~8.76 (d, J = 2.4 Hz, 1 H), 8.31 (s, 1 H), 6.90~6.96 (m, 1 H), 6.48~6.52 (m, 1 H), 4.19 (s, 3 H), 3.85~3.92 (m, 1 H), 3.45~3.48 (m, 1 H), 3.14 (m, 2 H), 3.12 (m, 2 H), 2.94 (s, 3 H), 2.82~2.94 (m, 1 H), 2.77~2.79 (m, 1 H).<br>MS: 521.1 ([M + H]⁺). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.145 | 6-[4-(dimethylamino)-5,6-difluoro-8-(methylamino)-9H-pyrido[2,3-b]indol-3-yl]-1-(3-hydroxy-1-methyl-propyl)-4-oxo-1,8-naphthyridine-3-carboxylic acid | CORE: Intermediate A3<br>AMINE: Dimethylamine hydrochloride<br>BORONIC REAGENT: Intermediate B41<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.78 (brs, 1H), 9.05 (m, 2H), 8.60 (br s, 1H), 8.38 (s, 1H), 8.25 (s, 1H), 6.59-6.55 (m, 1H), 5.98 (s, 1H), 5.74-5.70 (m, 1H), 4.58 (brs, 1H), 3.41-3.39 (m, 2H), 2.90 (d, J = 4.4 Hz, 3H), 2.71 (s, 6H), 2.20-2.12 (m, 2H), 1.60-1.59 (d, J = 5.6 Hz, 3H).<br>$^1$H NMR (400 MHz, DMSO-d6 + D$_2$O) δ ppm: 9.03-9.01 (m, 2H), 8.59 (s, 1H), 8.35 (s, 1H), 8.23 (s, 1H), 6.60-6.55 (m, 1H), 5.98 (s, 1H), 3.44 (m, 2H), 2.87 (s, 3H), 2.70 (s, 6H), 2.12 (m, 2H), 1.59 (d, 3H).<br>MS: 537.2 ([M + H]$^+$). |
| 1.146 | 6-(4-(dimethylamino)-5,6-difluoro-8-(methylamino)-9H-pyrido[2,3-b]indol-3-yl)-1-((1-hydroxy-cyclopropyl)methyl)-4-oxo-1,4-dihydro-1,8-naphthyridine-3-carboxylic acid | CORE: Intermediate A3<br>AMINE: Dimethylamine hydrochloride<br>BORONIC REAGENT: Intermediate B42<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.80 (s, 1H), 9.21 (s, 1H), 9.01 (d, J = 2.4 Hz, 1H), 8.66 (d, J = 2.4 Hz, 1H), 8.28 (s, 1H), 6.62-6.57 (m, 1H), 4.84 (s, 2H), 2.90 (s, 3H), 2.73 (s, 6H), 0.94-0.91 (m, 2H), 0.73-0.70 (m, 2H).<br>MS: 535.1 ([M + H]$^+$). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.147 | 6-(4-(dimethylamino)-5,6-difluoro-8-(methylamino)-9H-pyrido[2,3-b]indol-3-yl)-1-(2-morpholinoethyl)-4-oxo-1,4-dihydro-1,8-naphthyridine-3-carboxylic acid | CORE: Intermediate A3<br>AMINE: Dimethylamine hydrochloride<br>BORONIC REAGENT: Intermediate B43<br>CATALYST: cataCXium® A Pd G2 (Sigma-Aldrich, Catalog #: 761311)<br>SOLVENT: EtOH/H$_2$O | $^1$H NMR (400 MHz, DMSO-d6) δ ppm: 12.11 (s, 1H), 11.46 (s, 1H), 9.34 (s, 1H), 9.03-9.01 (d, J = 2.4 Hz, 1H), 8.63-8.61 (d, J = 2.4 Hz, 1H), 8.22 (s, 1H), 6.58-6.54 (m, 1H), 5.12 (m, 2H), 3.98 (m, 2H), 3.83 (m, 2H), 3.73 (m, 2H), 3.68-3.60 (m, 2H), 3.31-3.19 (m, 2H), 2.88 (s, 3H), 2.75 (s, 3H), 2.74 (s, 3H).<br>$^1$H NMR (400 MHz, DMSO-d6 + D$_2$O) δ ppm: 9.26 (s, 1H), 8.98-8.97 (d, J = 2.4 Hz, 1H), 8.58 (d, J = 2.4 Hz, 1H), 8.18 (s, 1H), 6.59-6.55 (m, 1H), 5.03 (s, 2H), 4.34-4.00 (m, 4H), 3.73-3.71 (m, 4H), 3.49 (m, 2H), 2.85 (s, 3H), 2.72 (s, 3H), 2.71 (s, 3H).<br>MS: 578.1 ([M + H]$^+$). |
| 1.148 | 6-(4-(dimethylamino)-5,6-difluoro-8-(methylamino)-9H-pyrido[2,3-b]indol-3-yl)-4-oxo-1-(2-(3-oxopiperazin-1-yl)ethyl)-1,4-dihydro-1,8-naphthyridine-3-carboxylic acid | CORE: Intermediate A3<br>AMINE: Dimethylamine hydrochloride<br>BORONIC REAGENT: Intermediate B44<br>CATALYST: cataCXium® A Pd G2 (Sigma-Aldrich, Catalog #: 761311)<br>SOLVENT: EtOH/H$_2$O | $^1$H NMR (400 MHz, DMSO-d6) δ ppm: 11.97 (s, 1H), 9.35 (s, 1H), 9.02 (d, J = 2.4 Hz, 1H), 8.64 (d, J = 2.4 Hz, 1H), 8.32 (s, 1H), 8.23 (s, 1H), 6.60 (m, 1H), 5.08 (s, 2H), 3.35 (m, 8H), 2.90 (s, 3H), 2.75 (s, 6H).<br>$^1$H NMR (400 MHz, DMSO-d6 + D$_2$O) δ ppm: 9.21 (s, 1H), 8.95 (d, J = 2.4 Hz, 1H), 8.59 (d, J = 2.4 Hz, 1H), 8.16 (s, 1H), 6.60 (m, 1H), 4 97 (s, 2H), 3.73 (m, 2H), 3.55 (m, 2H), 3.38 (m, 2H), 3.33 (m, 2H), 2.84 (s, 3H), 2.71 (s, 6H).<br>MS: 591.2 ([M + H]$^+$). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.149 | 6-(4-(2-((dimethylamino)methyl)morpholino)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C16<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.90 (s, 1H), 9.29 (s, 1H), 9.11 (s, 1H), 8.72 (s, 1 H), 8.22 (s, 2H), 6.63-6.58 (m, 1 H), 5.72 (brs, 1H), 4.17 (s, 3 H), 3.69 (m, 3H), 3.10 (m, 2H), 2.92 (m, 5H), 2.34-2.24 (m, 6H).<br>MS: 606.3 ([M + H]$^+$). |
| 1.150 | (S)-6-(4-(dimethylamino)-5,6-difluoro-8-(methylamino)-9H-pyrido[2,3-b]indol-3-yl)-4-oxo-1-(pyrrolidin-3-yl)-1,4-dihydro-1,8-naphthyridine-3-carboxylic acid | CORE: Intermediate A3<br>AMINE: Dimethylamine hydrochloride<br>BORONIC REAGENT: Intermediate B37<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) δ ppm 11.79 (s, 1 H), 9.32 (s, 1 H), 9.23 (s, 1 H), 9.04 (d, J = 2.38 Hz, 2 H), 8.65 (d, J = 2.38 Hz, 1 H), 8.24 (s, 1 H), 6.59 (dd, J = 13.42, 6.14 Hz, 1H), 5.96-6.08 (m, 1 H), 3.78 (d, J = 8.28 Hz, 3 H), 3.31-3.45 (m, 1 H), 2.90 (s, 3 H), 2.76 (d, J = 1.88 Hz, 6 H), 2.67 (m, 1 H) 2.52-2.60 (m, 1 H).<br>MS (ESI): 534.2 ([M + H]$^+$). |
| 1.151 | (R)-6-(5,6-difluoro-4-(3-hydroxypyrrolidin-1-yl)-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: (R)-pyrrolidin-3-ol<br>BORONIC REAGENT: Intermediate B2<br>CATALYST: Pd-Ad$_2$nBuP Biphenyl Precat (CAS#: 1375477-29-4)<br>SOLVENT: THF/H$_2$O | 1H NMR (400 MHz, DMSO-d6) δ ppm 12.04 (s, 1 H), 9.28 (s, 1 H), 9.16 (d, J = 2.38 Hz, 1 H), 8.71 (d, J = 2.38 Hz, 1 H), 8.24 (s, 1 H), 6.59 (dd, J = 13.49, 6.34 Hz, 1 H), 4.14-4.23 (m, 4 H), 3.49-3.50 (m, 1 H), 3.15-3.36 (m, 2 H), 3.01 (d, J = 10.04 Hz, 1 H), 2.89 (s, 3 H), 1.88-2.00 (m, 1 H), 1.66 (dd, J = 10.79, 5.52 Hz, 1 H).<br>MS (ESI): 521.2 ([M + H]$^+$) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.152 | 6-(4-trans-(3-(dimethylamino)-4-methylpyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid | CORE: Intermediate A1<br>AMINE: Intermediate C17<br>BORONIC REAGENT: Intermediate B2<br>CATALYST: Pd-Ad$_2$nBuP Biphenyl Precat (CAS#: 1375477-29-4)<br>SOLVENT: THF/H$_2$O | 1H NMR (400 MHz, DMSO-d6) δ ppm 11.67 (s, 1 H), 9.85-10.12 (m, 1 H), 9.30 (s, 1 H), 9.14 (d, J = 2.38 Hz, 1 H), 8.71 (d, J = 2.38 Hz, 1 H), 8.22 (s, 1 H), 6.81 (dd, J = 9.60, 1.94 Hz, 1 H), 6.49 (dd, J = 12.17, 2.01 Hz, 1 H), 4.18 (s, 3 H), 3.44-3.51 (m, 4 H,) 3.09-3.37 (m, 1 H), 2.93 (s, 3 H), 2.69-2.82 (m, 7 H), 1.17 (d, J = 6.78 Hz, 3 H). MS (ESI): 544.3 ([M + H]$^+$). |
| 1.153 | 6-[4-[(2S)-2-[(dimethylamino)methyl]pyrrolidin-1-yl]-6-fluoro-8-(methylamino)-9H-pyrido[2,3-b]indol-3-yl]-4-oxo-1-(2,2,2-trifluoroethylamino)-1,8-naphthyridine-3-carboxylic acid | CORE: Intermediate A1<br>AMINE: Intermediate C18<br>BORONIC REAGENT: Intermediate B45<br>CATALYST: Pd-Ad$_2$nBuP Biphenyl Precat (CAS#: 1375477-29-4)<br>SOLVENT: THF/H$_2$O | ¹H NMR (400 MHz, DMSO-d$_6$) δ = 11.50 (br s, 1H), 9.13 (br s, 1H), 8.94-8.67 (m, 2H), 8.41-8.07 (m, 2H), 6.72 (br s, 1H), 6.45 (br d, J = 7.5 Hz, 1H), 5.92 (br s, 1H), 4.11 (br s, 2H), 3.18 (br s, 6H), 2.98-2.87 (m, 1H), 2.92 (br s, 2H), 2.13-1.85 (m, 1H), 1.98 (br s, 4H), 1.80-1.54 (m, 6H) MS (ESI): 627.1 ([M + H]$^+$). |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.154 | 6-[4-[(2S)-2-[(dimethylamino)methyl]pyrrolidin-1-yl]-6-fluoro-8-(methylamino)-9H-pyrido[2,3-b]indol-3-yl]-4-oxo-1-(tetrahydropyran-4-ylamino)-1,8-naphthyridine-3-carboxylic acid | CORE: Intermediate A1<br>AMINE: Intermediate C18<br>BORONIC REAGENT: Intermediate B38<br>CATALYST: Pd-Ad₂nBuP Biphenyl Precat (CAS#: 1375477-29-4)<br>SOLVENT: THF/H₂O | ¹H NMR (400 MHz, DMSO-d₆) δ = 14.70-14.30 (m, 1H), 11.62 (s, 1H), 9.14 (d, J = 2.4 Hz, 1H), 9.06 (br s, 1H), 8.93 (s, 1H), 8.73 (d, J = 2.3 Hz, 1H), 8.36 (s, 1H), 7.71 (br s, 1H), 6.81 (dd, J = 2.0, 9.5 Hz, 1H), 6.48 (dd, J = 2.1, 12.3 Hz, 1H), 3.98-3.72 (m, 3H), 3.30-3.14 (m, 5H), 3.02-2.85 (m, 1H), 2.93 (s, 3H), 2.56 (br d, J = 3.6 Hz, 4H), 2.28 (br d, J = 3.4 Hz, 3H), 2.19-2.09 (m, 1H), 2.01 (td, J = 5.6, 11.5 Hz, 1H), 1.77 (br dd, J = 6.7, 19.0 Hz, 4H), 1.61-1.43 (m, 2H)<br>MS (ESI): 629.2 ([M + H]⁺). |
| 1.155 | (R)-6-(4-(dimethylamino)-5,6-difluoro-8-(methyl-amino)-9H-pyrido[2,3-b]indol-3-yl)-4-oxo-1-(pyrrolidin-3-yl)-1,4-dihydro-1,8-naphthyridine-3-carboxylic acid | CORE: Intermediate A3<br>AMINE: dimethylamine hydrochloride<br>BORONIC REAGENT: Intermediate B46<br>CATALYST: Pd-Ad₂nBuP Biphenyl Precat (CAS#: 1375477-29-4)<br>SOLVENT: THF/H₂O | 1H NMR (400 MHz, DMSO-d6) δ ppm 11.81 (s, 1 H), 9.35 (s, 1 H), 9.23 (s, 1 H), 9.04 (d, J = 2.51 Hz, 2 H), 8.65 (s, 1 H), 8.24 (s, 1 H), 6.59 (dd, J = 13.36, 6.09 Hz, 1 H), 5.97-6.06 (m, 1 H), 3.65-3.76 (m, 3 H), 3.38 (d, J = 4.89 Hz, 1 H), 2.90 (s, 3 H), 2.76 (d, J = 1.88 Hz, 6 H), 2.66 (td, J = 8.31, 4.45 Hz, 1 H), 2.53-2.60 (m, 1 H).<br>MS (ESI): 534.2 ([M + H]⁺). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.156 | (R)-6-(5,6-(difluoro-8-(methylamino)-4-(pyrrolidin-1-yl)-9H-pyrido[2,3-b]indol-3-yl)-4-oxo-1-(pyrrolidin-3-yl)-1,4-dihydro-1,8-naphthyridine-3-carboxylic acid | CORE: Intermediate A3<br>AMINE: pyrrolidine<br>BORONIC REAGENT: Intermediate B46<br>CATALYST: Pd-Ad$_2$nBuP Biphenyl Precat (CAS#: 1375477-29-4)<br>SOLVENT: THF/H$_2$O | 1H NMR (400 MHz, DMSO-d6) δ ppm 11.99-12.15 (m, 1 H), 9.32-9.50 (m, 1 H), 9.22 (s, 1 H), 9.02-9.14 (m, 2 H), 8.76 (d, J = 2.38 Hz, 1 H), 8.26 (s, 1 H), 6.59 (dd, J = 13.49, 6.21 Hz, 1 H), 5.94-6.04 (m, 1 H), 3.66-3.90 (m, 3 H), 3.38 (d, J = 5.65 Hz, 1 H), 3.23 (s, 4 H), 2.89 (s, 3 H), 2.61-2.71 (m, 1 H), 2.52-2.58 (m, 1 H), 1.78 (s, 4 H). MS (ESI): 560.2 ([M + H]$^+$). |
| 1.157 | (S)-6-(4-(6-((dimethylamino)methyl)-5-azaspiro[2.4]heptan-5-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C19<br>BORONIC REAGENT: Intermediate B2<br>CATALYST: Pd-Ad$_2$nBuP Biphenyl Precat (CAS#: 1375477-29-4)<br>SOLVENT: THF/H$_2$O | 1H NMR (400 MHz, DMSO-d6) δ ppm 11.91 (s, 1 H), 9.20-9.38 (m, 2 H) 9.12 (d, J = 2.26 Hz, 1 H), 8.73 (d, J = 2.13 Hz, 1 H), 8.35 (s, 1 H), 6.61 (dd, J = 13.55, 6.15 Hz, 1 H) 4.17 (s, 3 H), 3.17-3.42 (m, 2 H), 2.96-3.10 (m, 1 H), 2.90 (s, 4 H), 2.60 (d, J = 4.27 Hz, 3 H), 2.52 (d, J = 1.88 Hz, 1 H), 2.28-2.41 (m, 3 H), 1.53-1.84 (m, 2 H), 0.67 (s, 3 H), 0.47 (d, J = 8.66 Hz, 1 H). MS (ESI): 588.3 ([M + H]$^+$). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.158 | 6-(4-((3S,4S)-3-(dimethylamino)-4-methoxypyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C20<br>BORONIC REAGENT: Intermediate B2<br>CATALYST: Pd-Ad$_2$nBuP Biphenyl Precat (CAS#: 1375477-29-4)<br>SOLVENT: THF/H$_2$O | 1H NMR (400 MHz, DMSO-d6) δ ppm 11.97 (s, 1 H), 10.23 (s, 1 H), 9.28-9.32 (m, 1 H), 9.12-9.16 (m, 1 H), 8.69-8.72 (m, 1 H), 8.31 (s, 1 H), 6.63 (dd, J = 13.49, 6.21 Hz, 1 H), 4.06-4.27 (m, 5 H) 3.69-3.82 (m, 2 H), 3.43 (t, J = 7.78 Hz, 1 H), 3.19-3.25 (m, 4 H), 2.91 (s, 3 H), 2.81 (s, 3 H), 2.67-2.77 (m, 3 H).<br>MS (ESI): 578.2 ([M + H]$^+$). |
| 1.159 | 6-(4-((3S,4S)-3-(dimethylamino)-4-fluoropyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C21<br>BORONIC REAGENT: Intermediate B2<br>CATALYST: Pd-Ad$_2$nBuP Biphenyl Precat (CAS#: 1375477-29-4)<br>SOLVENT: THF/H$_2$O | 1H NMR (400 MHz, DMSO-d6) δ ppm 11.97 (s, 1 H), 9.28-9.32 (m, 1 H), 9.13 (d, J = 2.38 Hz, 1 H), 8.71 (d, J = 2.26 Hz, 1 H), 8.27 (s, 1 H), 6.63 (dd, J = 13.55, 6.27 Hz, 1 H), 5.34-5.53 (m, 1 H), 4.18 (s, 3 H), 4.03-4.15 (m, 2 H), 3.94 (t, J = 9.10 Hz, 1 H), 3.35-3.46 (m, 1 H), 3.20-3.33 (m, 1 H), 3.15 (t, J = 8.91 Hz, 1 H), 2.91 (s, 4 H), 2.69-2.84 (m, 4 H).<br>MS (ESI): 566.2 ([M + H]$^+$). |
| 1.160 | 6-(4-((3S,4S)-3-(dimethylamino)-4-methylpyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C22<br>BORONIC REAGENT: Intermediate B2<br>CATALYST: Pd-Ad$_2$nBuP Biphenyl Precat (CAS#: 1375477-29-4)<br>SOLVENT: THF/H$_2$O | 1H NMR (400 MHz, DMSO-d6) δ ppm 11.975 (s, 1 H), 9.95-10.22 (m, 1 H), 9.29 (d, J = 6.09 Hz, 1 H), 9.14 (s, 1 H), 8.70 (d, J = 4.39 Hz, 1 H), 8.25 (s, 1 H), 6.58-6.65 (m, 1 H), 4.17 (s, 3 H), 3.78 (t, J = 9.41 Hz, 1 H), 3.56 (s, 1 H), 3.17-3.26 (m, 2 H), 2.90 (s, 3 H), 2.66-2.78 (m, 7 H), 2.44 (d, J = 5.65 Hz, 1 H), 1.11 (d, J = 6.65 Hz, 3H).<br>MS (ESI): 562.3 ([M + H]$^+$). |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.161 | (S)-6-(4-(2-((trideuteriomethylamino)methyl)pyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A6 AMINE: Intermediate C18 BORONIC REAGENT: Intermediate B2 CATALYST: cataCXium ® A Pd G2 (Sigma-Aldrich, Catalog #: 761311) SOLVENT: THF/H$_2$O | ¹H NMR (400 MHz, DMSO-d$_6$) δ 14.75 (s, 1H), 11.91 (s, 1H), 9.32 (s, 1H), 9.10 (d, J = 2.1 Hz, 1H), 9.07-8.96 (m, 1H), 8.72 (d, J = 1.9 Hz, 1H), 8.39 (s, 1H), 6.62 (dd, J = 6.1, 13.4 Hz, 1H), 4.18 (s, 3H), 3.31 (d, J = 7.2 Hz, 1H), 2.93 (s, 1H), 2.76 (d, J = 8.8 Hz, 2H), 2.67 (s, 1H), 2.59 (d, J = 4.5 Hz, 3H), 2.34 (d, J = 4.5 Hz, 3H), 2.07 (s, 1H), 1.93 (s, 1H), 1.74 (s, 2H) MS (ESI): 565.3 ([M + H]⁺). |
| 1.162 | (S)-6-(4-(2-((dimethylamino)methyl)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid | CORE: Intermediate A1 AMINE: Intermediate C18 BORONIC REAGENT Intermediate B2 CATALYST Pd-Ad$_2$nBuP Biphenyl Precat (CAS#: 1375477-29-4) SOLVENT: THF/H$_2$O | ¹H NMR (400 MHz, DMSO-d$_6$) δ: 11.64 (br s, 1 H), 9.32 (s, 1 H), 9.07~9.13 (m, 2 H), 8.73~8.74 (d, J = 2.0 Hz, 1 H), 8.35 (s, 1 H), 6.80-6.83 (dd, J = 9.6, 2.0 Hz, 1 H), 6.47~6.51 (dd, J = 12.0, 2.0 Hz, 1 H), 4.18 (s, 3 H), 3.89 (m, 1 H) 3.34 (m, 1 H), 3.32 (m, 1 H), 2.94 (m, 4 H), 2.56~2.65 (m, 1 H), 2.52~2.53 (m, 3 H), 2.30~2.32 (m, 3 H) 2.03~2.12 (m, 2 H), 1.81 (m, 2 H) MS (ESI): 544.3 ([M + H]⁺), 272.8 ([M/2 + H]⁺). |
| 1.163 | (S)-6-(5,6-difluoro-4-(3-hydroxypyrrolidin-1-yl)-8-(methylamino)-9H-pyrido[2,3-b]indol-3-yl)-1-methyl-4-oxo-1,4-dihydro-1,8-naphthyridine-3-carboxylic acid | CORE: Intermediate A3 AMINE: (S)-pyrrolidin-3-ol hydrochloride BORONIC REAGENT: Intermediate B2 CATALYST: Pd-Ad$_2$nBuP Biphenyl Precat (CAS#: 1375477-29-4) SOLVENT: THF/H$_2$O | ¹H NMR (400 MHz, DMSO-d$_6$) δ: 11.93~11.96 (d, J = 10.4, 1H), 9.27 (s, 1H), 9.13~9.14 (d, J = 2.4, 1H), 8.70 (s, 1H), 8.23 (s, 1H), 6.56~6.61 (m, 1H), 4.16~4.21 (m, 4H), 3.23~3.28 (m, 1H), 2.97 (s, 1H), 2.89 (s, 3H), 2.52 (s, 1H), 2.47 (s, 1H), 1.95 (s, 1H), 1.66~1.68 (d, J = 3.2, 1H). MS (ESI): 521.0 ([M + H]⁺). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.164 | (S)-6-(5,6-difluoro-4-(3-hydroxymethyl)pyrrolidin-1-yl)-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: (S)-pyrrolidin-3-ylmethanol<br>BORONIC REAGENT: Intermediate B2<br>CATALYST: Pd-Ad$_2$nBuP Biphenyl Precat (CAS#: 1375477-29-4)<br>SOLVENT: THF/H$_2$O | 1H NMR (400 MHz, DMSO-d6) δ ppm 12.00 (s, 1 H), 9.28 (s, 1 H), 9.13 (d, J = 2.38 Hz, 1 H), 8.69 (d, J = 2.26 Hz, 1 H), 8.26 (s, 1 H), 6.59 (dd, J = 13.30, 5.90 Hz, 1 H), 4.17 (s, 3 H) 3.17-3.40 (m, 5 H) 2.97 (s, 1 H) 2.89 (s, 3 H) 2.26 (dt, J = 13.87, 6.87 Hz, 1 H) 1.86 (d, J = 5.90 Hz, 1 H) 1.47-1.57 (m, 1 H).<br>MS (ESI): 535.2 ([M + H]$^+$). |
| 1.165 | (S)-6-(5,6-difluoro-4-(3-hydroxymethyl)pyrrolidin-1-yl)-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: (R)-pyrrolidin-3-ylmethanol<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) δ ppm 14.79 (s, 1 H), 11.74 (s, 1 H), 9.27 (s, 1 H), 9.09 (d, J = 2.384 Hz, 1 H), 8.65 (d, J = 2.384 Hz, 1 H), 8.24 (s, 1 H), 6.58 (dd, J = 13.55, 6.27 Hz, 1 H), 5.66 (d, J = 4.89 Hz, 1 H), 4.50 (t, J = 4.76 Hz, 1 H), 4.17 (s, 3 H), 3.29~3.32 (m, 1 H), 3.24 (t, J = 7.90 Hz, 2 H), 3.11~3.20 (m, 2 H), 2.90 (d, J = 4.768 Hz, 3 H), 2.79 (t, J = 7.78 Hz, 1 H), 2.27~2.34 (m, 1 H), 1.83~1.95 (m, 1 H), 1.45~1.59 (m, 1 H).<br>MS (ESI): 535.2 ([M + H]$^+$). |
| 1.166 | (S)-6-(4-(2-((dimethylamino)methyl)pyrrolidin-1-yl)-8-(ethylamino)-5,6-difluoro-9H-pyrido[2,3-b]indol-3-yl)-1-methyl-4-oxo-1,4-dihydro-1,8-naphthyridine-3-carboxylic acid | CORE: Intermediate A7<br>AMINE: Intermediate C18<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO): δ 11.98 (s, 1 H), 9.33 (s, 1 H), 9.12 (m, 1 H), 9.06 (s, 1 H), 8.72~8.73 (m, 1 H), 8.40 (s, 1 H), 6.63~6.68 (m, 1 H), 4.19 (s, 3 H), 3.30~3.32 (m, 2 H), 3.22~3.27 (m, 2H), 2.98 (m, 1 H), 2.68~2.68 (m, 1 H), 2.59~2.60 (m, 3 H), 2.35 (m, 4 H), 2.34 (m, 1 H), 1.93 (m, 1 H), 1.75 (m, 2 H), 1.30~1.33 (m, 2 H).<br>MS: 548.1 ([M + H]$^+$). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.167 | 6-(4-trans-(3-(dimethylamino)-4-methylpyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3 AMINE: Intermediate C17 BORONIC REAGENT: Intermediate B2 CATALYST: Pd-Ad$_2$nBuP Biphenyl Precat (CAS#: 1375477-29-4) SOLVENT: THF/H$_2$O | 1H NMR (400 MHz, DMSO-d6) δ ppm 11.96 (s, 1 H), 10.05 (s, 1 H), 9.27 (s, 1 H), 9.13 (d, J = 2.38 Hz, 1 H), 8.70 (d, J = 2.38 Hz, 1 H), 8.25 (s, 1 H), 6.61 (dd, J = 13.49, 6.34 Hz, 1 H), 4.17 (s, 3 H), 3.784 (t, J = 9.47 Hz, 1 H), 3.56 (d, J = 5.65 Hz, 1 H), 3.15-3.30 (m, 2 H), 2.90 (s, 3 H), 2.65-2.79 (m, 7 H), 2.43 (dt, J = 12.49, 6.31 Hz, 1 H), 1.12 (d, J = 6.78 Hz, 3 H). MS (ESI): 562.3 ([M + H]$^+$). |
| 1.168 | 6-(4-trans-(3-(dimethylamino)-4-fluoropyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3 AMINE: Intermediate C24 BORONIC REAGENT: Intermediate B2 CATALYST: Pd-Ad$_2$nBuP Biphenyl Precat (CAS#: 1375477-29-4) SOLVENT: THF/H$_2$O | 1H NMR (400 MHz, DMSO-d6) δ ppm 11.98 (s, 1 H), 9.31 (s, 1 H), 9.13 (d, J = 2.38 Hz, 1 H), 8.71 (d, J = 2.38 Hz, 1 H), 8.27 (s, 1 H), 6.63 (dd, J = 13.55, 6.27 Hz, 1 H), 5.31-5.55 (m, 1 H), 4.18 (s, 3 H), 3.84-4.15 (m, 3 H), 3.33-3.46 (m, 1 H), 3.20-3.32 (m, 1 H), 3.15 (t, J = 8.97 Hz, 1 H), 2.91 (s, 3 H), 2.69-2.87 (m, 5 H). MS (ESI): 566.2 ([M + H]$^+$). |
| 1.169 | 6-(4-trans-(3-(dimethylamino)-4-fluoropyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid | CORE: Intermediate A1 AMINE: Intermediate C24 BORONIC REAGENT: Intermediate B2 CATALYST: Pd-Ad$_2$nBuP Biphenyl Precat (CAS#: 1375477-29-4) SOLVENT: THF/H$_2$O | 1H NMR (400 MHz, DMSO-d6) δ ppm 11.63 (s, 1 H), 9.32 (s, 1 H), 9.13 (d, J = 2.38 Hz, 1 H), 8.68-8.73 (m, 1 H), 8.21 (s, 1 H), 7.00 (dd, J = 9.60, 1.69 Hz, 1 H), 6.48 (dd, J = 12.17, 2.01 Hz, 1 H), 5.49-5.77 (m, 1 H), 4.05-4.33 (m, 4 H), 3.72 (s, 4 H), 3.29-3.46 (m, 1 H), 2.85-3.03 (m, 6 H), 2.57-2.72 (m, 2 H). MS (ESI): 548.2 ([M + H]$^+$). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.170 | 6-(4-trans--(3-(dimethylamino)-4-methoxypyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C25<br>BORONIC REAGENT: Intermediate B2<br>CATALYST: Pd-Ad$_2$nBuP Biphenyl Precat (CAS#: 1375477-29-4)<br>SOLVENT: THF/H$_2$O | 1H NMR (400 MHz, DMSO-d6) δ ppm 11.97 (s, 1 H), 10.33 (s, 1 H), 9.29 (s, 1 H), 9.13 (d, J = 2.38 Hz, 1 H), 8.69 (d, J = 2.38 Hz, 1 H), 8.30 (s, 1 H), 6.62 (dd, J = 13.43, 6.27 Hz, 1 H), 4.18 (s, 4 H), 3.61-3.87 (m, 2 H), 3.43 (t, J = 7.72 Hz, 1 H), 3.17-3.26 (m, 5 H), 2.90 (s, 3H), 2.81 (s, 3H), 2.71 (s, 3 H).<br>MS (ESI): 578.3 ([M + H]$^+$). |
| 1.171 | 6-(4-trans-(3-(dimethylamino)-4-methoxypyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid | CORE: Intermediate A1<br>AMINE: Intermediate C25<br>BORONIC REAGENT: Intermediate B2<br>CATALYST: Pd-Ad$_2$nBuP Biphenyl Precat (CAS#: 1375477-29-4)<br>SOLVENT: THF/H$_2$O | 1H NMR (400 MHz, DMSO-d6) δ ppm 11.654 (s, 1 H), 10.16 (s, 1 H), 9.31 (s, 1 H), 9.12 (d, J = 2.38 Hz, 1 H), 8.67 (d, J = 2.38 Hz, 1 H), 8.20 (s, 1 H), 7.18 (dd, J = 9.98, 2.07 Hz, 1 H), 6.47 (dd, J = 12.17, 2.13 Hz, 1 H), 4.18 (s, 4 H), 3.76 (s, 2 H), 3.48-3.57 (m, 1 H), 3.38 (s, 3 H), 3.28 (dd, J = 11.42, 5.90 Hz, 1 H), 2.93 (s, 3 H), 2.72-2.84 (m, 4 H), 2.58 (s, 3 H).<br>MS (ESI): 560.3 ([M + H]$^+$). |
| 1.172 | (S)-6-(4-(2-((dimethylamino)methyl)pyrrolidin-1-yl)-6,7-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A4<br>AMINE: Intermediate C18<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, Methanol-d4): δ 11.82 (s, 1 H), 9.31 (m, 1 H), 9.11~9.12 (m, 2 H), 8.718~8.724 (m, 1 H), 8.34 (m, 1 H), 7.04~7.08 (m, 1 H), 4.18 (s, 3 H), 3.30~3.34 (m, 1 H), 3.13~3.14 (m, 3 H), 3.00 (m, 1 H), 2.68 (m, 1 H), 2.55~2.56 (m, 3 H), 2.31~2.34 (m, 4 H), 2.03 (m, 1 H), 2.02 (m, 1 H), 1.79 (m, 2 H).<br>MS: 534.1 ([M + H]$^+$). |

| No. | Compound Name and Structure | CORE, AMINE, BORONIC REAGENT, CATALYST and SOLVENT | $^1$H NMR and MS (ESI) |
|---|---|---|---|
| 1.173 | (S)-6-(5,6-difluoro-8-(methylamino)-4-(3-(pyrrolidin-1-ylmethyl)pyrrolidin-1-yl)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C26<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 14.73 (br s, 1H), 11.84 (s, 1H), 9.31 (s, 1H), 9.24-9.18 (m, 1H), 9.14 (d, J = 2.4 Hz, 1H), 8.70 (d, J = 2.4 Hz, 1H), 8.33 (s, 1H), 6.64-6.59 (m, 1H), 4.19 (s, 3H), 3.39-3.36 (m, 2H), 3.25-3.21 (m, 2H), 3.16-3.03 (m, 2H), 3.03-2.93 (m, 2H), 2.91 (s, 3H), 2.89-2.86 (m, 1H), 2.59-2.56 (m, 2H), 2.14-2.09 (m 1H), 2.01-1.93 (m, 2H), 1.87-1.76 (m, 2H), 1.68-1.58 (m, 1H). MS: 588.2 ([M + H]$^+$). |
| 1.174 | (S)-6-(5,6-difluoro-8-(methylamino)-4-(3-(morpholinomethyl)pyrrolidin-1-yl)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C27<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 14.71 (br s, 1H), 11.88 (s, 1H), 9.50 (br s, 1H), 9.31 (s, 1H), 9.14 (d, J = 2.4 Hz, 1H), 8.71 (d, J = 2.4 Hz, 1H), 8.33 (s, 1H), 6.62 (m, 1H), 4.19 (s, 3H), 3.91-3.89 (m, 2H), 3.65-3.57 (m 2H), 3.47-3.38 (m, 2H), 3.36-3.32 (m, 1H), 3.27-3.20 (m, 2H), 3.16-3.11 (m, 2H), 3.10-3.02 (m, 2H), 2.91 (s, 4H), 2.66-2.58 (m, 1H), 2.16-2.12 (m, 1H), 1.70-1.57 (m, 1H). MS: 604.3 ([M + H]$^+$). |
| 1.175 | 6-(4-((3aR,4R,7aS)-4-(dimethylamino)hexahydro-1H-isoindol-2(3H)-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C28<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, MeOD-d4) δ ppm: 9.20-9.14 (m, 2H), 8.86 (d, J = 2.0 Hz, 1H), 8.19 (s, 1H), 6.65 (m, 1H), 4.23 (s, 3H), 3.87 (m, 1H), 3.53 (m, 1H), 3.46 (m, 2H), 3.04-2.94 (m, 5H), 2.80 (s, 6H), 2.28 (m, 1H), 2.05 (m, 1H), 1.92 (m, 1H), 1.55-1.42 (m, 2H), 1.41-1.18 (m, 2H). MS: 602.2 ([M + H]$^+$). |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.176 | 6-[8-(ethylamino)-6-fluoro-4-morpholino-9H-pyrido[2,3-b]indol-3-yl]-4-oxo-1-pyrrolidin-3-yl-1,8-naphthyridine-3-carboxylic acid | CORE: Intermediate A2<br>AMINE: morpholine<br>BORONIC REAGENT: Intermediate B6<br>CATALYST: Pd-Ad₂nBuP Biphenyl Precat (CAS#: 1375477-29-4)<br>SOLVENT: THF/H₂O | ¹H NMR (400 MHz, DMSO-d6): δ ppm: 11.66 (br s, 1H), 9.35 (s, 1H), 9.13 (d, 1H), 8.70 (d, 1H), 8.21 (s, 1H), 7.09-7.12 (m, 1H), 6.47-6.51 (m, 1H), 6.17-6.19 (m, 1H), 5.73-5.79 (m, 1H), 3.70-3.73 (m, 4H), 3.16-3.28 (m, 6H), 2.93-2.97 (m, 6H), 2.00-2.09 (m, 1H), 1.31-1.34 (m, 1H)<br>MS: 572.3 ([M + H]⁺) |
| 1.177 | 6-[5,6-difluoro-8-(methylamino)-4-morpholino-9H-pyrido[2,3-b]indol-3-yl]-1-(2,3-dihydroxypropyl)-4-oxo-1,8-naphthyridine-3-carboxylic acid | CORE: Intermediate A3<br>AMINE: morpholine<br>BORONIC REAGENT: Intermediate B47<br>CATALYST: Pd-Ad₂nBuP Biphenyl Precat (CAS#: 1375477-29-4)<br>SOLVENT: THF/H₂O | ¹H NMR (400 MHz, DMSO-d₆ + D2O): δ ppm: 9.06-9.14 (m, 1H), 9.04 (s, 1H), 8.72 (br s, 1H), 8.25 (br s, 1H), 6.63 (br dd, J = 5.75, 13.33 Hz, 1H), 5.73 (s, 1H), 5.18-5.21 (m, 2H), 4.91-4.94 (m, 1H), 4.24-4.30 (m, 1H), 3.96 (s, 1H), 3.46-3.59 (m, 6H), 2.90-2.94 (m, 7H)<br>MS: 581.2 ([M + H]⁺) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.178 | 9H-pyrido[2,3-b]indol-3-yl]-1-[2-(dimethylamino)-2-methyl-propyl]-4-oxo-1,8-naphthyridine-3-carboxylic acid | CORE: Intermediate A3<br>AMINE: N-methylmethanamine hydrochloride<br>BORONIC REAGENT: Intermediate B29<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 9.22 (s, 1H), 9.06 (s, 1H), 8.83 (s, 1H), 8.22 (br s, 1H), 6.64 (dd, J = 6.17, 13.14 Hz, 1H), 5.15 (br s, 2H), 3.13 (s, 6H), 3.00 (s, 6H), 2.87-2.96 (m, 6H), 1.57 (s, 6H)<br>MS: 563.9 ([M + H]$^+$) |
| 1.179 | 6-[4-(dimethylamino)-5,6-difluoro-8-(methylamino)-9H-pyrido[2,3-b]indol-3-yl]-1-morpholino-4-oxo-1,8-naphthyridine-3-carboxylic acid | CORE: Intermediate A3<br>AMINE: N-methylmethanamine hydrochloride<br>BORONIC REAGENT: Intermediate B30<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$ + D2O): δ ppm: 9.06 (s, 1H), 9.04 (s, 1H), 8.61 (d, J = 2.45 Hz, 1H), 8.25 (s, 1H), 6.60 (dd, J = 6.30, 13.51 Hz, 1H), 4.18 (br s, 2H), 3.92 (br s, 2H), 3.77 (br s, 3H), 3.34-3.43 (m, 1H), 2.90 (s, 3H), 2.74 (d, J = 1.96 Hz, 6H)<br>MS: 550.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.180 | 6-[5,6-difluoro-8-(methylamino)-4-morpholino-9H-pyrido[2,3-b]indol-3-yl]-1-(dimethylamino)-4-oxo-1,8-naphthyridine-3-carboxylic acid | CORE: Intermediate A3<br>AMINE: N-morpholine<br>BORONIC REAGENT: Intermediate B31<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$ + D2O): δ ppm: 9.06-9.14 (m, 1H), 9.04 (s, 1H), 8.70 (br s, 1H), 8.25 (br s, 1H), 6.63 (br dd, J = 5.75, 13.33 Hz, 1H), 3.58 (br s, 4H), 3.25 (br s, 6H), 2.95 (br s, 4H), 2.86-2.93 (m, 3H)<br>MS: 550.2 ([M + H]$^+$) |
| 1.181 | 6-[4-[2-[(dimethylamino)methyl]morpholin-4-yl]-5,6-difluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: N,N-dimethyl-1-morpholin-2-yl-methanamine<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 9.06-9.16 (m, 2H), 8.91 (br s, 1H), 8.52 (s, 1H), 8.31 (s, 1H), 6.64 (dd, J = 6.17, 13.02 Hz, 1H), 4.09 (br s, 1H), 3.78-3.88 (m, 1H), 3.64-3.78 (m, 1H), 3.12-3.27 (m, 2H), 3.07 (s,4H), 2.92-3.03 (m, 6H), 2.76 (s, 6H)<br>MS: 593.1 ([M + H]$^+$) |
| 1.182 | 6-[4-[4-(dimethylamino)-1-piperidyl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: N,N-dimethylpiperidin-4-amine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 9.10-9.23 (m, 1H), 9.00-9.09 (m, 1H), 8.81-8.94 (m, 1H), 8.53 (s, 1H), 8.19-8.40 (m, 1H), 6.63 (br dd, J = 6.11, 12.72 Hz, 1H), 4.21 (br s, 3H), 3.03-3.29 (m, 5H), 2.96-3.03 (m, 3H), 2.74 (s, 6H), 1.90 (br s, 2H), 1.61-1.85 (m, 2H)<br>MS: 562.1 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.183 | 6-[4-[4-[(dimethylamino)methyl]-1-piperidyl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: N,N-dimethyl-1-(4-piperidyl)methanamine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 9.16 (s, 1H), 9.05 (br s, 1H), 8.84-8.98 (m, 1H), 8.17-8.51 (m, 3H), 6.63 (br dd, J = 5.75, 12.23 Hz, 1H), 4.21 (s, 3H), 3.09-3.25 (m, 3H), 3.00 (s, 6H), 2.86 (s, 6H), 1.84 (br s, 1H), 1.65 (br d, J = 12.10 Hz, 2H), 1.30-1.54 (m, 2H)<br>MS: 576.1 ([M + H]$^+$) |
| 1.184 | 6-[6-fluoro-8-(methylamino)-4-(4-methylpiperazin-1-yl)-9H-pyrido[2,3-b]indol-3-yl]-1-methyl-4-oxo-1,8-naphthyridine-3-carboxylic acid | CORE: Intermediate A1<br>AMINE: 1-methylpiperazine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.58-14.87 (m, 1H), 11.54 (s, 1H), 9.28 (s, 1H), 9.09 (d, J = 2.32 Hz, 1H), 8.64 (d, J = 2.32 Hz, 1H), 8.17 (s, 1H), 7.08-7.22 (m, 1H), 6.38-6.52 (m, 1H), 5.81-6.00 (m, 1H), 4.15-4.21 (m, 3H), 2.87-3.02 (m, 7H), 2.43 (m, 4H) 2.18 (s, 3H)<br>MS: 516.3 ([M + H]$^+$) |
| 1.185 | 6-[6-fluoro-8-(methylamino)-4-(4-methyl-1,4-diazepan-1-yl)-9H-pyrido[2,3-b]indol-3-yl]-1-methyl-4-oxo-1,8-naphthyridine-3-carboxylic acid | CORE: Intermediate A1<br>AMINE: 1-1-methyl-1,4-diazepane<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 13.88-14.99 (m, 1H), 11.44-11.65 (m, 1H), 9.25 (br s, 1H), 8.95-9.17 (m, 1H), 8.61-8.80 (m, 1H), 8.28 (s, 1H), 7.40-7.58 (m, 1H), 6.45 (dd, J = 1.83, 11.98 Hz, 1H), 5.90 (br d, J = 4.03 Hz, 1H), 4.16 (br s, 3H), 3.11 (br s, 2H), 2.81-3.03 (m, 4H), 2.56-2.63 (m, 2H), 2.23-2.38 (m, 3H), 1.62-1.82 (m, 2H), 1.24 (s, 3H)<br>MS: 530.3 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.186 | 6-[4-[3-[(dimethylamino)methyl]-1-piperidyl]-5,6-difluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: N,N-dimethyl-1-(3-piperidyl)methanamine<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 9.19 (s, 1H), 9.12 (d, J = 2.32 Hz, 1H), 8.95 (d, J = 2.20 Hz, 1H), 8.34 (s, 1H), 6.67 (dd, J = 6.36, 13.08 Hz, 1H), 2.96-3.20 (m, 12H), 2.87 (d, J = 5.14 Hz, 6H), 2.26 (br s, 1H), 1.83 (br d, J = 9.78 Hz, 1H), 1.65 (br d, J = 13.33 Hz, 1H), 1.47 (br d, J = 10.03 Hz, 1H), 1.13-1.26 (m, 1H)<br>MS: 591.3 ([M + H]$^+$) |
| 1.187 | 6-[6-fluoro-8-(methylamino)-4-[cis-5-methyl-2,3,3a,4,6,6a-hexahydropyrrolo[2,3-c]pyrrol-1-yl]-9H-pyrido[2,3-b]indol-3-yl]-1-methyl-4-oxo-1,8-naphthyridine-3-carboxylic acid | CORE: Intermediate A1<br>AMINE: Intermediate C8<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 9.21 (s, 1H), 9.03-9.15 (m, 1H), 8.74-8.90 (m, 1H), 8.28 (s, 1H), 6.87-7.06 (m, 1H), 6.56 (br d, J = 11.49 Hz, 1H), 4.30-4.48 (m, 1H), 4.25 (s, 3H), 4.02-4.18 (m, 1H), 3.73-3.97 (m, 1H), 3.37-3.69 (m, 3H), 3.04 (s, 5H), 2.80 (br s, 4H), 2.26-2.55 (m, 1H), 1.95-2.15 (m, 1H)<br>MS: 542.0 ([M + H]$^+$) |
| 1.188 | 6-[6-fluoro-4-(cis-1-methyl-3,3a,4,6,7,7a-hexahydro-2H-pyrrolo[3,2-c]pyridin-5-yl)-8-(methylamino)-9H-pyrido[2,3-b]indol-3-yl]-1-methyl-4-oxo-1,8-naphthyridine-3-carboxylic acid | CORE: Intermediate A1<br>AMINE: cis-1-methyl-2,3,3a,4,5,6,7,7a-octahydropyrrolo[3,2-c]pyridine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 9.21 (s, 1H), 9.11 (s, 1H), 8.88 (s, 1H), 8.34 (s, 1H), 8.26 (s, 1H), 7.21 (br d, J = 9.29 Hz, 1H), 6.56 (br d, J = 11.74 Hz, 1H), 4.25 (s, 3H), 3.63-3.97 (m, 2H), 3.37-3.63 (m, 3H), 3.11-3.26 (m, 1H), 2.87-3.10 (m, 7H), 2.69-2.84 (m, 1H), 1.67-2.57 (m, 4H)<br>MS: 556.1 ([M + H]$^+$) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.189 | 6-[5,6-difluoro-8-(methylamino)-4-[cis-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylic acid | CORE: Intermediate A3<br>AMINE: Intermediate C8<br>BORONIC REAGENT: Intermediate B23<br>CATALYST: Pd-Ad₂nBuP Biphenyl Precat (CAS#: 1375477-29-4)<br>SOLVENT: THF/H₂O | ¹H NMR (400 MHz, METHANOL-d₄): δ ppm: 9.06 (s, 1H), 9.00 (s, 1H), 8.75 (s, 1H), 8.21 (br d, J = 18.34 Hz, 1H), 6.55 (dd, J = 6.36, 13.08 Hz, 1H), 4.12-4.38 (m, 1H), 3.67 (br s, 1H), 3.32-3.58 (m, 3H), 3.05-3.17 (m, 1H), 2.97 (s, 3H), 2.89 (s, 4H), 2.68-2.85 (m, 4H), 2.10-2.35 (m, 1H), 1.77-1.99 (m, 1H)<br>MS: 575.2 ([M + H]⁺) |
| 1.190 | 6-[5,6-difluoro-8-(methylamino)-4-(9-methyl-2,9-diazaspiro[4.5]decan-2-yl)-9H-pyrido[2,3-b]indol-3-yl]-1-methyl-4-oxo-1,8-naphthyridine-3-carboxylic acid | CORE: Intermediate A3<br>AMINE: 7-methyl-2,7-diazaspiro[4.5]decane<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, METHANOL-d₄): δ ppm: 9.09 (d, J = 2.20 Hz, 1H), 8.99 (s, 1H), 8.71 (s, 1H), 8.16 (d, J = 4.16 Hz, 1H), 6.49-6.56 (m, 1H), 4.12 (s, 3H), 3.23-3.48 (m, 3H), 2.94-3.19 (m, 4H), 2.80-2.94 (m, 3H), 2.66-2.80 (m, 3H), 1.62-2.00 (m, 4H), 1.47-1.61 (m, 1H), 1.16-1.41 (m, 2H)<br>MS: 588.1 ([M + H]⁺) |
| 1.191 | 6-[4-[3-(dimethylamino)-1-piperidyl]-5,6-difluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: N,N-dimethylpiperidin-3-amine<br>BORONIC REAGENT: Intermediate B23<br>CATALYST Pd-Ad₂nBuP Biphenyl Precat (CAS#: 1375477-29-4)<br>SOLVENT: THF/H₂O | ¹H NMR (400 MHz, DMSO-d₆): δ ppm: 14.62 (br s, 1H), 11.89 (br s, 1H), 9.16 (d, J = 2.32 Hz, 1H), 9.06 (s, 1H), 8.77 (d, J = 2.20 Hz, 1H), 8.33 (br s, 1H), 8.13 (s, 1H), 7.64 (q, J = 5.79 Hz, 1H), 6.63 (dd, J = 6.24, 13.45 Hz, 1H), 5.71 (br d, J = 4.65 Hz, 1H), 2.97 (d, J = 5.62 Hz, 5H), 2.91 (d, J = 4.89 Hz, 4H), 2.80 (br s, 1H), 2.34-2.45 (m, 2H), 2.11-2.31 (m, 5H), 1.82-2.01 (m, 1H), 1.54-1.67 (m, 1H), 1.34-1.51 (m, 1H), 1.03-1.21 (m, 1H)<br>MS: 577.5 ([M + H]⁺) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.192 | 6-[5,6-difluoro-8-(methylamino)-4-[cis-1-methyl-2,3,3a,4,6,6a-hexahydropyrrolo[2,3-c]pyrrol-5-yl]-9H-pyrido[2,3-b]indol-3-yl]-1-methyl-4-oxo-1,8-naphthyridine-3-carboxylic acid | CORE: Intermediate A3<br>AMINE: cis-1-methyl-3,3a,4,5,6,6a-hexahydro-2H-pyrrolo[2,3-c]pyrrole<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, DMSO-d₆): δ ppm: 14.84 (br s, 1H), 11.80 (s, 1H), 9.28 (s, 1H), 9.10 (d, J = 2.32 Hz, 1H), 8.69 (d, J = 2.32 Hz, 1H), 8.27 (s, 1H), 8.14 (s, 1H), 6.53-6.63 (m, 1H), 5.69 (br d, J = 4.52 Hz, 1H), 4.17 (s, 3H), 3.46-3.63 (m, 2H), 3.12 (br s, 1H), 2.76-2.97 (m, 6H), 2.64-2.75 (m, 1H), 2.38 (br s, 1H), 2.08 (br s, 3H), 1.87 (br s, 1H), 1.36 (br d, J = 6.72 Hz, 1H)<br>MS: 560.2 ([M + H]⁺) |
| 1.193 | 6-[5,6-difluoro-8-(methylamino)-4-[cis-1-methyl-2,3,3a,4,6,6a-hexahydropyrrolo[2,3-c]pyrrol-5-yl]-9H-pyrido[2,3-b]indol-3-yl]-1-(methylamino)-4-oxo-1,8-naphthyridine-3-carboxylic acid | CORE: Intermediate A3<br>AMINE: cis-1-methyl-3,3a,4,5,6,6a-hexahydro-2H-pyrrolo[2,3-c]pyrrole<br>BORONIC REAGENT: Intermediate B23<br>CATALYST: Pd-Ad₂nBuP Biphenyl Precat (CAS#: 1375477-29-4)<br>SOLVENT: THF/H₂O | ¹H NMR (400 MHz, DMSO-d₆): δ ppm: 14.69 (br s, 1H), 11.79 (br s, 1H), 9.12 (d, J = 2.32 Hz, 1H), 9.03 (s, 1H), 8.70 (d, J = 2.32 Hz, 1H), 8.28 (s, 1H), 7.59-7.66 (m, 1H), 6.55-6.63 (m, 1H), 5.69 (br d, J = 5.01 Hz, 1H), 3.44-3.60 (m, 2H), 2.96 (d, J = 5.62 Hz, 3H), 2.90 (d, J = 4.89 Hz, 3H), 2.73-2.87 (m, 3H), 2.62-2.71 (m, 2H), 2.14-2.24 (m, 1H), 1.94 (s, 3H), 1.76-1.85 (m, 1H), 1.23-1.34 (m, 1H)<br>MS: 575.3 ([M + H]⁺) |
| 1.194 | 6-[5,6-difluoro-4-[9-(2-hydroxyethyl)-2,9-diazaspiro[4.5]decan-2-yl]-8-(methylamino-9H-pyrido[2,3-b]indol-3-yl]-1-methyl-4-oxo-1,8-naphthyridine-3-carboxylic acid | CORE: Intermediate A3<br>AMINE: Intermediate C29<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, METHANOL-d₄): δ ppm: 9.14 (s, 1H), 9.05 (s, 1H), 8.78 (br s, 1H), 8.51 (s, 1H), 8.24 (s, 1H), 6.62 (dd, J = 6.24, 12.84 Hz, 1H), 4.23 (s, 3H), 3.70 (br s, 2H), 3.41 (br s, 2H), 3.15 (br d, J = 3.18 Hz, 3H), 3.01 (s, 3H), 2.82 (br s, 5H), 1.98 (br s, 1H), 1.86 (br s, 1H), 1.46-1.75 (m, 4H)<br>MS: 618.6 ([M + H]⁺) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.195 | 6-[5,6-difluoro-4-[9-(2-methoxyethyl)-2,9-diazaspiro[4.5]decan-2-yl]-8-(methylamino-9H-pyrido[2,3-b]indol-3-yl]-1-methyl-4-oxo-1,8-naphthyridine-3-carboxylic acid | CORE: Intermediate A3<br>AMINE: Intermediate C30<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.77 (s, 1H), 11.79 (s, 1H), 9.30 (s, 1H), 9.10 (d, J = 2.32 Hz, 1H), 8.65 (d, J = 2.32 Hz, 1H), 8.25 (s, 1H), 8.14 (s, 1H), 6.53-6.63 (m, 1H), 6.49-6.54 (m, 1H), 5.69 (br d, J = 4.65 Hz, 1H), 4.17 (s, 3H), 3.17-3.25 (m, 3H), 3.09-3.16 (m, 4H), 2.85-3.00 (m, 6H), 2.18-2.32 (m, 2H), 1.95-2.18 (m, 2H), 1.74-1.95 (m, 2H), 1.66 (br s, 1H), 1.36 (br s, 2H), 1.22 (br d, J = 14.31 Hz, 2H)<br>MS: 632.4 ([M + H]$^+$) |
| 1.196 | 6-[5,6-difluoro-4-(cis-1-methyl-3,3a,4,5,7,7a-hexahydro-2H-pyrrolo[2,3-c]pyridin-6-yl)-8-(methylamino)-9H-pyrido[2,3-b]indol-3-yl]-1-methyl-4-oxo-1,8-naphthyridine-3-carboxylic acid | CORE: Intermediate A3<br>AMINE: cis-1-methyl-2,3,3a,4,5,6,7,7a-octahydropyrrolo[2,3-c]pyridine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.86 (br s, 1H), 11.76-11.84 (m, 1H), 9.28 (s, 1H), 9.13 (d, J = 2.32 Hz, 1H), 8.75 (d, J = 2.32 Hz, 1H), 8.38 (s, 1H), 8.32 (s, 1H), 8.15 (s, 1H), 6.54-6.65 (m, 1H), 5.70 (br d, J = 4.89 Hz, 1H), 4.17 (s, 3H), 3.19 (br s, 1H), 3.12 (br dd, J = 5.01, 12.10 Hz, 2H), 2.86-2.93 (m, 4H), 2.72-2.86 (m, 3H), 2.14-2.24 (m, 2H), 2.04 (br d, J = 9.17 Hz, 1H), 1.82 (s, 4H), 1.66 (br d, J = 9.05 Hz, 1H), 1.56 (br s, 1H), 1.19-1.31 (m, 1H)<br>MS: 574.3 ([M + H]$^+$) |
| 1.197 | 6-[5,6-difluoro-4-[3-[2-methoxyethyl(methyl)amino]-1-piperidyl]-8-(methylamino)-9H-pyrido[2,3-b]indol-3-yl]-1-methyl-4-oxo-1,8-naphthyridine-3-carboxylic acid | CORE: Intermediate A3<br>AMINE: N-(2-methoxyethyl)-N-methyl-piperidin-3-amine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.78 (br s, 1H), 11.88 (br s, 1H), 9.31 (s, 1H), 9.13 (d, J = 2.32 Hz, 1H), 8.76 (d, J = 1.96 Hz, 1H), 8.29 (br s, 1H), 8.14 (s, 1H), 6.63 (dd, J = 6.24, 13.45 Hz, 1H), 5.70 (br d, J = 4.52 Hz, 1H), 4.18 (s, 3H), 3.22 (br s, 2H), 3.06-3.18 (m, 4H), 2.96 (br s, 2H), 2.86-2.94 (m, 4H), 2.81 (br s, 1H), 2.36-2.43 (m, 1H), 2.14 (br s, 3H), 1.64-1.97 (m, 2H), 1.56 (br s, 1H), 1.31-1.50 (m, 1H), 1.15 (br s, 1H)<br>MS: 606.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.198 | 6-[5,6-difluoro-4-[3-[2-methoxyethyl(methyl)amino]pyrrolidin-1-yl]-8-(methylamino)-9H-pyrido[2,3-b]indol-3-yl]-1-methyl-4-oxo-1,8-naphthyridine-3-carboxylic acid | CORE: Intermediate A3<br>AMINE: N-(2-methoxyethyl)-N-methyl-pyrrolidin-3-amine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$) δ ppm: 9.04 (s, 1H), 8.92-8.99 (m, 1H), 8.66 (br s, 1H), 8.31 (s, 1H), 8.19 (br s, 1H), 6.50 (br dd, J = 6.24, 13.08 Hz, 1H), 4.11 (s, 3H), 3.67 (br s, 1H), 3.54 (br s, 1H), 3.25-3.47 (m, 4H), 2.94-3.16 (m, 2H), 2.89 (s, 3H), 2.86 (br s, 2H), 2.78-2.86 (m, 2H), 2.46 (s, 3H), 2.18-2.38 (m, 1H), 1.89 (br s, 1H)<br>MS: 592.2 ([M + H]$^+$) |
| 1.199 | 6-[5,6-difluoro-4-(cis-1-methyl-3,3a,4,5,7,7a-hexahydro-2H-pyrrolo[2,3-c]pyridin-6-yl)-8-(methylamino)-9H-pyrido[2,3-b]indol-3-yl]-1-(methylamino)-4-oxo-1,8-naphthyridine-3-carboxylic acid | CORE: Intermediate A3<br>AMINE: cis-1-methyl-2,3,3a,4,5,6,7,7a-octahydropyrrolo[2,3-c]pyridine<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 9.07 (s, 1H), 9.01 (d, J = 1.96 Hz, 1H), 8.82 (s, 1H), 8.28 (s, 1H), 6.55 (dd, J = 6.48, 13.08 Hz, 1H), 3.49 (br d, J = 14.79 Hz, 2H), 3.29 (br s, 3H), 3.03 (br d, J = 1.71 Hz, 2H), 2.97 (s, 3H), 2.89 (s, 3H), 2.67 (s, 3H), 2.51 (br s, 1H), 2.16 (br s, 1H), 1.64-1.84 (m, 3H)<br>MS: 589.3 ([M + H]$^+$) |
| 1.200 | 6-[5,6-difluoro-4-[3-[2-hydroxyethyl(methyl)amino]pyrrolidin-1-yl]-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C33<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.79 (br s, 1H), 11.80 (br s, 1H), 9.29 (s, 1H), 9.12 (d, J = 2.32 Hz, 1H), 8.69 (d, J = 2.32 Hz, 1H), 8.29 (s, 1H), 8.14 (s, 1H), 6.53-6.65 (m, 1H), 5.69 (br d, J = 5.01 Hz, 1H), 4.28-4.60 (m, 1H), 4.18 (s, 3H), 3.38 (m, 3H), 3.21 (m, 3H), 2.90 (d, J = 4.65 Hz, 4H), 2.33-2.44 (m, 2H), 2.01-2.27 (m, 4H), 1.75 (s, 1H)<br>MS: 578.4 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.201 | 6-[5,6-difluoro-4-[3-[2-hydroxyethyl(methyl)amino]-1-piperidyl]-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C34<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) δ ppm: 14.79 (br s, 1H), 11.86 (br s, 1H), 9.29 (s, 1H), 9.13 (d, J = 2.32 Hz, 1H), 8.74 (d, J = 2.20 Hz, 1H), 8.28 (s, 1H), 8.15 (s, 1H), 6.62 (dd, J = 6.17, 13.39 Hz, 1H), 5.70 (br d, J = 5.01 Hz, 1H), 4.18 (s, 4H), 3.19-3.28 (m, 3H), 3.12 (br d, J = 8.80 Hz, 1H), 2.96 (br s, 1H), 2.90 (d, J = 4.65 Hz, 3H), 2.72-2.83 (m, 1H), 2.27-2.47 (m, 3H), 2.09 (s, 3H), 1.72-1.83 (m, 1H), 1.57 (br d, J = 12.35 Hz, 1H), 1.37-1.50 (m, 1H), 1.13 (br d, J = 11.86 Hz, 1H)<br>MS: 592.2 ([M + H]$^+$) |
| 1.202 | 6-[5,6-difluoro-8-(methylamino)-4-(9-methyl-6-oxa-2,9-diazaspiro[4.5]decan-2-yl)-9H-pyrido[2,3-b]indol-3-yl]-1-methyl-4-oxo-1,8-naphthyridine-3-carboxylic acid | CORE: Intermediate A3<br>AMINE: 9-methyl-6-oxa-2,9-diazaspiro[4.5]decane<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.79 (s, 1H), 11.80 (br s, 1H), 9.29 (s, 1H), 9.08 (d, J = 2.32 Hz, 1H), 8.67 (d, J = 2.08 Hz, 1H), 8.25 (s, 1H), 8.14 (s, 1H), 6.54-6.64 (m, 1H), 5.69 (br d, J = 4.77 Hz, 1H), 4.17 (s, 3H), 3.39-3.60 (m, 2H), 3.15-3.28 (m, 3H), 3.09 (br d, J = 9.66 Hz, 2H), 2.83-2.98 (m, 4H), 1.81-2.30 (m, 7H)<br>MS: 590.3 ([M + H]$^+$) |
| 1.203 | 6-[5,6-difluoro-8-(methylamino)-4-(4-pyrrolidin-1-yl-1-piperidyl)-9H-pyrido[2,3-b]indol-3-yl]-1-methyl-4-oxo-1,8-naphthyridine-3-carboxylic acid | CORE: Intermediate A3<br>AMINE: 2-[methyl(3-piperidyl)amino]ethanol<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.25-15.03 (m, 1H), 11.87 (br s, 1H), 9.30 (s, 1H), 9.11 (d, J = 2.20 Hz, 1H), 8.68 (d, J = 2.08 Hz, 1H), 8.20-8.25 (m, 1H), 8.18 (s, 1H), 6.62 (dd, J = 5.93, 13.39 Hz, 1H), 5.71 (br d, J = 3.55 Hz, 1H), 4.18 (s, 4H), 3.16 (br d, J = 11.98 Hz, 2H), 2.90 (br d, J = 4.40 Hz, 3H), 2.62-2.86 (m, 6H), 2.29-2.43 (m, 1H), 1.81 (br d, J = 10.64 Hz, 2H), 1.71 (br s, 4H), 1.56 (br d, J = 9.41 Hz, 2H)<br>MS: 588.3 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.204 | 6-[4-(4-cyclopropylpiperazin-1-yl)-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: 1-cyclopropylpiperazine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.76 (br s, 1H), 11.83 (br s, 1H), 9.29 (s, 1H), 9.10 (br s, 1H), 8.72 (br s, 1H), 8.12-8.20 (m, 1H), 6.61 (br dd, J = 5.87, 13.33 Hz, 1H), 5.68 (br s, 1H), 4.18 (s, 3H), 2.84-3.00 (m, 7H), 2.50 (m, 4H), 1.47-1.64 (m, 1H), 0.36 (br s, 2H), 0.23 (br s, 2H)<br>MS: 560.3 ([M + H]$^+$) |
| 1.205 | 6-[5,6-difluoro-8-(methylamino)-4-[cis-5-(2-hydroxyethyl)-2,3,3a,4,6,6a-hexahydropyrrolo[2,3-c]pyrrol-1-yl]-9H-pyrido[2,3-b]indol-3-yl]-1-methyl-4-oxo-1,8-naphthyridine-3-carboxylic acid | CORE: Intermediate A3<br>AMINE: Intermediate C35<br>BORONIC REAGENT: Intermediate B2<br>CATALYST Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 9.05-9.13 (m, 1H), 8.99-9.05 (m, 1H), 8.69-8.84 (m, 1H), 8.07-8.25 (m, 1H), 6.45-6.62 (m, 1H), 4.08-4.18 (m, 3H), 3.47-3.61 (m, 2H), 3.26-3.45 (m, 3H), 2.89 (s, 9H), 2.08-2.26 (m, 1H), 1.71-1.84 (m, 1H), 1.19 (s, 1H)<br>MS: 590.5 ([M + H]$^+$) |
| 1.206 | 6-[5,6-difluoro-8-(methylamino)-4-[cis-5-methyl-2,3,3a,4,6,6a-hexahydropyrrolo[2,3-c]pyrrol-1-yl]-9H-pyrido[2,3-b]indol-3-yl]-1-(2-hydroxy-1-methyl-ethyl)-4-oxo-1,8-naphthyridine-3-carboxylic acid | CORE: Intermediate A3<br>AMINE: Intermediate C8<br>BORONIC REAGENT: Intermediate B22<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.82 (br s, 1H), 11.75 (br s, 1H), 9.07-9.11 (m, 2H), 8.73 (dd, J = 2.32, 4.52 Hz, 1H), 8.11-8.19 (m, 1H), 6.59 (dd, J = 6.24, 13.45 Hz, 1H), 5.69 (br d, J = 4.89 Hz, 1H), 5.11 (br s, 1H), 4.87-4.99 (m, 1H), 4.22-4.45 (m, 2H), 4.02-4.22 (m, 1H), 2.94-3.13 (m, 2H), 2.87-2.94 (m, 3H), 2.76-2.87 (m, 1H), 2.25-2.41 (m, 1H), 2.12-2.23 (m, 3H), 1.88-2.04 (m, 2H), 1.63 (br s, 1H), 1.21 (dd, J = 4.28, 6.11 Hz, 4H)<br>MS: 604.5 ([M + H]$^+$) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.207 | 6-[4-[7-(dimethylamino)-5-azaspiro[2.4]heptan-5-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C36<br>BORONIC REAGENT: Intermediate B2<br>CATALYST: Pd-Ad$_2$nBuP Biphenyl Precat (CAS#: 1375477-29-4)<br>SOLVENT: THF/H$_2$O | ¹H NMR (400 MHz, DMSO-d$_6$): δ ppm: 14.65-14.91 (m, 1H), 11.93 (s, 1H), 9.32 (s, 1H), 9.16 (d, J = 2.32 Hz, 1H), 8.98-9.14 (m, 1H), 8.75 (d, J = 2.32 Hz, 1H), 8.31 (s, 1H), 6.64 (dd, J = 6.24, 13.57 Hz, 1H), 5.70 (br s, 1H), 4.17 (s, 3H), 3.87-3.95 (m, 2H), 3.63-3.74 (m, 1H), 2.98 (br d, J = 9.41 Hz, 1H), 2.91 (s, 3H), 2.63-2.74 (m, 4H), 2.59 (d, J = 4.89 Hz, 3H), 1.07-1.26 (m, 1H), 0.77-0.90 (m, 2H), 0.61-0.77 (m, 1H)<br>MS: 574.6 ([M + H]⁺) |
| 1.208 | 6-[5,6-difluoro-8-(methylamino)-4-pyrrolidin-1-yl-9H-pyrido[2,3-b]indol-3-yl]-1-methyl-4-oxo-1,8-naphthyridine-3-carboxylic acid | CORE: Intermediate A3<br>AMINE: pyrrolidine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | ¹H NMR (400 MHz, DMSO-d$_6$): δ ppm: 14.38-15.20 (m, 1H), 11.88 (br s, 1H), 9.28 (s, 1H), 9.12 (d, J = 2.45 Hz, 1H), 8.68 (d, J = 2.45 Hz, 1H), 8.26 (s, 1H), 6.59 (dd, J = 6.30, 13.51 Hz, 1H), 5.73 (br s, 1H), 4.17 (s, 3H), 3.16 (br s, 4H), 2.90 (s, 3H), 1.79 (br s, 4H)<br>MS: 505.2 ([M + H]⁺) |
| 1.209 | 6-[6-fluoro-8-(methylamino)-4-[cis-1-methyl-2,3,3a,4,6,6a-hexahydropyrrolo[2,3-c]pyrrol-5-yl]-9H-pyrido[2,3-b]indol-3-yl]-1-methyl-4-oxo-1,8-naphthyridine-3-carboxylic acid | CORE: Intermediate A1<br>AMINE: cis-1-methyl-3,3a,4,5,6,6a-hexahydro-2H-pyrrolo[2,3-c]pyrrole<br>BORONIC REAGENT: Intermediate B2<br>CATALYST: Pd-Ad$_2$nBuP Biphenyl Precat (CAS#: 1375477-29-4)<br>SOLVENT: THF/H$_2$O | ¹H NMR (400 MHz, DMSO-d$_6$): δ ppm: 14.78 (s, 1H), 11.47 (br s, 1H), 9.29 (s, 1H), 9.10 (d, J = 2.08 Hz, 1H), 8.64 (d, J = 2.20 Hz, 1H), 8.06-8.18 (m, 2H), 6.43 (br d, J = 11.86 Hz, 1H), 5.85 (br s, 1H), 4.18 (s, 3H), 3.53-3.94 (m, 1H), 3.00-3.23 (m, 2H), 2.85-3.00 (m, 1H), 2.92 (d, J = 4.65 Hz, 4H), 2.56-2.82 (m, 3H), 2.5 (m, 3H), 1.83-2.10 (m, 1H), 1.58 (br s, 1H)<br>MS: 542.5 ([M + H]⁺) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.210 | 6-[6-fluoro-8-(methylamino)-4-[cis-1-methyl-2,3,3a,4,6,6a-hexahydropyrrolo[2,3-c]pyrrol-5-yl]-9H-pyrido[2,3-b]indol-3-yl]-1-(methylamino)-4-oxo-1,8-naphthyridine-3-carboxylic acid | CORE: Intermediate A1<br>AMINE: cis-1-methyl-3,3a,4,5,6,6a-hexahydro-2H-pyrrolo[2,3-cpyrrole<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.53-14.80 (m, 1H), 11.39-11.64 (m, 1H), 9.14 (d, J = 2.08 Hz, 1H), 9.05 (s, 1H), 8.68 (d, J = 2.20 Hz, 1H), 8.19 (br s, 1H), 8.14 (s, 1H), 7.61 (q, J = 5.62 Hz, 2H), 6.45 (d, J = 11.31 Hz, 1H), 5.88 (br s, 1H), 3.02-3.29 (m, 4H), 2.89-3.02 (m, 8H), 2.71-2.88 (m, 2H), 2.54-2.66 (m, 3H), 1.90-2.16 (m, 1H), 1.51-1.73 (m, 1H)<br>MS: 557.4 ([M + H]$^+$) |
| 1.211 | 6-[6-fluoro-4-[cis-1-methyl-3,3a,4,5,7,7a-hexahydro-2H-pyrrolo[2,3-c]pyridin-6-yl)-8-(methylamino)-9H-pyrido[2,3-b]indol-3-yl]-1-methyl-4-oxo-1,8-naphthyridine-3-carboxylic acid | CORE: Intermediate A1<br>AMINE : cis-1-methyl-2,3,3a,4,5,6,7,7a-octahydropyrrolo[2,3-c]pyridine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.78 (br s, 1H), 11.54 (br s, 1H), 9.30 (s, 1H), 9.13 (d, J = 2.45 Hz, 1H), 8.70 (d, J = 2.45 Hz, 1H), 8.21 (s, 1H), 8.14 (s, 1H), 7.07-7.61 (m, 1H), 6.46 (dd, J = 2.02, 12.04 Hz, 1H), 5.74-6.03 (m, 1H), 4.19 (s, 3H), 3.12-3.25 (m, 2H), 2.92 (d, J = 4.77 Hz, 7H), 2.13-2.44 (m, 4H), 1.60-2.13 (m, 4H), 1.52 (br s, 1H)<br>MS: 556.3 ([M + H]$^+$) |
| 1.212 | 6-[6-fluoro-4-[cis-1-methyl-3,3a,4,5,7,7a-hexahydro-2H-pyrrolo[2,3-c]pyridin-6-yl)-8-(methylamino)-9H-pyrido[2,3-b]indol-3-yl]-1-(methylamino)-4-oxo-1,8-naphthyridine-3-carboxylic acid | CORE: Intermediate A1<br>AMINE: cis-1-methyl-2,3,3a,4,5,6,7,7a-octahydropyrrolo[2,3-c]pyridine<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.65 (br s, 1H), 11.56 (br s, 1H), 9.16 (d, J = 2.32 Hz, 1H), 9.06 (s, 1H), 8.73 (d, J = 2.32 Hz, 1H), 8.25 (s, 1H), 8.14 (s, 1H), 7.63 (q, J = 5.54 Hz, 1H), 7.33 (br s, 1H), 6.46 (dd, J = 1.90, 12.04 Hz, 1H), 5.90 (br d, J = 4.40 Hz, 1H), 3.12-3.26 (m, 2H), 2.85-3.12 (m, 10H), 2.70-2.84 (m, 1H), 1.92-2.46 (m, 5H), 1.39-1.86 (m, 3H)<br>MS: 571.5 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.213 | 6-[5,6-difluoro-8-(methylamino)-4-(cis-8-methyl-3,8-diazabicyclo[4.2.0]octan-3-yl)-9H-pyrido[2,3-b]indol-3-yl]-1-methyl-4-oxo-1,8-naphthyridine-3-carboxylic acid | CORE: Intermediate A3<br>AMINE: cis-8-methyl-3,8-diaza-bicyclo[4.2.0]octane<br>BORONIC REAGENT: Intermediate B2<br>CATALYST Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.92 (br s, 1H), 11.78 (s, 1H), 9.27 (s, 1H), 9.12 (d, J = 2.45 Hz, 1H), 8.79 (d, J = 2.32 Hz, 1H), 8.29 (s, 1H), 6.60 (dd, J = 6.36, 13.45 Hz, 1H), 5.68 (br d, J = 4.77 Hz, 1H), 4.17 (s, 3H), 3.41-3.50 (m, 1H), 3.03-3.22 (m, 2H), 2.90 (d, J = 4.89 Hz, 5H), 2.78 (br d, J = 19.32 Hz, 2H), 2.25-2.37 (m, 1H), 1.82 (br s, 4H), 1.73 (br s, 1H)<br>MS: 542.5 ([M + H]$^+$) |
| 1.214 | 6-[5,6-difluoro-8-(methylamino)-4-(cis-8-methyl-3,8-diazabicyclo[4.2.0]octan-3-yl)-9H-pyrido[2,3-b]indol-3-yl]-1-(methylamino)-4-oxo-1,8-naphthyridine-3-carboxylic acid | CORE: Intermediate A3<br>AMINE: cis-8-methyl-3,8-diaza-bicyclo[4.2.0]octane<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.79 (br s, 1H), 11.79 (s, 1H), 9.14 (d, J = 2.32 Hz, 1H), 9.03 (s, 1H), 8 81 (d, J = 2.32 Hz, 1H), 8.32 (s, 1H), 7.61 (q, J = 5.50 Hz, 1H), 6.53-6.64 (m, 1H), 5.69 (br d, J = 4.65 Hz, 1H), 3.43 (br dd, J = 3.06, 12.84 Hz, 1H), 3.14 (br d, J = 4.40 Hz, 2H), 2.97 (d, J = 5.62 Hz, 3H), 2.84-2.94 (m, 5H), 2.76-2.84 (m, 1H), 2.65-2.75 (m, 1H), 2.20-2.35 (m, 1H), 1.69-1.89 (m, 5H)<br>MS: 542.5 ([M + H]$^+$) |
| 1.215 | 6-[4-[3-(dimethylamino)-1-piperidyl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: N,N-dimethylpiperidin-3-amine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 8.79-8.92 (m, 2H), 8.71 (br s, 1H), 8.05 (s, 1H), 6.50 (br dd, J = 6.11, 13.08 Hz, 1H), 4.03 (s, 3H), 3.29 (br d, J = 8.93 Hz, 1H), 2.80-2.94 (m, 6H), 2.69 (br s, 1H), 2.31 (br s, 6H), 1.94 (br d, J = 10.76 Hz, 1H), 1.27-1.55 (m, 2H), 1.19 (s, 1H)<br>MS: 562.1 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.216 | 6-[6-fluoro-8-(methylamino)-4-morpholino-9H-pyrido[2,3-b]indol-3-yl]-1-[(1S)-2-hydroxy-1-methyl-ethyl]-4-oxo-1,8-naphthyridine-3-carboxylic acid | CORE: Intermediate A1<br>AMINE: morpholine<br>BORONIC REAGENT: Intermediate B52<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$ + D$_2$O): δ ppm: 9.12 (s, 1H), 9.09 (s, 1H), 8.71 (d, J = 2.45 Hz, 1H), 8.23 (s, 1H), 7.11 (dd, J = 2.14, 9.84 Hz, 1H), 6.49 (dd, J = 2.20, 12.10 Hz, 1H), 5.95 (br s, 1H), 3.79-3.97 (m, 2H), 3.68-3.76 (m, 4H), 2.95-3.03 (m, 4H), 2.90-2.95 (m, 3H), 1.60 (d, J = 6.97 Hz, 3H)<br>MS: 547.5 ([M + H]$^+$) |
| 1.217 | 6-[4-[(2S)-2-[(dimethylamino)methyl]pyrrolidin-1-yl]-5,6-difluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: N,N-dimethyl-1-[(2S)-pyrrolidin-2-yl]methanamine<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 9.07-9.15 (m, 1H), 9.06 (s, 1H), 8.83 (d, J = 2.08 Hz, 1H), 8.27 (s, 1H), 6.62 (dd, J = 6.36, 13.20 Hz, 1H), 3.83 (br s, 1H), 3.06 (s, 3H), 2.94-3.03 (m, 4H), 2.33-2.57 (m, 1H), 2.16-2.32 (m, 1H), 2.10 (br s, 1H), 1.95-2.05 (m, 8H), 1.72 (br d, J = 3.06 Hz, 1H), 0.00-0.00 (m, 1H)<br>MS: 577.2 ([M + H]$^+$) |
| 1.218 | 6-[4-cis-(4R)-[(dimethylamino)methyl]-3,3a,4,5,6,6a-hexahydro-1H-cyclopenta[c]pyrrol-2-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C37<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.58-14.95 (m, 1H), 11.85 (s, 1H), 9.23-9.41 (m, 1H), 9.05-9.20 (m, 2H), 8.68 (d, J = 2.32 Hz, 1H), 8.30 (s, 1H), 6.88-7.32 (m, 1H), 6.61 (dd, J = 6.17, 13.39 Hz, 1H), 4.17 (s, 4H), 2.83-3.03 (m, 6H), 2.56-2.81 (m, 10H), 2.19 (br d, J = 7.46 Hz, 1H), 1.60 (br d, J = 4.40 Hz, 2H), 1.09-1.21 (m, 2H)<br>MS: 602.3 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.219 | 6-[4-[(8aS)-3,4,6,7,8,8a-hexahydro-1H-pyrrolo[1,2-a]pyrazin-2-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3 AMINE: (8aS)-1,2,3,4,6,7,8,8a-octahydropyrrolo[1,2-a]pyrazine BORONIC REAGENT: Intermediate B2 CATALYST: Pd-Ad$_2$nBuP Biphenyl Precat (CAS#: 1375477-29-4) SOLVENT: THF/H$_2$O | $^1$H NMR (400 MHz, DMSO-d$_6$): δ ppm: 14.77 (br s, 1H), 11.86 (s, 1H), 9.29 (s, 1H), 9.11 (d, J = 2.32 Hz, 1H), 8.23 (s, 1H), 8.14 (s, 1H), 6.61 (dd, J = 6.05, 13.39 Hz, 1H), 5.69 (br d, J = 4.28 Hz, 1H), 4.18 (s, 3H), 3.04-3.21 (m, 3H), 2.82-3.03 (m, 5H), 2.54-2.63 (m, 1H), 1.98-2.31 (m, 3H), 1.62 (br s, 3H), 1.09 (br s, 1H) MS: 560.2 ([M + H]$^+$) |
| 1.220 | 6-[4-[(8aR)-3,4,6,7,8,8a-hexahydro-1H-pyrrolo[1,2-a]pyrazin-2-yl]-5,6-difluoro-8-(methylamino)-9H-pyrido[2,3-b]indol-3-yl]-1-methyl-4-oxo-1,8-naphthyridine-3-carboxylic acid Chiral | CORE: Intermediate A3 AMINE: (8aR)-1,2,3,4,6,7,8,8a-octahydropyrrolo[1,2-a]pyrazine BORONIC REAGENT: Intermediate B2 CATALYST: Pd-Ad$_2$nBuP Biphenyl Precat (CAS#: 1375477-29-4) SOLVENT: THF/H$_2$O | $^1$H NMR (400 MHz, DMSO-d$_6$): δ ppm: 14.76 (s, 1H), 11.88 (br s, 1H), 9.30 (s, 1H), 9.12 (d, J = 1.96 Hz, 1H), 8.72 (s, 1H), 8.24 (br s, 1H), 8.13 (s, 1H), 6.62 (br dd, J = 5.99, 13.45 Hz, 1H), 5.64-5.76 (m, 1H), 4.19 (s, 3H), 2.98-3.25 (m, 4H), 2.90 (br d, J = 4.65 Hz, 4H), 2.71-2.85 (m, 1H), 2.55-2.71 (m, 1H), 1.87-2.16 (m, 2H), 1.65 (br s, 2H), 1.75 (s, 1H), 1.11 (br s, 1H) MS: 560.3 ([M + H]$^+$) |
| 1.221 | 6-[4-cis-(4R)-(dimethylamino)-3,3a,4,5,6,6a-hexahydro-1H-cyclopenta[c]pyrrol-2-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3 AMINE: Intermediate C38 BORONIC REAGENT: Intermediate B2 CATALYST: Pd-Ad$_2$nBuP Biphenyl Precat (CAS#: 1375477-29-4) SOLVENT: THF/H$_2$O | $^1$H NMR (400 MHz, DMSO-d$_6$): δ ppm: 14.81 (br s, 1H), 11.63-11.90 (m, 1H), 9.29 (s, 1H), 9.11 (br s, 1H), 8.64 (s, 1H), 8.14-8.33 (m, 2H), 6.45-6.70 (m, 2H), 5.55-5.78 (m, 1H), 4.11-4.21 (m, 3H), 3.65 (br t, J = 8.62 Hz, 1H), 2.90 (br s, 6H), 2.70-2.83 (m, 3H), 2.13-2.20 (m, 2H), 1.91-1.97 (m, 6H), 1.49-1.60 (m, 2H) MS: 588.5 ([M + H]$^+$) |

| No. | Compound Name and Structure | CORE, AMINE, BORONIC REAGENT, CATALYST and SOLVENT | ¹H NMR and MS (ESI) |
|---|---|---|---|
| 1.223 | 6-[4-[cis-3-(dimethylamino)-4-hydroxy-pyrrolidin-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C39<br>BORONIC REAGENT: Intermediate B2<br>CATALYST: Pd-Ad$_2$nBuP Biphenyl Precat (CAS#: 1375477-29-4)<br>SOLVENT: THF/H$_2$O | ¹H NMR (400 MHz, DMSO-d$_6$): δ ppm: 11.82 (br s, 1H), 8.46 (br s, 1H), 8.23 (br s, 1H), 8.10-8.19 (m, 2H), 6.96-7.39 (m, 1H), 6.47-6.78 (m, 2H), 5.70 (br s, 1H), 5.25-5.41 (m, 1H), 3.55-3.66 (m, 3H), 2.79-2.95 (m, 8H), 2.41-2.48 (m, 3H), 1.92-2.06 (m, 2H), 1.73-1.80 (m, 1H), 1.38-1.53 (m, 1H)<br>MS: 564.2 ([M + H]⁺) |
| 1.224 | 6-[4-[cis-3-(dimethylamino)-4-hydroxy-pyrrolidin-1-yl]-5,6-difluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: Intermediate C39<br>BORONIC REAGENT: Intermediate B23<br>CATALYST: Pd-Ad$_2$nBuP Biphenyl Precat (CAS#: 1375477-29-4)<br>SOLVENT: THF/H$_2$O | ¹H NMR (400 MHz, DMSO-d$_6$): δ ppm: 14.69 (br s, 1H), 11.85 (s, 1H), 9.11 (s, 1H), 9.08 (s, 1H), 8.70 (d, J = 2.32 Hz, 1H), 8.28 (s, 1H), 8.14 (s, 1H), 7.52 (q, J = 5.62 Hz, 1H), 6.54-6.64 (m, 1H), 5.72 (br d, J = 4.52 Hz, 1H), 4.36 (br s, 1H), 3.59-3.79 (m, 2H), 3.51 (br s, 1H), 2.94-3.10 (m, 6H), 2.86-2.94 (m, 3H), 2.54-2.74 (m, 6H)<br>MS: 579.4 ([M + H]⁺) |
| 1.225 | 6-[5,6-difluoro-4-[2-(2-hydroxyethyl)morpholin-4-yl]-8-(methylamino)-9H-pyrido[2,3-b]indol-3-yl]-1-methyl-4-oxo-1,8-naphthyridine-3-carboxylic acid | CORE: Intermediate A3<br>AMINE: 2-morpholin-2-ylethanol<br>BORONIC REAGENT: Intermediate B2<br>CATALYST: cataCXium ® A Pd G2 (Sigma-Aldrich, Catalog #: 761311)<br>SOLVENT: Dioxane/H$_2$O | ¹H NMR (400 MHz, METHANOL-d4) δ ppm: 9.19 (s, 1H), 9.10 (d, J = 2.20 Hz, 1H), 8.85 (d, J = 1.96 Hz, 1H), 8.24 (s, 1H), 6.66 (dd, J = 5.99, 12.84 Hz, 1H), 4.25 (s, 3H), 3.75 (br d, J = 5.87 Hz, 2H), 3.46-3.63 (m, 2H), 3.10-3.31 (m, 2H), 2.96-3.07 (m, 4H), 2.88 (m, 2H), 1.53 (m, 2H)<br>MS: 565.2 ([M + H]⁺) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.226 | 6-[5,6-difluoro-8-(methylamino)-4-(4-methyl-piperazin-1-yl)-9H-pyrido[2,3-b]indol-3-yl]-1-methyl-4-oxo-1,8-naphthyridine-3-carboxylic acid | CORE: Intermediate A3<br>AMINE: 1-methylpiperazine<br>BORONIC REAGENT: Intermediate B2<br>CATALYST: cataCXium ® A Pd G2 (Sigma-Aldrich, Catalog #: 761311)<br>SOLVENT: Dioxane/H₂O | ¹H NMR (400 MHz, DMSO-d6) δ ppm: 9.31 (s, 1H), 9.12 (s, 1H), 8.71 (s, 1H), 8.21 (s, 1H), 8.14 (s, 1H), 6.62 (dd, J = 6.30, 13.39 Hz, 1H), 6.54 (s, 1H), 5.67-5.72 (m, 1H), 4.19 (s, 3H), 3.45-3.55 (m, 1H), 2.83-3.09 (m, 8H), 2.53-2.78 (m, 2H), 2.15-2.41 (m, 3H)<br>MS: 534.2 ([M + H]⁺) |
| 1.227 | 6-[5,6-difluoro-8-(methylamino)-4-[cis-2-methyl-1,3,3a,4,6,6a-hexahydropyrrolo[3,4-c]pyrrol-5-yl]-9H-pyrido[2,3-b]indol-3-yl]-1-methyl-4-oxo-1,8-naphthyridine-3-carboxylic acid | CORE: Intermediate A3<br>AMINE: cis-5-methyl-2,3,3a,4,6,6a-hexahydro-1H-pyrrolo[3,4-c]pyrrole<br>BORONIC REAGENT: Intermediate B2<br>CATALYST: cataCXium ® A Pd G2 (Sigma-Aldrich, Catalog #: 761311)<br>SOLVENT: Dioxane/H₂O | ¹H NMR (400 MHz, MEOD-d4) δ ppm: 9.20 (s, 1H), 9.12 (d, J = 2.20 Hz, 1H), 8.93 (d, J = 1.96 Hz, 1H), 8.41 (s, 1H), 8.32 (br s, 2H), 6.66 (dd, J = 6.54, 13.02 Hz, 1H), 4.25 (s, 3H), 3.73-3.93 (m, 2H), 3.58-3.73 (m, 2H), 2.85-3.07 (m, 12H)<br>MS: 560.2 ([M + H]⁺) |
| 1.228 | 6-[5,6-difluoro-8-(methylamino)-4-(2-methyl-2,6-diazaspiro[3.4]octan-6-yl)-9H-pyrido[2,3-b]indol-3-yl]-1-methyl-4-oxo-1,8-naphthyridine-3-carboxylic acid | CORE: Intermediate A3<br>AMINE: 2-methyl-2,7-diazaspiro[3.4]octane<br>BORONIC REAGENT: Intermediate B2<br>CATALYST cataCXium ® A Pd G2 (Sigma-Aldrich, Catalog #: 761311)<br>SOLVENT: Dioxane/H₂O | ¹H NMR (400 MHz, MeOD-d4) δ ppm: 9.13 (s, 1H), 9.02 (d, J = 1.96 Hz, 1H), 8.73 (d, J = 2.20 Hz, 1H), 8.50 (s, 1H), 8.25 (s, 1H), 6.60 (dd, J = 6.11, 13.20 Hz, 1H), 4.21 (s, 3H), 3.99-4.10 (m, 4H), 3.36-3.50 (m, 4H), 3.00 (s, 3H), 2.84 (s, 3H), 2.30 (br t, J = 6.85 Hz, 2H)<br>MS: 560.2 ([M + H]⁺) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.229 | 6-[5,6-difluoro-8-(methylamino)-4-(7-methyl-2,7-diazaspiro[4.4]nonan-2-yl)-9H-pyrido[2,3-b]indol-3-yl]-1-methyl-4-oxo-1,8-naphthyridine-3-carboxylic acid | CORE: Intermediate A3<br>AMINE: 2-methyl-2,7-diazaspiro[3.4]octane<br>BORONIC REAGENT: Intermediate B2<br>CATALYST: cataCXium ® A Pd G2 (Sigma-Aldrich, Catalog #: 761311)<br>SOLVENT: Dioxane/H₂O | ¹H NMR (400 MHz, MeOD-d4) δ ppm: 9.06 (s, 1H), 9.00 (d, J = 2.20 Hz, 1H), 8.68 (d, J = 2.32 Hz, 1H), 8.50 (s, 1H), 8.20 (s, 1H), 6.59 (dd, J = 6.36, 13.20 Hz, 1H), 4.19 (s, 3H), 3.35-3.51 (m, 3H), 3.21-3.30 (m, 4H), 3.12-3.21 (m, 1H), 3.00 (s, 3H), 2.82 (s, 3H), 1.98-2.15 (m, 4H)<br>MS: 574.2 ([M + H]⁺) |
| 1.230 | 6-[5,6-difluoro-8-(methylamino)-4-(1-methyl-1,8-diazaspiro[4.5]decan-8-yl)-9H-pyrido[2,3-b]indol-3-yl]-1-methyl-4-oxo-1,8-naphthyridine-3-carboxylic acid | CORE: Intermediate A3<br>AMINE: 2-methyl-2,7-diazaspiro[3.4]octane<br>BORONIC REAGENT: Intermediate B2<br>CATALYST: cataCXium ® A Pd G2 (Sigma-Aldrich, Catalog #: 761311)<br>SOLVENT: Dioxane/H₂O | ¹H NMR (400 MHz, MeOD-d4) δ ppm: 8.75-8.89 (m, 3H), 8.12 (s, 1H), 6.45-6.52 (m, 1H), 4.03 (s, 3H), 2.79-2.99 (m, 8H), 2.27 (s, 3H), 1.56-1.80 (m, 6H), 1.08-1.30 (m, 3H)<br>MS: 588.2 ([M + H]⁺) |
| 1.231 | 6-[5,6-difluoro-8-(methylamino)-4-(2-methyl-2,8-diazaspiro[4.5]decan-8-yl)-9H-pyrido[2,3-b]indol-3-yl]-1-methyl-4-oxo-1,8-naphthyridine-3-carboxylic acid | CORE: Intermediate A3<br>AMINE: 2-methyl-2,8-diazaspiro[4.5]decane<br>BORONIC REAGENT: Intermediate B2<br>CATALYST: cataCXium ® A Pd G2 (Sigma-Aldrich, Catalog #: 761311)<br>SOLVENT: Dioxane/H₂O | 1H NMR (400 MHz, MeOD-d4) δ ppm: 8.73 (s, 1H), 8.59-8.71 (m, 3H), 7.78-7.89 (m, 1H), 6.45-6.51 (m, 1H), 3.90-4.14 (m, 3H), 3.07-3.16 (m, 1H), 2.77-2.94 (m, 6H), 2.53-2.74 (m, 4H), 2.33-2.51 (m, 3H), 1.30-1.57 (m, 6H)<br>MS: 588.2 ([M + H]+) |

| No. | Compound Name and Structure | CORE, AMINE, BORONIC REAGENT, CATALYST and SOLVENT | ¹H NMR and MS (ESI) |
|---|---|---|---|
| 1.232 | 6-[5,6-difluoro-4-(1-methyl-3,4,4a,5,7,7a-hexahydro-2H-pyrrolo[3,4-b]pyridin-6-yl)-8-(methylamino)-9H-pyrido[2,3-b]indol-3-yl]-1-methyl-4-oxo-1,8-naphthyridine-3-carboxylic acid | CORE: Intermediate A3 AMINE: 1-methyl-2,3,4,4a,5,6,7,7a-octahydropyrrolo[3,4-b]pyridine BORONIC REAGENT Intermediate B2 CATALYST cataCXium® A Pd G2 (Sigma-Aldrich, Catalog #: 761311) SOLVENT: Dioxane/H₂O | 1H NMR (400 MHz, MeOD-d4) δ ppm: 8.91-8.98 (m, 2H), 8.65 (d, J = 2.20 Hz, 1H), 8.03 (s, 1H), 6.46 (dd, J = 5.99, 13.08 Hz, 1H), 4.08 (s, 3H), 3.23-3.48 (m, 2H), 2.85-2.92 (m, 5H), 2.32 (br d, J = 5.99 Hz, 2H), 2.10 (br d, J = 7.09 Hz, 1H), 1.79-1.96 (m, 3H), 1.27-1.51 (m, 5H) MS: 574.2 ([M + H]+) |
| 1.233 | 6-[4-(4-ethylpiperazin-1-yl)-5,6-difluoro-8-(methylamino)-9H-pyrido[2,3-b]indol-3-yl]-1-methyl-4-oxo-1,8-naphthyridine-3-carboxylic acid | CORE: Intermediate A3 AMINE: 1-ethylpiperazine BORONIC REAGENT: Intermediate B2 CATALYST: cataCXium® A Pd G2 (Sigma-Aldrich, Catalog #: 761311) SOLVENT: Dioxane/H₂O | 1H NMR (400 MHz, DMSO-d6) δ 9.10 (d, J = 2.45 Hz, 1H), 8.70 (d, J = 2.45 Hz, 1H), 8.18 (s, 1H), 6.60 (dd, J = 5.99, 13.45 Hz, 1H), 5.67 (br d, J = 5.14 Hz, 1H), 4.18 (s, 3H), 2.87-3.00 (m, 7H), 2.36 (br s, 4H), 2.27 (q, J = 6.93 Hz, 2H), 0.92 (t, J = 7.15 Hz, 3H) MS: 548.2 ([M + H]+) |
| 1.234 | 6-[5,6-difluoro-4-(4-isopropylpiperazin-1-yl)-8-(methylamino)-9H-pyrido[2,3-b]indol-3-yl]-1-methyl-4-oxo-1,8-naphthyridine-3-carboxylic acid | CORE: Intermediate A3 AMINE: 1-ethylpiperazine BORONIC REAGENT: Intermediate B2 CATALYST: cataCXium® A Pd G2 (Sigma-Aldrich, Catalog #: 761311) SOLVENT: Dioxane/H₂O | 1H NMR (400 MHz, DMSO-d6) δ ppm: 11.85 (s, 1H), 9.30 (s, 1H), 9.12 (d, J = 2.32 Hz, 1H), 8.74 (d, J = 2.32 Hz, 1H), 8.19 (s, 1H), 6.62 (dd, J = 5.93, 13.51 Hz, 1H), 5.69 (br d, J = 4.40 Hz, 1H), 4.18 (s, 4H), 4.04 (s, 1H), 3.02 (br s, 4H), 2.90 (d, J = 4.77 Hz, 4H), 2.67 (m, 2H), 0.96 (br d, J = 5.75 Hz, 6H) MS: 562.2 ([M + H]+) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.235 | 6-[5,6-difluoro-4-(4-methyl-2,3,4a,5,7,7a-hexahydro-pyrrolo[3,4-b][1,4]oxazin-6-yl)-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C40<br>BORONIC REAGENT: Intermediate B2<br>CATALYST: cataCXium ® A Pd G2 (Sigma-Aldrich, Catalog #: 761311)<br>SOLVENT: Dioxane/H$_2$O | 1H NMR (400 MHz, MeOD-d4) δ ppm: 9.17 (s, 1H), 9.06 (d, J = 2.32 Hz, 1H), 8.80 (s, 1H), 8.31 (s, 1H), 8.17-8.40 (m, 1H), 6.62 (dd, J = 6.30, 13.27 Hz, 1H), 4.63 (s, 1H), 4.24 (s, 3H), 3.94 (br d, J = 8.56 Hz, 1H), 3.76 (br d, J = 9.90 Hz, 2H), 3.42-3.58 (m, 2H), 3.08-3.23 (m, 2H), 3.01 (s, 3H), 2.77 (br d, J = 10.39 Hz, 1H), 2.40 (br d, J = 7.70 Hz, 1H), 2.24 (s, 1H), 2.12 (s, 2H)<br>MS: 576.2 ([M + H]+) |
| 1.236 | 6-[5,6-difluoro-4-(4-methyl-2,3,4a,5,7,7a-hexahydro-pyrrolo[3,4-b][1,4]oxazin-6-yl)-8-(methylamino)-9H-pyrido[2,3-b]indol-3-yl]-1-(methylamino)-4-oxo-1,8-naphthyridine-3-carboxylic acid | CORE: Intermediate A3<br>AMINE: Intermediate C40<br>BORONIC REAGENT Intermediate B23<br>CATALYST: cataCXium ® A Pd G2 (Sigma-Aldrich, Catalog #: 761311)<br>SOLVENT: Dioxane/H$_2$O | 1H NMR (400 MHz, MeOD-d4) δ ppm: 9.11-9.19 (m, 1H), 9.03-9.11 (m, 1H), 8.74-8.90 (m, 1H), 8.23-8.41 (m, 1H), 6.53-6.72 (m, 1H), 3.87-4.00 (m, 1H), 3.67-3.83 (m, 1H), 3.44-3.57 (m, 2H), 3.11-3.21 (m, 2H), 3.08 (s, 3H), 3.01 (s, 3H), 2.68-2.82 (m, 2H), 2.33-2.45 (m, 1H), 2.19-2.30 (m, 1H), 2.12 (s, 3H)<br>MS: 591.2 ([M + H]+) |
| 1.237 | 6-[5,6-difluoro-8-(methylamino)-4-(1-methyl-1,7-diazaspiro[3.4]octan-7-yl)-9H-pyrido[2,3-b]indol-3-yl]-1-methyl-4-oxo-1,8-naphthyridine-3-carboxylic acid | CORE: Intermediate A3<br>AMINE: 1-methyl-1,7-diazaspiro[3.4]octane<br>BORONIC REAGENT: Intermediate B2<br>CATALYST: cataCXium ® A Pd G2 (Sigma-Aldrich, Catalog #: 761311)<br>SOLVENT: Dioxane/H$_2$O | 1H NMR (400 MHz, MeOD-d4) δ ppm: 8.91-9.00 (m, 2H), 8.72 (d, J = 1.83 Hz, 1H), 8.20 (s, 1H), 6.58 (dd, J = 6.30, 13.39 Hz, 1H), 4.15 (s, 3H), 3.40-3.62 (m, 2H), 3.09-3.28 (m, 3H), 3.00 (s, 3H), 2.36 (br d, J = 11.62 Hz, 2H), 2.25 (s, 3H), 2.13 (br d, J = 7.34 Hz, 2H), 2.05 (br d, J = 6.97 Hz, 1H)<br>MS: 560.2 ([M + H]+) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.238 | 6-[5,6-difluoro-8-(methylamino)-4-(1-methyl-1,7-diazaspiro[3.4]octan-7-yl)-9H-pyrido[2,3-b]indol-3-yl]-1-(methylamino)-4-oxo-1,8-naphthyridine-3-carboxylic acid | CORE: Intermediate A3 AMINE: 1-methyl-1,7-diazaspiro[3.4]octane BORONIC REAGENT: Intermediate B23 CATALYST: cataCXium ® A Pd G2 (Sigma-Aldrich, Catalog #: 761311) SOLVENT: Dioxane/H$_2$O | 1H NMR (400 MHz, MeOD-d4) δ ppm: 8.99 (br s, 1H), 8.91 (br s, 1H), 8.76 (br s, 1H), 8.13-8.27 (m, 1H), 6.49-6.65 (m, 1H), 3.05-3.29 (m, 4H), 2.94-3.05 (m, 5H), 2.32 (br d, J = 9.29 Hz, 1H), 2.15-2.26 (m, 4H), 2.10 (m, 3H), 2.03 (m, 2H), MS: 575.2 ([M + H]+) |
| 1.239 | 6-[5,6-difluoro-8-(methylamino)-4-(1-methyl-1,7-diazaspiro[4.4]nonan-7-yl)-9H-pyrido[2,3-b]indol-3-yl]-1-methyl-4-oxo-1,8-naphthyridine-3-carboxylic acid | CORE: Intermediate A3 AMINE: 1-methyl-1,7-diazaspiro[4.4]nonane BORONIC REAGENT: Intermediate B2 CATALYST: cataCXium ® A Pd G2 (Sigma-Aldrich, Catalog #: 761311) SOLVENT: Dioxane/H$_2$O | 1H NMR (400 MHz, MeOD-d4) δ ppm: 8.95-9.04 (m, 2H), 8.76 (d, J = 2.32 Hz, 1H), 8.18 (s, 1H), 6.49-6.62 (m, 1H), 4.16 (s, 3H), 3.42-3.57 (m, 2H), 3.14-3.27 (m, 2H), 3.00 (s, 3H), 2.76-2.89 (m, 1H), 2.54-2.73 (m, 3H), 2.19 (s, 3H), 1.57-1.95 (m, 4H) MS: 574.2 ([M + H]+) |
| 1.240 | 6-[5,6-difluoro-8-(methylamino)-4-(1-methyl-1,7-diazaspiro[4.4]nonan-7-yl)-9H-pyrido[2,3-b]indol-3-yl]-1-(methylamino)-4-oxo-1,8-naphthyridine-3-carboxylic acid | CORE: Intermediate A3 AMINE: 1-methyl-1,7-diazaspiro[4.4]nonane BORONIC REAGENT: Intermediate B23 CATALYST: cataCXium ® A Pd G2 (Sigma-Aldrich, Catalog #: 761311) SOLVENT: Dioxane/H$_2$O | 1H NMR (400 MHz, MeOD-d4) δ ppm: 9.03 (s, 1H), 8.97 (d, J = 2.08 Hz, 1H), 8.78 (d, J = 2.08 Hz, 1H), 8.19 (s, 1H), 6.60 (dd, J = 6.24, 13.08 Hz, 1H), 3.35-3.59 (m, 2H), 3.25 (m, 1H), 3.03 (s, 3H), 3.00 (s, 3H), 2.83 (br d, J = 9.41 Hz, 1H), 2.61-2.73 (m, 2H), 2.16-2.27 (m, 4H), 1.86 (br m, 1H), 1.62-1.83 (m, 3H) MS: 589.2 ([M + H]+) |

| No. | Compound Name and Structure | CORE, AMINE, BORONIC REAGENT, CATALYST and SOLVENT | ¹H NMR and MS (ESI) |
|---|---|---|---|
| 1.241 | 6-[5,6-difluoro-4-(cis-4-methyl-2,3,4a,5,7,7a-hexahydro-pyrrolo[3,4-b][1,4]oxazin-6-yl)-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C41<br>BORONIC REAGENT: Intermediate B2<br>CATALYST: cataCXium ® A Pd G2 (Sigma-Aldrich, Catalog #: 761311)<br>SOLVENT: Dioxane/H$_2$O | 1H NMR (400 MHz, MeOD-d4) δ ppm: 9.14 (s, 1H), 9.07 (d, J = 2.45 Hz, 1H), 8.78 (d, J = 2.32 Hz, 1H), 8.27 (s, 1H), 6.49-6.70 (m, 1H), 4.23 (s, 3H), 4.01 (s, 1H), 3.69 (br d, J = 3.91 Hz, 3H), 3.37-3.61 (m, 3H), 3.01 (s, 3H), 2.91 (d, J = 10.64 Hz, 1H), 2.57-2.74 (m, 1H), 2.39-2.47 (m, 1H), 2.33 (s, 3H)<br>MS: 576.2 ([M + H]+) |
| 1.242 | 6-[5,6-difluoro-4-(cis-4-methyl-2,3,4a,5,7,7a-hexahydro-pyrrolo[3,4-b][1,4]oxazin-6-yl)-8-(methylamino)-9H-pyrido[2,3-b]indol-3-yl]-1-(methylamino)-4-oxo-1,8-naphthyridine-3-carboxylic acid | CORE: Intermediate A3<br>AMINE: Intermediate C41<br>BORONIC REAGENT: Intermediate B23<br>CATALYST: cataCXium ® A Pd G2 (Sigma-Aldrich, Catalog #: 761311)<br>SOLVENT: Dioxane/H$_2$O | 1H NMR (400 MHz, MeOD-d4) δ ppm: 9.13 (s, 1H), 9.09 (s, 1H), 8.80 (d, J = 2.20 Hz, 1H), 8.27 (s, 1H), 6.60 (dd, J = 6.42, 13.14 Hz, 1H), 4.02 (t, J = 3.55 Hz, 1H), 3.65-3.85 (m, 3H), 3.62 (br d, J = 6.85 Hz, 1H), 3.35-3.57 (m, 4H), 3.07 (s, 3H), 3.00 (s, 3H), 2.93 (d, J = 10.64 Hz, 1H), 2.65 (br d, J = 3.30 Hz, 1H), 2.41 (br d, J = 12.23 Hz, 1H), 2.33 (s, 3H)<br>MS: 591.2 ([M + H]+) |
| 1.243 | 6-[5,6-difluoro-4-(5-methyl-3,3a,4,6,7,7a-hexahydro-2H-pyrrolo[3,2-c]pyridin-1-yl)-8-(methylamino)-9H-pyrido[2,3-b]indol-3-yl]-1-methyl-4-oxo-1,8-naphthyridine-3-carboxylic acid | CORE: Intermediate A3<br>AMINE: 5-methyl-1,2,3,3a,4,6,7,7a-octahydropyrrolo[3,2-c]pyridine<br>BORONIC REAGENT: Intermediate B2<br>CATALYST: cataCXium ® A Pd G2 (Sigma-Aldrich, Catalog #: 761311)<br>SOLVENT: Dioxane/H$_2$O | 1H NMR (400 MHz, MeOD-d4) δ ppm: 9.14 (s, 1H), 9.05 (d, J = 2.32 Hz, 1H), 8.76 (d, J = 2.20 Hz, 1H), 8.28 (s, 1H), 6.66 (dd, J = 6.30, 13.02 Hz, 1H), 4.31 (s, 1H), 4.23 (s, 3H), 4.13 (br dd, J = 1.22, 7.46 Hz, 1H), 3.40-3.55 (m, 1H), 3.05-3.18 (m, 1H), 3.02 (s, 3H), 2.55-2.62 (m, 1H), 2.37-2.54 (m, 1H), 2.18-2.30 (m, 4H), 1.99-2.17 (m, 2H), 1.83 (dt, J = 1.96, 2.81 Hz, 1H), 1.46-1.67 (m, 1H), 1.16-1.42 (m, 1H)<br>MS: 574.2 ([M + H]+) |

TABLE 1-continued

Compound synthesis and characterization

| No. | Compound Name and Structure | CORE, AMINE, BORONIC REAGENT, CATALYST and SOLVENT | 1H NMR and MS (ESI) |
|---|---|---|---|
| 1.244 | 6-[5,6-difluoro-4-(5-methyl-3,3a,4,6,7,7a-hexahydro-2H-pyrrolo[3,2-c]pyridin-1-yl)-8-(methylamino)-9H-pyrido[2,3-b]indol-3-yl]-1-(methylamino)-4-oxo-1,8-naphthyridine-3-carboxylic acid | CORE: Intermediate A3<br>AMINE: 5-methyl-1,2,3,3a,4,6,7,7a-octahydropyrrolo[3,2-c]pyridine<br>BORONIC REAGENT: Intermediate B23<br>CATALYST: cataCXium ® A Pd G2 (Sigma-Aldrich, Catalog #: 761311)<br>SOLVENT: Dioxane/H₂O | 1H NMR (400 MHz, MeOD-d4) δ ppm: 9.00 (d, J = 8.38 Hz, 2H), 8.75 (d, J = 2.45 Hz, 1H), 8.25 (s, 1H), 6.62 (dd, J = 6.48, 13.08 Hz, 1H), 4.02-4.20 (m, 1H), 3.45 (br dd, J = 1.47, 3.42 Hz, 2H), 3.05-3.08 (m, 1H), 3.02 (s, 3H), 2.97 (s, 3H), 2.70-2.81 (m, 1H), 2.36-2.46 (m, 1H), 2.22-2.35 (m, 4H), 2.02-2.19 (m, 2H), 1.80 (br s, 1H), 1.52 (brs, 1H), 1.33-1.45 (m, 1H)<br>MS: 589.2 ([M + H]+) |
| 1.245 | 6-[5,6-difluoro-4-(cis-1-methyl-2,3,3a,5,6,6a-hexahydro-pyrrolo[3,2-b]pyrrol-4-yl)-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C42<br>BORONIC REAGENT: Intermediate B2<br>CATALYST: cataCXium ® A Pd G2 (Sigma-Aldrich, Catalog #: 761311)<br>SOLVENT: Dioxane/H₂O | 1H NMR (400 MHz, MeOD-d4) δ ppm: 9.12 (s, 1H), 9.04 (d, J = 2.20 Hz, 1H), 8.79 (d, J = 2.32 Hz, 1H), 8.12 (s, 1H), 6.59 (dd, J = 6.42, 13.14 Hz, 1H), 4.68 (br s, 1H), 4.21 (s, 3H), 3.08-3.17 (m, 1H), 3.00 (s, 3H), 2.90 (br s, 2H), 2.31-2.41 (m, 4H), 1.92-2.09 (m, 1H), 1.78 (br d, J = 12.23 Hz, 1H), 1.68 (br d, J = 3.91 Hz, 1H), 1.53 (m, 1H), 1.31 (m, 1H), 0.86-096 (m, 1H)<br>MS: 560.2 ([M + H]+) |
| 1.246 | 6-[5,6-difluoro-4-(4-methyl-3,3a,5,6,7,7a-hexahydro-2H-pyrrolo[3,2-b]pyridin-1-yl)-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C43<br>BORONIC REAGENT: Intermediate B2<br>CATALYST: cataCXium ® A Pd G2 (Sigma-Aldrich, Catalog #: 761311)<br>SOLVENT: Dioxane/H₂O | 1H NMR (400 MHz, MeOD-d4) δ ppm: 8.99 (s, 1H), 8.93 (d, J = 1.96 Hz, 1H), 8.78 (d, J = 2.20 Hz, 1H), 8.16 (s, 1H), 6.61 (dd, J = 6.05, 13.14 Hz, 1H), 4.16 (s, 3H), 3.98 (br s, 1H), 3.19-3.31 (m, 1H), 3.07-3.19 (m, 1H), 3.00 (s, 3H), 2.45 (br s, 1H), 2.25-2.33 (m, 4H), 2.21 (br s, 1H), 1.91-2.09 (m, 1H), 1.53 (m, 3H), 1.31-1.39 (m, 2H)<br>MS: 574.2 ([M + H]+) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.247 | 6-[5,6-difluoro-4-(4-methyl-3,3a,5,6,7,7a-hexahydro-2H-pyrrolo[3,2-b]pyridin-1-yl)-8-(methylamino)-9H-pyrido[2,3-b]indol-3-yl]-1-(methylamino)-4-oxo-1,8-naphthyridine-3-carboxylic acid | CORE: Intermediate A3<br>AMINE: Intermediate C43<br>BORONIC REAGENT: Intermediate B23<br>CATALYST: cataCXium ® A Pd G2 (Sigma-Aldrich, Catalog #: 761311)<br>SOLVENT: Dioxane/H$_2$O | 1H NMR (400 MHz, MeOD-d4) δ ppm: 9.07 (s, 1H), 9.01 (d, J = 2.32 Hz, 1H), 8.79 (d, J = 2.20 Hz, 1H), 8.21 (s, 1H), 6.61 (dd, J = 6.17, 13.14 Hz, 1H), 4.03 (m, 1H), 3.35-3.41 (m, 1H), 3.14-3.30 (m, 2H), 3.08 (s, 3H), 3.00 (s, 3H), 2.52 (m, 1H), 2.41 (m, 1H), 2.36 (s, 3H), 2.25 (m, 1H), 2.04 (m, 1H), 1.47-1.62 (m, 2H), 1.21-1.40 (m, 2H)<br>MS: 589.2 ([M + H]+) |
| 1.248 | 6-[5,6-difluoro-8-(methylamino)-4-(cis-6-methyl-2,6-diazabicyclo[3.2.0]heptan-2-yl)-9H-pyrido[2,3-b]indol-3-yl]-1-methyl-4-oxo-1,8-naphthyridine-3-carboxylic acid | CORE: Intermediate A3<br>AMINE: Intermediate C44<br>BORONIC REAGENT Intermediate B2<br>CATALYST: cataCXium ® A Pd G2 (Sigma-Aldrich, Catalog #: 761311)<br>SOLVENT: Dioxane/H$_2$O | 1H NMR (400 MHz, MeOD-d4) δ ppm: 9.23 (br s, 1H), 9.14 (br s, 1H), 8.87 (br s, 1H), 8.24 (s, 1H), 6.63 (m, 1H), 3.35-3.61 (m, 3H), 3.09-3.31 (m, 3H), 2.91-3.06 (m, 6H), 2.88 (br s, 2H), 2.08-2.45 (m, 3H)<br>MS: 546.2 ([M + H]+) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.249 | 6-[5,6-difluoro-4-(cis-1-methyl-2,3,3a,5,6,6a-hexahydropyrrolo[3,2-b]pyrrol-4-yl)-8-(methylamino)-9H-pyrido[2,3-b]indol-3-yl]-1-(methylamino)-4-oxo-1,8-naphthyridine-3-carboxylic acid | CORE: Intermediate A3<br>AMINE: Intermediate C42<br>BORONIC REAGENT: Intermediate B23<br>CATALYST: cataCXium ® A Pd G2 (Sigma-Aldrich, Catalog #: 761311)<br>SOLVENT: Dioxane/H$_2$O | 1H NMR (400 MHz, MeOD-d4) δ ppm: 9.23 (br s, 1H), 9.14 (br s, 1H), 8.87 (br s, 1H), 8.24 (s, 1H), 6.63 (dd, J = 6.36, 13.20 Hz, 1H), 3.35-3.61 (m, 3H), 3.09-3.31 (m, 4H), 2.91-3.06 (m, 6H), 2.88 (m, 3H), 2.08-2.45 (m, 3H)<br>MS: 575.2 ([M + H]+) |
| 1.250 | 6-[5,6-difluoro-8-(methylamino)-4-[(2S)-2-methylmorpholin-4-yl]-9H-pyrido[2,3-b]indol-3-yl]-4-oxo-1-[(1S)-2-hydroxy-1-methyl-ethyl]-1,8-naphthyridine-3-carboxylic acid | CORE: Intermediate A3<br>AMINE: (2S)-2-methylmorpholine<br>BORONIC REAGENT: Intermediate B52<br>CATALYST: cataCXium ® A Pd G2 (Sigma-Aldrich, Catalog #: 761311)<br>SOLVENT: Dioxane/H$_2$O | 1H NMR (400 MHz, DMSO-d6) δ ppm: 9.05-9.16 (m, 2H), 8.75 (d, J = 2.20 Hz, 1H), 8.27 (s, 1H), 6.63 (m, 1H), 5.94 (br s, 1H), 5.71 (br d, J = 4.65 Hz, 1H), 5.23 (br s, 1H), 3.90 (m, 1H), 3.82 (m, 1H), 3.64 (m, 1H), 3.05 (m, 1H), 2.91 (m, 5H), 2.54-2.64 (m, 2H), 2.33 (m, 1H), 1.76 (s, 1H), 1.60 (d, J = 6.97 Hz, 3H), 0.92 (d, J = 6.24 Hz, 3H)<br>MS: 579.2 ([M + H]+) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.251 | (1R)-6-[5,6-difluoro-8-(methylamino)-4-[(2S)-2-methyl-morpholin-4-yl]-9H-pyrido[2,3-b]indol-3-yl]-4-oxo-1-pyrrolidin-3-yl-1,8-naphthyridine-3-carboxylic acid | CORE: Intermediate A3<br>AMINE: (2S)-2-methylmorpholine<br>BORONIC REAGENT: Intermediate B37<br>CATALYST: cataCXium® A Pd G2 (Sigma-Aldrich, Catalog #: 761311)<br>SOLVENT: Dioxane/H$_2$O | 1H NMR (400 MHz, MeOD-d4) δ ppm: 8.94 (s, 1H), 8.82-8.87 (m, 1H), 8.68-8.76 (m, 1H), 8.45 (s, 1H), 8.00-8.15 (m, 1H), 6.44-6.58 (m, 1H), 3.57-3.71 (m, 2H), 3.29-3.43 (m, 2H), 2.94-3.08 (m, 2H), 2.89 (s, 3H), 2.60-2.71 (m, 1H), 2.39-2.50 (m, 2H), 2.13-2.28 (m, 1H), 1.14-1.28 (m, 2H), 0.83-0.94 (m, 5H)<br>MS: 590.2 ([M + H]+) |
| 1.252 | 6-[5,6-difluoro-8-(methylamino)-4-[cis--6-methyl-3,6-diazabicyclo[3.2.0]heptan-3-yl]-9H-pyrido[2,3-b]indol-3-yl]-1-methyl-4-oxo-1,8-naphthyridine-3-carboxylic acid | CORE: Intermediate A3<br>AMINE: (cis-6-methyl-3,6-diaza-bicyclo[3.2.0]heptane<br>BORONIC REAGENT: Intermediate B2<br>CATALYST: cataCXium® A Pd G2 (Sigma-Aldrich, Catalog #: 761311)<br>SOLVENT: Dioxane/H$_2$O | 1H NMR (400 MHz, MeOD-d4) δ ppm: 9.28 (s, 1H), 9.21 (br s, 1H), 8.93 (d, J = 2.32 Hz, 1H), 8.52 (s, 1H), 6.70 (dd, J = 6.11, 13.33 Hz, 1H), 4.25 (s, 3H), 3.69 (m, 2H), 3.50 (m, 2H), 3.25 (m, 2H), 3.05 (m, 2H), 3.03 (s, 3H), 2.11 (m, 3H)<br>MS: 546.2 ([M + H]+) |
| 1.253 | 6-[4-[(3S)-3-(dimethylamino)pyrrolidin-1-yl]-6-fluoro-8-(methylamino)-9H-pyrido[2,3-b]indol-3-yl]-1-methyl-4-oxo-1,8-naphthyridine-3-carboxylic acid | CORE: Intermediate A1<br>AMINE: (3S)-N,N-dimethylpyrrolidin-3-amine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: $^1$H NMR (DMSO-d$_6$) δ: 11.55 (s, 1H), 9.29 (s, 1H), 9.12 (d, 1H), 8.67 (d, 1H), 8.23 (s, 1H), 6.87 (br d, 1H), 6.46 (m, 1H), 5.92 (br d, 1H), 4.18 (s, 3H), 3.26-3.16 (m, 4H), 3.14-3.02 (m, 2H), 2.93 (d, 3H), 2.33 (br s, 6H), 2.19 (br s, 1H)<br>MS: 530.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.254 | 6-[4-[(3S)-3-(dimethylamino)pyrrolidin-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: (3S)-N,N-dimethylpyrrolidin-3-amine<br>BORONIC REAGENT: Intermediate B2<br>CATALYST: Pd-Ad$_2$nBuP Biphenyl Precat (CAS#: 1375477-29-4)<br>SOLVENT: EtOH/H$_2$O | $^1$H NMR (400 MHz, DMSO-d6): δ ppm: 11.85 (s, 1H), 9.25 (s, 1H), 9.07 (d, 1H), 8.64 (d, 1H), 8.26 (s, 1H), 6.56 (m, 1H), 4.12 (s, 3H), 3.86-3.74 (m, 1H), 3.54 (br m, 1H), 3.11 (br s, 2H), 3.00 (m, 1H), 2.84 (s, 3H), 2.68 (d, 3H), 2.56 (br d, 3H), 2.29-2.20 (m, 1H), 1.94-1.82 (m, 1H)<br>MS: 548.3 ([M + H]$^+$) |
| 1.255 | 6-[4-[(3S)-3-[(dimethylamino)methyl]pyrrolidin-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: (R)-N,N-dimethyl-1-(pyrrolidin-3-yl)methanamine dihydrochloride<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 11.85 (s, 1H), 9.31 (s, 1H), 9.13 (d, 2H), 8.70 (d, 1H), 8.32 (s, 1H), 6.61 (m, 1H), 4.18 (s, 3H), 3.25-3.26 (m, 3H), 3.03-3.11 (m, 2H), 2.83-2.93 (m, 5H), 2.72 (m, 6H), 2.09 (br s, 1H), 1.56-1.65 (m, 1H)<br>MS: 562.2 ([M + H]$^+$) |
| 1.256 | 6-[4-[(3R)-3-[(dimethylamino)methyl]pyrrolidin-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: (S)-N,N-dimethyl-1-(pyrrolidin-3-yl)methanamine dihydrochloride<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 8.87 (s, 2H), 8.62 (s, 1H), 8.10 (s, 1H), 6.47 (m, 1H), 4.04 (s, 3H), 3.46-3.33 (m, 1H), 3.17-2.95 (m, 2H), 2.94-2.71 (m, 4H), 2.51 (m, 3H), 2.29 (s, 6H), 1.97 (br d, 1H), 1.54 (br d, 1H)<br>MS: 562.3 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.257 | 6-[4-[(3R)-3-(dimethylamino)pyrrolidin-1-yl]-5,6-difluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: (3R)-N,N-dimethylpyrrolidin-3-amine<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 11.88 (s, 1H), 9.73 (br s, 1H), 9.65-9.79 (m, 1H), 8.94-9.15 (m, 2H), 8.58-8.72 (m, 1H), 8.58-8.72 (m, 1H), 8.66 (d, 1H), 8.29 (s, 1H), 6.57 (m, 1H), 3.76-3.86 (m, 1H), 3.30 (m, 1H), 3.11 (br d, 2H), 3.00-2.89 (m, 4H), 2.84 (m, 3H), 2.67 (br d, 3H), 2.56 (br d, 3H), 2.26 (m, 1H), 1.90 (m, 1H)<br>MS: 563.3 ([M + H]$^+$) |
| 1.258 | 6-[4-[(3R)-3-(dimethylamino)pyrrolidin-1-yl]-5,6-difluoro-8-(methylamino)-9H-pyrido[2,3-b]indol-3-yl]-1-(ethylamino)-4-oxo-1,8-naphthyridine-3-carboxylic acid | CORE: Intermediate A3<br>AMINE: (3R)-N,N-dimethylpyrrolidin-3-amine<br>BORONIC REAGENT: Intermediate B35<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 11.86 (s, 1H), 9.63 (br s, 1H), 9.09 (d, 1H), 8.96 (s, 1H), 8.65 (d, 1H), 8.28 (s, 1H), 6.57 (m, 1H), 3.81 (br m, 1H), 3.53 (m, 1H), 3.23 (m, 1H), 3.11 (m, 1H), 2.95 (m, 1H), 2.84 (s, 3H), 2.67 (br d, 3H), 2.55 (br d, 3H), 2.26 (m, 2H), 1.92 (m, 2H), 1.08 (m, 3H)<br>MS: 577.4 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.259 | 6-[6-fluoro-8-(methylamino)-4-pyrrolidin-1-yl-9H-pyrido[2,3-b]indol-3-yl]-4-oxo-1-pyrrolidin-3-yl-1,8-naphthyridine-3-carboxylic acid | CORE: Intermediate A1<br>AMINE: pyrrolidine<br>BORONIC REAGENT: Intermediate B6<br>CATALYST: Xphos Pd G2(CAS: 1310584-14-5)<br>SOLVENT: THF/H$_2$O | $^1$H NMR (400 MHz, DMSO-d6): δ ppm: 11.72 (br s, 1H), 9.23 (s, 1H), 9.11 (d, 1H), 8.73 (d, 1H), 8.22 (s, 1H), 6.81 (m, 1H), 6.46 (m, 1H), 5.93-6.08 (m, 1H), 3.77 (br d, 3H), 3.20-3.27 (m, 5H), 2.87-2.97 (m, 4H), 2.60-2.70 (m, 1H), 1.79-1.91 (m, 5H)<br>MS: 542.3 ([M + H]$^+$) |
| 1.260 | 6-[4-[cis-1-(3-hydroxypropyl)-2,3,3a,4,6,6a-hexahydropyrrolo[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C45<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, MeOD-d4) δ ppm: 9.17 (m, 1H), 9.11 (m, 1H), 8.81 (m, 1H), 8.35 (m, 1H), 6.66 (m, 1H), 4.36 (m, 1H), 4.24 (s, 3H), 3.98 (m, 1H), 3.55 (m, 4H), 3.36 (m, 3H), 3.31-3.24 (m, 2H), 3.11 (m, 1H), 3.01 (s, 3H), 2.36 (m, 1H), 1.85 (m, 3H).<br>MS: 604.3 ([M + H]$^+$). |
| 1.261 | 6-[4-[cis-1-(2-hydroxyethyl)-2,3,3a,4,6,6a-hexahydropyrrolo[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C46<br>BORONIC REAGENT Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.91 (m, 1H), 9.45 (m, 1H), 9.31 (m, 1H), 9.12 (m, 1H), 8.79 (m, 1H), 8.28 (m, 1H), 6.63 (m, 1H), 4.32 (m, 1H), 4.19 (m, 3H), 3.83 (m, 1H), 3.70-3.62 (m, 4H), 3.25-3.07 (m, 4H), 2.91 (s, 3H), 2.82 (m, 1H), 2.53 (m, 2H), 2.15 (m, 1H), 1.61 (m, 1H).<br>$^1$H NMR (400 MHz, DMSO-d6, T = 80° C.) δ ppm: 11.73 (s, 1H), 9.21 (s, 1H), 9.13 (d, J = 2.4 Hz, 1H), 8.74 (d, J = 2.4 Hz, 1H), 8.35 (s, 1H), 6.65-6.58 (m, 1H), 6.62 (m, 1H), 4.39 (br s, 1H), 4.21 (s, 3H), 3.83 (m, 1H), 3.74-3.58 (m, 4H), 3.23-3.22 (m, 4H), 2.95 (s, 3H), 2.94-2.87 (m, 1H), 2.53 (m, 2H), 2.18 (m, 1H), 1.64 (m, 1H).<br>MS: 590.3 ([M + H]$^+$). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.262 | 6-(4-(1-(dimethylamino)-6-azaspiro[3.4]octan-6-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C47<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6) δ ppm 14.54~14.96 (m, 1 H), 11.86 (s, 1 H), 9.30 (s, 1 H), 9.28~9.35 (m, 1 H), 9.06~9.10 (m, 1 H), 8.62~8.65 (m, 1 H), 8.30 (s, 1 H), 6.54~6.68 (m, 1 H), 4.17 (s, 3 H) 3.16~3.26 (m, 1 H), 2.99~3.06 (m, 1 H), 2.91 (s, 3 H) 2.75~2.79 (m, 1 H), 2.66~2.70 (m, 1 H), 2.60 (br s, 6 H) 2.33 (s, 1 H), 2.07~2.08 (m, 1 H), 2.02~2.06 (m, 1 H), 1.90~1.99 (m, 2 H), 1.69~1.77 (m, 1 H), 1.36~1.46 (m, 1 H).<br>MS: 534.2 ([M + H]+) |
| 1.263 | 6-(4-((1R,5S,6S)-6-(dimethylamino)-3-azabicyclo[3.1.0]hexan-3-yl)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: Intermediate C48<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6) δ ppm: 11.78 (s, 1H), 9.43 (s, 1H), 9.07 (d = 2.4 Hz, 1H), 8.62 (d, J = 2.4 Hz, 1H), 8.38 (s, 1H), 8.27 (s, 1H), 7.37 (s, 1H), 6.62-6.57 (m, 1H), 6.08 (s, 2H), 2.91 (s, 3H), 2.73 (s, 6H).<br>MS: 546.4 ([M + H]$^+$). |
| 1.264 | 6-[4-[cis-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-(methylamino)-4-oxo-1,8-naphthyridine-3-carboxylic acid | CORE: Intermediate A11<br>AMINE: IntermediaeC8<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 11.75 (s, 1 H) 9.03-9.21 (m, 2 H) 8.73 (br d, J = 12.3 Hz, 1 H) 8.24 (br s, 1 H) 7.01-7.27 (m, 2 H) 6.61 (s, 1 H) 4.17 (br s, 1 H) 3.99 (br s, 1 H) 3.81 (br s, 1 H) 3.69 (br s, 1 H) 3.14-3.31 (m, 1 H) 2.99 (s, 1 H) 2.97-3.04 (m, 1 H) 2.97-3.04 (m, 1 H) 2.94 (s, 3 H) 2.77 (br s, 1 H) 2.67 (br d, J = 8.3 Hz, 3 H) 2.33 (br s, 1 H) 2.17 (br s, 1 H) 1.94 (br s, 1 H) 1.84 (br s, 1 H)<br>MS: 573.3 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.265 | 6-[4-[cis-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-methyl-4-oxo-1,8-naphthyridine-3-carboxylic acid | CORE: Intermediate A11<br>AMINE: Intermediate C8<br>BORONIC REAGENT: Intermediate B2<br>CATALYST Pd-Ad$_2$nBuP Biphenyl Precat (CAS#: 1375477-29-4)<br>SOLVENT: THF/H$_2$O | $^1$H NMR (400 MHz, Methanol-d4): δ ppm: 11.76 (s, 1 H), 9.73 (s, 1 H), 9.31 (s, 1 H), 9.10-9.15 (m, 1 H), 8.67-8.72 (m, 1 H), 8.19-8.22 (m, 1 H), 7.12-7.17 (m, 1 H), 6.61 (s, 1 H), 4.19 (m, 1 H), 4.00 (m, 1 H), 3.98 (m, 1 H), 3.41 (m, 2 H), 3.23-3.27 (m, 1 H), 2.99-3.01 (m, 1 H), 2.94 (s, 3 H), 2.78 (m, 1 H), 2.64-2.69 (m, 3 H), 2.29-2.33 (m, 1 H), 2.13 (m, 1 H), 1.96 (m, 1 H)<br>MS: 558.3 ([M + H]$^+$) |
| 1.266 | 6-[4-[cis-5-methyl-2,3,3a,4,6,6a-hexahydropyrrolo[2,3-c]pyrrol-1-yl]-6-chloro-5-fluoro-8-(methylamino)-9H-pyrido[2,3-b]indol-3-yl]-1-(methylamino)-4-oxo-1,8-naphthyridine-3-carboxylic acid | CORE: Intermediate A14<br>AMINE: Intermediate C8<br>BORONIC REAGENT: Intermediate B23<br>CATALYST 1: cataCXium ® A Pd G2 (Sigma-Aldrich, Catalog #: 761311)<br>SOLVENT: THF/H$_2$O | $^1$H NMR (400 MHz, DMSO-d$_6$) δ = 12.13 (br d, J = 17.2 Hz, 1H), 9.83 (br s, 1H), 9.34 (br s, 1H), 9.14 (br d, J = 5.3 Hz, 1H), 9.08 (s, 1H), 8.73 (s, 1H), 8.35-8.25 (m, 1H), 6.72-6.55 (m, 1H), 4.27-4.05 (m, 1H), 3.44-3.40 (m, 2H), 3.21-3.07 (m, 2H), 2.99 (s, 3H), 2.92 (s, 3H), 2.88-2.76 (m, 2H), 2.69-2.60 (m, 2H), 2.71-2.60 (m, 1H), 2.20-2.03 (m, 1H), 1.91-1.71 (m, 1H)<br>MS: 591.2 ([M + H]$^+$) |
| 1.267 | 6-[4-[cis-5-methyl-2,3,3a,4,6,6a-hexahydropyrrolo[2,3-c]pyrrol-1-yl]-6-chloro-5-fluoro-8-(methylamino)-9H-pyrido[2,3-b]indol-3-yl]-1-methyl-4-oxo-1,8-naphthyridine-3-carboxylic acid | CORE: Intermediate A14<br>AMINE: Intermediate C8<br>BORONIC REAGENT: Intermediate B2<br>CATALYST 1: cataCXium ® A Pd G2 (Sigma-Aldrich, Catalog #: 761311)<br>SOLVENT: THF/H$_2$O | $^1$H NMR (400 MHz, DMSO-d$_6$) δ = 12.12 (br d, J = 17.2 Hz, 1H), 9.82 (br s, 1H), 9.36 (br s, 1H), 9.31 (s, 1H), 9.13 (br s, 1H), 8.70 (s, 1H), 8.35-8.19 (m, 1H), 6.63 (br t, J = 5.5 Hz, 1H), 4.29-3.90 (m, 4H), 3.17-3.08 (m, 3H), 2.91 (s, 4H), 2.83 (br s, 2H), 2.67 (br s, 4H), 2.24-1.97 (m, 1H), 1.88-1.75 (m, 1H)<br>MS: 576.2 ([M + H]$^+$) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.268 | 6-[4-[cis-5-methyl-2,3,3a,4,6,6a-hexahydropyrrolo[2,3-c]pyrrol-1-yl]-5-chloro-6-fluoro-8-(methylamino)-9H-pyrido[2,3-b]indol-3-yl]-1-(methylamino)-4-oxo-1,8-naphthyridine-3-carboxylic acid | CORE: Intermediate A20<br>AMINE: Intermediate C8<br>BORONIC REAGENT: Intermediate B23<br>CATALYST: Pd-Ad₂nBuP Biphenyl Precat (CAS#: 1375477-29-4)<br>SOLVENT: THF/H₂O | ¹H NMR (400 MHz, DMSO-d₆) δ ppm: 11.99 (br s, 1 H), 9.63 (br s, 1 H), 9.22 (br s, 1 H), 9.06 (s, 1 H), 8.75 (s, 1 H), 8.09 (br s, 1 H), 6.64 (d, J = 12.4 Hz, 1 H), 4.63-4.85 (m, 1 H), 3.09-3.28 (m, 5 H), 2.98 (s, 3 H), 2.92 (s, 3 H), 2.69 (br s, 5 H), 1.91-2.18 (m, 2 H), 1.55-1.70 (m, 1 H).<br>MS: 591.2 ([M + H]⁺) |
| 1.269 | 6-(5-chloro-6-fluoro-8-(methylamino)-4-morpholino-9H-pyrido[2,3-b]indol-3-yl)-1-methyl-4-oxo-1,4-dihydro-1,8-naphthyridine-3-carboxylic acid | CORE: Intermediate A20<br>AMINE: morpholine<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, DMSO-d₆) δ ppm: 11.84 (br s, 1 H), 9.24 (s, 1 H), 9.14 (s, 1 H), 8.78 (s, 1 H), 8.09 (s, 1 H), 6.61 (d, J = 12.2 Hz, 1 H), 4.16 (s, 3 H), 3.00-3.21 (m, 5 H), 2.95 (br s, 2 H), 2.91 (s, 3 H).<br>MS: 537.2 ([M + H]⁺) |
| 1.270 | 6-[4-[cis-5-methyl-2,3,3a,4,6,6a-hexahydropyrrolo[2,3-c]pyrrol-1-yl]-5-chloro-6-fluoro-8-(methylamino)-9H-pyrido[2,3-b]indol-3-yl]-1-methyl-4-oxo-1,8-naphthyridine-3-carboxylic acid | CORE: Intermediate A20<br>AMINE: Intermediate C8<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, DMSO-d₆) δ ppm: 11.93 (br s, 1 H) 9.51 (br s, 1 H) 9.06-9.34 (m, 2 H) 8.71 (br s, 1 H) 8.05 (br s, 1 H) 6.64 (br d, J = 12.3 Hz, 1 H) 4.18 (s, 3 H) 2.92 (s, 3 H) 2.63-2.71 (m, 3 H) 2.59-2.80 (m, 1 H) 1.88-2.19 (m, 1 H) 1.60 (br s, 1 H)<br>MS: 576.3 ([M + H]⁺) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.272 | 6-[4-(3a,5-dimethyl-3,4,6,6a-tetrahydro-2H-pyrrolo[2,3-c]pyrrol-1-yl)-6-fluoro-8-(methylamino)-9H-pyrido[2,3-b]indol-3-yl]-1-methyl-4-oxo-1,8-naphthyridine-3-carboxylic acid | CORE: Intermediate A1<br>AMINE: Intermediate C49<br>BORONIC REAGENT: Intermediate B2<br>CATALYST: Pd-Ad₂nBuP Biphenyl Precat (CAS#: 1375477-29-4)<br>SOLVENT: dioxane/H₂O | ¹H NMR (400 MHz, DMSO-d6) δ ppm 9.19 (s, 1 H), 9.12 (d, J = 2.3 Hz, 1 H), 8.74 (d, J = 2.3 Hz, 1 H), 8.22 (s, 1 H), 6.53 (dd, J = 12.0, 2.0 Hz, 1 H), 4.21 (s, 3 H), 3.25~3.77 (m, 5 H), 2.90~3.23 (m, 5 H), 2.60 (br s, 3 H), 2.13~2.47 (m, 1 H), 1.81~1.93 (m, 1 H), 0.94~1.25 (m, 3 H) MS (ESI): 556.3 ([M + H]⁺), 278.8 ([M/2 + H]⁺). |
| 1.273 | 6-[4-(3a,5-dimethyl-3,4,6,6a-tetrahydro-2H-pyrrolo[2,3-c]pyrrol-1-yl)-6-fluoro-8-(methylamino)-9H-pyrido[2,3-b]indol-3-yl]-1-(methylamino)-4-oxo-1,8-naphthyridine-3-carboxylic acid | CORE: Intermediate A1<br>AMINE: Intermediate C49<br>BORONIC REAGENT: Intermediate B23<br>CATALYST: Pd-Ad₂nBuP Biphenyl Precat (CAS#: 1375477-29-4)<br>SOLVENT: dioxane/H₂O | ¹H NMR (400 MHz, DMSO-d6) δ ppm 9.13 (s, 1 H), 9.04 (s, 1 H), 8.78 (d, J = 1.8 Hz, 1 H), 8.23 (s, 1 H), 6.54 (br d, J = 11.8 Hz, 1 H), 3.19-3.72 (m, 5 H), 2.92-3.15 (m, 7 H), 2.61 (br s, 3 H), 2.05-2.49 (m, 1 H), 1.77-1.94 (m, 1 H), 1.14 (br s, 3 H) MS (ESI): 571.3 ([M + H]⁺), 286.4 ([M/2 + H]⁺). |
| 1.274 | 6-[4-[cis-5-methyl-2,3,3a,4,6,6a-hexahydropyrrolo[2,3-c]pyrrol-1-yl]-5-cyano-6-fluoro-8-(methylamino)-9H-pyrido[2,3-b]indol-3-yl]-1-methyl-4-oxo-1,8-naphthyridine-3-carboxylic acid | CORE: Intermediate A16<br>AMINE: Intermediate C8<br>BORONIC REAGENT: Intermediate B2<br>CATALYST: Pd-Ad₂nBuP Biphenyl Precat (CAS#: 1375477-29-4)<br>SOLVENT: dioxane/H₂O | ¹H NMR (400 MHz, DMSO-d6) δ ppm 9.21 (s, 1 H), 9.15 (d, J = 2.0 Hz, 1 H), 8.73 (d, J = 2.3 Hz, 1 H), 8.17 (s, 1 H), 6.66 (d, J = 13.1 Hz, 1 H), 4.60 (br d, J = 6.8 Hz, 1 H), 4.22 (s, 3 H), 2.96~3.63 (m, 9 H), 2.75 (s, 3 H), 2.52~2.57 (m, 1 H), 2.11~2.28 (m, 1 H), 1.86 (br s, 1 H). MS (ESI): 567.2 ([M + H]⁺), 284.2 ([M/2 + H]⁺). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.275 | 6-[4-[cis-5-methyl-2,3,3a,4,6,6a-hexahydropyrrolo[2,3-c]pyrrol-1-yl]-5-cyano-6-fluoro-8-(methylamino)-9H-pyrido[2,3-b]indol-3-yl]-1-(methylamino)-4-oxo-1,8-naphthyridine-3-carboxylic acid | CORE: Intermediate A16<br>AMINE: Intermediate C8<br>BORONIC REAGENT: Intermediate B23<br>CATALYST: Pd-Ad$_2$nBuP Biphenyl Precat (CAS#: 1375477-29-4)<br>SOLVENT: dioxane/H$_2$O | $^1$H NMR (400 MHz, DMSO-d6) δ ppm 9.16 (d, J = 2.3 Hz, 1 H), 9.01~9.08 (m, 1 H), 8.76 (d, J = 2.3 Hz, 1H), 8.19 (s, 1 H), 6.66 (d, J = 13.1 Hz, 1 H), 4.60 (q, J = 6.5 Hz, 1 H), 3.29~3.53 (m, 3 H), 2.926~3.305 (m, 10 H), 2.75 (s, 3 H), 2.14~2.27 (m, 1 H), 1.87 (br s, 1 H).<br>MS (ESI): 582.2 ([M + H]$^+$), 291.8 ([M/2 + H]$^+$). |
| 1.276 | 6-[6-chloro-4-(cis-3-hydroxy-2,3,3a,4,6,6a-hexahydro-furo[2,3-c]pyrrol-5-yl]-8-(methylamino)-9H-pyrido[2,3-b]indol-3-yl]-1-methyl-4-oxo-1,8-naphthyridine-3-carboxylic acid | CORE: Intermediate A11<br>AMINE: Intermediate C52<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.48-15.06 (m, 1H), 11.67 (s, 1H), 9.29 (s, 1H), 9.12 (d, J = 2.45 Hz, 1H), 8.67 (d, J = 2.45 Hz, 1H), 8.17 (s, 1H), 7.71 (d, J = 1.47 Hz, 1H), 6.56 (d, J = 1.71 Hz, 1H), 5.65-6.16 (m, 1H), 4.73-5.09 (m, 1H), 4.59 (br t, J = 4.77 Hz, 1H), 4.27 (q, J = 5.99 Hz, 1H), 4.18 (s, 3H), 3.73-3.82 (m, 2H), 3.63 (dd, J = 5.99, 8.56 Hz, 1H), 3.22-3.31 (m, 1H), 2.93 (s, 3H), 2.74-2.85 (m, 2H)<br>MS: 561.2 ([M + H]$^+$) |
| 1.277 | 6-[6-chloro-4-[cis-3-(dimethylamino)-2,3,3a,4,6,6a-hexahydro-furo[2,3-c]pyrrol-5-yl]-8-(methylamino)-9H-pyrido[2,3-b]indol-3-yl]-1-methyl-4-oxo-1,8-naphthyridine-3-carboxylic acid | CORE: Intermediate A11<br>AMINE: Intermediate C51<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.79 (br s, 1H), 11.73 (s, 1H), 9.45 (br s, 1H), 9.32 (s, 1H), 9.12 (d, J = 2.32 Hz, 1H), 8.68 (d, J = 2.32 Hz, 1H), 8.27 (s, 1H), 7.66 (s, 1H), 6.59 (d, J = 1.59 Hz, 1H), 5.89 (br s, 1H), 4.81 (br s, 1H), 4.19 (s, 4H), 3.86-4.08 (m, 3H), 3.26-3.33 (m, 1H), 3.21 (br d, J = 10.03 Hz, 1H), 3.13 (br s, 1H), 2.97-3.05 (m, 1H), 2.90-2.97 (m, 3H), 2.75 (br d, J = 8.56 Hz, 6H)<br>MS: 588.3 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.278 | 6-[6-chloro-8-(methylamino)-4-(cis-8-methyl-3,8-diazabicyclo[4.2.0]octan-3-yl)-9H-pyrido[2,3-b]indol-3-yl]-1-methyl-4-oxo-1,8-naphthyridine-3-carboxylic acid | CORE: Intermediate A11<br>AMINE: cis-8-methyl-3,8-diaza-bicyclo[4.2.0]octane<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.76 (s, 1H), 11.61 (br s, 1H), 9.30 (s, 1H), 9.09 (br s, 1H), 8.66 (br s, 1H), 8.18 (br s, 1H), 8.14 (s, 1H), 6.53-6.61 (m, 1H), 5.81 (br s, 1H), 4.19 (s, 4H), 3.60-3.82 (m, 1H), 3.06 (br s, 3H), 2.93 (d, J = 4.77 Hz, 3H), 2.74 (br s, 2H), 2.31-2.46 (m, 2H), 2.07-2.26 (m, 1H), 1.72-2.05 (m, 3H)<br>MS: 588.2 ([M + H]$^+$) |
| 1.279 | 6-[4-[(cis-5-ethyl-2,3,3a,4,6,6a-hexahydropyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C53<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.23-15.27 (m, 1H), 11.77 (br s, 1H), 9.26 (s, 1H), 9.17 (d, J = 2.32 Hz, 1H), 8.70 (d, J = 2.20 Hz, 1H), 8.25 (s, 1H), 8.14 (s, 1H), 6.58 (dd, J = 6.24, 13.45 Hz, 1H), 5.70 (br s, 1H), 4.47 (br s, 1H), 4.16 (s, 3H), 2.99 (br s, 2H), 2.77-2.93 (m, 5H), 2.07-2.27 (m, 3H), 1.92-2.07 (m, 1H), 1.68-1.83 (m, 1H), 1.54-1.68 (m, 1H), 1.23 (br s, 1H), 0.84-0.95 (m, 3H)<br>MS: 574.3 ([M + H]$^+$) |

TABLE 1-continued

Compound synthesis and characterization

| No. | Compound Name and Structure | CORE, AMINE, BORONIC REAGENT, CATALYST and SOLVENT | ¹H NMR and MS (ESI) |
|---|---|---|---|
| 1.280 | 6-[4-(dimethylamino)-5,6-difluoro-8-(methylamino)-9H-pyrido[2,3-b]indol-3-yl]-1-[(3S)-1-ethylpyrrolidin-3-yl]-4-oxo-1,8-naphthyridine-3-carboxylic acid | CORE: Intermediate A3<br>AMINE: N-methylmethanamine hydrochloride<br>BORONIC REAGENT: Intermediate B51<br>CATALYST: Pd-Ad₂nBuP Biphenyl Precat (CAS#: 1375477-29-4)<br>SOLVENT: THF/H₂O | ¹H NMR (400 MHz, DMSO-d₆): δ ppm: 14.71 (br s, 1H), 11.74 (br s, 1H), 9.55 (s, 1H), 9.06 (d, J = 2.32 Hz, 1H), 8.61 (d, J = 2.32 Hz, 1H), 8.25 (s, 1H), 8.14 (s, 1H), 6.51-6.67 (m, 1H), 6.25 (br s, 1H), 5.66 (br d, J = 4.52 Hz, 1H), 2.90 (br d, J = 4.65 Hz, 3H), 2.73 (d, J = 1.83 Hz, 6H), 2.56-2.69 (m, 4H), 2.26 (br d, J = 8.31 Hz, 1H), 1.93-2.08 (m, 2H), 1.23 (br s, 2H), 1.11-1.20 (m, 3H)<br>MS: 562.2 ([M + H]⁺) |
| 1.281 | 6-[4-[cis-1-cyclopropyl-2,3,3a,4,6,6a-hexahydropyrrolo[2,3-c]pyrrol-5-yl]-5,6-difluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: Intermediate C54<br>BORONIC REAGENT: Intermediate B23<br>CATALYST: Pd-Ad₂nBuP Biphenyl Precat (CAS#: 1375477-29-4)<br>SOLVENT: THF/H₂O | ¹H NMR (400 MHz, DMSO-d₆): δ ppm: 9.11 (br s, 1H), 9.03 (s, 1H), 8.69 (br s, 1H), 8.29 (s, 1H), 7.61 (br s, 1H), 6.60 (dd, J = 6.24, 13.45 Hz, 1H), 5.72 (br d, J = 4.65 Hz, 1H), 3.51-3.64 (m, 1H), 3.36-3.50 (m, 2H), 2.87-3.02 (m, 6H), 2.70-2.87 (m, 3H), 2.62 (br s, 1H), 1.73-1.88 (m, 1H), 1.40-1.59 (m, 1H), 1.18-1.33 (m, 2H), 0.10-0.23 (m, 2H), −0.09-−0.01 (m, 1H), −0.24-−0.09 (m, 1H)<br>MS: 601.2 ([M + H]⁺) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.282 | 6-[4-[3-[(dimethylamino)methyl]-3-fluoro-1-piperidyl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C55<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.79 (s, 1H), 11.94 (s, 1H), 9.29 (s, 1H), 9.13 (d, J = 2.32 Hz, 1H), 8.72 (d, J = 2.32 Hz, 1H), 8.32 (s, 1H), 8.13 (s, 1H), 6.64 (dd, J = 6.30, 13.39 Hz, 1H), 5.73 (br d, J = 4.16 Hz, 1H), 4.17 (s, 3H), 3.22-3.26 (m, 1H), 3.15 (br s, 2H), 2.95-3.05 (m, 1H), 2.87-2.95 (m, 4H), 2.83 (br s, 1H), 2.14-2.38 (m, 1H), 2.00 (br s, 4H), 1.67-1.86 (m, 2H), 1.41-1.66 (m, 3H)<br>MS: 594.2 ([M + H]$^+$) |
| 1.283 | 6-[4-[cis-1-cyclopropyl-2,3,3a,4,6,6a-hexahydro-pyrrolo[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C54<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.29-15.07 (m, 1H), 11.78 (br s, 1H), 9.29 (s, 1H), 9.09 (d, J = 2.20 Hz, 1H), 8.67 (d, J = 2.20 Hz, 1H), 8 26 (s, 1H), 6.54-6.65 (m, 1H), 5.69 (br d, J = 4.65 Hz, 1H), 4.17 (s, 3H), 3.55 (br t, J = 9.23 Hz, 1H), 3.35-3.49 (m, 2H), 2.90 (d, J = 4.89 Hz, 3H), 2.70-2.87 (m, 3H), 2.54-2.66 (m, 1H), 1.73-1.92 (m, 1H), 1.43-1.65 (m, 1H), 1.14-1.36 (m, 2H), 0.11-0.24 (m, 2H), −0.05-−0.01 (m, 1H), −0.20-−0.05 (m, 1H)<br>MS: 586.2 ([M + H]$^+$) |
| 1.284 | 6-[5,6-difluoro-8-(methylamino)-4-[cis-(4R)-4-(dimethylamino)-3,3a,4,5,6,6a-hexahydro-1H-cyclopenta[c]pyrrol-2-yl]-9H-pyrido[2,3-b]indol-3-yl]-1-(methylamino)-4-oxo-1,8-naphthyridine-3-carboxylic acid | CORE: Intermediate A3<br>AMINE: Intermediate C38<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.65 (br s, 1H), 11.78 (s, 1H), 9.12 (d, J = 2.20 Hz, 1H), 9.05 (s, 1H), 8.67 (d, J = 2.20 Hz, 1H), 8.28 (s, 1H), 7.63 (q, J = 5.46 Hz, 1H), 6.52-6.63 (m, 1H), 5.68 (br d, J = 4.77 Hz, 1H), 3.69 (br t, J = 7.95 Hz, 1H), 3.08-3.21 (m, 1H), 2.83-3.01 (m, 7H), 2.70-2.83 (m, 2H), 2.13 (br s, 1H), 1.92 (br s, 6H), 1.45-1.65 (m, 2H), 1.07-1.30 (m, 3H)<br>MS: 603.2 ([M + H]$^+$) |

| No. | Compound Name and Structure | CORE, AMINE, BORONIC REAGENT, CATALYST and SOLVENT | ¹H NMR and MS (ESI) |
|---|---|---|---|
| 1.285 | 6-[6-chloro-8-(methylamino)-4-[cis-(4R)-(dimethylamino)-3,3a,4,5,6,6a-hexahydro-1H-cyclopenta[c]pyrrol-2-yl]-9H-pyrido[2,3-b]indol-3-yl]-1-methyl-4-oxo-1,8-naphthyridine-3-carboxylic acid | CORE: Intermediate A11<br>AMINE: Intermediate C38<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, DMSO-d₆): δ ppm: 14.80 (br s, 1H), 11.75 (s, 1H), 9.31 (s, 1H), 9.11-9.25 (m, 2H), 8.69 (d, J = 2.45 Hz, 1H), 8.34 (s, 1H), 7.01-7.11 (m, 1H), 6.60 (d, J = 1.59 Hz, 1H), 6.55-6.64 (m, 1H), 6.55-6.64 (m, 1H), 5.93 (br s, 1H), 4.19 (s, 3H), 3.51-3.64 (m, 2H), 3.05-3.17 (m, 2H), 2.94 (s, 3H), 2.90 (br s, 1H), 2.78 (dd, J = 4.65, 8.56 Hz, 7H), 1.96-2.09 (m, 2H), 1.76-1.88 (m, 1H), 1.61-1.72 (m, 1H), 1.47-1.55 (m, 1H)<br>MS: 585.9 ([M + H]⁺) |
| 1.286 | 6-[4-[cis-3-(dimethylamino)-2,3,3a,4,6,6a-hexahydro-furo[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C51<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, DMSO-d₆): δ ppm: 14.77 (s, 1H), 11.89 (br s, 1H), 9.40 (br s, 1H), 9.24 (s, 1H), 9.08 (d, J = 2.32 Hz, 1H), 8.66 (br s, 1H), 8.39 (br s, 1H), 6.57 (br dd, J = 6.17, 13.39 Hz, 1H), 5.67 (br s, 1H), 4.65 (br s, 1H), 4.12 (s, 3H), 3.97 (br s, 2H), 3.57 (br dd, J = 2.87, 5.69 Hz, 3H), 3.14-3.22 (m, 1H), 2.97 (br s, 1H), 2.84 (br s, 4H), 2.62-2.78 (m, 5H), 1.89 (br s, 1H)<br>MS: 590.3 ([M + H]⁺) |
| 1.287 | 6-[5,6-difluoro-4-(cis-3-hydroxy-2,3,3a,4,6,6a-hexahydro-furo[2,3-c]pyrrol-5-yl]-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C52<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, DMSO-d₆): δ ppm: 14.77 (br s, 1H), 11.78 (s, 1H), 9.21 (s, 1H), 9.06 (d, J = 2.45 Hz, 1H), 8.61 (d, J = 2.45 Hz, 1H), 8.23 (s, 1H), 6.54 (dd, J = 6.36, 13.45 Hz, 1H), 5.65 (br s, 1H), 4.77 (br s, 1H), 4.48-4.54 (m, 1H), 4.06-4.20 (m, 4H), 3.51-3.64 (m, 2H), 3.16-3.22 (m, 2H), 2.79-2.92 (m, 5H)<br>MS: 563.3 ([M + H]⁺) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.288 | 6-[5,6-difluoro-8-(methylamino)-4-[cis-(4S)-4-(dimethyl-amino)-3,3a,4,5,6,6a-hexahydro-1H-cyclopenta[c]pyrrol-2-yl]-9H-pyrido[2,3-b]indol-3-yl]-1-methyl-4-oxo-1,8-naphthyridine-3-carboxylic acid 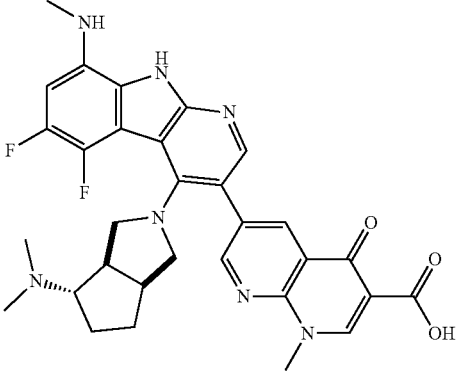 | CORE: Intermediate A3 AMINE: Intermediate C56 BORONIC REAGENT: Intermediate B2 CATALYST: Pd-Ad$_2$nBuP Biphenyl Precat (CAS#: 1375477-29-4) SOLVENT: THF/H$_2$O | $^1$H NMR (400 MHz, DMSO-d$_6$): δ ppm: 14.09-15.07 (m, 1H), 11.80 (s, 1H), 9.23 (s, 1H), 9.06 (d, J = 2.32 Hz, 1H), 8.66 (d, J = 2.32 Hz, 1H), 8.30 (s, 1H), 8.08 (s, 1H), 6.55 (dd, J = 6.36, 13.45 Hz, 1H), 5.64 (br d, J = 4.52 Hz, 1H), 4.11 (s, 3H), 3.51-3.62 (m, 1H), 3.43 (dt, J = 2.57, 8.31 Hz, 1H), 2.84 (d, J = 4.77 Hz, 3H), 2.63-2.79 (m, 2H), 2.47-2.62 (m, 2H), 2.20 (br s, 1H), 2.09 (br s, 5H), 1.60-1.77 (m, 3H), 1.32-1 47 (m, 1H), 0.93-1.09 (m, 1H) MS: 588.3 ([M + H]$^+$) |
| 1.289 | 6-[4-[cis-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-ethyl-4-oxo-1,8-naphthyridine-3-carboxylic acid 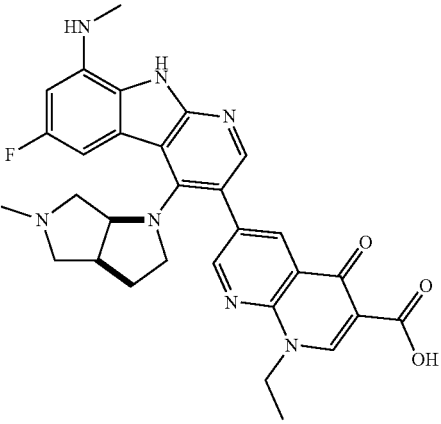 | CORE: Intermediate A1 AMINE: Intermediate C8 BORONIC REAGENT: Intermediate B23 CATALYST: Xphos Pd G2(CAS: 1310584-14-5) SOLVENT: THF/H$_2$O | $^1$H NMR (400 MHz, DMSO-d6): δ ppm: 11.50 (s, 1H), 9.28 (s, 1H), 9.11-9.07 (m, 1H), 8.71 (d, 1H), 8.23-8.18 (m, 2H), 7.01 (br d, 1H), 6.45 (m, 1H), 5.89 (br s, 1H), 4.74 (m, 2H), 3.97-3.91 (m, 1H), 3.13-3.07 (m, 1H), 2.95-2.88 (m, 3H), 2.76-2.66 (m, 2H), 2.58 (br d, 1H), 2.20-2.10 (m, H), 2.10-2.07 (m, 3H), 1.76 (br m, 2H), 1.49 (br m, 3H) MS: 556.2 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.290 | 6-[4-[cis-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-(ethylamino)-4-oxo-1,8-naphthyridine-3-carboxylic acid | CORE: Intermediate A1<br>AMINE: Intermediate C8<br>BORONIC REAGENT: Intermediate B35<br>CATALYST: Xphos Pd G2(CAS: 1310584-14-5)<br>SOLVENT: THF/H$_2$O | $^1$H NMR (400 MHz, DMSO-d6): δ ppm: 11.54 (s, 1H), 9.04 (br s, 1H), 8.96 (s, 1H), 8.64 (br s, 1H), 8.16 (s, 1H), 7.56 (m, 1H), 6.87 (br d, 1H), 6.41 (m, 1H), 5.87 (br s, 1H), 4.11-3.58 (m, 3H), 3.42 (br s, 1H), 3.18-3.02 (m, 1H), 2.86 (br d, 4H), 2.66-2.50 (m, 4H), 2.29-2.01 (m, 2H), 1.98-1.68 (m, 1H), 1.09 (m, 3H)<br>MS: 571.4 ([M + H]$^+$) |
| 1.291 | 6-[4-[cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-(ethylamino)-4-oxo-1,8-naphthyridine-3-carboxylic acid | CORE: Intermediate A3<br>AMINE: Intermediate C8<br>BORONIC REAGENT: Intermediate B35<br>CATALYST: Xphos Pd G2(CAS: 1310584-14-5)<br>SOLVENT: THF/H$_2$O | $^1$H NMR (400 MHz, DMSO-d6): δ ppm: 11.84 (br s, 1H), 9.07 (d, 1H), 8.96 (s, 1H), 8.66 (d, 1H), 8.21 (br s, 1H), 7.56 (m, 1H), 6.56 (m, 1H), 5.67 (br d, 1H), 4.09 (br s, 1H), 3.24-3.19 (m, 3H), 3.17-3.10 (m, 1H), 2.88-2.80 (m, 4H), 2.52 (br s, 3H), 2.01 (br s, 1H), 1.70 (br d, 1H), 1.09 (m, 3H)<br>MS: 589.4 ([M + H]$^+$) |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.292 | 6-(5,6-dichloro-4-(cis-(4R)-4-(dimethylamino)hexa-hydrocyclopenta[c]pyrrol-2(1H)-yl)-8-(methylamino)-9H-pyrido[2,3-b]indol-3-yl)-1-methyl-4-oxo-1,4-dihydro-1,8-naphthyridine-3-carboxylic acid | CORE: Intermediate A18<br>AMINE: Intermediate C38<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 12.10 (s, 1H), 9.33 (s, 1H), 9.28 (s, 1H), 9.13 (s 1H), 8.67 (s, 1H), 8.18 (s, 1H), 6.74 (s, 1H), 4.16 (s, 3H), 3.20 (m, 3H), 2.92 (s, 3H), 2.69 (s, 3H), 2.66 (m, 2H), 2.62 (m, 3H), 2.53 (m, 1H), 1.96 (m, H), 1.79 (m, 1H), 1.67 (m, 1H), 1.35 (m, 1H).<br>MS: 624.0([{$^{37}$Cl + $^{37}$Cl}M + H]$^+$), 622.0([{$^{37}$Cl + $^{35}$Cl}M + H]$^+$), 620.0([{$^{35}$Cl + $^{35}$Cl}M + H]$^+$). |
| 1.293 | 6-[4-[cis-5-methyl-2,3,3a,4,6,6a-hexahydropyrrolo[2,3-c]pyrrol-1-yl]-5,6-dichloro-8-(methylamino)-9H-pyrido[2,3-b]indol-3-yl]-1-methyl-4-oxo-1,8-naphthyridine-3-carboxylic acid | CORE: Intermediate A18<br>AMINE: Intermediate C8<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 14.74 (s, 1H), 11.93 (s, 1H), 9.31 (s, 1H), 9.22 (s, 1H), 8.71 (s 1H), 8.07 (s, 1H), 6.75 (s, 1H), 5.96 (s, 1H), 4.69 (s, 1H), 4.19 (s, 3H), 3.64 (m, 1H), 3.23 (m, 2H), 3.12 (m, 2H), 2.93 (s, 3H), 2.70 (d, 3H), 2.64 (m, 1H), 2.07 (m, H), 1.95 (m, 1H), 1.60 (m, 1H).<br>MS: 596.0([{$^{37}$Cl + $^{37}$Cl}M + H]$^+$), 594.0([{$^{37}$Cl + $^{35}$Cl}M + H]$^+$), 592.0([{$^{35}$Cl + $^{35}$Cl}M + H]$^+$). |
| 1.294 | 6-[4-[cis-5-methyl-2,3,3a,4,6,6a-hexahydropyrrolo[2,3-c]pyrrol-1-yl]-6-fluoro-5-methoxy-8-(methylamino)-9H-pyrido[2,3-b]indol-3-yl]-1-methyl-4-oxo-1,8-naphthyridine-3-carboxylic acid | CORE: Intermediate A17<br>AMINE: Intermediate C8<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.74 (s, 1H), 9.44 (s, 1H), 9.30 (s, 1H), 9.18 (s 1H), 8.75 (s, 1H), 8.08 (s, 1H), 6.56-6.52 (d, J = 13.6 Hz, 1H), 4.95 (m, 1H), 4.19 (s, 3H), 3.70 (m, 1H), 3.68 (s, 3H), 3.25 (m, 3H), 3.16 (m, 1H), 2.89 (s, 3H), 2.74 (s, 3H), 2.65 (m, 1H), 2.52 (m, 1H), 1.90 (m, 1H), 1.59 (m, 1H).<br>MS: 572.1 ([M + H]$^+$). |

TABLE 1-continued

Compound synthesis and characterization

| No. | Compound Name and Structure | CORE, AMINE, BORONIC REAGENT, CATALYST and SOLVENT | $^1$H NMR and MS (ESI) |
|---|---|---|---|
| 1.295 | 6-[4-[cis-1-methyl-2,3,3a,4,6,6a-hexahydropyrrolo[2,3-c]pyrrol-5-yl]-6-fluoro-5-methoxy-8-(methylamino)-9H-pyrido[2,3-b]indol-3-yl]-1-methyl-4-oxo-1,8-naphthyridine-3-carboxylic acid | CORE: Intermediate A17<br>AMINE: cis-1-methyl-octahydropyrrolo[2,3-c]pyrrole<br>BORONIC REAGENT: Intermediate B2<br>CATALYST: cataCXium ® A Pd G2 (Sigma-Aldrich, Catalog #: 761311)<br>SOLVENT: THF/H$_2$O | $^1$H NMR (400 MHz, DMSO-d6) δ ppm: 11.82 (s, 1H), 9.84 (s, 1H), 9.30 (s, 1H), 9.18 (s 1H), 8.74 (s, 1H), 8.15 (s, 1H), 6.56-6.52 (d, J = 13.6 Hz, 1H), 4.46 (m, 1H), 4.18 (s, 3H), 3.68 (s, 3H), 3.37 (m, 2H), 3.22 (m, 2H), 3.02 (m, 1H), 2.98 (s, 3H), 2.77 (s, 3H), 2.65 (m, 1H), 2.52 (m, 1H), 2.16 (m, 1H), 1.53 (m, 1H).<br>MS: 572.1 ([M + H]$^+$). |
| 1.296 | 6-(6-fluoro-8-(methylamino)-4-(5-oxa-2,8-diazaspiro[3.5]nonan-8-yl)-9H-pyrido[2,3-b]indol-3-yl)-1-methyl-4-oxo-1,4-dihydro-1,8-naphthyridine-3-carboxylic acid | CORE: Intermediate A1<br>AMINE: tert-butyl 5-oxa-2,8-diazaspiro[3.5]nonane-2-carboxylate<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) δ ppm 14.50-15.02 (m, 1 H), 11.74 (s, 1 H), 9.35 (s, 1 H), 9.13 (d, J = 2.38 Hz, 1 H), 8.71 (d, J = 2.38 Hz, 2 H), 8.35 (s, 2 H), 6.92-7.01 (m, 1 H), 6.44-6.55 (m, 1 H), 4.20 (s, 3 H), 3.93 (br s, 3 H), 3.15-3.36 (m, 5 H), 2.94 (s, 3 H), 2.65-2.71 (m, 1 H), 2.31-2.36 (m, 1 H).<br>MS: 544.2 ([M + H]+) |
| 1.297 | 6-(6-fluoro-8-(methylamino)-4-(cis-6-methylhexahydropyrrolo[3,4-b][1,4]oxazin-4(4aH)-yl)-9H-pyrido[2,3-b]indol-3-yl)-1-methyl-4-oxo-1,4-dihydro-1,8-naphthyridine-3-carboxylic acid | CORE: Intermediate A1<br>AMINE: Intermediate C58<br>BORONIC REAGENT: Intermediate B2<br>CATALYST: Pd-Ad$_2$nBuP Biphenyl Precat (CAS#: 1375477-29-4)<br>SOLVENT: THF/H$_2$O | 1H NMR (400 MHz, DMSO-d6) δ ppm 11.69 (s, 1 H), 9.54-10.24 (m, 1 H), 9.32 (s, 1 H), 9.12-9.22 (m, 1 H), 8.72-8.91 (m, 1 H), 8.22 (d, J = 4.64 Hz, 1 H), 6.96-7.10 (m, 1 H), 6.50 (dd, J = 12.17, 2.01 Hz, 1 H), 4.19 (s, 3 H), 3.74-3.95 (m, 4 H), 3.11-3.20 (m, 1 H), 3.06 (s, 1 H), 2.93 (s, 3 H), 2.83 (s, 1 H), 2.66-2.72 (m, 2 H), 2.51-2.57 (m, 5 H).<br>MS: 558.3 ([M + H]$^+$). |

| No. | Compound Name and Structure | CORE, AMINE, BORONIC REAGENT, CATALYST and SOLVENT | $^1$H NMR and MS (ESI) |
|---|---|---|---|
| 1.298 | 6-[4-[(3aS,6aS)-5-methyl-2,3,3a,4,6,6a-hexahydro-pyrrolo[2,3-c]pyrrol-1-yl]-5-cyano-6-fluoro-8-(methylamino)-9H-pyrido[2,3-b]indol-3-yl]-1-methyl-4-oxo-1,8-naphthyridine-3-carboxylic acid | CORE: Intermediate A16<br>AMINE: (3aS,6aS)-5-methyloctahydro-pyrrolo[2,3-c]pyrrole<br>BORONIC REAGENT: Intermediate B2<br>CATALYST: Pd-Ad$_2$nBuP Biphenyl Precat (CAS#: 1375477-29-4)<br>SOLVENT: dioxane/H$_2$O | $^1$H NMR (400 MHz, DMSO-d6) δ ppm 9.21 (s, 1 H), 9.15 (d, J = 2.3 Hz, 1 H), 8.72 (d, J = 2.5 Hz, 1 H), 8.16 (s, 1 H), 6.66 (d, J = 13.1 Hz, 1 H), 4.61 (br d, J = 6.0 Hz, 1 H), 4.21 (s, 3 H), 2.93-3.45 (m, 10 H), 2.74 (s, 3 H), 2.09-2.25 (m, 1 H), 1.84 (br s, 1 H).<br>MS (ESI): 567.3 ([M + H]$^+$), 284.2 ([M/2 + H]$^+$). |
| 1.299 | 6-[4-[(3aS,6aS)-5-methyl-2,3,3a,4,6,6a-hexahydro-pyrrolo[2,3-c]pyrrol-1-yl]-5-cyano-6-fluoro-8-(methyl-amino)-9H-pyrido[2,3-b]indol-3-yl]-1-(methyl-amino)-4-oxo-1,8-naphthyridine-3-carboxylic acid | CORE: Intermediate A16<br>AMINE: (3aS,6aS)-5-methyloctahydro-pyrrolo[2,3-c]pyrrole<br>BORONIC REAGENT: Intermediate B23<br>CATALYST: Pd-Ad$_2$nBuP Biphenyl Precat (CAS#: 1375477-29-4)<br>SOLVENT: dioxane/H$_2$O | $^1$H NMR (400 MHz, DMSO-d6) δ ppm 9.17 (d, J = 2.3 Hz, 1 H), 9.05 (s, 1 H), 8.75 (d, J = 2.3 Hz, 1 H), 8.18 (s, 1 H), 6.65 (d, J = 13.1 Hz, 1 H), 4.61 (br d, J = 6.3 Hz, 1 H), 3.04 (d, J = 1.8 Hz, 11 H), 2.74 (s, 3 H), 2.12-2.26 (m, 1 H), 1.76-1.90 (m, 1 H)<br>MS (ESI): 582.2 ([M + H]$^+$), 291.8 ([M/2 + H]$^+$). |

Example 2.01

6-[4-(3,3-Difluoropyrrolidin-1-yl)-5,6-difluoro-8-(methylamino)-9H-pyrido[2,3-b]indol-3-yl]-1-methyl-4-oxo-1,8-naphthyridine-3-carboxylic acid

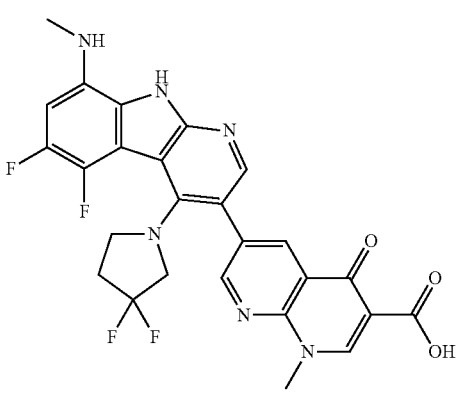 [SMILES: CNc1cc(F)c(F)c2c1[nH]c1ncc(-c3cnc4c(c3)c(=O)c(C(=O)O)cn4C)c(N3CCC(F)(F)C3)c12]

Step (a) Preparation of tert-butyl N-[3-chloro-4-(3,3-difluoropyrrolidin-1-yl)-5,6-difluoro-9H-pyrido[2,3-b]indol-8-yl]-N-methyl-carbamate

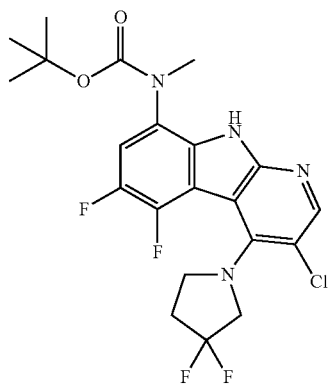 [SMILES: CN(C(=O)OC(C)(C)C)c1cc(F)c(F)c2c1[nH]c1ncc(Cl)c(N3CCC(F)(F)C3)c12]

A solution of tert-butyl N-(3,4-dichloro-5,6-difluoro-9H-pyrido[2,3-b]indol-8-yl)-N-methyl-carbamate (Intermediate A3, 800 mg, 1.99 mmol, as the "CORE" in Table 2), 3,3-difluoropyrrolidine hydrochloride (857.0 mg, 5.97 mmol, as the "AMINE" in Table 2), SPhos Pd G1, Methyl t-Butyl Ether Adduct (151.0 mg, 0.199 mmol, as the "CATALYST 1" in Table 2, Sigma-Aldrich, Catalog number: 704946) and potassium tert-butoxide (1.11 g, 9.95 mmol) in THF (10.0 mL) was stirred at 80° C. under $N_2$ atmosphere for 18 h. After cooled to room temperature, the reaction mixture was poured into water (80 mL), and extracted with EtOAc (80 mL) three times. The combined organic layer was washed with brine (100 mL), dried over anhy. $Na_2SO_4$, filtered, and concentrated in vacuo to give a crude product, which was purified by Prep-HPLC to give tert-butyl N-[3-chloro-4-(3,3-difluoropyrrolidin-1-yl)-5,6-difluoro-9H-pyrido[2,3-b]indol-8-yl]-N-methyl-carbamate (350.0 mg, 37% yield) as a yellow solid. MS (ESI): 473.1 ([$\{^{35}Cl\}$M+H]$^+$), 475.1 ([$\{^{37}Cl\}$M+H]$^+$).

Step (b) Preparation of ethyl 6-[8-[tert-butoxycarbonyl(methyl)amino]-4-(3,3-difluoropyrrolidin-1-yl)-5,6-difluoro-9H-pyrido[2,3-b]indol-3-yl]-1-methyl-4-oxo-1,8-naphthyridine-3-carboxylate

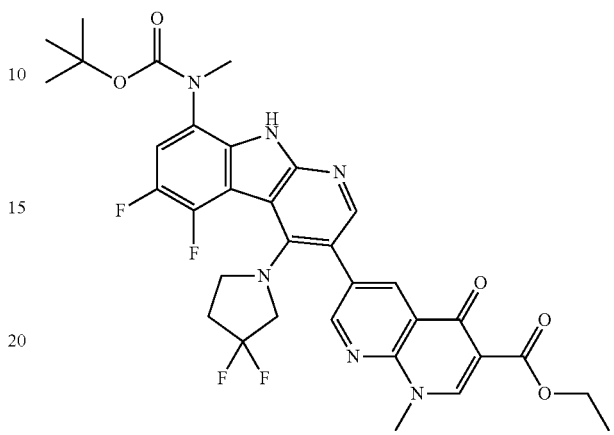

A mixture of tert-Butyl N-[3-chloro-4-(3,3-difluoropyrrolidin-1-yl)-5,6-difluoro-9H-pyrido[2,3-b]indol-8-yl]-N-methyl-carbamate (47.2 mg, 0.10 mmol), (6-ethoxycarbonyl-8-methyl-5-oxo-1,8-naphthyridin-3-yl)boronic acid (Intermediate B2, 33.1 mg, 0.12 mmol, as the "BORONIC REAGENT" in Table 2), XPhos Pd G2 (15.7 mg, 0.020 mmol, as the "CATALYST 2" in Table 2, Sigma-Aldrich, Catalog number: 741825), and $K_3PO_4$ (84.9 mg, 0.40 mmol) were dissolved in a mixture of THF/water (2.0 mL, V/V=10/1, as the "SOLVENT" in table 2). The resulting reaction mixture was stirred under argon atmosphere at 70° C. for 12 h before it was cooled to room temperature. Precipitate was removed by filtration through thin silica pad. The filtrate was concentrated in vacuo to give a crude product, which was purified by Prep-HPLC to give ethyl 6-[8-[tert-butoxycarbonyl(methyl)amino]-4-(3,3-difluoropyrrolidin-1-yl)-5,6-difluoro-9H-pyrido[2,3-b]indol-3-yl]-1-methyl-4-oxo-1,8-naphthyridine-3-carboxylate as a yellow solid (52.3 mg, 78% yield). MS (ESI): 669.3 ([M+H]$^+$).

Step (c) Preparation of 6-[8-[tert-butoxycarbonyl(methyl)amino]-4-(3,3-difluoropyrrolidin-1-yl)-5,6-difluoro-9H-pyrido[2,3-b]indol-3-yl]-1-methyl-4-oxo-1,8-naphthyridine-3-carboxylic acid

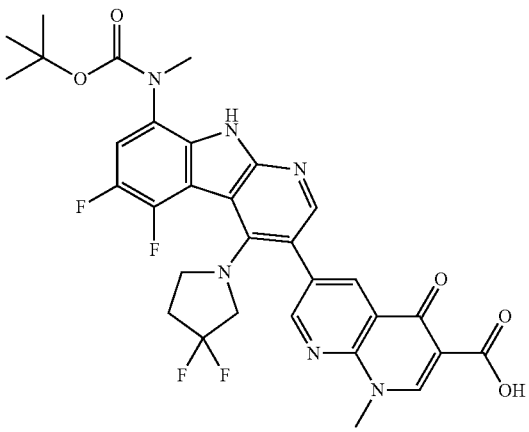 [SMILES: CN(C(=O)OC(C)(C)C)c1cc(F)c(F)c2c1[nH]c1ncc(-c3cnc4c(c3)c(=O)c(C(=O)O)cn4C)c(N3CCC(F)(F)C3)c12]

A solution of ethyl 6-[8-[tert-butoxycarbonyl(methyl)amino]-4-(3,3-difluoropyrrolidin-1-yl)-5,6-difluoro-9H-pyrido[2,3-b]indol-3-yl]-1-methyl-4-oxo-1,8-naphthyridine-3-carboxylate (46.5 mg, 0.070 mmol), LiBr (17.9 mg, 0.21 mmol), and Et$_3$N (21.3 mg, 0.21 mmol) were dissolved in a mixture of MeCN/H$_2$O (3.6 mL, V/V=5/1) and the resulting reaction mixture was stirred at 25° C. for 4 d. The reaction mixture was then diluted with H$_2$O (50 mL), adjusted to pH=6 with 1N HCl aqueous solution, and extracted with EtOAc (50 mL) three times. The combined organic layer was washed with brine (50 mL) two times, dried over anhy. Na$_2$SO$_4$, filtered, and concentrated in vacuo to give a crude product of 6-[8-[tert-butoxycarbonyl(methyl)amino]-4-(3,3-difluoropyrrolidin-1-yl)-5,6-difluoro-9H-pyrido[2,3-b]indol-3-yl]-1-methyl-4-oxo-1,8-naphthyridine-3-carboxylic acid (31.5 mg, 80% yield) as an off-white solid, which was used directly in the next step without further purification. MS (ESI): 641.0 (M+H)$^+$.

Step (d) Preparation of 6-[4-(3,3-difluoropyrrolidin-1-yl)-5,6-difluoro-8-(methylamino)-9H-pyrido[2,3-b]indol-3-yl]-1-methyl-4-oxo-1,8-naphthyridine-3-carboxylic acid The above crude 6-[8-[tert-butoxycarbonyl(methyl)amino]-4-(3,3-difluoropyrrolidin-1-yl)-5,6-difluoro-9H-pyrido[2,3-b]indol-3-yl]-1-methyl-4-oxo-1,8-naphthyridine-3-carboxylic acid (25.9 mg, 0.040 mmol) was dissolved in the mixture of DCM (2.0 mL) and TFA (0.4 mL). The reaction mixture was stirred at 20° C. for 12 h before it was concentrated in vacuo. The residue was purified by Prep-HPLC to give 6-[4-(3,3-difluoropyrrolidin-1-yl)-5,6-difluoro-8-(methylamino)-9H-pyrido[2,3-b]indol-3-yl]-1-methyl-4-oxo-1,8-naphthyridine-3-carboxylic acid (15.6 mg, 72% yield) as a yellow solid. $^1$H NMR (400 MHz, DMSO-d6): δ 14.77 (s, 1H), 11.92 (s, 1H), 9.28 (s, 1H), 9.13 (s, 1H), 8.72 (s, 1H), 8.31 (s, 1H), 6.62 (m, 1H), 4.17 (s, 3H), 3.48 (m, 4H), 2.91 (s, 3H), 2.38 (m, 2H). MS (ESI): 540.9 ([M+H]$^+$).

The following examples were prepared in analogy to Example 2.01, replacing tert-butyl N-(3,4-dichloro-5,6-difluoro-9H-pyrido[2,3-b]indol-8-yl)-N-methyl-carbamate (Intermediate A3) with the "CORE" in step (a), SPhos Pd G1 with the "CATALYST 1" in step (a), 3,3-difluoropyrrolidine hydrochloride with the "AMINE" in step (a), THF/H$_2$O with the "SOLVENT" in step (b), XPhos Pd G2 with the "CATALYST 2" in step (b), and (6-ethoxycarbonyl-8-methyl-5-oxo-1,8-naphthyridin-3-yl)boronic acid with the "BORONIC REAGENT" in step (b) by the reagents indicated in Table 2.

TABLE 2

Compound synthesis and characterization

| No. | Compound Name and Structure | CORE, AMINE, BORONIC REAGENT, CATALYST1, CATALYST2, and SLOVENT | $^1$H NMR and MS (ESI) |
|---|---|---|---|
| 2.02 | 6-[4-(3,3-Difluoropyrrolidin-1-yl)-5,6-difluoro-8-(methylamino)-9H-pyrido[2,3-b]indol-3-yl]-1-[2-(dimethylamino)ethyl]-4-oxo-1,8-naphthyridine-3-carboxylic acid | CORE: Intermediate A3<br>AMINE: Difluoropyrrolidine hydrochloride<br>BORONIC REAGENT: Intermediate B11<br>CATALYST 1: SPhos Pd G1, Methyl t-Butyl Ether Adduct (Sigma-Aldrich, Catalog #: 704946)<br>CATALYST 2: XPhos Pd G2 (Sigma-Aldrich, Catalog #: 741825)<br>SOLVENT: THF/H$_2$O | $^1$H NMR (400 MHz, DMSO-d6) δ ppm: 11.93 (s, 1H), 9.58 (m, 1H), 9.363 (s, 1H), 9.10 (d, J = 2.4 Hz, 1H), 8.76 (d, J = 2.4 Hz, 1H), 8.32 (s, 1H), 6.64 (m, 1H), 5.07 (m, 2H), 3.42 (m, 4H), 2.94 (s, 3H), 2.92 (s, 6H), 2.37 (m, 4H).<br>MS: 598.1 ([M + H]$^+$) |

TABLE 2-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
|---|---|---|---|
| 2.03 | 6-(4-(3,3-difluoropyrrolidin-1-yl)-5,6-difluoro-8-(methylamino)-9H-pyrido[2,3-b]indol-3-yl)-1-(1-methylpyrrolidin-3-yl)-4-oxo-1,4-dihydro-1,8-naphthyridine-3-carboxylic acid | CORE: Intermediate A3 AMINE: Difluoropyrrolidine hydrochloride BORONIC REAGENT: Intermediate B9 CATALYST 1: SPhos Pd G2, Methyl t-Butyl Ether Adduct (Sigma-Aldrich, Catalog #: 704946) CATALYST 2: XPhos Pd G2 (Sigma-Aldrich, Catalog #: 741825) SOLVENT: THF/H$_2$O | $^1$H NMR (400 MHz, DMSO-d6) δ 11.97 (s, 1 H), 9.26~9.30 (s, 1 H), 9.13~9.14 (d, J = 2.0 Hz, 1 H), 8.77 (d, J = 2.0 Hz, 1 H), 8.32~8.34 (s, 1 H), 6.61~6.66 (dd, J = 13.2, 6.0 Hz, 1 H), 6.09 (br s, 1 H), 4.12~4.53 (m, 2 H), 3.73 (m, 2 H), 3.42~3.49 (m, 5 H), 2.91~3.00 (m, 6 H), 2.79 (m, 1 H), 2.55 (m, 1 H), 2.29-2.41(m, 2 H). MS (ESI): 610.2 (M + H)$^+$, 305.6 (M/2 + H)$^+$. |

Example 3.01A

6-[5,6-difluoro-8-(methylamino)-4-[(3aS,6aS)-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylic acid (Example 3.01A)

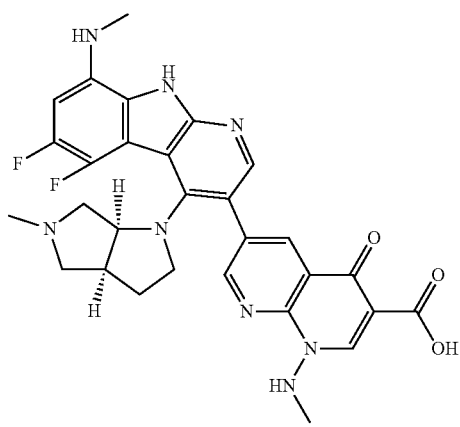 [SMILES: CNc1cc(F)c(F)c2c1[nH]c1ncc(-c3cnc4c(c3)c(=O)c(C(=O)O)cn4NC)c(N3CC[C@H]4CN(C)C[C@H]43)c12]

Step (a) Preparation of tert-butyl N-[3-chloro-5,6-difluoro-4-[cis-(3a,6a)-5-methyl-2,3,3a,4,6,6a-hexahydropyrrolo[2,3-c]pyrrol-1-yl]-9H-pyrido[2,3-b]indol-8-yl]-N-methyl-carbamate

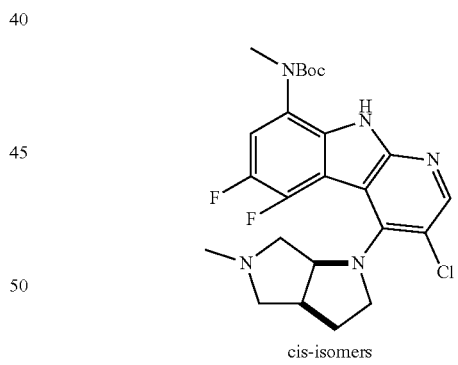

cis-isomers

To a solution of tert-Butyl N-(3,4-dichloro-5,6-difluoro-9H-pyrido[2,3-b]indol-8-yl)-N-methyl-carbamate (Intermediate A3, 2 g, 4.97 mmol, as the "CORE" in table 3) and DIPEA (1.93, 2.61 mmol) in DMSO (2.0 mL) was added cis-(3a,6a)-5-methyl-2,3,3a,4,6,6a-hexahydro-1H-pyrrolo[2,3-c]pyrrole (1.13 g, 8.95 mmol, as the "AMINE" in table 3), and the resulting reaction solution was stirred at 125° C. for 15 h. After cooled to room temperature, the mixture was poured into water (100 mL) and extracted by EtOAc (150 mL) two times. The combined organic layer was washed by brine (50 mL) two times, dried over anhy. Na$_2$SO$_4$, filtered, and concentrated under reduced pressure to give a crude product of cis-tert-butyl N-[3-chloro-5,6-difluoro-4-[cis- (3a,6a)-5-methyl-2,3,3a,4,6,6a-hexahydropyrrolo[2,3-c]pyrrol-1-yl]-9H-pyrido[2,3-b]indol-8-yl]-N-methyl-carbamate (2.4 g, 97.9% yield) as a yellow solid. MS (ESI): 493.2 (M+H)⁺.

Step (b) Preparation of tert-butyl N-[4-[(3aS,6aS)-5-methyl-2,3,3a,4,6,6a-hexahydropyrrolo[2,3-c]pyrrol-1-yl]-3-chloro-5,6-difluoro-9H-pyrido[2,3-b]indol-8-yl]-N-methyl-carbamate (Compound 3.01a) and tert-butyl N-[4-[(3aR,6aR)-5-methyl-2,3,3a,4,6,6a-hexahydropyrrolo[2,3-c]pyrrol-1-yl]-3-chloro-5,6-difluoro-9H-pyrido[2,3-b]indol-8-yl]-N-methyl-carbamate (Compound 3.01b)

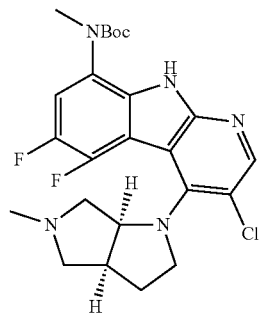

Compound 3.01a

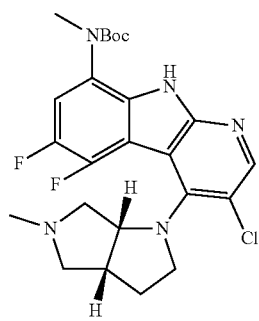

Compound 3.01b

The crude product tert-butyl N-[3-chloro-5,6-difluoro-4-[cis-(3a,6a)-5-methyl-2,3,3a,4,6,6a-hexahydropyrrolo[2,3-c]pyrrol-1-yl]-9H-pyrido[2,3-b]indol-8-yl]-N-methyl-carbamate (2.4 g) was purified by chiral SFC to afford tert-butyl N-[4-[(3aS,6aS)-5-methyl-2,3,3a,4,6,6a-hexahydropyrrolo[2,3-c]pyrrol-1-yl]-3-chloro-5,6-difluoro-9H-pyrido[2,3-b]indol-8-yl]-N-methyl-carbamate (compound 3.01a, 850 mg, 34.7% yield) and tert-butyl N-[4-[(3aR,6aR)-5-methyl-2,3,3a,4,6,6a-hexahydropyrrolo[2,3-c]pyrrol-1-yl]-3-chloro-5,6-difluoro-9H-pyrido[2,3-b]indol-8-yl]-N-methyl-carbamate (compound 3.01b, 860 mg, 35.2% yield).

SFC Method: Column: Daicel OD-H Column 30×250 mm Mobile Phase: $CO_2$+0.5% $NH_3$ in Ethanol Temperature: 35° C. Compound 3.01a was obtained at Rf=11.282/15 min, MS (ESI): 493.2 (M+H)⁺, Compound 3.01b was obtained at Rf=11.809/15 min, MS (ESI): 493.2 (M+H)⁺).

Step (c) Preparation of ethyl 6-[8-[tert-butoxycarbonyl(methyl)amino]-5,6-difluoro-4-[(3aS,6aS)-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylate

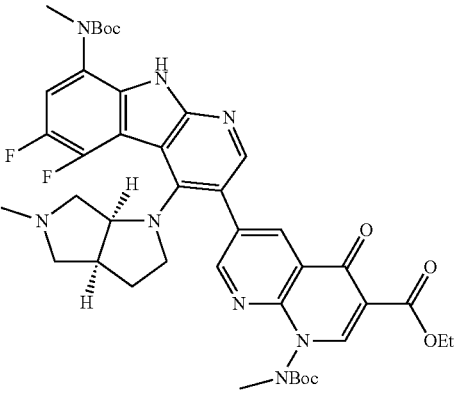 [SMILES: CCOC(=O)c1cn(N(C)C(=O)OC(C)(C)C)c2ncc(-c3cnc4[nH]c5c(N(C)C(=O)OC(C)(C)C)cc(F)c(F)c5c4c3N3CC[C@H]4CN(C)C[C@H]43)cc2c1=O]

A mixture of tert-butyl N-[4-[(3aS,6aS)-5-methyl-2,3,3a,4,6,6a-hexahydropyrrolo[2,3-c]pyrrol-1-yl]-3-chloro-5,6-difluoro-9H-pyrido[2,3-b]indol-8-yl]-N-methyl-carbamate (compound 3.01a, 270 mg, 549 μmol), [8-[tert-Butoxycarbonyl(methyl)amino]-6-ethoxycarbonyl-5-oxo-1,8-naphthyridin-3-yl]boronic acid (Intermediate 23, 644 mg, 1.65 mmol, as the "BORONIC REAGENT" in table 3) and $K_3PO_4$ (349 mg, 1.65 mmol) were dissolved in THF/$H_2O$ (4.0 mL, v/v=20:1 as the "SOLVENT" in table 1), followed by the addition of $Ad_2nBuP$ Biphenyl (147 mg, 220 μmol, as the "CATALYST" in table 3) to the mixture under nitrogen. The resulting reaction mixture was stirred at 72° C. for 15 h under nitrogen, before it was poured into water (50 mL) and extracted by EtOAc (100 mL) two times. The combined organic layer was washed with brine (50 mL) two times, dried with anhy. $Na_2SO_4$, filtered, and concentrated under reduced pressure to give a crude product, which was purified by silica gel flash chromatography (0% to 10% MeOH in DCM) to give ethyl 6-[8-[tert-butoxycarbonyl(methyl)amino]-5,6-difluoro-4-[(3aS,6aS)-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylate (430 mg, 97.6% yield) as a yellow solid. MS (ESI): 803 (M+H)⁺.

Step (d) Preparation of 6-[8-[tert-butoxycarbonyl(methyl)amino]-5,6-difluoro-4-[(3aS,6aS)-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylic acid

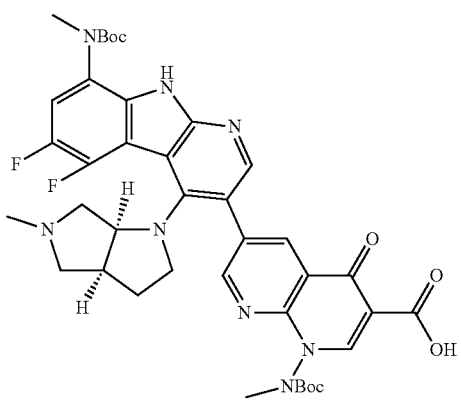 [SMILES: CN1C[C@@H]2CCN(c3c(-c4cnc5c(c4)c(=O)c(C(=O)O)cn5N(C)C(=O)OC(C)(C)C)cnc4[nH]c5c(N(C)C(=O)OC(C)(C)C)cc(F)c(F)c5c34)[C@@H]2C1]

A mixture of ethyl 6-[8-[tert-butoxycarbonyl(methyl)amino]-5,6-difluoro-4-[(3aS,6aS)-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylate (430 mg, 536 µmol) and NaOH (214 mg, 5.36 mmol) were dissolved in a mixture of EtOH/H$_2$O (25 mL, V/V=3/2). The resulting reaction mixture was stirred at rt for 1 h before concentrated under reduced pressure to give a crude product of 6-[8-[tert-butoxycarbonyl(methyl)amino]-5,6-difluoro-4-[(3aS,6aS)-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylic acid (415 mg, 100% yield) as a yellow solid, which was used directly in the next step without further purification. MS (ESI): 775.4 (M+H)$^+$.

Step (e) Preparation of 6-[5,6-difluoro-8-(methylamino)-4-[(3aS,6aS)-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylic acid (Example 3.01A)

To a solution of 6-[8-[tert-butoxycarbonyl(methyl)amino]-5,6-difluoro-4-[(3 aS,6aS)-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylic acid (415 mg, 536 µmol) in dry DCM (12.0 mL) was added TFA (6.11 g, 53.6 mmol). The resulting reaction mixture was stirred at room temperature for 1 h, and then concentrated in vacuo to give a crude product, which was purified by Prep-HPLC to give 6-[5,6-difluoro-8-(methylamino)-4-[(3aS,6aS)-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylic acid (110 mg, 35% yield) as a yellow solid. $^1$H NMR (400 MHz, DMSO-d$_6$) δ: 14.69 (s, 1H) 11.76 (s, 1H) 9.16 (s, 1H) 9.03 (s, 1H) 8.75 (s, 1H) 8.18 (s, 1H) 7.60-7.62 (m, 1H) 6.58-6.62 (m, 1H) 5.68-5.70 (s, 1H) 4.40 (s, 1H) 3.31 (m, 2H) 3.15-2.97 (m, 5H), 2.91-2.89 (d, 3H) 2.83 (m, 1H) 2.50 (m, 2H) 2.12 (m, 1H) 1.99 (m, 1H) 1.64 (m, 1H). MS (ESI): 575.3 (M+H)$^+$.

Example 3.01B

6-[5,6-difluoro-8-(methylamino)-4-[(3aR,6aR)-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylic acid (Example 3.01B)

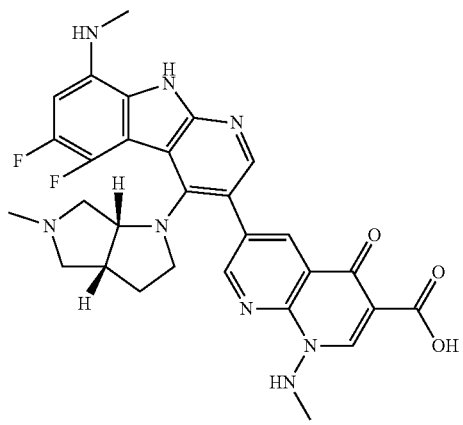 [SMILES: CNc1cc(F)c(F)c2c1[nH]c1ncc(-c3cnc4c(c3)c(=O)c(C(=O)O)cn4NC)c(N3CC[C@@H]4CN(C)C[C@@H]43)c12]

The Example 3.01B was prepared in analogy to Example 3.01A by replacing compound 3.01a with compound 3.01b in step (c).

The absolute configuration of Example 3.01A was determined by crystal analysis and was shown as FIGURE.

The following examples were prepared in analogy to Example 3.01A and 3.01B, by replacing tert-butyl N-(3,4-dichloro-5,6-difluoro-9H-pyrido[2,3-b]indol-8-yl)-N-methyl-carbamate (Intermediate A3) with the "CORE" in step (a), cis-(3a,6a)-5-methyl-2,3,3a,4,6,6a-hexahydro-1H-pyrrolo[2,3-c]pyrrole with the "AMINE" in step (a), THF/H$_2$O with the "SOLVENT" in step (b), Ad$_2$nBuP Biphenyl with the "CATALYST" in step (b) and [8-[tert-butoxycarbonyl(methyl)amino]-6-ethoxycarbonyl-5-oxo-1,8-naphthyridin-3-yl]boronic acid with the "BORONIC REAGENT" in step (c) by the reagents indicated in Table 3.

TABLE 3

| | | Compound synthesis and characterization | |
|---|---|---|---|
| No. | Compound Name and Structure | CORE, AMINE, BORONIC REAGENT, CATALYST1, CATALYST2, and SLOVENT | $^1$H NMR and MS (ESI) |
| 3.02A | 6-[4-[(2S)-2-[(dimethylamino)methyl]morpholin-4-yl]-6-fluoro-8-(methylamino)-9H-pyrido[2,3-b]indol-3-yl]-1-methyl-4-oxo-1,8-naphthyridine-3-carboxylic acid | CORE: Intermediate A1<br>AMINE: N,N-dimethyl-1-morpholin-2-yl-methanamine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 9.06 (s, 1H), 8.96 (s, 1H), 8.64-8.78 (m, 1H), 8.30 (s, 1H), 8.13 (br s, 1H), 7.05-7.21 (m, 1H), 6.31-6.51 (m, 1H), 6.31-6.51 (m, 1H), 4.02-4.17 (m, 4H), 3.78-4.02 (m, 2H), 3.08 (br s, 3H), 2.98-3.02 (m, 1H), 2.92 (s, 4H), 2.73 (s, 7H) MS: 560.2 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
|---|---|---|---|
| 3.02B | 6-[4-[(2R)-2-[(dimethylamino)methyl]morpholin-4-yl]-6-fluoro-8-(methylamino)-9H-pyrido[2,3-b]indol-3-yl]-1-methyl-4-oxo-1,8-naphthyridine-3-carboxylic acid 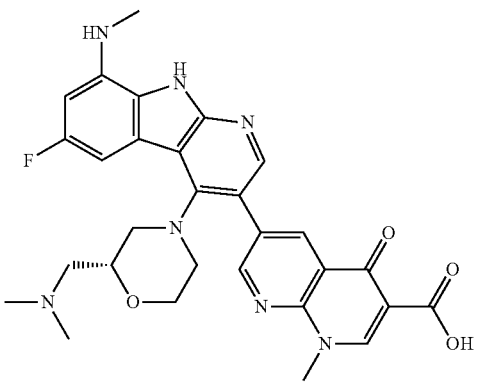 | CORE: Intermediate A1<br>AMINE: N,N-dimethyl-1-morpholin-2-yl-methanamine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 9.05 (s, 1H), 8.96 (s, 1H), 8.71 (br s, 1H), 8.24 (s, 1H), 8.13 (s, 1H), 7.13 (br d, J = 8.44 Hz, 1H), 6.41 (br d, J = 10.27 Hz, 1H), 4.11 (s, 4H), 3.80-4.03 (m, 2H), 2.94-3.16 (m, 5H), 2.91 (s, 3H), 2.75 (s, 6H), 2.67 (br s, 1H)<br>MS: 560.2 ([M + H]$^+$) |
| 3.03A | 6-[4-[(3aS,6aS)-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid 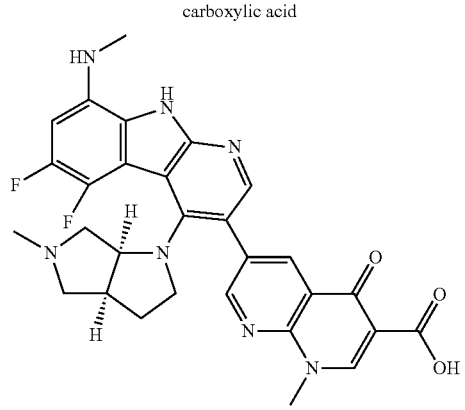 | CORE: Intermediate A3<br>AMINE: Intermediate C8<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.85 (br s, 1H), 11.73 (br s, 1H), 9.26 (s, 1H), 9.14 (d, J = 2.32 Hz, 1H), 8.72 (d, J = 2.20 Hz, 1H), 8.12 (s, 1H), 6.58 (dd, J = 6.17, 13.51 Hz, 1H), 5.68 (br d, J = 5.01 Hz, 1H), 4.46 (br s, 1H), 4.17 (s, 3H), 2.94 (br d, J = 7.46 Hz, 1H), 2.87-2.92 (m, 4H), 2.81 (br d, J = 7.58 Hz, 1H), 2.37-2.47 (m, 2H), 2.15 (br t, J = 8.25 Hz, 1H), 2.07-2.12 (m, 3H), 1.88-2.02 (m, 1H), 1.75-1.84 (m, 1H), 1.61 (br d, J = 5.75 Hz, 1H)<br>MS: 560.1 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
|---|---|---|---|
| 3.03B | 6-[4-[(3aR,6aR)-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C8<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) δ ppm 9.20 (s, 1 H), 9.09 (d, J = 2.5 Hz, 1 H), 8.72 (d, J = 2.3 Hz, 1 H), 8.28 (s, 1 H), 6.62 (dd, J = 13.3, 6.3 Hz, 1 H), 4.22 (s, 4 H), 4.03 (br d, J = 6.5 Hz, 1 H), 3.63 (br d, J = 6.5 Hz, 2 H), 3.41~3.47 (m, 2 H), 2.88~3.03 (m, 5 H), 2.70 (s, 3 H), 2.09~2.22 (m, 1 H), 1.87 (br dd, J = 11.7, 5.6 Hz, 1 H)<br>MS (ESI): 560.3 ([M + H]$^+$) |
| 3.04A | 6-[4-[(3aS,6aS)-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-methyl-4-oxo-1,8-naphthyridine-3-carboxylic acid | CORE: Intermediate A1<br>AMINE: Intermediate C8<br>BORONIC REAGENT: Intermediate B23<br>CATALYST: Xphos Pd G2(CAS: 1310584-14-5)<br>SOLVENT: THF/H$_2$O | $^1$H NMR (400 MHz, DMSO-d6): δ ppm: 11.45 (br s, 1H), 9.06 (d, 1H), 8.95 (s, 1H), 8.65 (d, 1H), 8.15 (s, 1H), 7.49-7.57 (m, 1H), 6.94 (m, 1H), 6.38 (m, 1H), 5.83 (br d, 1H), 3.87 (m, 1H), 3.47 (m, 1H), 3.03 (m, 1H), 2.90 (d, 3H), 2.86 (d, 3H), 2.67 (br d, 1H), 2.51 (br d, 1H), 2.35 (br d, 1H), 2.12-2.03 (m, 2H), 2.01 (s, 3H), 1.75-1.65 (m, 2H)<br>MS: 542.3 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
| --- | --- | --- | --- |
| 3.05A | 6-[4-[(3aS,6aS)-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-(methylamino)-4-oxo-1,8-naphthyridine-3-carboxylic acid | CORE: Intermediate A1<br>AMINE: Intermediate C8<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: 11.43 (s, 1H), 9.19 (s, 1H), 9.03 (d, 1H), 8.63 (s, 1H), 8.11 (s, 1H), 6.92 (m, 1H), 6.38 (m, 1H), 5.82 (br d, 1H), 4.10 (s, 3H), 3.89 (br s, 1H), 3.42-3.51 (m, 1H), 2.96-3.04 (m, 1H), 2.86 (d, 3H), 2.71-2.56 (m, 1H), 2.51 (br d, 1H), 2.36 (br d, 1H), 2.12-1.97 (m, 5H), 1.69 (br m, 2H)<br>MS: 557.4 ([M + H]$^+$) |
| 3.06A | 6-[4-[(3R)-3-(dimethylamino)-1-piperidyl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: N,N-dimethylpiperidin-3-amine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.78 (br s, 1H), 11.84 (s, 1H), 9.29 (s, 1H), 9.13 (d, J = 2.32 Hz, 1H), 8.74 (d, J = 2.32 Hz, 1H), 8.26 (s, 1H), 6.62 (dd, J = 6.30, 13.39 Hz, 1H), 5.69 (br d, J = 5.01 Hz, 1H), 4.18 (s, 3H), 3.13-3.28 (m, 2H), 2.99 (br d, J = 11.62 Hz, 1H), 2.90 (d, J = 4.77 Hz, 3H), 2.76-2.87 (m, 1H), 2.63-2.74 (m, 1H), 2.10 (br s, 1H), 1.99 (s, 6H), 1.70-1.95 (m, 1H), 1.49-1.61 (m, 1H), 1.36-1.49 (m, 1H)<br>MS: 562.4 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
|---|---|---|---|
| 3.06B | 6-[4-[(3S)-3-(dimethylamino)-1-piperidyl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: N,N-dimethylpiperidin-3-amine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.60-15.03 (m, 1H), 11.85 (br s, 1H), 9.29 (s, 1H), 9.13 (d, J = 2.20 Hz, 1H), 8.74 (d, J = 2.20 Hz, 1H), 8.26 (s, 1H), 6.62 (dd, J = 6.17, 13.39 Hz, 1H), 5.69 (br d, J = 4.65 Hz, 1H), 4.18 (s, 3H), 3.10-3.28 (m, 2H), 2.99 (br d, J = 10.03 Hz, 1H), 2.90 (d, J = 4.77 Hz, 3H), 2.84 (br s, 1H), 2.59-2.75 (m, 1H), 2.03-2.19 (m, 1H), 1.98 (s, 6H), 1.67-1.86 (m, 1H), 1.48-1.65 (m, 1H), 1.35-1.48 (m, 1H)<br>MS: 562.4 ([M + H]$^+$) |
| 3.07A | 6-[4-[(3aR,6aR)-1-methyl-2,3,3a,4,6,6a-hexahydropyrrolo[2,3-c]pyrrol-5-yl]-5,6-difluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: cis-1-methyl-3,3a,4,5,6,6a-hexahydro-2H-pyrrolo[2,3-c]pyrrole<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.71 (br s, 1H), 11.79 (s, 1H), 9.12 (d, J = 2.32 Hz, 1H), 9.03 (s, 1H), 8.70 (d, J = 2.32 Hz, 1H), 8.29 (s, 1H), 7.63 (q J = 5.50 Hz, 1H), 6.60 (dd, J = 6.24, 13.45 Hz, 1H), 3.45-3.59 (m, 2H), 2.96 (d, J = 5.62 Hz, 3H), 2.90 (d, J = 4.89 Hz, 3H), 2.73-2.86 (m, 3H), 2.63-2.71 (m, 1H), 2.21 (br d, J = 8.44 Hz, 1H), 1.95 (s, 3H), 1.75-1.89 (m, 1H), 1.23-1.35 (m, 1H)<br>MS: 575.6 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
|---|---|---|---|
| 3.07B | 6-[4-[(3aS,6aS)-1-methyl-2,3,3a,4,6,6a-hexahydropyrrolo[2,3-c]pyrrol-5-yl]-5,6-difluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: cis-1-methyl-3,3a,4,5,6,6a-hexahydro-2H-pyrrolo[2,3-c]pyrrole<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.71 (br s, 1H), 11.79 (br s, 1H), 9.12 (d, J = 2.20 Hz, 1H), 9.03 (s, 1H), 8.70 (d, J = 2.32 Hz, 1H), 8.28 (s, 1H), 7.63 (q, J = 5.62 Hz, 1H), 6.60 (dd, J = 6.17, 13.51 Hz, 1H), 5.69 (br d, J = 4.77 Hz, 1H), 3.43-3.62 (m, 2H), 2.86-2.99 (m, 7H), 2.74-2.86 (m, 3H), 2.63-2.71 (m, 1H), 2.20 (q, J = 8.35 Hz, 1H), 1.95 (s, 3H), 1.75-1.89 (m, 1H), 1.23-1.35 (m, 1H)<br>MS: 575.6 ([M + H]$^+$) |
| 3.08A | 6-[4-[(3aR,6aR)-1-methyl-2,3,3a,4,6,6a-hexahydropyrrolo[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: cis-1-methyl-3,3a,4,5,6,6a-hexahydro-2H-pyrrolo[2,3-c]pyrrole<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.66 (br s, 1H), 12.02 (br s, 1H), 9.15 (br s, 1H), 8.98-9.06 (m, 1H), 8.57-8.66 (m, 1H), 8.21 (s, 1H), 6.57 (dd, J = 6.24, 13.45 Hz, 1H), 5.85 (br s, 1H), 4.12 (s, 3H), 3.41-3.57 (m, 2H), 2.90 (br d, J = 4.77 Hz, 4H), 2.74-2.85 (m, 3H), 2.60-2.70 (m, 1H), 2.15-2.26 (m, 1H), 1.91-2.08 (m, 3H), 1.74-1.85 (m, 1H), 1.20-1.36 (m, 1H)<br>MS: 560.2 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | ¹H NMR and MS (ESI) |
|---|---|---|---|
| 3.09A | 6-[4-[(3aR,6aR)-3a-fluoro-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A12<br>AMINE: Intermediate C12<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, DMSO-d₆) δ ppm 9.17 (s, 1 H), 9.10 (d, J = 2.3 Hz, 1 H), 8.74 (d, J = 2.5 Hz, 1 H), 8.28 (s, 1 H), 6.70 (dd, J = 13.3, 6.5 Hz, 1 H), 4.20 (s, 3 H), 3.87~3.93 (m, 2 H), 3.68-3.76 (m, 2 H), 3.36~3.58 (m, 2 H), 2.94 (s, 4 H), 2.68 (s, 3 H), 2.53~2.60 (m, 1 H), 2.23~2.37 (m, 1 H)<br>¹⁹FNMR (400 MHz, DMSO-d6) δ ppm −145.14 (br s, 1 F), −147.57 (br d, J = 24.1 Hz, 1 F), −153.19 (br s, 1 F). EE >97.2%.<br>MS (ESI): 578.3 ([M + H] +), 289.6 ([M/2 + H] +). |
| 3.09B | 6-[4-[(3aS,6aS)-3a-fluoro-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C12<br>BORONIC REAGENT: Intermediate B2<br>CATALYST: Pd-Ad₂nBuP Biphenyl Precat (CAS#: 1375477-29-4)<br>SOLVENT: THF /H₂O | ¹H NMR (400 MHz, DMSO-d₆) δ ppm 8.97 (br s, 2 H) 8.54-8.68 (m, 1 H) 8.14 (br s, 1 H) 6.56 (br s, 1 H) 6.04 (br s, 1 H) 4.06 (br s, 4 H) 3.93 (br s, 1 H) 2.90 (br s, 3 H) 2.75 (br s, 1 H) 2.27 (br s, 2 H) 2.06 (br s, 3 H) 1.73-1.78 (m, 1 H) 1.63 (br s, 1 H) 1.52 (br s, 1 H) 1.21 (br s, 1 H) 1.05-1.09 (m, 1 H)<br>MS: 578.0 ([M + H]⁺) |

TABLE 3-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
|---|---|---|---|
| 3.10A | 6-[4-[(3aR,6aR)-3a-fluoro-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-(methylamino)-4-oxo-1,8-naphthyridine-3-carboxylic acid | CORE: Intermediate A12<br>AMINE: Intermediate C12<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) δ ppm 9.12 (d, J = 2.0 Hz, 1 H), 9.03 (s, 1 H), 8.76 (d, J = 2.3 Hz, 1 H), 8.31 (s, 1 H), 6.69 (dd, J = 13.3, 6.5 Hz, 1 H), 3.91-3.94 (m, 3 H), 3.69-3.77 (m, 1 H), 3.35-3.57 (m, 2 H), 3.03 (s, 3 H), 2.94 (s, 4 H), 2.67 (s, 3 H), 2.54-2.62 (m, 1 H), 2.22-2.38 (m, 1 H)<br>$^{19}$FNMR (400 MHz, DMSO-d6) δ ppm −145.11 (br s, 1 F), −147.64 (br d, J = 24.1 Hz, 1 F), −153.48 (br s, 1 F). EE >97.8%.<br>MS (ESI): 593.2 ([M + H]$^+$), 297.2 ([M/2 + H]$^+$). |
| 3.10B | 6-[4-[(3aS,6aS)-3a-fluoro-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: Intermediate C12<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm: $^1$H NMR (400 MHz, DMSO-d$_6$) δ ppm 9.11 (d, J = 2.3 Hz, 1 H) 8.99 (s, 1 H) 8.75 (d, J = 2.3 Hz, 1 H) 8.23 (s, 1 H) 7.54 (q, J = 5.5 Hz, 1 H) 6.59 (dd, J = 13.6, 6.3 Hz, 1 H) 5.85 (br d, J = 4.5 Hz, 1 H) 3.91-4.06 (m, 1 H) 3.46-3.51 (m, 2 H) 2.96 (d, J = 5.5 Hz, 3 H) 2.87-2.93 (m, 3 H) 2.78 (br t, J = 10.5 Hz, 1 H) 2.47 (br d, J = 10.0 Hz, 1 H) 2.23 (br d, J = 9.0 Hz, 2 H) 2.09-2.19 (m, 2 H) 2.04 (s, 3 H).<br>MS: 593.0 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
|---|---|---|---|
| 3.11A | 6-[4-[(3aS,6aS)-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-methyl-4-oxo-1,8-naphthyridine-3-carboxylic acid 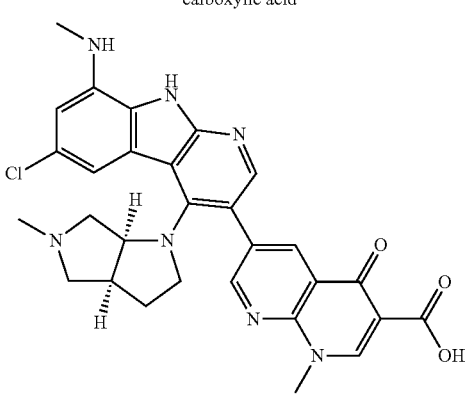 | CORE: Intermediate A11<br>AMINE: Intermediate C8<br>BORONIC REAGENT: Intermediate B2<br>CATALYST: Pd-Ad$_2$nBuP Biphenyl Precat (CAS#: 1375477-29-4)<br>SOLVENT: THF/H$_2$O<br>SFC Method:<br>Column: AD-3S (250 mm*30 mm, 10 um),<br>Flowing Phase: CO$_2$ + 0.1% NH$_3$•H$_2$O in IPA,<br>Temperature: 35° C.,<br>Flowrate (mL/min): 60 | $^1$H NMR (400 MHz, Methanol-d4): δ ppm 11.76 (s, 1 H) 9.51-9.75 (m, 1 H) 9.32 (s, 1 H) 9.11 (dd, J = 13.9, 2.1 Hz, 1 H) 8.69 (dd, J = 12.0, 2.3 Hz 1 H) 8.22 (s, 1 H) 7.16-7.30 (m, 1 H) 6.97-7.13 (m, 1 H) 6.61 (s, 1 H) 4.19 (s, 3 H) 3.99 (br s, 1 H) 3.82 (br s, 1 H) 3.69 (br s, 2 H) 3.14-3.29 (m, 1 H) 2.97-3.08 (m, 1 H) 2.97-3.08 (m, 1 H) 2.87-2.97 (m, 3 H) 2.62-2.74 (m, 3 H) 2.28-2.35 (m, 1 H) 2.07-2.20 (m, 1 H) 1.95 (br s, 1 H) 1.86 (br s, 1 H)<br>MS: 558.1 ([M + H]$^+$) |
| 3.11B | 6-[4-[(3aR,6aR)-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-methyl-4-oxo-1,8-naphthyridine-3-carboxylic acid 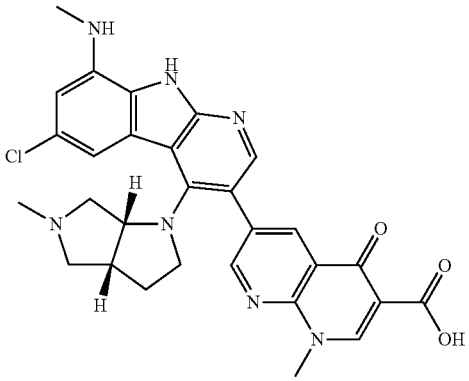 | CORE: Intermediate A11<br>AMINE: Intermediate C8<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, Methanol-d4): δ ppm 11.76 (s, 1 H) 9.72 (br s, 1 H) 9.31 (s, 1 H) 9.11 (dd, J = 12.9, 2.1 Hz, 1 H) 8.63-8.74 (m, 1 H) 8.22 (s, 1 H) 7.14 (br d, J = 16.6 Hz, 1 H) 6.61 (d, J = 1.5 Hz, 1 H) 4.19 (s, 3 H) 4.01 (br dd, J = 14.6, 7.8 Hz, 1 H) 3.82 (br d, J = 6.5 Hz, 1 H) 3.69 (br s, 2 H) 3.24-3.32 (m, 1 H) 2.97-3.06 (m, 1 H) 2.94 (s, 3 H) 2.64-2.74 (m, 3 H) 2.24-2.36 (m, 1 H) 2.07-2.20 (m, 1 H) 1.91-2.01 (m, 1 H) 1.86 (br s, 1 H).<br>MS: 558.1 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
|---|---|---|---|
| 3.12A | 6-[4-[(3aS,6aS)-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-(methylamino)-4-oxo-1,8-naphthyridine-3-carboxylic acid | CORE: Intermediate A11<br>AMINE: Intermediate C8<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm 11.77 (s, 1 H) 9.71 (br s, 1 H) 9.04-9.21 (m, 2 H) 8.73 (dd, J = 11.3, 2.3 Hz, 1 H) 8.25 (d, J = 2.5 Hz, 1 H) 7.15 (br d, J = 18.6 Hz, 1 H) 6.61 (d, J = 1.5 Hz, 1 H) 4.17 (br d, J = 7.5 Hz, 1 H) 3.94-4.05 (m, 1 H) 3.82 (br d, J = 6.8 Hz, 1 H) 3.69-3.75 (m, 1 H) 3.70 (br s, 1 H) 3.19-3.30 (m, 1 H) 2.99 (br d, J = 2.0 Hz, 4 H) 2.94 (s, 4 H) 2.60-2.73 (m, 4 H) 2.24-2.35 (m, 1 H) 2.06-2.21 (m, 1 H) 2.06-2.21 (m, 1 H) 1.97 (br d, J = 9.3 Hz, 1 H) 1.86 (br s, 1 H)<br>MS: 572.1 ([M + H]$^+$) |
| 3.12B | 6-[4-[(3aR,6aR)-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-(methylamino)-4-oxo-1,8-naphthyridine-3-carboxylic acid | CORE: Intermediate A11<br>AMINE: Intermediate C8<br>BORONIC REAGENT: Intermediate B23<br>CATALYST: Pd-Ad$_2$nBuP Biphenyl Precat (CAS#: 1375477-29-4)<br>SOLVENT: THF/H$_2$O | $^1$H NMR (400 MHz, DMSO-d6): δ ppm 11.80 (s, 1 H) 9.78 (br s, 1 H) 9.01-9.20 (m, 2 H) 8.72 (br d, J = 8.8 Hz, 1 H) 8.12-8.35 (m, 1 H) 7.15 (br d, J = 16.6 Hz, 1 H) 6.61 (d, J = 1.5 Hz, 1 H) 4.06-4.24 (m, 1 H) 4.17 (br d, J = 7.5 Hz, 1 H) 3.97 (br d, J = 7.3 Hz, 2 H) 3.16-3.34 (m, 1 H) 2.96-3.09 (m, 4 H) 2.94 (s, 3 H) 2.62-2.73 (m, 4 H) 2.31 (br d, J = 17.3 Hz, 1 H) 2.05-2.21 (m, 1 H) 2.05-2.21 (m, 1 H) 1.96 (br s, 1 H) 1.72-1.90 (m, 1 H)<br>MS: 573.2 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
|---|---|---|---|
| 3.13A | 6-[4-[(4aS,7aR)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: Intermediate C41<br>BORONIC REAGENT: Intermediate B23<br>CATALYST: cataCXium ® A Pd G2 (Sigma-Aldrich, Catalog #: 761311)<br>SOLVENT: Dioxane/H$_2$O | 1H NMR (400 MHz, MeOD-d4) δ ppm: 9.13 (s, 1H), 9.08-9.10 (m, 1H), 8.78 (d, J = 2.32 Hz, 1H), 8.28 (s, 1H), 6.60 (dd, J = 6.42, 13.39 Hz, 1H), 4.03 (t, J = 3.48 Hz, 1H), 3.58-3.73 (m, 4H), 3.46-3.56 (m, 2H), 3.08 (s, 3H), 3.01 (s, 3H), 2.90 (d, J = 10.39 Hz, 1H), 2.73 (m, 1H), 2.48 (br d, J = 12.10 Hz, 1H), 2.39 (s, 3H), 2.04-2.13 (m, 1H), 1.73-1.85 (m, 1H), 1.31 (s, 1H)<br>MS: 591.2 ([M + H]$^+$) |
| 3.13B | 6-[4-[(4aR,7aS)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-(methylamino)-4-oxo-1,8-naphthyridine-3-carboxylic acid | CORE: Intermediate A3<br>AMINE: Intermediate C41<br>BORONIC REAGENT: Intermediate B23<br>CATALYST: cataCXium ® A Pd G2 (Sigma-Aldrich, Catalog #: 761311)<br>SOLVENT: Dioxane/H$_2$O | 1H NMR (400 MHz, MeOD-d4) δ ppm: 9.13 (s, 1H), 9.08-9.10 (m, 1H), 8.78 (d, J = 2.32 Hz, 1H), 8.28 (s, 1H), 6.60 (dd, J = 6.42, 13.39 Hz, 1H), 4.03 (t, J = 3.48 Hz, 1H), 3.58-3.73 (m, 4H), 3.46-3.56 (m, 2H), 3.08 (s, 3H), 3.01 (s, 3H), 2.90 (d, J = 10.39 Hz, 1H), 2.73 (m, 1H), 2.48 (br d, J = 12.10 Hz, 1H), 2.39 (s, 3H), 2.04-2.13 (m, 1H), 1.73-1.85 (m, 1H), 1.31 (s, 1H)<br>MS: 591.2 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
|---|---|---|---|
| 3.14A | 6-[4-[(4aS,7aR)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C41<br>BORONIC REAGENT: Intermediate B2<br>CATALYST: cataCXium ® A Pd G2 (Sigma-Aldrich, Catalog #: 761311)<br>SOLVENT: Dioxane/H$_2$O | 1H NMR (400 MHz, MeOD-d4) δ ppm: 9.11 (s, 1H), 9.05 (d, J = 2.32 Hz, 1H), 8.70 (d, J = 2.45 Hz, 1H), 8.26 (s, 1H), 6.59 (dd, J = 6.42, 13.14 Hz, 1H), 4.22 (s, 3H), 3.90-4.10 (m, 1H), 3.58-3.70 (m, 4H), 3.36-3.54 (m, 2H), 3.01 (s, 3H), 2.86 (d, J = 10.51 Hz, 1H), 2.70 (br d, J = 2.93 Hz, 1H), 2.41-2.44 (m, 1H), 2.36 (s, 3H)<br>MS: 576.2 ([M + H]$^+$) |
| 3.14B | 6-[4-[(4aR,7aS)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C41<br>BORONIC REAGENT: Intermediate B2<br>CATALYST: cataCXium ® A Pd G2 (Sigma-Aldrich, Catalog #: 761311)<br>SOLVENT: Dioxane/H$_2$O | 1H NMR (400 MHz, MeOD-d4) δ ppm: 9.11 (s, 1H), 9.05 (d, J = 2.32 Hz, 1H), 8.70 (d, J = 2.45 Hz, 1H), 8.26 (s, 1H), 6.59 (dd, J = 6.42, 13.14 Hz, 1H), 4.22 (s, 3H), 3.90-4.10 (m, 1H), 3.58-3.70 (m, 4H), 3.36-3.54 (m, 2H), 3.01 (s, 3H), 2.86 (d, J = 10.51 Hz, 1H), 2.70 (br d, J = 2.93 Hz, 1H), 2.41-2.44 (m, 1H), 2.36 (s, 3H)<br>MS: 576.2 ([M + H]+) |

TABLE 3-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
|---|---|---|---|
| 3.15A | 6-[4-[(3aR,6aR)-1-methyl-2,3,3a,4,6,6a-hexahydropyrrolo[2,3-c]pyrrol-5-yl]-6-chloro-8-(methylamino)-9H-pyrido[2,3-b]indol-3-yl]-1-methyl-4-oxo-1,8-naphthyridine-3-carboxylic acid | CORE: Intermediate A11<br>AMINE: cis-1-methyl-3,3a,4,5,6,6a-hexahydro-2H-pyrrolo[2,3-c]pyrrole<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.77 (br s, 1H), 11.61 (br s, 1H), 9.30 (s, 1H), 9.11 (s, 1H), 8.65 (d, J = 2.20 Hz, 1H), 8.26-8.47 (m, 1H), 8.14 (s, 1H), 6.47-6.66 (m, 1H), 5.82 (br s, 1H), 4.18 (s, 3H), 3.59-4.00 (m, 1H), 3.13-3.28 (m, 2H), 2.86-3.13 (m, 7H), 2.61-2.85 (m, 3H), 2.14-2.40 (m, 1H), 1.94 (br s, 1H), 1.46-1.76 (m, 1H)<br>MS: 558.2 ([M + H]$^+$) |
| 3.15B | 6-[4-[(3aS,6aS)-1-methyl-2,3,3a,4,6,6a-hexahydropyrrolo[2,3-c]pyrrol-5-yl]-6-chloro-8-(methylamino)-9H-pyrido[2,3-b]indol-3-yl]-1-methyl-4-oxo-1,8-naphthyridine-3-carboxylic acid | CORE: Intermediate A11<br>AMINE: cis-1-methyl-3,3a,4,5,6,6a-hexahydro-2H-pyrrolo[2,3-c]pyrrole<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.77 (s, 1H), 11.63 (br s, 1H), 9.31 (s, 1H), 9.12 (br s, 1H), 8.66 (s, 1H), 8.11-8.25 (m, 2H), 6.57 (s, 1H), 5.84 (br s, 1H), 4.19 (s, 3H), 3.81 (br s, 1H), 3.20 (br s, 3H), 3.10 (br s, 2H), 2.83-2.96 (m, 4H), 2.55-2.81 (m, 3H), 2.10-2.34 (m, 1H), 1.94 (br s, 1H), 1.42-1.77 (m, 1H)<br>MS: 558.2 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | ¹H NMR and MS (ESI) |
|---|---|---|---|
| 3.16A | 6-[5,6-difluoro-8-(methylamino)-4-[(5R)-9-methyl-6-oxa-2,9-diazaspiro[4.5]decan-2-yl]-9H-pyrido[2,3-b]indol-3-yl]-1-methyl-4-oxo-1,8-naphthyridine-3-carboxylic acid | CORE: Intermediate A3<br>AMINE: 9-methyl-6-oxa-2,9-diazaspiro[4.5]decane<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, DMSO-d₆): δ ppm: 14.79 (s, 1H), 11.79 (br s, 1H), 9.29 (s, 1H), 9.08 (d, J = 2.20 Hz, 1H), 8.67 (s, 1H), 8.25 (br s, 1H), 8.13 (s, 1H), 6.60 (dd, J = 6.24, 13.57 Hz, 1H), 5.70 (br s, 1H), 4.17 (s, 3H), 3.38-3.65 (m, 2H), 3.21-3.30 (m, 2H), 3.14-3.21 (m, 1H), 3.01-3.13 (m, 2H), 2.90 (d, J = 4.77 Hz, 3H), 2.70-2.81 (m, 1H), 2.12 (br s, 2H), 1.82-2.10 (m, 5H)<br>MS: 590.2 ([M + H]⁺) |
| 3.16B | 6-[5,6-difluoro-8-(methylamino)-4-[(5S)-9-methyl-6-oxa-2,9-diazaspiro[4.5]decan-2-yl]-9H-pyrido[2,3-b]indol-3-yl]-1-methyl-4-oxo-1,8-naphthyridine-3-carboxylic acid | CORE: Intermediate A3<br>AMINE: 9-methyl-6-oxa-2,9-diazaspiro[4.5]decane<br>BORONIC REAGENT: Intermediate B2<br>CATALYST: Pd-Ad₂nBuP Biphenyl Precat (CAS#: 1375477-29-4)<br>SOLVENT: THF/H₂O | ¹H NMR (400 MHz, DMSO-d₆): δ ppm: 14.79 (s, 1H), 11.81 (br s, 1H), 9.29 (s, 1H), 9.08 (br s, 1H), 8.68 (br s, 1H), 8.26 (br s, 1H), 8.13 (s, 1H), 6.53-6.64 (m, 1H), 5.70 (br s, 1H), 4.17 (s, 3H), 3.39-3.91 (m, 3H), 3.17-3.30 (m, 3H), 3.09 (br s, 1H), 2.90 (d, J = 4.65 Hz, 4H), 2.64-2.81 (m, 1H), 1.81-2.28 (m, 6H)<br>MS: 590.2 ([M + H]⁺) |

TABLE 3-continued

Compound synthesis and characterization

| No. | Compound Name and Structure | CORE, AMINE, BORONIC REAGENT, CATALYST1, CATALYST2, and SLOVENT | ¹H NMR and MS (ESI) |
|---|---|---|---|
| 3.17A | 6-[4-[(3aR,6aR)-1-methyl-2,3,3a,4,6,6a-hexahydropyrrolo[2,3-c]pyrrol-5-yl]-6-fluoro-8-(methylamino)-9H-pyrido[2,3-b]indol-3-yl]-1-(methylamino)-4-oxo-1,8-naphthyridine-3-carboxylic acid | CORE: Intermediate A1<br>AMINE: cis-1-methyl-3,3a,4,5,6,6a-hexahydro-2H-pyrrolo[2,3-c]pyrrole<br>BORONIC REAGENT: Intermediate B23<br>CATALYST: Pd-Ad₂nBuP Biphenyl Precat (CAS#: 1375477-29-4)<br>SOLVENT: THF/H₂O | ¹H NMR (400 MHz, DMSO-d₆): δ ppm: 14.64 (s, 1H), 11.43 (br s, 1H), 9.11 (d, J = 2.32 Hz, 1H), 9.03 (s, 1H), 8.66 (d, J = 2.32 Hz, 1H), 8.13 (br d, J = 6.48 Hz, 1H), 8.02 (br s, 1H), 7.62 (q, J = 5.58 Hz, 1H), 6.42 (dd, J = 1.77, 11.80 Hz, 1H), 5.82 (br s, 1H), 3.82 (br s, 1H), 2.82-3.09 (m, 10H), 2.58-2.77 (m, 2H), 2.40 (br s, 3H), 2.20-2.33 (m, 1H), 1.89 (br s, 1H), 1.52 (br s, 1H)<br>MS: 557.2 ([M + H]⁺) |
| 3.17B | 6-[4-[(3aS,6aS)-1-methyl-2,3,3a,4,6,6a-hexahydropyrrolo[2,3-c]pyrrol-5-yl]-6-fluoro-8-(methylamino)-9H-pyrido[2,3-b]indol-3-yl]-1-(methylamino)-4-oxo-1,8-naphthyridine-3-carboxylic acid | CORE: Intermediate A1<br>AMINE: cis-1-methyl-3,3a,4,5,6,6a-hexahydro-2H-pyrrolo[2,3-c]pyrrole<br>BORONIC REAGENT: Intermediate B23<br>CATALYST: Pd-Ad₂nBuP Biphenyl Precat (CAS#: 1375477-29-4)<br>SOLVENT: THF/H₂O | ¹H NMR (400 MHz, DMSO-d₆): δ ppm: 14.64 (br s, 1H), 11.47 (br s, 1H), 9.07-9.16 (m, 1H), 8.96-9.05 (m, 1H), 8.63-8.81 (m, 1H), 8.08-8.23 (m, 1H), 7.78 (dd, J = 4.52, 8.07 Hz, 1H), 7.50-7.65 (m, 1H), 6.43 (br d, J = 11.74 Hz, 1H), 5.85 (br s, 1H), 3.72 (br s, 1H), 2.87-3.18 (m, 10H), 2.61-2.83 (m, 3H), 2.40-2.48 (m, 2H), 2.33 (br d, J = 1.83 Hz, 1H), 1.95 (br s, 1H), 1.56 (br s, 1H)<br>MS: 557.2 ([M + H]⁺) |

TABLE 3-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
|---|---|---|---|
| 3.18A | 6-[4-[(3aR,7aR)-1-methyl-3,3a,4,5,7,7a-hexahydro-2H-pyrrolo[2,3-c]pyridin-6-yl]-6-fluoro-8-(methylamino)-9H-pyrido[2,3-b]indol-3-yl]-1-methyl-4-oxo-1,8-naphthyridine-3-carboxylic acid | CORE: Intermediate A1<br>AMINE: cis-1-methyl-2,3,3a,4,5,6,7,7a-octahydropyrrolo[2,3-c]pyridine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.78 (br s, 1H), 11.52 (br s, 1H), 9.29 (s, 1H), 9.13 (d, J = 2.08 Hz, 1H), 8.66-8.73 (m, 1H), 8.20 (s, 1H), 8.14 (s, 1H), 7.44 (br s, 1H), 6.42-6.54 (m, 1H), 5.86 (br s, 1H), 4.18 (s, 3H), 2.75-3.23 (m, 9H), 2.07-2.36 (m, 3H), 1.84-2.05 (m, 2H), 1.58-1.79 (m, 2H), 1.47 (br s, 1H), 1.16-1.32 (m, 1H). MS: 556.2 ([M + H]$^+$) |
| 3.18B | 6-[4-[(3aS,7aS)-1-methyl-3,3a,4,5,7,7a-hexahydro-2H-pyrrolo[2,3-c]pyridin-6-yl]-6-fluoro-8-(methylamino)-9H-pyrido[2,3-b]indol-3-yl]-1-methyl-4-oxo-1,8-naphthyridine-3-carboxylic acid | CORE: Intermediate A1<br>AMINE: cis-1-methyl-2,3,3a,4,5,6,7,7a-octahydropyrrolo[2,3-c]pyridine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.79 (br s, 1H), 11.47 (s, 1H), 9.28 (s, 1H), 9.13 (d, J = 2.32 Hz, 1H), 8.69 (d, J = 2.32 Hz, 1H), 8.18 (s, 1H), 8.14 (s, 1H), 7.59 (br d, J = 9.41 Hz, 1H), 6.44 (dd, J = 2.14, 12.04 Hz, 1H), 5.84 (br d, J = 4.40 Hz, 1H), 4.18 (s, 3H), 3.11-3.26 (m, 1H), 2.98-3.11 (m, 3H), 2.92 (d, J = 4.77 Hz, 3H), 2.76 (br s, 1H), 2.28-2.38 (m, 1H), 2.23 (br d, J = 7.70 Hz, 1H), 2.09 (s, 4H), 1.81-1.96 (m, 1H), 1.62 (br d, J = 4.28 Hz, 2H), 1.30-1.45 (m, 1H)<br>MS: 556.2 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | ¹H NMR and MS (ESI) |
|---|---|---|---|
| 3.19A | 6-[5,6-difluoro-8-(methylamino)-4-[(3aR,4R,6aS)-4-(dimethylamino)-3,3a,4,5,6,6a-hexahydro-1H-cyclopenta[c]pyrrol-2-yl]-9H-pyrido[2,3-b]indol-3-yl]-1-(methylamino)-4-oxo-1,8-naphthyridine-3-carboxylic acid | CORE: Intermediate A3<br>AMINE: Intermediate C38<br>BORONIC REAGENT: Intermediate B23<br>CATALYST: Pd-Ad₂nBuP Biphenyl Precat (CAS#: 1375477-29-4)<br>SOLVENT: THF/H₂O | ¹H NMR (400 MHz, DMSO-d₆): δ ppm: 14.66 (br s, 1H), 11.80 (s, 1H), 9.13 (d, J = 2.32 Hz, 1H), 9.06 (s, 1H), 8.68 (d, J = 2.20 Hz, 1H), 8.30 (s, 1H), 8.14 (s, 1H), 7.63 (q, J = 5.67 Hz, 1H), 6.52-6.67 (m, 1H), 5.69 (br d, J = 4.77 Hz, 1H), 3.62-3.73 (m, 1H), 3.18 (br t, J = 8.56 Hz, 1H), 2.97 (d, J = 5.62 Hz, 3H), 2.67-2.93 (m, 6H), 2.53-2.61 (m, 1H), 2.25 (br s, 1H), 1.99 (br s, 6H), 1.44-1.70 (m, 2H), 1.13-1.29 (m, 2H)<br>MS: 603.3 ([M + H]⁺) |
| 3.19B | 6-[5,6-difluoro-8-(methylamino)-4-[(3aS,4R,6aR)-4-(dimethylamino)-3,3a,4,5,6,6a-hexahydro-1H-cyclopenta[c]pyrrol-2-yl]-9H-pyrido[2,3-b]indol-3-yl]-1-(methylamino)-4-oxo-1,8-naphthyridine-3-carboxylic acid | CORE: Intermediate A3<br>AMINE: Intermediate C38<br>BORONIC REAGENT: Intermediate B23<br>CATALYST: Pd-Ad₂nBuP Biphenyl Precat (CAS#: 1375477-29-4)<br>SOLVENT: THF/H₂O | ¹H NMR (400 MHz, DMSO-d₆): δ ppm: 14.66 (br s, 1H), 11.80 (br s, 1H), 9.13 (d, J = 2.32 Hz, 1H), 9.06 (s, 1H), 8.68 (d, J = 2.20 Hz, 1H), 8.29 (s, 1H), 8.15 (s, 1H), 7.64 (q, J = 5.62 Hz, 1H), 6.60 (dd, J = 6.17, 13.51 Hz, 1H), 5.69 (br d, J = 4.77 Hz, 1H), 3.70 (br t, J = 8.62 Hz, 1H), 3.17 (br t, J = 8.80 Hz, 1H), 2.97 (d, J = 5.62 Hz, 3H), 2.73-2.93 (m, 6H), 2.56 (br d, J = 6.60 Hz, 1H), 2.21 (br s, 1H), 1.97 (s, 6H), 1.50-1.66 (m, 2H), 1.11-1.26 (m, 2H)<br>MS: 603.3 ([M + H]⁺) |

TABLE 3-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
|---|---|---|---|
| 3.20A | 6-[4-[(3aR,4S,6aS)-4-(dimethylamino)-3,3a,4,5,6,6a-hexahydro-1H-cyclopenta[c]pyrrol-2-yl]-6-chloro-8-(methylamino)-9H-pyrido[2,3-b]indol-3-yl]-1-methyl-4-oxo-1,8-naphthyridine-3-carboxylic acid | CORE: Intermediate A11<br>AMINE: Intermediate C56<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 14.80 (br s, 1H), 11.66 (br s, 1H), 9.30 (s, 1H), 9.14 (d, J = 2.20 Hz, 1H), 8.65 (d, J = 2.08 Hz, 1H), 8.27 (s, 1H), 8.14 (s, 1H), 7.08 (s, 1H), 6.54-6.60 (m, 1H), 5.89 (br d, J = 4.77 Hz, 1H), 4.18 (s, 3H), 3.54 (br t, J = 8.74 Hz, 1H), 3.05-3.15 (m, 1H), 2.88-3.00 (m, 4H), 2.74-2.87 (m, 2H), 2.57 (br d, J = 15.04 Hz, 2H), 2.01-2.45 (m, 5H), 1.62-1.90 (m, 2H), 1.33-1.58 (m, 2H)<br>MS: 586.2 ([M + H]$^+$) |
| 3.20B | 6-[4-[(3aS,4S,6aR)-4-(dimethylamino)-3,3a,4,5,6,6a-hexahydro-1H-cyclopenta[c]pyrrol-2-yl]-6-chloro-8-(methylamino)-9H-pyrido[2,3-b]indol-3-yl]-1-methyl-4-oxo-1,8-naphthyridine-3-carboxylic acid | CORE: Intermediate A11<br>AMINE: Intermediate C56<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): ppm: 14.80 (s, 1H), 11.67 (br s, 1H), 9.31 (s, 1H), 9.14 (d, J = 2.08 Hz, 1H), 8.66 (s, 1H), 8.28 (br s, 1H), 8.14 (s, 1H), 7.08 (s, 1H), 6.54-6.63 (m, 1H), 5.90 (br d, J = 4.03 Hz, 1H), 4.19 (s, 3H), 3.54 (br s, 1H), 3.05-3.14 (m, 2H), 2.88-2.99 (m, 4H), 2.58-2.88 (m, 4H), 1.91-2.19 (m, 4H), 1.63-1.83 (m, 2H), 1.44 (br s, 2H), 1.24 (br s, 1H)<br>MS: 586.4 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
|---|---|---|---|
| 3.21A | 6-[5,6-difluoro-8-(methylamino)-4-[(4aR,7aR)-4-hydroxy-1-methyl-3,4,4a,5,7,7a-hexahydro-2H-pyrrolo[3,4-b]pyridin-6-yl]-9H-pyrido[2,3-b]indol-3-yl]-1-methyl-4-oxo-1,8-naphthyridine-3-carboxylic acid | CORE: Intermediate A3<br>AMINE: Intermediate C57<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 9.12 (s, 1H), 9.03-9.09 (m, 1H), 8.71 (br s, 1H), 8.31 (br s, 1H), 8.27 (s, 1H), 6.61 (br dd, J = 6.30, 13.02 Hz, 1H), 4.23 (s, 3H), 3.91-4.11 (m, 1H), 3.78 (br s, 1H), 3.39-3.61 (m, 3H), 2.94-3.19 (m, 6H), 2.60 (br s, 3H), 2.30 (br s, 1H), 1.88 (br d, J = 11.13 Hz, 1H), 1.64 (br d, J = 9.90 Hz, 1H)<br>MS: 590.3 ([M + H]$^+$) |
| 3.21B | 6-[5,6-difluoro-8-(methylamino)-4-[(4aS,7aS)-4-hydroxy-1-methyl-3,4,4a,5,7,7a-hexahydro-2H-pyrrolo[3,4-b]pyridin-6-yl]-9H-pyrido[2,3-b]indol-3-yl]-1-methyl-4-oxo-1,8-naphthyridine-3-carboxylic acid | CORE: Intermediate A3<br>AMINE: Intermediate C57<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, METHANOL-d$_4$): δ ppm: 9.13-9.26 (m, 1H), 9.09 (br s, 1H), 8.79 (br s, 1H), 8.20 (br d, J = 12.47 Hz, 1H), 6.56-6.66 (m, 1H), 4.23 (br s, 3H), 3.97 (br s, 1H), 3.88 (br s, 1H), 3.59 (br s, 1H), 3.21-3.30 (m, 2H), 3.14 (br d, J = 11.86 Hz, 1H), 3.00 (s, 3H), 2.81-2.96 (m, 2H), 2.71 (br s, 1H), 2.36 (br s, 3H), 1.82 (br s, 2H)<br>MS: 590.3 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | ¹H NMR and MS (ESI) |
|---|---|---|---|
| 3.22A | 6-[6-fluoro-8-(methylamino)-4-[(4aS,7aR)-4-methyl-2,3,4a,5,7,7a-hexahydropyrrolo[3,4-b][1,4]oxazin-6-yl]-9H-pyrido[2,3-b]indol-3-yl]-1-methyl-4-oxo-1,8-naphthyridine-3-carboxylic acid | CORE: Intermediate A1<br>AMINE: Intermediate C10<br>BORONIC REAGENT: Intermediate B2<br>CATALYST: Xphos Pd G2(CAS: 1310584-14-5)<br>SOLVENT: THF/H$_2$O | ¹H NMR (400 MHz, DMSO-d6): δ ppm: 11.58 (s, 1H), 9.23 (s, 1H), 9.08 (d, 1H), 8.65 (d, 1H), 8.27 (s, 1H), 7.01 (m, 1H), 6.41 (m, 1H), 4.28 (br d, 1H), 4.11 (s, 3H), 4.03-3.79 (m, 3H), 3.26-2.99 (m, 2H), 2.86 (s, 3H), 2.72-2.51 (m, 2H)<br>MS: 558.3 ([M + H]$^+$) |
| 3.22B | 6-[4-[(4aR,7aS)-4-methyl-2,3,4a,5,7,7a-hexahydropyrrolo[3,4-b][1,4]oxazin-6-yl]-6-fluoro-8-(methylamino)-9H-pyrido[2,3-b]indol-3-yl]-1-methyl-4-oxo-1,8-naphthyridine-3-carboxylic acid | CORE: Intermediate A1<br>AMINE: Intermediate C10<br>BORONIC REAGENT: Intermediate B2<br>CATALYST: Xphos Pd G2(CAS: 1310584-14-5)<br>SOLVENT: THF/H$_2$O | ¹H NMR (400 MHz, DMSO-d6): δ ppm: 11.57 (s, 1H), 9.24 (s, 1H), 9.08 (d, 1H), 8.66 (d, 1H), 8.27 (br s, 1H), 8.33-8.20 (m, 1H), 7.05-6.95 (m, 1H), 6.41 (m, 1H), 4.31-4.17 (m, 1H), 4.11 (s, 3H), 4.03-3.84 (m, 2H), 3.60 (br d, 2H), 3.25-2.97(m, 5H), 2.86 (s, 3H), 2.60 (br s, 2H)<br>MS: 558.3 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | $^1$H NMR and MS (ESI) |
| --- | --- | --- | --- |
| 3.23A | 6-[6-fluoro-8-(methylamino)-4-[(4aS,7aR)-4-methyl-2,3,4a,5,7,7a-hexahydropyrrolo[3,4-b][1,4]oxazin-6-yl]-9H-pyrido[2,3-b]indol-3-yl]-1-(methylamino)-4-oxo-1,8-naphthyridine-3-carboxylic acid | CORE: Intermediate A1<br>AMINE: Intermediate C10<br>BORONIC REAGENT: Intermediate B23<br>CATALYST: Xphos Pd G2(CAS: 1310584-14-5)<br>SOLVENT: THF/H$_2$O | $^1$H NMR (400 MHz, DMSO-d6): δ ppm: 11.58 (s, 1H), 9.09 (d, 1H), 9.02-8.96 (m, 1H), 8.68 (d, 1H), 8.28 (br s, 1H), 7.03-6.93 (m, 1H), 6.41 (m, 1H), 4.28 (br s, 1H), 4.05-3.80 (m, 3H), 3.65 (br s, 2H), 3.24 (br d, 3H), 3.19-2.98 (m, 3H), 2.91 (s, 3H), 2.86 (s, 3H), 2.60 (br s, 2H)<br>MS: 573.3 ([M + H]$^+$) |
| 3.23B | 6-[4-[(4aR,7aS)-4-methyl-2,3,4a,5,7,7a-hexahydropyrrolo[3,4-b][1,4]oxazin-6-yl]-6-fluoro-8-(methylamino)-9H-pyrido[2,3-b]indol-3-yl]-1-(methylamino)-4-oxo-1,8-naphthyridine-3-carboxylic acid | CORE: Intermediate A1<br>AMINE: Intermediate C10<br>BORONIC REAGENT: Intermediate B23<br>CATALYST: Xphos Pd G2(CAS: 1310584-14-5)<br>SOLVENT: THF/H$_2$O | $^1$H NMR (400 MHz, DMSO-d6): δ ppm: 11.59 (br s, 1H), 9.09 (d, 1H), 8.99 (s, 1H), 8.68 (d, 1H), 8.28 (s, 1H), 7.00 (br d, 1H), 6.41 (m, 1H), 4.29 (br s, 1H), 4.05-3.80 (m, 3H), 3.64 (br s, 3H), 3.24 (br d, 2H), 3.19-3.09 (m, 2H), 3.09-2.97 (m, 2H), 2.91 (s, 3H), 2.86 (s, 3H), 2.61 (br s, 2H)<br>MS: 573.2 ([M + H]$^+$) |

TABLE 3-continued

Compound synthesis and characterization

| No. | Compound Name and Structure | CORE, AMINE, BORONIC REAGENT, CATALYST1, CATALYST2, and SLOVENT | ¹H NMR and MS (ESI) |
|---|---|---|---|
| 3.24A | 6-[4-[(4aS,7aS)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C50<br>BORONIC REAGENT: Intermediate B2<br>CATALYST: cataCXium ® A Pd G2 (Sigma-Aldrich, Catalog #: 761311)<br>SOLVENT: Dioxane/H₂O | 1H NMR (400 MHz, MeOD-d4) δ ppm: 9.16 (s, 1H), 9.05 (d, J = 2.32 Hz, 1H), 8.76 (d, J = 2.32 Hz, 1H), 8.30 (s, 1H), 6.58-6.63 (m, 1H), 4.24 (s, 3H), 3.94 (m, 1H), 3.67-3.82 (m, 2H), 3.40-3.58 (m, 2H), 3.20-3.30 (m, 1H), 3.10-3.20 (t, J = 8.93 Hz, 2H), 3.00 (s, 3H), 2.72-2.85 (m, 1H), 2.38 (m, 1H), 2.26 (m, 1H), 2.13 (s, 3H)<br>MS: 576.2 ([M + H]⁺) |
| 3.24B | 6-[4-[(4aR,7aR)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-methyl-4-oxo-1,8-naphthyridine-3-carboxylic acid | CORE: Intermediate A3<br>AMINE: Intermediate C50<br>BORONIC REAGENT: Intermediate B2<br>CATALYST: cataCXium ® A Pd G2 (Sigma-Aldrich, Catalog #: 761311)<br>SOLVENT: Dioxane/H₂O | 1H NMR (400 MHz, MeOD-d4) δ ppm: 9.16 (s, 1H), 9.05 (d, J = 2.32 Hz, 1H), 8.76 (d, J = 2.32 Hz, 1H), 8.30 (s, 1H), 6.58-6.63 (m, 1H), 4.24 (s, 3H), 3.94 (m, 1H), 3.67-3.82 (m, 2H), 3.40-3.58 (m, 2H), 3.20-3.30 (m, 1H), 3.10-3.20 (t, J = 8.93 Hz, 2H), 3.00 (s, 3H), 2.72-2.85 (m, 1H), 2.38 (m, 1H), 2.26 (m, 1H), 2.13 (s, 3H)<br>MS: 576.2 ([M + H]+) |

Example 4.01A (S)-6-(5,6-Difluoro-8-(methylamino)-4-(3-(trifluoromethyl)piperazin-1-yl)-9H-pyrido[2,3-b]indol-3-yl)-1-methyl-4-oxo-1,4-dihydro-1,8-naphthyridine-3-carboxylic acid (Example 4.01A)

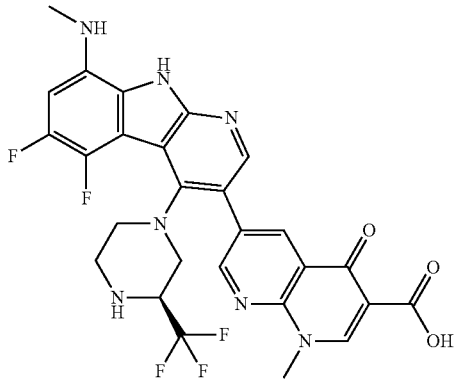 [SMILES: CNc1cc(F)c(F)c2c1[nH]c1ncc(-c3cnc4c(c3)c(=O)c(C(=O)O)cn4C)c(N3CCN[C@H](C(F)(F)F)C3)c12]

Step (a) Preparation of tert-butyl (3-chloro-5,6-difluoro-4-(3-(trifluoromethyl)piperazin-1-yl)-9H-pyrido[2,3-b]indol-8-yl)(methyl)carbamate

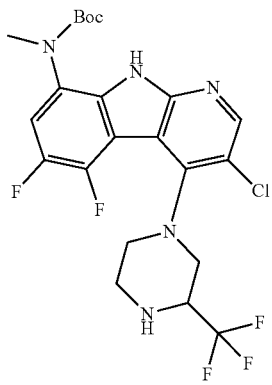 [SMILES: CN(C(=O)OC(C)(C)C)c1cc(F)c(F)c2c1[nH]c1ncc(Cl)c(N3CCNC(C(F)(F)F)C3)c12]

To a solution of tert-butyl (3,4-dichloro-5,6-difluoro-9H-pyrido[2,3-b]indol-8-yl)(methyl)carbamate (Intermediate A3, 200 mg, 0.497 mmol, as the "CORE" in table 4) in DMSO (2.0 mL) was added 2-(trifluoromethyl)piperazine (90 mg, 0.584 mmol, as the "AMINE" in table 4) and DIPEA (150 mg, 1.16 mmol), and the resulting solution was stirred at 110° C. for 18 h. After cooled down to room temperature, the mixture was poured into water (50 mL) and extracted with EtOAc (30 mL) twice. The combined organic layer was washed with brine (30 mL) three times, dried over anhy. Na$_2$SO$_4$, filtered and concentrated in vacuo to give a crude product, which was purified by Prep-TLC (petroleum ether/EtOAc=3/1) to give tert-butyl (3-chloro-5,6-difluoro-4-(3-(trifluoromethyl)piperazin-1-yl)-9H-pyrido[2,3-b]indol-8-yl)(methyl)carbamate (120 mg, 46.4% yield) as a yellow solid. MS (ESI): 520.0 ([{$^{35}$Cl}M+H]$^+$), 522.0 ([{$^{37}$Cl}M+H]$^+$).

Step (b) Preparation of ethyl 6-(8-((tert-butoxycarbonyl)(methyl)amino)-5,6-difluoro-4-(3-(trifluoromethyl)piperazin-1-yl)-9H-pyrido[2,3-b]indol-3-yl)-1-methyl-4-oxo-1,4-dihydro-1,8-naphthyridine-3-carboxylate

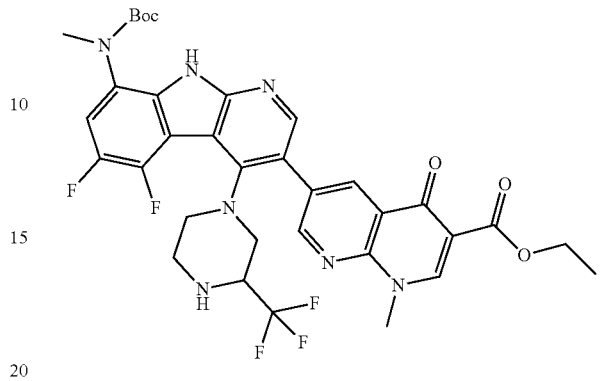

To a solution of tert-butyl (3-chloro-5,6-difluoro-4-(3-(trifluoromethyl)piperazin-1-yl)-9H-pyrido[2,3-b]indol-8-yl)(methyl)carbamate (120 mg, 0.231 mmol), (6-ethoxycarbonyl-8-methyl-5-oxo-1,8-naphthyridin-3-yl)boronic acid (Intermediate B2, 160 mg, 0.447 mmol, as the "BORONIC REAGENT" in table 4) in THF/H$_2$O (6.3 mL, v/v=20:1 as the "SOLVENT" in table 4) was added Pd-Ad$_2$nBuP Biphenyl Precat (40 mg, 0.059 mmol, as the "CATALYST" in table 4) and K$_3$PO$_4$ (154 mg, 0.726 mmol), then the resulting reaction mixture was stirred at 80° C. for 18 h under argon. After cooled down to room temperature, the mixture was poured into water (50 mL) and extracted with EtOAc (30 mL) twice. The combined organic layer was washed with brine (30 mL) three times, dried over anhy. Na$_2$SO$_4$, filtered and concentrated in vacuo to give a crude material, which was purified by Prep-TLC (petroleum ether/EtOAc=1/2) to give ethyl 6-(8-((tert-butoxycarbonyl)(methyl)amino)-5,6-difluoro-4-(3-(trifluoromethyl)piperazin-1-yl)-9H-pyrido[2,3-b]indol-3-yl)-1-methyl-4-oxo-1,4-dihydro-1,8-naphthyridine-3-carboxylate (120.0 mg, 72.6% yield) as a yellow solid. MS (ESI): 716.2 ([M+H]$^+$).

Step (c) (S)-Ethyl 6-(8-((tert-butoxycarbonyl)(methyl)amino)-5,6-difluoro-4-(3-(trifluoromethyl)piperazin-1-yl)-9H-pyrido[2,3-b]indol-3-yl)-1-methyl-4-oxo-1,4-dihydro-1,8-naphthyridine-3-carboxylate (Compound 4.01a) and (R)-ethyl 6-(8-((tert-butoxycarbonyl)(methyl)amino)-5,6-difluoro-4-(3-(trifluoromethyl)piperazin-1-yl)-9H-pyrido[2,3-b]indol-3-yl)-1-methyl-4-oxo-1,4-dihydro-1,8-naphthyridine-3-carboxylate (Compound 4.01b)

Compound 4.01a

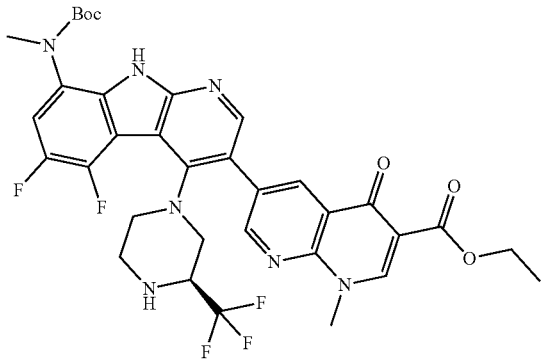

-continued

Compound 4.01b

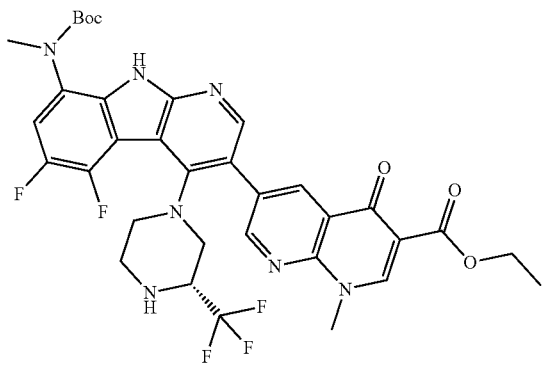

120 mg of ethyl 6-(8-(((tert-butoxycarbonyl)(methyl) amino)-5,6-difluoro-4-(3-(trifluoromethyl)piperazin-1-yl)-9H-pyrido[2,3-b]indol-3-yl)-1-methyl-4-oxo-1,4-dihydro-1,8-naphthyridine-3-carboxylate was separate by chiral SFC to give (S)-ethyl 6-(8-(((tert-butoxycarbonyl)(methyl) amino)-5,6-difluoro-4-(3-(trifluoromethyl)piperazin-1-yl)-9H-pyrido[2,3-b]indol-3-yl)-1-methyl-4-oxo-1,4-dihydro-1,8-naphthyridine-3-carboxylate (compound 4.01a, 55 mg, 45.8% yield) as a yellow solid and (R)-ethyl 6-(8-(((tert-butoxycarbonyl)(methyl)amino)-5,6-difluoro-4-(3-(trifluoromethyl)piperazin-1-yl)-9H-pyrido[2,3-b]indol-3-yl)-1-methyl-4-oxo-1,4-dihydro-1,8-naphthyridine-3-carboxylate (compound 4.01b, 53 mg, 44.1% yield).

SFC Method: Column: AD (250 mm×30 mm, 10 μm), Flowing Phase: $CO_2$+0.1% $NH_3 \cdot H_2O$ in IPA, Temperature: 35° C. Compound 4.01a was obtained at Rf=1.496/5 min, compound 4.01b was obtained at Rf=2.137/5 min (as "Chiral SFC condition" in table 4).

Step (d) (S)-6-(8-(((tert-Butoxycarbonyl)(methyl) amino)-5,6-difluoro-4-(3-(trifluoromethyl)piperazin-1-yl)-9H-pyrido[2,3-b]indol-3-yl)-1-methyl-4-oxo-1,4-dihydro-1,8-naphthyridine-3-carboxylic acid

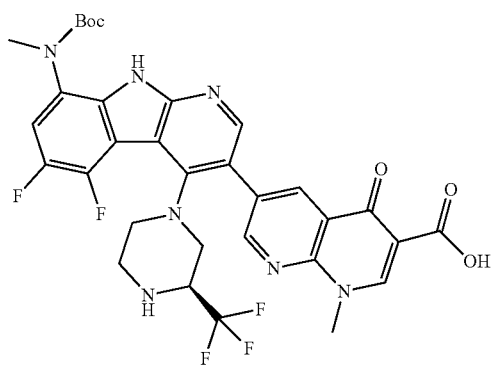 [SMILES: CN(C(=O)OC(C)(C)C)c1cc(F)c(F)c2c1[nH]c1ncc(-c3cnc4c(c3)c(=O)c(C(=O)O)cn4C)c(N3CCN[C@H](C(F)(F)F)C3)c12]

To a solution of (S)-ethyl 6-(8-(((tert-butoxycarbonyl)(methyl)amino)-5,6-difluoro-4-(3-(trifluoromethyl)piperazin-1-yl)-9H-pyrido[2,3-b]indol-3-yl)-1-methyl-4-oxo-1,4-dihydro-1,8-naphthyridine-3-carboxylate (50.0 mg, 0.07 mmol) in EtOH (5.0 mL) was added NaOH (aq., 1 N, 2.0 mL), and the resulting reaction mixture was stirred at 28° C. for 30 min. Then the reaction mixture was diluted with $H_2O$ (40 mL) and extracted with EtOAc (20 mL) three times. The aqueous layer was further acidified with 1 N HCl to pH=5~6 and extracted with DCM (40 mL) three times. The combined organic layer was washed with brine (40 mL) three times, dried over anhy. $Na_2SO_4$, filtered and concentrated in vacuo to give a crude product of (S)-6-(8-(((tert-butoxycarbonyl) (methyl)amino)-5,6-difluoro-4-(3-(trifluoromethyl)piperazin-1-yl)-9H-pyrido[2,3-b]indol-3-yl)-1-methyl-4-oxo-1,4-dihydro-1,8-naphthyridine-3-carboxylic acid (60.0 mg) as a yellow solid, which was used directly in the next step without further purification. MS (ESI): 688.6 ([M+H]$^+$).

Step (e) (S)-6-(5,6-Difluoro-8-(methylamino)-4-(3-(trifluoromethyl)piperazin-1-yl)-9H-pyrido[2,3-b] indol-3-yl)-1-methyl-4-oxo-1,4-dihydro-1,8-naphthyridine-3-carboxylic acid (Example 4.01A)

To a solution of (S)-6-(8-(((tert-butoxycarbonyl)(methyl) amino)-5,6-difluoro-4-(3-(trifluoromethyl)piperazin-1-yl)-9H-pyrido[2,3-b]indol-3-yl)-1-methyl-4-oxo-1,4-dihydro-1,8-naphthyridine-3-carboxylic acid (60.0 mg, 0.07 mmol) in DCM (3.0 mL) was added TFA (0.5 mL), and the resulting reaction mixture was stirred at 28° C. for 1 h. Afterwards, the reaction mixture was concentrated in vacuo to give a crude product, which was and purified by Prep-HPLC (water-CAN, 0.225% formic acid as additive) to give (S)-6-(5,6-difluoro-8-(methylamino)-4-(3-(trifluoromethyl)piperazin-1-yl)-9H-pyrido[2,3-b]indol-3-yl)-1-methyl-4-oxo-1,4-dihydro-1,8-naphthyridine-3-carboxylic acid (14.6 mg, 35.6% yield) as a yellow solid. MS (ESI): 588.0 ([M+H]$^+$). $^1$H NMR (400 MHz, DMSO-d$_6$) δppm: 11.92 (s, 1H), 9.28 (s, 1H), 9.13 (d, J=2.4 Hz, 1H), 8.73 (d, J=2.4 Hz, 1H), 8.25 (s, 1H), 6.65-6.60 (m, 1H), 5.71 (s, 1H), 4.18 (s, 3H), 3.28 (m, 2H), 2.91 (s, 3H), 2.87-2.84 (m, 1H), 2.72-2.66 (m, 4H). $^1$H NMR (400 MHz, DMSO-d$_6$+D$_2$O) δppm: 9.05 (s, 1H), 9.00 (s, 1H), 8.51 (s, 1H), 8.15 (s, 1H), 6.58-6.54 (m, 1H), 4.10 (s, 3H), 3.40-3.37 (m, 2H), 2.85 (s, 3H), 2.73 (m, 1H), 2.67-2.65 (m, 4H).

Example 4.01B (R)-6-(5,6-Difluoro-8-(methylamino)-4-(3-(trifluoromethyl)piperazin-1-yl)-9H-pyrido[2,3-b]indol-3-yl)-1-methyl-4-oxo-1,4-dihydro-1,8-naphthyridine-3-carboxylic acid (Example 3.01-B)

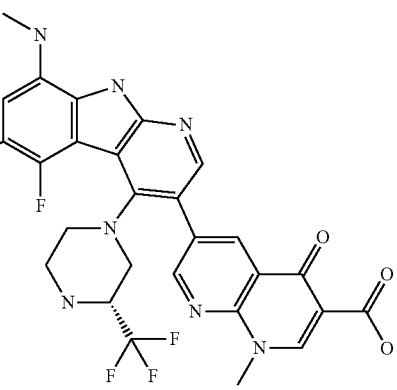

The Example 4.01B was prepared in analogy to Example 4.01A by replacing compound 4.01a with compound 4.01b in step (d).

The following examples were prepared in analogy to Example 4.01A and 4.01B, by replacing tert-butyl (3,4-dichloro-5,6-difluoro-9H-pyrido[2,3-b]indol-8-yl)(methyl)carbamate (Intermediate A3) with the "CORE" in step (a), 2-(trifluoromethyl)piperazine with the "AMINE" in step (a), THF/H$_2$O with the "SOLVENT" in step (b), Ad$_2$nBuP Biphenyl with the "CATALYST" in step (b), (6-ethoxycarbonyl-8-methyl-5-oxo-1,8-naphthyridin-3-yl)boronic acid with the "BORONIC REAGENT" in step (b) and similar chiral SFC separation in step (c) as indicated in Table 4.

TABLE 4

| No. | Compound Name and Structure | CORE, AMINE, BORONIC REAGENT, CATALYST, SLOVENT and SFC Condition | $^1$H NMR and MS (ESI) |
|---|---|---|---|
| 4.02A | (R)-6-(4-(2-((dimethylamino)methyl)morpholino)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: N,N-dimethyl-1-(morpholin-2-yl)methanamine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 11.90 (s, 1H), 9.27 (s, 1H), 9.11 (d, J = 2.4 Hz, 1H), 8.71 (d, J = 2.4 Hz, 1H), 8.24 (s, 1H), 8.21 (s, 1H), 6.62-6.57 (m, 1H), 5.72 (s, 1H), 4.18 (s, 3H), 3.67-3.64 (m, 3H), 3.16 (m, 1H), 2.90-2.89 (d, 3H), 2.85 (s, 2H), 2.67-2.65 (d, 1H), 2.26 (s, 2H), 2.12 (s, 6H).<br>MS: 578.1 ([M + H]$^+$). |
| 4.02B | (S)-6-(4-(2-((dimethylamino)methyl)morpholino)-5,6-difluoro-8-(methylamino)-9H-pyrido[2,3-b]indol-3-yl)-1-methyl-4-oxo-1,4-dihydro-1,8-naphthyridine-3-carboxylic acid | CORE: Intermediate A3<br>AMINE: N,N-dimethyl-1-(morpholin-2-yl)methanamine<br>BORONIC REAGENT: Intermediate B2<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$): δ ppm: 11.88 (s, 1H), 9.29 (s, 1H), 9.12 (d, J = 2.4 Hz, 1H), 8.74 (d, J = 2.4 Hz, 1H), 8.24 (s, 1H), 8.17 (s, 1H), 6.62-6.57 (m, 1H), 5.70 (s, 1H), 4.18 (s, 3H), 3.67-3.64 (m, 3H), 3.16 (m, 1H), 2.90-2.89 (d, 3H), 2.85 (s, 2H), 2.67-2.65 (d, 1H), 2.26 (s, 2H), 2.12 (s, 6H).<br>MS: 578.1 ([M + H]$^+$). |

Example 5.01

6-[4-[cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-(2-methoxyethylamino)-4-oxo-1,8-naphthyridine-3-carboxylic acid

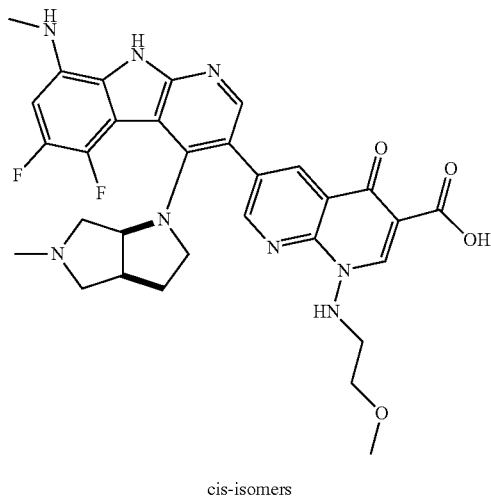

cis-isomers

Step (a) Preparation of tert-butyl N-[3-bromo-5,6-difluoro-4-[cis-5-methyl-2,3,3a,4,6,6a-hexahydropyrrolo[2,3-c]pyrrol-1-yl]-9H-pyrido[2,3-b]indol-8-yl]-N-methyl-carbamate

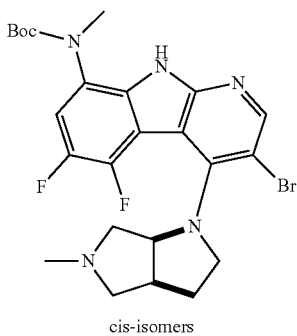

cis-isomers

To a solution of cis-5-methyloctahydropyrrolo[2,3-c]pyrrole (200 mg, 1.58 mmol, as the "AMINE" in table 5) in DMSO (5 mL) was added N,N-diisopropylethylamine (620 mg, 4.8 mmol) and tert-butyl (3-bromo-4-chloro-5,6-difluoro-9H-pyrido[2,3-b]indol-8-yl)(methyl)carbamate (Intermediate A12, 567 mg, 1.27 mmol, as the "CORE" in table 5), and the resulting reaction mixture was stirred at 110° C. for 16 h. After cooled down to room temperature, the mixture solution was diluted with EtOAc (80 mL), washed with brine (50 mL) three times. The organic layer was then dried over anhy. Na$_2$SO$_4$, filtered, and concentrated under reduced pressure to give a crude product, which was purified by Prep-TLC (petroleum ether/EtOAc=3/1) to give tert-butyl N-[3-bromo-5,6-difluoro-4-[cis-5-methyl-2,3,3a,4,6,6a-hexahydropyrrolo[2,3-c]pyrrol-1-yl]-9H-pyrido[2,3-b]indol-8-yl]-N-methyl-carbamate (300 mg, 34.94% yield) as a white solid. MS (ESI): 538.2 ([{$^{81}$Br}M+H]$^+$), 536.2 ([{$^{79}$Br}M+H]$^+$).

Step (b) Preparation of [8-[tert-butoxycarbonyl(methyl)amino]-5,6-difluoro-4-[cis-5-methyl-2,3,3a,4,6,6a-hexahydropyrrolo[2,3-c]pyrrol-1-yl]-9H-pyrido[2,3-b]indol-3-yl]boronic acid

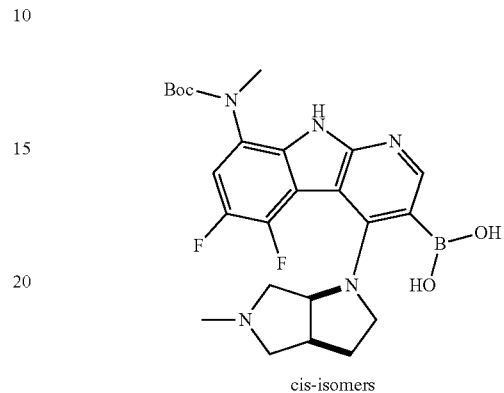

cis-isomers

After a solution of tert-butyl N-[3-bromo-5,6-difluoro-4-[cis-5-methyl-2,3,3a,4,6,6a-hexahydropyrrolo[2,3-c]pyrrol-1-yl]-9H-pyrido[2,3-b]indol-8-yl]-N-methyl-carbamate in THF (3 mL) was degassed under vacuum and purged with Ar for 3 times, 1,1-dimethylpropylmagnesium chloride (2.15 mL, 2.8 mmol, 1M in THF) was added slowly and the resulting reaction mixture was stirred at 25° C. for 3 h before 2-isopropoxy-4, 4, 5, 5-tetramethyl-1, 3,2-dioxaborolane (520 mg, 2.8 mmol) was added. The mixture was stirred at 25° C. for another 1 h under Ar. The reaction was quenched with addition of aq. NH$_4$Cl solution (15 mL), followed by the extraction with EtOAc (30 mL) twice. The combined organic phase was washed with brine (30 mL), dried over anhy. Na$_2$SO$_4$, filtered, and concentrated under reduced pressure to give a crude product, which was purified by trituration (petroleum Ether, 5 mL) to give [8-[tert-butoxycarbonyl(methyl)amino]-5,6-difluoro-4-[cis-5-methyl-2,3,3a,4,6,6a-hexahydropyrrolo[2,3-c]pyrrol-1-yl]-9H-pyrido[2,3-b]indol-3-yl]boronic acid (220 mg, 78.46% yield) as a white solid. MS: 502.3 ([M+H]$^+$).

Step (c) Ethyl 6-bromo-1-((tert-butoxycarbonyl)amino)-4-oxo-1,4-dihydro-1,8-naphthyridine-3-carboxylate

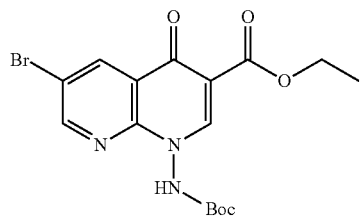 [SMILES: CCOC(=O)c1cn(NC(=O)OC(C)(C)C)c2ncc(Br)cc2c1=O]

The title compound was prepared in analogy to Intermediate B36 by replacing oxazol-5-ylmethanamine with tert-butyl hydrazine carboxylate in step (a). MS (ESI): 414.1 ([{$^{81}$Br}M+H]$^+$), 412.1 ([{$^{79}$Br}M+H]$^+$).

Step (d) Ethyl 6-bromo-1-((tert-butoxycarbonyl)(2-methoxyethyl)amino)-4-oxo-1,4-dihydro-1,8-naphthyridine-3-carboxylate

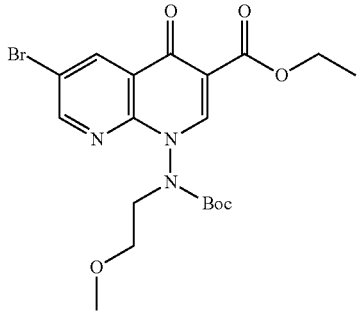 [SMILES: CCOC(=O)c1cn(N(CCOC)C(=O)OC(C)(C)C)c2ncc(Br)cc2c1=O]

To a solution of 2-bromoethyl methyl ether (152 mg, 1.09 mmol) in CH$_3$CN (5 mL) was added cesium carbonate (712 mg, 2.19 mmol) and ethyl 6-bromo-1-((tert-butoxycarbonyl)amino)-4-oxo-1,4-dihydro-1,8-naphthyridine-3-carboxylate (300 mg, 0.73 mmol), and the resulting reaction mixture was stirred at 70° C. for 16 h. After cooled down to room temperature, the mixture solution was diluted with EtOAc (80 mL), washed with water (30 mL) and brine (30 mL). The organic layer was then dried over with anhy. Na$_2$SO$_4$, filtered, and concentrated under reduced pressure to give a crude product, which was purified by Prep-TLC (petroleum ether:EtOAc=2:1) to give ethyl 6-bromo-1-((tert-butoxycarbonyl)(2-methoxyethyl)amino)-4-oxo-1,4-dihydro-1,8-naphthyridine-3-carboxylate (150 mg, 40.32% yield) as yellow oil. MS (ESI): 472.0 ([{$^{81}$Br}M+H]$^+$), 470.0 ([{$^{79}$Br}M+H]$^+$).

Step (e) ethyl 1-[tert-butoxycarbonyl(2-methoxyethyl)amino]-6-[8-[tert-butoxycarbonyl(methyl)amino]-5,6-difluoro-4-[cis-5-methyl-2,3,3a,4,6,6a-hexahydropyrrolo[2,3-c]pyrrol-1-yl]-9H-pyrido[2,3-b]indol-3-yl]-4-oxo-1,8-naphthyridine-3-carboxylate

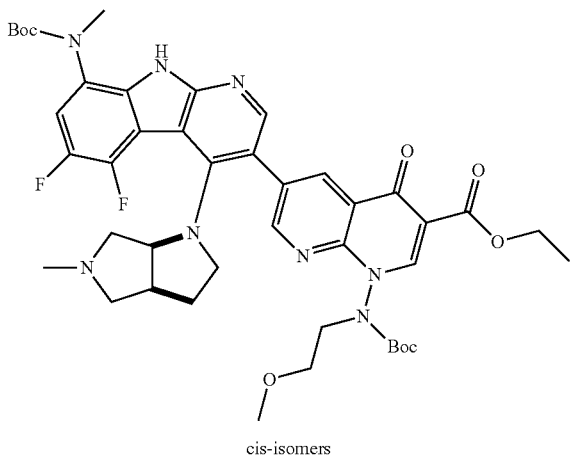

cis-isomers

A mixture solution of ethyl 6-bromo-1-((tert-butoxycarbonyl)amino)-4-oxo-1,4-dihydro-1,8-naphthyridine-3-carboxylate (75 mg, 0.16 mmol, the "BROMIDE REAGENT" reagent in table 5), [8-[tert-butoxycarbonyl(methyl)amino]-5,6-difluoro-4-[cis-5-methyl-2,3,3a,4,6,6a-hexahydropyrrolo[2,3-c]pyrrol-1-yl]-9H-pyrido[2,3-b]indol-3-yl]boronic acid (80 mg, 0.16 mmol), Pd-Ad$_2$nBuP Biphenyl Precat (43 mg, 0.06 mmol, as the "CATALYST" in table 5) and K$_3$PO$_4$ (102 mg, 0.48 mmol) in THF/H$_2$O (1.1 mL, v/v=20:1, as the "SOLVENT" in table 5) and water (0.1 mL) was degassed under vacuum and purged with Argon for 3 times before it was stirred at 60° C. for 16 h under Ar. After cooled down to room temperature, the mixture was diluted with EtOAc (80 mL), washed with water (30 mL), and brine (30 mL). The organic layer was then dried over anhy. Na$_2$SO$_4$, filtered, and concentrated under reduced pressure to give a crude product, which was purified by Prep-TLC (DCM:MeOH=10:1) to give ethyl 1-[tert-butoxycarbonyl(2-methoxyethyl)amino]-6-[8-[tert-butoxycarbonyl(methyl)amino]-5,6-difluoro-4-[cis-5-methyl-2,3,3a,4,6,6a-hexahydropyrrolo[2,3-c]pyrrol-1-yl]-9H-pyrido[2,3-b]indol-3-yl]-4-oxo-1,8-naphthyridine-3-carboxylate (70 mg, 51.8% yield) as a yellow solid. MS (ESI): 847.4 ([M+H]$^+$).

Step (f) 1-[tert-butoxycarbonyl(2-methoxyethyl)amino]-6-[8-[tert-butoxycarbonyl(methyl)amino]-5,6-difluoro-4-[cis-5-methyl-2,3,3a,4,6,6a-hexahydropyrrolo[2,3-c]pyrrol-1-yl]-9H-pyrido[2,3-b]indol-3-yl]-4-oxo-1,8-naphthyridine-3-carboxylic acid

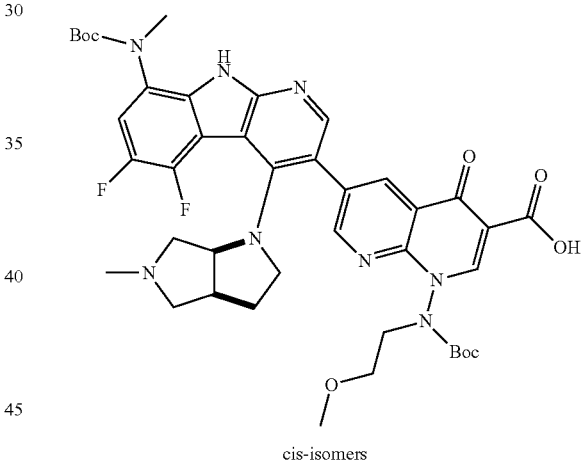

cis-isomers

To a solution of ethyl 1-[tert-butoxycarbonyl(2-methoxyethyl)amino]-6-[8-[tert-butoxycarbonyl(methyl)amino]-5,6-difluoro-4-[cis-5-methyl-2,3,3a,4,6,6a-hexahydropyrrolo[2,3-c]pyrrol-1-yl]-9H-pyrido[2,3-b]indol-3-yl]-4-oxo-1,8-naphthyridine-3-carboxylate (70 mg, 0.08 mmol) in ethanol (5 mL) was added sodium hydroxide in water (1.5 mL, 3 mmol), and the resulting mixture was stirred at 25° C. for 2 h. The mixture was then diluted with water (20 mL), acidified with 1N HCl to pH=5, and extracted with EtOAc (30 mL) twice. The organic layer was washed with brine (20 mL), dried over anhy. Na$_2$SO$_4$, filtered, and concentrated under reduced pressure to give 1-[tert-butoxycarbonyl(2-methoxyethyl)amino]-6-[8-[tert-butoxycarbonyl(methyl)amino]-5,6-difluoro-4-[cis-5-methyl-2,3,3a,4,6,6a-hexahydropyrrolo[2,3-c]pyrrol-1-yl]-9H-pyrido[2,3-b]indol-3-yl]-4-oxo-1,8-naphthyridine-3-carboxylic acid (80 mg, 94.56% yield) as a yellow solid. MS (ESI): 819.3 ([M+H]$^+$). It was used directly in the next step without further purification.

Step (g) 6-[4-[cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-(2-methoxyethylamino)-4-oxo-1,8-naphthyridine-3-carboxylic acid To a solution of 1-[tert-butoxycarbonyl(2-methoxyethyl)amino]-6-[8-[tert-butoxycarbonyl(methyl)amino]-5,6-difluoro-4-[cis-5-methyl-2,3,3a,4,6,6a-hexahydropyrrolo[2,3-c]pyrrol-1-yl]-9H-pyrido[2,3-b]indol-3-yl]-4-oxo-1,8-naphthyridine-3-carboxylic acid (80 mg, 0.1 mmol) in DCM (5 mL) was added trifluoroacetic acid (1.5 mL, 19.47 mmol), and the resulting reaction mixture was stirred at 25° C. for 0.5 h. Afterwards, the mixture solution was concentrated in vacuo to give a crude product, which was purified by prep-HPLC (water-CH$_3$CN, 0.225% formic acid as additive) to give 6-[4-[cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-(2-methoxyethylamino)-4-oxo-1,8-naphthyridine-3-carboxylic acid (32.8 mg, 45.47% yield) as a yellow solid. MS (ESI): 619.3 ([M+H]$^+$). $^1$H NMR (400 MHz, MeOD-d$_4$) δ ppm: 9.17 (s, 1H), 9.09 (s, 1H), 8.83 (br s, 1H), 8.31 (brs, 1H), 6.65 (m, 1H), 4.20-4.45 (m, 1H), 3.62-3.85 (m, 3H), 3.50 (m, 5H), 3.36 (s, 3H), 3.05-3.26 (m, 2H), 2.99 (s, 3H), 2.84-2.92 (m, 1H), 2.81 (m, 3H), 2.19-2.42 (m, 1H), 1.94 (m, 1H).

The following examples were prepared in analogy to Example 5.01, by replacing tert-butyl (3-bromo-4-chloro-5,6-difluoro-9H-pyrido[2,3-b]indol-8-yl)(methyl)carbamate (Intermediate A12) with the "CORE" in step (a), cis-5-methyloctahydropyrrolo[2,3-c]pyrrole with the "AMINE" in step (a), THF/H$_2$O with the "SOLVENT" in step (e), Ad$_2$nBuP Biphenyl with the "CATALYST" in step (e) and 6-bromo-1-((tert-butoxycarbonyl)(2-methoxyethyl)amino)-4-oxo-1,4-dihydro-1,8-naphthyridine-3-carboxylate with the "BROMIDE REAGENT" in step (e) with the reagents indicated in Table 5.

TABLE 5

Compound synthesis and characterization

| No. | Compound Name and Structure | CORE, AMINE, BROMIDE REAGENT, CATALYST and SLOVENT | $^1$H NMR and MS (ESI) |
|---|---|---|---|
| 5.02 | 6-[4-[(cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-amino-4-oxo-1,8-naphthyridine-3-carboxylic acid | CORE: Intermediate A12<br>AMINE: Intermediate C8<br>BROMIDE REAGENT: Intermediate 5.1<br>CATALYST: Pd-Ad$_2$nBuP Biphenyl Precat (CAS#: 1375477-29-4)<br>SOLVENT: THF/H$_2$O | $^1$H NMR (400 MHz, Methanol-d4): δ ppm: 9.11 (m, 2H), 8.82 (m, 1H), 8.32 (m, 1H), 6.65 (m, 1H), 4.27 (m, 1H), 3.45-3.77 (m, 3H), 3.05-3.30 (m, 4H), 2.99 (s, 3H), 2.81 (m, 3H), 2.17-2.42 (m, 1H), 1.93 (m, 1H). MS: 562.1 ([M + H]$^+$) |
| 5.03 | 6-(4-(dimethylamino)-5,6-difluoro-8-(methylamino)-9H-pyrido[2,3-b]indol-3-yl)-4-oxo-1-((2,2,2-trifluoroethyl)amino)-1,4-dihydro-1,8-naphthyridine-3-carboxylic acid | CORE: Intermediate A12<br>AMINE: dimethylamine hydrochloride<br>BORONIC REAGENT: Intermediate B48<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) δ11.79 (s, 1H), 9.07 (d, J = 2.3 Hz, 1H), 8.87 (s, 1H), 8.63 (d, J = 2.3 Hz, 1H), 8.33 (br s, 1H), 8.25 (s, 1H), 6.59 (dd, J = 6.2, 13.5 Hz, 1H), 4.12 (br dd, J = 4.0, 9.8 Hz, 2H), 2.89 (s, 3H), 2.74 (d, J = 1.8 Hz, 6H) MS (ESI): 662.1 ([M + H]$^+$). |

TABLE 5-continued

Compound synthesis and characterization

| No. | Compound Name and Structure | CORE, AMINE, BROMIDE REAGENT, CATALYST and SLOVENT | $^1$H NMR and MS (ESI) |
|---|---|---|---|
| 5.04 | 6-(4-(dimethylamino)-5,6-difluoro-8-(methylamino)-9H-pyrido[2,3-b]indol-3-yl)-1-(2-methyl-1-(methylamino)propan-2-yl)-4-oxo-1,4-dihydro-1,8-naphthyridine-3-carboxylic acid | CORE: Intermediate A12<br>AMINE: Dimethylamine hydrochloride<br>BROMIDE REAGENT: Intermediate B49<br>CATALYST: cataCXium ® A Pd G2 (Sigma-Aldrich, Catalog #: 761311)<br>SOLVENT: THF/H$_2$O | $^1$H NMR (400 MHz, MeOD-d4) δ ppm: 9.19 (br s, 1 H), 9.03 (br s, 1 H), 8.77 (br s, 1 H), 8.17 (br s, 1 H), 6.61 (br dd, J = 13.08, 5.99 Hz, 1 H), 4.28 (br s, 2 H), 2.98 (s, 3 H), 2.92 (s, 6 H), 2.76 (br s, 3 H), 2.09 (s, 6 H). MS: 550.2 [(M + H)$^+$]. |
| 5.05 | 6-[4-[(cis-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-amino-4-oxo-1,8-naphthyridine-3-carboxylic acid | CORE: Intermediate A13<br>AMINE: Intermediate C8<br>BORONIC REAGENT: Intermediate 5.1<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) δ ppm: 11.65 (s, 1 H) 9.71 (br s, 1 H) 9.10 (br s, 1 H) 9.00 (s, 1 H) 8.64-8.74 (m, 1 H) 8.22 (s, 1 H) 6.93 (br s, 1 H) 6.47 (dd, J = 12.2, 2.0 Hz, 1 H) 3.19 (br d, J = 10.8 Hz, 2 H) 3.04-3.14 (m, 2 H) 2.97 (br d, J = 7.9 Hz, 2 H) 2.92 (s, 3 H) 2.65 (br d, J = 9.4 Hz, 4 H) 2.27 (br s, 3 H) MS: 543.2 ([M + H]$^+$) |
| 5.06 | 6-[4-[cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-(methoxymethyl)-4-oxo-1,8-naphthyridine-3-carboxylic acid | CORE: Intermediate A12<br>AMINE: Intermediate C8<br>BORONIC REAGENT: Intermediate B50<br>CATALYST: Pd-Ad$_2$nBuP Biphenyl Precat (CAS#: 1375477-29-4)<br>SOLVENT: THF/H$_2$O | $^1$H NMR (400 MHz, DMSO-d$_6$) δ ppm 9.25 (s, 1 H), 9.08 (d, J = 2.3 Hz, 1 H), 8.72 (d, J = 2.5 Hz, 1 H), 8.30 (s, 1 H), 6.62 (dd, J = 13.4, 6.4 Hz, 1 H), 6.03~6.10 (m, 2 H), 4.13-4.26 (m, 1 H), 3.58~3.71 (m, 1 H), 3.39~3.54 (m, 4 H), 2.95 (s, 4 H), 2.68 (s, 3 H), 2.47~2.50 (m, 3 H), 2.15 (br s, 1 H), 1.88 (br s, 1 H) MS (ESI): 590.3 ([M + H]$^+$), 295.7 ([M/2 + H]$^+$). |

Example 6.01

6-(4-(trans-2-(Dimethylamino)-5-azaspiro[2.4]heptan-5-yl)-5,6-difluoro-8-(methylamino)-9H-pyrido[2,3-b]indol-3-yl)-1-methyl-4-oxo-1,4-dihydro-1,8-naphthyridine-3-carboxylic acid

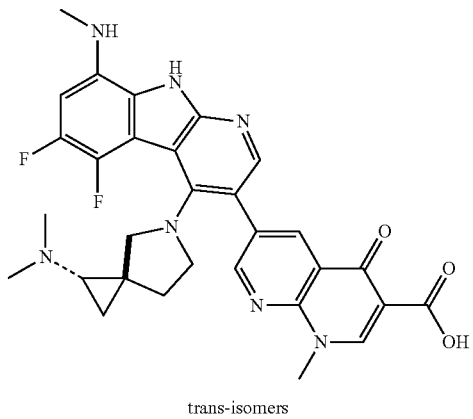

trans-isomers

Step (a) Preparation of tert-butyl (4-(2-((tert-butoxycarbonyl)amino)-5-azaspiro[2.4]heptan-5-yl)-3-chloro-5,6-difluoro-9H-pyrido[2,3-b]indol-8-yl)(methyl)carbamate

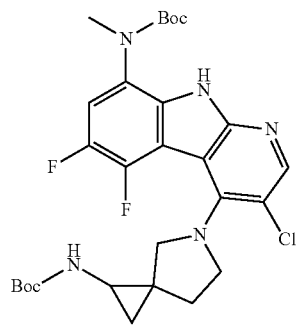 [SMILES: CN(C(=O)OC(C)(C)C)c1cc(F)c(F)c2c1[nH]c1ncc(Cl)c(N3CCC4(CC4NC(=O)OC(C)(C)C)C3)c12]

A mixture solution of tert-butyl N-(3,4-dichloro-5,6-difluoro-9H-pyrido[2,3-b]indol-8-yl)-N-methyl-carbamate (Intermediate A3, 1000 mg, 2.49 mmol), tert-butyl N-(5-azaspiro[2.4]heptan-2-yl)carbamate (634 mg, 2.98 mmol), and triethylamine (1.04 mL, 7.46 mmol) in DMSO (5 mL) was stirred at 120° C. for 16 h. After cooled down to room temperature, the reaction mixture was diluted with EtOAc (100 mL) and washed with brine (30 mL) twice. The organic layer was dried over anhy. Na$_2$SO$_4$, filtered and concentrated in vacuo to give a crude product, which was purified by silica gel flash chromatography (2-20% EtOAc in petroleum ether) to give tert-butyl (4-(1-((tert-butoxycarbonyl)amino)-5-azaspiro[2.4]heptan-5-yl)-3-chloro-5,6-difluoro-9H-pyrido[2,3-b]indol-8-yl)(methyl)carbamate (850 mg, 59.14% yield) as a yellow solid. MS (ESI): 578.3 ([{$^{35}$Cl}M+H]$^+$), 580.3 ([{$^{37}$Cl}M+H]$^+$).

Step (b) Preparation of 4-(2-amino-5-azaspiro[2.4]heptan-5-yl)-3-chloro-5,6-difluoro-N-methyl-9H-pyrido[2,3-b]indol-8-amine

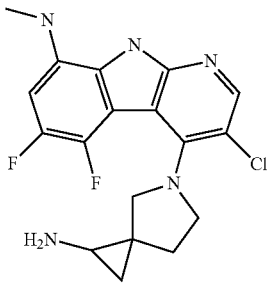 [SMILES: CNc1cc(F)c(F)c2c1[nH]c1ncc(Cl)c(N3CCC4(CC4N)C3)c12]

To a solution of tert-butyl (4-(2-((tert-butoxycarbonyl)amino)-5-azaspiro[2.4]heptan-5-yl)-3-chloro-5,6-difluoro-9H-pyrido[2,3-b]indol-8-yl)(methyl)carbamate (260 mg, 0.450 mmol) in EtOAc (5 mL) was added HCl in EtOAc (1.0 mL, 4 mmol), and the mixture was stirred at 30° C. for 16 h. Afterwards, the mixture solution was concentrated in vacuo to give a crude product of 4-(1-amino-5-azaspiro[2.4]heptan-5-yl)-3-chloro-5,6-difluoro-N-methyl-9H-pyrido[2,3-b]indol-8-amine (150 mg, 88.27% yield) as a yellow solid, which was used directly in the next step without further purification. MS (ESI): 378.0 ([{$^{35}$Cl}M+H]$^+$), 380.0 ([{$^{37}$Cl}M+H]$^+$).

Step (c) Preparation of 3-chloro-4-(2-(dimethylamino)-5-azaspiro[2,4]heptan-5-yl)-5,6-difluoro-N-methyl-9H-pyrido[2,3-b]indol-8-amine

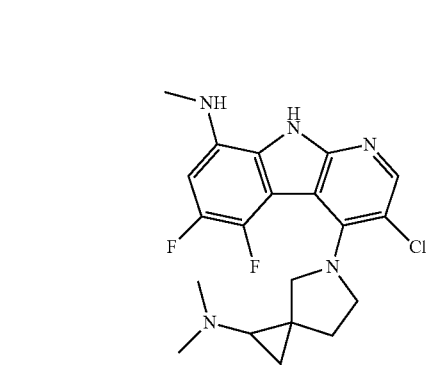 [SMILES: CNc1cc(F)c(F)c2c1[nH]c1ncc(Cl)c(N3CCC4(CC4N(C)C)C3)c12]

To a solution of 4-(2-amino-5-azaspiro[2.4]heptan-5-yl)-3-chloro-5,6-difluoro-N-methyl-9H-pyrido[2,3-b]indol-8-amine (150 mg, 0.400 mmol) and formaldehyde (83 mg, 0.830 mmol, 37% in water) in MeOH (5 mL) was added sodium cyanoborohydride (52 mg, 0.830 mmol), and the resulting mixture was stirred at 15° C. for 16 h. Afterwards, the mixture solution was concentrated in vacuo to give a crude product of 3-chloro-4-(1-(dimethylamino)-5-azaspiro[2.4]heptan-5-yl)-5,6-difluoro-N-methyl-9H-pyrido[2,3-b]indol-8-amine (300 mg), which was used directly in the next step without further purification. MS (ESI): 406.0 ([{$^{35}$Cl}M+H]$^+$), 408.0 ([{$^{37}$Cl}M+H]$^+$).

Step (d) 3-chloro-4(trans-2-(dimethylamino)-5-azaspiro[2.4]heptan-5-yl)-5,6-difluoro-N-methyl-9H-pyrido[2,3-b]indol-8-amine and 3-chloro-4-(cis-2-(dimethylamino)-5-azaspiro[2.4]heptan-5-yl)-5,6-difluoro-N-methyl-9H-pyrido[2,3-b]indol-8-amine

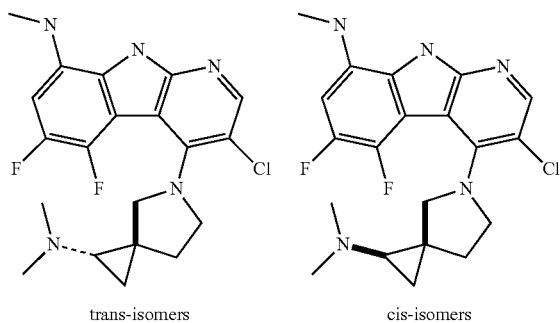

300 mg of crude 3-chloro-4-(2-(dimethylamino)-5-azaspiro[2.4]heptan-5-yl)-5,6-difluoro-N-methyl-9H-pyrido[2,3-b]indol-8-amine was separated by prep-HPLC (Column: Phenomenex Gemini 150×25 mm×10 m; Mobile Phase: water (0.05% ammonia hydroxide v/v)-MeCN (from 63% MeCN in water (0.05% ammonia hydroxide) to 90% MeCN in water (0.05% ammonia hydroxide)); Gradient Time (min): 12 min; Flow Rate: 25 mL/min) to give trans-3-chloro-4-(2-(dimethylamino)-5-azaspiro[2.4]heptan-5-yl)-5,6-difluoro-N-methyl-9H-pyrido[2,3-b]indol-8-amine (15 mg, early eluted at 8.5 min) as a yellow solid and cis-3-chloro-4-(1-(dimethylamino)-5-azaspiro[2.4]heptan-5-yl)-5,6-difluoro-N-methyl-9H-pyrido[2,3-b]indol-8-amine (40 mg, later eluted at 9.15 min) as a yellow solid.

Step (e) tert-butyl (3-chloro-4-(trans-2-(dimethylamino)-5-azaspiro[2.4]heptan-5-yl)-5,6-difluoro-9H-pyrido[2,3-b]indol-8-yl)(methyl)carbamate

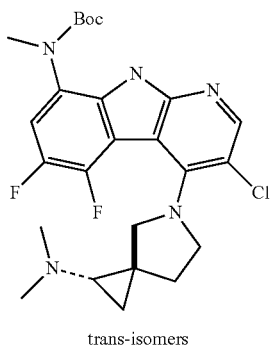 [SMILES: CN(C(=O)OC(C)(C)C)c1cc(F)c(F)c2c1[nH]c1ncc(Cl)c(N3CC[C@@]4(C[C@@H]4N(C)C)C3)c12]

A mixture solution of 3-chloro-4-(trans-2-(dimethylamino)-5-azaspiro[2.4]heptan-5-yl)-5,6-difluoro-N-methyl-9H-pyrido[2,3-b]indol-8-amine (15 mg, 0.037 mmol), di-t-butyldicarbonate (10 mg, 0.044 mmol), triethylamine (8 mg, 0.074 mmol), and 4-dimethylaminopyridine (3 mg, 0.025 mmol) in DCM (1 mL) was stirred at 25° C. for 16 h. Afterwards, the reaction mixture was diluted with DCM (10 mL), and washed with satd. aq. NH$_4$Cl solution (10 mL) twice and brine (10 mL). The organic layer was then dried over anhy. Na$_2$SO$_4$, filtered, and concentrated in vacuo to give trans-tert-butyl (3-chloro-4-(1-(dimethylamino)-5-azaspiro[2.4]heptan-5-yl)-5,6-difluoro-9H-pyrido[2,3-b]indol-8-yl)(methyl)carbamate (15 mg, 80.21% yield) as a yellow solid. MS (ESI): 506.1 ([{$^{35}$Cl}M+H]$^+$), 508.1 ([{$^{37}$Cl}M+H]$^+$).

Step (f) Preparation of ethyl 6-[8-[tert-butoxycarbonyl(methyl)amino]-4-[trans-2-(dimethylamino)-5-azaspiro[2.4]heptan-5-yl]-5,6-difluoro-9H-pyrido[2,3-b]indol-3-yl]-1-methyl-4-oxo-1,8-naphthyridine-3-carboxylate

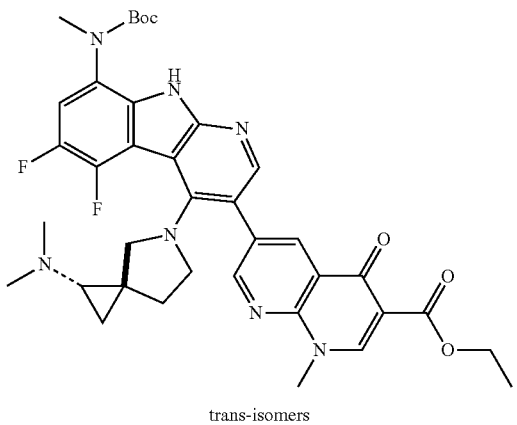

A mixture solution of (6-ethoxycarbonyl-8-methyl-5-oxo-1,8-naphthyridin-3-yl)boronic acid (10 mg, 0.036 mmol), tert-butyl (3-chloro-4-(trans-1-(dimethylamino)-5-azaspiro[2.4]heptan-5-yl)-5,6-difluoro-9H-pyrido[2,3-b]indol-8-yl)(methyl)carbamate (15 mg, 0.03 mmol), Pd-Ad$_2$nBuP Biphenyl Precat (2 mg, 0.003 mmol), K$_3$PO$_4$ (20 mg, 0.1 mmol) in THF (1 mL), and water (0.10 mL) was stirred at 70° C. for 16 h under N$_2$. After cooled down to room temperature, the reaction mixture was filtered and the filtrated was concentrated in vacuo to give a crude product, which was purified by Prep-TLC (petroleum/EtOAc=1:3) to give ethyl 6-[8-[tert-butoxycarbonyl(methyl)amino]-4-[trans-2-(dimethylamino)-5-azaspiro[2.4]heptan-5-yl]-5,6-difluoro-9H-pyrido[2,3-b]indol-3-yl]-1-methyl-4-oxo-1,8-naphthyridine-3-carboxylate (15 mg, 72.1% yield) as a yellow solid. MS (ESI): 702.4 ([M+H]$^+$).

Step (g) Preparation of 6-[8-[tert-butoxycarbonyl(methyl)amino]-4-[trans-2-(dimethylamino)-5-azaspiro[2.4]heptan-5-yl]-5,6-difluoro-9H-pyrido[2,3-b]indol-3-yl]-1-methyl-4-oxo-1,8-naphthyridine-3-carboxylic acid

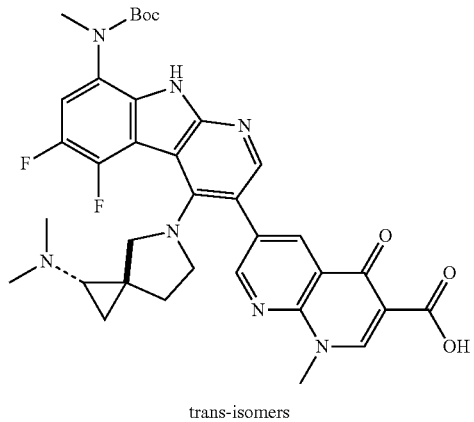

To a solution of ethyl 6-[8-[tert-butoxycarbonyl(methyl)amino]-4-[trans-2-dimethylamino)-5-azaspiro[2.4]heptan-5-yl]-5,6-difluoro-9H-pyrido[2,3-b]indol-3-yl]-1-methyl-4-oxo-1,8-naphthyridine-3-carboxylate (50.0 mg, 0.07 mmol) in EtOH (5.0 mL) was added NaOH (aq., 1 N, 2.0 mL), and the resulting reaction mixture was stirred at 28° C. for 30 min. Then the reaction mixture was diluted with H₂O (40 mL) and extracted with EtOAc (20 mL) three times. The aqueous layer was further acidified with 1 N HCl to pH=5~6 and extracted with DCM (40 mL) three times. The combined organic layer was washed with brine (40 mL) three times, dried over anhy. Na₂SO₄, filtered and concentrated in vacuo to give a crude product of 6-[8-[tert-butoxycarbonyl(methyl)amino]-4-[trans-2-(dimethylamino)-5-azaspiro[2.4]heptan-5-yl]-5,6-difluoro-9H-pyrido[2,3-b]indol-3-yl]-1-methyl-4-oxo-1,8-naphthyridine-3-carboxylic acid (60.0 mg) as a yellow solid, which was used directly in the next step without further purification. MS (ESI): 674.2 ([M+H]⁺).

Step (h) 6-(4-(trans-2-(dimethylamino)-5-azaspiro[2.4]heptan-5-yl)-5,6-difluoro-8-(methylamino)-9H-pyrido[2,3-b]indol-3-yl)-1-methyl-4-oxo-1,4-dihydro-1,8-naphthyridine-3-carboxylic acid Example 6.01

To a solution of 6-[8-[tert-butoxycarbonyl(methyl)amino]-4-[trans-2-(dimethylamino)-5-azaspiro[2.4]heptan-5-yl]-5,6-difluoro-9H-pyrido[2,3-b]indol-3-yl]-1-methyl-4-oxo-1,8-naphthyridine-3-carboxylic acid (15 mg, 0.025 mmol) in DCM (5 mL) was added trifluoroacetic acid (1.0 mL, 12.98 mmol), and the resulting reaction mixture was stirred at 15° C. for 1 h. Afterwards, the mixture solution was concentrated in vacuo to give a crude product, which was purified by Prep-HPLC to give 6-(4-(trans-2-(dimethylamino)-5-azaspiro[2.4]heptan-5-yl)-5,6-difluoro-8-(methylamino)-9H-pyrido[2,3-b]indol-3-yl)-1-methyl-4-oxo-1,4-dihydro-1,8-naphthyridine-3-carboxylic acid (2.3 mg, 15.6% yield) as a yellow solid. MS (ESI): 574.4 ([M+H]⁺). ¹H NMR (400 MHz, DMSO-d₆) δ ppm: 12.91 (s, 1H), 10.55 (s, 1H), 9.26 (s, 1H), 9.18 (s, 1H), 8.72 (s, 1H), 8.25 (s, 1H), 6.61 (m, 1H), 4.16 (s, 3H), 3.48 (m, 1H), 3.43 (m, 2H), 3.17 (m, 1H), 2.91 (m, 2H), 2.87 (s, 3H), 2.77 (s, 6H), 2.61 (m, 1H), 2.23 (m, 2H), 1.10 (m, 1H), 1.05-0.96 (m, 1H).

Example 6.02

6-(4-cis-(2-(dimethylamino)-5-azaspiro[2.4]heptan-5-yl)-5,6-difluoro-8-(methylamino)-9H-pyrido[2,3-b]indol-3-yl)-1-methyl-4-oxo-1,4-dihydro-1,8-naphthyridine-3-carboxylic acid

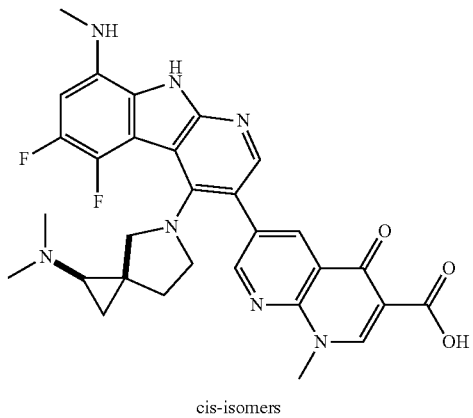

cis-isomers

The title compound was prepared in analogy to Example 6.01 by replacing 3-chloro-4(trans-2-(dimethylamino)-5-azaspiro[2.4]heptan-5-yl)-5,6-difluoro-N-methyl-9H-pyrido[2,3-b]indol-8-amine with 3-chloro-4-(cis-2-(dimethylamino)-5-azaspiro[2.4]heptan-5-yl)-5,6-difluoro-N-methyl-9H-pyrido[2,3-b]indol-8-amine in step (e). MS (ESI): 574.0 ([M+H]⁺). ¹H NMR (400 MHz, DMSO-d₆) δppm: 11.87 (s, 1H), 9.32 (s, 1H), 9.16 (d, 1H), 9.03-8.86 (m, 1H), 8.73 (d, 1H), 8.29 (s, 1H), 6.64-6.60 (m, 1H), 4.19 (s, 3H), 3.30-3.24 (m, 2H), 3.21-3.15 (m, 2H), 2.91 (s, 4H), 2.83 (s, 3H), 2.75 (s, 3H), 1.96 (m, 1H), 1.77 (m, 1H), 1.14 (m, 1H), 0.85 (m, 1H).

Example 7.01

6-(4-((2S,4S)-2-((Dimethylamino)methyl)-4-fluoro-pyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid

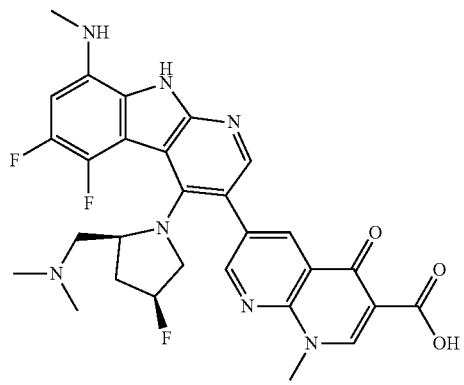 [SMILES: CNc1cc(F)c(F)c2c1[nH]c1ncc(-c3cnc4c(c3)c(=O)c(C(=O)O)cn4C)c(N3C[C@@H](F)C[C@H]3CN(C)C)c12]

Step (a) Preparation of tert-butyl (3-chloro-4-((2S,4S)-2-((dimethylamino)methyl)-4-fluoropyrrolidin-1-yl)-5,6-difluoro-9H-pyrido[2,3-b]indol-8-yl)(methyl)carbamate

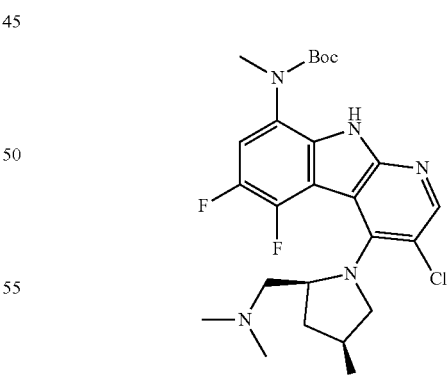

To a solution of 1-((2S,4S)-4-fluoropyrrolidin-2-yl)-N,N-dimethylmethanamine hydrochloride (Intermediate C23, 327.1 mg, 2.24 mmol) in sulfolane (0.5 mL, 0.750 mmol) was added tert-butyl (3,4-dichloro-5,6-difluoro-9H-pyrido[2,3-b]indol-8-yl)(methyl)carbamate (300.0 mg, 0.750 mmol) and N,N-diisopropylethylamine (0.39 mL, 2.24 mmol), and the resulting reaction mixture was stirred at 120°

C. for 18 h. After LCMS showed the starting material was consumed completely, the mixture was evaporated to dryness under reduced pressure. The crude product was purified by prep-HPLC (TFA as additive) to give tert-butyl (3-chloro-4-((2S,4S)-2-((dimethylamino)methyl)-4-fluoropyrrolidin-1-yl)-5,6-difluoro-9H-pyrido[2,3-b]indol-8-yl)(methyl)carbamate (320 mg, 54.47% yield) as a yellow solid. MS (ESI): 512.2 ([{$^{35}$Cl}M+H]$^+$), 514.2 ([{$^{37}$Cl}+H]$^+$).

Step (b) Preparation of tert-butyl (3-chloro-4-((2S,4S)-2-((dimethylamino)methyl)-4-fluoropyrrolidin-1-yl)-5,6-difluoro-9-((2-(trimethylsilyl)ethoxy)methyl)-9H-pyrido[2,3-b]indol-8-yl)(methyl)carbamate

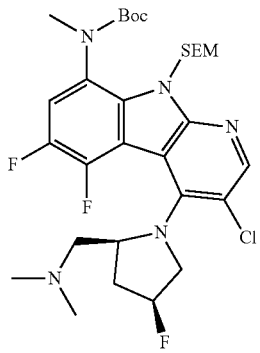 [SMILES: CN(C)C[C@@H]1C[C@H](F)CN1c1c(Cl)cnc2c1c1c(F)c(F)cc(N(C)C(=O)OC(C)(C)C)c1n2COCC[Si](C)(C)C]

To a solution of SEMCl (0.08 mL, 0.440 mmol) in DMF (2 mL) was added sodium hydride (60% dispersion in mineral oil, 35.15 mg, 0.880 mmol) at 0° C., and the resulting mixture was stirred at 0° C. for 10 min before tert-butyl (3-chloro-4-((2S,4S)-2-((dimethylamino)methyl)-4-fluoropyrrolidin-1-yl)-5,6-difluoro-9H-pyrido[2,3-b]indol-8-yl)(methyl)carbamate (150.0 mg, 0.290 mmol) was added. The mixture then was stirred at 15° C. for additional 3 h. After TLC (petroleum ether/ethyl acetate=2:1, $R_f$=0.2) showed that the starting material was consumed completely, the mixture solution was poured into 30 mL satd. aq. NH$_4$Cl solution (30 mL) and extracted with EtOAc (20 mL) three times. The combined organic layer was dried over anhy. Na$_2$SO$_4$, filtered, and concentrated in vacuo to give a crude product, which was then purified by Prep-TLC (petroleum ether/ethyl acetate=3:2, $R_f$=0.3) to give tert-butyl (3-chloro-4-((2S,4S)-2-((dimethylamino)methyl)-4-fluoropyrrolidin-1-yl)-5,6-difluoro-9-((2-(trimethyl silyl)ethoxy) methyl)-9H-pyrido[2,3-b]indol-8-yl)(methyl)carbamate (130.0 mg, 62.18%) as yellow oil. MS (ESI): 642.3 ([{$^{35}$Cl}M+H]$^+$), 644.3 ([{$^{37}$Cl}+H]$^+$).

Step (C) Preparation of ethyl 6-(8-((tert-butoxycarbonyl)(methyl)amino)-4-((2S,4S)-2-((dimethylamino)methyl)-4-fluoropyrrolidin-1-yl)-5,6-difluoro-9-((2-(trimethylsilyl)ethoxy)methyl)-9H-pyrido[2,3-b]indol-3-yl)-1-methyl-4-oxo-1,4-dihydro-1,8-naphthyridine-3-carboxylate

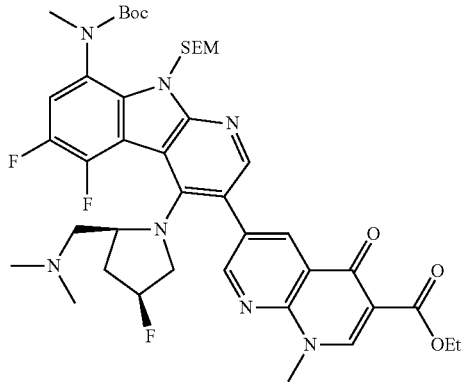 [SMILES: CCOC(=O)c1cn(C)c2ncc(-c3cnc4c(c3N3C[C@@H](F)C[C@H]3CN(C)C)c3c(F)c(F)cc(N(C)C(=O)OC(C)(C)C)c3n4COCC[Si](C)(C)C)cc2c1=O]

To a solution of tert-butyl (3-chloro-4-((2S,4S)-2-((dimethylamino)methyl)-4-fluoropyrrolidin-1-yl)-5,6-difluoro-9-((2-(trimethylsilyl)ethoxy)methyl)-9H-pyrido[2,3-b]indol-8-yl)(methyl)carbamate (120 mg, 0.190 mmol) in THF (1 mL) and water (0.10 mL) was added ethyl 1-methyl-4-oxo-6-(4,4,5,5-tetramethyl-1,3,2-dioxaborolan-2-yl)-1,4-dihydro-1,8-naphthyridine-3-carboxylate (Intermediate B2, 100.4 mg, 0.280 mmol), K$_3$PO$_4$ (118.99 mg, 0.560 mmol), and Pd-Ad$_2$nBuP Biphenyl Precat (CAS: 1375477-29-4, 24.99 mg, 0.040 mmol, 0.200 eq) in glove box. The resulting mixture was stirred at 65° C. for 18 h under Ar until LCMS showed that the starting material was consumed completely. After cooled down to room temperature, the mixture solution was concentrated in vacuo to give a crude product, which was purified by Prep-TLC (DCM/MeOH=10:1, $R_f$=0.6) to give ethyl 6-(8-((tert-butoxycarbonyl)(methyl)amino)-4-((2S,4S)-2-((dimethylamino)methyl)-4-fluoropyrrolidin-1-yl)-5,6-difluoro-9-((2-(trimethylsilyl)ethoxy)methyl)-9H-pyrido[2,3-b]indol-3-yl)-1-methyl-4-oxo-1,4-dihydro-1,8-naphthyridine-3-carboxylate (150.0 mg, 86.22% yield) as yellow oil. MS (ESI): 838.4 ([M+H]$^+$).

Step (d) Preparation of 6-(8-((tert-butoxycarbonyl)(methyl)amino)-4-((2S,4S)-2-((dimethylamino)methyl)-4-fluoropyrrolidin-1-yl)-5,6-difluoro-9-((2-(trimethylsilyl)ethoxy)methyl)-9H-pyrido[2,3-b]indol-3-yl)-1-methyl-4-oxo-1,4-dihydro-1,8-naphthyridine-3-carboxylic acid

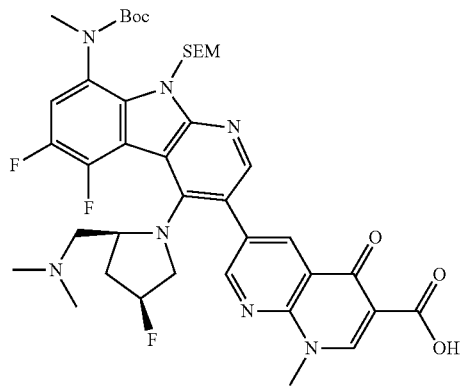 [SMILES: CN(C)C[C@@H]1C[C@H](F)CN1c1c(-c2cnc3c(c2)c(=O)c(C(=O)O)cn3C)cnc2c1c1c(F)c(F)cc(N(C)C(=O)OC(C)(C)C)c1n2COCC[Si](C)(C)C]

To a solution of ethyl 6-(8-((tert-butoxycarbonyl)(methyl)amino)-4-((2S,4S)-2-((dimethylamino)methyl)-4-fluoropyrrolidin-1-yl)-5,6-difluoro-9-((2-(trimethylsilyl)ethoxy)methyl)-9H-pyrido[2,3-b]indol-3-yl)-1-methyl-4-oxo-1,4-dihydro-1,8-naphthyridine-3-carboxylate (140 mg, 0.17 mmol) in THF (0.50 mL) was added NaOH (133.6 mg, 3.34 mmol) and water (0.05 mL). The resulting reaction mixture was then stirred at 15° C. for 2 h before LCMS showed that the starting material was consumed completely. The reaction mixture was acidified with aq. HCl solution (3 N) to pH=3~4, and then extracted with DCM (30 mL) three times. The combined organic phase was then concentrated in vacuo to give a crude product of 6-(8-((tert-butoxycarbonyl)(methyl)amino)-4-((2S,4S)-2-((dimethylamino)methyl)-4-fluoropyrrolidin-1-yl)-5,6-difluoro-9-((2-(trimethylsilyl)ethoxy)methyl)-9H-pyrido[2,3-b]indol-3-yl)-1-methyl-4-oxo-1,4-dihydro-1,8-naphthyridine-3-carboxylic acid (130 mg, 0.160 mmol, 57.64% yield) as yellow oil, which was used directly in the next step without further purification. MS(ESI): 810.4 ([M+H]$^+$).

Step (e) Preparation of 6-(4-((2S,4S)-2-((dimethylamino)methyl)-4-fluoropyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid To a solution of 6-(8-((tert-butoxycarbonyl)(methyl)amino)-4-((2S,4S)-2-((dimethylamino)methyl)-4-fluoropyrrolidin-1-yl)-5,6-difluoro-9-((2-(trimethylsilyl)ethoxy)methyl)-9H-pyrido[2,3-b]indol-3-yl)-1-methyl-4-oxo-1,4-dihydro-1,8-naphthyridine-3-carboxylic acid (135.3 mg, 0.170 mmol) in DCM (3 mL) was added trifluoroacetic acid (1.03 mL, 13.37 mmol), and the resulting mixture was stirred at 15° C. for 2 h. The mixture solution was then concentrated in vacuo to give a crude product, which was purified by prep-HPLC (TFA as additive) to give 6-(4-((2S,4S)-2-((dimethylamino)methyl)-4-fluoropyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid (22.5 mg, 18.89% yield) as a yellow solid. MS (ESI): 580.2 ([M+H]$^+$). 1H NMR (400 MHz, DMSO-d6) δ ppm 12.009 (s, 1H), 9.36 (s, 1H), 9.29 (s, 1H), 9.10 (s, 1H), 8.70 (s, 1H), 8.42 (s, 1H), 6.64 (dd, J=13.30, 6.15 Hz, 1H), 5.31-5.55 (m, 1H), 4.17 (s, 3H), 3.72 (d, J=8.66 Hz, 1H), 3.64 (d, J=8.41 Hz, 1H), 2.91 (s, 5H), 2.60 (d, J=3.64 Hz, 3H), 2.41 (d, J=3.51 Hz, 4H), 1.99-2.21 (m, 2H).

Biological Examples

Example 8

50% Growth Inhibitory Concentration (IC$_{50}$) Determination Assay:

The in vitro antimicrobial activity of the compounds against *S. aureus* (ATCC29213), *K. pneumoniae* (ATCC10031), and *A. baumannii* (ATCC17978), was determined according to the following procedure:

The assay used a 10-points Iso-Sensitest broth medium to measure quantitatively the in vitro activity of the compounds against *S. aureus* ATCC29213, *K. pneumoniae* ATCC10031, and *A. baumannii* ATCC17978.

Stock compounds in DMSO were serially two-fold diluted (range from 50 to 0.097 μM final concentration) in 384 wells microtiter plates and inoculated with 49 μL the bacterial suspension in Iso-Sensitest broth medium to have a final cell concentration of ~5×10$^5$ CFU/mL in a final volume/well of 50 μL/well. Microtiter plates were incubated at 35±2° C.

Bacterial cell growth was determined with the measurement of optical density at λ=600 nm each 20 minutes over a time course of 16 h.

Growth inhibition was calculated during the logarithmic growth of the bacterial cells with determination of the concentration inhibiting 50% (IC$_{50}$) of the growth.

GP-6 (Example 4.131 disclosed in WO 2012/125746 A1) was used as the reference compound in Table 6-8.

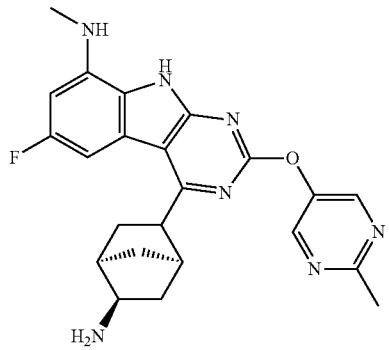

(GP-6)

Compounds of the present invention were tested for their concentration inhibiting 50% (IC$_{50}$). The data of IC$_{50}$ over *S. aureus* (ATCC29213), *K. pneumoniae* (ATCC10031), and *A. baumannii* (ATCC17978) are illustrated in Table 6. Particular compounds of the present invention were found to have IC$_{50}$≤1 μM.

TABLE 6

IC$_{50}$ values of the compounds of this invention against *S. aureus*, *K. pneumoniae* and *A. baumannii*

| Example No. | IC50 (μM) | | |
|---|---|---|---|
| | *S. aureus* ATCC29213 | *K. pneumoniae* ATCC10031 | *A. baumannii* ATCC17978 |
| GP-6 | <<0.098** | <<0.098** | <<0.098** |
| 1.01 | <0.098* | <0.098* | <0.098* |
| 1.02 | <0.098* | <0.098* | 0.693 |
| 1.03 | <0.098* | <0.098* | 0.437 |
| 1.04 | <0.098* | 0.101 | 0.935 |
| 1.05 | <0.098* | <0.098* | 0.725 |
| 1.06 | <0.098* | 0.170 | 0.849 |
| 1.08 | <0.098* | <0.098* | 0.155 |
| 1.09 | <0.098* | 0.104 | 0.818 |
| 1.10 | N.A. | N.A. | 0.192 |
| 1.11 | N.A. | N.A. | 0.847 |
| 1.12 | 0.110 | <0.098* | 0.294 |
| 1.14 | <0.098* | <0.098* | 0.154 |
| 1.15 | <0.098* | <0.098* | 0.403 |
| 1.16 | <0.098* | <0.098* | 0.308 |
| 1.17 | <0.098* | 0.101 | 0.515 |
| 1.18 | <0.098* | 0.132 | 0.326 |
| 1.19 | <0.098* | 0.145 | 0.283 |
| 1.20 | <0.098* | 0.141 | 0.209 |
| 1.21 | <0.098* | 0.154 | 0.469 |
| 1.22 | <0.098* | <0.098* | 0.118 |
| 1.23 | <0.098* | <0.098* | 0.507 |
| 1.24 | <0.098* | 0.238 | 0.519 |
| 1.26 | <0.098* | <0.098* | 0.569 |
| 1.27 | <0.098* | N.A. | 0.602 |
| 1.29 | <0.098* | <0.098* | 0.405 |
| 1.30 | <0.098* | N.A. | 0.242 |
| 1.32 | <0.098* | <0.098* | 0.353 |

TABLE 6-continued

IC$_{50}$ values of the compounds of this invention against
S. aureus, K. pneumoniae and A. baumannii

| | IC50 (μM) | | |
|---|---|---|---|
| Example No. | S. aureus ATCC29213 | K. pneumoniae ATCC10031 | A. baumannii ATCC17978 |
| 1.33 | <0.098* | <0.098* | 0.252 |
| 1.35 | <0.098* | <0.098* | 0.663 |
| 1.36 | <0.098* | <0.098* | 0.147 |
| 1.38 | 0.181 | <0.098* | 0.883 |
| 1.39 | <0.098* | 0.190 | 0.363 |
| 1.40 | <0.098* | 0.264 | 0.364 |
| 1.43 | <0.098* | <0.098* | 0.663 |
| 1.45 | <0.098* | <0.098* | 0.472 |
| 1.46 | <0.098* | <0.098* | 0.277 |
| 1.48 | <0.098* | <0.098* | 0.110 |
| 1.49 | <0.098* | <0.098* | 0.112 |
| 1.50 | <0.098* | <0.098* | 0.112 |
| 1.51 | <0.098* | <0.098* | 0.533 |
| 1.52 | <0.098* | <0.098* | 0.233 |
| 1.53 | <0.098* | <0.098* | 0.764 |
| 1.54 | <0.098* | <0.098* | 0.461 |
| 1.55 | 0.101 | N.A. | 0.334 |
| 1.57 | <0.098* | N.A. | 0.198 |
| 1.58 | <0.098* | N.A. | 0.643 |
| 1.59 | <0.098* | <0.098* | 0.658 |
| 1.60 | <0.098* | <0.098* | 0.248 |
| 1.61 | 0.139 | <0.098* | 0.817 |
| 1.64 | <0.098* | <0.098* | 0.320 |
| 1.65 | <0.098* | <0.098* | 0.378 |
| 1.66 | <0.098* | <0.098* | 0.415 |
| 1.67 | <0.098* | <0.098* | 0.729 |
| 1.69 | <0.098* | <0.098* | 0.438 |
| 1.70 | <0.098* | <0.098* | 0.619 |
| 1.71 | <0.098* | <0.098* | 0.923 |
| 1.72 | <0.098* | <0.098* | <0.098* |
| 1.73 | <0.098* | <0.098* | 0.238 |
| 1.75 | 0.108 | <0.098* | 0.108 |
| 1.76 | <0.098* | <0.098* | 0.643 |
| 1.77 | <0.098* | 0.111 | 0.291 |
| 1.78 | 0.343 | <0.098* | 0.326 |
| 1.79 | <0.098* | <0.098* | 0.173 |
| 1.80 | <0.098* | <0.098* | 0.132 |
| 1.81 | <0.098* | <0.098* | 0.164 |
| 1.82 | <0.098* | <0.098* | 0.748 |
| 1.83 | <0.098* | <0.098* | 0.519 |
| 1.84 | <0.098* | 0.110 | 0.326 |
| 1.85 | <0.098* | <0.098* | 0.089 |
| 1.86 | 0.150 | <0.098* | 0.175 |
| 1.87 | <0.098* | 0.122 | 0.490 |
| 1.88 | <0.098* | <0.098* | 0.289 |
| 1.89 | <0.098* | <0.098* | 0.315 |
| 1.90 | 0.216 | <0.098* | 0.411 |
| 1.91 | <0.098* | 0.165 | 0.237 |
| 1.92 | <0.098* | <0.098* | 0.140 |
| 1.93 | <0.098* | <0.098* | 0.094 |
| 1.94 | <0.098* | <0.098* | 0.155 |
| 1.95 | <0.098* | 0.282 | 0.276 |
| 1.96 | <0.098* | <0.098* | 0.269 |
| 1.97 | <0.098* | 0.257 | 0.507 |
| 1.98 | 8.842 | 0.107 | 0.744 |
| 1.99 | <0.098* | <0.098* | 0.771 |
| 1.100 | 0.272 | <0.098* | 0.900 |
| 1.101 | <0.098* | <0.098* | 0.150 |
| 1.102 | <0.098* | <0.098* | 0.134 |
| 1.103 | N.A. | N.A. | 0.130 |
| 1.104 | <0.098* | <0.098* | 0.137 |
| 1.105 | 5.218 | <0.098* | 0.216 |
| 1.106 | <0.098* | <0.098* | 0.244 |
| 1.107 | 0.189 | <0.098* | 0.699 |
| 1.108 | <0.098* | <0.098* | 0.088 |
| 1.109 | <0.098* | <0.098* | 0.066 |
| 1.110 | <0.098* | <0.098* | 0.074 |
| 1.111 | <0.098* | <0.098* | 0.115 |
| 1.112 | <0.098* | <0.098* | 0.334 |
| 1.113 | <0.098* | <0.098* | 0.586 |
| 1.114 | <0.098* | <0.098* | 0.103 |
| 1.115 | <0.098* | <0.098* | 0.049 |
| 1.116 | N.A. | N.A. | 0.355 |
| 1.117 | N.A. | N.A. | 0.164 |
| 1.118 | N.A. | N.A. | 0.521 |
| 1.119 | N.A. | N.A. | 0.840 |
| 1.120 | <0.098* | <0.098* | 0.169 |
| 1.121 | <0.098* | <0.098* | 0.215 |
| 1.122 | <0.098* | <0.098* | 0.195 |
| 1.123 | <0.098* | <0.098* | 0.696 |
| 1.124 | <0.098* | <0.098* | 0.074 |
| 1.125 | <0.098* | <0.098* | 0.079 |
| 1.129 | <0.098* | N.A. | 0.302 |
| 1.130 | <0.098* | <0.098* | 0.132 |
| 1.132 | <0.098* | <0.098* | 0.286 |
| 1.135 | <0.098* | <0.098* | 0.153 |
| 1.136 | <0.098* | <0.098* | 0.172 |
| 1.137 | <0.098* | <0.098* | 0.151 |
| 1.138 | <0.098* | <0.098* | 0.302 |
| 1.139 | <0.098* | <0.098* | 0.116 |
| 1.140 | <0.098* | <0.098* | 0.631 |
| 1.141 | <0.098* | <0.098* | 0.485 |
| 1.142 | <0.098* | <0.098* | 0.195 |
| 1.143 | <0.098* | <0.098* | 0.109 |
| 1.144 | <0.098* | <0.098* | 0.551 |
| 1.145 | <0.098* | 0.202 | 0.341 |
| 1.146 | <0.098* | 0.411 | 0.525 |
| 1.149 | <0.098* | <0.098* | 0.362 |
| 1.150 | <0.098* | <0.098* | 0.273 |
| 1.151 | <0.098* | <0.098* | 0.311 |
| 1.152 | <0.098* | <0.098* | 0.305 |
| 1.153 | 0.372 | <0.098* | 0.388 |
| 1.155 | 3.802 | <0.098* | 0.328 |
| 1.156 | <0.098* | <0.098* | 0.478 |
| 1.157 | <0.098* | <0.098* | 0.299 |
| 1.158 | N.A. | N.A. | 0.230 |
| 1.159 | N.A. | N.A. | 0.189 |
| 1.160 | <0.098* | <0.098* | 0.131 |
| 1.161 | 0.155 | <0.098* | 0.202 |
| 1.162 | 0.162 | <0.098* | 0.283 |
| 1.163 | <0.098* | <0.098* | 0.171 |
| 1.164 | <0.098* | <0.098* | 0.472 |
| 1.165 | <0.098* | <0.098* | 0.336 |
| 1.166 | <0.098* | <0.098* | 0.146 |
| 1.167 | <0.098* | <0.098* | 0.143 |
| 1.168 | <0.098* | <0.098* | 0.287 |
| 1.169 | <0.098* | <0.098* | 0.229 |
| 1.170 | <0.098* | <0.098* | 0.292 |
| 1.171 | <0.098* | <0.098* | 0.445 |
| 1.172 | 0.213 | <0.098* | 0.182 |
| 1.173 | <0.098* | <0.098* | 0.216 |
| 1.174 | <0.098* | 0.224 | 0.784 |
| 1.175 | <0.098* | <0.098* | 0.277 |
| 1.178 | <0.098* | <0.098* | 0.235 |
| 1.180 | <0.098* | 0.112 | 0.353 |
| 1.181 | 0.444 | <0.098* | 0.916 |
| 1.182 | 0.177 | <0.098* | 0.423 |
| 1.183 | <0.098* | <0.098* | 0.103 |
| 1.184 | <0.098* | <0.098* | 0.148 |
| 1.185 | 0.321 | <0.098* | 0.524 |
| 1.186 | <0.098* | <0.098* | 0.236 |
| 1.187 | <0.098* | <0.098* | 0.096 |
| 1.188 | 0.232 | <0.098* | 0.307 |
| 1.189 | <0.098* | <0.098* | 0.095 |
| 1.190 | 12.188 | <0.098* | 0.143 |
| 1.191 | 0.195 | <0.098* | 0.197 |
| 1.192 | <0.098* | <0.098* | 0.105 |
| 1.193 | <0.098* | <0.098* | 0.096 |
| 1.194 | <0.098* | <0.098* | 0.199 |
| 1.195 | <0.098* | <0.098* | 0.499 |
| 1.196 | <0.098* | <0.098* | 0.102 |
| 1.197 | <0.098* | <0.098* | 0.245 |
| 1.198 | <0.098* | <0.098* | 0.215 |
| 1.199 | <0.098* | <0.098* | 0.151 |

TABLE 6-continued

IC$_{50}$ values of the compounds of this invention against S. aureus, K. pneumoniae and A. baumannii

| Example No. | S. aureus ATCC29213 | K. pneumoniae ATCC10031 | A. baumannii ATCC17978 |
|---|---|---|---|
| 1.200 | 0.100 | <0.098* | 0.570 |
| 1.201 | 0.189 | <0.098* | 0.852 |
| 1.202 | <0.098* | <0.098* | 0.160 |
| 1.203 | 0.208 | <0.098* | 0.778 |
| 1.204 | <0.098* | <0.098* | 0.201 |
| 1.205 | <0.098* | <0.098* | 0.143 |
| 1.206 | <0.098* | <0.098* | 0.277 |
| 1.207 | 0.101 | <0.098* | 0.203 |
| 1.208 | <0.098* | 0.160 | 0.780 |
| 1.209 | <0.098* | <0.098* | 0.076 |
| 1.210 | <0.098* | <0.098* | <0.098* |
| 1.211 | <0.098* | <0.098* | 0.110 |
| 1.212 | 0.168 | <0.098* | 0.180 |
| 1.213 | <0.098* | <0.098* | 0.102 |
| 1.214 | <0.098* | <0.098* | 0.111 |
| 1.215 | 0.114 | 0.103 | 0.252 |
| 1.216 | <0.098* | <0.098* | 0.424 |
| 1.217 | 0.120 | <0.098* | 0.187 |
| 1.218 | <0.098* | <0.098* | 0.497 |
| 1.219 | N.A. | N.A. | 0.267 |
| 1.220 | N.A. | N.A. | 0.141 |
| 1.221 | <0.098* | <0.098* | 0.081 |
| 1.223 | <0.098* | <0.098* | 0.298 |
| 1.224 | 0.183 | <0.098* | 0.621 |
| 1.226 | 0.110 | <0.098* | 0.207 |
| 1.227 | 0.132 | <0.098* | 0.294 |
| 1.229 | <0.098* | <0.098* | 0.297 |
| 1.230 | 0.099 | <0.098* | 0.376 |
| 1.231 | <0.098* | <0.098* | 0.542 |
| 1.232 | <0.098* | <0.098* | 0.049 |
| 1.233 | 0.169 | <0.098* | 0.300 |
| 1.234 | 0.283 | <0.098* | 0.821 |
| 1.237 | <0.098* | <0.098* | 0.194 |
| 1.238 | <0.098* | <0.098* | 0.308 |
| 1.239 | <0.098* | <0.098* | 0.104 |
| 1.240 | <0.098* | <0.098* | 0.151 |
| 1.241 | <0.098* | <0.098* | 0.095 |
| 1.242 | <0.098* | <0.098* | 0.189 |
| 1.243 | 0.712 | 0.403 | 0.961 |
| 1.245 | <0.098* | <0.098* | 0.293 |
| 1.246 | 0.193 | <0.098* | 0.317 |
| 1.247 | 0.217 | <0.098* | 0.344 |
| 1.248 | 0.199 | <0.098* | 0.729 |
| 1.249 | <0.098* | <0.098* | 0.272 |
| 1.250 | <0.098* | 0.140 | 0.476 |
| 1.252 | <0.098* | <0.098* | 0.361 |
| 1.253 | <0.098* | <0.098* | 0.092 |
| 1.254 | <0.098* | <0.098* | 0.164 |
| 1.255 | <0.098* | <0.098* | 0.130 |
| 1.256 | <0.098* | <0.098* | 0.219 |
| 1.257 | N.A. | N.A. | 0.201 |
| 1.258 | <0.098* | <0.098* | <0.098* |
| 1.259 | <0.098* | <0.098* | 0.533 |
| 1.260 | <0.098* | <0.098* | 0.558 |
| 1.261 | <0.098* | <0.098* | 0.215 |
| 1.263 | <0.098* | <0.098* | 0.088 |
| 1.264 | <0.098* | <0.098* | 0.267 |
| 1.266 | <0.098* | <0.098* | 0.066 |
| 1.267 | <0.098* | <0.098* | 0.072 |
| 1.268 | <0.098* | <0.098* | 0.065 |
| 1.269 | <0.098* | <0.098* | 0.088 |
| 1.270 | <0.098* | <0.098* | 0.048 |
| 1.272 | <0.098* | <0.098* | 0.112 |
| 1.273 | <0.098* | <0.098* | 0.254 |
| 1.274 | N.A. | N.A. | 0.117 |
| 1.275 | N.A. | N.A. | 0.281 |
| 1.277 | <0.098* | <0.098* | 0.480 |
| 1.278 | <0.098* | <0.098* | 0.126 |
| 1.279 | <0.098* | <0.098* | 0.215 |
| 1.284 | <0.098* | <0.098* | 0.111 |
| 1.285 | N.A. | N.A. | 0.253 |
| 1.286 | N.A. | N.A. | 0.143 |
| 1.287 | N.A. | N.A. | 0.502 |
| 1.288 | N.A. | N.A. | 0.269 |
| 1.289 | <0.098* | <0.098* | 0.210 |
| 1.290 | <0.098* | <0.098* | 0.148 |
| 1.291 | <0.098* | <0.098* | 0.157 |
| 2.02 | <0.098* | 0.167 | 0.992 |
| 2.03 | <0.098* | <0.098* | 0.562 |
| 5.01 | N.A. | N.A. | 0.190 |
| 5.03 | <0.098* | 0.275 | 0.745 |
| 5.06 | <0.098* | <0.098* | 0.295 |
| 6.01 | <0.098* | 0.118 | 0.257 |
| 6.02 | <0.098* | 0.166 | 0.389 |
| 7.01 | <0.098* | <0.098* | 0.280 |
| 3.01A | <0.098* | <0.098* | 0.034 |
| 3.01B | 0.168 | <0.098* | 0.560 |
| 3.02A | <0.098* | <0.098* | 0.268 |
| 3.02B | <0.098* | <0.098* | 0.444 |
| 3.03A | <0.098* | <0.098* | 0.039 |
| 3.04A | <0.098* | <0.098* | 0.035 |
| 3.05A | <0.098* | <0.098* | 0.055 |
| 3.06A | <0.098* | <0.098* | 0.102 |
| 3.06B | <0.098* | <0.098* | 0.176 |
| 3.07A | <0.098* | <0.098* | 0.076 |
| 3.07B | 0.122 | <0.098* | 0.155 |
| 3.08A | <0.098* | <0.098* | 0.049 |
| 3.10A | <0.098* | <0.098* | 0.068 |
| 3.10B | <0.098* | <0.098* | 0.727 |
| 3.11A | N.A. | N.A. | 0.122 |
| 3.12A | N.A. | N.A. | 0.081 |
| 3.13A | <0.098* | <0.098* | 0.152 |
| 3.13B | <0.098* | <0.098* | 0.160 |
| 3.14A | <0.098* | <0.098* | 0.075 |
| 3.14B | <0.098* | <0.098* | 0.103 |
| 3.15A | <0.098* | <0.098* | 0.208 |
| 3.15B | <0.098* | <0.098* | 0.094 |
| 3.16A | <0.098* | <0.098* | 0.161 |
| 3.16B | <0.098* | <0.098* | 0.190 |
| 3.17A | <0.098* | <0.098* | 0.087 |
| 3.17B | <0.098* | <0.098* | 0.075 |
| 3.18A | <0.098* | <0.098* | 0.081 |
| 3.18B | 0.133 | <0.098* | 0.275 |
| 3.20A | N.A. | N.A. | 0.149 |
| 3.20B | N.A. | N.A. | 0.252 |
| 3.22A | <0.098* | <0.098* | 0.363 |
| 3.22B | <0.098* | <0.098* | 0.256 |
| 3.23A | <0.098* | <0.098* | 0.865 |
| 3.23B | <0.098* | <0.098* | 0.789 |
| 3.24A | <0.098* | <0.098* | 0.315 |
| 3.24B | <0.098* | <0.098* | 0.371 |
| 4.01A | N.A. | N.A. | 0.393 |
| 4.01B | N.A. | N.A. | 0.352 |
| 4.02A | 0.197 | <0.098* | 0.437 |
| 4.02B | 0.207 | <0.098* | 0.408 |

"*": the detection limit;
"N.A.": not available.

Example 9

Lyophilisation Solubility Assay (LYSA):

The solubility of compounds of present invention was assessed by LYSA assay. Samples were prepared in duplicate from 10 mM DMSO stock solutions (20 µL) diluted in 30 µL pure DMSO. After evaporation of DMSO with a centrifugal vacuum evaporator, the residue was dissolved in 0.05 M phosphate buffer (150 µL, pH 6.5), which was stirred for one hour and shook for two hours. After one night, the solution was filtered using a microtiter filter plate. Then the filtrate and its 1/10 dilution were analyzed by HPLC-UV. In addition a four-point calibration curve was prepared from the 10 mM stock solutions and used for the solubility determination of the compounds. The results were in g/mL and summarized in Table 7. Particular compounds of the present invention were found to have LYSA>10 μg/mL with much improved solubility compared to GP-6.

TABLE 7

Solubility data of Examples

| Example No. | Lysa (μg/mL) |
|---|---|
| GP-6 | <1.0* |
| 1.04 | 32 |
| 1.12 | 321 |
| 1.13 | 389 |
| 1.14 | 407 |
| 1.38 | 15 |
| 1.61 | 600 |
| 1.71 | 11 |
| 1.75 | 152 |
| 1.78 | 530 |
| 1.85 | 101 |
| 1.86 | >805 |
| 1.88 | 485 |
| 1.90 | 700 |
| 1.92 | 88 |
| 1.93 | 105 |
| 1.94 | 301 |
| 1.96 | 169 |
| 1.100 | 632 |
| 1.101 | 214 |
| 1.103 | 11 |
| 1.106 | 19 |
| 1.110 | 71 |
| 1.111 | 112 |
| 1.120 | 37 |
| 1.121 | 58 |
| 1.122 | 76 |
| 1.123 | 48 |
| 1.124 | 151 |
| 1.125 | 262 |
| 1.134 | 11 |
| 1.135 | 266 |
| 1.138 | 91 |
| 1.139 | 20 |
| 1.141 | 485 |
| 1.144 | 22 |
| 1.149 | 530 |
| 1.152 | 49 |
| 1.153 | 201 |
| 1.157 | 42 |
| 1.158 | 49 |
| 1.160 | 43 |
| 1.161 | >830 |
| 1.162 | 695 |
| 1.166 | 330 |
| 1.170 | 119 |
| 1.171 | 46 |
| 1.172 | 475 |
| 1.173 | 106 |
| 1.175 | 113 |
| 1.181 | 70 |
| 1.182 | 147 |
| 1.183 | 96 |
| 1.184 | 52 |
| 1.186 | 104 |
| 1.187 | >730 |
| 1.188 | 20 |
| 1.189 | 255 |
| 1.190 | 62 |
| 1.191 | 181 |
| 1.192 | 58 |
| 1.193 | 16 |
| 1.195 | 29 |
| 1.196 | 25 |
| 1.197 | 407 |
| 1.198 | 56 |

TABLE 7-continued

Solubility data of Examples

| Example No. | Lysa (μg/mL) |
|---|---|
| 1.200 | 69 |
| 1.201 | 124 |
| 1.203 | 303 |
| 1.205 | 192 |
| 1.206 | 273 |
| 1.207 | 73 |
| 1.209 | 63 |
| 1.211 | 205 |
| 1.213 | 26 |
| 1.215 | 48 |
| 1.217 | 190 |
| 1.219 | 73 |
| 1.220 | 79 |
| 1.221 | 49 |
| 1.223 | 472 |
| 1.224 | 570 |
| 1.227 | 12 |
| 1.229 | 12 |
| 1.230 | 19 |
| 1.232 | 23 |
| 1.236 | 55 |
| 1.237 | 145 |
| 1.242 | 24 |
| 1.243 | 151 |
| 1.244 | 254 |
| 1.245 | 542 |
| 1.246 | >612 |
| 1.247 | 516 |
| 1.248 | 222 |
| 1.249 | 487 |
| 1.252 | 41 |
| 1.253 | 209 |
| 1.254 | 23 |
| 1.255 | 99 |
| 1.256 | 202 |
| 1.258 | 17 |
| 1.259 | 17 |
| 1.260 | 277 |
| 1.264 | 159 |
| 1.266 | 241 |
| 1.267 | 104 |
| 1.268 | 24 |
| 1.272 | >632 |
| 1.273 | 468 |
| 1.274 | 118 |
| 1.279 | 151 |
| 1.289 | 113 |
| 1.290 | 247 |
| 1.291 | 138 |
| 5.01 | 425 |
| 5.02 | 174 |
| 5.05 | 250 |
| 5.06 | 366 |
| 7.01 | 330 |
| 3.01A | 264 |
| 3.01B | 265 |
| 3.02A | 480 |
| 3.02B | 455 |
| 3.03A | 137 |
| 3.03B | 180 |
| 3.04A | 485 |
| 3.05A | 535 |
| 3.06A | 66 |
| 3.06B | 85 |
| 3.07A | 20 |
| 3.07B | 33 |
| 3.08A | 119 |
| 3.10A | 58 |
| 3.10B | 16 |
| 3.17A | 118 |
| 3.17B | 125 |
| 3.18A | 172 |
| 3.18B | 338 |

TABLE 7-continued

Solubility data of Examples

| Example No. | Lysa (µg/mL) |
|---|---|
| 3.23A | 49 |
| 3.23B | 58 |

Example 10

Cytotoxicity Assay:

The cytotoxicity of compounds of present invention was assessed by HepG2 assay. HepG2 cells (ATCC HB-8065™) were seeded into 96-well plates ($1.2 \times 10^4$ cells per well) and treated with compounds for 3 days, cell viability was measured at day 3 post compound treatment using the CellTiter-Blue® Cell Viability Assay (Promega, Cat. No. G8082). 20 µL of Cell titer blue buffer were added to each well of the cells, which were incubated for 3 hours at 37° C., and the fluorescence value was measured by a plate reader (Molecular Device SpectraMax M2). The $CC_{50}$ value of each compound is plotted with GraphPad Prism using four parameter logistic equation. Results of cytotoxicity are given in Table 8.

TABLE 8

$CC_{50}$ of Examples

| Example No. | $CC_{50}$ (µM) |
|---|---|
| GP-6 | 5.6 |
| 1.02 | >100.0* |
| 1.03 | 38.08 |
| 1.11 | >100.0* |
| 1.12 | 39.18 |
| 1.14 | 29.10 |
| 1.15 | >100.0* |
| 1.23 | >100.0* |
| 1.25 | 62.58 |
| 1.26 | 32.50 |
| 1.27 | 28.19 |
| 1.31 | 49.03 |
| 1.32 | 50.08 |
| 1.34 | >100.0* |
| 1.35 | 76.92 |
| 1.37 | 55.49 |
| 1.38 | >100.0* |
| 1.41 | 90.20 |
| 1.42 | >100.0* |
| 1.43 | 39.31 |
| 1.44 | >100.0* |
| 1.45 | >100.0* |
| 1.47 | >100.0* |
| 1.51 | >100.0* |
| 1.53 | >100.0* |
| 1.54 | >100.0* |
| 1.55 | 49.76 |
| 1.57 | 35.88 |
| 1.58 | >100.0* |
| 1.59 | 27.86 |
| 1.61 | >100.0* |
| 1.64 | >100.0* |
| 1.67 | >100.0* |
| 1.68 | 26.47 |
| 1.71 | >100.0* |
| 1.75 | 68.50 |
| 1.78 | 42.52 |
| 1.80 | 27.46 |
| 1.82 | >100.0* |
| 1.83 | 26.38 |
| 1.84 | 26.75 |
| 1.85 | 35.15 |
| 1.86 | 43.35 |
| 1.90 | >100.0* |
| 1.94 | 38.74 |
| 1.98 | >100.0* |
| 1.106 | 91.27 |
| 1.113 | >100.0* |
| 1.128 | 27.06 |
| 1.134 | >100.0* |
| 1.135 | 29.31 |
| 1.138 | 47.33 |
| 1.140 | >100.0* |
| 1.149 | 66.65 |
| 1.150 | >100.0* |
| 1.151 | 37.18 |
| 1.161 | >100.0* |
| 1.162 | 67.60 |
| 1.163 | 28.85 |
| 1.164 | 99.29 |
| 1.165 | >100.0* |
| 1.172 | 31.52 |
| 1.173 | 44.92 |
| 1.181 | >100.0* |
| 1.182 | 91.70 |
| 1.184 | 28.66 |
| 1.186 | 45.57 |
| 1.188 | 51.65 |
| 1.189 | 41.25 |
| 1.191 | 29.12 |
| 1.193 | >100.0* |
| 1.194 | 72.03 |
| 1.212 | 33.93 |
| 1.214 | 40.77 |
| 1.216 | >100.0* |
| 1.217 | 27.81 |
| 1.227 | 28.02 |
| 1.228 | >100.0* |
| 1.229 | 53.10 |
| 1.230 | >100.0* |
| 1.231 | 37.23 |
| 1.239 | 32.91 |
| 1.251 | >100.0* |
| 1.254 | 36.09 |
| 1.268 | 33.42 |
| 1.269 | 40.75 |
| 5.01 | 43.48 |
| 3.01A | 54.14 |
| 3.01B | 39.40 |
| 3.02A | >100.0* |
| 3.02B | >100.0* |
| 3.03A | 38.40 |
| 3.04A | 49.53 |
| 3.05A | 54.47 |
| 3.06A | 52.52 |
| 3.06B | 40.21 |
| 3.07A | >100.0* |

"*": the detection limit.

Example 11

Single Dose PK Study (SDPK) in Female CD-1 Mouse:

The single dose PK in female CD-1 mouse was performed to assess compound's pharmacokinetic properties. One group of animals were dosed via bolus intravenous (IV) of the respective compound. Blood samples (approximately 30 µL) were collected via saphenous vein at 5 mins, 15 min, 30 min, 1 hr, 2 hr, 4 hr and 7 hr. For last time point (24 hr), samples were collected via cardiac puncture while the mouse was under anesthesia. Blood samples were placed into tubes containing EDTA-K2 anticoagulant (2 µL of 0.5M per tube) and centrifuged at 3000 rpm for 10 minutes at 4° C. within half an hour to separate plasma from the samples. Following centrifugation, plasma samples were stored in polypropylene tubes, quick frozen over dry ice and kept at −70±10° C. until LC/MS/MS analysis. The pharmacokinetic parameters were calculated using non-compartmental module of WinNonlin® Professional 6.4. Results of SDPK assay are given in Table 9.

TABLE 9

SDPK data of Examples

| Example No. | PK Conditions: MOUSE IV | CL total (mL/min/kg) | AUC total (h * ng/mL) |
|---|---|---|---|
| GP6 | 1.0 mg/kg-Solution | 132.1 | 126.2 |
| 1.02 | 1.0 mg/kg-Solution | 58.8 | 291.0 |
| 1.05 | 1.0 mg/kg-Solution | 100.0 | 162.7 |
| 1.07 | 0.7 mg/kg-Solution | 45.8 | 260.7 |
| 1.22 | 1.0 mg/kg-Solution | 91.3 | 179.9 |
| 1.43 | 1.0 mg/kg-Solution | 66.3 | 235.1 |
| 1.52 | 1.0 mg/kg-Solution | 57.4 | 305.8 |
| 1.53 | 1.0 mg/kg-Solution | 83.5 | 211.3 |
| 1.55 | 1.0 mg/kg-Solution | 98.7 | 165.9 |
| 1.57 | 0.7 mg/kg-Solution | 84.6 | 190.8 |
| 1.85 | 1.0 mg/kg-Solution | 94.8 | 177.0 |
| 1.86 | 1.0 mg/kg-Solution | 86.46 | 194.1 |
| 1.192 | 1.0 mg/kg-Solution | 69.63 | 235.0 |
| 1.196 | 1.0 mg/kg-Solution | 98.38 | 177.4 |
| 1.202 | 1.0 mg/kg-Solution | 98.10 | 167.5 |
| 1.207 | 1.0 mg/kg-Solution | 85.71 | 188.3 |
| 1.241 | 1.0 mg/kg-Solution | 84.27 | 196.3 |
| 1.298 | 1.0 mg/kg-Solution | 62.7 | 274.0 |
| 3.01A | 1.0 mg/kg-Solution | 81.90 | 195.4 |
| 3.01B | 1.0 mg/kg-Solution | 105.3 | 156.1 |
| 3.03A | 1.0 mg/kg-Solution | 66.90 | 249.6 |
| 3.04A | 1.0 mg/kg-Solution | 68.93 | 241.6 |
| 3.05A | 1.0 mg/kg-Solution | 50.48 | 356.4 |
| 3.07A | 1.0 mg/kg-Solution | 77.40 | 214.0 |
| 3.08A | 1.0 mg/kg-Solution | 86.73 | 190.5 |

Example 12

Minimal Inhibitory Concentration (MIC) and MIC90 Determination:

The MIC of antibacterial compounds against multiple species and strains was determined using the broth microdilution method according to M07-A10 Clinical and Laboratory Standards Institute (CLSI) guidelines (CLSI (2015) Methods for dilution antimicrobial susceptibility tests for bacteria that grow aerobically; Approved Standard, Tenth Edition. CLSI Document M7-A10 (ISBN 1-56238-987-4). Wayne, Pa.: Clinical and Laboratory Standards Institute, 19087, USA.). In short, bacterial strain preparation was performed on D1 and D2. The bacterial strains were revived from storage frozen two days before the MIC screening, and streaked onto surface of agar plates, incubated in an ambient-air incubator with humidity for 20-24 hr at 35±2° C. 5-10 well-isolated colonies of similar morphology were selected and re-streaked onto fresh agar plates using sterile loops and incubated for 20-24 hr at 35±2° C. Bacterial strains were subcultured two times to ensure fresh inoculums for MIC screening. On the day of MIC assay (Day 3), colonies were transferred from fresh culture plates into 5 mL of saline with sterile loops and mixed well, which was measured and adjusted turbidity to 0.5 McFarland barium sulfate standard ($1-2\times10^8$ Colony Forming Units (CFU)/mL) using a turbidity meter. Alternatively, 1-2 colonies were transferred into 500 µL of saline and OD600 was adjusted to ~0.1 using an OD meter. Bacterial inoculum was diluted by 1:280 for Gram-positive strains and 1:400 for Gram-negative strains into corresponding medium broth (CAMHB, CAMHB+3% lysed horse blood, HTM) (e.g. 35.6 µL of inoculum into 10 mL of CAMHB or 25 µL of inoculum into 10 mL of CAMHB). For compound plate, the compound stock solutions were prepared in 100% DMSO on the day of MIC screening and used immediately. Compound stock concentration=[(highest testing concentration)×100 µL/2 µL] (e.g. if the required highest testing concentration is 64 µg/mL in assay plates, stock concentration=64 µg/mL×100 µL/2 µL=3.2 mg/mL). The compound plates were prepared by dispensing 100 µL of each stock solution in the first well of a 96 well microtiter plate (MTP) at a concentration 100-fold higher than the final concentration desired in broth. Eleven serial 2-fold dilutions of the highest concentration were made in DMSO for new compounds and for reference compounds (GP-6 and ciprofloxacin). 1 µL of each well was transferred in a new MTP, which served as the test plate by subsequent inoculation. The bacterial suspension prepared above is dispensed at 98 µL/well within 15 minutes after preparation. Negative controls (lack of bacterial cells) and growth control wells (lack of compound) were included in all plates. MTPs were incubated for 18-24 hours at 35±2° C. in ambient air. The MIC was recorded and CFUs were calculated on Day 4. The assay plate was placed on the top of MIC reader, and the magnification mirror was adjusted to read each wells, recording growth status as raw data. Photo images of each assay plates were recorded using Q Count 530 (Spiral Biotech). The MIC value of each compound, expressed as g/mL, was determined as the lowest concentration required for complete growth inhibition (no visible growth). Results of MIC were summarized in Table 10.

TABLE 10

MIC of antibacterial compounds against multiple species

| Ex. | S1 | S2 | S3 | S4 | S5 | S6 | S7 | S8 | S9 |
|---|---|---|---|---|---|---|---|---|---|
| Cip | 2 | 16 | 0.5 | <0.0625 | 0.5 | >64 | 0.5 | 2 | 0.5 |
| GP6 | 0.339 | 0.339 | 0.169 | <0.021 | 1.358 | 2.715 | 0.678 | 1.358 | 1.358 |
| 1.02 | 0.832 | 1.667 | 1.667 | 0.052 | 6.669 | >26.676 | 6.669 | 1.667 | 3.335 |
| 1.14 | 0.876 | 1.755 | 0.438 | 0.055 | 7.02 | 3.51 | 3.51 | 3.51 | 7.02 |
| 1.85 | 0.436 | 0.436 | 0.436 | 0.055 | 3.497 | 1.749 | 1.749 | 1.749 | 6.995 |
| 1.189 | 0.537 | 0.537 | 0.537 | 0.067 | 4.304 | 4.304 | 2.152 | 4.304 | 4.304 |
| 1.274 | 0.531 | 0.531 | 0.531 | 0.067 | 2.127 | 2.127 | 2.127 | 4.254 | 8.508 |
| 1.275 | 1.085 | 1.085 | 1.085 | <0.034 | 8.695 | 4.348 | 4.348 | 4.348 | 4.348 |
| 1.286 | 0.248 | 0.496 | 0.992 | 0.062 | 1.986 | 1.986 | 3.973 | 0.992 | 3.973 |
| 1.298 | 0.265 | 0.531 | 0.531 | <0.033 | 2.127 | 2.127 | 1.062 | 2.127 | 17.016 |
| 3.01A | 0.112 | 0.224 | 0.224 | <0.028 | 1.796 | 1.796 | 0.896 | 1.796 | 1.796 |
| 3.03A | 0.109 | 0.109 | 0.218 | <0.027 | 0.873 | 0.873 | 0.873 | 0.873 | 1.749 |

TABLE 10-continued

MIC of antibacterial compounds against multiple species

| 3.04A | 0.422 | 0.845 | 0.422 | <0.026 | 3.385 | 3.385 | 3.385 | 3.385 | 6.77 |
| 3.05A | 0.868 | 0.868 | 0.868 | <0.027 | 6.957 | 3.479 | 3.479 | 3.479 | 6.957 |

| Ex. | S10 | S11 | S12 | S13 | S14 | S15 | S16 | S17 |
|---|---|---|---|---|---|---|---|---|
| CiP | 0.25 | 0.5 | 1 | <0.0625 | <0.0625 | >64 | | |
| GP6 | <0.021 | <0.021 | 0.043 | 0.169 | 0.169 | 1.358 | 0.127 | 0.127 |
| 1.02 | 0.104 | 0.104 | 0.208 | 0.416 | 0.832 | 1.667 | 0.313 | 0.625 |
| 1.14 | 0.219 | 0.11 | 0.219 | 0.876 | 1.755 | 1.755 | 0.329 | 0.329 |
| 1.85 | 0.055 | <0.027 | 0.055 | 0.218 | 0.436 | 0.873 | 0.328 | 0.164 |
| 1.189 | 0.067 | 0.067 | 0.067 | 1.074 | 0.537 | 1.074 | 0.202 | 0.101 |
| 1.274 | 0.067 | <0.033 | 0.067 | 0.265 | 0.531 | 1.062 | 0.199 | 0.199 |
| 1.275 | 0.136 | 0.068 | 0.136 | 0.543 | 1.085 | 1.085 | 0.408 | 0.204 |
| 1.286 | <0.031 | <0.031 | <0.031 | 0.248 | 0.496 | 0.496 | 0.186 | 0.186 |
| 1.298 | 0.067 | <0.033 | <0.033 | 0.265 | 0.265 | 0.531 | 0.399 | 0.199 |
| 3.01A | <0.028 | <0.028 | <0.028 | 0.112 | 0.224 | 0.448 | 0.084 | 0.084 |
| 3.03A | <0.027 | <0.027 | <0.027 | 0.109 | 0.109 | 0.218 | 0.082 | 0.082 |
| 3.04A | 0.106 | 0.053 | 0.106 | 0.211 | 0.422 | 0.845 | 0.159 | 0.159 |
| 3.05A | 0.434 | 0.217 | 0.434 | 0.217 | 0.868 | 1.739 | 0.163 | 0.163 |

Ex.: Example Number
S1: *A. baumannii* ATCC 19606
S2: *A. baumannii* ATCC 51432
S3: *A. baumannii* ATCC BAA-747
S4: *K. pneumoniae* ATCC 10031
S5: *K. pneumoniae* ATCC 700603
S6: *K. pneumoniae* ATCC BAA-2146
S7: *P. aeruginosa* ATCC 27853
S8: *P. aeruginosa* ATCC BAA-2108
S9: *P. aeruginosa* ATCC BAA-2113
S10: *S. aureus* ATCC 9144
S11: *S. aureus* ATCC 29213
S12: *S. aureus* ATCC 43300
S13: *E. coli* ATCC 29181
S14: *E. coli* ATCC 35218
S15: *E. coli* ATCC BAA-2340
S16: *E. coli* ATCC 25922
S17: *E. coli* ΔtolC of BW25113

The invention claimed is:

1. A compound of formula (I), wherein
R$^1$ is wherein
R$^7$ is H;
R$^8$ is carboxy;
R$^9$ is H;
R$^{10}$ is (C$_{1-6}$alkyl)$_2$(C$_{1-6}$alkylamino)C$_{1-6}$alkyl, (C$_{1-6}$alkyl)$_2$(pyrrolidinyl)C$_{1-6}$alkyl, (C$_{1-6}$alkyl)$_2$amino, (C$_{1-6}$alkyl)$_2$amino(phenyl)C$_{1-6}$alkyl, (C$_{1-6}$alkyl)$_2$aminoC$_{1-6}$alkyl, (C$_{1-6}$alkylamino)C$_{1-6}$alkyl, (C$_{1-6}$alkylpiperazinyl)C$_{1-6}$alkyl, (C$_{1-6}$alkylpiperidinyl)C$_{1-6}$alkyl, (C$_{1-6}$alkylpyrrolidinyl)C$_{1-6}$alkyl, (hydroxyC$_{1-6}$alkyl)$_2$C$_{1-6}$alkyl, (hydroxyC$_{1-6}$alkyl)C$_{1-6}$alkyl, (hydroxyC$_{3-7}$cycloalkyl)C$_{1-6}$alkyl, amino, aminoC$_{1-6}$alkyl, C$_{1-6}$alkoxyC$_{1-6}$alkyl, C$_{1-6}$alkoxyC$_{1-6}$alkylamino, C$_{1-6}$alkyl, C$_{1-6}$alkylamino, C$_{1-6}$alkylheterocyclyl, C$_{3-7}$cycloalkyl, C$_{3-7}$cycloalkylamino, dihydroxyC$_{1-6}$alkyl, haloC$_{1-6}$alkylamino, hydroxyC$_{1-6}$alkyl, heterocyclylC$_{1-6}$alkyl, heterocyclyl or heterocyclylamino;
R$^{11}$ is H;
R$^2$ is (C$_{1-6}$alkyl)$_2$amino, C$_{1-6}$alkylamino, C$_{1-6}$alkoxyC$_{1-6}$alkyl(C$_{1-6}$alkyl)amino or heterocyclyl;
R$^3$ is H, halogen, cyano or C$_{1-6}$alkoxy;
R$^4$ is H, halogen or haloC$_{1-6}$alkyl;
R$^5$ is H or halogen; and
R$^6$ is C$_{1-6}$alkyl;
or a pharmaceutically acceptable salt, or enantiomer or diastereomer thereof.

2. A compound according to claim 1, wherein R$^1$ is

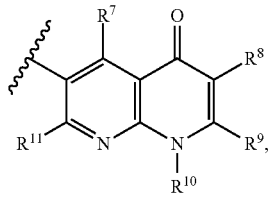

wherein
R$^7$ is H;
R$^8$ is carboxy;
R$^9$ is H;
R$^{10}$ is (C$_{1-6}$alkyl)$_2$(C$_{1-6}$alkylamino)C$_{1-6}$alkyl, (C$_{1-6}$alkyl)$_2$(pyrrolidinyl)C$_{1-6}$alkyl, (C$_{1-6}$alkyl)$_2$amino, (C$_{1-6}$alkyl)$_2$amino(phenyl)C$_{1-6}$alkyl, (C$_{1-6}$alkyl)$_2$aminoC$_{1-6}$alkyl, (C$_{1-6}$alkylamino)C$_{1-6}$alkyl, (C$_{1-6}$alkylpiperazinyl)C$_{1-6}$alkyl, (C$_{1-6}$alkylpiperidinyl)C$_{1-6}$alkyl, (C$_{1-6}$alkylpyrrolidinyl)C$_{1-6}$alkyl, (hydroxyC$_{1-6}$alkyl)$_2$C$_{1-6}$ alkyl, (hydroxyC$_{1-6}$ alkyl)C$_{1-6}$alkyl, (hydroxyC$_{3-7}$cycloalkyl)C$_{1-6}$alkyl, amino, aminoC$_{1-6}$alkyl, C$_{1-6}$alkoxyC$_{1-6}$alkyl, C$_{1-6}$alkoxy C$_{1-6}$alkylamino, C$_{1-6}$alkyl, C$_{1-6}$alkylamino, C$_{1-6}$alkylpyrrolidinyl, C$_{3-7}$cycloalkyl, C$_{3-7}$cycloalkylamino, dihydroxyC$_{1-6}$alkyl, haloC$_{1-6}$alkylamino, hydroxy C$_{1-6}$alkyl, morpholinyl, morpholinylC$_{1-6}$alkyl, oxazolylC$_{1-6}$alkyl, oxopiperazinylC$_{1-6}$alkyl, pyrazinylC$_{1-6}$alkyl, pyridinylC$_{1-6}$alkyl, pyrrolidinyl, pyrrolidinylC$_{1-6}$ alkyl, tetrahydrofuranyl, tetrahydrofuranylC$_{1-6}$ alkyl or tetrahydropyranylamino;
R$^{11}$ is H;
R$^2$ is (C$_{1-6}$alkyl)$_2$amino; C$_{1-6}$alkoxyC$_{1-6}$alkyl(C$_{1-6}$alkyl)amino; C$_{1-6}$alkylamino;
1,3,3a,4,6,6a-hexahydrofuro[3,4-c]pyrrolyl; 1,3,3a,4,6,6a-hexahydropyrrolo[3,4-c]pyrrolyl substituted by C$_{1-6}$alkyl; 1,4-diazepanyl substituted by C$_{1-6}$ alkyl; 1,4-oxazepanyl substituted by (C$_{1-6}$alkyl)$_2$amino C$_{1-6}$alkyl; 1,7-diazaspiro[3.4]octanyl substituted by C$_{1-6}$alkyl; 1,7-diazaspiro[4.4]nonanyl substituted by C$_{1-6}$alkyl; 2,3,3a,4,6,6a-hexahydrofuro[2,3-c]pyrrolyl substituted by (C$_{1-6}$alkyl)$_2$amino, (C$_{1-6}$ alkyl)$_2$aminoC$_{1-6}$ alkyl or hydroxy; 2,3,3a,4,6,6a-hexahydropyrrolo[2,3-c]pyrrolyl substituted by one or two substituents independently selected from halo C$_{1-6}$alkyl, halogen, hydroxyC$_{1-6}$alkyl, C$_{1-6}$ alkoxyC$_{1-6}$ alkyl, C$_{3-7}$cycloalkyl and C$_{1-6}$ alkyl; 2,3,3a,5,6,6a-hexahydropyrrolo[3,2-b]pyrrolyl substituted by C$_{1-6}$ alkyl; 2,3,4a,5,7,7a-hexahydropyrrolo[3,4-b][1,4]oxazinyl substituted by C$_{1-6}$alkyl; 2,6-diazabicyclo[3.2.0]heptanyl substituted by C$_{1-6}$ alkyl; 2,6-diazaspiro[3.4] octanyl substituted by C$_{1-6}$alkyl; 2,7-diazaspiro[4.4] nonanyl substituted by C$_{1-6}$alkyl; 2,8-diazaspiro[4.5] decanyl substituted by C$_{1-6}$alkyl; 2,9-diazaspiro[4.5] decanyl substituted by hydroxyC$_{1-6}$alkyl, C$_{1-6}$ alkoxyC$_{1-6}$ alkyl or C$_{1-6}$ alkyl; 3,3a,4,5,6,6a-hexahydro-1H-cyclopenta[c]pyrrolyl substituted by (C$_{1-6}$alkyl)$_2$aminoC$_{1-6}$alkyl or (C$_{1-6}$alkyl)$_2$amino; 3,3a,4,5,7,7a-hexahydro-2H-pyrrolo[2,3-c]pyridinyl substituted by C$_{1-6}$ alkyl; 3,3a,4,6,7,7a-hexahydro-2H-pyrrolo[3,2-c]pyridinyl substituted by C$_{1-6}$ alkyl; 3,3a,5,6,7,7a-hexahydro-2H-pyrrolo[3,2-b]pyridinyl substituted by C$_{1-6}$ alkyl; 3,4,4a,5,7,7a-hexahydro-2H-pyrrolo[3,4-b]pyridinyl substituted by one or two substituents independently selected from hydroxy and C$_{1-6}$ alkyl; 3,4,6,6a-tetrahydro-2H-pyrrolo[2,3-c]pyrrolyl substituted twice by C$_{1-6}$ alkyl; 3,4,6,6a-tetrahydro-2H-pyrrolo[3,4-b]pyrrolyl substituted by one or two substituents independently selected from halogen and C$_{1-6}$alkyl; 3,4,6,7,8,8a-hexahydro-1H-pyrrolo[1,2-a] pyrazinyl; 3,6-diazabicyclo[3.2.0]heptanyl substituted by C$_{1-6}$alkyl; 3,8-diazabicyclo[4.2.0]octanyl substituted by C$_{1-6}$alkyl; 3-azabicyclo[3.1.0]hexanyl substituted by (C$_{1-6}$alkyl)$_2$amino; 5-azaspiro[2.4]heptanyl substituted by (C$_{1-6}$alkyl)$_2$aminoC$_{1-6}$alkyl or (C$_{1-6}$alkyl)$_2$amino; 5-oxa-2,8-diazaspiro[3.5]nonanyl; 6-azaspiro[3.4]octanyl substituted by (C$_{1-6}$ alkyl)$_2$amino; 6-oxa-2,9-diazaspiro[4.5]decanyl substituted by C$_{1-6}$alkyl; hexahydro-1H-isoindol-2(3H)-yl substituted by (C$_{1-6}$alkyl)$_2$amino; hexahydro-1H-pyrrolo[3,4-b]pyridin-6(2H)-yl substituted by C$_{1-6}$alkyl; hexahydropyrazino[2,1-c][1,4]oxazin-8(1H)-yl; hexahydropyrrolo[3,4-b][1,4]oxazin-6(2H)-yl substituted by C$_{1-6}$alkyl; morpholinyl, said morpholinyl being unsubstituted or substituted by (C$_{1-6}$alkyl)$_2$amino C$_{1-6}$alkyl, hydroxyC$_{1-6}$alkyl, C$_{1-6}$alkoxyC$_{1-6}$alkyl or C$_{1-6}$alkyl; oxaazabicyclo[2.2.1]heptanyl; oxaazabicyclo[3.1.1]heptanyl; oxazepanyl; piperazinyl substituted by haloC$_{1-6}$alkyl, C$_{3-7}$cycloalkyl or C$_{1-6}$alkyl; piperidinyl, said piperidinyl being unsubstituted or substituted with one or two substituents independently selected from (C$_{1-6}$alkyl)$_2$amino, (C$_{1-6}$alkyl)$_2$aminoC$_{1-6}$alkyl, C$_{1-6}$alkoxy, C$_{1-6}$alkoxyC$_{1-6}$alkyl(C$_{1-6}$alkyl)amino, halogen, hydroxy, hydroxyC$_{1-6}$ alkyl(C$_{1-6}$ alkyl)amino and pyrrolidinyl; pyrazolyl substituted once or twice by substituents independently selected from amino C$_{1-6}$alkyl and haloC$_{1-6}$alkyl; pyrrolidinyl said pyrrolidinyl being unsubstituted or substituted with one, two or three substituents independently selected from (C$_{1-6}$alkoxyC$_{1-6}$alkyl(C$_{1-6}$alkyl)amino)C$_{1-6}$alkyl, (C$_{1-6}$alkyl)$_2$amino, (C$_{1-6}$alkyl)$_2$aminoC$_{1-6}$alkyl, (C$_{3-7}$cycloalkyl(C$_{1-6}$alkyl)amino)C$_{1-6}$alkyl, (C$_{3-7}$cycloalkylamino)C$_{1-6}$alkyl, amino, aminoC$_{1-6}$alkyl, C$_{1-6}$alkoxy, C$_{1-6}$alkoxyC$_{1-6}$alkyl(C$_{1-6}$alkyl)amino, C$_{1-6}$alkyl, C$_{3-7}$cycloalkyl(C$_{1-6}$alkyl)amino, C$_{3-7}$cycloalkylamino, haloC$_{1-6}$alkyl, halogen, hydroxy, hydroxyC$_{1-6}$alkyl, hydroxyC$_{1-6}$alkyl(C$_{1-6}$alkyl)amino, morpholinoC$_{1-6}$alkyl and pyrrolidinylC$_{1-6}$alkyl; or thiomorpholinyl;
R$^3$ is H, halogen, cyano or C$_{1-6}$alkoxy;
R$^4$ is H, halogen or haloC$_{1-6}$ alkyl;
R$^5$ is H or halogen; and
R$^6$ is C$_{1-6}$alkyl;
or a pharmaceutically acceptable salt, or enantiomer or diastereomer thereof.
3. A compound according to claim 2, wherein R$^1$ is

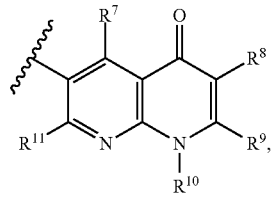

wherein
R$^7$ is H;
R$^8$ is carboxy;

R⁹ is H;

R¹⁰ is (diethylamino)ethyl, (dimethylamino)butyl, (diethylamino)ethyl, (dimethylamino)isopentyl, (dimethylamino)isopropyl, (dimethylamino)methylpropyl, (ethylpyrrolidinyl)methyl, (hydroxycyclopropyl) methyl, (hydroxymethyl)₂ethyl, (hydroxymethyl)ethyl, (methylamino)ethyl, (methylpiperazinyl)ethyl, (methylpiperidinyl)methyl, amino, amino(methyl)propyl, aminoisopentyl, cyclopropyl, cyclopropylamino, dihydroxypropyl, dimethyl(methylamino)ethyl, dimethyl (pyrrolidinyl)ethyl, dimethylamino, dimethylamino (phenyl)ethyl, ethyl, ethylamino, ethylpyrrolidinyl, hydroxy(methyl)propyl, hydroxypropyl, methoxyethyl, methoxyethylamino, methoxymethyl, methyl, methylamino, methylpyrrolidinyl, morpholinylethyl, morpholinyl, morpholinylmethyl, oxazolylmethyl, oxopiperazinylethyl, pyrazinylmethyl, pyridinylmethyl, pyrrolidinyl, pyrrolidinylmethyl, tetrahydrofuranyl, tetrahydrofuranylmethyl, tetrahydropyranylamino or trifluoroethylamino;

R¹¹ is H;

R² is dimethylamino; ((cyclopropyl(methyl)amino)methyl)pyrrolidinyl; ((cyclopropylamino)methyl)pyrrolidinyl; ((diethylamino)methyl)morpholinyl; ((dimethylamino)methyl)fluoropiperidinyl; ((dimethylamino) methyl)fluoropyrrolidinyl; ((dimethylamino)methyl) hydroxypyrrolidinyl; ((dimethylamino)methyl) methylpyrrolidinyl; ((dimethylamino)methyl) morpholinyl; ((dimethylamino)methyl)piperidinyl; ((dimethylamino)methyl)pyrrolidinyl; ((methoxyethyl (methyl)amino)methyl)pyrrolidinyl; (cyclopropyl (methyl)amino)pyrrolidinyl; (cyclopropylamino)pyrrolidinyl; (dimethylamino)fluoropyrrolidinyl; (dimethylamino)hexahydro-1H-isoindol-2(3H)-yl; (dimethylamino)hydroxypyrrolidinyl; (dimethylamino) methoxypyrrolidinyl; (dimethylamino)methyl-1,4-oxazepanyl; (dimethylamino)methyl-2,3,3a,4,6,6a-hexahydrofuro[2,3-c]pyrrolyl; (dimethylamino) methyl-3,3a,4,5,6,6a-hexahydro-1H-cyclopenta[c] pyrrolyl; (dimethylamino)methyl-3,3-difluoropyrrolidinyl; (dimethylamino)methyl-5-azaspiro[2.4]heptanyl; (dimethylamino) methylpyrrolidinyl; (dimethylamino)piperidinyl; (dimethylamino)pyrrolidinyl; (hydroxyethyl(methyl) amino)piperidinyl; (hydroxyethyl(methyl)amino)pyrrolidinyl; (hydroxyethyl)morpholinyl; (hydroxyethyl) pyrrolidinyl; (hydroxymethyl)pyrrolidinyl; (methoxyethyl(methyl)amino)piperidinyl; (methoxyethyl(methyl)amino)pyrrolidinyl; (methoxymethyl) morpholinyl; (morpholinylmethyl)pyrrolidinyl; (pyrrolidinylmethyl)pyrrolidinyl; (trifluoromethyl) piperazinyl; (trifluoromethyl)pyrazolyl; 1,3,3a,4,6,6a-hexahydrofuro[3,4-c]pyrrolyl; 3,4,6,7,8,8a-hexahydro-1H-pyrrolo[1,2-a]pyrazinyl; 3a-(fluoromethyl)-5-methyl-2,3,3a,4,6,6a-hexahydropyrrolo[2,3-c]pyrrolyl; 3a-fluoro-5-methyl-2,3,3a,4,6,6a-hexahydropyrrolo[2,3-c]pyrrolyl; 5-oxa-2,8-diazaspiro[3.5]nonanyl; amino (trifluoromethyl)pyrrolidinyl; aminomethyl(trifluoromethyl)pyrazolyl; cyclopropyl-2,3,3a,4,6,6a-hexahydropyrrolo[2,3-c]pyrrolyl; cyclopropylpiperazinyl; difluoropyrrolidinyl; dimethyl-3,4,6,6a-tetrahydro-2H-pyrrolo[2,3-c]pyrrolyl; dimethylamino-2,3,3a,4,6,6a-hexahydrofuro[2,3-c] pyrrolyl; dimethylamino-3,3a,4,5,6,6a-hexahydro-1H-cyclopenta[c]pyrrolyl; dimethylamino-3-azabicyclo [3.1.0]hexanyl; dimethylamino-5-azaspiro[2.4] heptanyl; dimethylamino-6-azaspiro[3.4]octanyl; ethyl-2,3,3a,4,6,6a-hexahydropyrrolo[2,3-c]pyrrolyl; ethylpiperazinyl; fluoro(aminomethyl)pyrrolidinyl; fluoro(hydroxy)pyrrolidinyl; fluoro(methyl)-3,4,6,6a-tetrahydro-2H-pyrrolo[3,4-b]pyrrolyl; hexahydropyrazino[2,1-c][1,4]oxazin-8(1H)-yl; hydroxy(methyl)-3,4,4a,5,7,7a-hexahydro-2H-pyrrolo[3,4-b]pyridinyl; hydroxy(methyl)pyrrolidinyl; hydroxy(trifluoromethyl)pyrrolidinyl; hydroxy-2,3,3a,4,6,6a-hexahydrofuro[2,3-c]pyrrolyl; hydroxyethyl-2,3,3a,4,6,6a-hexahydropyrrolo[2,3-c]pyrrolyl; hydroxyethyl-2,9-diazaspiro[4.5]decanyl; hydroxymethyl(methyl) pyrrolidinyl; hydroxypiperidinyl; hydroxypropyl-2,3,3a,4,6,6a-hexahydropyrrolo[2,3-c]pyrrolyl; hydroxypyrrolidinyl; isopropylpiperazinyl; methoxyethyl(methyl)amino; methoxyethyl-2,3,3a,4,6,6a-hexahydropyrrolo[2,3-c]pyrrolyl; methoxyethyl-2,9-diazaspiro[4.5]decanyl; methoxypiperidinyl; methyl (propyl)amino; methyl-1,3,3a,4,6,6a-hexahydropyrrolo [3,4-c]pyrrolyl; methyl-1,4-diazepanyl; methyl-1,7-diazaspiro[3.4]octanyl; methyl-1,7-diazaspiro[4.4] nonanyl; methyl-2,3,3a,4,6,6a-hexahydropyrrolo[2,3-c]pyrrolyl; methyl-2,3,3a,5,6,6a-hexahydropyrrolo[3,2-b]pyrrolyl; methyl-2,3,4a,5,7,7a-hexahydropyrrolo [3,4-b][1,4]oxazinyl; methyl-2,6-diazabicyclo[3.2.0] heptanyl; methyl-2,6-diazaspiro[3.4]octanyl; methyl-2,7-diazaspiro[4.4]nonanyl; methyl-2,8-diazaspiro[4.5] decanyl; methyl-2,9-diazaspiro[4.5]decanyl; methyl-3,3a,4,5,7,7a-hexahydro-2H-pyrrolo[2,3-c]pyridinyl; methyl-3,3a,4,6,7,7a-hexahydro-2H-pyrrolo[3,2-c] pyridinyl; methyl-3,3a, 5,6,7,7a-hexahydro-2H-pyrrolo [3,2-b]pyridinyl; methyl-3,4,4a,5,7,7a-hexahydro-2H-pyrrolo[3,4-b]pyridinyl; methyl-3,6-diazabicyclo [3.2.0]heptanyl; methyl-3,8-diazabicyclo[4.2.0] octanyl; methyl-6-oxa-2,9-diazaspiro[4.5]decanyl; methylamino; methylhexahydro-1H-pyrrolo[3,4-b] pyridin-6(2H)-yl; methylhexahydropyrrolo[3,4-b][1,4] oxazin-6(2H)-yl; methylmorpholinyl; methylpiperazinyl; methylpyrrolidinyl; morpholinyl; oxaazabicyclo [2.2.1]heptanyl; oxaazabicyclo[3.1.1]heptanyl; oxazepanyl; piperidinyl; pyrrolidinyl; pyrrolidinylpiperidinyl; or thiomorpholinyl;

R³ is H, fluoro, chloro, cyano or methoxy;

R⁴ is H, fluoro, chloro or trifluoromethyl;

R⁵ is H, fluoro or chloro; and

R⁶ is methyl or ethyl;

or a pharmaceutically acceptable salt, or enantiomer or diastereomer thereof.

4. A compound according to claim 2, or a pharmaceutically acceptable salt, or enantiomer or diastereomer thereof, wherein R¹⁰ is $C_{1-6}$alkyl or $C_{1-6}$alkylamino.

5. A compound according to claim 4, or a pharmaceutically acceptable salt, or enantiomer or diastereomer thereof, wherein R¹⁰ is methyl or methylamino.

6. A compound according to claim 4, or a pharmaceutically acceptable salt, or enantiomer or diastereomer thereof, wherein R² is 2,3,3a,4,6,6a-hexahydropyrrolo[2,3-c]pyrrolyl substituted by $C_{1-6}$ alkyl; pyrrolidinyl substituted by $(C_{1-6}alkyl)_2$amino; 3,3a,4,5,6,6a-hexahydro-1H-cyclopenta [c]pyrrolyl substituted by $(C_{1-6}alkyl)_2$amino; 2,3,3a,4,6,6a-hexahydrofuro[2,3-c]pyrrolyl substituted by $(C_{1-6}alkyl)_2$amino; or 2,3,4a,5,7,7a-hexahydropyrrolo[3,4-b][1,4] oxazinyl substituted by $C_{1-6}$ alkyl.

7. A compound according to claim 6, or a pharmaceutically acceptable salt, or enantiomer or diastereomer thereof, wherein R² is (dimethylamino)pyrrolidinyl; methyl-2,3,3a, 4,6,6a-hexahydropyrrolo[2,3-c]pyrrolyl; dimethylamino-3, 3a,4,5,6,6a-hexahydro-1H-cyclopenta[c]pyrrolyl; dimethylamino-2,3,3a,4,6,6a-hexahydrofuro[2,3-c]pyrrolyl; or methyl-2,3,4a,5,7,7a-hexahydropyrrolo[3,4-b][1,4]oxazinyl.

8. A compound according to claim 6, or a pharmaceutically acceptable salt, or enantiomer or diastereomer thereof, wherein $R^4$ is halogen.

9. A compound according to claim 8, or a pharmaceutically acceptable salt, or enantiomer or diastereomer thereof, wherein $R^4$ is fluoro or chloro.

10. A compound according to claim 8, or a pharmaceutically acceptable salt, or enantiomer or diastereomer thereof, wherein $R^5$ is H.

11. A compound according to claim 2, wherein $R^1$ is

[chemical structure]

wherein
$R^7$ is H;
$R^8$ is carboxy;
$R^9$ is H;
$R^{10}$ is $C_{1-6}$alkyl or $C_{1-6}$alkylamino;
$R^{11}$ is H;
$R^2$ is 2,3,3a,4,6,6a-hexahydropyrrolo[2,3-c]pyrrolyl substituted by $C_{1-6}$alkyl; pyrrolidinyl substituted by $(C_{1-6}$alkyl$)_2$amino; 3,3a,4,5,6,6a-hexahydro-1H-cyclopenta[c]pyrrolyl substituted by $(C_{1-6}$alkyl$)_2$amino; 2,3,3a,4,6,6a-hexahydrofuro[2,3-c]pyrrolyl substituted by $(C_{1-6}$alkyl$)_2$amino; or 2,3,4a,5,7,7a-hexahydropyrrolo[3,4-b][1,4]oxazinyl substituted by $C_{1-6}$alkyl;
$R^3$ is H, halogen or cyano;
$R^4$ is halogen;
$R^5$ is H; and
$R^6$ is $C_{1-6}$alkyl;
or a pharmaceutically acceptable salt, or enantiomer or diastereomer thereof.

12. A compound according to claim 11, wherein $R^1$ is

[chemical structure]

wherein
$R^7$ is H;
$R^8$ is carboxy;
$R^9$ is H;
$R^{10}$ is methyl or methylamino;
$R^{11}$ is H;
$R^2$ is (dimethylamino)pyrrolidinyl; methyl-2,3,3a,4,6,6a-hexahydropyrrolo[2,3-c]pyrrolyl; dimethylamino-3,3a,4,5,6,6a-hexahydro-1H-cyclopenta[c]pyrrolyl; dimethylamino-2,3,3a,4,6,6a-hexahydrofuro[2,3-c]pyrrolyl; or methyl-2,3,4a,5,7,7a-hexahydropyrrolo[3,4-b][1,4]oxazinyl;
$R^3$ is H, fluoro, chloro or cyano;
$R^4$ is fluoro or chloro;
$R^5$ is H; and
$R^6$ is methyl;
or a pharmaceutically acceptable salt, or enantiomer or diastereomer thereof.

13. A compound according to claim 2, wherein $R^1$ is

[chemical structure]

wherein
$R^7$ is H;
$R^8$ is carboxy;
$R^9$ is H;
$R^{10}$ is $(C_{1-6}$alkylpyrrolidinyl$)C_{1-6}$alkyl, (hydroxy$C_{1-6}$alkyl$)C_{1-6}$alkyl, amino, $C_{1-6}$alkoxy$C_{1-6}$alkyl, $C_{1-6}$alkoxy$C_{1-6}$alkylamino, $C_{1-6}$alkyl, $C_{1-6}$alkylamino, halo$C_{1-6}$alkylamino, morpholinyl or pyrrolidinyl;
$R^{11}$ is H;
$R^2$ is $(C_{1-6}$ alkyl$)_2$amino; 1,3,3a,4,6,6a-hexahydropyrrolo[3,4-c]pyrrolyl substituted by $C_{1-6}$alkyl; 1,4-oxazepanyl substituted by $(C_{1-6}$alkyl$)_2$amino$C_{1-6}$alkyl; 1,7-diazaspiro[3.4]octanyl substituted by $C_{1-6}$ alkyl; 2,3,3a,4,6,6a-hexahydrofuro[2,3-c]pyrrolyl substituted by $(C_{1-6}$alkyl$)_2$amino$C_{1-6}$alkyl; 2,3,3a,4,6,6a-hexahydropyrrolo[2,3-c]pyrrolyl substituted by one or two substituents independently selected from halo$C_{1-6}$ alkyl, halogen, hydroxy$C_{1-6}$ alkyl, $C_{1-6}$alkoxy$C_{1-6}$ alkyl and $C_{1-6}$ alkyl; 2,3,3a,5,6,6a-hexahydropyrrolo[3,2-b]pyrrolyl substituted by $C_{1-6}$ alkyl; 2,3,4a,5,7,7a-hexahydropyrrolo[3,4-b][1,4]oxazinyl substituted by $C_{1-6}$alkyl; 2,6-diazabicyclo[3.2.0]heptanyl substituted by $C_{1-6}$alkyl; 2,7-diazaspiro[4.4]nonanyl substituted by $C_{1-6}$alkyl; 2,8-diazaspiro[4.5]decanyl substituted by $C_{1-6}$alkyl; 2,9-diazaspiro[4.5]decanyl substituted by $C_{1-6}$alkoxy$C_{1-6}$alkyl or $C_{1-6}$alkyl; 3,3a,4,5,6,6a-hexahydro-1H-cyclopenta[c]pyrrolyl substituted by $(C_{1-6}$alkyl$)_2$amino; 3,3a,4,5,7,7a-hexahydro-2H-pyrrolo[2,3-c]pyridinyl substituted by $C_{1-6}$alkyl; 3,3a,4,6,7,7a-hexahydro-2H-pyrrolo[3,2-c]pyridinyl substituted by $C_{1-6}$alkyl; 3,3a,5,6,7,7a-hexahydro-2H-pyrrolo[3,2-b]pyridinyl substituted by $C_{1-6}$ alkyl; 3,4,4a,5,7,7a-hexahydro-2H-pyrrolo[3,4-b]pyridinyl substituted by $C_{1-6}$ alkyl; 3,4,6,6a-tetrahydro-2H-pyrrolo[2,3-c]pyrrolyl substituted twice by $C_{1-6}$ alkyl; 3,4,6,6a-tetrahydro-2H-pyrrolo[3,4-b]pyrrolyl substituted by one or two substituents independently selected from halogen and $C_{1-6}$alkyl; 3,4,6,7,8,8a-hexahydro-1H-pyrrolo[1,2-a]pyrazinyl; 3,6-diazabicyclo[3.2.0]heptanyl substituted by $C_{1-6}$alkyl; 3,8-diazabicyclo[4.2.0]octanyl substituted by $C_{1-6}$alkyl; 5-azaspiro[2.4]heptanyl substituted by $(C_{1-6}$alkyl$)_2$amino$C_{1-6}$alkyl or $(C_{1-6}$alkyl$)_2$amino; hexahydro-1H-isoindol-2(3H)-yl substituted by $(C_{1-6}$alkyl$)_2$amino; hexahydro-1H-pyrrolo[3,4-b]pyridin-6(2H)-yl substituted by $C_{1-6}$ alkyl; hexahydropyrazino[2,1-c][1,4]oxazin-8(1H)-yl; morpholinyl, said morpholinyl being unsubstituted or substituted by $(C_{1-6}alkyl)_2aminoC_{1-6}alkyl$; piperazinyl substituted by $C_{1-6}alkyl$; piperidinyl substituted by $(C_{1-6}alkyl)_2amino$, $(C_{1-6}alkyl)_2aminoC_{1-6}alkyl$, $C_{1-6}alkoxyC_{1-6}alkyl(C_{1-6}alkyl)amino$, $hydroxyC_{1-6}alkyl(C_{1-6}alkyl)amino$ or pyrrolidinyl; or pyrrolidinyl substituted by one, two or three substituents independently selected from $(C_{1-6}alkyl)_2amino$, $(C_{1-6}alkoxyC_{1-6}alkyl(C_{1-6}alkyl)amino)C_{1-6}alkyl$, $(C_{1-6}alkyl)_2amino$, $(C_{1-6}alkyl)_2aminoC_{1-6}alkyl$, $C_{1-6}alkoxy$, $C_{1-6}alkoxyC_{1-6}alkyl(C_{1-6}alkyl)amino$, $C_{1-6}alkyl$, halogen, hydroxy, $hydroxyC_{1-6}alkyl(C_{1-6}alkyl)amino$ and $pyrrolidinylC_{1-6}alkyl$;

$R^3$ is H, halogen or cyano;
$R^4$ is H, halogen or $haloC_{1-6}alkyl$;
$R^5$ is H or halogen; and
$R^6$ is $C_{1-6}alkyl$;

or a pharmaceutically acceptable salt, or enantiomer or diastereomer thereof.

14. A compound according to claim 13, wherein $R^1$ is wherein
$R^7$ is H;
$R^8$ is carboxy;
$R^9$ is H;
$R^{10}$ is amino, $C_{1-6}alkoxyC_{1-6}alkyl$, $C_{1-6}alkoxyC_{1-6}alkylamino$, $C_{1-6}alkyl$, $C_{1-6}alkylamino$, $haloC_{1-6}alkylamino$ or $hydroxyC_{1-6}alkyl$;
$R^{11}$ is H;
$R^2$ is 1,4-oxazepanyl substituted by $(C_{1-6}alkyl)_2amino$ $C_{1-6}alkyl$; 1,7-diazaspiro[3.4]octanyl substituted by $C_{1-6}alkyl$; 2,3,3a,4,6,6a-hexahydrofuro[2,3-c]pyrrolyl substituted by $(C_{1-6}alkyl)_2aminoC_{1-6}alkyl$; 2,3,3a,4,6,6a-hexahydropyrrolo[2,3-c]pyrrolyl substituted by one or two substituents independently selected from $haloC_{1-6}alkyl$, halogen, $hydroxyC_{1-6}alkyl$, $C_{1-6}alkoxyC_{1-6}alkyl$ and $C_{1-6}alkyl$; 2,3,3a,5,6,6a-hexahydropyrrolo[3,2-b]pyrrolyl substituted by $C_{1-6}alkyl$; 2,6-diazabicyclo[3.2.0]heptanyl substituted by $C_{1-6}alkyl$; 3,3a,4,5,7,7a-hexahydro-2H-pyrrolo[2,3-c]pyridinyl substituted by $C_{1-6}alkyl$; 3,3a,4,6,7,7a-hexahydro-2H-pyrrolo[3,2-c]pyridinyl substituted by $C_{1-6}alkyl$; 3,3a,5,6,7,7a-hexahydro-2H-pyrrolo[3,2-b]pyridinyl substituted by $C_{1-6}alkyl$; 3,4,6,6a-tetrahydro-2H-pyrrolo[2,3-c]pyrrolyl substituted twice by $C_{1-6}alkyl$; 3,4,6,6a-tetrahydro-2H-pyrrolo[3,4-b]pyrrolyl substituted by one or two substituents independently selected from halogen and $C_{1-6}alkyl$; hexahydro-1H-isoindol-2(3H)-yl substituted by $(C_{1-6}alkyl)_2amino$; hexahydro-1H-pyrrolo[3,4-b]pyridin-6(2H)-yl substituted by $C_{1-6}alkyl$; morpholinyl substituted by $(C_{1-6}alkyl)_2aminoC_{1-6}alkyl$; piperidinyl substituted by $(C_{1-6}alkyl)_2amino$, $(C_{1-6}alkyl)_2aminoC_{1-6}alkyl$, $C_{1-6}alkoxyC_{1-6}alkyl(C_{1-6}alkyl)amino$, hydroxy $C_{1-6}alkyl(C_{1-6}alkyl)amino$ or pyrrolidinyl; or pyrrolidinyl substituted by one or two substituents independently selected from $(C_{1-6}alkoxyC_{1-6}alkyl(C_{1-6}alkyl)amino)C_{1-6}alkyl$, $(C_{1-6}alkyl)_2amino$, $(C_{1-6}alkyl)_2aminoC_{1-6}alkyl$, $C_{1-6}alkoxy$, $C_{1-6}alkyl$, halogen, hydroxy and $pyrrolidinylC_{1-6}alkyl$;

$R^3$ is H, halogen or cyano;
$R^4$ is H or halogen;
$R^5$ is H or halogen; and
$R^6$ is $C_{1-6}alkyl$;

or a pharmaceutically acceptable salt, or enantiomer or diastereomer thereof.

15. A compound according to claim 14, wherein $R^1$ is wherein
$R^7$ is H;
$R^8$ is carboxy;
$R^9$ is H;
$R^{10}$ is (hydroxymethyl)ethyl, amino, ethyl, ethylamino, methoxyethylamino, methoxymethyl, methyl, methylamino or trifluoroethylamino;
$R^{11}$ is H;
$R^2$ is ((diethylamino)methyl)morpholinyl; ((dimethylamino)methyl)fluoropyrrolidinyl; ((dimethylamino)methyl)hydroxypyrrolidinyl; ((dimethylamino)methyl)methylpyrrolidinyl; ((dimethylamino)methyl)morpholinyl; ((dimethylamino)methyl)piperidinyl; ((dimethylamino)methyl)pyrrolidinyl; ((methoxyethyl(methyl)amino)methyl)pyrrolidinyl; (dimethylamino)hexahydro-1H-isoindol-2(3H)-yl; (dimethylamino)hydroxypyrrolidinyl; (dimethylamino)methoxypyrrolidinyl; (dimethylamino)methyl-1,4-oxazepanyl; (dimethylamino)methyl-2,3,3a,4,6,6a-hexahydrofuro[2,3-c]pyrrolyl; (dimethylamino)methylpyrrolidinyl; (dimethylamino)piperidinyl; (dimethylamino)pyrrolidinyl; (hydroxyethyl(methyl)amino)piperidinyl; (methoxyethyl(methyl)amino)piperidinyl; (pyrrolidinylmethyl)pyrrolidinyl; 3a-(fluoromethyl)-5-methyl-2,3,3a,4,6,6a-hexahydropyrrolo[2,3-c]pyrrolyl; dimethyl-3,4,6,6a-tetrahydro-2H-pyrrolo[2,3-c]pyrrolyl; ethyl-2,3,3a,4,6,6a-hexahydropyrrolo[2,3-c]pyrrolyl; fluoro(methyl)-3,4,6,6a-tetrahydro-2H-pyrrolo[3,4-b]pyrrolyl; hydroxyethyl-2,3,3a,4,6,6a-hexahydropyrrolo[2,3-c]pyrrolyl; hydroxypropyl-2,3,3a,4,6,6a-hexahydropyrrolo[2,3-c]pyrrolyl; methoxyethyl-2,3,3a,4,6,6a-hexahydropyrrolo[2,3-c]pyrrolyl; methyl-1,7-diazaspiro[3.4]octanyl; methyl-2,3,3a,4,6,6a-hexahydropyrrolo[2,3-c]pyrrolyl; methyl-2,3,3a,5,6,6a-hexahydropyrrolo[3,2-b]pyrrolyl; methyl-2,6-diazabicyclo[3.2.0]heptanyl; methyl-3,3a,4,5,7,7a-hexahydro-2H-pyrrolo[2,3-c]pyridinyl; methyl-3,3a,4,6,7,7a-hexahydro-2H-pyrrolo[3,2-c]pyridinyl; methyl-3,3a,5,6,7,7a-hexahydro-2H-pyrrolo[3,2-b]pyridinyl; methylhexahydro-1H-pyrrolo[3,4-b]pyridin-6(2H)-yl; or pyrrolidinylpiperidinyl;

$R^3$ is H, fluoro or cyano;
$R^4$ is H, fluoro or chloro;
$R^5$ is H or fluoro; and
$R^6$ is methyl or ethyl;
or a pharmaceutically acceptable salt, or enantiomer or diastereomer thereof.

16. A compound according to claim 2, wherein $R^1$ is

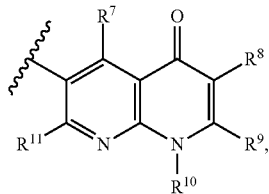

wherein
$R^7$ is H;
$R^8$ is carboxy;
$R^9$ is H;
$R^{10}$ is ($C_{1-6}$alkylamino)$C_{1-6}$alkyl, ($C_{1-6}$alkylpiperidinyl)$C_{1-6}$alkyl, (hydroxy$C_{1-6}$alkyl)$_2C_{1-6}$alkyl, (hydroxy $C_{1-6}$alkyl)$C_{1-6}$alkyl, amino$C_{1-6}$alkyl, $C_{1-6}$alkoxy $C_{1-6}$alkylamino, $C_{1-6}$alkyl, $C_{1-6}$alkylamino, hydroxy$C_{1-6}$alkyl, morpholinyl, morpholinyl$C_{1-6}$alkyl, pyrazinyl$C_{1-6}$alkyl, pyrrolidinyl or pyrrolidinyl $C_{1-6}$alkyl;
$R^{11}$ is H;
$R^2$ is ($C_{1-6}$alkyl)$_2$amino; $C_{1-6}$alkoxy$C_{1-6}$alkyl($C_{1-6}$alkyl)amino; $C_{1-6}$alkylamino; 1,4-oxazepanyl substituted by ($C_{1-6}$alkyl)$_2$amino$C_{1-6}$alkyl; 1,7-diazaspiro[3.4]octanyl substituted by $C_{1-6}$alkyl; 2,3,3a,4,6,6a-hexahydropyrrolo[2,3-c]pyrrolyl substituted by $C_{1-6}$alkyl; 2,6-diazaspiro[3.4]octanyl substituted by $C_{1-6}$alkyl; 2,7-diazaspiro[4.4]nonanyl substituted by $C_{1-6}$alkyl; 2,8-diazaspiro[4.5]decanyl substituted by $C_{1-6}$alkyl; 2,9-diazaspiro[4.5]decanyl substituted by hydroxy $C_{1-6}$alkyl; 3,3a,4,5,7,7a-hexahydro-2H-pyrrolo[2,3-c]pyridinyl substituted by $C_{1-6}$alkyl; 3,3a,4,6,7,7a-hexahydro-2H-pyrrolo[3,2-c]pyridinyl substituted by $C_{1-6}$alkyl; 3,8-diazabicyclo[4.2.0]octanyl substituted by $C_{1-6}$alkyl; hexahydropyrazino[2,1-c][1,4]oxazin-8(1H)-yl; hexahydropyrrolo[3,4-b][1,4]oxazin-6(2H)-yl substituted by $C_{1-6}$alkyl; morpholinyl, said morpholinyl being unsubstituted or substituted by ($C_{1-6}$alkyl)$_2$amino$C_{1-6}$alkyl or $C_{1-6}$alkyl; piperidinyl substituted by hydroxy, ($C_{1-6}$alkyl)$_2$amino$C_{1-6}$alkyl or ($C_{1-6}$alkyl)$_2$amino; pyrazolyl substituted twice by amino$C_{1-6}$alkyl and halo$C_{1-6}$alkyl; pyrrolidinyl substituted by ($C_{1-6}$alkyl)$_2$amino, ($C_{1-6}$alkyl)$_2$amino $C_{1-6}$alkyl, amino$C_{1-6}$alkyl, $C_{1-6}$alkyl, halo$C_{1-6}$alkyl, halogen, hydroxy, hydroxy$C_{1-6}$alkyl or pyrrolidinyl $C_{1-6}$alkyl; or thiomorpholinyl;
$R^3$ is H, halogen or cyano;
$R^4$ is H or halogen;
$R^5$ is H or halogen; and
$R^6$ is $C_{1-6}$alkyl;
or a pharmaceutically acceptable salt, or enantiomer or diastereomer thereof.

17. A compound according to claim 16, wherein $R^1$ is

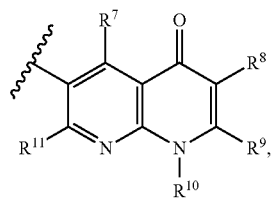

wherein
$R^7$ is H;
$R^8$ is carboxy;
$R^9$ is H;
$R^{10}$ is (hydroxymethyl)$_2$ethyl, (hydroxymethyl)ethyl, (methylamino)ethyl, (methylpiperidinyl)methyl, amino(methyl)propyl, aminoisopentyl, ethyl, hydroxy(methyl)propyl, hydroxypropyl, methoxyethylamino, methyl, methylamino, morpholinyl, morpholinylmethyl, pyrazinylmethyl, pyrrolidinyl or pyrrolidinylmethyl;
$R^{11}$ is H;
$R^2$ is ((diethylamino)methyl)morpholinyl; ((dimethylamino)methyl)morpholinyl; ((dimethylamino)methyl)piperidinyl; ((dimethylamino)methyl)pyrrolidinyl; (dimethylamino)methyl-1,4-oxazepanyl; (dimethylamino)methylpyrrolidinyl; (dimethylamino)piperidinyl; (dimethylamino)pyrrolidinyl; (hydroxyethyl)pyrrolidinyl; (hydroxymethyl)pyrrolidinyl; (pyrrolidinylmethyl)pyrrolidinyl; aminomethyl(trifluoromethyl)pyrazolyl; dimethylamino; fluoro(aminomethyl)pyrrolidinyl; fluoro(hydroxy)pyrrolidinyl; hexahydropyrazino[2,1-c][1,4]oxazin-8(1H)-yl; hydroxy(trifluoromethyl)pyrrolidinyl; hydroxyethyl-2,9-diazaspiro[4.5]decanyl; hydroxypiperidinyl; hydroxypyrrolidinyl; methoxyethyl(methyl)amino; methyl-1,7-diazaspiro[4.4]nonanyl; methyl-2,3,3a,4,6,6a-hexahydropyrrolo[2,3-c]pyrrolyl; methyl-2,6-diazaspiro[3.4]octanyl; methyl-2,7-diazaspiro[4.4]nonanyl; methyl-2,8-diazaspiro[4.5]decanyl; methyl-3,3a,4,5,7,7a-hexahydro-2H-pyrrolo[2,3-c]pyridinyl; methyl-3,3a,4,6,7,7a-hexahydro-2H-pyrrolo[3,2-c]pyridinyl; methyl-3,8-diazabicyclo[4.2.0]octanyl; methylamino; methylhexahydropyrrolo[3,4-b][1,4]oxazin-6(2H)-yl; methylmorpholinyl; morpholinyl; or thiomorpholinyl;
$R^3$ is H, fluoro, chloro or cyano;
$R^4$ is H, fluoro or chloro;
$R^5$ is H or fluoro; and
$R^6$ is methyl or ethyl;
or a pharmaceutically acceptable salt, or enantiomer or diastereomer thereof.

18. A compound according to claim 1, selected from
6-[4-(dimethylamino)-5,6-difluoro-8-(methylamino)-9H-pyrido[2,3-b]indol-3-yl]-1-methyl-4-oxo-1,8-naphthyridine-3-carboxylic acid;
6-[4-(dimethylamino)-5,6-difluoro-8-(methylamino)-9H-pyrido[2,3-b]indol-3-yl]-4-oxo-1-pyrrolidin-3-yl-1,8-naphthyridine-3-carboxylic acid;
6-[4-(dimethylamino)-5,6-difluoro-8-(methylamino)-9H-pyrido[2,3-b]indol-3-yl]-1-(morpholin-3-ylmethyl)-4-oxo-1,8-naphthyridine-3-carboxylic acid;
6-[4-(dimethylamino)-5,6-difluoro-8-(methylamino)-9H-pyrido[2,3-b]indol-3-yl]-1-[(1-ethylpyrrolidin-2-yl)methyl]-4-oxo-1,8-naphthyridine-3-carboxylic acid;
6-[5,6-difluoro-8-(methylamino)-4-(2-oxa-5-azabicyclo[2.2.1]heptan-5-yl)-9H-pyrido[2,3-b]indol-3-yl]-1-ethyl-4-oxo-1,8-naphthyridine-3-carboxylic acid;

6-[5,6-difluoro-4-[2-methoxyethyl(methyl)amino]-8-(methylamino)-9H-pyrido[2,3-b]indol-3-yl]-1-ethyl-4-oxo-1,8-naphthyridine-3-carboxylic acid;

6-[5,6-difluoro-8-(methylamino)-4-[methyl(propyl)amino]-9H-pyrido[2,3-b]indol-3-yl]-1-ethyl-4-oxo-1,8-naphthyridine-3-carboxylic acid;

6-[5,6-difluoro-8-(methylamino)-4-morpholino-9H-pyrido[2,3-b]indol-3-yl]-1-methyl-4-oxo-1,8-naphthyridine-3-carboxylic acid;

6-[5,6-difluoro-8-(methylamino)-4-[3-(trifluoromethyl)piperazin-1-yl]-9H-pyrido[2,3-b]indol-3-yl]-1-methyl-4-oxo-1,8-naphthyridine-3-carboxylic acid;

6-[5,6-difluoro-4-[2-(methoxymethyl)morpholin-4-yl]-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-morpholino-9H-pyrido[2,3-b]indol-3-yl]-4-oxo-1-(pyrrolidin-2-ylmethyl)-1,8-naphthyridine-3-carboxylic acid;

6-[4-[2-[(dimethylamino)methyl]pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-[(2R)-2-[(dimethylamino)methyl]pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-[(2S)-2-[(dimethylamino)methyl]pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-[4-(aminomethyl)-3-(trifluoromethyl)pyrazol-1-yl]-8-(ethylamino)-6-fluoro-9H-pyrido[2,3-b]indol-3-yl]-1-ethyl-4-oxo-1,8-naphthyridine-3-carboxylic acid;

6-[4-(3,3-difluoropyrrolidin-1-yl)-6-fluoro-8-(methylamino)-9H-pyrido[2,3-b]indol-3-yl]-1-methyl-4-oxo-1,8-naphthyridine-3-carboxylic acid;

6-[4-(Dimethylamino)-6-fluoro-8-(methylamino)-9H-pyrido[2,3-b]indol-3-yl]-1-(1,1-dimethyl-2-pyrrolidin-1-yl-ethyl)-4-oxo-1,8-naphthyridine-3-carboxylic acid;

6-[4-(Dimethylamino)-5,6-difluoro-8-(methylamino)-9H-pyrido[2,3-b]indol-3-yl]-1-ethyl-4-oxo-1,8-naphthyridine-3-carboxylic acid;

6-[4-(Dimethylamino)-6-fluoro-8-(methylamino)-9H-pyrido[2,3-b]indol-3-yl]-1-ethyl-4-oxo-1,8-naphthyridine-3-carboxylic acid;

6-[4-(Dimethylamino)-6,7-difluoro-8-(methylamino)-9H-pyrido[2,3-b]indol-3-yl]-1-ethyl-4-oxo-1,8-naphthyridine-3-carboxylic acid;

6-[4-(Dimethylamino)-5,6-difluoro-8-(methylamino)-9H-pyrido[2,3-b]indol-3-yl]-4-oxo-1-tetrahydrofuran-3-yl-1,8-naphthyridine-3-carboxylic acid;

6-[4-(Dimethylamino)-5,6-difluoro-8-(methylamino)-9H-pyrido[2,3-b]indol-3-yl]-1-[2-(dimethylamino)ethyl]-4-oxo-1,8-naphthyridine-3-carboxylic acid;

6-[4-[3-(Aminomethyl)-3-fluoro-pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-(Dimethylamino)-5,6-difluoro-8-(methylamino)-9H-pyrido[2,3-b]indol-3-yl]-1-(2-methoxyethyl)-4-oxo-1,8-naphthyridine-3-carboxylic acid;

6-[6-Fluoro-4-[3-hydroxy-3-(trifluoromethyl)pyrrolidin-1-yl]-8-(methylamino)-9H-pyrido[2,3-b]indol-3-yl]-1-methyl-4-oxo-1,8-naphthyridine-3-carboxylic acid;

6-[4-(Dimethylamino)-5,6-difluoro-8-(methylamino)-9H-pyrido[2,3-b]indol-3-yl]-1-[2-(methylamino)ethyl]-4-oxo-1,8-naphthyridine-3-carboxylic acid;

6-[4-[3-Amino-3-(trifluoromethyl)pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[8-(Ethyl amino)-6-fluoro-4-[3-(trifluoromethyl)pyrazol-1-yl]-9H-pyrido[2,3-b]indol-3-yl]-4-oxo-1-pyrrolidin-3-yl-1,8-naphthyridine-3-carboxylic acid;

6-[4-(Dimethylamino)-5,6-difluoro-8-(methylamino)-9H-pyrido[2,3-b]indol-3-yl]-1-[2-(4-methylpiperazin-1-yl)ethyl]-4-oxo-1,8-naphthyridine-3-carboxylic acid;

6-[4-(Dimethylamino)-5,6-difluoro-8-(methylamino)-9H-pyrido[2,3-b]indol-3-yl]-4-oxo-1-(4-pyridylmethyl)-1,8-naphthyridine-3-carboxylic acid;

6-[5,6-Difluoro-8-(methylamino)-4-morpholino-9H-pyrido[2,3-b]indol-3-yl]-1-(morpholin-3-ylmethyl)-4-oxo-1,8-naphthyridine-3-carboxylic acid;

6-[4-(Dimethylamino)-5,6-difluoro-8-(methylamino)-9H-pyrido[2,3-b]indol-3-yl]-1-[(1-methyl-4-piperidyl)methyl]-4-oxo-1,8-naphthyridine-3-carboxylic acid;

6-[5,6-Difluoro-4-[2-methoxyethyl(methyl)amino]-8-(methylamino)-9H-pyrido[2,3-b]indol-3-yl]-1-methyl-4-oxo-1,8-naphthyridine-3-carboxylic acid;

6-[8-(Ethylamino)-6-fluoro-4-morpholino-9H-pyrido[2,3-b]indol-3-yl]-4-oxo-1-pyrrolidin-3-yl-1,8-naphthyridine-3-carboxylic acid;

6-[5,6-Difluoro-8-(methylamino)-4-morpholino-9H-pyrido[2,3-b]indol-3-yl]-1-(2-hydroxy-2-methyl-propyl)-4-oxo-1,8-naphthyridine-3-carboxylic acid;

6-[5,6-Difluoro-8-(methylamino)-4-[(2S)-2-methylmorpholin-4-yl]-9H-pyrido[2,3-b]indol-3-yl]-1-methyl-4-oxo-1,8-naphthyridine-3-carboxylic acid;

6-[6-Fluoro-4,8-bis(methylamino)-9H-pyrido[2,3-b]indol-3-yl]-1-(morpholin-3-ylmethyl)-4-oxo-1,8-naphthyridine-3-carboxylic acid;

1-(2-Amino-2-methyl-propyl)-6-[5,6-difluoro-8-(methylamino)-4-morpholino-9H-pyrido[2,3-b]indol-3-yl]-4-oxo-1,8-naphthyridine-3-carboxylic acid;

6-[5,6-Difluoro-8-(methylamino)-4-morpholino-9H-pyrido[2,3-b]indol-3-yl]-4-oxo-1-(tetrahydrofuran-2-ylmethyl)-1,8-naphthyridine-3-carboxylic acid;

6-[5,6-Difluoro-4-(4-methoxy-1-piperidyl)-8-(methylamino)-9H-pyrido[2,3-b]indol-3-yl]-1-methyl-4-oxo-1,8-naphthyridine-3-carboxylic acid;

6-[5,6-Difluoro-4-[2-methoxyethyl(methyl)amino]-8-(methylamino)-9H-pyrido[2,3-b]indol-3-yl]-1-(morpholin-3-ylmethyl)-4-oxo-1,8-naphthyridine-3-carboxylic acid;

6-[5,6-Difluoro-8-(methylamino)-4-morpholino-9H-pyrido[2,3-b]indol-3-yl]-1-(morpholin-2-ylmethyl)-4-oxo-1,8-naphthyridine-3-carboxylic acid;

6-[5,6-Difluoro-4-(4-hydroxy-1-piperidyl)-8-(methylamino)-9H-pyrido[2,3-b]indol-3-yl]-1-methyl-4-oxo-1,8-naphthyridine-3-carboxylic acid;

6-[6-Fluoro-8-(methylamino)-4-morpholino-9H-pyrido[2,3-b]indol-3-yl]-1-[2-hydroxy-1-(hydroxymethyl)-1-methyl-ethyl]-4-oxo-1,8-naphthyridine-3-carboxylic acid;

6-[6-Fluoro-8-(methylamino)-4-morpholino-9H-pyrido[2,3-b]indol-3-yl]-1-(2-hydroxy-1-methyl-ethyl)-4-oxo-1,8-naphthyridine-3-carboxylic acid;

6-[6-Fluoro-8-(methylamino)-4-pyrrolidin-1-yl-9H-pyrido[2,3-b]indol-3-yl]-1-methyl-4-oxo-1,8-naphthyridine-3-carboxylic acid;

6-[6-Fluoro-4-(3-hydroxypyrrolidin-1-yl)-8-(methylamino)-9H-pyrido[2,3-b]indol-3-yl]-1-methyl-4-oxo-1,8-naphthyridine-3-carboxylic acid;

6-[6-Fluoro-8-(methylamino)-4-morpholino-9H-pyrido[2,3-b]indol-3-yl]-1-methyl-4-oxo-1,8-naphthyridine-3-carboxylic acid;

6-[6-Fluoro-8-(methylamino)-4-[(2R)-2-methylmorpholin-4-yl]-9H-pyrido[2,3-b]indol-3-yl]-1-methyl-4-oxo-1,8-naphthyridine-3-carboxylic acid;

6-[6-Fluoro-8-(methylamino)-4-[(2S)-2-methylmorpholin-4-yl]-9H-pyrido[2,3-b]indol-3-yl]-1-methyl-4-oxo-1,8-naphthyridine-3-carboxylic acid;

6-[5,6-Difluoro-8-(methylamino)-4-morpholino-9H-pyrido[2,3-b]indol-3-yl]-1-(2-hydroxy-1-methyl-ethyl)-4-oxo-1,8-naphthyridine-3-carboxylic acid;

6-[6-Fluoro-8-(methylamino)-4-morpholino-9H-pyrido[2,3-b]indol-3-yl]-1-(methylamino)-4-oxo-1,8-naphthyridine-3-carboxylic acid;

6-[6-Fluoro-8-(methylamino)-4-morpholino-9H-pyrido[2,3-b]indol-3-yl]-1-(2-hydroxypropyl)-4-oxo-1,8-naphthyridine-3-carboxylic acid;

6-[6-Fluoro-4-[3-(hydroxymethyl)pyrrolidin-1-yl]-8-(methylamino)-9H-pyrido[2,3-b]indol-3-yl]-1-methyl-4-oxo-1,8-naphthyridine-3-carboxylic acid;

6-[4-(Dimethylamino)-6,7-difluoro-8-(methylamino)-9H-pyrido[2,3-b]indol-3-yl]-4-oxo-1-pyrrolidin-3-yl-1,8-naphthyridine-3-carboxylic acid;

6-[6-Fluoro-8-(methylamino)-4-(1-piperidyl)-9H-pyrido[2,3-b]indol-3-yl]-1-methyl-4-oxo-1,8-naphthyridine-3-carboxylic acid;

1-(2-Amino-3-methyl-butyl)-6-[5,6-difluoro-8-(methylamino)-4-morpholino-9H-pyrido[2,3-b]indol-3-yl]-4-oxo-1,8-naphthyridine-3-carboxylic acid;

6-[6-Fluoro-8-(methylamino)-4-morpholino-9H-pyrido[2,3-b]indol-3-yl]-4-oxo-1-(pyrazin-2-ylmethyl)-1,8-naphthyridine-3-carboxylic acid;

6-[6-Fluoro-4-(3-hydroxy-3-methyl-pyrrolidin-1-yl)-8-(methylamino)-9H-pyrido[2,3-b]indol-3-yl]-1-methyl-4-oxo-1,8-naphthyridine-3-carboxylic acid;

6-[6-Fluoro-8-(methylamino)-4-(1,4-oxazepan-4-yl)-9H-pyrido[2,3-b]indol-3-yl]-1-methyl-4-oxo-1,8-naphthyridine-3-carboxylic acid;

6-[4-[2-[(Dimethylamino)methyl]morpholin-4-yl]-5,6-difluoro-8-(methylamino)-9H-pyrido[2,3-b]indol-3-yl]-1-methyl-4-oxo-1,8-naphthyridine-3-carboxylic acid;

6-[4-(1,3,3a,4,6,6a-Hexahydrofuro[3,4-c]pyrrol-5-yl)-6-fluoro-8-(methylamino)-9H-pyrido[2,3-b]indol-3-yl]-1-methyl-4-oxo-1,8-naphthyridine-3-carboxylic acid;

6-[7-Chloro-6-fluoro-8-(methylamino)-4-morpholino-9H-pyrido[2,3-b]indol-3-yl]-1-methyl-4-oxo-1,8-naphthyridine-3-carboxylic acid;

6-[5,6-Difluoro-8-(methylamino)-4-pyrrolidin-1-yl-9H-pyrido[2,3-b]indol-3-yl]-4-oxo-1-pyrrolidin-3-yl-1,8-naphthyridine-3-carboxylic acid;

6-[6-Fluoro-8-(methylamino)-4-thiomorpholino-9H-pyrido[2,3-b]indol-3-yl]-1-methyl-4-oxo-1,8-naphthyridine-3-carboxylic acid;

6-[6-Fluoro-4-[3-(2-hydroxyethyl)pyrrolidin-1-yl]-8-(methylamino)-9H-pyrido[2,3-b]indol-3-yl]-1-methyl-4-oxo-1,8-naphthyridine-3-carboxylic acid;

6-[7-Chloro-4-(dimethylamino)-6-fluoro-8-(methylamino)-9H-pyrido[2,3-b]indol-3-yl]-4-oxo-1-pyrrolidin-3-yl-1,8-naphthyridine-3-carboxylic acid;

1-[2-(Dimethylamino)-2-methyl-propyl]-6-[6-fluoro-8-(methylamino)-4-morpholino-9H-pyrido[2,3-b]indol-3-yl]-4-oxo-1,8-naphthyridine-3-carboxylic acid;

1-[2-(Dimethylamino)-1-methyl-ethyl]-6-[6-fluoro-8-(methylamino)-4-morpholino-9H-pyrido[2,3-b]indol-3-yl]-4-oxo-1,8-naphthyridine-3-carboxylic acid;

6-[6-Fluoro-8-(methylamino)-4-morpholino-9H-pyrido[2,3-b]indol-3-yl]-1-morpholino-4-oxo-1,8-naphthyridine-3-carboxylic acid;

6-[4-(Dimethylamino)-5,6-difluoro-8-(methylamino)-9H-pyrido[2,3-b]indol-3-yl]-1-(methylamino)-4-oxo-1,8-naphthyridine-3-carboxylic acid;

1-[2-(Diethylamino)ethyl]-6-[5,6-difluoro-8-(methylamino)-4-morpholino-9H-pyrido[2,3-b]indol-3-yl]-4-oxo-1,8-naphthyridine-3-carboxylic acid;

6-[5,6-Difluoro-8-(methylamino)-4-morpholino-9H-pyrido[2,3-b]indol-3-yl]-1-[2-(dimethylamino)-2-phenyl-ethyl]-4-oxo-1,8-naphthyridine-3-carboxylic acid;

6-[4-[3-(Dimethylamino)pyrrolidin-1-yl]-6-fluoro-8-(methylamino)-9H-pyrido[2,3-b]indol-3-yl]-1-methyl-4-oxo-1,8-naphthyridine-3-carboxylic acid;

6-[6,7-Difluoro-8-(methylamino)-4-pyrrolidin-1-yl-9H-pyrido[2,3-b]indol-3-yl]-4-oxo-1-pyrrolidin-3-yl-1,8-naphthyridine-3-carboxylic acid;

6-[5,6-Difluoro-4-[(2 S)-2-(hydroxymethyl)pyrrolidin-1-yl]-8-(methylamino)-9H-pyrido[2,3-b]indol-3-yl]-1-methyl-4-oxo-1,8-naphthyridine-3-carboxylic acid;

6-[4-[2-[(Dimethylamino)methyl]morpholin-4-yl]-6,7-difluoro-8-(methylamino)-9H-pyrido[2,3-b]indol-3-yl]-1-methyl-4-oxo-1,8-naphthyridine-3-carboxylic acid;

6-[5,6-Difluoro-8-(methylamino)-4-morpholino-9H-pyrido[2,3-b]indol-3-yl]-1-[2-(dimethylamino)butyl]-4-oxo-1,8-naphthyridine-3-carboxylic acid;

6-[4-[3-[(Dimethylamino)methyl]-1-piperidyl]-5,6-difluoro-8-(methylamino)-9H-pyrido[2,3-b]indol-3-yl]-1-methyl-4-oxo-1,8-naphthyridine-3-carboxylic acid;

6-[6-Fluoro-8-(methylamino)-4-morpholino-9H-pyrido[2,3-b]indol-3-yl]-1-(1-methylpyrrolidin-3-yl)-4-oxo-1,8-naphthyridine-3-carboxylic acid;

6-[5,6-Difluoro-4-[trans-3-fluoro-4-hydroxy-pyrrolidin-1-yl]-8-(methylamino)-9H-pyrido[2,3-b]indol-3-yl]-1-methyl-4-oxo-1,8-naphthyridine-3-carboxylic acid;

6-[5,6-difluoro-4-[trans-hydroxy-4-methyl-pyrrolidin-1-yl]-8-(methylamino)-9H-pyrido[2,3-b]indol-3-yl]-1-methyl-4-oxo-1,8-naphthyridine-3-carboxylic acid;

6-[5,6-Difluoro-4-[3-(hydroxymethyl)-3-methyl-pyrrolidin-1-yl]-8-(methylamino)-9H-pyrido[2,3-b]indol-3-yl]-1-methyl-4-oxo-1,8-naphthyridine-3-carboxylic acid;

6-[4-[cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-[cis-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-(methylamino)-4-oxo-1,8-naphthyridine-3-carboxylic acid;

6-[4-(dimethylamino)-5,6-difluoro-8-(methylamino)-9H-pyrido[2,3-b]indol-3-yl]-1-(oxazol-5-ylmethyl)-4-oxo-1,8-naphthyridine-3-carboxylic acid;

6-[4-[cis-3-[(dimethylamino)methyl]-2,3,3a,4,6,6a-hexahydrofuro[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid;

(S)-6-(5,6-difluoro-8-(methylamino)-4-(pyrrolidin-1-yl)-9H-pyrido[2,3-b]indol-3-yl)-4-oxo-1-(pyrrolidin-3-yl)-1,4-dihydro-1,8-naphthyridine-3-carboxylic acid;

6-(4-(6-((dimethylamino)methyl)-1,4-oxazepan-4-yl)-6-fluoro-8-(methylamino)-9H-pyrido[2,3-b]indol-3-yl)-1-methyl-4-oxo-1,4-dihydro-1,8-naphthyridine-3-carboxylic acid;

6-(4-(dimethylamino)-5,6-difluoro-8-(methylamino)-9H-pyrido[2,3-b]indol-3-yl)-4-oxo-1-((tetrahydro-2H-pyran-4-yl)amino)-1,4-dihydro-1,8-naphthyridine-3-carboxylic acid;

6-(4-(3-((dimethylamino)methyl)-3-fluoropyrrolidin-1-yl)-6-fluoro-8-(methylamino)-9H-pyrido[2,3-b]indol-3-yl)-1-(methylamino)-4-oxo-1,4-dihydro-1,8-naphthyridine-3-carboxylic acid;

6-(4-(3-((dimethylamino)methyl)-3-fluoropyrrolidin-1-yl)-5,6-difluoro-8-(methylamino)-9H-pyrido[2,3-b]indol-3-yl)-1-(methylamino)-4-oxo-1,4-dihydro-1,8-naphthyridine-3-carboxylic acid;

6-(4-(3-((dimethylamino)methyl)piperidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

1-cyclopropyl-6-[4-(dimethylamino)-5,6-difluoro-8-(methylamino)-9H-pyrido[2,3-b]indol-3-yl]-4-oxo-1,8-naphthyridine-3-carboxylic acid;

6-[4-[(cis-5-(2-methoxyethyl)-2,3,3a,4,6,6a-hexahydropyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-(5,6-difluoro-8-(methylamino)-4-thiomorpholino-9H-pyrido[2,3-b]indol-3-yl)-1-methyl-4-oxo-1,4-dihydro-1,8-naphthyridine-3-carboxylic acid;

6-(5,6-difluoro-8-(methylamino)-4-thiomorpholino-9H-pyrido[2,3-b]indol-3-yl)-4-oxo-1-(pyrrolidin-3-yl)-1,4-dihydro-1,8-naphthyridine-3-carboxylic acid;

6-(4-(3-((cyclopropyl(methyl)amino)methyl)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-(4-(3-((dimethylamino)methyl)-3-hydroxypyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-(3-((dimethylamino)methyl)-3-methylpyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-(3-((dimethylamino)methyl)-3-methylpyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-[4-[cis-5-methyl-2,3,3a,4,6,6a-hexahydropyrrolo[2,3-c]pyrrol-1-yl]-6,'7-difluoro-8-(methylamino)-9H-pyrido[2,3-b]indol-3-yl]-1-methyl-4-oxo-1,8-naphthyridine-3-carboxylic acid;

6-(4-(3-(dimethylamino)pyrrolidin-1-yl)-8-(ethylamino)-5,6-difluoro-9H-pyrido[2,3-b]indol-3-yl)-1-methyl-4-oxo-1,4-dihydro-1,8-naphthyridine-3-carboxylic acid;

6-(5,7-difluoro-8-(methylamino)-4-morpholino-9H-pyrido[2,3-b]indol-3-yl)-1-methyl-4-oxo-1,4-dihydro-1,8-naphthyridine-3-carboxylic acid;

6-(4-(3-((dimethylamino)methyl)pyrrolidin-1-yl)-8-(ethylamino)-5,6-difluoro-9H-pyrido[2,3-b]indol-3-yl)-1-methyl-4-oxo-1,4-dihydro-1,8-naphthyridine-3-carboxylic acid;

6-(4-(dimethylamino)-5,7-difluoro-8-(methylamino)-9H-pyrido[2,3-b]indol-3-yl)-4-oxo-1-(pyrrolidin-3-yl)-1,4-dihydro-1,8-naphthyridine-3-carboxylic acid;

6-(4-(3-((dimethylamino)methyl)-3-fluoropyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-(3-((dimethylamino)methyl)-3-fluoropyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-(6-fluoro-8-(methylamino)-4-(cis-1-methylhexahydro-1H-pyrrolo[3,4-b]pyridin-6(2H)-yl)-9H-pyrido[2,3-b]indol-3-yl)-1-methyl-4-oxo-1,4-dihydro-1,8-naphthyridine-3-carboxylic acid;

6-(6-fluoro-8-(methylamino)-4-(cis-1-methylhexahydro-1H-pyrrolo[3,4-b]pyridin-6(2H)-yl)-9H-pyrido[2,3-b]indol-3-yl)-1-(methylamino)-4-oxo-1,4-dihydro-1,8-naphthyridine-3-carboxylic acid;

6-(6-fluoro-8-(methylamino)-4-(cis-4-methylhexahydropyrrolo[3,4-b][1,4]oxazin-6(2H)-yl)-9H-pyrido[2,3-b]indol-3-yl)-1-methyl-4-oxo-1,4-dihydro-1,8-naphthyridine-3-carboxylic acid;

6-(6-fluoro-8-(methylamino)-4-(cis-4-methylhexahydropyrrolo[3,4-b][1,4]oxazin-6(2H)-yl)-9H-pyrido[2,3-b]indol-3-yl)-1-(methylamino)-4-oxo-1,4-dihydro-1,8-naphthyridine-3-carboxylic acid;

6-(4-(3-(cyclopropyl amino)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-(4-(3-(cyclopropyl amino)pyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-(3-(cyclopropyl(methyl)amino)pyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(5-chloro-4-(dimethylamino)-6-fluoro-8-(methylamino)-9H-pyrido[2,3-b]indol-3-yl)-1-methyl-4-oxo-1,4-dihydro-1,8-naphthyridine-3-carboxylic acid;

6-(4-(3-(cyclopropyl(methyl)amino)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

1-(cyclopropyl amino)-6-(4-(dimethylamino)-5,6-difluoro-8-(methylamino)-9H-pyrido[2,3-b]indol-3-yl)-4-oxo-1,4-dihydro-1,8-naphthyridine-3-carboxylic acid;

6-[4-(3a-fluoro-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-(3a-fluoro-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-(methylamino)-4-oxo-1,8-naphthyridine-3-carboxylic acid;

6-(5-chloro-4-(3-((dimethylamino)methyl)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-[4-[cis-5-methyl-2,3,3a,4,6,6a-hexahydropyrrolo[2,3-c]pyrrol-1-yl]-8-(ethylamino)-6-(trifluoromethyl)-9H-pyrido[2,3-b]indol-3-yl]-1-(methylamino)-4-oxo-1,8-naphthyridine-3-carboxylic acid;

6-[4-[3a-(fluoromethyl)-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-[3a-(fluoromethyl)-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-(methylamino)-4-oxo-1,8-naphthyridine-3-carboxylic acid;

6-(4-(3,3-difluoropyrrolidin-1-yl)-6-fluoro-8-(methylamino)-9H-pyrido[2,3-b]indol-3-yl)-1-ethyl-4-oxo-1,4-dihydro-1,8-naphthyridine-3-carboxylic acid;

6-(8-(ethylamino)-6-fluoro-4-(3-(trifluoromethyl)-1H-pyrazol-1-yl)-9H-pyrido[2,3-b]indol-3-yl)-1-methyl-4-oxo-1,4-dihydro-1,8-naphthyridine-3-carboxylic acid;

6-(4-(6-oxa-3-azabicyclo[3.1.1]heptan-3-yl)-5,6-difluoro-8-(methylamino)-9H-pyrido[2,3-b]indol-3-yl)-1-ethyl-4-oxo-1,4-dihydro-1,8-naphthyridine-3-carboxylic acid;

6-(5,6-difluoro-4-(3-hydroxy-3-(trifluoromethyl)pyrrolidin-1-yl)-8-(methylamino)-9H-pyrido[2,3-b]indol-3-yl)-1-methyl-4-oxo-1,4-dihydro-1,8-naphthyridine-3-carboxylic acid;

6-(4-(dimethylamino)-5,6-difluoro-8-(methylamino)-9H-pyrido[2,3-b]indol-3-yl)-1-(1-methylpyrrolidin-3-yl)-4-oxo-1,4-dihydro-1,8-naphthyridine-3-carboxylic acid;

6-(5,6-difluoro-4-((2-methoxyethyl)(methyl)amino)-8-(methylamino)-9H-pyrido[2,3-b]indol-3-yl)-1-methyl-4-oxo-1,4-dihydro-1,8-naphthyridine-3-carboxylic acid;

6-(6-fluoro-8-(methylamino)-4-(3-methylpyrrolidin-1-yl)-9H-pyrido[2,3-b]indol-3-yl)-1-methyl-4-oxo-1,4-dihydro-1,8-naphthyridine-3-carboxylic acid;

6-(5,6-difluoro-4-(hexahydropyrazino[2,1-c][1,4]oxazin-8(1H)-yl)-8-(methylamino)-9H-pyrido[2,3-b]indol-3-yl)-1-methyl-4-oxo-1,4-dihydro-1,8-naphthyridine-3-carboxylic acid;

6-(4-(3-((dimethylamino)methyl)pyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-(3-((cyclopropylamino)methyl)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-(4-(3-((cyclopropylamino)methyl)pyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(6-chloro-4-(2-((dimethylamino)methyl)morpholino)-8-(methylamino)-9H-pyrido[2,3-b]indol-3-yl)-1-methyl-4-oxo-1,4-dihydro-1,8-naphthyridine-3-carboxylic acid;

6-(6-chloro-4-(3-(dimethylamino)pyrrolidin-1-yl)-8-(methylamino)-9H-pyrido[2,3-b]indol-3-yl)-1-methyl-4-oxo-1,4-dihydro-1,8-naphthyridine-3-carboxylic acid;

6-(4-(dimethylamino)-8-(ethylamino)-5,6-difluoro-9H-pyrido[2,3-b]indol-3-yl)-4-oxo-1-(pyrrolidin-3-yl)-1,4-dihydro-1,8-naphthyridine-3-carboxylic acid;

6-(6-fluoro-4-(3-(((2-methoxyethyl)(methyl)amino)methyl)pyrrolidin-1-yl)-8-(methylamino)-9H-pyrido[2,3-b]indol-3-yl)-1-methyl-4-oxo-1,4-dihydro-1,8-naphthyridine-3-carboxylic acid;

6-(5,6-difluoro-4-(3-(((2-methoxyethyl)(methyl)amino)methyl)pyrrolidin-1-yl)-8-(methylamino)-9H-pyrido[2,3-b]indol-3-yl)-1-methyl-4-oxo-1,4-dihydro-1,8-naphthyridine-3-carboxylic acid;

6-(4-(4-((dimethylamino)methyl)-3,3-difluoropyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-(4-((dimethylamino)methyl)-3,3-difluoropyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-[4-(dimethylamino)-5,6-difluoro-8-(methylamino)-9H-pyrido[2,3-b]indol-3-yl]-1-(3-hydroxy-1-methyl-propyl)-4-oxo-1,8-naphthyridine-3-carboxylic acid;

6-(4-(dimethylamino)-5,6-difluoro-8-(methylamino)-9H-pyrido[2,3-b]indol-3-yl)-1-((1-hydroxycyclopropyl)methyl)-4-oxo-1,4-dihydro-1,8-naphthyridine-3-carboxylic acid;

6-(4-(dimethylamino)-5,6-difluoro-8-(methylamino)-9H-pyrido[2,3-b]indol-3-yl)-1-(2-morpholinoethyl)-4-oxo-1,4-dihydro-1,8-naphthyridine-3-carboxylic acid;

6-(4-(dimethylamino)-5,6-difluoro-8-(methylamino)-9H-pyrido[2,3-b]indol-3-yl)-4-oxo-1-(2-(3-oxopiperazin-1-yl)ethyl)-1,4-dihydro-1,8-naphthyridine-3-carboxylic acid;

6-(4-(2-((diethylamino)methyl)morpholino)-5,6-difluoro-8-(methylamino)-9H-pyrido[2,3-b]indol-3-yl)-1-methyl-4-oxo-1,4-dihydro-1,8-naphthyridine-3-carboxylic acid;

(S)-6-(4-(dimethylamino)-5,6-difluoro-8-(methylamino)-9H-pyrido[2,3-b]indol-3-yl)-4-oxo-1-(pyrrolidin-3-yl)-1,4-dihydro-1,8-naphthyridine-3-carboxylic acid;

(R)-6-(5,6-difluoro-4-(3-hydroxypyrrolidin-1-yl)-8-(methylamino)-9H-pyrido[2,3-b]indol-3-yl)-1-methyl-4-oxo-1,4-dihydro-1,8-naphthyridine-3-carboxylic acid;

6-(4-trans-(3-(dimethylamino)-4-methylpyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-[4-[(2S)-2-[(dimethylamino)methyl]pyrrolidin-1-yl]-6-fluoro-8-(methylamino)-9H-pyrido[2,3-b]indol-3-yl]-4-oxo-1-(2,2,2-trifluoroethylamino)-1,8-naphthyridine-3-carboxylic acid;

6-[4-[(2 S)-2-[(dimethylamino)methyl]pyrrolidin-1-yl]-6-fluoro-8-(methylamino)-9H-pyrido[2,3-b]indol-3-yl]-4-oxo-1-(tetrahydropyran-4-ylamino)-1,8-naphthyridine-3-carboxylic acid;

(R)-6-(4-(dimethylamino)-5,6-difluoro-8-(methylamino)-9H-pyrido[2,3-b]indol-3-yl)-4-oxo-1-(pyrrolidin-3-yl)-1,4-dihydro-1,8-naphthyridine-3-carboxylic acid;

(R)-6-(5,6-difluoro-8-(methylamino)-4-(pyrrolidin-1-yl)-9H-pyrido[2,3-b]indol-3-yl)-4-oxo-1-(pyrrolidin-3-yl)-1,4-dihydro-1,8-naphthyridine-3-carboxylic acid;

(S)-6-(4-(6-((dimethylamino)methyl)-5-azaspiro[2.4]heptan-5-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-((3 S,4S)-3-(dimethylamino)-4-methoxypyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-((3 S,4 S)-3-(dimethylamino)-4-fluoropyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-((3R,4S)-3-(dimethylamino)-4-methylpyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

(S)-6-(4-(2-((dimethylamino)methyl)pyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

(S)-6-(5,6-difluoro-4-(3-hydroxypyrrolidin-1-yl)-8-(methylamino)-9H-pyrido[2,3-b]indol-3-yl)-1-methyl-4-oxo-1,4-dihydro-1,8-naphthyridine-3-carboxylic acid;

(S)-6-(5,6-difluoro-4-(3-(hydroxymethyl)pyrrolidin-1-yl)-8-(methylamino)-9H-pyrido[2,3-b]indol-3-yl)-1-methyl-4-oxo-1,4-dihydro-1,8-naphthyridine-3-carboxylic acid;

(R)-6-(5,6-difluoro-4-(3-(hydroxymethyl)pyrrolidin-1-yl)-8-(methylamino)-9H-pyrido[2,3-b]indol-3-yl)-1-methyl-4-oxo-1,4-dihydro-1,8-naphthyridine-3-carboxylic acid;

(S)-6-(4-(2-((dimethylamino)methyl)pyrrolidin-1-yl)-8-(ethylamino)-5,6-difluoro-9H-pyrido[2,3-b]indol-3-yl)-1-methyl-4-oxo-1,4-dihydro-1,8-naphthyridine-3-carboxylic acid;

6-(4-trans-(3-(dimethylamino)-4-methylpyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-trans-(3-(dimethylamino)-4-fluoropyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-trans-(3-(dimethylamino)-4-fluoropyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

6-(4-trans-(3-(dimethylamino)-4-methoxypyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-trans-(3-(dimethylamino)-4-methoxypyrrolidin-1-yl)-6-fluoro-8-(methylamino)-9H-pyrido[2,3-b]indol-3-yl)-1-methyl-4-oxo-1,4-dihydro-1,8-naphthyridine-3-carboxylic acid;

(S)-6-(4-(2-((dimethylamino)methyl)pyrrolidin-1-yl)-6,7-difluoro-8-(methylamino)-9H-pyrido[2,3-b]indol-3-yl)-1-methyl-4-oxo-1,4-dihydro-1,8-naphthyridine-3-carboxylic acid;

(S)-6-(5,6-difluoro-8-(methylamino)-4-(3-(pyrrolidin-1-ylmethyl)pyrrolidin-1-yl)-9H-pyrido[2,3-b]indol-3-yl)-1-methyl-4-oxo-1,4-dihydro-1,8-naphthyridine-3-carboxylic acid;

(S)-6-(5,6-difluoro-8-(methylamino)-4-(3-(morpholinomethyl)pyrrolidin-1-yl)-9H-pyrido[2,3-b]indol-3-yl)-1-methyl-4-oxo-1,4-dihydro-1,8-naphthyridine-3-carboxylic acid;

6-(4-((3 aR,4R,7aS)-4-(dimethylamino)hexahydro-1H-isoindol-2(3H)-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-[8-(ethylamino)-6-fluoro-4-morpholino-9H-pyrido[2,3-b]indol-3-yl]-4-oxo-1-pyrrolidin-3-yl-1,8-naphthyridine-3-carboxylic acid;

6-[5,6-difluoro-8-(methylamino)-4-morpholino-9H-pyrido[2,3-b]indol-3-yl]-1-(2,3-dihydroxypropyl)-4-oxo-1,8-naphthyridine-3-carboxylic acid;

6-[4-(dimethylamino)-5,6-difluoro-8-(methylamino)-9H-pyrido[2,3-b]indol-3-yl]-1-[2-(dimethylamino)-2-methyl-propyl]-4-oxo-1,8-naphthyridine-3-carboxylic acid;

6-[4-(dimethylamino)-5,6-difluoro-8-(methylamino)-9H-pyrido[2,3-b]indol-3-yl]-1-morpholino-4-oxo-1,8-naphthyridine-3-carboxylic acid;

6-[5,6-difluoro-8-(methylamino)-4-morpholino-9H-pyrido[2,3-b]indol-3-yl]-1-(dimethylamino)-4-oxo-1,8-naphthyridine-3-carboxylic acid;

6-[4-[2-[(dimethylamino)methyl]morpholin-4-yl]-5,6-difluoro-8-(methylamino)-9H-pyrido[2,3-b]indol-3-yl]-1-(methylamino)-4-oxo-1,8-naphthyridine-3-carboxylic acid;

6-[4-[4-(dimethylamino)-1-piperidyl]-5,6-difluoro-8-(methylamino)-9H-pyrido[2,3-b]indol-3-yl]-1-methyl-4-oxo-1,8-naphthyridine-3-carboxylic acid;

6-[4-[4-[(dimethylamino)methyl]-1-piperidyl]-5,6-difluoro-8-(methylamino)-9H-pyrido[2,3-b]indol-3-yl]-1-methyl-4-oxo-1,8-naphthyridine-3-carboxylic acid;

6-[6-fluoro-8-(methylamino)-4-(4-methylpiperazin-1-yl)-9H-pyrido[2,3-b]indol-3-yl]-1-methyl-4-oxo-1,8-naphthyridine-3-carboxylic acid;

6-[6-fluoro-8-(methylamino)-4-(4-methyl-1,4-diazepan-1-yl)-9H-pyrido[2,3-b]indol-3-yl]-1-methyl-4-oxo-1,8-naphthyridine-3-carboxylic acid;

6-[4-[3-[(dimethylamino)methyl]-1-piperidyl]-5,6-difluoro-8-(methylamino)-9H-pyrido[2,3-b]indol-3-yl]-1-(methylamino)-4-oxo-1,8-naphthyridine-3-carboxylic acid;

6-[6-fluoro-8-(methylamino)-4-[cis-5-methyl-2,3,3a,4,6,6a-hexahydropyrrolo[2,3-c]pyrrol-1-yl]-9H-pyrido[2,3-b]indol-3-yl]-1-methyl-4-oxo-1,8-naphthyridine-3-carboxylic acid;

6-[6-fluoro-4-(cis-1-methyl-3,3a,4,6,7,7a-hexahydro-2H-pyrrolo[3,2-c]pyridin-5-yl)-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-[cis-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylic acid;

6-[5,6-difluoro-8-(methylamino)-4-(9-methyl-2,9-diazaspiro[4.5]decan-2-yl)-9H-pyrido[2,3-b]indol-3-yl]-1-methyl-4-oxo-1,8-naphthyridine-3-carboxylic acid;

6-[4-[3-(dimethylamino)-1-piperidyl]-5,6-difluoro-8-(methylamino)-9H-pyrido[2,3-b]indol-3-yl]-1-(methylamino)-4-oxo-1,8-naphthyridine-3-carboxylic acid;

6-[5,6-difluoro-8-(methylamino)-4-[cis-1-methyl-2,3,3a,4,6,6a-hexahydropyrrolo[2,3-c]pyrrol-5-yl]-9H-pyrido[2,3-b]indol-3-yl]-1-methyl-4-oxo-1,8-naphthyridine-3-carboxylic acid;

6-[5,6-difluoro-8-(methylamino)-4-[cis-1-methyl-2,3,3a,4,6,6a-hexahydropyrrolo[2,3-c]pyrrol-5-yl]-9H-pyrido[2,3-b]indol-3-yl]-1-(methylamino)-4-oxo-1,8-naphthyridine-3-carboxylic acid;

6-[5,6-difluoro-4-[9-(2-hydroxyethyl)-2,9-diazaspiro[4.5]decan-2-yl]-8-(methylamino)-9H-pyrido[2,3-b]indol-3-yl]-1-methyl-4-oxo-1,8-naphthyridine-3-carboxylic acid;

6-[5,6-difluoro-4-[9-(2-methoxyethyl)-2,9-diazaspiro[4.5]decan-2-yl]-8-(methylamino)-9H-pyrido[2,3-b]indol-3-yl]-1-methyl-4-oxo-1,8-naphthyridine-3-carboxylic acid;

6-[5,6-difluoro-4-(cis-1-methyl-3,3a,4,5,7,7a-hexahydro-2H-pyrrolo[2,3-c]pyridin-6-yl)-8-(methylamino)-9H-pyrido[2,3-b]indol-3-yl]-1-methyl-4-oxo-1,8-naphthyridine-3-carboxylic acid;

6-[5,6-difluoro-4-[3-[2-methoxyethyl(methyl)amino]-1-piperidyl]-8-(methylamino)-9H-pyrido[2,3-b]indol-3-yl]-1-methyl-4-oxo-1,8-naphthyridine-3-carboxylic acid;

6-[5,6-difluoro-4-[3-[2-methoxyethyl(methyl)amino]pyrrolidin-1-yl]-8-(methylamino)-9H-pyrido[2,3-b]indol-3-yl]-1-methyl-4-oxo-1,8-naphthyridine-3-carboxylic acid;

6-[5,6-difluoro-4-(cis-1-methyl-3,3a,4,5,7,7a-hexahydro-2H-pyrrolo[2,3-c]pyridin-6-yl)-8-(methylamino)-9H-pyrido[2,3-b]indol-3-yl]-1-(methylamino)-4-oxo-1,8-naphthyridine-3-carboxylic acid;

6-[5,6-difluoro-4-[3-[2-hydroxyethyl(methyl)amino]pyrrolidin-1-yl]-8-(methylamino)-9H-pyrido[2,3-b]indol-3-yl]-1-methyl-4-oxo-1,8-naphthyridine-3-carboxylic acid;

6-[5,6-difluoro-4-[3-[2-hydroxyethyl(methyl)amino]-1-piperidyl]-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-(9-methyl-6-oxa-2,9-diazaspiro[4.5]decan-2-yl)-9H-pyrido[2,3-b]indol-3-yl]-1-methyl-4-oxo-1,8-naphthyridine-3-carboxylic acid;

6-[5,6-difluoro-8-(methylamino)-4-(4-pyrrolidin-1-yl-1-piperidyl)-9H-pyrido[2,3-b]indol-3-yl]-1-methyl-4-oxo-1,8-naphthyridine-3-carboxylic acid;

6-[4-(4-cyclopropylpiperazin-1-yl)-5,6-difluoro-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-[cis-5-(2-hydroxyethyl)-2,3,3a,4,6,6a-hexahydropyrrolo[2,3-c]pyrrol-1-yl]-9H-pyrido[2,3-b]indol-3-yl]-1-methyl-4-oxo-1,8-naphthyridine-3-carboxylic acid;

6-[5,6-difluoro-8-(methylamino)-4-[cis-5-methyl-2,3,3a,4,6,6a-hexahydropyrrolo[2,3-c]pyrrol-1-yl]-9H-pyrido[2,3-b]indol-3-yl]-1-(2-hydroxy-1-methyl-ethyl)-4-oxo-1,8-naphthyridine-3-carboxylic acid;

6-[4-[7-(dimethylamino)-5-azaspiro[2.4]heptan-5-yl]-5,6-difluoro-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-pyrrolidin-1-yl-9H-pyrido[2,3-b]indol-3-yl]-1-methyl-4-oxo-1,8-naphthyridine-3-carboxylic acid;

6-[6-fluoro-8-(methylamino)-4-[cis-1-methyl-2,3,3a,4,6,6a-hexahydropyrrolo[2,3-c]pyrrol-5-yl]-9H-pyrido[2,3-b]indol-3-yl]-1-methyl-4-oxo-1,8-naphthyridine-3-carboxylic acid;

6-[6-fluoro-8-(methylamino)-4-[cis-1-methyl-2,3,3a,4,6,6a-hexahydropyrrolo[2,3-c]pyrrol-5-yl]-9H-pyrido[2,3-b]indol-3-yl]-1-(methylamino)-4-oxo-1,8-naphthyridine-3-carboxylic acid;

6-[6-fluoro-4-(cis-1-methyl-3,3a,4,5,7,7a-hexahydro-2H-pyrrolo[2,3-c]pyridin-6-yl)-8-(methylamino)-9H-pyrido[2,3-b]indol-3-yl]-1-methyl-4-oxo-1,8-naphthyridine-3-carboxylic acid;

6-[6-fluoro-4-(cis-1-methyl-3,3a,4,5,7,7a-hexahydro-2H-pyrrolo[2,3-c]pyridin-6-yl)-8-(methylamino)-9H-pyrido[2,3-b]indol-3-yl]-1-(methylamino)-4-oxo-1,8-naphthyridine-3-carboxylic acid;

6-[5,6-difluoro-8-(methylamino)-4-(cis-8-methyl-3,8-diazabicyclo[4.2.0]octan-3-yl)-9H-pyrido[2,3-b]indol-3-yl]-1-methyl-4-oxo-1,8-naphthyridine-3-carboxylic acid;

6-[5,6-difluoro-8-(methylamino)-4-(cis-8-methyl-3,8-diazabicyclo[4.2.0]octan-3-yl)-9H-pyrido[2,3-b]indol-3-yl]-1-(methylamino)-4-oxo-1,8-naphthyridine-3-carboxylic acid;

6-[4-[3-(dimethylamino)-1-piperidyl]-5,6-difluoro-8-(methylamino)-9H-pyrido[2,3-b]indol-3-yl]-1-methyl-4-oxo-1,8-naphthyridine-3-carboxylic acid;

6-[6-fluoro-8-(methylamino)-4-morpholino-9H-pyrido[2,3-b]indol-3-yl]-1-[(1 S)-2-hydroxy-1-methyl-ethyl]-4-oxo-1,8-naphthyridine-3-carboxylic acid;

6-[4-[(2S)-2-[(dimethylamino)methyl]pyrrolidin-1-yl]-5,6-difluoro-8-(methylamino)-9H-pyrido[2,3-b]indol-3-yl]-1-(methylamino)-4-oxo-1,8-naphthyridine-3-carboxylic acid;

6-[4-cis-(4R)-[(dimethylamino)methyl]-3,3a,4,5,6,6a-hexahydro-1H-cyclopenta[c]pyrrol-2-yl]-5,6-difluoro-8-(methylamino)-9H-pyrido[2,3-b]indol-3-yl]-1-methyl-4-oxo-1,8-naphthyridine-3-carboxylic acid;

6-[4-[(8aS)-3,4,6,7,8,8a-hexahydro-1H-pyrrolo[1,2-a]pyrazin-2-yl]-5,6-difluoro-8-(methylamino)-9H-pyrido[2,3-b]indol-3-yl]-1-methyl-4-oxo-1,8-naphthyridine-3-carboxylic acid;

6-[4-[(8aR)-3,4,6,7,8,8a-hexahydro-1H-pyrrolo[1,2-a]pyrazin-2-yl]-5,6-difluoro-8-(methylamino)-9H-pyrido[2,3-b]indol-3-yl]-1-methyl-4-oxo-1,8-naphthyridine-3-carboxylic acid;

6-[4-cis-(4R)-(dimethylamino)-3,3a,4,5,6,6a-hexahydro-1H-cyclopenta[c]pyrrol-2-yl]-5,6-difluoro-8-(methylamino)-9H-pyrido[2,3-b]indol-3-yl]-1-methyl-4-oxo-1,8-naphthyridine-3-carboxylic acid;

6-[4-[cis-3-(dimethylamino)-4-hydroxy-pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-[cis-3-(dimethylamino)-4-hydroxy-pyrrolidin-1-yl]-5,6-difluoro-8-(methylamino)-9H-pyrido[2,3-b]indol-3-yl]-1-(methylamino)-4-oxo-1,8-naphthyridine-3-carboxylic acid;

6-[5,6-difluoro-4-[2-(2-hydroxyethyl)morpholin-4-yl]-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-(4-methylpiperazin-1-yl)-9H-pyrido[2,3-b]indol-3-yl]-1-methyl-4-oxo-1,8-naphthyridine-3-carboxylic acid;

6-[5,6-difluoro-8-(methylamino)-4-[cis-2-methyl-1,3,3a,4,6,6a-hexahydropyrrolo[3,4-c]pyrrol-5-yl]-9H-pyrido[2,3-b]indol-3-yl]-1-methyl-4-oxo-1,8-naphthyridine-3-carboxylic acid;

6-[5,6-difluoro-8-(methylamino)-4-(2-methyl-2,6-diazaspiro[3.4]octan-6-yl)-9H-pyrido[2,3-b]indol-3-yl]-1-methyl-4-oxo-1,8-naphthyridine-3-carboxylic acid;

6-[5,6-difluoro-8-(methylamino)-4-(7-methyl-2,7-diazaspiro[4.4]nonan-2-yl)-9H-pyrido[2,3-b]indol-3-yl]-1-methyl-4-oxo-1,8-naphthyridine-3-carboxylic acid;

6-[5,6-difluoro-8-(methylamino)-4-(1-methyl-1,8-diazaspiro[4.5]decan-8-yl)-9H-pyrido[2,3-b]indol-3-yl]-1-methyl-4-oxo-1,8-naphthyridine-3-carboxylic acid;

6-[5,6-difluoro-8-(methylamino)-4-(2-methyl-2,8-diazaspiro[4.5]decan-8-yl)-9H-pyrido[2,3-b]indol-3-yl]-1-methyl-4-oxo-1, 8-naphthyridine-3-carboxylic acid;

6-[5,6-difluoro-4-(1-methyl-3,4,4a, 5,7,7a-hexahydro-2H-pyrrolo[3,4-b]pyridin-6-yl)-8-(methylamino)-9H-pyrido[2,3-b]indol-3-yl]-1-methyl-4-oxo-1, 8-naphthyridine-3-carboxylic acid;

6-[4-(4-ethylpiperazin-1-yl)-5, 6-difluoro-8-(methylamino)-9H-pyrido[2,3-b]indol-3-yl]-1-methyl-4-oxo-1, 8-naphthyridine-3-carboxylic acid;

6-[5,6-difluoro-4-(4-isopropylpiperazin-1-yl)-8-(methylamino)-9H-pyrido[2,3-b]indol-3-yl]-1-methyl-4-oxo-1,8-naphthyridine-3-carboxylic acid;

6-[5,6-difluoro-4-(4-methyl-2,3,4a, 5,7,7a-hexahydropyrrolo[3,4-b][1,4]oxazin-6-yl)-8-(methylamino)-9H-pyrido[2,3-b]indol-3-yl]-1-methyl-4-oxo-1, 8-naphthyridine-3-carboxylic acid;

6-[5,6-difluoro-4-(4-methyl-2,3,4a, 5,7,7a-hexahydropyrrolo[3,4-b][1,4]oxazin-6-yl)-8-(methylamino)-9H-pyrido[2,3-b]indol-3-yl]-1-(methylamino)-4-oxo-1, 8-naphthyridine-3-carboxylic acid;

6-[5,6-difluoro-8-(methylamino)-4-(1-methyl-1,7-diazaspiro[3.4]octan-7-yl)-9H-pyrido[2,3-b]indol-3-yl]-1-methyl-4-oxo-1, 8-naphthyridine-3-carboxylic acid;

6-[5,6-difluoro-8-(methylamino)-4-(1-methyl-1,7-diazaspiro[3.4]octan-7-yl)-9H-pyrido[2,3-b]indol-3-yl]-1-(methylamino)-4-oxo-1, 8-naphthyridine-3-carboxylic acid;

6-[5,6-difluoro-8-(methylamino)-4-(1-methyl-1,7-diazaspiro[4.4]nonan-7-yl)-9H-pyrido[2,3-b]indol-3-yl]-1-methyl-4-oxo-1,8-naphthyridine-3-carboxylic acid;

6-[5,6-difluoro-8-(methylamino)-4-(1-methyl-1,7-diazaspiro[4.4]nonan-7-yl)-9H-pyrido[2,3-b]indol-3-yl]-1-(methylamino)-4-oxo-1,8-naphthyridine-3-carboxylic acid;

6-[5,6-difluoro-4-(cis-4-methyl-2,3,4a,5,7,7a-hexahydropyrrolo[3,4-b][1,4]oxazin-6-yl)-8-(methylamino)-9H-pyrido[2,3-b]indol-3-yl]-1-methyl-4-oxo-1,8-naphthyridine-3-carboxylic acid;

6-[5,6-difluoro-4-(cis-4-methyl-2,3,4a,5,7,7a-hexahydropyrrolo[3,4-b][1,4]oxazin-6-yl)-8-(methylamino)-9H-pyrido[2,3-b]indol-3-yl]-1-(methylamino)-4-oxo-1,8-naphthyridine-3-carboxylic acid;

6-[5,6-difluoro-4-(5-methyl-3,3a,4,6,7,7a-hexahydro-2H-pyrrolo[3,2-c]pyridin-1-yl)-8-(methylamino)-9H-pyrido[2,3-b]indol-3-yl]-1-methyl-4-oxo-1,8-naphthyridine-3-carboxylic acid;

6-[5,6-difluoro-4-(5-methyl-3,3a,4,6,7,7a-hexahydro-2H-pyrrolo[3,2-c]pyridin-1-yl)-8-(methylamino)-9H-pyrido[2,3-b]indol-3-yl]-1-(methylamino)-4-oxo-1,8-naphthyridine-3-carboxylic acid;

6-[5,6-difluoro-4-(cis-1-methyl-2,3,3a,5,6,6a-hexahydropyrrolo[3,2-b]pyrrol-4-yl)-8-(methylamino)-9H-pyrido[2,3-b]indol-3-yl]-1-methyl-4-oxo-1,8-naphthyridine-3-carboxylic acid;

6-[5,6-difluoro-4-(4-methyl-3,3a,5,6,7,7a-hexahydro-2H-pyrrolo[3,2-b]pyridin-1-yl)-8-(methylamino)-9H-pyrido[2,3-b]indol-3-yl]-1-methyl-4-oxo-1,8-naphthyridine-3-carboxylic acid;

6-[5,6-difluoro-4-(4-methyl-3,3a,5,6,7,7a-hexahydro-2H-pyrrolo[3,2-b]pyridin-1-yl)-8-(methylamino)-9H-pyrido[2,3-b]indol-3-yl]-1-(methylamino)-4-oxo-1,8-naphthyridine-3-carboxylic acid;

6-[5,6-difluoro-8-(methylamino)-4-(cis-6-methyl-2,6-diazabicyclo[3.2.0]heptan-2-yl)-9H-pyrido[2,3-b]indol-3-yl]-1-methyl-4-oxo-1,8-naphthyridine-3-carboxylic acid;

6-[5,6-difluoro-4-(cis-1-methyl-2,3,3a,5,6,6a-hexahydropyrrolo[3,2-b]pyrrol-4-yl)-8-(methylamino)-9H-pyrido[2,3-b]indol-3-yl]-1-(methylamino)-4-oxo-1,8-naphthyridine-3-carboxylic acid;

6-[5,6-difluoro-8-(methylamino)-4-[(2S)-2-methylmorpholin-4-yl]-9H-pyrido[2,3-b]indol-3-yl]-4-oxo-1-[(1S)-2-hydroxy-1-methyl-ethyl]-1,8-naphthyridine-3-carboxylic acid;

(1R)-6-[5,6-difluoro-8-(methylamino)-4-[(2S)-2-methylmorpholin-4-yl]-9H-pyrido[2,3-b]indol-3-yl]-4-oxo-1-pyrrolidin-3-yl-8-naphthyridine-3-carboxylic acid;

6-[5,6-difluoro-8-(methylamino)-4-[cis-6-methyl-3,6-diazabicyclo[3.2.0]heptan-3-yl]-9H-pyrido[2,3-b]indol-3-yl]-1-methyl-4-oxo-1,8-naphthyridine-3-carboxylic acid;

6-[4-[(3 S)-3-(dimethylamino)pyrrolidin-1-yl]-6-fluoro-8-(methylamino)-9H-pyrido[2,3-b]indol-3-yl]-1-methyl-4-oxo-1,8-naphthyridine-3-carboxylic acid;

6-[4-[(3 S)-3-(dimethylamino)pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-[(3 S)-3-[(dimethylamino)methyl]pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-[(3R)-3-[(dimethylamino)methyl]pyrrolidin-1-yl]-5,6-difluoro-8-(methylamino)-9H-pyrido[2,3-b]indol-3-yl]-1-methyl-4-oxo-1,8-naphthyridine-3-carboxylic acid;

6-[4-[(3R)-3-(dimethylamino)pyrrolidin-1-yl]-5,6-difluoro-8-(methylamino)-9H-pyrido[2,3-b]indol-3-yl]-1-(methylamino)-4-oxo-1,8-naphthyridine-3-carboxylic acid;

6-[4-[(3R)-3-(dimethylamino)pyrrolidin-1-yl]-5,6-difluoro-8-(methylamino)-9H-pyrido[2,3-b]indol-3-yl]-1-(ethylamino)-4-oxo-1,8-naphthyridine-3-carboxylic acid;

6-[6-fluoro-8-(methylamino)-4-pyrrolidin-1-yl-9H-pyrido[2,3-b]indol-3-yl]-4-oxo-1-pyrrolidin-3-yl-1,8-naphthyridine-3-carboxylic acid;

6-[4-[cis-1-(3-hydroxypropyl)-2,3,3a,4,6,6a-hexahydropyrrolo[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid;

6-[4-[cis-1-(2-hydroxyethyl)-2,3,3a,4,6,6a-hexahydropyrrolo[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid;

6-(4-(1-(dimethylamino)-6-azaspiro[3.4]octan-6-yl)-5,6-difluoro-8-(methylamino)-9H-pyrido[2,3-b]indol-3-yl)-1-methyl-4-oxo-1,4-dihydro-1, 8-naphthyridine-3-carboxylic acid;

6-(4-((1R,5 S,6S)-6-(dimethylamino)-3-azabicyclo[3.1.0]hexan-3-yl)-5, 6-difluoro-8-(methylamino)-9H-pyrido[2,3-b]indol-3-yl)-1-methyl-4-oxo-1,4-dihydro-1, 8-naphthyridine-3-carboxylic acid;

6-[4-[cis-5-methyl-2,3,3a,4, 6,6a-hexahydropyrrolo[2,3-c]pyrrol-1-yl]-6-chloro-8-(methylamino)-9H-pyrido[2, 3-b]indol-3-yl]-1-(methylamino)-4-oxo-1, 8-naphthyridine-3-carboxylic acid;

6-[4-[cis-5-methyl-2,3,3a,4, 6,6a-hexahydropyrrolo[2,3-c]pyrrol-1-yl]-6-chloro-8-(methylamino)-9H-pyrido[2, 3-b]indol-3-yl]-1-methyl-4-oxo-1, 8-naphthyridine-3-carboxylic acid;

6-[4-[cis-5-methyl-2,3,3a,4, 6,6a-hexahydropyrrolo[2,3-c]pyrrol-1-yl]-6-chloro-5-fluoro-8-(methylamino)-9H-pyri do[2,3-b]indol-3-yl]-1-(methylamino)-4-oxo-1, 8-naphthyridine-3-carboxylic acid;

6-[4-[cis-5-methyl-2,3,3a,4, 6,6a-hexahydropyrrolo[2,3-c]pyrrol-1-yl]-6-chloro-5-fluoro-8-(methylamino)-9H-pyrido[2, 3-b]indol-3-yl]-1-methyl-4-oxo-1, 8-naphthyridine-3-carboxylic acid;

6-[4-[cis-5-methyl-2,3,3a,4, 6,6a-hexahydropyrrolo[2,3-c]pyrrol-1-yl]-5-chloro-6-fluoro-8-(methylamino)-9H-pyri do[2,3-b]indol-3-yl]-1-(methylamino)-4-oxo-1, 8-naphthyridine-3-carboxylic acid;

6-(5-chloro-6-fluoro-8-(methylamino)-4-morpholino-9H-pyrido[2,3-b]indol-3-yl)-1-methyl-4-oxo-1,4-dihydro-1,8-naphthyridine-3-carboxylic acid;

6-[4-[cis-5-methyl-2,3,3a,4,6,6a-hexahydropyrrolo[2,3-c]pyrrol-1-yl]-5-chloro-6-fluoro-8-(methylamino)-9H-pyrido[2,3-b]indol-3-yl]-1-methyl-4-oxo-1,8-naphthyridine-3-carboxylic acid;

6-[4-(3a,5-dimethyl-3,4,6,6a-tetrahydro-2H-pyrrolo[2,3-c]pyrrol-1-yl)-6-fluoro-8-(methylamino)-9H-pyrido[2,3-b]indol-3-yl]-1-methyl-4-oxo-1,8-naphthyridine-3-carboxylic acid;

6-[4-(3a,5-dimethyl-3,4,6,6a-tetrahydro-2H-pyrrolo[2,3-c]pyrrol-1-yl)-6-fluoro-8-(methylamino)-9H-pyrido[2,3-b]indol-3-yl]-1-(methylamino)-4-oxo-1,8-naphthyridine-3-carboxylic acid;

6-[4-[cis-5-methyl-2,3,3a,4,6,6a-hexahydropyrrolo[2,3-c]pyrrol-1-yl]-5-cyano-6-fluoro-8-(methylamino)-9H-pyrido[2,3-b]indol-3-yl]-1-methyl-4-oxo-1,8-naphthyridine-3-carboxylic acid;

6-[4-[cis-5-methyl-2,3,3a,4,6,6a-hexahydropyrrolo[2,3-c]pyrrol-1-yl]-5-cyano-6-fluoro-8-(methylamino)-9H-pyrido[2,3-b]indol-3-yl]-1-(methylamino)-4-oxo-1,8-naphthyridine-3-carboxylic acid;

6-[6-chloro-4-(cis-3-hydroxy-2,3,3a,4,6,6a-hexahydrofuro[2,3-c]pyrrol-5-yl)-8-(methylamino)-9H-pyrido[2,3-b]indol-3-yl]-1-methyl-4-oxo-1,8-naphthyridine-3-carboxylic acid;

6-[6-chloro-4-[cis-3-(dimethylamino)-2,3,3a,4,6,6a-hexahydrofuro[2,3-c]pyrrol-5-yl]-8-(methylamino)-9H-pyrido[2,3-b]indol-3-yl]-1-methyl-4-oxo-1,8-naphthyridine-3-carboxylic acid;

6-[6-chloro-8-(methylamino)-4-(cis-8-methyl-3,8-diazabicyclo[4.2.0]octan-3-yl)-9H-pyrido[2,3-b]indol-3-yl]-1-methyl-4-oxo-1,8-naphthyridine-3-carboxylic acid;

6-[4-[(cis-5-ethyl-2,3,3a,4,6,6a-hexahydropyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-(dimethylamino)-5,6-difluoro-8-(methylamino)-9H-pyrido[2,3-b]indol-3-yl]-1-[(3S)-1-ethylpyrrolidin-3-yl]-4-oxo-1,8-naphthyridine-3-carboxylic acid;

6-[4-[cis-1-cyclopropyl-2,3,3a,4,6,6a-hexahydropyrrolo[2,3-c]pyrrol-5-yl]-5,6-difluoro-8-(methylamino)-9H-pyrido[2,3-b]indol-3-yl]-1-(methylamino)-4-oxo-1,8-naphthyridine-3-carboxylic acid;

6-[4-[3-[(dimethylamino)methyl]-3-fluoro-1-piperidyl]-5,6-difluoro-8-(methylamino)-9H-pyrido[2,3-b]indol-3-yl]-1-methyl-4-oxo-1,8-naphthyridine-3-carboxylic acid;

6-[4-[cis-1-cyclopropyl-2,3,3a,4,6,6a-hexahydropyrrolo[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-[cis-(4R)-4-(dimethylamino)-3,3a,4,5,6,6a-hexahydro-1H-cyclopenta[c]pyrrol-2-yl]-9H-pyrido[2,3-b]indol-3-yl]-1-(methylamino)-4-oxo-1,8-naphthyridine-3-carboxylic acid;

6-[6-chloro-8-(methylamino)-4-[cis-(4R)-(dimethylamino)-3,3a,4,5,6,6a-hexahydro-1H-cyclopenta[c]pyrrol-2-yl]-9H-pyrido[2,3-b]indol-3-yl]-1-methyl-4-oxo-1,8-naphthyridine-3-carboxylic acid;

6-[4-[cis-3-(dimethylamino)-2,3,3a,4,6,6a-hexahydrofuro[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid;

6-[5,6-difluoro-4-(cis-3-hydroxy-2,3,3a,4,6,6a-hexahydrofuro[2,3-c]pyrrol-5-yl)-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-[cis-(4S)-4-(dimethylamino)-3,3a,4,5,6,6a-hexahydro-1H-cyclopenta[c]pyrrol-2-yl]-9H-pyrido[2,3-b]indol-3-yl]-1-methyl-4-oxo-1,8-naphthyridine-3-carboxylic acid;

6-[4-[cis-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-ethyl-4-oxo-1,8-naphthyridine-3-carboxylic acid;

6-[4-[cis-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-(ethylamino)-4-oxo-1,8-naphthyridine-3-carboxylic acid;

6-[4-[cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-(ethylamino)-4-oxo-1,8-naphthyridine-3-carboxylic acid;

6-(5,6-dichloro-4-(cis-(4R)-4-(dimethylamino)hexahydrocyclopenta[c]pyrrol-2(1H)-yl)-8-(methylamino)-9H-pyrido[2,3-b]indol-3-yl)-1-methyl-4-oxo-1,4-dihydro-1,8-naphthyridine-3-carboxylic acid;

6-[4-[cis-5-methyl-2,3,3a,4,6,6a-hexahydropyrrolo[2,3-c]pyrrol-1-yl]-5,6-dichloro-8-(methylamino)-9H-pyrido[2,3-b]indol-3-yl]-1-methyl-4-oxo-1,8-naphthyridine-3-carboxylic acid;

6-[4-[cis-5-methyl-2,3,3a,4,6,6a-hexahydropyrrolo[2,3-c]pyrrol-1-yl]-6-fluoro-5-methoxy-8-(methylamino)-9H-pyrido[2,3-b]indol-3-yl]-1-methyl-4-oxo-1,8-naphthyridine-3-carboxylic acid;

6-[4-[cis-1-methyl-2,3,3a,4,6,6a-hexahydropyrrolo[2,3-c]pyrrol-5-yl]-6-fluoro-5-methoxy-8-(methylamino)-9H-pyrido[2,3-b]indol-3-yl]-1-methyl-4-oxo-1,8-naphthyridine-3-carboxylic acid;

6-(6-fluoro-8-(methylamino)-4-(5-oxa-2,8-diazaspiro[3.5]nonan-8-yl)-9H-pyrido[2,3-b]indol-3-yl)-1-methyl-4-oxo-1,4-dihydro-1,8-naphthyridine-3-carboxylic acid;

6-(6-fluoro-8-(methylamino)-4-(cis-6-methylhexahydropyrrolo[3,4-b][1,4]oxazin-4(4aH)-yl)-9H-pyrido[2,3-b]indol-3-yl)-1-methyl-4-oxo-1,4-dihydro-1,8-naphthyridine-3-carboxylic acid;

6-[4-[(3aS,6aS)-5-methyl-2,3,3a,4,6,6a-hexahydropyrrolo[2,3-c]pyrrol-1-yl]-5-cyano-6-fluoro-8-(methylamino)-9H-pyrido[2,3-b]indol-3-yl]-1-methyl-4-oxo-1,8-naphthyridine-3-carboxylic acid;

6-[4-[(3aS,6aS)-5-methyl-2,3,3a,4,6,6a-hexahydropyrrolo[2,3-c]pyrrol-1-yl]-5-cyano-6-fluoro-8-(methylamino)-9H-pyrido[2,3-b]indol-3-yl]-1-(methylamino)-4-oxo-1,8-naphthyridine-3-carboxylic acid;

6-[4-(3,3-Difluoropyrrolidin-1-yl)-5,6-difluoro-8-(methylamino)-9H-pyrido[2,3-b]indol-3-yl]-1-methyl-4-oxo-1,8-naphthyridine-3-carboxylic acid;

6-[4-(3,3-Difluoropyrrolidin-1-yl)-5,6-difluoro-8-(methylamino)-9H-pyrido[2,3-b]indol-3-yl]-1-[2-(dimethylamino)ethyl]-4-oxo-1,8-naphthyridine-3-carboxylic acid;

6-(4-(3,3-difluoropyrrolidin-1-yl)-5,6-difluoro-8-(methylamino)-9H-pyrido[2,3-b]indol-3-yl)-1-(1-methylpyrrolidin-3-yl)-4-oxo-1,4-dihydro-1,8-naphthyridine-3-carboxylic acid;

6-[4-[cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-(2-methoxyethylamino)-4-oxo-1,8-naphthyridine-3-carboxylic acid;

6-[4-[(cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-amino-4-oxo-1,8-naphthyridine-3-carboxylic acid;

6-(4-(dimethylamino)-5,6-difluoro-8-(methylamino)-9H-pyrido[2,3-b]indol-3-yl)-4-oxo-1-((2,2,2-trifluoroethyl)amino)-1,4-dihydro-1,8-naphthyridine-3-carboxylic acid;

6-(4-(dimethylamino)-5,6-difluoro-8-(methylamino)-9H-pyrido[2,3-b]indol-3-yl)-1-(2-methyl-1-(methylamino)propan-2-yl)-4-oxo-1,4-dihydro-1,8-naphthyridine-3-carboxylic acid;

6-[4-[(cis-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-amino-4-oxo-1,8-naphthyridine-3-carboxylic acid;

6-[4-[cis-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-(methoxymethyl)-4-oxo-1,8-naphthyridine-3-carboxylic acid;

6-(4-(trans-1-(dimethylamino)-5-azaspiro[2.4]heptan-5-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-(cis-1-(dimethylamino)-5-azaspiro[2.4]heptan-5-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-(4-((2S,4S)-2-((dimethylamino)methyl)-4-fluoropyrrolidin-1-yl)-5,6-difluoro-8-(methylamino)-9H-pyrido[2,3-b]indol-3-yl)-1-methyl-4-oxo-1,4-dihydro-1,8-naphthyridine-3-carboxylic acid;

6-[5,6-difluoro-8-(methylamino)-4-[(3aS,6aS)-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylic acid;

6-[5,6-difluoro-8-(methylamino)-4-[(3aR,6aR)-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylic acid;

6-[4-[(2S)-2-[(dimethylamino)methyl]morpholin-4-yl]-6-fluoro-8-(methylamino)-9H-pyrido[2,3-b]indol-3-yl]-1-methyl-4-oxo-1,8-naphthyridine-3-carboxylic acid;

6-[4-[(2R)-2-[(dimethylamino)methyl]morpholin-4-yl]-6-fluoro-8-(methylamino)-9H-pyrido[2,3-b]indol-3-yl]-1-methyl-4-oxo-1,8-naphthyridine-3-carboxylic acid;

6-[4-[(3 aS,6aS)-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-[(3 aR,6aR)-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-[(3 aS,6aS)-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-methyl-4-oxo-1,8-naphthyridine-3-carboxylic acid;

6-[4-[(3 aS,6aS)-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-(methylamino)-4-oxo-1,8-naphthyridine-3-carboxylic acid;

6-[4-[(3R)-3-(dimethylamino)-1-piperidyl]-5,6-difluoro-8-(methylamino)-9H-pyrido[2,3-b]indol-3-yl]-1-methyl-4-oxo-1,8-naphthyridine-3-carboxylic acid;

6-[4-[(3 S)-3-(dimethylamino)-1-piperidyl]-5,6-difluoro-8-(methylamino)-9H-pyrido[2,3-b]indol-3-yl]-1-methyl-4-oxo-1,8-naphthyridine-3-carboxylic acid;

6-[4-[(3 aR,6aR)-1-methyl-2,3,3a,4,6,6a-hexahydropyrrolo[2,3-c]pyrrol-5-yl]-5,6-difluoro-8-(methylamino)-9H-pyrido[2,3-b]indol-3-yl]-1-(methylamino)-4-oxo-1,8-naphthyridine-3-carboxylic acid;

6-[4-[(3 aS,6aS)-1-methyl-2,3,3a,4,6,6a-hexahydropyrrolo[2,3-c]pyrrol-5-yl]-5,6-difluoro-8-(methylamino)-9H-pyrido[2,3-b]indol-3-yl]-1-(methylamino)-4-oxo-1,8-naphthyridine-3-carboxylic acid;

6-[4-[(3 aR,6aR)-1-methyl-2,3,3a,4,6,6a-hexahydropyrrolo[2,3-c]pyrrol-5-yl]-5,6-difluoro-8-(methylamino)-9H-pyrido[2,3-b]indol-3-yl]-1-methyl-4-oxo-1,8-naphthyridine-3-carboxylic acid;

6-[4-[(3 aR,6aR)-3a-fluoro-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-[(3 aS, 6aS)-3a-fluoro-5-methyl-3,4,6, 6a-tetrahydro-2H-pyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-[(3aR,6aR)-3a-fluoro-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-(methylamino)-4-oxo-1,8-naphthyridine-3-carboxylic acid;

6-[4-[(3aS,6aS)-3a-fluoro-5-methyl-3,4,6,6a-tetrahydro-2H-pyrrolo[2,3-c]pyrrol-1-yl]-5,6-difluoro-8-(methylamino)-9H-pyrido[2,3-b]indol-3-yl]-1-(methylamino)-4-oxo-1,8-naphthyridine-3-carboxylic acid;

6-[4-[(3aS,6aS)-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-methyl-4-oxo-1,8-naphthyridine-3-carboxylic acid;

6-[4-[(3aR,6aR)-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-methyl-4-oxo-1,8-naphthyridine-3-carboxylic acid;

6-[4-[(3aS,6aS)-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-(methylamino)-4-oxo-1,8-naphthyridine-3-carboxylic acid;

6-[4-[(3aR,6aR)-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-(methylamino)-4-oxo-1,8-naphthyridine-3-carboxylic acid;

6-[4-[(4aS,7aR)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-(methylamino)-4-oxo-1,8-naphthyridine-3-carboxylic acid;

6-[4-[(4aR,7aS)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-(methylamino)-4-oxo-1,8-naphthyridine-3-carboxylic acid;

6-[4-[(4aS,7aR)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-methyl-4-oxo-1,8-naphthyridine-3-carboxylic acid;

6-[4-[(4aR,7aS)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-methyl-4-oxo-1,8-naphthyridine-3-carboxylic acid;

6-[4-[(3aR,6aR)-1-methyl-2,3,3a,4,6,6a-hexahydropyrrolo[2,3-c]pyrrol-5-yl]-6-chloro-8-(methylamino)-9H-pyrido[2,3-b]indol-3-yl]-1-methyl-4-oxo-1,8-naphthyridine-3-carboxylic acid;

6-[4-[(3aS,6aS)-1-methyl-2,3,3a,4,6,6a-hexahydropyrrolo[2,3-c]pyrrol-5-yl]-6-chloro-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-[(5R)-9-methyl-6-oxa-2,9-diazaspiro[4.5]decan-2-yl]-9H-pyrido[2,3-b]indol-3-yl]-1-methyl-4-oxo-1,8-naphthyridine-3-carboxylic acids;

6-[5,6-difluoro-8-(methylamino)-4-[(5S)-9-methyl-6-oxa-2,9-diazaspiro[4.5]decan-2-yl]-9H-pyrido[2,3-b]indol-3-yl]-1-methyl-4-oxo-1,8-naphthyridine-3-carboxylic acid;

6-[4-[(3aR,6aR)-1-methyl-2,3,3a,4,6,6a-hexahydropyrrolo[2,3-c]pyrrol-5-yl]-6-fluoro-8-(methylamino)-9H-pyrido[2,3-b]indol-3-yl]-1-(methylamino)-4-oxo-1,8-naphthyridine-3-carboxylic acid;

6-[4-[(3aS,6aS)-1-methyl-2,3,3a,4,6,6a-hexahydropyrrolo[2,3-c]pyrrol-5-yl]-6-fluoro-8-(methylamino)-9H-pyrido[2,3-b]indol-3-yl]-1-(methylamino)-4-oxo-1,8-naphthyridine-3-carboxylic acid;

6-[4-[(3aR,7aR)-1-methyl-3,3a,4,5,7,7a-hexahydro-2H-pyrrolo[2,3-c]pyridin-6-yl]-6-fluoro-8-(methylamino)-9H-pyrido[2,3-b]indol-3-yl]-1-methyl-4-oxo-1,8-naphthyridine-3-carboxylic acid;

6-[4-[(3aS,7aS)-1-methyl-3,3a,4,5,7,7a-hexahydro-2H-pyrrolo[2,3-c]pyridin-6-yl]-6-fluoro-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-[(3aR,4R,6aS)-4-(dimethylamino)-3,3a,4,5,6,6a-hexahydro-1H-cyclopenta[c]pyrrol-2-yl]-9H-pyrido[2,3-b]indol-3-yl]-1-(methylamino)-4-oxo-1,8-naphthyridine-3-carboxylic acid;

6-[5,6-difluoro-8-(methylamino)-4-[(3aS,4R,6aS)-4-(dimethylamino)-3,3a,4,5,6,6a-hexahydro-1H-cyclopenta[c]pyrrol-2-yl]-9H-pyrido[2,3-b]indol-3-yl]-1-(methylamino)-4-oxo-1,8-naphthyridine-3-carboxylic acid;

6-[4-[(3aR,4S,6aS)-4-(dimethylamino)-3,3a,4,5,6,6a-hexahydro-1H-cyclopenta[c]pyrrol-2-yl]-6-chloro-8-(methylamino)-9H-pyrido[2,3-b]indol-3-yl]-1-methyl-4-oxo-1,8-naphthyridine-3-carboxylic acid;

6-[4-[(3aS,4S,6aR)-4-(dimethylamino)-3,3a,4,5,6,6a-hexahydro-1H-cyclopenta[c]pyrrol-2-yl]-6-chloro-8-(methylamino)-9H-pyrido[2,3-b]indol-3-yl]-1-methyl-4-oxo-1,8-naphthyridine-3-carboxylic acid;

6-[5,6-difluoro-8-(methylamino)-4-[(4aR,7aR)-4-hydroxy-1-methyl-3,4,4a,5,7,7a-hexahydro-2H-pyrrolo[3,4-b]pyridin-6-yl]-9H-pyrido[2,3-b]indol-3-yl]-1-methyl-4-oxo-1,8-naphthyridine-3-carboxylic acid;

6-[5,6-difluoro-8-(methylamino)-4-[(4aS,7aS)-4-hydroxy-1-methyl-3,4,4a,5,7,7a-hexahydro-2H-pyrrolo[3,4-b]pyridin-6-yl]-9H-pyrido[2,3-b]indol-3-yl]-1-methyl-4-oxo-1,8-naphthyridine-3-carboxylic acid;

6-[6-fluoro-8-(methylamino)-4-[(4aR,7aR)-4-methyl-2,3,4a,5,7,7a-hexahydropyrrolo[3,4-b][1,4]oxazin-6-yl]-9H-pyrido[2,3-b]indol-3-yl]-1-methyl-4-oxo-1,8-naphthyridine-3-carboxylic acid;

6-[4-[(4aR,7aS)-4-methyl-2,3,4a,5,7,7a-hexahydropyrrolo[3,4-b][1,4]oxazin-6-yl]-6-fluoro-8-(methylamino)-9H-pyrido[2,3-b]indol-3-yl]-1-methyl-4-oxo-1,8-naphthyridine-3-carboxylic acid;

6-[6-fluoro-8-(methylamino)-4-[(4aS,7aR)-4-methyl-2,3,4a,5,7,7a-hexahydropyrrolo[3,4-b][1,4]oxazin-6-yl]-9H-pyrido[2,3-b]indol-3-yl]-1-(methylamino)-4-oxo-1,8-naphthyridine-3-carboxylic acid;

6-[4-[(4aR,7aS)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-methyl-4-oxo-1,8-naphthyridine-3-carboxylic acid;

6-[4-[(4aR,7aR)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-methyl-4-oxo-1,8-naphthyridine-3-carboxylic acid;

(S)-6-(5,6-difluoro-8-(methylamino)-4-(3-(trifluoromethyl)piperazin-1-yl)-9H-pyrido[2,3-b]indol-3-yl)-1-methyl-4-oxo-1,4-dihydro-1, 8-naphthyridine-3-carboxylic acid;

(R)-6-(5,6-difluoro-8-(methylamino)-4-(3-(trifluoromethyl)piperazin-1-yl)-9H-pyrido[2,3-b]indol-3-yl)-1-methyl-4-oxo-1,4-dihydro-1, 8-naphthyridine-3-carboxylic acid;

(R)-6-(4-(2-((dimethylamino)methyl)morpholino)-5,6-difluoro-8-(methylamino)-9H-pyrido[2,3-b]indol-3-yl)-1-methyl-4-oxo-1,4-dihydro-1, 8-naphthyridine-3-carboxylic acid; and (S)-6-(4-(2-((dimethylamino)methyl)morpholino)-5,6-difluoro-8-(methylamino)-9H-pyrido[2,3-b]indol-3-yl)-1-methyl-4-oxo-1,4-dihydro-1, 8-naphthyridine-3-carboxylic acid;

or a pharmaceutically acceptable salt, or enantiomer or diastereomer thereof.

19. A compound according to claim 1, selected from 6-(6-chloro-4-(3-(dimethylamino)pyrrolidin-1-yl)-8-(methylamino)-9H-pyrido[2,3-b]indol-3-yl)-1-methyl-4-oxo-1,4-dihydro-1,8-naphthyridine-3-carboxylic acid;

6-[4-cis-(4R)-(dimethylamino)-3,3a,4,5,6,6a-hexahydro-1H-cyclopenta[c]pyrrol-2-yl]-5,6-difluoro-8-(methylamino)-9H-pyrido[2,3-b]indol-3-yl]-1-methyl-4-oxo-1,8-naphthyridine-3-carboxylic acid;

6-[4-[cis-5-methyl-2,3,3a,4,6,6a-hexahydropyrrolo[2,3-c]pyrrol-1-yl]-5-chloro-6-fluoro-8-(methylamino)-9H-pyrido[2,3-b]indol-3-yl]-1-methyl-4-oxo-1,8-naphthyridine-3-carboxylic acid;

6-[6-chloro-8-(methylamino)-4-[cis-(4R)-(dimethylamino)-3,3a,4, 5,6,6a-hexahydro-1H-cyclopenta[c]pyrrol-2-yl]-9H-pyrido[2,3-b]indol-3-yl]-1-methyl-4-oxo-1,8-naphthyridine-3-carboxylic acid;

6-[4-[cis-5-methyl-2,3,3a,4,6,6a-hexahydropyrrolo[2,3-c]pyrrol-1-yl]-5,6-dichloro-8-(methylamino)-9H-pyrido[2,3-b]indol-3-yl]-1-methyl-4-oxo-1,8-naphthyridine-3-carboxylic acid;

6-[4-[(3 aS,6aS)-5-methyl-2,3,3a,4,6,6a-hexahydropyrrolo[2,3-c]pyrrol-1-yl]-5-cyano-6-fluoro-8-(methylamino)-9H-pyrido[2,3-b]indol-3-yl]-1-methyl-4-oxo-1,8-naphthyridine-3-carboxylic acid;

6-[4-[(3 aS,6aS)-5-methyl-2,3,3a,4,6,6a-hexahydropyrrolo[2,3-c]pyrrol-1-yl]-5-cyano-6-fluoro-8-(methylamino)-9H-pyrido[2,3-b]indol-3-yl]-1-(methylamino)-4-oxo-1,8-naphthyridine-3-carboxylic acid;

6-[5,6-difluoro-8-(methylamino)-4-[(3aS,6aS)-5-methyl-2,3,3a,4,6,6a-hexahydropyrrolo[2,3-c]pyrrol-1-yl]-9H-pyrido[2,3-b]indol-3-yl]-1-(methylamino)-4-oxo-1,8-naphthyridine-3-carboxylic acid;

6-[4-[(3aS,6aS)-5-methyl-2,3,3a,4,6,6a-hexahydropyrrolo[2,3-c]pyrrol-1-yl]-5,6-difluoro-8-(methylamino)-9H-pyrido[2,3-b]indol-3-yl]-1-methyl-4-oxo-1,8-naphthyridine-3-carboxylic acid;

6-[4-[(3aS,6aS)-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-methyl-4-oxo-1,8-naphthyridine-3-carboxylic acid;

6-[4-[(3aS,6aS)-5-methyl-2,3,3a,4,6,6a-hexahydropyrrolo[2,3-c]pyrrol-1-yl]-6-fluoro-8-(methylamino)-9H-pyrido[2,3-b]indol-3-yl]-1-(methylamino)-4-oxo-1,8-naphthyridine-3-carboxylic acid;

6-[4-[(3aR,6aR)-1-methyl-2,3,3a,4,6,6a-hexahydropyrrolo[2,3-c]pyrrol-5-yl]-5,6-difluoro-8-(methylamino)-9H-pyrido[2,3-b]indol-3-yl]-1-(methylamino)-4-oxo-1,8-naphthyridine-3-carboxylic acid;

6-[4-[(3aS,6aS)-5-methyl-2,3,3a,4,6,6a-hexahydropyrrolo[2,3-c]pyrrol-1-yl]-6-chloro-8-(methylamino)-9H-pyrido[2,3-b]indol-3-yl]-1-methyl-4-oxo-1,8-naphthyridine-3-carboxylic acid;

6-[4-[(4aS,7aR)-4-methyl-2,3,4a,5,7,7a-hexahydropyrrolo[3,4-b][1,4]oxazin-6-yl]-5,6-difluoro-8-(methylamino)-9H-pyrido[2,3-b]indol-3-yl]-1-(methylamino)-4-oxo-1,8-naphthyridine-3-carboxylic acid; and 6-[4-[(3aR,6aR)-1-methyl-2,3,3a,4,6,6a-hexahydropyrrolo[2,3-c]pyrrol-5-yl]-6-chloro-8-(methylamino)-9H-pyrido[2,3-b]indol-3-yl]-1-methyl-4-oxo-1,8-naphthyridine-3-carboxylic acid;

or a pharmaceutically acceptable salt, or enantiomer or diastereomer thereof.

20. A pharmaceutical composition comprising a compound according to claim 1, or a pharmaceutically acceptable salt, or enantiomer or diastereomer thereof, and a therapeutically inert carrier.

21. A compound according to claim 1, or a pharmaceutically acceptable salt, or enantiomer or diastereomer thereof, manufactured according to a process comprising reacting compound of formula (Ii),

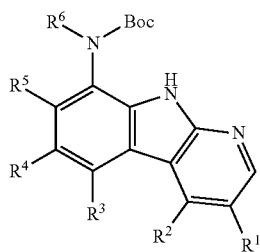

(Ii)

with an acid.

22. A process for the preparation of a compound according to claim 1, or a pharmaceutically acceptable salt, or enantiomer or diastereomer thereof, comprising the reaction of compound of formula (Ii),

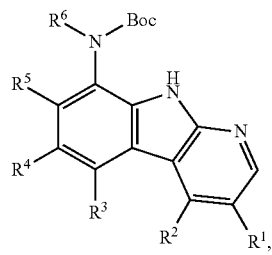

(Ii)

with an acid.

23. A method for the treatment of bacterial infection in a subject, which method comprises administering to said subject an effective amount of a compound according to claim 1, or a pharmaceutically acceptable salt, or enantiomer or diastereomer thereof.

24. The method according to claim 23, wherein the bacterial infection is caused by *Streptococcus pneumoniae*, *Streptococcus pyogenes*, *Enterococcus faecalis*, *Enterococcus faecium*, *Enterobacter* spp. species, *Proteus* spp. species, *Serratia marcescens*, *Staphylococcus aureus*, Coag. Neg. Staphylococci, *Haemophilus influenzae*, *Bacillus anthraces*, *Mycoplasma pneumoniae*, *Moraxella catarrhalis*, *Chlamydophila pneumoniae*, *Chlamydia trachomatis*, *Legionella pneumophila*, *Mycobacterium tuberculosis*, *Helicobacter pylori*, *Staphylococcus saprophyticus*, *Staphylococcus epidermidis*, *Francisella tularensis*, *Yersinia pestis*, *Clostridium difficile*, *Bacteroides* spp. species *Neisseria gonorrhoeae*, *Neisseria meningitidis*, *Burkholderia pseudomallei*, *Burkholderia mallei*, *Borrelia burgdorferi*, *Mycobacterium avium* complex, *Mycobacterium abscessus*, *Mycobacterium kansasii*, *E. coli* or *Mycobacterium ulcerans*.

25. The method according to claim 23, wherein the bacterial infection is caused by *Acinetobacter baumannii*, *Klebsiella pneumoniae*, *Pseudomonas aeruginosa*, *Staphylococcus aureus* or *E. coli*.

26. A method for inhibiting DNA gyrase or topoisomerase IV in a subject, which method comprises administering to said subject an effective amount of a compound according to claim 1, or a pharmaceutically acceptable salt, or enantiomer or diastereomer thereof.

27. A method for inhibiting DNA gyrase and topoisomerase IV in a subject, which method comprises administering to said subject an effective amount of a compound according to claim 1, or a pharmaceutically acceptable salt, or enantiomer or diastereomer thereof.

* * * * *